United States Patent
Quddus et al.

(10) Patent No.: US 11,655,246 B2
(45) Date of Patent: May 23, 2023

(54) AMINOTHIAZOLE COMPOUNDS AS INHIBITORS OF CTPS1

(71) Applicant: STEP PHARMA S.A.S., Paris (FR)

(72) Inventors: Abdul Quddus, Nottingham (GB); Andrew Novak, Nottingham (GB); David Cousin, Nottingham (GB); Elli Chatzopoulou, Nottingham (GB); Emma Blackham, Nottingham (GB); Geraint Jones, Nottingham (GB); Jennifer Thomas, Nottingham (GB); Joseph Wrigglesworth, Nottingham (GB); Lorna Duffy, Nottingham (GB); Louise Birch, Nottingham (GB); Pascal George, Nottingham (GB); Saleh Ahmed, Nottingham (GB)

(73) Assignee: STEP PHARMA S.A.S., Paris (FR)

( * ) Notice: Subject to any disclaimer, the term of this patent is extended or adjusted under 35 U.S.C. 154(b) by 0 days.

(21) Appl. No.: 16/767,338

(22) PCT Filed: Nov. 30, 2018

(86) PCT No.: PCT/EP2018/083169
§ 371 (c)(1),
(2) Date: May 27, 2020

(87) PCT Pub. No.: WO2019/106156
PCT Pub. Date: Jun. 6, 2019

(65) Prior Publication Data
US 2021/0002269 A1     Jan. 7, 2021

(30) Foreign Application Priority Data

Nov. 30, 2017 (EP) ...................... 17204796
Mar. 23, 2018 (EP) ...................... 18163766

(51) Int. Cl.
*C07D 417/14* (2006.01)
*C07D 277/52* (2006.01)
*C07D 417/12* (2006.01)

(52) U.S. Cl.
CPC ......... *C07D 417/14* (2013.01); *C07D 277/52* (2013.01); *C07D 417/12* (2013.01)

(58) Field of Classification Search
CPC ... C07D 417/14; C07D 277/52; C07D 417/12
See application file for complete search history.

(56) References Cited

U.S. PATENT DOCUMENTS

| 6,048,884 | A * | 4/2000 | Maruyama | ........... | C07D 471/04 |
| | | | | | 514/342 |
| 11,505,547 | B2 * | 11/2022 | Novak | ............ | C07D 213/22 |
| 2003/0176476 | A1 * | 9/2003 | Barf | ............ | A61P 25/28 |
| | | | | | 514/370 |
| 2008/0139557 | A1 | 6/2008 | Blomgren et al. | | |
| 2016/0152583 | A1 | 6/2016 | Arisawa et al. | | |
| 2021/0024507 | A1 | 1/2021 | Quddus et al. | | |
| 2021/0380575 | A1 | 12/2021 | Novak et al. | | |
| 2021/0387965 | A1 | 12/2021 | Quddus et al. | | |
| 2022/0324837 | A1 * | 10/2022 | Quddus | ................ | C07D 239/38 |

FOREIGN PATENT DOCUMENTS

| CN | 104262071 | | 1/2015 |
| EP | 1659113 | | 5/2006 |
| EP | 2292603 | A1 | 3/2011 |
| GB | 1555007 | A | 11/1979 |
| GB | 1575803 | | 10/1980 |
| WO | WO 2006/010751 | A1 | 2/2006 |
| WO | WO 2009/075874 | A1 | 6/2009 |
| WO | WO 2014/090715 | A1 | 6/2014 |
| WO | WO 2014/170435 | A2 | 10/2014 |
| WO | WO 2019/106146 | A1 | 6/2019 |
| WO | WO 2019/106156 | A1 | 6/2019 |
| WO | WO 2019/179652 | A1 | 9/2019 |
| WO | WO 2019/180244 | A1 | 9/2019 |
| WO | WO 2020/083975 | A1 | 4/2020 |
| WO | WO 2020/245664 | A1 | 12/2020 |
| WO | WO 2020/245665 | A1 | 12/2020 |
| WO | WO 2021/053402 | A2 | 3/2021 |
| WO | WO 2021/053403 | A1 | 3/2021 |
| WO | WO 2022/087634 | | 4/2022 |

OTHER PUBLICATIONS

Lee; Antiviral Research 2017, 139, 49-58. DOI: 10.1016/j.antiviral.2016.12.016 (Year: 2016).*
Lubbers; Bioorg. Med. Chem. Lett. 2011, 21, 6554-6558. DOI: 10.1016/j.bmcl.2011.08.060 (Year: 2011).*
Tang; Arteriosclerosis, Thrombosis, and Vascular Biology 2013, 33, 2336-2344. DOI: 10.1161/ATVBAHA.113.301561 (Year: 2013).*
National Center for Biotechnology Information. PubChem Substance Record for SID 69002076, ZINC29974483, Available May 29, 2009, Source: ZINC. https://pubchem.ncbi.nlm.nih.gov/substance/69002076. (Year: 2009).*
International Search Report & Written Opinion PCT Application No. PCT/EP2018/083140, dated Jun. 6, 2019, 12 pages.
International Search Report & Written Opinion PCT Application No. PCT/EP2018/083169, dated Jun. 6, 2019, 12 pages.

(Continued)

*Primary Examiner* — Daniel R Carcanague
(74) *Attorney, Agent, or Firm* — Morgan, Lewis & Bockius LLP

(57) ABSTRACT

Compounds of formula (I): (I) and related aspects.

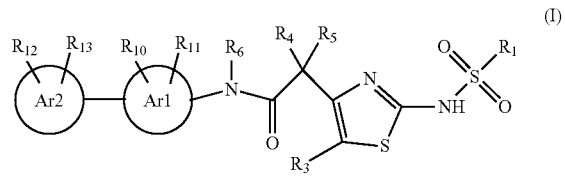

19 Claims, No Drawings
Specification includes a Sequence Listing.

(56) References Cited

OTHER PUBLICATIONS

Klapers, et al., "Copper-Catalyzed Halogen Exchange in Aryl Halides: An Aromatic Finkelstein Reaction," J. Am. Chem. Soc., vol. 124, pp. 14844-14845, 2002.

Lai, et al., "A biocompatible inverse electron demand Diels-Alder reaction of aldehyde and tetrazine promoted by proline," New J. Chem. vol. 40, pp. 8194-8197, 2016.

Mccluskey, et al., "Exploring the Potent Inhibition of CTP Synthase by Gemcitabine-5'-Triphosphate," ChemBioChem., vol. 17, pp. 2240-2249, 2016.

Meng, et al., "Carboxylation of Aromatic and Aliphatic Bromides and Tritiates with $CO_2$ by Dual Visible-Light-Nickel Catalysis," Angew. Chem. Int. Ed., vol. 56, pp. 13426-13430, 2017.

Sakamoto, et al., "Identification of cytidine-5-triphosphate synthaseI-selective inhibitory peptide from random peptide library displayed on T7 phage," Peptides, vol. 94, pp. 56-63, 2017.

Thirumoorthi, et al., "A practical metal-free homolytic aromatic alkylation protocol for the synthesis of 3-(pyrazine-2-yl)bicycle[1.1.1]pentane-1-carboxylic acid," Org. Biomol. Chem., vol. 14, pp. 9485-9489, 2016.

Wang, et al., "Diamondoid-structured polymolybdate-based metal-organic frameworks as high-capacity anodes for lithium-ion batteries," Chem. Commun., vol. 53, pp. 5204-5207, 2017.

Zhao, et al., "Design, synthesis and evaluation of aromatic heterocyclic derivatives as potent antifungal agents," European Journal of Medicinal Chemistry, vol. 137, pp. 96-107, 2017.

U.S. Appl. No. 17/615,879, Quddus, et al.

U.S. Appl. No. 17/615,873, Quddus, et al.

Lynch, et al., "Structural basis for isoform-specific inhibition of human CTPS1," PNAS, vol. 118, No. 40, 9 pages, 2021.

U.S. Appl. No. 17/760,861, Novak et al.

U.S. Appl. No. 17/760,886, Novak et al.

Ananthakrishnanadar et al., "The Effects of Substituents on the Rate of Saponification of Biphenyl-4-carboxylates," Journal of the Chemical Society, Perkin Transactions 2: Physical Organic Chemistry, 11 (1): 35-37 (1984).

Database Registry, Chemical Abstracts Service, XP055772827, Feb 20, 2014.

Database Registry, Chemical Abstracts Service, XP055772837, Jun. 10, 2009.

Database Registry, Chemical Abstracts Service, XP055772841, Dec. 4, 2017.

Database Registry, Chemical Abstracts Service, XP055772832, Jun. 10, 2009.

Database Registry, Chemical Abstracts Service, XP055772844, Nov. 10, 2011.

Database Registry, Chemical Abstracts Service, XP002801975, Mar. 8, 2019.

Database Registry, Chemical Abstracts Service, XP002801976, Dec. 10, 2013.

Database Registry, Chemical Abstracts Service, XP002801977, Nov. 1, 2013.

Database Registry, Chemical Abstracts Service, XP002801978, Nov. 4, 2013.

Database Registry, Chemical Abstracts Service, XP002801979, Dec. 2, 2013.

Database Registry, Chemical Abstracts Service, XP002801980, Dec. 8, 2013.

Database Registry, Chemical Abstracts Service, XP002801981, Dec. 13, 2013.

Database Registry, Chemical Abstracts Service, XP002801982, Dec. 15, 2013.

Database Registry, Chemical Abstracts Service, XP002801983, Dec. 19, 2013.

Novak, Andrew, et al., Journal of Medicinal Chemistry "Discovery and Optimization of Potent and Orally Available CTP Synthetase Inhibitors Use in Treatment of Diseases Driven by Abberrant Immune Cell Proliferation," published online Nov. 30, 2022, 11 pages.

Schimmel, K.J.M., et al., Current Cancer Drug Targets, "Cyclopentenyl Cytosine (CPEC): An overview of its in vitro and in vivo Activity," dated May 28, 2007, pp. 504-509.

\* cited by examiner

AMINOTHIAZOLE COMPOUNDS AS INHIBITORS OF CTPS1

RELATED APPLICATIONS

This application is a U.S. National Phase Application under 35 U.S.C. § 371 of International Application No. PCT/EP2018/083169, filed Nov. 30, 2018, which claims priority to, and the benefit of, European Application No. 17204796.1, filed Nov. 30, 2017, and European Application No. 18163766.1, filed Mar. 23, 2018. The contents of each of these applications are incorporated herein by reference in their entirety.

INCORPORATION BY REFERENCE OF SEQUENCE LISTING

The present application is being filed with a Sequence Listing in electronic format. The Sequence Listing is provided as a file entitled "STP-P2245US—Sequence listing_ST25," created on Oct. 29, 2021, and is 4.00 kilobytes in size. The information in electronic format of the Sequence Listing is incorporated by reference in its entirety.

FIELD OF THE INVENTION

The invention relates to novel aminothiazole compounds, processes for the manufacture of such compounds, related intermediates, compositions comprising such compounds and the use of such compounds as cytidine triphosphate synthase 1 inhibitors, particularly in the treatment or prophylaxis of disorders associated with cell proliferation.

BACKGROUND OF THE INVENTION

Nucleotides are a key building block for cellular metabolic processes such as deoxyribonucleic acid (DNA) and ribonucleic acid (RNA) synthesis. There are two classes of nucleotides, that contain either purine or pyrimidine bases, both of which are important for metabolic processes. Based on this, many therapies have been developed to target different aspects of nucleotide synthesis, with some inhibiting generation of purine nucleotides and some pyrimidine nucleotides, or both.

The pyrimidine nucleotide cytidine 5' triphosphate (CTP) is a precursor required not just for the metabolism of DNA and RNA but also phospholipids and sialyation of proteins. CTP originates from two sources: a salvage pathway and a de novo synthesis pathway that depends on two enzymes, the CTP synthases (or synthetases) 1 and 2 (CTPS1 and CTPS2) (Evans and Guy 2004; Higgins, et al. 2007; Ostrander, et al. 1998).

CTPS1 and CTPS2 catalyse the conversion of uridine triphosphate (UTP) and glutamine into cytidine triphosphate (CTP) and L-glutamate:

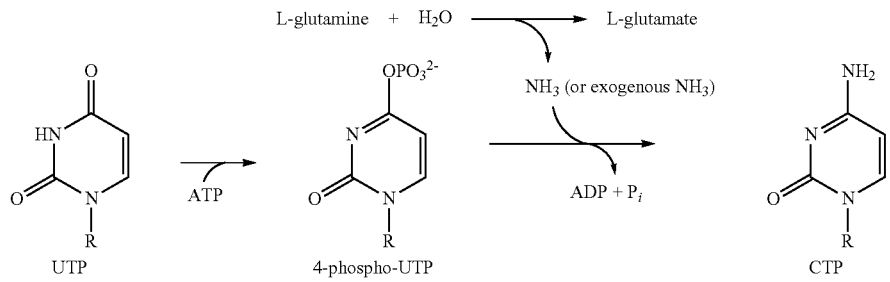

Both enzymes have two domains, an N-terminal synthetase domain and a C-terminal glutaminase domain (Kursula, et al. 2006). The synthetase domain transfers a phosphate from adenosine triphosphate (ATP) to the 4-position of UTP to create an activated intermediate, 4-phospho-UTP. The glutaminase domain generates ammonia from glutamine, via a covalent thioester intermediate with a conserved active site cysteine, generating glutamate. This ammonium is transferred from the glutaminase domain to the synthetase domain via a tunnel or can be derived from external ammonium. This ammonium is then used by the synthetase domain to generate CTP from the 4-phospho-UTP (Lieberman, 1956).

Although CTPS exists as two isozymes in humans and other eukaryotic organisms, CTPS1 and CTPS2, functional differences between the two isozymes are not yet fully elucidated (van Kuilenburg, et al. 2000).

The immune system provides protection from infections and has therefore evolved to rapidly respond to the wide variety of pathogens that the individual may be exposed to. This response can take many forms, but the expansion and differentiation of immune populations is a critical element and is hence closely linked to rapid cell proliferation. Within this, CTP synthase activity appears to play an important role in DNA synthesis and the rapid expansion of lymphocytes following activation (Fairbanks, et al. 1995; van den Berg, et al. 1995).

Strong clinical validation that CTPS1 is the critical enzyme in human lymphocyte proliferation came with the identification of a loss-of-function homozygous mutation (rs145092287) in this enzyme that causes a distinct and life-threatening immunodeficiency, characterized by an impaired capacity of activated T- and B-cells to proliferate in response to antigen receptor-mediated activation. Activated CTPS1-deficient cells were shown to have decreased levels of CTP. Normal T-cell proliferation was restored in CTPS1-deficient cells by expressing wild-type CTPS1 or by addition of exogenous CTP or its nucleoside precursor, cytidine. CTPS1 expression was found to be low in resting lymphocytes, but rapidly upregulated following activation of these cells. Expression of CTPS1 in other tissues was generally low. CTPS2 seems to be ubiquitously expressed in a range of cells and tissues but at low levels, and the failure of CTPS2, which is still intact in the patients, to compensate for the mutated CTPS1, supports CTPS1 being the critical enzyme for the immune populations affected in the patients (Martin, et al. 2014).

Overall, these findings suggest that CTPS1 is a critical enzyme necessary to meet the demands for the supply of CTP required by several important immune cell populations.

Normally the immune response is tightly regulated to ensure protection from infection, whilst controlling any response targeting host tissues. In certain situations, the control of this process is not effective, leading to immune-mediated pathology. A wide range of human diseases are thought to be due to such inappropriate responses mediated by different elements of the immune system.

Given the role that cell populations, such as T and B lymphocytes, are thought to play in a wide range of auto-immune and other diseases, CTPS1 represents a target for a new class of immunosuppressive agents. Inhibition of CTPS1 therefore provides a novel approach to the inhibition of activated lymphocytes and selected other immune cell populations such as Natural Killer cells, Mucosal-Associated Invariant T (MAIT) and Invariant Natural Killer T cells, highlighted by the phenotype of the human mutation patients (Martin, et al. 2014).

Cancer can affect multiple cell types and tissues but the underlying cause is a breakdown in the control of cell division. This process is highly complex, requiring careful coordination of multiple pathways, many of which remain to be fully characterised. Cell division requires the effective replication of the cell's DNA and other constituents. Interfering with a cell's ability to replicate by targeting nucleic acid synthesis has been a core approach in cancer therapy for many years. Examples of therapies acting in this way are 6-thioguanine, 6-mecaptopurine, 5-fluorouracil, cytarabine, gemcitabine and pemetrexed.

As indicated above, pathways involved in providing the key building blocks for nucleic acid replication are the purine and pyrimidine synthesis pathways, and pyrimidine biosynthesis has been observed to be up-regulated in tumors and neoplastic cells.

CTPS activity is upregulated in a range of tumour types of both haematological and non-haematological origin, although heterogeneity is observed among patients. Linkages have also been made between high enzyme levels and resistance to chemotherapeutic agents.

Currently, the precise role that CTPS1 and CTPS2 may play in cancer is not completely clear. Several non-selective CTPS inhibitors have been developed for oncology indications up to phase I/II clinical trials, but were stopped due to toxicity and efficacy issues.

Most of the developed inhibitors are nucleoside-analogue prodrugs (3-deazauridine, CPEC, carbodine), which are converted to the active triphosphorylated metabolite by the kinases involved in pyrimidine biosynthesis: uridine/cytidine kinase, nucleoside monophosphate-kinase (NMP-kinase) and nucleoside diphosphatekinase (NDP-kinase). The remaining inhibitors (acivicin, DON) are reactive analogues of glutamine, which irreversibly inhibit the glutaminase domain of CTPS. Gemcitibine is also reported to have some inhibitory activity against CTPS (McClusky et al., 2016).

CTPS therefore appears to be an important target in the cancer field. The nature of all of the above compounds is such that effects on other pathways are likely to contribute to the efficacy they show in inhibiting tumours.

Selective CTPS inhibitors therefore offer an attractive alternative approach for the treatment of tumours. Compounds with different potencies against CTPS1 and CTPS2 may offer important opportunities to target different tumours depending upon their relative dependence on these enzymes.

CTPS1 has also been suggested to play a role in vascular smooth muscle cell proliferation following vascular injury or surgery (Tang et al., 2013).

As far as is known to date, no selective CTPS1 inhibitors have been developed. Recently, the CTPS1 selective inhibitory peptide CTpep-3 has been identified. The inhibitory effects of CTpep-3 however, were seen in cell free assays but not in the cellular context. This was not unexpected though, since the peptide is unlikely to enter the cell and hence is not easily developable as a therapeutic (Sakamoto, et al. 2017).

In summary, the available information and data strongly suggest that inhibitors of CTPS1 will reduce the proliferation of a number of immune and cancer cell populations, with the potential for an effect on other selected cell types such as vascular smooth muscle cells as well. Inhibitors of CTPS1 may therefore be expected to have utility for treatment or prophylaxis in a wide range of indications where the pathology is driven by these populations.

CTPS1 inhibitors represent a novel approach for inhibiting selected components of the immune system in various tissues, and the related pathologies or pathological conditions such as, in general terms, rejection of transplanted cells and tissues, Graft-related diseases or disorders, allergies and autoimmune diseases. In addition, CTPS1 inhibitors offer therapeutic potential in a range of cancer indications and in enhancing recovery from vascular injury or surgery and reducing morbidity and mortality associated with neointima and restenosis.

SUMMARY OF THE INVENTION

The invention provides a compound of formula (I):

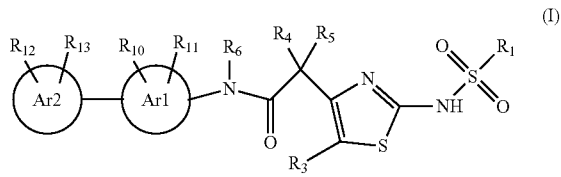

wherein $R_1$ is $C_{1-5}$alkyl, $C_{0-2}$alkylene$C_{3-5}$cycloalkyl which cycloalkyl is optionally substituted by $CH_3$, $C_{1-3}$alkyleneOC$_{1-2}$alkyl, or $CF_3$;

$R_3$ is H, halo, $CH_3$, $OC_{1-2}$alkyl or $CF_3$;

or $R_3$ together with $R_5$ forms a 5- or 6-membered cycloalkyl or 5 or 6 membered oxygen-containing heterocycloalkyl;

$R_4$ and $R_5$ are each independently H, halo, $C_{1-6}$alkyl, $C_{0-2}$alkyleneC$_{3-6}$cycloalkyl, $C_{0-2}$alkyleneC$_{3-6}$heterocycloalkyl, $OC_{1-6}$alkyl, $OC_{0-2}$alkyleneC$_{3-6}$cycloalkyl, $OC_{0-2}$alkyleneC$_{3-6}$heterocycloalkyl, $C_{1-3}$alkyleneOC$_{1-3}$alkyl, $C_{1-6}$alkylOH, $C_{1-6}$haloalkyl, $OC_{1-6}$haloalkyl or $NR_{21}R_{22}$, or $R_4$ is H and $R_5$ together with $R_3$ form a 5- or 6-membered cycloalkyl or 5 or 6 membered oxygen-containing heterocycloalkyl, or $R_4$ and $R_5$ together with the carbon atom to which they are attached form a $C_{3-6}$cycloalkyl or $C_{3-6}$heterocycloalkyl, or $R_4$ is H and $R_5$ and $R_6$ are a $C_{2-3}$alkylene chain forming a 5- or 6-membered ring;
or $R_4$ is O and $R_5$ is absent;
$R_6$ is H or $C_{1-3}$alkyl,
or $R_6$ together with $R_{11}$ when in the ortho-position to the amide are a $C_2$alkylene chain forming a 5-membered ring,
or $R_5$ and $R_6$ are a $C_{2-3}$alkylene chain forming a 5- or 6-membered ring and $R_4$ is H;
Ar1 is 6-membered aryl or heteroaryl;
Ar2 is a 6-membered aryl or heteroaryl and is attached to Ar1 in the para position relative to the amide;
$R_{10}$ is H, halo, $C_{1-3}$alkyl, $OC_{1-2}$alkyl, $C_{1-2}$haloalkyl, $OC_{1-2}$haloalkyl or CN;
$R_{11}$ is H, F, C, $CH_3$, ethyl, $OCH_3$, $CF_3$, $OCF_3$ or CN,
or $R_{11}$, when in the ortho-position to the amide, together with $R_6$ are a $C_2$alkylene chain forming a 5-membered ring;
$R_{12}$ is attached to Ar2 in the ortho or meta position relative to Ar1 and $R_{12}$ is H, halo, $C_{1-4}$ alkyl, $C_{2-4}$alkynyl, $C_{0-2}$alkylene$C_{3-8}$cycloalkyl, $OC_{1-4}$alkyl, $OC_{0-2}$alkylene$C_{3-8}$cycloalkyl, $OCH_2CH_2N(CH_3)_2$, OH, $C_{1-4}$alkylOH, CN, $C_{1-3}$alkyleneO$C_{1-3}$alkyl, $C_{1-4}$haloalkyl, $OC_{1-4}$ haloalkyl, C(=O)$C_{1-2}$alkyl, $NR_{23}R_{24}$, $SO_2$$C_{1-4}$alkyl, $SOC_{1-4}$alkyl, $SC_{1-4}$alkyl, SH, C(O)N(CH_3)_2$, NHC(O)$C_{1-3}$alkyl, $C_{3-6}$heterocycloalkyl comprising one nitrogen located at the point of attachment to Ar2, or $R_{12}$ together with a nitrogen atom to which it is attached forms an N-oxide ($N^+$—$O^-$);
$R_{13}$ is H, halo, $CH_3$ or $OCH_3$;
$R_{21}$ is H, $C_{1-5}$alkyl, C(O)$C_{1-5}$alkyl, C(O)O$C_{1-5}$alkyl;
$R_{22}$ is H or $CH_3$;
$R_{23}$ is H or $C_{1-2}$alkyl; and
$R_{24}$ is H or $C_{1-2}$alkyl.
Suitably, the invention provides a compound of formula (I):

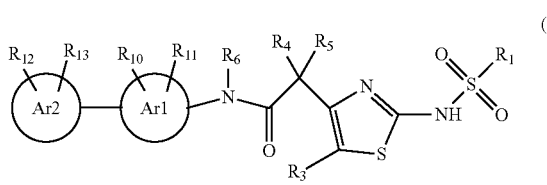

wherein
$R_1$ is $C_{1-5}$alkyl, $C_{1-2}$alkyleneO$C_{1-2}$alkyl, $C_{0-2}$alkylene-$C_{3-5}$cycloalkyl which cycloalkyl is optionally substituted by $CH_3$, or $CF_3$;
$R_3$ is H, halo, $CH_3$, $CF_3$ or $OCH_3$;
or $R_3$ together with $R_5$ forms a 5- or 6-membered cycloalkyl;
$R_4$ and $R_5$ are each independently H, F, $C_{1-6}$alkyl, $C_{0-2}$alkylene$C_{3-6}$cycloalkyl, $OC_{1-6}$alkyl, $OC_{0-2}$alkylene$C_{3-6}$cycloalkyl, $C_{1-3}$alkyleneO$C_{1-3}$alkyl, $C_{1-6}$alkylOH, $C_{1-6}$haloalkyl, $OC_{1-6}$ haloalkyl or $NR_{21}R_{22}$,
or $R_4$ is H and $R_5$ together with $R_3$ form a 5- or 6-membered cycloalkyl,
or $R_4$ and $R_5$ together with the carbon atom to which they are attached form a $C_{3-6}$cycloalkyl,
or $R_4$ is O and $R_5$ is absent;
$R_6$ is H or $C_{1-3}$alkyl,
or $R_6$ together with $R_{11}$ in the ortho-position to the amide are a $C_2$alkylene chain forming a 5-membered ring;
Ar1 is 6-membered aryl or heteroaryl;
Ar2 is a 6-membered aryl or heteroaryl and is attached to Ar1 in the para position relative to the amide;
$R_{10}$ is H, halo, $C_{1-2}$alkyl, $OC_{1-2}$alkyl, $C_{1-2}$haloalkyl, $OC_{1-2}$haloalkyl or CN;
$R_{11}$ is H, F, Cl, $CH_3$, ethyl, $OCH_3$, $CF_3$, $OCF_3$ or CN,
or $R_{11}$, when in the ortho-position to the amide, together with $R_6$ are a $C_2$alkylene chain forming a 5-membered ring;
$R_{12}$ is attached to Ar2 in the ortho or meta position relative to Ar1 and $R_{12}$ is H, halo, $C_{1-4}$alkyl, $C_{2-4}$alkynyl, $C_{0-2}$alkylene$C_{3-5}$cycloalkyl, $OC_{1-4}$alkyl, $OC_{0-2}$alkylene$C_{3-5}$cycloalkyl, $OCH_2CH_2N(CH_3)_2$, OH, $C_{1-4}$alkylOH, CN, $C_{1-3}$alkyleneO$C_{1-3}$alkyl, $C_{1-4}$haloalkyl, $OC_{1-4}$haloalkyl, $N(CH_3)_2$, $SO_2CH_3$, C(O)N(CH_3)_2$, NHC(O)$C_{1-3}$alkyl or a $C_{3-6}$heterocycloalkyl comprising one nitrogen located at the point of attachment to Ar2;
$R_{13}$ is H, F, $CH_3$ or $OCH_3$;
$R_{21}$ is H, $C_{1-5}$alkyl, C(O)$C_{1-5}$alkyl, C(O)O$C_{1-5}$alkyl; and
$R_{22}$ is H or $CH_3$.
The invention also provides a compound of formula (I):

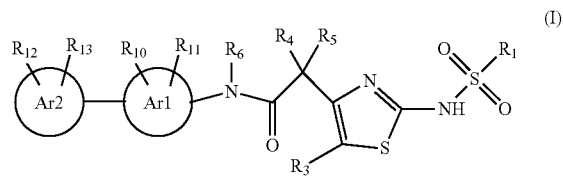

wherein
$R_1$ is $C_{1-5}$alkyl, $C_{0-2}$alkylene$C_{3-5}$cycloalkyl which cycloalkyl is optionally substituted by $CH_3$, or $CF_3$;
$R_3$ is H, halo, $CH_3$ or $CF_3$,
or $R_3$ together with $R_5$ forms a 5- or 6-membered cycloalkyl;
$R_4$ and $R_5$ are each independently H, F, $C_{1-6}$alkyl, $C_{0-2}$alkylene$C_{3-5}$cycloalkyl, $OC_{1-6}$alkyl, $OC_{0-2}$alkylene$C_{3-6}$cycloalkyl, $C_{1-3}$alkyleneO$C_{1-3}$alkyl, $C_{1-6}$haloalkyl or $OC_{1-6}$haloalkyl,
or $R_4$ is H and $R_5$ together with $R_3$ form a 5- or 6-membered cycloalkyl,
or $R_4$ and $R_5$ together with the carbon atom to which they are attached form a $C_{3-6}$cycloalkyl,
or $R_4$ is O and $R_5$ is absent;
$R_6$ is H or $C_{1-3}$alkyl,
or $R_6$ together with $R_{11}$ in the ortho-position to the amide are a $C_2$alkylene chain forming a 5-membered ring;
Ar1 is 6-membered aryl or heteroaryl;
Ar2 is a 6-membered aryl or heteroaryl and is attached to Ar1 in the para position relative to the amide;
$R_{10}$ is H, halo, $C_{1-2}$alkyl, $OC_{1-2}$alkyl, $C_{1-2}$haloalkyl, $OC_{1-2}$haloalkyl or CN;
$R_{11}$ is H, F, Cl, $CH_3$, $OCH_3$, $CF_3$, $OCF_3$ or CN,
or $R_{11}$, when in the ortho-position to the amide, together with $R_6$ are a $C_2$alkylene chain forming a 5-membered ring;
$R_{12}$ is attached to Ar2 in the ortho or meta position relative to Ar1 and $R_{12}$ is H, halo, $C_{1-4}$ alkyl, $C_{2-4}$alkynyl, $C_{0-2}$alkylene$C_{3-5}$cycloalkyl, $OC_{1-4}$alkyl, $OC_{0-2}$alkylene$C_{3-5}$cycloalkyl, $OCH_2CH_2N(CH_3)_2$, $C_{1-4}$alkylOH, CN, $C_{1-3}$alkyleneO$C_{1-3}$alkyl, $C_{1-4}$haloalkyl, $OC_{1-4}$haloalkyl, $N(CH_3)_2$, $SO_2CH_3$, C(O)N(CH_3)_2$, NHC(O)$C_{1-3}$alkyl or a $C_{3-6}$heterocycloalkyl comprising one nitrogen located at the point of attachment to Ar2; and
$R_{13}$ is H, F, $CH_3$ or $OCH_3$.

A compound of formula (I) may be provided in the form of a salt and/or solvate thereof and/or derivative thereof. Suitably, the compound of formula (I) may be provided in the form of a pharmaceutically acceptable salt and/or solvate thereof and/or derivative thereof. In particular, the compound of formula (I) may be provided in the form of a pharmaceutically acceptable salt and/or solvate, such as a pharmaceutically acceptable salt.

Also provided is a compound of formula (I), or a pharmaceutically acceptable salt and/or solvate thereof and/or derivative thereof, for use as a medicament, in particular for use in the inhibition of CTPS1 in a subject or the prophylaxis or treatment of associated diseases or disorders, such as those in which a reduction in T-cell and/or B-cell proliferation would be beneficial.

Further, there is provided a method for the inhibition of CTPS1 in a subject or the prophylaxis or treatment of associated diseases or disorders, such as those in which a reduction in T-cell and/or B-cell proliferation would be beneficial, by administering to a subject in need thereof a compound of formula (I) or a pharmaceutically acceptable salt and/or solvate thereof and/or derivative thereof.

Additionally provided is the use of a compound of formula (I), or a pharmaceutically acceptable salt and/or solvate thereof and/or derivative thereof, in the manufacture of a medicament for the inhibition of CTPS1 in a subject or the prophylaxis or treatment of associated diseases or disorders, such as those in which a reduction in T-cell and/or B-cell proliferation would be beneficial.

Suitably the disease or disorder is selected from: inflammatory skin diseases such as psoriasis or lichen planus; acute and/or chronic GVHD such as steroid resistant acute GVHD; acute lymphoproliferative syndrome (ALPS); systemic lupus erythematosus, lupus nephritis or cutaneous lupus; and transplantation. In addition, the disease or disorder may be selected from myasthenia gravis, multiple sclerosis, and scleroderma/systemic sclerosis.

Also provided is a compound of formula (I), or a pharmaceutically acceptable salt and/or solvate thereof and/or derivative thereof, for use in the treatment of cancer.

Further, there is provided a method for treating cancer in a subject, by administering to a subject in need thereof a compound of formula (I) or a pharmaceutically acceptable salt and/or solvate thereof and/or derivative thereof.

Additionally provided is the use of a compound of formula (I), or a pharmaceutically acceptable salt and/or solvate thereof and/or derivative thereof, in the manufacture of a medicament for the treatment of cancer in a subject.

Also provided is a compound of formula (I), or a pharmaceutically acceptable salt and/or solvate thereof and/or derivative thereof, for use in enhancing recovery from vascular injury or surgery and reducing morbidity and mortality associated with neointima and restenosis in a subject.

Further, there is provided a method for enhancing recovery from vascular injury or surgery and reducing morbidity and mortality associated with neointima and restenosis in a subject, by administering to a subject in need thereof a compound of formula (I) or a pharmaceutically acceptable salt and/or solvate thereof and/or derivative thereof.

Additionally provided is the use of a compound of formula (I), or a pharmaceutically acceptable salt and/or solvate thereof and/or derivative thereof, in the manufacture of a medicament for enhancing recovery from vascular injury or surgery and reducing morbidity and mortality associated with neointima and restenosis in a subject.

Also provided are pharmaceutical compositions containing a compound of formula (I), or a pharmaceutically acceptable salt and/or solvate thereof and/or derivative thereof, and a pharmaceutically acceptable carrier or excipient.

Also provided are processes for preparing compounds of formula (I) and novel intermediates of use in the preparation of compounds of formula (I).

DETAILED DESCRIPTION OF THE INVENTION

The invention provides a compound of formula (I):

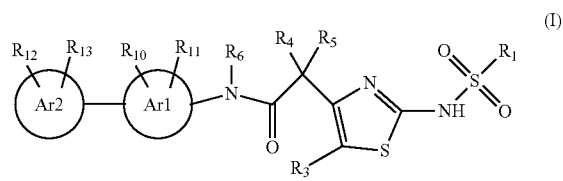

wherein $R_1$ is $C_{1-5}$alkyl, $C_{0-2}$alkylene$C_{3-5}$cycloalkyl which cycloalkyl is optionally substituted by $CH_3$, $C_{1-3}$alkyleneOC$_{1-2}$alkyl, or $CF_3$;

$R_3$ is H, halo, $CH_3$, $OC_{1-2}$alkyl or $CF_3$;
  or $R_3$ together with $R_5$ forms a 5- or 6-membered cycloalkyl or 5 or 6 membered oxygen-containing heterocycloalkyl;

$R_4$ and $R_5$ are each independently H, halo, $C_{1-6}$alkyl, $C_{0-2}$alkylene$C_{3-6}$cycloalkyl, $C_{0-2}$alkylene$C_{3-6}$heterocycloalkyl, $OC_{1-6}$alkyl, $OC_{0-2}$alkylene$C_{3-6}$cycloalkyl, $OC_{0-2}$alkylene$C_{3-6}$heterocycloalkyl, $C_{1-3}$alkyleneOC$_{1-3}$alkyl, $C_{1-6}$alkylOH, $C_{1-6}$haloalkyl, $OC_{1-6}$haloalkyl or $NR_{21}R_{22}$,
  or $R_4$ is H and $R_5$ together with $R_3$ form a 5- or 6-membered cycloalkyl or 5 or 6 membered oxygen-containing heterocycloalkyl,
  or $R_4$ and $R_5$ together with the carbon atom to which they are attached form a $C_{3-6}$cycloalkyl or $C_{3-6}$heterocycloalkyl,
  or $R_4$ is H and $R_5$ and $R_6$ are a $C_{2-3}$alkylene chain forming a 5- or 6-membered ring;
  or $R_4$ is O and $R_5$ is absent;

$R_6$ is H or $C_{1-3}$alkyl,
  or $R_6$ together with $R_{11}$ when in the ortho-position to the amide are a $C_2$alkylene chain forming a 5-membered ring,
  or $R_5$ and $R_6$ are a $C_{2-3}$alkylene chain forming a 5- or 6-membered ring and $R_4$ is H;

Ar1 is 6-membered aryl or heteroaryl;

Ar2 is a 6-membered aryl or heteroaryl and is attached to Ar1 in the para position relative to the amide;

$R_{10}$ is H, halo, $C_{1-3}$alkyl, $OC_{1-2}$alkyl, $C_{1-2}$haloalkyl, $OC_{1-2}$haloalkyl or CN;

$R_{11}$ is H, F, Cl, $CH_3$, ethyl, $OCH_3$, $CF_3$, $OCF_3$ or CN,
  or $R_{11}$, when in the ortho-position to the amide, together with $R_6$ are a $C_2$alkylene chain forming a 5-membered ring;

$R_{12}$ is attached to Ar2 in the ortho or meta position relative to Ar1 and $R_{12}$ is H, halo, $C_{1-4}$alkyl, $C_{2-4}$alkynyl, $C_{0-2}$alkylene$C_{3-5}$cycloalkyl, $OC_{1-4}$alkyl, $OC_{0-2}$alkyleneC$_{3-5}$cycloalkyl, $OCH_2CH_2N(CH_3)_2$, OH, $C_{1-4}$alkylOH, CN, $C_{1-3}$alkyleneOC$_{1-3}$alkyl, $C_{1-4}$haloalkyl, $OC_{1-4}$ haloalkyl, C(=O)$C_{1-2}$alkyl, $NR_{23}R_{24}$, $SO_2$ $C_{1-4}$alkyl, $SOC_{1-4}$alkyl, $SC_{1-4}$alkyl, SH, $C(O)N(CH_3)_2$, $NHC(O)C_{1-3}$alkyl, $C_{3-6}$heterocycloalkyl comprising one nitrogen located at the point of attachment to Ar2, or $R_{12}$ together with a nitrogen atom to which it is attached forms an N-oxide ($N^+$—$O^-$);

$R_{13}$ is H, halo, $CH_3$ or $OCH_3$;
$R_{21}$ is H, $C_{1-5}$alkyl, $C(O)C_{1-5}$alkyl, $C(O)OC_{1-5}$alkyl;
$R_{22}$ is H or $CH_3$;
$R_{23}$ is H or $C_{1-2}$alkyl; and
$R_{24}$ is H or $C_{1-2}$alkyl;

or a salt and/or solvate thereof and/or derivative thereof.

Suitably, the invention provides a compound of formula (I):

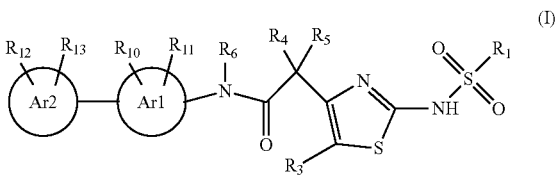

wherein $R_1$ is $C_{1-5}$alkyl, $C_{1-2}$alkyleneOC$_{1-2}$alkyl, $C_{0-2}$alkylene $C_{3-5}$cycloalkyl which cycloalkyl is optionally substituted by $CH_3$, or $CF_3$;

$R_3$ is H, halo, $CH_3$, $CF_3$ or $OCH_3$;

or $R_3$ together with $R_5$ forms a 5- or 6-membered cycloalkyl;

$R_4$ and $R_5$ are each independently H, F, $C_{1-6}$alkyl, $C_{0-2}$alkylene$C_{3-6}$cycloalkyl, $OC_{1-6}$alkyl, $OC_{0-2}$alkylene $C_{3-6}$cycloalkyl, $C_{1-3}$alkyleneOC$_{1-3}$alkyl, $C_{1-6}$alkylOH, $C_{1-6}$haloalkyl, $OC_{1-6}$ haloalkyl or $NR_{21}R_{22}$, or $R_4$ is H and $R_5$ together with $R_3$ form a 5- or 6-membered cycloalkyl, or $R_4$ and $R_5$ together with the carbon atom to which they are attached form a $C_{3-6}$cycloalkyl, or $R_4$ is O and $R_5$ is absent;

$R_6$ is H or $C_{1-3}$alkyl, or $R_6$ together with $R_{11}$ in the ortho-position to the amide are a $C_2$alkylene chain forming a 5-membered ring;

Ar1 is 6-membered aryl or heteroaryl;

Ar2 is a 6-membered aryl or heteroaryl and is attached to Ar1 in the para position relative to the amide;

$R_{10}$ is H, halo, $C_{1-3}$alkyl, $OC_{1-2}$alkyl, $C_{1-2}$haloalkyl, $OC_{1-2}$haloalkyl or CN;

$R_{11}$ is H, F, C, $CH_3$, ethyl, $OCH_3$, $CF_3$, $OCF_3$ or CN, or $R_{11}$, when in the ortho-position to the amide, together with $R_6$ are a $C_2$alkylene chain forming a 5-membered ring;

$R_{12}$ is attached to Ar2 in the ortho or meta position relative to Ar1 and $R_{12}$ is H, halo, $C_{1-4}$ alkyl, $C_{2-4}$alkynyl, $C_{0-2}$alkylene$C_{3-5}$cycloalkyl, $OC_{1-4}$alkyl, $OC_{0-2}$alkylene$C_{3-5}$cycloalkyl, $OCH_2CH_2N(CH_3)_2$, OH, $C_{1-4}$alkylOH, CN, $C_{1-3}$alkyleneOC$_{1-3}$alkyl, $C_{1-4}$haloalkyl, $OC_{1-4}$ haloalkyl, $N(CH_3)_2$, $SO_2CH_3$, $C(O)N(CH_3)_2$, $NHC(O)C_{1-3}$alkyl or a $C_{3-6}$heterocycloalkyl comprising one nitrogen located at the point of attachment to Ar2;

$R_{13}$ is H, F, $CH_3$ or $OCH_3$;
$R_{21}$ is H, $C_{1-5}$alkyl, $C(O)C_{1-5}$alkyl, $C(O)OC_{1-5}$alkyl; and
$R_{22}$ is H or $CH_3$;

or a salt and/or solvate thereof and/or derivative thereof.

The invention also provides a compound of formula (I):

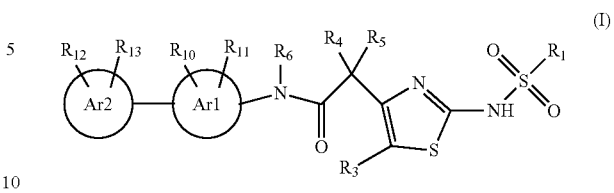

wherein $R_1$ is $C_{1-5}$alkyl, $C_{0-2}$alkylene$C_{3-5}$cycloalkyl which cycloalkyl is optionally substituted by $CH_3$, or $CF_3$;

$R_3$ is H, halo, $CH_3$ or $CF_3$, or $R_3$ together with $R_5$ forms a 5- or 6-membered cycloalkyl;

$R_4$ and $R_5$ are each independently H, F, $C_{1-6}$alkyl, $C_{0-2}$alkylene$C_{3-5}$cycloalkyl, $OC_{1-6}$alkyl, $OC_{0-2}$alkylene $C_{3-6}$cycloalkyl, $C_{1-3}$alkyleneOC$_{1-3}$alkyl, $C_{1-6}$haloalkyl or $OC_{1-6}$haloalkyl, or $R_4$ is H and $R_5$ together with $R_3$ form a 5- or 6-membered cycloalkyl, or $R_4$ and $R_5$ together with the carbon atom to which they are attached form a $C_{3-6}$cycloalkyl, or $R_4$ is O and $R_5$ is absent;

$R_6$ is H or $C_{1-3}$alkyl, or $R_6$ together with $R_1$ in the ortho-position to the amide are a $C_2$alkylene chain forming a 5-membered ring;

Ar1 is 6-membered aryl or heteroaryl;

Ar2 is a 6-membered aryl or heteroaryl and is attached to Ar1 in the para position relative to the amide;

$R_{10}$ is H, halo, $C_{1-2}$alkyl, $OC_{1-2}$alkyl, $C_{1-2}$haloalkyl, $OC_{1-2}$haloalkyl or CN;

$R_{11}$ is H, F, C, $CH_3$, $OCH_3$, $CF_3$, $OCF_3$ or CN, or $R_{11}$, when in the ortho-position to the amide, together with $R_6$ are a $C_2$alkylene chain forming a 5-membered ring;

$R_{12}$ is attached to Ar2 in the ortho or meta position relative to Ar1 and $R_{12}$ is H, halo, $C_{1-4}$alkyl, $C_{2-4}$alkynyl, $C_{0-2}$alkylene$C_{3-5}$cycloalkyl, $OC_{1-4}$alkyl, $OC_{0-2}$alkylene$C_{3-5}$cycloalkyl, $OCH_2CH_2N(CH_3)_2$, $C_{1-4}$alkylOH, CN, $C_{1-3}$alkyleneOC$_{1-3}$alkyl, $C_{1-4}$haloalkyl, $OC_{1-4}$haloalkyl, $N(CH_3)_2$, $SO_2CH_3$, $C(O)N(CH_3)_2$, $NHC(O)C_{1-3}$alkyl or a $C_{3-6}$heterocycloalkyl comprising one nitrogen located at the point of attachment to Ar2; and $R_{13}$ is H, F, $CH_3$ or $OCH_3$;

or a salt and/or solvate thereof and/or derivative thereof.

The term 'alkyl' as used herein, such as in $C_{1-3}$alkyl, $C_{1-4}$alkyl or $C_{1-5}$alkyl, whether alone or forming part of a larger group such as an Oalkyl group (e.g. $OC_{1-3}$alkyl, $OC_{1-4}$alkyl and $OC_{1-5}$alkyl), is a straight or a branched fully saturated hydrocarbon chain containing the specified number of carbon atoms. Examples of alkyl groups include the $C_{1-5}$alkyl groups methyl, ethyl, n-propyl, iso-propyl, n-butyl, iso-butyl, sec-butyl, tert-butyl and n-pentyl, sec-pentyl and 3-pentyl, in particular the $C_{1-3}$alkyl groups methyl, ethyl, n-propyl and iso-propyl. Reference to "propyl" includes n-propyl and iso-propyl, and reference to "butyl" includes n-butyl, isobutyl, sec-butyl and tert-butyl. Examples of Oalkyl groups include the $OC_{1-4}$alkyl groups methoxy, ethoxy, propoxy (which includes n-propoxy and iso-propoxy) and butoxy (which includes n-butoxy, iso-butoxy, sec-butoxy and tert-butoxy). $C_6$alkyl groups as used herein, whether alone or forming part of a larger group such as an $OC_6$alkyl group is a straight or a branched fully saturated hydrocarbon chain containing six carbon atoms.

Examples of $C_6$alkyl groups include n-hexyl, 2-methylpentyl, 3-methylpentyl, 2,2-dimethylbutyl and 2,3-dimethylbutyl.

The term 'alkylene' as used herein, such as in $C_{0-2}$alkylene$C_{3-5}$cycloalkyl or $C_{1-3}$alkyleneO$C_{1-2}$alkyl such as $C_{1-2}$alkyleneO$C_{1-2}$alkyl is a bifunctional straight or a branched fully saturated hydrocarbon chain containing the specified number of carbon atoms. Examples of $C_{0-2}$alkylene groups are where the group is absent (i.e. $C_0$), methylene ($C_1$) and ethylene ($C_2$).

The term 'alkynyl' as used herein, such as in $C_{2-4}$alkynyl is a branched or unbranched unsaturated hydrocarbon chain containing the specified number of carbon atoms, two of which are linked by a carbon-carbon triple bond.

The term 'cycloalkyl' as used herein, such as in $C_{3-5}$cycloalkyl or $C_{3-6}$cycloalkyl, whether alone or forming part of a larger group such as O$C_{3-5}$cycloalkyl or $C_{0-2}$alkylene $C_{3-5}$cycloalkyl is a fully saturated hydrocarbon ring containing the specified number of carbon atoms. Examples of cycloalkyl groups include the $C_{3-6}$cycloalkyl groups cyclopropyl, cyclobutyl, cyclopentyl and cyclohexyl, in particular the $C_{3-5}$cycloalkyl groups cyclopropyl, cyclobutyl and cyclopentyl:

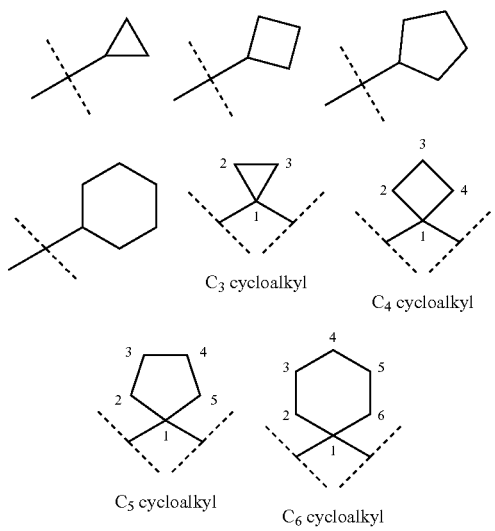

The term 'heterocycloalkyl' as used herein, such as in $C_{3-6}$heterocycloalkyl or $C_{0-2}$alkylene$C_{3-6}$heterocycloalkyl is a fully saturated hydrocarbon ring containing the specified number of carbon atoms wherein at least one of the carbon atoms is replaced by a heteroatom such as N, S or O. As required by valency, any nitrogen atom(s) may be connected to a hydrogen atom to form an NH group. Alternatively any nitrogen atom(s) may be substituted (such as one nitrogen atom is substituted), for example by $C_{1-4}$alkyl, C(O)H, C(O)$C_{1-4}$alkyl, C(O)O$C_{1-4}$alkyl, C(O)O$C_{1-4}$alkylaryl such as C(O)OBz, C(O)NH$C_{1-4}$alkyl, C(O)NH$C_{1-4}$alkylaryl such as C(O)NHBz, an Fmoc group, C(O)$C_{1-4}$haloalkyl, C(O)O$C_{1-4}$haloalkyl or C(O)NH$C_{1-4}$haloalkyl such as C(O)OtBu. Wherein a ring heteroatom is S, the term 'heterocycloalkyl' includes wherein the S atom(s) is substituted (such as one S atom is substituted) by one or two oxygen atoms (i.e. S(O) or S(O)$_2$). Alternatively, any sulphur atom(s) in the $C_{3-6}$heterocycloalkyl ring is not substituted. Examples of $C_{3-6}$heterocycloalkyl include those comprising one nitrogen atom such as containing one heteroatom (i.e. nitrogen) or containing two heteroatoms (e.g. two nitrogen atoms or one nitrogen atom and one oxygen atom). Particular examples of $C_{3-6}$heterocycloalkyl comprising one nitrogen atom include pyrrolidinyl, pyrazolidinyl, piperidinyl, piperazinyl, morpholinyl and thiomorpholinyl, especially, pyrrolidinyl and morpholinyl. Examples of $C_{3-6}$heterocycloalkyl include those comprising one oxygen atom such as containing one oxygen atom, or containing two oxygen atoms. Particular examples of $C_{3-6}$heterocycloalkyl comprising one oxygen atom include oxiranyl, oxetanyl, 3-dioxolanyl, morpholinyl, 1,4-oxathianyl, tetrahydropyranyl, 1,4-thioxanyl and 1,3,5-trioxanyl.

Desirably, the term 'heterocycloalkyl' as used herein, such as in $C_{3-6}$heterocycloalkyl is a fully saturated hydrocarbon ring containing the specified number of carbon atoms wherein at least one of the carbon atoms is replaced by a heteroatom such as N, S or O. Examples of $C_{3-6}$heterocycloalkyl include those comprising one nitrogen atom such as containing one heteroatom (i.e. nitrogen) or containing two heteroatoms (e.g. two nitrogen atoms or one nitrogen atom and one oxygen atom).

The term '5- or 6-membered oxygen-containing heterocycloalkyl' as used herein, is a fully saturated hydrocarbon ring containing the specified number of ring atoms (i.e. 5 or 6), wherein at least one ring atom is an oxygen atom and the ring does not contain heteroatoms other than oxygen. Examples of oxygen-containing heterocycloalkyl groups are oxiranyl, oxetanyl, tetrahydrofuranyl, 3-dioxolanyl, tetrahydropyranyl, and 1,3,5-trioxanyl, such as tetrahydrofuranyl and tetrahydropyranyl.

The heterocycloalkyl groups may have the following structures:

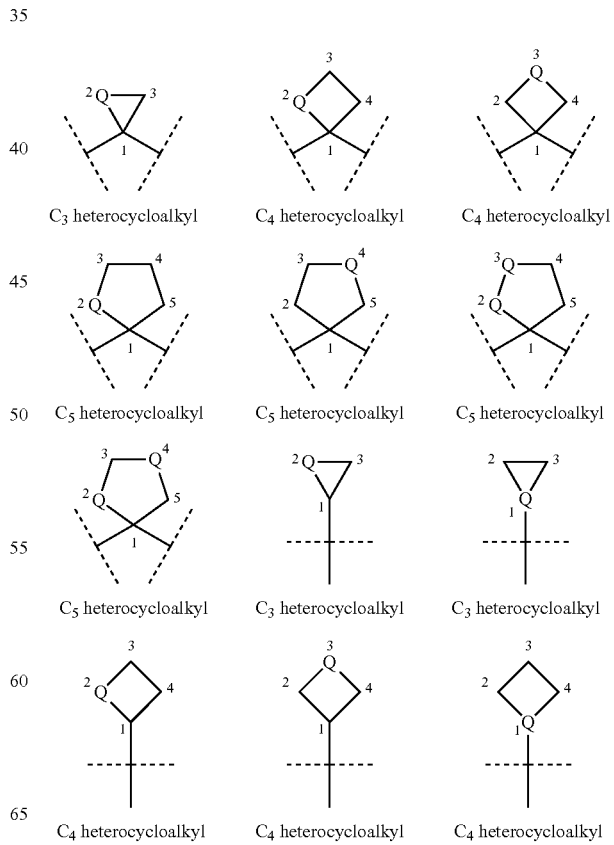

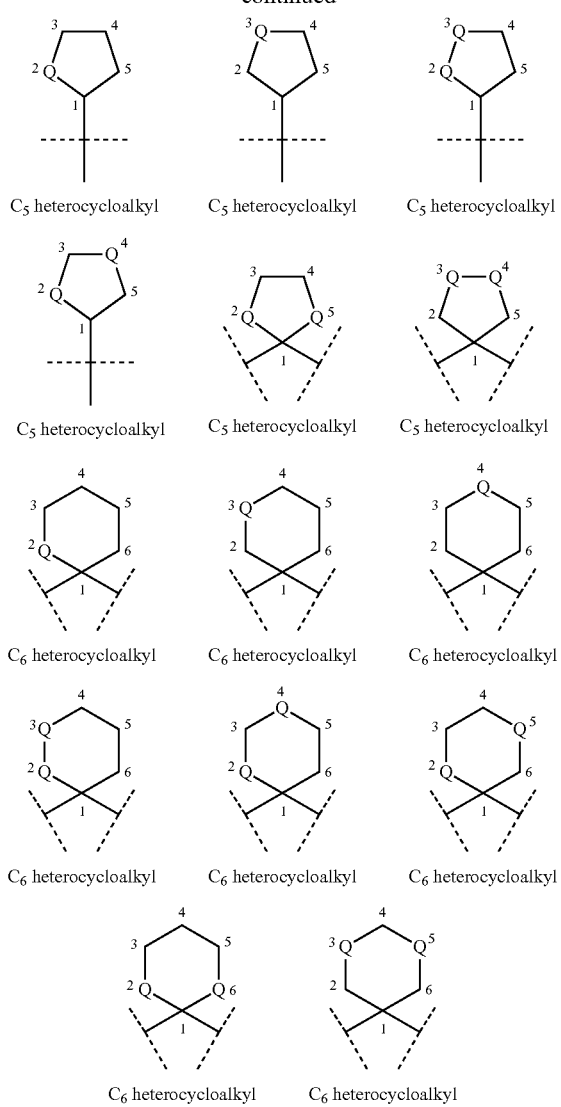

wherein each Q is independently selected from O, N or S, such as O or N. When Q is N, as required by valency, the nitrogen atom(s) may be connected to a hydrogen atom to form an NH group. Alternatively the nitrogen atom(s) may be substituted (such as one nitrogen atom is substituted), for example by $C_{1-4}$alkyl, C(O)H, C(O)$C_{1-4}$alkyl, C(O)O$C_{1-4}$alkyl, C(O)O$C_{1-4}$alkylaryl such as C(O)OBz, C(O)NH$C_{1-4}$alkyl, C(O)NH$C_{1-4}$alkylaryl such as C(O)NHBz, an Fmoc group, C(O)$C_{1-4}$haloalkyl, C(O)O$C_{1-4}$haloalkyl or C(O)NH$C_{1-4}$haloalkyl such as C(O)OtBu. When any Q is S, the S atoms can be substituted (such as one S atom is substituted) by one or two oxygen atoms (i.e. S(O) or S(O)$_2$). Alternatively, any sulphur atom(s) in the $C_{3-6}$heterocycloalkyl ring is not substituted.

Suitably, heterocycloalkyl is a fully saturated hydrocarbon ring containing the specified number of carbon atoms wherein at least one of the carbon atoms is replaced by a heteroatom such as N, S or O. Suitably, as required by valency, any nitrogen atom is connected to a hydrogen atom. Suitably any S atom is not present as an oxide. In particular, any nitrogen atom is connected to a hydrogen arom and any S atom is not present as an oxide.

The term 'halo' or 'halogen' as used herein, refers to fluorine, chlorine, bromine or iodine. Particular examples of halo are fluorine and chlorine, especially fluorine.

The term 'haloalkyl' as used herein, such as in $C_{1-4}$haloalkyl, whether alone or forming part of a larger group such as an Ohaloalkyl group, such as in O$C_{1-4}$haloalkyl, is a straight or a branched fully saturated hydrocarbon chain containing the specified number of carbon atoms and at least one halogen atom, such as fluoro or chloro, especially fluoro. An example of haloalkyl is $CF_3$. Further examples of haloalkyl are $CHF_2$ and $CH_2CF_3$. Examples of Ohaloalkyl include $OCF_3$, $OCHF_2$ and $OCH_2CF_3$.

The term '6-membered aryl' as used herein refers to a phenyl ring.

The term '6-membered heteroaryl' as used herein refers to 6-membered aromatic rings containing at least one heteroatom (e.g. nitrogen). Exemplary 6-membered heteroaryls include one nitrogen atom (pyridinyl), two nitrogen atoms (pyridazinyl, pyrimidinyl or pyrazinyl) and three nitrogen atoms (triazinyl).

The phrase 'in the para position relative to the amide' as used herein, such as in relation to the position of Ar2, means that compounds with the following substructure are formed:

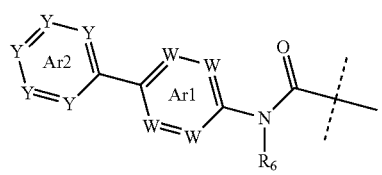

wherein W may be N, CH, $CR_{10}$ or $CR_{11}$, and Y may be N, CH, $CR_{12}$ or $CR_{13}$ as allowed by the definitions provided for compounds of formula (I).

The terms 'ortho' and 'meta' as used herein, such as when used in respect of defining the position of $R_{12}$ on Ar2 is with respect to Ar1:

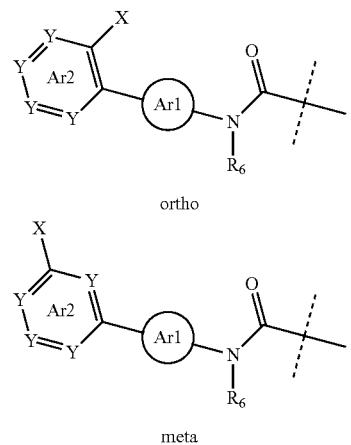

In one embodiment of the invention $R_1$ is $C_{1-5}$alkyl. When $R_1$ is $C_{1-5}$alkyl, $R_1$ may be methyl, ethyl, propyl (n-propyl or isopropyl), butyl (n-butyl, isobutyl, sec-butyl or tert-butyl) or pentyl (e.g. n-pentyl, sec-pentyl or 3-pentyl). Suitably, when $R_1$ is $C_{1-5}$alkyl, $R_1$ may be methyl, ethyl, propyl (e.g. isopropyl) or butyl (e.g. sec-butyl or tert-butyl), especially methyl, ethyl or isopropyl and in particular methyl.

In a second embodiment of the invention R$_1$ is C$_{0-2}$alkyleneC$_{3-5}$cycloalkyl which cycloalkyl is optionally substituted by CH$_3$. In some embodiments, R$_1$ is C$_{0-2}$alkylene C$_{3-5}$cycloalkyl. In other embodiments, R$_1$ is C$_{0-2}$alkylene C$_{3-5}$cycloalkyl which cycloalkyl is substituted by CH$_3$. R$_1$ may be C$_{3-5}$cycloalkyl, which cycloalkyl is optionally substituted by CH$_3$. R$_1$ may be C$_1$alkyleneC$_{3-5}$cycloalkyl, which cycloalkyl is optionally substituted by CH$_3$. R$_1$ may be C$_2$alkyleneC$_{3-5}$cycloalkyl, which cycloalkyl is optionally substituted by CH$_3$. R$_1$ may be C$_{0-2}$alkyleneC$_3$cycloalkyl, which cycloalkyl is optionally substituted by CH$_3$. R$_1$ may be C$_{0-2}$alkyleneC$_4$cycloalkyl, which cycloalkyl is optionally substituted by CH$_3$. R$_1$ may be C$_{0-2}$alkyleneC$_5$cycloalkyl, which cycloalkyl is optionally substituted by CH$_3$. Suitably, where C$_{0-2}$alkyleneC$_{3-5}$cycloalkyl is optionally substituted by CH$_3$, the CH$_3$ is at the point of attachment of the C$_{3-5}$cycloalkyl to the C$_{0-2}$alkylene.

In a third embodiment of the invention R$_1$ is CF$_3$.

In a fourth embodiment of the invention R$_1$ is C$_{1-3}$alkyleneOC$_{1-2}$alkyl such as C$_{1-2}$alkyleneOC$_{1-2}$alkyl. When R$_1$ is C$_{1-3}$alkyleneOC$_{1-2}$alkyl, R$_1$ may be methoxymethyl, methoxyethyl, ethoxymethyl, ethoxyethyl, propoxymethyl or propoxyethyl. When R$_1$ is C$_{1-2}$alkyleneOC$_{1-2}$alkyl, R$_1$ may be methoxymethyl, methoxyethyl, ethoxymethyl or ethoxyethyl.

Suitably R$_1$ is cyclopropyl, cyclopropyl substituted by CH$_3$ at the point of attachment, cyclobutyl, CH$_3$, isopropyl, sec-butyl, tert-butyl or CF$_3$. In particular R$_1$ is cyclopropyl, cyclopropyl substituted by CH$_3$ at the point of attachment, cyclobutyl, CH$_3$, isopropyl, sec-butyl or tert-butyl, especially cyclopropyl, cyclopropyl substituted by CH$_3$ at the point of attachment, cyclobutyl or isopropyl, such as cyclopropyl or cyclopropyl substituted by CH$_3$ at the point of attachment.

Additionally of interest is when R$_1$ is cyclopentyl, methyl, ethyl, cyclopropylmethylene and methoxyethyl, in particular cyclopentyl, methyl, ethyl and cyclopropylmethylene, especially ethyl and methyl, such as methyl.

Consequently, suitably R$_1$ is cyclopropyl, cyclopropyl substituted by CH$_3$ at the point of attachment, cyclopropylmethylene, cyclobutyl, cyclopentyl, CH$_3$, ethyl, isopropyl, sec-butyl, tert-butyl, methoxyethyl or CF$_3$. In particular R$_1$ is cyclopropyl, cyclopropyl substituted by CH$_3$ at the point of attachment, cyclopropylmethylene, cyclobutyl, cyclopentyl, CH$_3$, ethyl, isopropyl, sec-butyl or tert-butyl, especially cyclopropyl, cyclopropyl substituted by CH$_3$ at the point of attachment, cyclobutyl, CH$_3$, ethyl or isopropyl, such as cyclopropyl, cyclopropyl substituted by CH$_3$ at the point of attachment, ethyl or methyl such as cyclopropyl, cyclopropyl substituted by CH$_3$ at the point of attachment or methyl.

In one embodiment R$_3$ is H. In a second embodiment R$_3$ is halo, in particular chloro or fluoro, especially chloro. In a third embodiment R$_3$ is CH$_3$. In a fourth embodiment R$_3$ is CF$_3$. In a fifth embodiment R$_3$ together with R$_5$ forms a 5- or 6-membered cycloalkyl, in particular a 5-membered cycloalkyl. In a sixth embodiment R$_3$ is OC$_{1-2}$alkyl such as OCH$_3$. In a seventh embodiment R$_3$ together with R$_5$ forms a 5- or 6-membered oxygen-containing heterocycloalkyl, in particular a 5-membered heterocycloalkyl.

The phrase 'R$_3$ together with R$_5$ forms a 5- or 6-membered cycloalkyl' means that compounds with the following substructure are formed:

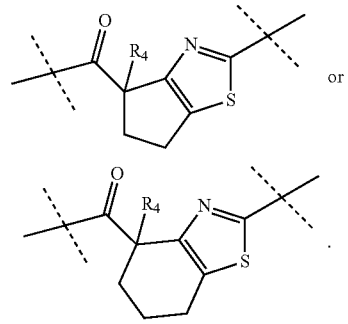

The phrase 'R$_3$ together with R$_5$ forms a 5- or 6-membered oxygen containing heterocycloalkyl' means that compounds with the following substructure are formed:

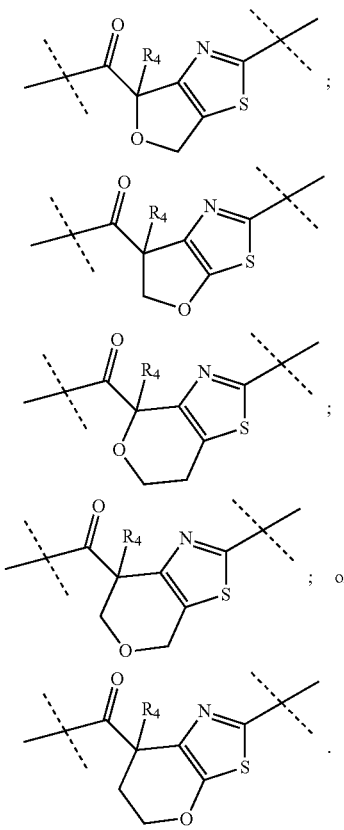

In particular R$_3$ is H, CH$_3$ or R$_3$ together with R$_5$ forms a 5- or 6-membered cycloalkyl, especially H, CH$_3$ or R$_3$ together with R$_5$ forms a 5-membered cycloalkyl, such as R$_3$ is H or CH$_3$, e.g. H.

In one embodiment R$_4$ is O and R$_5$ is absent. The person skilled in the art will appreciate that in this embodiment, the following moiety forms, in order to retain the correct carbon valency of 4:

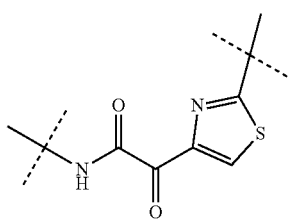

R₄ = O R₅ = absent

In a second embodiment, R₄ and R₅ together with the carbon atom to which they are attached form a C₃₋₆cycloalkyl, such as cyclopropyl, cyclobutyl or cyclopentyl. In a third embodiment R₄ is C₁₋₆alkyl, in particular C₁₋₄alkyl such as methyl, ethyl, propyl (n-propyl or isopropyl) or butyl (n-butyl, isobutyl, sec-butyl or tert-butyl). In a fourth embodiment R₄ is C₀₋₂alkyleneC₃₋₆cycloalkyl, in particular C₀₋₂alkyleneC₃₋₅cycloalkyl, such as C₃₋₅cycloalkyl, C₁alkyleneC₃₋₅cycloalkyl or C₂alkyleneC₃₋₅cycloalkyl. In a fifth embodiment R₄ is OC₁₋₆alkyl, in particular OC₁₋₄alkyl, such as methoxy, ethoxy, propoxy (n-propoxy or isopropoxy) or butoxy (n-butoxy, isobutoxy, sec-butoxy or tert-butoxy). In a sixth embodiment R₄ is OC₀₋₂alkylene C₃₋₆cycloalkyl, such as OC₃₋₆cycloalkyl, OC₁alkylene C₃₋₆cycloalkyl or OC₂alkyleneC₃₋₆cycloalkyl. In a seventh embodiment R₄ is C₁₋₃ alkyleneOC₁₋₃alkyl, in particular C₁₋₂alkyleneOC₁₋₂alkyl such as C₁alkyleneOC₁alkyl, C₂alkyleneOC₁alkyl, C₁alkyleneOC₂alkyl or C₂alkyleneOC₂alkyl. In an eighth embodiment R₄ is C₁₋₆haloalkyl, in particular C₁₋₄haloalkyl. In a ninth embodiment R₄ is OC₁₋₆haloalkyl, in particular OC₁₋₄haloalkyl. In a tenth embodiment R₄ is H. In an eleventh embodiment R₄ is halo such as fluoro. In a twelfth embodiment R₄ is C₁₋₆alkylOH, such as CH₂OH or CH₂CH₂OH, in particular CH₂CH₂OH. In a thirteenth embodiment R₄ is NR₂₁R₂₂. In a fourteenth embodiment, R₄ is C₀₋₂alkyleneC₃₋₆heterocycloalkyl such as C₀₋₂alkyleneC₃heterocycloalkyl, C₀₋₂alkyleneC₄heterocycloalkyl, C₀₋₂alkyleneC₅heterocycloalkyl, C₀₋₂alkylene C₆heterocycloalkyl, C₀alkyleneC₃₋₆heterocycloalkyl, C₁alkyleneC₃₋₆heterocycloalkyl and C₂alkyleneC₃₋₆heterocycloalkyl. Suitably the heterocycloalkyl is a heterocyclopropyl, heterocyclobutyl, heterocyclopentyl or heterocyclohexyl ring such as a heterocyclohexyl ring. Suitably, the heterocyclopentyl ring is tetrahydrofuranyl or pyrrolidinyl. Suitably, the heterocyclohexyl ring is tetrahydropyranyl or piperidinyl. Any nitrogen atom(s) (such as one nitrogen atom) in the C₃₋₆heterocycloalkyl ring may be substituted, for example by C₁₋₄alkyl, C(O)H, C(O)C₁₋₄alkyl, C(O)OC₁₋₄alkyl, C(O)OC₁₋₄alkylaryl such as C(O)OBz, C(O)NHC₁₋₄alkyl, C(O)NHC₁₋₄alkylaryl such as C(O)NHBz, an Fmoc group, C(O)C₁₋₄haloalkyl, C(O)OC₁₋₄haloalkyl or C(O)NHC₁₋₄ haloalkyl such as C(O)OtBu. Suitably, any nitrogen atom in the C₃₋₆heterocycloalkyl ring is not substituted. In a fifteenth embodiment, R₄ and R₅ together with the carbon atom to which they are attached form a C₃₋₆heterocycloalkyl, such as tetrahydrofuranyl, tetrahydropyranyl, pyrrolidinyl or piperidinyl, such as tetrahydrofuranyl or piperidinyl. If the C₃₋₆heterocycloalkyl group comprises (e.g. contains) a nitrogen atom, independently the nitrogen atom(s) may be unsubstituted (NH) or the nitrogen atom(s) may be substituted, for example substituted by a group selected from the following: C₁₋₄alkyl, C(O)H, C(O) C₁₋₄alkyl, C(O)OC₁₋₄alkyl, C(O)OC₁₋₄alkylaryl such as C(O)OBz, C(O)NHC₁₋₄alkyl, C(O)NHC₁₋₄alkylaryl such as C(O)NHBz, an Fmoc group, C(O)C₁₋₄haloalkyl, C(O) OC₁₋₄haloalkyl or C(O)NHC₁₋₄haloalkyl such as C(O) OtBu. In a fifteenth embodiment, R₄ is H and R₅ and R₆ are a C₂₋₃alkylene chain forming a 5- or 6-membered ring. In a sixteenth embodiment, R₄ is OC₀₋₂alkyleneC₃₋₆heterocycloalkyl such as OC₀₋₂alkyleneC₃heterocycloalkyl, OC₀₋₂alkyleneC₄heterocycloalkyl, OC₀₋₂alkyleneC₅heterocycloalkyl, OC₀₋₂alkyleneC₆heterocycloalkyl, OC₀alkyleneC₃₋₆heterocycloalkyl, OC₁alkyleneC₃₋₆heterocycloalkyl and OC₂alkyleneC₃₋₆heterocycloalkyl. Suitably the heterocycloalkyl is a heterocyclopropyl, heterocyclobutyl, heterocyclopentyl or heterocyclohexyl ring such as a heterocyclohexyl ring. Suitably, the heterocyclopentyl ring is tetrahydrofuranyl or pyrrolidinyl. Suitably, the heterocyclohexyl ring is tetrahydropyranyl or piperidinyl. Any nitrogen atom(s) (such as one nitrogen atom) in the C₃₋₆heterocycloalkyl ring may be substituted, for example by C₁₋₄alkyl, C(O)H, C(O)C₁₋₄alkyl, C(O)OC₁₋₄alkyl, C(O)OC₁₋₄alkylaryl such as C(O)OBz, C(O)NHC₁₋₄alkyl, C(O)NHC₁₋₄alkylaryl such as C(O)NHBz, an Fmoc group, C(O)C₁₋₄haloalkyl, C(O)OC₁₋₄haloalkyl or C(O)NHC₁₋₄haloalkyl such as C(O)OtBu. Suitably, any nitrogen atom in the C₃₋₆heterocycloalkyl ring is not substituted.

When R₄ is H and R₅ and R₆ are a C₂₋₃alkylene chain forming a 5- or 6-membered ring, suitably a 5-membered ring, compounds comprising one of the following moieties are formed:

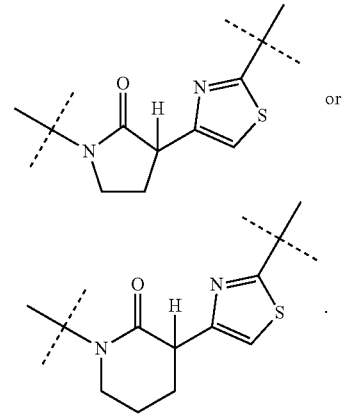

When R₄ is NR₂₁R₂₂, in one embodiment R₂₁ is H. In a second embodiment R₂₁ is C₁₋₅alkyl, such as methyl, ethyl or propyl, especially methyl. In a third embodiment R₂₁ is C(O)C₁₋₅alkyl, such as C(O)CH₃. In a fourth embodiment R₂₁ is C(O)OC₁₋₅alkyl, such as C(O)OCH₃ or C(O)Otert-butyl.

When R₄ is NR₂₁R₂₂, in one embodiment R₂₂ is H. In a second embodiment R₂₂ is methyl.

Suitably R₄ is H, CH₃, ethyl, isopropyl, fluoro, OCH₃, isopropoxy or CH₂CH₂OCH₃, in particular H, CH₃, ethyl, fluoro, OCH₃, isopropoxy or CH₂CH₂OCH₃, especially H, CH₃, ethyl, OCH₃ or CH₂CH₂OCH₃.

Additionally of interest is when R₄ is NH₂, N(CH₃)₂, NHC(O)CH₃, NHC(O)OCH₃, NHC(O)Otert-butyl and CH₂CH₂OH, especially, N(CH₃)₂, NHC(O)CH₃, NHC(O) OCH₃.

Suitably, R₂₁ is C(O)OCH₃ and R₂₂ is H. Suitably, R₂₁ is C(O)CH₃ and R₂₂ is H. Suitably, R₂₁ and R₂₂ are both CH₃. Suitably, R₂₁ and R₂₂ are both H.

Consequently, suitably $R_4$ is H, $CH_3$, ethyl, isopropyl, fluoro, $OCH_3$, isopropoxy, $CH_2CH_2OCH_3$, $NH_2$, $N(CH_3)_2$, $NHC(O)CH_3$, $NHC(O)OCH_3$, $NHC(O)$Otert-butyl or $CH_2CH_2OH$, in particular H, $CH_3$, ethyl, fluoro, $OCH_3$, isopropoxy, $CH_2CH_2OCH_3$, $NH_2$, $N(CH_3)_2$, $NHC(O)CH_3$, $NHC(O)OCH_3$, $NHC(O)$Otert-butyl or $CH_2CH_2OH$, especially H, $CH_3$, ethyl, $OCH_3$, $CH_2CH_2OCH_3$, $N(CH_3)_2$, $NHC(O)CH_3$ or $NHC(O)OCH_3$.

Suitably $R_4$ may be C=O and $R_5$ is absent.

Suitably $R_4$ and $R_5$ together with the carbon atom to which they are attached form a cyclopropyl or cyclopentyl, in particular a cyclopentyl.

Suitably $R_4$ is H and $R_3$ together with $R_5$ forms a 5- or 6-membered cycloalkyl, in particular a 5-membered cycloalkyl, especially $R_4$ is H and $R_3$ together with $R_5$ forms a 5- or 6-membered cycloalkyl, such as a 5-membered cycloalkyl.

In one embodiment $R_5$ is $C_{1-6}$alkyl, in particular $C_{1-4}$alkyl, such as methyl, ethyl, propyl (n-propyl or isopropyl) or butyl (n-butyl, isobutyl, sec-butyl or tert-butyl). In a second embodiment $R_5$ is $C_{0-2}$alkylene$C_{3-6}$cycloalkyl, in particular $C_{0-2}$alkylene$C_{3-5}$cycloalkyl, such as $C_{3-5}$cycloalkyl, $C_1$alkylene$C_{3-5}$cycloalkyl or $C_2$alkylene$C_{3-5}$cycloalkyl. In a third embodiment $R_5$ is $OC_{1-6}$alkyl, in particular $OC_{1-4}$alkyl, such as methoxy, ethoxy, propoxy (n-propoxy or isopropoxy) or butoxy (n-butoxy, isobutoxy, sec-butoxy or tert-butoxy). In a fourth embodiment $R_5$ is $OC_{0-2}$alkylene$C_{3-6}$cycloalkyl, such as $OC_{3-6}$cycloalkyl, $OC_1$alkylene$C_{3-6}$cycloalkyl or $OC_2$alkylene$C_{3-6}$cycloalkyl. In a fifth embodiment $R_5$ is $C_{1-3}$alkyleneO$C_{1-3}$alkyl, in particular $C_{1-2}$alkyleneO$C_{1-2}$alkyl such as $C_1$alkyleneO$C_1$alkyl, $C_2$alkyleneO$C_1$alkyl, $C_1$alkyleneO$C_2$alkyl or $C_2$alkyleneO$C_2$alkyl. In a sixth embodiment $R_5$ is $C_{1-6}$haloalkyl, in particular $C_{1-4}$haloalkyl. In a seventh embodiment $R_5$ is $OC_{1-6}$haloalkyl, in particular $OC_{1-4}$haloalkyl. In an eighth embodiment $R_5$ is H. In a ninth embodiment $R_5$ is halo such as fluoro. In a tenth embodiment $R_5$ is $C_{1-6}$alkylOH, such as $CH_2OH$ or $CH_2CH_2OH$, in particular $CH_2CH_2OH$. In an eleventh embodiment $R_5$ is $NR_{21}R_{22}$. In a twelfth embodiment, $R_5$ is $C_{0-2}$alkylene$C_{3-6}$heterocycloalkyl such as $C_{0-2}$alkylene$C_3$heterocycloalkyl, $C_{0-2}$alkylene$C_4$heterocycloalkyl, $C_{0-2}$alkylene$C_5$heterocycloalkyl, $C_{0-2}$alkylene$C_6$heterocycloalkyl, $C_0$alkylene$C_{3-6}$heterocycloalkyl, $C_1$alkylene$C_{3-6}$heterocycloalkyl and $C_2$alkylene$C_{3-6}$heterocycloalkyl. Suitably the heterocycloalkyl is a heterocyclopropyl, heterocyclobutyl, heterocyclopentyl or heterocyclohexyl ring such as a heterocyclohexyl ring. Suitably, the heterocyclopentyl ring is tetrahydrofuranyl or pyrrolidinyl. Suitably, the heterocyclohexyl ring is tetrahydropyranyl or piperidinyl. Any nitrogen atom(s) in the $C_{3-6}$heterocycloalkyl ring may be substituted (such as one nitrogen atom is substituted), for example by $C_{1-4}$alkyl, C(O)H, C(O)$C_{1-4}$alkyl, C(O)O$C_{1-4}$alkyl, C(O)O$C_{1-4}$alkylaryl such as C(O)OBz, C(O)NH$C_{1-4}$alkyl, C(O)NH$C_{1-4}$ alkylaryl such as C(O)NHBz, an Fmoc group, C(O)$C_{1-4}$haloalkyl, C(O)O$C_{1-4}$haloalkyl or C(O)NH$C_{1-4}$haloalkyl such as C(O)OtBu. Suitably, any nitrogen atom in the $C_{3-6}$heterocycloalkyl ring is not substituted. In a thirteenth embodiment, $R_5$ is $OC_{0-2}$alkylene$C_{3-6}$heterocycloalkyl such as $OC_{0-2}$alkylene$C_3$heterocycloalkyl, $OC_{0-2}$alkylene$C_4$heterocycloalkyl, $OC_{0-2}$alkylene$C_5$heterocycloalkyl, $OC_{0-2}$alkylene$C_6$heterocycloalkyl, $OC_0$alkylene$C_{3-5}$heterocycloalkyl, $OC_1$alkylene$C_{3-6}$heterocycloalkyl and $OC_2$alkylene$C_{3-6}$heterocycloalkyl. Suitably the heterocycloalkyl is a heterocyclopropyl, heterocyclobutyl, heterocyclopentyl or heterocyclohexyl ring such as a heterocyclohexyl ring. Suitably, the heterocyclopentyl ring is tetrahydrofuranyl or pyrrolidinyl. Suitably, the heterocyclohexyl ring is tetrahydropyranyl or piperidinyl. Any nitrogen atom(s) (such as one nitrogen atom) in the $C_{3-6}$heterocycloalkyl ring may be substituted, for example by $C_{1-4}$alkyl, C(O)H, C(O)$C_{1-4}$alkyl, C(O)O$C_{1-4}$alkyl, C(O)O$C_{1-4}$alkylaryl such as C(O)OBz, C(O)NH$C_{1-4}$alkyl, C(O)NH$C_{1-4}$alkylaryl such as C(O)NHBz, an Fmoc group, C(O)$C_{1-4}$haloalkyl, C(O)O$C_{1-4}$haloalkyl or C(O)NH$C_{1-4}$haloalkyl such as C(O)OtBu. Suitably, any nitrogen atom in the $C_{3-6}$heterocycloalkyl ring is not substituted.

Suitably $R_5$ is H, $CH_3$, ethyl, isopropyl or fluoro, in particular $R_5$ is H, methyl or ethyl.

Suitably $R_4$ is H, $CH_3$, ethyl, fluoro, $OCH_3$, propoxy or $CH_2CH_2OCH_3$ and $R_5$ is H, $CH_3$, ethyl or fluoro, in particular $R_4$ is H, $CH_3$, ethyl or $OCH_3$ and $R_5$ is H, methyl or ethyl. For example, $R_4$ and $R_5$ are H, $R_4$ and $R_5$ are methyl, $R_4$ and $R_5$ are ethyl, $R_4$ is $CH_2CH_2OCH_3$ and $R_5$ is H or $R_4$ and $R_5$ are fluoro.

Suitably, when $R_4$ is other than H, methyl, ethyl or fluoro, then $R_5$ is H.

In one embodiment $R_6$ is H. In a second embodiment $R_6$ is $C_{1-3}$alkyl, in particular methyl. In a third embodiment $R_6$ together with $R_{11}$ in the ortho-position to the amide are a $C_2$alkylene chain forming a 5-membered ring. In a fourth embodiment, $R_4$ is H and $R_5$ and $R_6$ are a $C_{2-3}$alkylene chain forming a 5- or 6-membered ring in particular a 5-membered ring.

Suitably $R_6$ is H, methyl or $R_6$ together with $R_{11}$ when in the ortho-position to the amide are a $C_2$alkylene chain forming a 5-membered ring. In particular $R_6$ is H or $R_6$ together with $R_{11}$ in the ortho-position to the amide are a $C_2$alkylene chain forming a 5-membered ring, especially $R_6$ is H.

The term '$R_6$ together with $R_{11}$ in the ortho-position to the amide are a $C_2$alkylene chain forming a 5-membered ring' as used herein means that compounds with the following substructure are formed:

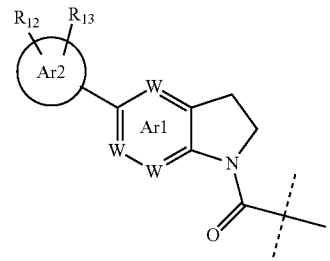

wherein W may be N or $CR_{10}$.

In one embodiment Ar1 is a 6-membered aryl, i.e. phenyl. In a second embodiment Ar1 is a 6-membered heteroaryl, in particular containing one nitrogen atom (pyridyl) or two nitrogen atoms (pyridazinyl, pyrimidinyl or pyrazinyl).

In particular Ar1 is phenyl, 2-pyridyl, 3-pyridyl or 2,6-pyrimidinyl, especially phenyl, 2-pyridyl or 3-pyridyl, such as phenyl or 2-pyridyl. The position numbering for Ar1 is in respect of the amide, with the carbon at the point of attachment designated position 1 and other numbers providing the relative location of the nitrogen atoms, for example:

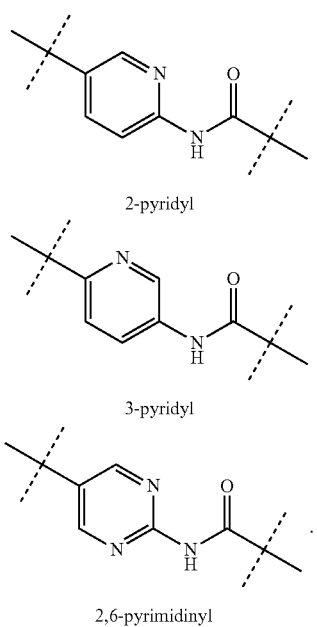

2-pyridyl 3-pyridyl 2,6-pyrimidinyl

In one embodiment $R_{10}$ is H. In a second embodiment $R_{10}$ is halo, for example fluoro or chloro. In a third embodiment $R_{10}$ is $C_{1-3}$alkyl, such as $CH_3$, ethyl or isopropyl, in particular $C_{1-2}$alkyl, such as $CH_3$ or ethyl. In a fourth embodiment $R_{10}$ is $OC_{1-2}$alkyl, such as $OCH_3$ or ethoxy. In a fifth embodiment $R_{10}$ is $C_{1-2}$haloalkyl, such as $CF_3$. In a sixth embodiment $R_{10}$ is $OC_{1-2}$haloalkyl, such as $OCF_3$. In a seventh embodiment $R_{10}$ is CN.

Suitably $R_{10}$ is H, fluoro, chloro, $CH_3$, $OCH_3$, ethoxy, $OCF_3$ or CN, in particular H, fluoro, chloro, $CH_3$, $OCH_3$, ethoxy or $OCF_3$, especially or H, fluoro, chloro, $CH_3$, $OCH_3$ or $OCF_3$, such as H, fluoro or $CH_3$.

Additionally of interest are compounds wherein $R_{10}$ is ethyl, isopropyl and $CF_3$, in particular isopropyl and $CF_3$. Additionally of interest are compounds when $R_{10}$ is CN.

Consequently, suitably $R_{10}$ is H, fluoro, chloro, $CH_3$, ethyl, isopropyl, $OCH_3$, ethoxy, $OCF_3$, $CF_3$ or CN, in particular H, fluoro, chloro, $CH_3$, isopropyl, $OCH_3$, ethoxy, $OCF_3$ or $CF_3$, especially or H, fluoro, chloro, $CH_3$, isopropyl, $OCH_3$, $OCF_3$ or $CF_3$, such as H, fluoro or $CH_3$.

In one embodiment $R_{11}$ is H. In a second embodiment $R_{11}$ is F. In a third embodiment, $R_{11}$ is $CH_3$. In a fourth embodiment $R_6$ together with $R_{11}$ in the ortho-position to the amide are a $C_2$alkylene chain forming a 5-membered ring. In a fifth embodiment $R_{11}$ is ethyl. In a sixth embodiment $R_{11}$ is Cl. In a seventh embodiment $R_{11}$ is $OCH_3$. In an eighth embodiment, $R_{11}$ is $CF_3$. In a ninth embodiment, $R_{11}$ is $OCF_3$. In a tenth embodiment, $R_{11}$ is CN. In an eleventh embodiment $R_6$ together with $R_{11}$ in the ortho-position to the amide are a $C_2$alkylene chain forming a 5-membered ring.

Suitably, $R_{10}$ and $R_{11}$ are both $CH_3$. Suitably, $R_{10}$ and $R_{11}$ are both H. Suitably, $R_{10}$ and $R_{11}$ are both fluoro.

In one embodiment, $R_{10}$ is in the ortho position with respect to the amide. In another embodiment, $R_{10}$ is in the meta position with respect to the amide. Suitably $R_{10}$ is in the ortho position with respect to the amide.

In one embodiment, $R_{11}$ is in the ortho position with respect to the amide. In another embodiment, $R_{11}$ is in the meta position with respect to the amide. Suitably $R_{11}$ is in the ortho position with respect to the amide.

In one embodiment Ar2 is a 6-membered aryl, i.e. phenyl. In a second embodiment Ar2 is a 6-membered heteroaryl, in particular containing one nitrogen atom (pyridyl) or two nitrogen atoms (pyridazinyl, pyrimidinyl or pyrazinyl).

The position numbering for Ar2 is in respect of the point of attachment to Ar1, for example:

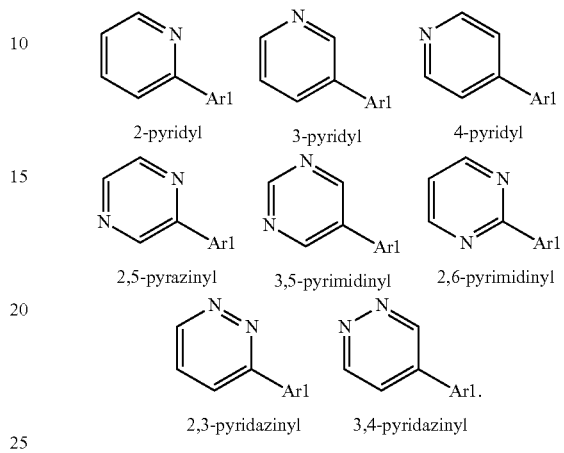

2-pyridyl   3-pyridyl   4-pyridyl 2,5-pyrazinyl   3,5-pyrimidinyl   2,6-pyrimidinyl 2,3-pyridazinyl   3,4-pyridazinyl.

In particular Ar2 is phenyl, 2-pyridyl, 3-pyridyl, 4-pyridyl, 2,3-pyridazinyl, 3,4-pyridazinyl, 3,5-pyrimidinyl or 2,5-pyrazinyl, especially 3-pyridyl, 3,5-pyrimidinyl or 2,5-pyrazinyl, such as 3-pyridyl or 2,5-pyrazinyl.

In one embodiment $R_{12}$ is H. In a second embodiment $R_{12}$ is halo, for example fluoro or chloro. In a third embodiment $R_{12}$ is $C_{1-4}$alkyl, such as methyl, ethyl, propyl (n-propyl or isopropyl) or butyl (n-butyl, isobutyl, sec-butyl or tert-butyl). In a fourth embodiment $R_{12}$ is $C_{2-4}$alkynyl, such as C≡CH. In a fifth embodiment $R_{12}$ is $C_{0-2}$alkylene$C_{3-5}$cycloalkyl, such as $C_{3-5}$cycloalkyl (e.g. cyclopropyl), $C_1$alkylene$C_{3-5}$cycloalkyl or $C_2$alkylene$C_{3-5}$cycloalkyl. In a sixth embodiment $R_{12}$ is $OC_{1-4}$alkyl, such as $OCH_3$, ethoxy, isopropoxy or n-propoxy. In a seventh embodiment $R_{12}$ is $OC_{0-2}$alkylene$C_{3-5}$cycloalkyl, such as $OC_{3-5}$cycloalkyl (e.g. cyclopropoxy or cyclobutoxy), $OC_1$alkylene$C_{3-5}$cycloalkyl or $OC_2$alkylene$C_{3-5}$cycloalkyl. In an eighth embodiment $R_{12}$ is $OCH_2CH_2N(CH_3)_2$. In a ninth embodiment $R_{12}$ is $C_{1-4}$alkylOH, such as $CH_2OH$ or $C(CH_3)_2OH$. In a tenth embodiment $R_{12}$ is CN. In an eleventh embodiment $R_{12}$ is $C_{1-3}$alkyleneO$C_{1-3}$alkyl. In a twelfth embodiment $R_{12}$ is $C_{1-4}$haloalkyl, such as $CF_3$. In a thirteenth embodiment $R_{12}$ is $OC_{1-4}$haloalkyl, such as $OCF_3$, $OCHF_2$ or $OCH_2CF_3$. In a fourteenth embodiment $R_{12}$ is $NR_{23}R_{24}$ such as $N(CH_3)_2$.

In a fifteenth embodiment $R_{12}$ is $S(O)_2C_{1-4}$alkyl such as $SO_2CH_3$. In a sixteenth embodiment $R_{12}$ is $C(O)N(CH_3)_2$. In a seventeenth embodiment $R_{12}$ is $NHC(O)C_{1-3}$alkyl such as $NHC(O)CH_3$. In an eighteenth embodiment $R_{12}$ is a $C_{3-6}$heterocycloalkyl comprising one nitrogen located at the point of attachment to Ar2, such as a $C_5$heterocycloalkyl, in particular pyrrolidinyl, or a $C_6$heterocycloalkyl such as morpholinyl. In a nineteenth embodiment $R_{12}$ is OH. In a twentieth embodiment $R_{12}$ is C(=O)$C_{1-2}$alkyl. In a twentyfirst embodiment $R_{12}$ is S(O)$C_{1-4}$alkyl. In a twentysecond embodiment $R_{12}$ is S$C_{1-4}$alkyl. In a twentythird embodiment $R_{12}$ is SH. In a twentyfourth embodiment, $R_{12}$ together with a nitrogen atom to which it is attached forms an N-oxide ($N^+$—$O^-$).

$R_{12}$ is suitably H, fluoro, chloro, $CH_3$, cyclopropyl, C≡CH, $OCH_3$, ethoxy, n-propoxy, isopropoxy, cyclopropoxy, cyclobutoxy, CN, $CF_3$, $OCF_3$, $OCHF_2$, $OCH_2CF_3$, $CH_2OH$, $N(CH_3)_2$, $NHC(O)CH_3$, $SO_2CH_3$, $C(O)N(CH_3)_2$ or pyrrolidinyl, in particular H, fluoro, chloro, $CH_3$, cyclopropyl, C≡CH, $OCH_3$, ethoxy, n-propoxy, isopropoxy, cyclopropoxy, cyclobutoxy, CN, $CF_3$, $OCF_3$, $OCHF_2$, $OCH_2CF_3$, $CH_2OH$, $C(O)N(CH_3)_2$ or pyrrolidinyl, especially H, fluoro, chloro, $CH_3$, cyclopropyl, C≡CH, $OCH_3$, ethoxy, n-propoxy, isopropoxy, cyclopropoxy, CN, $CF_3$, $OCHF_2$, $OCH_2CF_3$ or pyrrolidinyl, such as H, fluoro, chloro, $CH_3$, C≡CH, $OCH_3$, ethoxy, n-propoxy, isopropoxy, cyclopropoxy, CN, $CF_3$, $OCHF_2$ or $OCH_2CF_3$.

Additionally of interest are ethyl, 2-methoxyisopropyl and OH, especially ethyl.

In one embodiment, $R_{23}$ is H. In another embodiment, $R_{23}$ is $C_{1-2}$alkyl such as methyl.

In one embodiment, $R_{24}$ is H. In another embodiment $R_{24}$ is $C_{1-2}$alkyl such as methyl.

Suitably, $R_{23}$ is H and $R_{24}$ is ethyl. Suitably, $R_{23}$ is $CH_3$ and $R_{24}$ is $CH_3$.

Consequently, suitably $R_{12}$ is H, fluoro, chloro, $CH_3$, ethyl, cyclopropyl, C≡CH, $OCH_3$, ethoxy, n-propoxy, isopropoxy, cyclopropoxy, cyclobutoxy, CN, $CF_3$, $OCF_3$, $OCHF_2$, $OCH_2CF_3$, OH, $CH_2OH$, $N(CH_3)_2$, $NHC(O)CH_3$, $SO_2CH_3$, $C(O)N(CH_3)_2$ or pyrrolidinyl, in particular H, fluoro, chloro, $CH_3$, ethyl, cyclopropyl, C≡CH, $OCH_3$, ethoxy, n-propoxy, isopropoxy, cyclopropoxy, cyclobutoxy, CN, $CF_3$, $OCF_3$, $OCHF_2$, $OCH_2CF_3$, $CH_2OH$, $C(O)N(CH_3)_2$ or pyrrolidinyl, especially H, fluoro, chloro, $CH_3$, ethyl, cyclopropyl, C≡CH, $OCH_3$, ethoxy, n-propoxy, isopropoxy, cyclopropoxy, CN, $CF_3$, $OCHF_2$, $OCH_2CF_3$ or pyrrolidinyl, such as H, fluoro, chloro, $CH_3$, C≡CH, $OCH_3$, ethoxy, n-propoxy, isopropoxy, cyclopropoxy, CN, $CF_3$, $OCHF_2$ or $OCH_2CF_3$.

Suitably $R_{12}$ is suitably in the meta position of Ar2. Alternatively, $R_{12}$ is in the ortho position of Ar2.

The present invention provides N-oxides of the compound of formula (I). Suitably, when $R_{12}$ together with a nitrogen atom to which it is attached forms an N-oxide ($N^+$—$O^-$), the example following structures are formed:

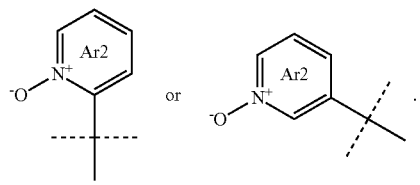

In one embodiment $R_{13}$ is methyl. In a second embodiment $R_{13}$ is H. In a third embodiment $R_{13}$ is methoxy. In a fourth embodiment $R_{13}$ is halo such as fluoro.

In one embodiment, $R_{13}$ is in the ortho position with respect to Ar1. In another embodiment, $R_{13}$ is in the para position with respect to Ar1.

In one embodiment, Ar1 is 2-pyridyl:

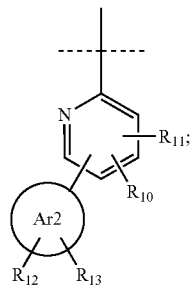

$R_1$ is cyclopropyl or sec-butyl; $R_3$ is H or forms a 5-membered ring with $R_5$; $R_4$ and $R_5$ are independently H, $CH_3$, ethyl, $OCH_3$, isopropoxy or $CH_2CH_2OCH_3$, or $R_4$ is H and $R_5$ and $R_3$ join to form a 5-membered cycloalkyl ring; $R_6$ is H; Ar2 is 3-pyridyl, phenyl, 2,5-pyrazinyl or 3,5-pyrimidinyl; $R_{10}$ is H or F and $R_{11}$ is H; $R_{12}$ is in the meta position and is selected from the group consisting of H, F, C, $CH_3$, CN, $CF_3$, $OCF_3$, $OCH_2CF_3$, $OCH_3$, ethoxy, n-propoxy, isopropoxy, cyclopropoxy and cyclobutoxy; and $R_{13}$ is H.

Suitably, Ar2 is 3-pyridyl or 2,5-pyrazinyl (e.g. 2,5-pyrazinyl); and $R_{12}$ is selected from the group consisting of H, F, C, $CH_3$, CN, $CF_3$, $OCH_2CF_3$, $OCH_3$, ethoxy, n-propoxy, isopropoxy, cyclopropoxy and cyclobutoxy.

More suitably, $R_3$ is H; $R_4$ and $R_5$ are independently H, $CH_3$, ethyl, $OCH_3$, isopropoxy or $CH_2CH_2OMe$ (e.g. H, $CH_3$, ethyl, $CH_2CH_2OCH_3$ or $OCH_3$); and $R_{12}$ is selected from the group consisting of F, C, $CH_3$, CN, $CF_3$, $OCH_2CF_3$, $OCH_3$, ethoxy, n-propoxy, isopropoxy and cyclopropoxy (e.g. $CF_3$, $OCH_3$, OEt, OnPr, OiPr and OCyclethoxy, n-propoxy, isopropoxy and cyclopropoxy).

In one embodiment, Ar1 is 3-pyridyl:

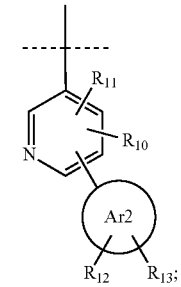

$R_1$ is cyclopropyl; $R_3$ is H; $R_4$ and $R_5$ are independently H or $CH_3$ (e.g. $CH_3$); $R_6$ is H; Ar2 is 3-pyridyl, phenyl or 3,5-pyrimidinyl (e.g. 3-pyridyl or 3,5-pyrimidinyl); and $R_{10}$, $R_{11}$, $R_{12}$ and $R_{13}$ are H.

In one embodiment, Ar1 is phenyl:

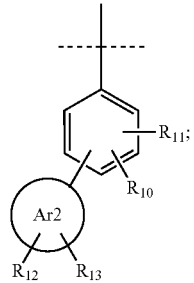

$R_1$ is cyclopropyl, cyclopropyl substituted by $CH_3$ at the point of attachment, cyclobutyl, $CH_3$, isopropyl, sec-butyl, tert-butyl or $CF_3$; $R_3$ is H, $CH_3$ or forms a 5- or 6-membered ring with $R_5$; Ar2 is selected from the group consisting of 3-pyridyl, phenyl, 2,5-pyrazinyl, 2-pyridyl, 3,5-pyrimidinyl and 2,3-pyridazinyl; and when Ar2 is 3-pyridyl, $R_1$ is cyclopropyl, cyclopropyl substituted by $CH_3$ at the point of attachment, cyclobutyl or $CH_3$;

$R_4$ and $R_5$ are independently selected from the list consisting of H, $CH_3$, ethyl, isopropyl, F, $OCH_3$, isopropoxy and $CH_2CH_2OCH_3$; or $R_4$ is H and $R_5$ and $R_3$ join to form a 5- or 6-membered cycloalkyl ring; or $R_4$ is O and $R_5$ is absent;

$R_6$ is H or $CH_3$;

$R_{10}$ is H, F, $CH_3$, C, $OCH_3$, ethoxy, $OCF_3$ or CN;

$R_{11}$ is H, F or $CH_3$;

$R_{12}$ is selected from the group consisting of H, $CH_3$, F, C, $OCH_3$, ethoxy, n-propoxy, isopropoxy, CN, $CH_2OH$, $CF_3$, $OCHF_2$, $OCH_2CF_3$, $N(CH_3)_2$ and $SO_2CH_3$; and $R_{13}$ is H; or when Ar2 is phenyl, $R_1$ is cyclopropyl;

$R_4$ and $R_5$ are independently H, $CH_3$, ethyl or F;

$R_6$ is H;

$R_{12}$ is H, $OCH_3$, CN and Cl; and $R_{10}$, $R_{11}$ and $R_{13}$ are H; or when Ar2 is 2,5-pyrazinyl, $R_1$ is cyclopropyl, cyclopropyl substituted by $CH_3$ at the point of attachment, cyclobutyl, isopropyl, sec-butyl, tert-butyl or $CF_3$;

$R_4$ and $R_5$ are independently H, $CH_3$, ethyl, isopropyl, $OCH_3$ and $CH_2CH_2OCH_3$ or join together to form a $C_5$cycloalkyl ring;

$R_6$ is H or $R_6$ together with $R_{11}$, when in the ortho-position to the amide, is covalently linked by an alkylene chain to form a 5-membered ring;

$R_{10}$ is H, F, $OCH_3$ or CN;

$R_{11}$ is H or when in the ortho-position to the amide, together with $R_6$ is covalently linked by an alkylene chain to form a 5-membered ring; and $R_{12}$ is selected from the group consisting of H, $CH_3$, cyclopropyl, C≡CH, C, $CF_3$, $OCH_2CF_3$, $CH_2OH$, CN, $OCH_3$, ethoxy, isopropoxy, cyclopropoxy, n-propoxy, cyclobutoxy, $C(O)N(CH_3)_2$, $NHC(O)CH_3$ and pyrrolidinyl;

$R_{13}$ is H or $CH_3$; or when Ar2 is 2-pyridyl, $R_1$ is cyclopropyl;

$R_4$ and $R_5$ are $CH_3$;

$R_6$ is H;

$R_{12}$ is $OCH_3$, C or $CF_3$; and $R_{10}$ and $R_{11}$ are H;

$R_{13}$ is H; or when Ar2 is 3,5-pyrimidinyl, $R_1$ is cyclopropyl;

$R_4$ and $R_5$ are independently H, $CH_3$ or isopropyl; and $R_6$, $R_{10}$, $R_{11}$, $R_{12}$ and $R_{13}$ are H; or when Ar2 is 2,3-pyridazinyl, $R_1$ is cyclopropyl;

$R_4$ and $R_5$ are $CH_3$; and $R_6$, $R_{10}$, $R_{11}$, $R_{12}$ and $R_{13}$ are H.

In this embodiment, suitably Ar2 is selected from the group consisting of 3-pyridyl, 2,5-pyrazinyl, 2-pyridyl and 3,5-pyrimidinyl; and when Ar2 is 3-pyridyl, $R_4$ and $R_5$ are independently selected from the group consisting of H, $CH_3$, ethyl, isopropyl, F, $OCH_3$, isopropoxy and $CH_2CH_2OCH_3$;

or $R_4$ is H and $R_5$ and $R_3$ join to form a 5- or 6-membered cycloalkyl ring;

$R_{10}$ is H, F, Cl, $CH_3$, $OCH_3$ or $OCF_3$ (e.g. H, F or $CH_3$); and $R_{12}$ is selected from the group consisting of H, $CH_3$, F, Cl, $CF_3$, $OCHF_2$, $OCH_2CF_3$, CN, $OCH_3$, ethoxy, n-propoxy and isopropoxy; or when Ar2 is 2-pyridyl, $R_{12}$ is C or $CF_3$; or when Ar2 is 3,5-pyrimidinyl, $R_4$ and $R_5$ are independently H or $CH_3$; or when Ar2 is 2,5-pyrazinyl, $R_{10}$ is H, F or $OCH_3$;

$R_{12}$ is selected from the group consisting of H, $CH_3$, cyclopropyl, C≡CH, C, $CF_3$, $OCH_2CF_3$, $CH_2OH$, CN, $OCH_3$, ethoxy, isopropoxy, cyclopropoxy, n-propoxy, cyclobutoxy, $C(O)N(CH_3)_2$ and pyrrolidinyl;

$R_{13}$ is H or $CH_3$.

More suitably, $R_1$ is cyclopropyl, cyclopropyl substituted by $CH_3$ at the point of attachment, cyclobutyl or isopropyl (e.g. cyclopropyl or cyclopropyl substituted by $CH_3$ at the point of attachment); $R_3$ is H or forms a 5- or 6-membered ring with $R_5$ (e.g. H); Ar2 is 3-pyridyl, 2,5-pyrazinyl or 3,5-pyrimidinyl (e.g. 3-pyridyl or 2,5-pyrazinyl); and when Ar2 is 3-pyridyl, $R_4$ and $R_5$ are independently selected from the group consisting of H, F, $CH_3$, ethyl, $OCH_3$, isopropoxy and $CH_2CH_2OCH_3$ (e.g. H, $CH_3$, ethyl or $OCH_3$), or $R_4$ is H and $R_5$ and $R_3$ join to form a 5-membered cycloalkyl ring; and $R_6$ is H; and $R_{11}$ is H or $CH_3$ (e.g. H);

$R_{12}$ is selected from the group consisting of H, $CH_3$, F, C, $CF_3$, $OCHF_2$, CN, $OCH_3$, ethoxy, isopropoxy and n-propoxy (e.g. H, F, C, $CF_3$, $OCHF_2$, CN, $CH_3$, $OCH_3$, ethoxy or isopropoxy); or when Ar2 is 3,5-pyrimidinyl, $R_4$ and $R_5$ are $CH_3$; or when Ar2 is 2,5-pyrazinyl, $R_4$ and $R_5$ are independently H, $CH_3$, ethyl, $OCH_3$ and $CH_2CH_2OCH_3$ or join together to form a $C_5$cycloalkyl ring (e.g. H, $CH_3$, ethyl or $OCH_3$);

$R_6$ is H or $R_6$ together with $R_{11}$, when in the ortho-position to the amide, is covalently linked by an alkylene chain to form a 5-membered ring (e.g. H);

$R_{10}$ is H or F;

$R_{12}$ is selected from the group consisting of H, $CH_3$, cyclopropyl, C≡CH, Cl, $CF_3$, $OCH_2CF_3$, $OCH_3$, ethoxy, isopropoxy, cyclopropoxy, n-propoxy and pyrrolidinyl (e.g. H, C≡CH, Cl, $CF_3$, $OCH_2CF_3$, $OCH_3$, ethoxy, isopropoxy or cyclopropoxy); and $R_{13}$ is H.

In one embodiment, Ar1 is 2,6-pyrimidinyl:

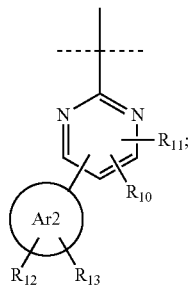

$R_1$ is cyclopropyl; $R_3$ is H; $R_4$ and $R_5$ are $CH_3$; $R_6$ is H; $R_{10}$ is H; $R_{11}$ is H; Ar2 is 3-pyridyl; $R_{12}$ is H, F, CN, $CF_3$ or $OCH_3$; and $R_{13}$ is H.

Throughout the specification Ar1 and Ar2 may be depicted as follows:

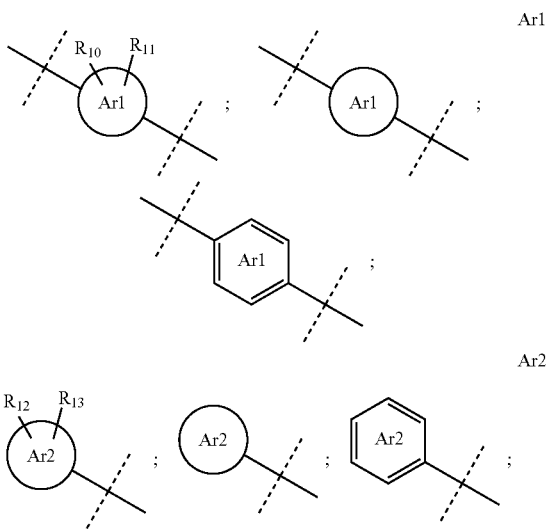

All depictions with respect to Ar1 are equivalent and all depictions with respect to Ar2 are equivalent, unless the context requires otherwise, depictions of Ar1 and Ar2 should not be taken to exclude the presence of heteroatoms or substitutions.

The present invention provides the compounds described in any one of Examples T1 to T322. Also of interest are the compounds described in any one of Examples T1 to T416, such as T325 to T416. Also of interest are the compounds described in any one of Examples T417 to T465.

The present invention provides the following compounds:
N-([1,1'-biphenyl]-4-yl)-2-(2-(methylsulfonamido)thiazol-4-yl)acetamide;
N-([1,1'-biphenyl]-4-yl)-2-(2-(cyclopropanesulfonamido)thiazol-4-yl)acetamide;
2-(2-(cyclopropanesulfonamido)thiazol-4-yl)-2-ethyl-N-(5-(pyrazin-2-yl)pyridin-2-yl)butanamide;
2-(2-(cyclopropanesulfonamido)thiazol-4-yl)-2-methyl-N-(4-(pyrimidin-2-yl)phenyl)propanamide;
2-(2-(cyclopropanesulfonamido)thiazol-4-yl)-N-(4-(pyridin-3-yl)phenyl)butanamide (racemic);
(R)-2-(2-(cyclopropanesulfonamido)thiazol-4-yl)-N-(4-(pyridin-3-yl)phenyl)butanamide;
(S)-2-(2-(cyclopropanesulfonamido)thiazol-4-yl)-N-(4-(pyridin-3-yl)phenyl)butanamide;
2-(2-(cyclopropanesulfonamido)thiazol-4-yl)-N-(4-(5-fluoropyridin-3-yl)phenyl)butanamide (racemic);
(R)-2-(2-(cyclopropanesulfonamido)thiazol-4-yl)-N-(4-(5-fluoropyridin-3-yl)phenyl)butanamide;
(S)-2-(2-(cyclopropanesulfonamido)thiazol-4-yl)-N-(4-(5-fluoropyridin-3-yl)phenyl)butanamide;
2-(2-(cyclopropanesulfonamido)thiazol-4-yl)-3-methyl-N-(4-(pyrimidin-5-yl)phenyl)butanamide;
2-(2-(cyclopropanesulfonamido)thiazol-4-yl)-3-methyl-N-(4-(pyridin-3-yl)phenyl)butanamide;
2-(2-(cyclopropanesulfonamido)thiazol-4-yl)-N-(4-(5-methoxypyridin-3-yl)phenyl)-2-methylpropanamide;
N-(2-chloro-4-(pyridin-3-yl)phenyl)-2-(2-(cyclopropanesulfonamido)thiazol-4-yl)acetamide;
2-(2-(cyclopropanesulfonamido)-5-methylthiazol-4-yl)-2-methyl-N-(4-(6-(trifluoromethyl) pyrazin-2-yl)phenyl)propanamide;
2-(2-(cyclopropanesulfonamido)thiazol-4-yl)-2-methyl-N-(4-(pyrimidin-5-yl)phenyl)propanamide;
6-(4-(2-(2-(cyclopropanesulfonamido)thiazol-4-yl)-2-methylpropanamido)phenyl)-N,N-dimethylpyrazine-2-carboxamide;
N-(5-(5-cyanopyridin-3-yl)pyrimidin-2-yl)-2-(2-(cyclopropanesulfonamido)thiazol-4-yl)-2-methylpropanamide;
N-([1,1'-biphenyl]-4-yl)-2-(5-chloro-2-(cyclopropanesulfonamido)thiazol-4-yl)acetamide;
2-(2-(cyclopropanesulfonamido)thiazol-4-yl)-N-(4-(6-ethynylpyrazin-2-yl)phenyl)butanamide;
2-(2-(cyclopropanesulfonamido)thiazol-4-yl)-N-(6-(pyrimidin-5-yl)pyridin-3-yl)acetamide;
2-(2-(cyclopropanesulfonamido)thiazol-4-yl)-N-(5-phenylpyridin-2-yl)acetamide;
2-(2-(cyclopropanesulfonamido)thiazol-4-yl)-N-(4'-fluoro-[1,1'-biphenyl]-4-yl)acetamide;
2-(2-(cyclopropanesulfonamido)thiazol-4-yl)-N-methyl-N-(4-(pyridin-3-yl)phenyl)acetamide;
N-([2,3'-bipyridin]-5-yl)-2-(2-(cyclopropanesulfonamido)thiazol-4-yl)propanamide;
2-(2-(cyclopropanesulfonamido)thiazol-4-yl)-N-(3'-methoxy-[1,1'-biphenyl]-4-yl)-2-methylpropanamide;
2-(2-(cyclopropanesulfonamido)thiazol-4-yl)-2-methyl-N-(4-(pyridin-3-yl)phenyl)propanamide;
2-(2-(cyclopropanesulfonamido)thiazol-4-yl)-2-methyl-N-(4-(5-methylpyridin-3-yl)phenyl)propanamide;
2-(2-(cyclopropanesulfonamido)thiazol-4-yl)-2-methyl-N-(4-(pyridazin-4-yl)phenyl)propanamide;
2-(2-(cyclopropanesulfonamido)thiazol-4-yl)-2-methyl-N-(4-(pyrazin-2-yl)phenyl)propanamide;
2-(2-(cyclopropanesulfonamido)thiazol-4-yl)-N-(4-(6-methoxypyrazin-2-yl)phenyl)butanamide;
N-(3-cyano-4-(pyrazin-2-yl)phenyl)-2-(2-(cyclopropanesulfonamido)thiazol-4-yl)-2-methylpropanamide;
2-(2-(cyclopropanesulfonamido)thiazol-4-yl)-2-methyl-N-(5-(6-(trifluoromethyl)pyrazin-2-yl)pyridin-2-yl)propanamide;
2-(2-(cyclopropanesulfonamido)thiazol-4-yl)-N-(2,3-difluoro-4-(pyridin-3-yl)phenyl)-2-methylpropanamide;
2-(2-(cyclopropanesulfonamido)thiazol-4-yl)-2-methyl-N-(5-(pyridin-3-yl)pyrimidin-2-yl)propanamide;
2-(2-(cyclopropanesulfonamido)thiazol-4-yl)-2-methyl-N-(5-(6-propoxypyrazin-2-yl)pyridin-2-yl)propanamide;
2-(2-(cyclopropanesulfonamido)thiazol-4-yl)-N-(3-fluoro-4-(pyrazin-2-yl)phenyl)-2-methylpropanamide;
2-(2-(cyclopropanesulfonamido)thiazol-4-yl)-2-methyl-N-(4-(pyridin-3-yl)-2-(trifluoromethoxy)phenyl)propanamide;

N-(2-chloro-4-(pyridin-3-yl)phenyl)-2-(2-(cyclopropane-sulfonamido)thiazol-4-yl)-2-methylpropanamide;
2-(2-(cyclopropanesulfonamido)thiazol-4-yl)-N-(2-fluoro-4-(pyridin-3-yl)phenyl)-2-methylpropanamide;
2-(2-(cyclopropanesulfonamido)thiazol-4-yl)-N-(3-methoxy-4-(pyrazin-2-yl)phenyl)-2-methylpropanamide;
2-(2-(cyclopropanesulfonamido)thiazol-4-yl)-N-(4-(2-methoxypyridin-3-yl)phenyl)-2-methylpropanamide;
2-(2-(cyclopropanesulfonamido)thiazol-4-yl)-N-(4-(5-(hydroxymethyl)pyridin-3-yl)phenyl)acetamide;
2-(2-(cyclopropanesulfonamido)thiazol-4-yl)-N-(4-(6-methoxypyridin-3-yl)phenyl)-2-methylpropanamide;
N-(4-(5-cyanopyridin-3-yl)phenyl)-2-(2-(cyclopropane-sulfonamido)thiazol-4-yl)-2-methylpropanamide;
2-(2-(cyclopropanesulfonamido)thiazol-4-yl)-2-methyl-N-(4-(5-(trifluoromethyl)pyridin-3-yl)phenyl)propanamide;
2-(2-(cyclopropanesulfonamido)thiazol-4-yl)-2-methyl-N-(4-(5-(methylsulfonyl)pyridin-3-yl)phenyl)propanamide;
2-(2-(cyclopropanesulfonamido)thiazol-4-yl)-N-(2-methoxy-4-(5-methoxypyridin-3-yl)phenyl)-2-methylpropanamide;
2-(2-(cyclopropanesulfonamido)thiazol-4-yl)-2-methyl-N-(5'-(trifluoromethyl)-[3,3'-bipyridin]-6-yl)propanamide;
2-(2-(cyclopropanesulfonamido)thiazol-4-yl)-N-(4-(6-ethoxypyrazin-2-yl)phenyl)-2-methylpropanamide;
2-(2-(cyclopropanesulfonamido)thiazol-4-yl)-2-methyl-N-(4-(6-morpholinopyrazin-2-yl)phenyl)propanamide;
N-(4-(6-cyclobutoxypyrazin-2-yl)phenyl)-2-(2-(cyclopropanesulfonamido)thiazol-4-yl)-2-methylpropanamide;
2-(2-(cyclopropanesulfonamido)thiazol-4-yl)-2-methyl-N-(4-(6-propoxypyrazin-2-yl)phenyl)propanamide;
2-(2-(cyclopropanesulfonamido)thiazol-4-yl)-N-(2-fluoro-4-(5-methoxypyridin-3-yl)phenyl)-2-methylpropanamide;
2-(2-(cyclopropanesulfonamido)thiazol-4-yl)-2-methoxy-N-(4-(6-methoxypyrazin-2-yl)phenyl)acetamide;
N-(4-(5-chloropyridin-3-yl)phenyl)-2-(2-(cyclopropane-sulfonamido)thiazol-4-yl)-2-isopropoxyacetamide;
2-(2-(cyclopropanesulfonamido)thiazol-4-yl)-4-methoxy-N-(5-(6-(trifluoromethyl)pyrazin-2-yl)pyridin-2-yl)butanamide;
N-([1,1'-biphenyl]-4-yl)-2-(2-(cyclopropanesulfonamido)thiazol-4-yl)-2,2-difluoroacetamide;
2-(2-(cyclobutanesulfonamido)thiazol-4-yl)-N-(4-(6-methoxypyrazin-2-yl)phenyl)acetamide;
N-([3,3'-bipyridin]-6-yl)-2-(2-(cyclopropanesulfonamido)thiazol-4-yl)butanamide;
2-(2-(cyclopropanesulfonamido)thiazol-4-yl)-2-methyl-N-(5-phenylpyridin-2-yl)propanamide;
2-(2-(cyclopropanesulfonamido)thiazol-4-yl)-N-(5-(pyrimidin-5-yl)pyridin-2-yl)acetamide;
N-([3,3'-bipyridin]-6-yl)-2-(2-(cyclopropanesulfonamido)thiazol-4-yl)acetamide;
2-(2-(cyclopropanesulfonamido)thiazol-4-yl)-N-(6-phenylpyridin-3-yl)acetamide;
N-([2,3'-bipyridin]-5-yl)-2-(2-(cyclopropanesulfonamido)thiazol-4-yl)acetamide;
2-(2-(cyclopropanesulfonamido)thiazol-4-yl)-2-methyl-N-(4-(pyridazin-3-yl)phenyl)propanamide;
2-(2-(cyclopropanesulfonamido)thiazol-4-yl)-N-(4-(pyridazin-4-yl)phenyl)butanamide;
2-(2-(cyclopropanesulfonamido)thiazol-4-yl)-N-(4-(pyrazin-2-yl)phenyl)butanamide;
N-(4-(5-chloropyridin-3-yl)phenyl)-2-(2-(cyclopropane-sulfonamido)thiazol-4-yl)-4-methoxybutanamide;
2-(2-(cyclopropanesulfonamido)thiazol-4-yl)-N-(4-(5-fluoropyridin-3-yl)phenyl)butanamide;
2-(2-(cyclopropanesulfonamido)thiazol-4-yl)-N-(4-(6-(trifluoromethyl)pyrazin-2-yl)phenyl)butanamide;
2-(2-(cyclopropanesulfonamido)thiazol-4-yl)-3-methyl-N-(4-(pyrazin-2-yl)phenyl)butanamide;
2-(2-(cyclopropanesulfonamido)thiazol-4-yl)-N-(4-(6-propoxypyrazin-2-yl)phenyl)butanamide;
2-(2-(cyclopropanesulfonamido)thiazol-4-yl)-N-(4-(6-isopropoxypyrazin-2-yl)phenyl)butanamide;
2-(2-(cyclopropanesulfonamido)thiazol-4-yl)-N-(4-(6-cyclopropoxypyrazin-2-yl)phenyl)butanamide:
N-(4-(6-chloropyrazin-2-yl)phenyl)-2-(2-(cyclopropane-sulfonamido)thiazol-4-yl)butanamide;
N-(4-(6-cyanopyrazin-2-yl)phenyl)-2-(2-(cyclopropane-sulfonamido)thiazol-4-yl)butanamide;
2-(2-(cyclopropanesulfonamido)thiazol-4-yl)-N-(4-(6-(trifluoromethyl)pyrazin-2-yl)phenyl)butanamide;
2-(2-(cyclopropanesulfonamido)thiazol-4-yl)-N-(4-(6-methoxypyrazin-2-yl)phenyl)acetamide;
2-(2-(cyclopropanesulfonamido)thiazol-4-yl)-N-(4-(pyrazin-2-yl)phenyl)acetamide;
N-([1,1'-biphenyl]-4-yl)-2-(cyclopropanesulfonamido)-4,5,6,7-tetrahydrobenzo[d]thiazole-4-carboxamide;
2-(cyclopropanesulfonamido)-N-(4-(pyridin-3-yl)phenyl)-4,5,6,7-tetrahydrobenzo[d]thiazole-4-carboxamide;
N-([1,1'-biphenyl]-4-yl)-2-(2-(cyclopropanesulfonamido)thiazol-4-yl)butanamide;
N-([1,1'-biphenyl]-4-yl)-2-(2-(cyclopropanesulfonamido)thiazol-4-yl)-3-methylbutanamide;
N-(3'-chloro-[1,1'-biphenyl]-4-yl)-2-(2-(cyclopropanesulfonamido)thiazol-4-yl)-2-methylpropanamide;
N-(3'-cyano-[1,1'-biphenyl]-4-yl)-2-(2-(cyclopropanesulfonamido)thiazol-4-yl)-2-methylpropanamide;
2-(2-(cyclopropanesulfonamido)thiazol-4-yl)-2,2-difluoro-N-(4-(pyridin-3-yl)phenyl)acetamide;
N-(4-(5-fluoropyridin-3-yl)phenyl)-2-(2-(cyclopropane-sulfonamido)thiazol-4-yl)butanamide;
2-(2-(cyclopropanesulfonamido)thiazol-4-yl)-2-ethyl-N-(4-(pyridin-3-yl)phenyl)butanamide;
N-(4-(5-cyanopyridin-3-yl)phenyl)-2-(2-(cyclopropane-sulfonamido)thiazol-4-yl)-2-ethylbutanamide;
2-(2-(cyclopropanesulfonamido)thiazol-4-yl)-N-(4-(5-ethoxypyridin-3-yl)phenyl)propanamide;
N-(4-(5-chloropyridin-3-yl)phenyl)-2-(2-(cyclopropane-sulfonamido)thiazol-4-yl)propanamide;
2-(2-(cyclopropanesulfonamido)thiazol-4-yl)-N-(4-(5-ethoxypyridin-3-yl)phenyl)butanamide;
N-([1,1'-biphenyl]-4-yl)-2-(2-(cyclopropanesulfonamido)thiazol-4-yl)-2-methylpropanamide;
2-(2-(cyclopropanesulfonamido)thiazol-4-yl)-N-(4-(4-methylpyridin-3-yl)phenyl)acetamide;
2-(2-(cyclopropanesulfonamido)thiazol-4-yl)-N-(4-(5-methylpyridin-3-yl)phenyl)acetamide;
2-(2-(cyclopropanesulfonamido)thiazol-4-yl)-N-(4-(2-methylpyridin-3-yl)phenyl)acetamide;
2-(2-(cyclopropanesulfonamido)thiazol-4-yl)-N-(4-(6-methylpyridin-3-yl)phenyl)acetamide;
2-(2-(cyclopropanesulfonamido)thiazol-4-yl)-N-(4-(pyridin-3-yl)phenyl)propanamide;
2-(2-(cyclopropanesulfonamido)thiazol-4-yl)-2-methyl-N-(4-(2-methylpyridin-3-yl)phenyl)propanamide;
2-(2-(cyclopropanesulfonamido)thiazol-4-yl)-2-oxo-N-(4-(pyridin-3-yl)phenyl)acetamide;
2-(2-(cyclopropanesulfonamido)thiazol-4-yl)-2-methyl-N-(4-(6-methylpyridin-3-yl)phenyl)propanamide;
2-(2-(cyclopropanesulfonamido)thiazol-4-yl)-N-(4-(6-(trifluoromethyl)pyrazin-2-yl)phenyl)butanamide:

(R)-2-(2-(cyclopropanesulfonamido)thiazol-4-yl)-2-methoxy-N-(4-(6-methoxypyrazin-2-yl)phenyl)acetamide;
(S)-2-(2-(cyclopropanesulfonamido)thiazol-4-yl)-2-methoxy-N-(4-(6-methoxypyrazin-2-yl)phenyl)acetamide;
2-(2-(cyclopropanesulfonamido)thiazol-4-yl)-2-methyl-N-(5-(6-(2,2,2-trifluoroethoxy)pyrazin-2-yl)pyridin-2-yl)propanamide;
2-(2-(cyclopropanesulfonamido)thiazol-4-yl)-N-(3-fluoro-5-(pyrazin-2-yl) pyridin-2-yl)-2-methylpropanamide;
2-(2-(cyclopropanesulfonamido)thiazol-4-yl)-N-(5-(6-ethoxypyrazin-2-yl)-3-fluoropyridin-2-yl)-2-methylpropanamide;
2-(2-(cyclopropanesulfonamido)thiazol-4-yl)-N-(3-fluoro-5-(6-(trifluoromethyl)pyrazin-2-yl)pyridin-2-yl)-2-methylpropanamide;
N-(5-(6-cyanopyrazin-2-yl)-3-fluoropyridin-2-yl)-2-(2-(cyclopropanesulfonamido)thiazol-4-yl)-2-methylpropanamide;
2-(2-(cyclopropanesulfonamido)thiazol-4-yl)-2-methyl-N-(5'-(2,2,2-trifluoroethoxy)-[3,3'-bipyridin]-6-yl)propanamide;
2-(2-(cyclopropanesulfonamido)thiazol-4-yl)-N-(5'-(difluoromethoxy)-[3,3'-bipyridin]-6-yl)-2-methylpropanamide;
N-([2,3'-bipyridin]-5-yl)-2-(2-(cyclopropanesulfonamido)thiazol-4-yl)-2-methylpropanamide;
2-(2-(cyclopropanesulfonamido)thiazol-4-yl)-2-methyl-N-(6-(pyrimidin-5-yl)pyridin-3-yl)propanamide;
2-(2-(cyclopropanesulfonamido)thiazol-4-yl)-N-(4-(5-(difluoromethoxy)pyridin-3-yl)phenyl)-2-methylpropanamide;
2-(2-(cyclopropanesulfonamido)thiazol-4-yl)-2-ethyl-N-(4-(6-methoxypyrazin-2-yl)phenyl)butanamide;
N-(4-(5-chloropyridin-3-yl)phenyl)-2-(2-(cyclopropanesulfonamido)thiazol-4-yl)-2-ethylbutanamide;
2-(2-(cyclopropanesulfonamido)thiazol-4-yl)-2-ethyl-N-(2-fluoro-4-(pyridin-3-yl)phenyl)butanamide;
2-(2-(cyclopropanesulfonamido)thiazol-4-yl)-2-ethyl-N-(4-(pyrazin-2-yl)phenyl)butanamide;
2-(2-(cyclopropanesulfonamido)thiazol-4-yl)-2-ethyl-N-(4-(6-propoxypyrazin-2-yl)phenyl)butanamide;
2-(2-(cyclopropanesulfonamido)thiazol-4-yl)-N-(2-fluoro-4-(6-(trifluoromethyl)pyrazin-2-yl)phenyl)-2-methylpropanamide;
2-(2-(cyclopropanesulfonamido)thiazol-4-yl)-N-(4-(5-ethoxypyridin-3-yl)-2-fluorophenyl)-2-methylpropanamide;
2-(2-(cyclopropanesulfonamido)thiazol-4-yl)-N-(2-fluoro-4-(5-fluoropyridin-3-yl)phenyl)-2-methylpropanamide;
2-(2-(cyclopropanesulfonamido)thiazol-4-yl)-2-methyl-N-(4-(6-(2,2,2-trifluoroethoxy)pyrazin-2-yl)phenyl)propanamide;
N-(4-(5-chloropyridin-3-yl)-2-fluorophenyl)-2-(2-(cyclopropanesulfonamido)thiazol-4-yl)-2-methylpropanamide;
N-(4-(5-cyanopyridin-3-yl)-2-fluorophenyl)-2-(2-(cyclopropanesulfonamido)thiazol-4-yl)-2-methylpropanamide;
1-(2-(cyclopropanesulfonamido)thiazol-4-yl)-N-(4-(6-methoxypyrazin-2-yl)phenyl)cyclopentane-1-carboxamide;
2-(2-(cyclopropanesulfonamido)thiazol-4-yl)-N-(2-fluoro-4-(6-(2,2,2-trifluoroethoxy)pyrazin-2-yl)phenyl)-2-methylpropanamide;
2-(2-(cyclopropanesulfonamido)thiazol-4-yl)-N-(2-fluoro-4-(5-(2,2,2-trifluoroethoxy)pyridin-3-yl)phenyl)-2-methylpropanamide;
2-(2-(cyclopropanesulfonamido)thiazol-4-yl)-N-(2-fluoro-4-(5-(trifluoromethyl)pyridin-3-yl)phenyl)-2-methylpropanamide;
2-(2-(cyclopropanesulfonamido)thiazol-4-yl)-N-(4-(6-ethoxypyrazin-2-yl)-2-fluorophenyl)-2-methylpropanamide;
2-(2-(cyclopropanesulfonamido)thiazol-4-yl)-2-methyl-N-(4-(5-(2,2,2-trifluoroethoxy)pyrazin-2-yl)pyridin-3-yl)phenyl)propanamide;
2-(2-(cyclopropanesulfonamido)thiazol-4-yl)-N-(4-(6-ethynylpyrazin-2-yl)phenyl)-2-methylpropanamide;
2-(2-(cyclopropanesulfonamido)thiazol-4-yl)-N-(4-(6-ethoxypyrazin-2-yl)-2-methylphenyl)-2-methylpropanamide;
N-(4-(6-chloropyrazin-2-yl)-2-methylphenyl)-2-(2-(cyclopropanesulfonamido)thiazol-4-yl)-2-methylpropanamide;
2-(2-(cyclopropanesulfonamido)thiazol-4-yl)-N-(4-(5-(difluoromethoxy)pyridin-3-yl)-2-fluorophenyl)-2-methylpropanamide;
2-(2-(cyclopropanesulfonamido)thiazol-4-yl)-2-methyl-N-(5-(pyrazin-2-yl)pyridin-2-yl)propanamide;
N-(5-(6-cyclobutoxypyrazin-2-yl)pyridin-2-yl)-2-(2-(cyclopropanesulfonamido)thiazol-4-yl)-2-methylpropanamide;
2-(2-(cyclopropanesulfonamido)thiazol-4-yl)-N-(5-(6-cyclopropoxypyrazin-2-yl)pyridin-2-yl)-2-methylpropanamide;
2-(2-(cyclopropanesulfonamido)thiazol-4-yl)-N-(5-(6-isopropoxypyrazin-2-yl)pyridin-2-yl)-2-methylpropanamide;
N-([3,3'-bipyridin]-6-yl)-2-(2-(cyclopropanesulfonamido)thiazol-4-yl)-2-ethylbutanamide;
2-(2-(cyclopropanesulfonamido)thiazol-4-yl)-N-(5'-ethoxy-[3,3'-bipyridin]-6-yl)-2-ethylbutanamide;
2-(2-(cyclopropanesulfonamido)thiazol-4-yl)-2-methyl-N-(5'-propoxy-[3,3'-bipyridin]-6-yl)propanamide;
2-(2-(cyclopropanesulfonamido)thiazol-4-yl)-2-ethyl-N-(5-(6-(trifluoromethyl)pyrazin-2-yl)pyridin-2-yl)butanamide;
N-([3,3'-bipyridin]-6-yl)-2-(2-(cyclopropanesulfonamido)thiazol-4-yl)-2-methylpropanamide;
2-(2-(cyclopropanesulfonamido)thiazol-4-yl)-N-(2-methoxy-4-(pyridin-3-yl)phenyl)-2-methylpropanamide;
2-(2-(cyclopropanesulfonamido)thiazol-4-yl)-N-(3-methoxy-4-(pyridin-3-yl)phenyl)-2-methylpropanamide;
2-(2-(cyclopropanesulfonamido)thiazol-4-yl)-N-(3-fluoro-4-(pyridin-3-yl)phenyl)-2-methylpropanamide;
N-(3-cyano-4-(pyridin-3-yl)phenyl)-2-(2-(cyclopropanesulfonamido)thiazol-4-yl)-2-methylpropanamide;
N-(3-chloro-4-(pyridin-3-yl)phenyl)-2-(2-(cyclopropanesulfonamido)thiazol-4-yl)-2-methylpropanamide;
N-(4-(6-cyanopyrazin-2-yl)phenyl)-2-(2-(cyclopropanesulfonamido)thiazol-4-yl)-2-methylpropanamide;
N-(4-(6-chloropyrazin-2-yl)phenyl)-2-(2-(cyclopropanesulfonamido)thiazol-4-yl)-2-methylpropanamide;
2-(2-(cyclopropanesulfonamido)thiazol-4-yl)-2-ethyl-N-(4-(5-fluoropyridin-3-yl)phenyl)butanamide;
2-(2-(cyclopropanesulfonamido)thiazol-4-yl)-2-methyl-N-(4-(5-propoxypyridin-3-yl)phenyl)propanamide;
2-(2-(cyclopropanesulfonamido)thiazol-4-yl)-N-(4-(5-isopropoxypyridin-3-yl)phenyl)-2-methylpropanamide;
2-(2-(cyclopropanesulfonamido)thiazol-4-yl)-N-(2-fluoro-4-(5-isopropoxypyridin-3-yl)phenyl)-2-methylpropanamide;
N-(4-(6-chloropyrazin-2-yl)phenyl)-2-(2-(cyclopropanesulfonamido)thiazol-4-yl)-2-ethylbutanamide;
N-(4-(6-cyanopyrazin-2-yl)phenyl)-2-(2-(cyclopropanesulfonamido)thiazol-4-yl)-2-ethylbutanamide;

2-methyl-2-(2-(methylsulfonamido)thiazol-4-yl)-N-(4-(pyridin-3-yl)phenyl) propanamide;
2-(2-(cyclopropanesulfonamido)thiazol-4-yl)-N,2-dimethyl-N-(4-(pyridin-3-yl)phenyl)propanamide;
2-(cyclopropanesulfonamido)-N-(5-(6-(trifluoromethyl)pyrazin-2-yl)pyridin-2-yl)-5,6-dihydro-4H-cyclopenta[d]thiazole-4-carboxamide;
2-(2-(cyclopropanesulfonamido)thiazol-4-yl)-4-methoxy-N-(5-(pyrazin-2-yl)pyridin-2-yl)butanamide;
2-(2-(cyclopropanesulfonamido)thiazol-4-yl)-4-methoxy-N-(5'-methoxy-[3,3'-bipyridin]-6-yl)butanamide;
2-(2-(cyclopropanesulfonamido)thiazol-4-yl)-2-isopropoxy-N-(5-(6-(trifluoromethyl)pyrazin-2-yl)pyridin-2-yl)acetamide;
2-(2-(cyclopropanesulfonamido)thiazol-4-yl)-N-(5-(6-propoxypyrazin-2-yl)pyridin-2-yl)butanamide;
2-(2-(cyclopropanesulfonamido)thiazol-4-yl)-N-(5-(6-isopropoxypyrazin-2-yl)pyridin-2-yl)butanamide;
2-(2-(cyclopropanesulfonamido)thiazol-4-yl)-N-(5-(6-(trifluoromethyl)pyrazin-2-yl)pyridin-2-yl)butanamide;
2-(2-(cyclopropanesulfonamido)thiazol-4-yl)-N-(5-(6-methoxypyrazin-2-yl)pyridin-2-yl)butanamide;
2-(2-(cyclopropanesulfonamido)thiazol-4-yl)-N-(5-(6-ethoxypyrazin-2-yl)pyridin-2-yl)butanamide;
N-(5-(6-cyanopyrazin-2-yl)pyridin-2-yl)-2-(2-(cyclopropanesulfonamido)thiazol-4-yl)butanamide;
2-(2-(cyclopropanesulfonamido)thiazol-4-yl)-N-(5'-fluoro-[3,3'-bipyridin]-6-yl)butanamide;
N-(5'-cyano-[3,3'-bipyridin]-6-yl)-2-(2-(cyclopropanesulfonamido)thiazol-4-yl)butanamide;
2-(2-(cyclopropanesulfonamido)thiazol-4-yl)-N-(5-phenylpyridin-2-yl)butanamide;
2-(2-(cyclopropanesulfonamido)thiazol-4-yl)-N-(5-(6-(2,2,2-trifluoroethoxy)pyrazin-2-yl)pyridin-2-yl)butanamide;
2-(2-(cyclopropanesulfonamido)thiazol-4-yl)-N-(5-(6-ethoxypyrazin-2-yl)-3-fluoropyridin-2-yl)butanamide;
N-(5-(6-cyanopyrazin-2-yl)-3-fluoropyridin-2-yl)-2-(2-(cyclopropanesulfonamido)thiazol-4-yl)butanamide;
2-(2-(cyclopropanesulfonamido)thiazol-4-yl)-N-(5'-(2,2,2-trifluoroethoxy)-[3,3'-bipyridin]-6-yl)butanamide;
2-(2-(cyclopropanesulfonamido)thiazol-4-yl)-N-(5'-(difluoromethoxy)-[3,3'-bipyridin]-6-yl)butanamide;
N-(5-(6-chloropyrazin-2-yl)pyridin-2-yl)-2-(2-(cyclopropanesulfonamido)thiazol-4-yl)butanamide;
2-(2-(cyclopropanesulfonamido)thiazol-4-yl)-N-(2,3-difluoro-4-(pyridin-3-yl)phenyl)acetamide;
2-(2-(cyclopropanesulfonamido)thiazol-4-yl)-N-(4-(6-ethoxypyrazin-2-yl)phenyl)butanamide (racemic);
2-(2-(cyclopropanesulfonamido)thiazol-4-yl)-4-methoxy-N-(4-(6-methoxypyrazin-2-yl)phenyl)butanamide: 2-(2-(cyclopropanesulfonamido)thiazol-4-yl)-N-(4-(5-fluoropyridin-3-yl)phenyl)-4-methoxybutanamide;
2-(2-(cyclopropanesulfonamido)thiazol-4-yl)-N-(4-(6-ethoxypyrazin-2-yl)phenyl)propanamide;
2-(2-(cyclopropanesulfonamido)thiazol-4-yl)-N-(4-(5-(trifluoromethyl)pyridin-3-yl)phenyl)butanamide;
N-(4-(5-cyanopyridin-3-yl)phenyl)-2-(2-(cyclopropanesulfonamido)thiazol-4-yl)butanamide;
2-(2-(cyclopropanesulfonamido)thiazol-4-yl)-N-(4-(6-(2,2,2-trifluoroethoxy)pyrazin-2-yl)phenyl)butanamide;
2-(2-(cyclopropanesulfonamido)thiazol-4-yl)-N-(2-fluoro-4-(pyrazin-2-yl)phenyl)butanamide;
2-(2-(cyclopropanesulfonamido)thiazol-4-yl)-N-(2-fluoro-4-(6-(trifluoromethyl)pyrazin-2-yl)phenyl)butanamide;
2-(2-(cyclopropanesulfonamido)thiazol-4-yl)-N-(4-(6-ethoxypyrazin-2-yl)-2-fluorophenyl)butanamide;
2-(2-(cyclopropanesulfonamido)thiazol-4-yl)-N-(4-(5-ethoxypyridin-3-yl)-2-fluorophenyl)butanamide;
2-(2-(cyclopropanesulfonamido)thiazol-4-yl)-N-(2-fluoro-4-(5-fluoropyridin-3-yl)phenyl)butanamide;
2-(2-(cyclopropanesulfonamido)thiazol-4-yl)-N-(2-fluoro-4-(pyridin-3-yl)phenyl)butanamide;
N-(4-(5-cyanopyridin-3-yl)-2-fluorophenyl)-2-(2-(cyclopropanesulfonamido)thiazol-4-yl)butanamide;
N-(4-(5-chloropyridin-3-yl)-2-fluorophenyl)-2-(2-(cyclopropanesulfonamido)thiazol-4-yl)butanamide;
(R)-2-(2-(cyclopropanesulfonamido)thiazol-4-yl)-N-(4-(6-ethoxypyrazin-2-yl)phenyl)butanamide;
(S)-2-(2-(cyclopropanesulfonamido)thiazol-4-yl)-N-(4-(6-ethoxypyrazin-2-yl)phenyl)butanamide;
N-(4-(1-(5-(6-ethoxypyrazin-2-yl)indolin-1-yl)-1-oxobutan-2-yl)thiazol-2-yl)cyclopropanesulfonamide;
2-(2-(cyclopropanesulfonamido)thiazol-4-yl)-N-(2-fluoro-4-(6-(2,2,2-trifluoroethoxy)pyrazin-2-yl)phenyl)butanamide;
2-(2-(cyclopropanesulfonamido)thiazol-4-yl)-N-(2-fluoro-4-(6-methoxypyrazin-2-yl)phenyl)butanamide;
2-(2-(cyclopropanesulfonamido)thiazol-4-yl)-N-(4-(5-(difluoromethoxy)pyridin-3-yl)-2-fluorophenyl)butanamide;
2-(2-(cyclopropanesulfonamido)thiazol-4-yl)-N-(4-(5-(difluoromethoxy)pyridin-3-yl)phenyl)butanamide;
2-(2-(cyclopropanesulfonamido)thiazol-4-yl)-N-(4-(5-(2,2,2-trifluoroethoxy)pyridin-3-yl)phenyl)butanamide;
2-(2-(cyclopropanesulfonamido)thiazol-4-yl)-N-(2-fluoro-4-(5-(2,2,2-trifluoroethoxy)pyridin-3-yl)phenyl)butanamide;
2-(cyclopropanesulfonamido)-N-(4-(pyridin-3-yl)phenyl)-5,6-dihydro-4H-cyclopenta[d]thiazole-4-carboxamide;
2-(2-(cyclopropanesulfonamido)thiazol-4-yl)-2-methoxy-N-(5-(6-(trifluoromethyl)pyrazin-2-yl)pyridin-2-yl)acetamide;
2-(2-(cyclopropanesulfonamido)thiazol-4-yl)-N-(2-methoxy-4-(pyridin-3-yl)phenyl)acetamide;
2-(2-(cyclopropanesulfonamido)thiazol-4-yl)-N-(2-fluoro-4-(pyridin-3-yl)phenyl)acetamide;
N-(4-(5-cyanopyridin-3-yl)phenyl)-2-(cyclopropanesulfonamido)-5,6-dihydro-4H-cyclopenta[d]thiazole-4-carboxamide;
2-(cyclopropanesulfonamido)-N-(4-(5-fluoropyridin-3-yl)phenyl)-5,6-dihydro-4H-cyclopenta[d]thiazole-4-carboxamide;
2-(2-(cyclopropanesulfonamido)thiazol-4-yl)-2-methoxy-N-(4-(pyridin-3-yl)phenyl)acetamide;
2-(2-(cyclopropanesulfonamido)thiazol-4-yl)-N-(2-fluoro-4-(pyridin-3-yl)phenyl)-2-methoxyacetamide;
N-(2-chloro-4-(pyridin-3-yl)phenyl)-2-(2-(cyclopropanesulfonamido)thiazol-4-yl)butanamide;
2-(2-(cyclopropanesulfonamido)thiazol-4-yl)-N-(4-(6-(2,2,2-trifluoroethoxy)pyrazin-2-yl)phenyl)butanamide;
2-(2-(cyclopropanesulfonamido)thiazol-4-yl)-N-(4-(6-(2,2,2-trifluoroethoxy)pyrazin-2-yl)phenyl)butanamide;
2-(2-(cyclopropanesulfonamido)thiazol-4-yl)-N-(5'-methoxy-[3,3'-bipyridin]-6-yl)-2-methylpropanamide;
N-(5'-chloro-[3,3'-bipyridin]-6-yl)-2-(2-(cyclopropanesulfonamido)thiazol-4-yl)-2-methylpropanamide;
N-(5'-cyano-[3,3'-bipyridin]-6-yl)-2-(2-(cyclopropanesulfonamido)thiazol-4-yl)-2-methylpropanamide;
2-(2-(cyclopropanesulfonamido)thiazol-4-yl)-N-(5'-fluoro-[3,3'-bipyridin]-6-yl)-2-methylpropanamide;
N-(5'-cyano-5-fluoro-[3,3'-bipyridin]-6-yl)-2-(2-(cyclopropanesulfonamido)thiazol-4-yl)-2-methylpropanamide;
N-(5'-chloro-5-fluoro-[3,3'-bipyridin]-6-yl)-2-(2-(cyclopropanesulfonamido)thiazol-4-yl)-2-methylpropanamide;

2-(2-(cyclopropanesulfonamido)thiazol-4-yl)-N-(5,5'-difluoro-[3,3'-bipyridin]-6-yl)-2-methylpropanamide;

N-(5-(3-chloro-5-methylphenyl)pyridin-2-yl)-2-(2-(cyclopropanesulfonamido)thiazol-4-yl)-2-methylpropanamide;

2-(2-(cyclopropanesulfonamido)thiazol-4-yl)-N-(5-(3-methoxyphenyl)pyridin-2-yl)-2-methylpropanamide;

2-(2-(cyclopropanesulfonamido)thiazol-4-yl)-N-(5-(3-fluoro-5-methoxyphenyl)pyridin-2-yl)-2-methylpropanamide;

2-(2-(cyclopropanesulfonamido)thiazol-4-yl)-N-(5-(3,5-dimethoxyphenyl)pyridin-2-yl)-2-methylpropanamide;

2-(2-(cyclopropanesulfonamido)thiazol-4-yl)-2-methyl-N-(5-(3-(trifluoromethyl)phenyl)pyridin-2-yl)propanamide;

2-(2-(cyclopropanesulfonamido)thiazol-4-yl)-2-methyl-N-(5-(3-(trifluoromethoxy)phenyl)pyridin-2-yl)propanamide;

2-(2-(cyclopropanesulfonamido)thiazol-4-yl)-N-(5-(3-(2-hydroxypropan-2-yl)phenyl)pyridin-2-yl)-2-methylpropanamide;

2-(2-(cyclopropanesulfonamido)thiazol-4-yl)-2-methyl-N-(5-(3-morpholinophenyl)pyridin-2-yl)propanamide;

2-(2-(cyclopropanesulfonamido)thiazol-4-yl)-2-methyl-N-(6-phenylpyridin-3-yl)propanamide;

2-(2-(cyclopropanesulfonamido)thiazol-4-yl)-N-(4-(2-fluoropyridin-3-yl)phenyl)-2-methylpropanamide;

2-(2-(cyclopropanesulfonamido)thiazol-4-yl)-N-(4-(5-(hydroxymethyl)pyridin-3-yl)phenyl)-2-methylpropanamide;

2-(2-(cyclopropanesulfonamido)thiazol-4-yl)-N-(4-(2-methoxypyrimidin-5-yl)phenyl)acetamide;

N-(4'-(tert-butyl)-[1,1'-biphenyl]-4-yl)-2-(2-(cyclopropanesulfonamido)thiazol-4-yl)acetamide;

2-(2-(cyclopropanesulfonamido)thiazol-4-yl)-N-(4-(pyridin-3-yl)phenyl)acetamide;

2-(2-(cyclopropanesulfonamido)thiazol-4-yl)-N-(4-(pyridin-4-yl)phenyl)acetamide;

2-(2-(cyclopropanesulfonamido)thiazol-4-yl)-N-(2'-methoxy-[1,1'-biphenyl]-4-yl)acetamide;

2-(2-(cyclopropanesulfonamido)thiazol-4-yl)-N-(4-(pyrimidin-5-yl)phenyl)acetamide;

2-(2-(cyclopropanesulfonamido)thiazol-4-yl)-2-methyl-N-(4-(2-(trifluoromethyl)pyridin-3-yl)phenyl)propanamide;

2-(2-(cyclopropanesulfonamido)thiazol-4-yl)-2-methyl-N-(5'-methyl-[3,3'-bipyridin]-6-yl)propanamide;

2-(2-(cyclopropanesulfonamido)thiazol-4-yl)-N-(4-(2-methoxy-4-methylpyridin-3-yl)phenyl)-2-methylpropanamide;

2-(2-(cyclopropanesulfonamido)thiazol-4-yl)-N-(4-(6-methoxy-5-methylpyridin-3-yl)phenyl)-2-methylpropanamide;

N-(4-(5-chloropyridin-3-yl)phenyl)-2-(2-(cyclopropanesulfonamido)thiazol-4-yl)-2-methylpropanamide;

2-(2-(cyclopropanesulfonamido)thiazol-4-yl)-N-(4-(5-fluoropyridin-3-yl)phenyl)-2-methylpropanamide;

2-(2-(cyclopropanesulfonamido)thiazol-4-yl)-2-methyl-N-(4-(4-methylpyridin-3-yl)phenyl)propanamide;

2-(2-(cyclopropanesulfonamido)thiazol-4-yl)-2-methyl-N-(4-(4-(trifluoromethyl)pyridin-3-yl)phenyl)propanamide;

N-(4-(5-chloropyridin-3-yl)-2-methoxyphenyl)-2-(2-(cyclopropanesulfonamido)thiazol-4-yl)-2-methylpropanamide;

2-(2-(cyclopropanesulfonamido)thiazol-4-yl)-N-(4-(5-(dimethylamino)pyridin-3-yl)phenyl)-2-methylpropanamide;

2-(2-(cyclopropanesulfonamido)thiazol-4-yl)-N-(2-methoxy-4-(5-methylpyridin-3-yl)phenyl)-2-methylpropanamide;

2-(2-(cyclopropanesulfonamido)thiazol-4-yl)-N-(2-methoxy-4-(5-(trifluoromethyl)pyridin-3-yl)phenyl)-2-methylpropanamide;

2-(2-(cyclopropanesulfonamido)thiazol-4-yl)-N-(4-(6-methoxypyridin-3-yl)phenyl)acetamide;

2-(2-(cyclopropanesulfonamido)thiazol-4-yl)-N-(5'-fluoro-[3,3'-bipyridin]-6-yl)-2-methylpropanamide;

N-(5-(6-chloropyrazin-2-yl) pyridin-2-yl)-2-(2-(cyclopropanesulfonamido)thiazol-4-yl)-2-methylpropanamide;

N-(5-(6-cyanopyrazin-2-yl)pyridin-2-yl)-2-(2-(cyclopropanesulfonamido)thiazol-4-yl)-2-methylpropanamide;

2-(2-(cyclopropanesulfonamido)thiazol-4-yl)-2-methyl-N-(5-(pyrimidin-5-yl)pyridin-2-yl)propanamide;

2-(2-(cyclopropanesulfonamido)thiazol-4-yl)-N-(4-(6-methoxypyrazin-2-yl)phenyl)-2-methylpropanamide;

2-(2-(cyclopropanesulfonamido)thiazol-4-yl)-2-methyl-N-(4-(6-methylpyrazin-2-yl)phenyl)propanamide;

2-(2-(cyclopropanesulfonamido)thiazol-4-yl)-2-methyl-N-(4-(6-(trifluoromethyl)pyrazin-2-yl)phenyl)propanamide;

N-(4-(6-chloropyridin-2-yl)phenyl)-2-(2-(cyclopropanesulfonamido)thiazol-4-yl)-2-methylpropanamide;

2-(2-(cyclopropanesulfonamido)thiazol-4-yl)-N-(4-(6-methoxypyridin-2-yl)phenyl)-2-methylpropanamide;

2-(2-(cyclopropanesulfonamido)thiazol-4-yl)-2-methyl-N-(4-(6-(trifluoromethyl)pyridin-2-yl)phenyl)propanamide;

2-(2-(cyclopropanesulfonamido)thiazol-4-yl)-N-(4-(4-methoxypyridin-2-yl)phenyl)-2-methylpropanamide;

2-(2-(cyclopropanesulfonamido)thiazol-4-yl)-N-(4-(6-isopropoxypyrazin-2-yl)phenyl)-2-methylpropanamide;

2-(2-(cyclopropanesulfonamido)thiazol-4-yl)-N-(4-(6-cyclopropoxypyrazin-2-yl)phenyl)-2-methylpropanamide;

2-(2-(cyclopropanesulfonamido)thiazol-4-yl)-N-(2-fluoro-4-(pyrazin-2-yl)phenyl)-2-methylpropanamide;

2-(2-(cyclopropanesulfonamido)thiazol-4-yl)-N-(2-fluoro-4-(6-methoxypyrazin-2-yl)phenyl)-2-methylpropanamide;

N-(4-(6-chloro-3-methylpyrazin-2-yl)phenyl)-2-(2-(cyclopropanesulfonamido)thiazol-4-yl)-2-methylpropanamide;

N-(4-(6-chloro-5-methylpyrazin-2-yl)phenyl)-2-(2-(cyclopropanesulfonamido)thiazol-4-yl)-2-methylpropanamide;

2-(2-(cyclopropanesulfonamido)thiazol-4-yl)-2-methyl-N-(4-(6-(pyrrolidin-1-yl)pyrazin-2-yl)phenyl)propanamide;

2-(2-(cyclopropanesulfonamido)thiazol-4-yl)-N-(4-(6-(2-(dimethylamino)ethoxy)pyrazin-2-yl)phenyl)-2-methylpropanamide;

2-(2-(cyclopropanesulfonamido)thiazol-4-yl)-2-methyl-N-(4-(3-methylpyrazin-2-yl)phenyl)propanamide;

N-(4-(6-acetamidopyrazin-2-yl)phenyl)-2-(2-(cyclopropanesulfonamido)thiazol-4-yl)-2-methylpropanamide;

2-(2-(cyclopropanesulfonamido)thiazol-4-yl)-N-(4-(5,6-dimethylpyrazin-2-yl)phenyl)-2-methylpropanamide;

2-(2-(cyclopropanesulfonamido)thiazol-4-yl)-N-(4-(6-(hydroxymethyl) pyrazin-2-yl)phenyl)-2-methylpropanamide;

2-(2-(cyclopropanesulfonamido)thiazol-4-yl)-N-(4-(3,6-dimethylpyrazin-2-yl)phenyl)-2-methylpropanamide;

2-(2-(cyclopropanesulfonamido)thiazol-4-yl)-N-(4-(5-methoxypyridin-3-yl)-2-methylphenyl)-2-methylpropanamide;

N-(4-(5-cyanopyridin-3-yl)-2-methylphenyl)-2-(2-(cyclopropanesulfonamido)thiazol-4-yl)-2-methylpropanamide;

2-(2-(cyclopropanesulfonamido)thiazol-4-yl)-N-(4-(5-fluoropyridin-3-yl)-2-methylphenyl)-2-methylpropanamide;

N-(4-(5-chloropyridin-3-yl)-3-methylphenyl)-2-(2-(cyclopropanesulfonamido)thiazol-4-yl)-2-methylpropanamide;

N-(4-(5-cyanopyridin-3-yl)-3-ethoxyphenyl)-2-(2-(cyclopropanesulfonamido)thiazol-4-yl)-2-methylpropanamide;

2-(2-(cyclopropanesulfonamido)thiazol-4-yl)-N-(4-(5-ethoxypyridin-3-yl)phenyl)-2-methylpropanamide;
2-(2-(cyclopropanesulfonamido)thiazol-4-yl)-N-(4-(6-cyclopropylpyrazin-2-yl)phenyl)butanamide:
2-(2-(cyclopropanesulfonamido)thiazol-4-yl)-N-(5-(5-methoxypyridin-3-yl)pyrimidin-2-yl)-2-methylpropanamide;
2-(2-(cyclopropanesulfonamido)thiazol-4-yl)-N-(5-(5-fluoropyridin-3-yl)pyrimidin-2-yl)-2-methylpropanamide;
2-(2-(cyclopropanesulfonamido)thiazol-4-yl)-2-methyl-N-(5-(5-(trifluoromethyl)pyridin-3-yl)pyrimidin-2-yl)propanamide;
N-(5-(6-ethoxypyrazin-2-yl)pyridin-2-yl)-2-methyl-2-(2-((2-methylpropyl)sulfonamido)thiazol-4-yl)propanamide;
N-(4-(6-ethoxypyrazin-2-yl)phenyl)-2-methyl-2-(2-((trifluoromethyl)sulfonamido)thiazol-4-yl)propanamide;
2-methyl-2-(2-((1-methylethyl)sulfonamido)thiazol-4-yl)-N-(4-(pyridin-3-yl)phenyl)propanamide;
N-(4-(6-ethoxypyrazin-2-yl)phenyl)-2-methyl-2-(2-((1-methylethyl)sulfonamido)thiazol-4-yl)propanamide;
2-methyl-2-(2-((1-methylcyclopropane)-1-sulfonamido)thiazol-4-yl)-N-(4-(pyridin-3-yl)phenyl)propanamide;
N-(4-(5-chloropyridin-3-yl)phenyl)-2-methyl-2-(2-((1-methylcyclopropane)-1-sulfonamido)thiazol-4-yl)propanamide;
N-(4-(6-ethoxypyrazin-2-yl)phenyl)-2-methyl-2-(2-((1-methylcyclopropane)-1-sulfonamido)thiazol-4-yl)propanamide;
2-methyl-2-(2-((1-methylcyclopropane)-1-sulfonamido)thiazol-4-yl)-N-(4-(6-(trifluoromethyl)pyrazin-2-yl)phenyl)propanamide;
2-(2-((1,1-dimethylethyl)sulfonamido)thiazol-4-yl)-2-methyl-N-(4-(pyridin-3-yl)phenyl)propanamide;
2-(2-((1,1-dimethylethyl)sulfonamido)thiazol-4-yl)-N-(4-(6-ethoxypyrazin-2-yl)phenyl)-2-methylpropanamide;
2-(2-((1,1-dimethylethyl)sulfonamido)thiazol-4-yl)-2-methyl-N-(4-(6-(trifluoromethyl)pyrazin-2-yl)phenyl)propanamide;
2-(2-(cyclobutanesulfonamido)thiazol-4-yl)-2-methyl-N-(4-(pyridin-3-yl)phenyl)propanamide;
2-(2-(cyclobutanesulfonamido)thiazol-4-yl)-N-(4-(6-ethoxypyrazin-2-yl)phenyl)-2-methylpropanamide;
2-(2-(cyclobutanesulfonamido)thiazol-4-yl)-2-methyl-N-(4-(6-(trifluoromethyl)pyrazin-2-yl)phenyl)propanamide;
N-(4-(5-cyanopyridin-3-yl)phenyl)-2-(2-(cyclopropanesulfonamido)thiazol-4-yl)-N,2-dimethylpropanamide;
2-(2-(cyclopropanesulfonamido)thiazol-4-yl)-N,2-dimethyl-N-(4-(6-(trifluoromethyl)pyrazin-2-yl)phenyl)propanamide;
2-methyl-2-(2-((2-methylpropyl)sulfonamido)thiazol-4-yl)-N-(4-(pyridin-3-yl)phenyl)propanamide;
N-(4-(6-ethoxypyrazin-2-yl)phenyl)-2-methyl-2-(2-((2-methylpropyl)sulfonamido)thiazol-4-yl)propanamide;
2-methyl-2-(2-((2-methylpropyl)sulfonamido)thiazol-4-yl)-N-(4-(6-(trifluoromethyl)pyrazin-2-yl)phenyl)propanamide;
N-(4-(5-chloropyridin-3-yl)phenyl)-2-(2-(cyclopropanesulfonamido)-5-methylthiazol-4-yl)-2-methylpropanamide;
2-(2-(cyclopropanesulfonamido)thiazol-4-yl)-N-methyl-N-(4-(pyridin-3-yl)phenyl)butanamide;
N-(4-(5-cyanopyridin-3-yl)phenyl)-2-(2-(cyclopropanesulfonamido)thiazol-4-yl)-N-methylbutanamide;
2-(2-(cyclopropanesulfonamido)-5-methylthiazol-4-yl)-N-(4-(6-ethoxypyrazin-2-yl)phenyl)-2-methylpropanamide;
N-(4-(5-chloropyridin-3-yl)phenyl)-2-(2-(cyclopropanesulfonamido)thiazol-4-yl)-N,2-dimethylpropanamide;
2-(2-(cyclopropanesulfonamido)-5-methylthiazol-4-yl)-2-methyl-N-(4-(pyridin-3-yl)phenyl)propanamide;
N-(4-(5-cyanopyridin-3-yl)-2,6-dimethylphenyl)-2-(2-(cyclopropanesulfonamido)thiazol-4-yl)-2-methylpropanamide;
N-(4-(5-chloropyridin-3-yl)-2,6-dimethylphenyl)-2-(2-(cyclopropanesulfonamido)thiazol-4-yl)-2-methylpropanamide; and
N-(4-(5-cyanopyridin-3-yl)-3-methylphenyl)-2-(2-(cyclopropanesulfonamido)thiazol-4-yl)-2-methylpropanamide.

Additionally of interest are the compounds:
2-(2-(cyclopropanesulfonamido)thiazol-4-yl)-N-(4-(pyridin-3-yl)phenyl)butanamide;
2-(2-(cyclopropanesulfonamido)thiazol-4-yl)-N-(4-(5-fluoropyridin-3-yl)phenyl)butanamide;
2-(2-(cyclopropanesulfonamido)thiazol-4-yl)-2-methoxy-N-(4-(6-methoxypyrazin-2-yl)phenyl)acetamide; and
2-(2-(cyclopropanesulfonamido)thiazol-4-yl)-N-(4-(6-ethoxypyrazin-2-yl)phenyl)butanamide.

Also of interest are the compounds:
2-amino-2-(2-(cyclopropanesulfonamido)thiazol-4-yl)-N-(4-(6-ethoxypyrazin-2-yl)phenyl)acetamide;
2-acetamido-2-(2-(cyclopropanesulfonamido)thiazol-4-yl)-N-(4-(6-ethoxypyrazin-2-yl)phenyl)acetamide;
methyl(1-(2-(cyclopropanesulfonamido)thiazol-4-yl)-2-((4-(6-ethoxypyrazin-2-yl)phenyl)amino)-2-oxoethyl)carbamate:
2-(2-(cyclopropanesulfonamido)thiazol-4-yl)-2-(dimethylamino)-N-(4-(6-ethoxypyrazin-2-yl)phenyl)acetamide;
2-(2-(cyclopropanesulfonamido)thiazol-4-yl)-N-(4-(6-ethoxypyrazin-2-yl)phenyl)-4-hydroxybutanamide;
2-(2-(cyclopropanesulfonamido)thiazol-4-yl)-N-(4-(6-ethoxypyrazin-2-yl)phenyl)-2-methoxyacetamide;
(R)-2-(2-(cyclopropanesulfonamido)thiazol-4-yl)-N-(4-(6-ethoxypyrazin-2-yl)phenyl)-2-methoxyacetamide;
(S)-2-(2-(cyclopropanesulfonamido)thiazol-4-yl)-N-(4-(6-ethoxypyrazin-2-yl)phenyl)-2-methoxyacetamide;
2-(2-((2-methoxyethyl)sulfonamido)thiazol-4-yl)-2-methyl-N-(5-(6-(trifluoromethyl)pyrazin-2-yl)pyridin-2-yl)propanamide;
2-(2-(cyclopentanesulfonamido)thiazol-4-yl)-2-methyl-N-(4-(pyridin-3-yl)phenyl)propanamide;
2-(2-(cyclopentanesulfonamido)thiazol-4-yl)-2-methyl-N-(4-(6-(trifluoromethyl)pyrazin-2-yl)phenyl)propanamide;
2-(2-(cyclopentanesulfonamido)thiazol-4-yl)-N-(4-(6-ethoxypyrazin-2-yl)phenyl)-2-methylpropanamide;
2-(2-(cyclopropanesulfonamido)thiazol-4-yl)-N-(5-(6-isopropylpyrazin-2-yl)pyridin-2-yl)-2-methylpropanamide;
2-(2-(cyclopropanesulfonamido)thiazol-4-yl)-N-(5'-ethoxy-[3,3'-bipyridin]-6-yl)-2-methylpropanamide;
2-(2-(cyclopropanesulfonamido)thiazol-4-yl)-N-(5-(6-(2-hydroxypropan-2-yl)pyrazin-2-yl)pyridin-2-yl)-2-methylpropanamide;
2-(2-(cyclopropanesulfonamido)thiazol-4-yl)-N-(5-(6-(2-methoxypropan-2-yl)pyrazin-2-yl)pyridin-2-yl)-2-methylpropanamide;
2-(2-(cyclopropanesulfonamido)-5-methylthiazol-4-yl)-2-methyl-N-(5-(6-(trifluoromethyl)pyrazin-2-yl)pyridin-2-yl)propanamide;
2-(2-(cyclopropanesulfonamido)thiazol-4-yl)-N-(5-(6-ethoxypyrazin-2-yl)pyridin-2-yl)-2-methylpropanamide;
2-(2-(cyclopropanesulfonamido)-5-methylthiazol-4-yl)-N-(5-(6-ethoxypyrazin-2-yl)pyridin-2-yl)-2-methylpropanamide;

N-(4-(5-chloropyridin-3-yl)-2-(trifluoromethyl)phenyl)-2-(2-(cyclopropanesulfonamido)thiazol-4-yl)-2-methylpropanamide;

N-(4-(5-cyanopyridin-3-yl)-2-(trifluoromethyl)phenyl)-2-(2-(cyclopropanesulfonamido)thiazol-4-yl)-2-methylpropanamide;

2-(2-(cyclopropanesulfonamido)thiazol-4-yl)-N-(4-(5-fluoropyridin-3-yl)-2-(trifluoromethyl)phenyl)-2-methylpropanamide;

2-(2-(cyclopropanesulfonamido)thiazol-4-yl)-2-methyl-N-(2-(trifluoromethyl)-4-(6-(trifluoromethyl)pyrazin-2-yl)phenyl)propanamide;

2-(2-(cyclopropanesulfonamido)thiazol-4-yl)-N-(4-(6-ethoxypyrazin-2-yl)-2-(trifluoromethyl)phenyl)-2-methylpropanamide;

N-(4-(5-chloropyridin-3-yl)-2,6-diethylphenyl)-2-(2-(cyclopropanesulfonamido)thiazol-4-yl)-2-methylpropanamide;

N-(4-(5-cyanopyridin-3-yl)-2,6-diethylphenyl)-2-(2-(cyclopropanesulfonamido)thiazol-4-yl)-2-methylpropanamide;

2-(2-(cyclopropanesulfonamido)-5-methylthiazol-4-yl)-N-(2-fluoro-4-(5-(trifluoromethyl)pyridin-3-yl)phenyl)-2-methylpropanamide;

N-(4-(5-chloropyridin-3-yl)-2,6-difluorophenyl)-2-(2-(cyclopropanesulfonamido)thiazol-4-yl)-2-methylpropanamide;

N-(4-(5-chloropyridin-3-yl)-2-fluoro-5-methylphenyl)-2-(2-(cyclopropanesulfonamido)thiazol-4-yl)-2-methylpropanamide;

2-(2-(cyclopropanesulfonamido)thiazol-4-yl)-N-(2-fluoro-4-(6-(2-methoxypropan-2-yl)pyrazin-2-yl)phenyl)-2-methylpropanamide;

2-(2-(cyclopropanesulfonamido)-5-methylthiazol-4-yl)-N-(2-fluoro-4-(6-(trifluoromethyl)pyrazin-2-yl)phenyl)-2-methylpropanamide;

N-(4-(6-cyanopyrazin-2-yl)-2-fluorophenyl)-2-(2-(cyclopropanesulfonamido)thiazol-4-yl)-2-methylpropanamide;

2-(2-(cyclopropanesulfonamido)thiazol-4-yl)-N-(4-(6-ethylpyrazin-2-yl)-2-fluorophenyl)-2-methylpropanamide;

2-(2-(cyclopropanesulfonamido)thiazol-4-yl)-N-(2-fluoro-4-(6-isopropoxypyrazin-2-yl)phenyl)-2-methylpropanamide;

2-(2-(cyclopropanesulfonamido)-5-methylthiazol-4-yl)-N-(4-(6-ethoxypyrazin-2-yl)-2-fluorophenyl)-2-methylpropanamide;

N-(4-(5-chloropyridin-3-yl)-2-isopropylphenyl)-2-(2-(cyclopropanesulfonamido)thiazol-4-yl)-2-methylpropanamide;

N-(4-(5-cyanopyridin-3-yl)-2-isopropylphenyl)-2-(2-(cyclopropanesulfonamido)thiazol-4-yl)-2-methylpropanamide;

2-(2-(cyclopropanesulfonamido)thiazol-4-yl)-N-(2-isopropyl-4-(6-(trifluoromethyl)pyrazin-2-yl)phenyl)-2-methylpropanamide;

2-(2-(cyclopropanesulfonamido)thiazol-4-yl)-N-(4-(6-ethoxypyrazin-2-yl)-2-isopropylphenyl)-2-methylpropanamide;

N-(4-(5-chloropyridin-3-yl)-3-fluoro-2-methylphenyl)-2-(2-(cyclopropanesulfonamido)thiazol-4-yl)-2-methylpropanamide;

N-(4-(5-chloropyridin-3-yl)-5-fluoro-2-methylphenyl)-2-(2-(cyclopropanesulfonamido)thiazol-4-yl)-2-methylpropanamide;

N-(4-(5-chloropyridin-3-yl)-2,3-dimethylphenyl)-2-(2-(cyclopropanesulfonamido)thiazol-4-yl)-2-methylpropanamide;

N-(4-(5-chloropyridin-3-yl)-2,5-dimethylphenyl)-2-(2-(cyclopropanesulfonamido)thiazol-4-yl)-2-methylpropanamide;

N-(4-(5-cyanopyridin-3-yl)-3-fluoro-2-methylphenyl)-2-(2-(cyclopropanesulfonamido)thiazol-4-yl)-2-methylpropanamide;

2-(2-(cyclopropanesulfonamido)thiazol-4-yl)-2-methyl-N-(2-methyl-4-(6-(trifluoromethyl)pyrazin-2-yl)phenyl)propanamide;

N-(4-(5-chloropyridin-3-yl)-5-fluoro-2-methoxyphenyl)-2-(2-(cyclopropanesulfonamido)thiazol-4-yl)-2-methylpropanamide;

N-(4-(5-chloropyridin-3-yl)-3-(trifluoromethyl)phenyl)-2-(2-(cyclopropanesulfonamido)thiazol-4-yl)-2-methylpropanamide;

2-(2-(cyclopropanesulfonamido)thiazol-4-yl)-N-(4-(6-ethoxypyrazin-2-yl)-3-methylphenyl)-2-methylpropanamide;

N-(4-(5-chloropyridin-3-yl)-3-ethoxyphenyl)-2-(2-(cyclopropanesulfonamido)thiazol-4-yl)-2-methylpropanamide;

N-(4-(5-chloropyridin-3-yl)phenyl)-1-(2-(cyclopropanesulfonamido)thiazol-4-yl)cyclopropane-1-carboxamide;

N-(4-(5-cyanopyridin-3-yl)phenyl)-2-(2-(cyclopropanesulfonamido)-5-methylthiazol-4-yl)-2-methylpropanamide;

2-(2-(cyclopropanesulfonamido)thiazol-4-yl)-N-(4-(6-(2-methoxypropan-2-yl)pyrazin-2-yl)phenyl)-2-methylpropanamide;

2-(5-chloro-2-(cyclopropanesulfonamido)thiazol-4-yl)-N-(4-(6-ethoxypyrazin-2-yl)phenyl)-2-methylpropanamide;

2-(2-(cyclopropanesulfonamido)-5-methoxythiazol-4-yl)-N-(4-(6-ethoxypyrazin-2-yl)phenyl)-2-methylpropanamide;

N-(4-(6-(cyclopentylmethoxy)pyrazin-2-yl)phenyl)-2-(2-(cyclopropanesulfonamido)thiazol-4-yl)-2-methylpropanamide;

2-(2-(cyclopropanesulfonamido)thiazol-4-yl)-N-(4-(6-hydroxypyrazin-2-yl)phenyl)-2-methylpropanamide;

2-(2-(ethylsulfonamido)thiazol-4-yl)-2-methyl-N-(5'-(trifluoromethyl)-[3,3'-bipyridin]-6-yl)propanamide;

2-(2-(ethylsulfonamido)thiazol-4-yl)-2-methyl-N-(5-(6-(trifluoromethyl)pyrazin-2-yl)pyridin-2-yl)propanamide;

N-(5-(6-ethoxypyrazin-2-yl)pyridin-2-yl)-2-(2-(ethylsulfonamido)thiazol-4-yl)-2-methylpropanamide;

2-(2-(ethylsulfonamido)thiazol-4-yl)-N-(2-fluoro-4-(6-isopropoxypyrazin-2-yl)phenyl)-2-methylpropanamide;

N-(4-(5-cyanopyridin-3-yl)phenyl)-2-(2-(ethylsulfonamido)thiazol-4-yl)-2-methylpropanamide;

2-(2-(ethylsulfonamido)thiazol-4-yl)-N-(4-(5-fluoropyridin-3-yl)phenyl)-2-methylpropanamide;

2-(2-(ethylsulfonamido)thiazol-4-yl)-2-methyl-N-(4-(pyridin-3-yl)phenyl)propanamide;

2-(2-(ethylsulfonamido)thiazol-4-yl)-2-methyl-N-(4-(6-(trifluoromethyl)pyrazin-2-yl)phenyl)propanamide;

2-(2-(ethylsulfonamido)thiazol-4-yl)-N-(4-(6-isopropoxypyrazin-2-yl)phenyl)-2-methylpropanamide;

2-methyl-2-(2-(methylsulfonamido)thiazol-4-yl)-N-(5'-(trifluoromethyl)-[3,3'-bipyridin]-6-yl)propanamide;

N-(5-(6-ethoxypyrazin-2-yl)pyridin-2-yl)-2-methyl-2-(2-(methylsulfonamido)thiazol-4-yl)propanamide;

N-(2-fluoro-4-(6-(trifluoromethyl)pyrazin-2-yl)phenyl)-2-methyl-2-(2-(methylsulfonamido)thiazol-4-yl)propanamide;

N-(2-fluoro-4-(6-isopropoxypyrazin-2-yl)phenyl)-2-methyl-2-(2-(methylsulfonamido)thiazol-4-yl)propanamide;

N-(4-(5-chloropyridin-3-yl)phenyl)-2-methyl-2-(2-(methylsulfonamido)thiazol-4-yl)propanamide;
2-methyl-2-(2-(methylsulfonamido)thiazol-4-yl)-N-(4-(6-(trifluoromethyl)pyrazin-2-yl)phenyl)propanamide;
N-(4-(6-isopropoxypyrazin-2-yl)phenyl)-2-methyl-2-(2-(methylsulfonamido)thiazol-4-yl)propanamide;
2-(2-((cyclopropylmethyl)sulfonamido)thiazol-4-yl)-2-methyl-N-(5-(6-(trifluoromethyl)pyrazin-2-yl)pyridin-2-yl)propanamide;
1-(2-(cyclopropanesulfonamido)thiazol-4-yl)-N-(4-(6-(trifluoromethyl)pyrazin-2-yl)phenyl)cyclopropane-1-carboxamide;
1-(2-(cyclopropanesulfonamido)thiazol-4-yl)-N-(4-(6-ethoxypyrazin-2-yl)phenyl)cyclopropane-1-carboxamide;
2-(2-(cyclopropanesulfonamido)thiazol-4-yl)-N-(2-fluoro-4-(6-(trifluoromethyl)pyrazin-2-yl)phenyl)-4-methoxybutanamide;
2-(2-(cyclopropanesulfonamido)thiazol-4-yl)-N-(2-fluoro-4-(6-isopropoxypyrazin-2-yl)phenyl)-4-methoxybutanamide;
2-(2-(cyclopropanesulfonamido)thiazol-4-yl)-N-(5-(6-isopropylpyrazin-2-yl)pyridin-2-yl)butanamide;
2-(2-(cyclopropanesulfonamido)thiazol-4-yl)-N-(5-(6-(2-methoxypropan-2-yl)pyrazin-2-yl)pyridin-2-yl)butanamide;
2-(2-(cyclopropanesulfonamido)thiazol-4-yl)-N-(2-fluoro-4-(6-(2-methoxypropan-2-yl)pyrazin-2-yl)phenyl)butanamide;
N-(4-(6-cyanopyrazin-2-yl)-2-fluorophenyl)-2-(2-(cyclopropanesulfonamido)thiazol-4-yl)butanamide;
2-(2-(cyclopropanesulfonamido)thiazol-4-yl)-N-(4-(6-ethylpyrazin-2-yl)-2-fluorophenyl)butanamide;
2-(2-(cyclopropanesulfonamido)thiazol-4-yl)-N-(4-(6-(2-methoxypropan-2-yl)pyrazin-2-yl)phenyl)butanamide;
tert-butyl-(1-(2-(cyclopropanesulfonamido)thiazol-4-yl)-2-((4-(6-ethoxypyrazin-2-yl)phenyl)amino)-2-oxoethyl)carbamate;
2-(2-(cyclopropanesulfonamido)thiazol-4-yl)-N-(2-fluoro-4-(6-(trifluoromethyl)pyrazin-2-yl)phenyl)-2-methoxyacetamide;
2-(2-(cyclopropanesulfonamido)thiazol-4-yl)-N-(4-(6-ethoxypyrazin-2-yl)-2-fluorophenyl)-2-methoxyacetamide;
2-(2-(cyclopropanesulfonamido)thiazol-4-yl)-N-(4-(6-ethoxypyrazin-2-yl)phenyl)-2-methoxyacetamide;
2-(2-(cyclopropanesulfonamido)thiazol-4-yl)-N-(4-(6-isopropoxypyrazin-2-yl)phenyl)-2-methoxyacetamide;
2-(2-(cyclopropanesulfonamido)thiazol-4-yl)-N-(4-(6-ethoxypyrazin-2-yl)-2-fluorophenyl)butanamide;
(R)-2-(2-(cyclopropanesulfonamido)thiazol-4-yl)-N-(4-(6-ethoxypyrazin-2-yl)-2-fluorophenyl)butanamide;
(S)-2-(2-(cyclopropanesulfonamido)thiazol-4-yl)-N-(4-(6-ethoxypyrazin-2-yl)-2-fluorophenyl)butanamide;
2-(2-(cyclopropanesulfonamido)thiazol-4-yl)-N-(5-(6-(trifluoromethyl)pyrazin-2-yl)pyridin-2-yl)butanamide; and
2-(2-(cyclopropanesulfonamido)thiazol-4-yl)-N-(2-fluoro-4-(5-(trifluoromethyl)pyridin-3-yl)phenyl)butanamide;
(R)-2-(2-(cyclopropanesulfonamido)thiazol-4-yl)-N-(2-fluoro-4-(5-(trifluoromethyl)pyridin-3-yl)phenyl)butanamide;
(S)-2-(2-(cyclopropanesulfonamido)thiazol-4-yl)-N-(2-fluoro-4-(5-(trifluoromethyl)pyridin-3-yl)phenyl)butanamide.

Also of interest are the compounds:
2-Amino-2-(2-(cyclopropanesulfonamido)thiazol-4-yl)-N-(5-(6-(trifluoromethyl)pyrazin-2-yl)pyridin-2-yl)acetamide hydrochloride;
2-Amino-2-(2-(cyclopropanesulfonamido)thiazol-4-yl)-N-(2-fluoro-4-(6-(trifluoromethyl)pyrazin-2-yl)phenyl)acetamide;
2-Amino-2-(2-(cyclopropanesulfonamido)thiazol-4-yl)-N-(4-(6-ethoxypyrazin-2-yl)-2-fluorophenyl)acetamide hydrochloride;
2-(2-(Cyclopropanesulfonamido)thiazol-4-yl)-2-(dimethylamino)-N-(2-fluoro-4-(6-(trifluoromethyl)pyrazin-2-yl)phenyl)acetamide;
2-(2-(Cyclopropanesulfonamido)thiazol-4-yl)-2-(dimethylamino)-N-(4-(6-ethoxypyrazin-2-yl)-2-fluorophenyl)acetamide;
2-(2-(cyclopropanesulfonamido)thiazol-4-yl)-N-(5-(6-ethoxypyrazin-2-yl)pyridin-2-yl)-2,2-difluoroacetamide;
2-(2-(cyclopropanesulfonamido)thiazol-4-yl)-N-(4-(6-ethoxypyrazin-2-yl)-2-fluorophenyl)acetamide;
2-(2-(cyclopropanesulfonamido)thiazol-4-yl)-N-(4-(6-ethoxypyrazin-2-yl)phenyl)acetamide;
2-methyl-2-(2-(methylsulfonamido)thiazol-4-yl)-N-(5-(6-(trifluoromethyl)pyrazin-2-yl)pyridin-2-yl)propanamide;
N-(2-fluoro-4-(5-(trifluoromethyl)pyridin-3-yl)phenyl)-2-methyl-2-(2-(methylsulfonamido)thiazol-4-yl)propanamide;
2-(2-((cyclopropylmethyl)sulfonamido)thiazol-4-yl)-N-(2-fluoro-4-(5-(trifluoromethyl)pyridin-3-yl)phenyl)-2-methylpropanamide;
N-(4-(5-chloro-4-methylpyridin-3-yl)phenyl)-2-(2-(cyclopropanesulfonamido)thiazol-4-yl)-2-methylpropanamide;
N-(4-(6-ethoxypyrazin-2-yl)-2-(trifluoromethyl)phenyl)-2-methyl-2-(2-(methylsulfonamido)thiazol-4-yl)propanamide;
2-(2-((cyclopropylmethyl)sulfonamido)thiazol-4-yl)-N-(2-fluoro-4-(6-(trifluoromethyl)pyrazin-2-yl)phenyl)-2-methylpropanamide;
N-(4-(6-ethoxypyrazin-2-yl)-2-fluorophenyl)-2-methyl-2-(2-(methylsulfonamido)thiazol-4-yl)propanamide;
N-(4-(6-ethoxypyrazin-2-yl)-2-fluorophenyl)-2-(2-((2-methoxyethyl)sulfonamido)thiazol-4-yl)-2-methylpropanamide;
2-(2-((cyclopropylmethyl)sulfonamido)thiazol-4-yl)-N-(4-(6-ethoxypyrazin-2-yl)-2-fluorophenyl)-2-methylpropanamide;
N-(4-(6-ethoxypyrazin-2-yl)phenyl)-2-methyl-2-(2-(methylsulfonamido)thiazol-4-yl)propanamide;
2-(2-(cyclopropanesulfonamido)thiazol-4-yl)-N-(5-(6-ethoxypyrazin-2-yl)-3-fluoropyridin-2-yl)-4-methoxybutanamide;
2-(2-(cyclopropanesulfonamido)thiazol-4-yl)-N-(5-(6-ethoxypyrazin-2-yl)pyridin-2-yl)-4-methoxybutanamide;
2-(2-(cyclopropanesulfonamido)thiazol-4-yl)-4-methoxy-N-(4-(6-(trifluoromethyl)pyrazin-2-yl)phenyl)butanamide;
2-(2-(cyclopropanesulfonamido)thiazol-4-yl)-N-(5-(6-ethoxypyrazin-2-yl)-3-methylpyridin-2-yl)butanamide;
N-(2-chloro-4-(6-ethoxypyrazin-2-yl)phenyl)-2-(2-(cyclopropanesulfonamido)thiazol-4-yl)butanamide;
N-(2-cyano-4-(6-ethoxypyrazin-2-yl)phenyl)-2-(2-(cyclopropanesulfonamido)thiazol-4-yl)butanamide;
2-(2-(cyclopropanesulfonamido)thiazol-4-yl)-N-(4-(6-ethoxypyrazin-2-yl)-2-methylphenyl)butanamide;
2-(2-(cyclopropanesulfonamido)thiazol-4-yl)-N-(4-(6-ethoxypyrazin-2-yl)-2-(trifluoromethoxy)phenyl)butanamide;

2-(2-(cyclopropanesulfonamido)thiazol-4-yl)-N-(4-(6-ethoxypyrazin-2-yl)-2-methoxyphenyl)butanamide;

2-(2-(Cyclopropanesulfonamido)thiazol-4-yl)-N-(4-(6-(ethylamino)pyrazin-2-yl)phenyl)butanamide;

2-(2-(cyclopropanesulfonamido)thiazol-4-yl)-N-(5-(6-ethoxypyrazin-2-yl)-3-fluoropyridin-2-yl)-2-methoxyacetamide;

2-(2-(cyclopropanesulfonamido)thiazol-4-yl)-N-(5-(6-ethoxypyrazin-2-yl)pyridin-2-yl)-2-methoxyacetamide;

2-(2-(cyclopropanesulfonamido)thiazol-4-yl)-N-(4-(5-fluoropyridin-3-yl)-2-(trifluoromethyl)phenyl)-2-methoxyacetamide;

2-(2-(cyclopropanesulfonamido)thiazol-4-yl)-N-(2-fluoro-4-(5-(trifluoromethyl)pyridin-3-yl)phenyl)-2-methoxyacetamide;

2-(2-(cyclopropanesulfonamido)thiazol-4-yl)-N-(4-(6-ethoxypyrazin-2-yl)-2-(trifluoromethyl)phenyl)-2-methoxyacetamide;

N-(2-chloro-4-(6-ethoxypyrazin-2-yl)phenyl)-2-(2-(cyclopropanesulfonamido)thiazol-4-yl)-2-methoxyacetamide;

N-(2-cyano-4-(6-ethoxypyrazin-2-yl)phenyl)-2-(2-(cyclopropanesulfonamido)thiazol-4-yl)-2-methoxyacetamide;

N-(2-fluoro-4-(6-(trifluoromethyl)pyrazin-2-yl)phenyl)-2-methoxy-2-(2-(methylsulfonamido)thiazol-4-yl)acetamide;

2-(2-(cyclopropanesulfonamido)thiazol-4-yl)-N-(4-(6-ethoxypyrazin-2-yl)-2,6-difluorophenyl)-2-methoxyacetamide;

2-(2-(cyclopropanesulfonamido)thiazol-4-yl)-N-(4-(6-ethoxypyrazin-2-yl)-2-(trifluoromethoxy)phenyl)-2-methoxyacetamide;

N-(4-(6-ethoxypyrazin-2-yl)phenyl)-2-methoxy-2-(2-(methylsulfonamido)thiazol-4-yl)acetamide;

2-(2-(cyclopropanesulfonamido)thiazol-4-yl)-N-(5-(6-ethoxypyrazin-2-yl)-3-fluoropyridin-2-yl)butanamide (R enantiomer);

2-(2-(cyclopropanesulfonamido)thiazol-4-yl)-N-(5-(6-ethoxypyrazin-2-yl)-3-fluoropyridin-2-yl)butanamide (S enantiomer);

2-(2-(cyclopropanesulfonamido)thiazol-4-yl)-N-(2-fluoro-4-(6-(trifluoromethyl)pyrazin-2-yl)phenyl)-2-methoxyacetamide (R enantiomer);

2-(2-(cyclopropanesulfonamido)thiazol-4-yl)-N-(2-fluoro-4-(6-(trifluoromethyl)pyrazin-2-yl)phenyl)-2-methoxyacetamide (S enantiomer);

4-(2-(cyclopropanesulfonamido)thiazol-4-yl)-N-(4-(6-ethoxypyrazin-2-yl)-2-fluorophenyl)tetrahydro-2H-pyran-4-carboxamide;

4-(2-(cyclopropanesulfonamido)thiazol-4-yl)-N-(5-(6-(trifluoromethyl)pyrazin-2-yl)pyridin-2-yl)tetrahydro-2H-pyran-4-carboxamide;

4-(2-(cyclopropanesulfonamido)thiazol-4-yl)-N-(5-(6-ethoxypyrazin-2-yl)pyridin-2-yl)tetrahydro-2H-pyran-4-carboxamide;

N-(4-(1-(4-(5-methoxypyridin-3-yl)phenyl)-2-oxopyrrolidin-3-yl)thiazol-2-yl)cyclopropanesulfonamide;

2-(2-(cyclopropanesulfonamido)thiazol-4-yl)-2-methyl-N-(5-(6-methylpyrazin-2-yl)pyridin-2-yl)propanamide; and N-(4-(6-cyanopyrazin-2-yl)-2-methylphenyl)-2-(2-(cyclopropanesulfonamido)thiazol-4-yl)-2-methylpropanamide.

The compounds of the invention may be provided in the form of a pharmaceutically acceptable salt and/or solvate thereof and/or derivative thereof. In particular, the compound of formula (I) may be provided in the form of a pharmaceutically acceptable salt and/or solvate, such as a pharmaceutically acceptable salt.

Compounds of the invention of particular interest are those demonstrating an $IC_{50}$ of 1 uM or lower, especially 100 nM or lower, in respect of CTPS1 enzyme, using the methods of the examples (or comparable methods).

Compounds of the invention of particular interest are those demonstrating a selectivity for CTPS1 over CTPS2 of 2-30 fold, suitably >30-60 fold or more suitably >60 fold, using the methods of the examples (or comparable methods).

It will be appreciated that for use in medicine the salts of the compounds of formula (I) should be pharmaceutically acceptable. Non-pharmaceutically acceptable salts of the compounds of formula (I) may be of use in other contexts such as during preparation of the compounds of formula (I). Suitable pharmaceutically acceptable salts will be apparent to those skilled in the art. Pharmaceutically acceptable salts include those described by Berge et al. (1977). Such pharmaceutically acceptable salts include acid and base addition salts. Pharmaceutically acceptable acid additional salts may be formed with inorganic acids e.g. hydrochloric, hydrobromic, sulphuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates, may be used, for example in the isolation of compounds of formula (I) and are included within the scope of this invention.

Certain compounds of formula (I) may form acid or base addition salts with one or more equivalents of the acid or base. The present invention includes within its scope all possible stoichiometric and non-stoichiometric forms.

The compounds of formula (I) may be prepared in crystalline or non-crystalline form and, if crystalline, may optionally be solvated, e.g. as the hydrate. This invention includes within its scope stoichiometric solvates (e.g. hydrates) as well as compounds containing variable amounts of solvent (e.g. water).

It will be understood that the invention includes pharmaceutically acceptable derivatives of compounds of formula (I) and that these are included within the scope of the invention.

As used herein "pharmaceutically acceptable derivative" includes any pharmaceutically acceptable prodrug such as an ester or salt of such ester of a compound of formula (I) which, upon administration to the recipient is capable of providing (directly or indirectly) a compound of formula (I) or an active metabolite or residue thereof.

It is to be understood that the present invention encompasses all isomers of formula (I) and their pharmaceutically acceptable derivatives, including all geometric, tautomeric and optical forms, and mixtures thereof (e.g. racemic mixtures). Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

The present disclosure includes all isotopic forms of the compounds of the invention provided herein, whether in a form (i) wherein all atoms of a given atomic number have a mass number (or mixture of mass numbers) which predominates in nature (referred to herein as the "natural isotopic form") or (ii) wherein one or more atoms are replaced by atoms having the same atomic number, but a mass number different from the mass number of atoms which predominates in nature (referred to herein as an "unnatural variant isotopic form"). It is understood that an atom may naturally exists as a mixture of mass numbers. The term "unnatural variant isotopic form" also includes embodiments in which the proportion of an atom of given atomic number having a mass number found less commonly in nature (referred to herein as an "uncommon isotope") has been increased relative to that which is naturally occurring e.g. to the level of >20%, >50%, >75%, >90%, >95% or >99% by number of the atoms of that atomic number (the latter embodiment referred to as an "isotopically enriched variant form"). The term "unnatural variant isotopic form" also includes embodiments in which the proportion of an uncommon isotope has been reduced relative to that which is naturally occurring. Isotopic forms may include radioactive forms (i.e. they incorporate radioisotopes) and non-radioactive forms. Radioactive forms will typically be isotopically enriched variant forms.

An unnatural variant isotopic form of a compound may thus contain one or more artificial or uncommon isotopes such as deuterium ($^2$H or D), carbon-11 ($^{11}$C), carbon-13 ($^{13}$C), carbon-14 ($^{14}$C), nitrogen-13 ($^{13}$N), nitrogen-15 ($^{15}$N), oxygen-15 ($^{15}$O), oxygen-17 ($^{17}$O), oxygen-18 ($^{18}$O), phosphorus-32 ($^{32}$P), sulphur-35 ($^{35}$S), chlorine-36 ($^{36}$Cl), chlorine-37 ($^{37}$Cl), fluorine-18 ($^{18}$F) iodine-123 ($^{123}$I), iodine-125 ($^{125}$I) in one or more atoms or may contain an increased proportion of said isotopes as compared with the proportion that predominates in nature in one or more atoms.

Unnatural variant isotopic forms comprising radioisotopes may, for example, be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Unnatural variant isotopic forms which incorporate deuterium i.e $^2$H or D may afford certain therapeutic advantages resulting from greater metabolic stability, for example, increased in vivo half-life or reduced dosage requirements, and hence may be preferred in some circumstances. Further, unnatural variant isotopic forms may be prepared which incorporate positron emitting isotopes, such as $^{11}$C, $^{18}$F, $^{15}$O and $^{13}$N, and would be useful in Positron Emission Topography (PET) studies for examining substrate receptor occupancy.

In one embodiment, the compounds of the invention are provided in a natural isotopic form.

In one embodiment, the compounds of the invention are provided in an unnatural variant isotopic form. In a specific embodiment, the unnatural variant isotopic form is a form in which deuterium (i.e. $^2$H or D) is incorporated where hydrogen is specified in the chemical structure in one or more atoms of a compound of the invention. In one embodiment, the atoms of the compounds of the invention are in an isotopic form which is not radioactive. In one embodiment, one or more atoms of the compounds of the invention are in an isotopic form which is radioactive. Suitably radioactive isotopes are stable isotopes. Suitably the unnatural variant isotopic form is a pharmaceutically acceptable form.

In one embodiment, a compound of the invention is provided whereby a single atom of the compound exists in an unnatural variant isotopic form. In another embodiment, a compound of the invention is provided whereby two or more atoms exist in an unnatural variant isotopic form.

Unnatural isotopic variant forms can generally be prepared by conventional techniques known to those skilled in the art or by processes described herein e.g. processes analogous to those described in the accompanying Examples for preparing natural isotopic forms. Thus, unnatural isotopic variant forms could be prepared by using appropriate isotopically variant (or labelled) reagents in place of the normal reagents employed in the Examples. Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

In general, the compounds of formula (I) may be made according to the organic synthesis techniques known to those skilled in this field, as well as by the representative methods set forth below, those in the Examples, and modifications thereof.

General Routes:

Generic routes by which compound examples of the invention may be conveniently prepared are summarised below.

Scheme 1

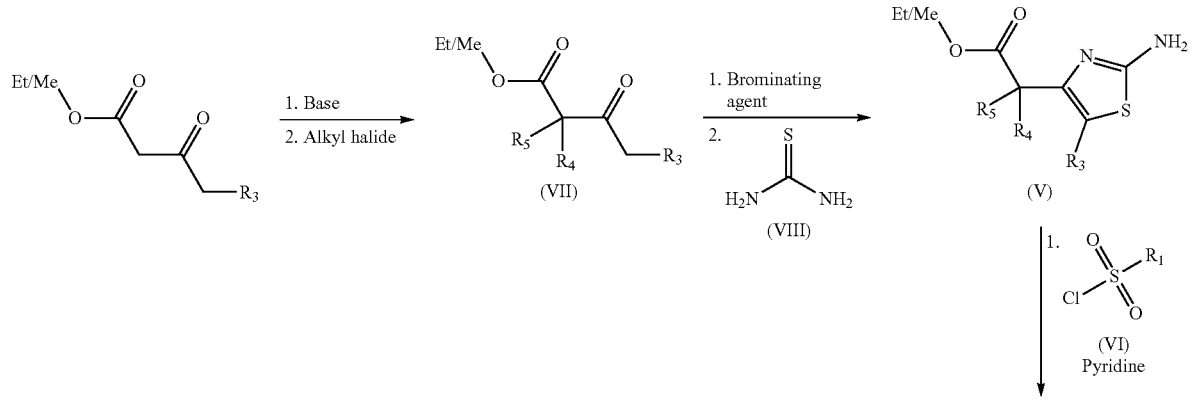

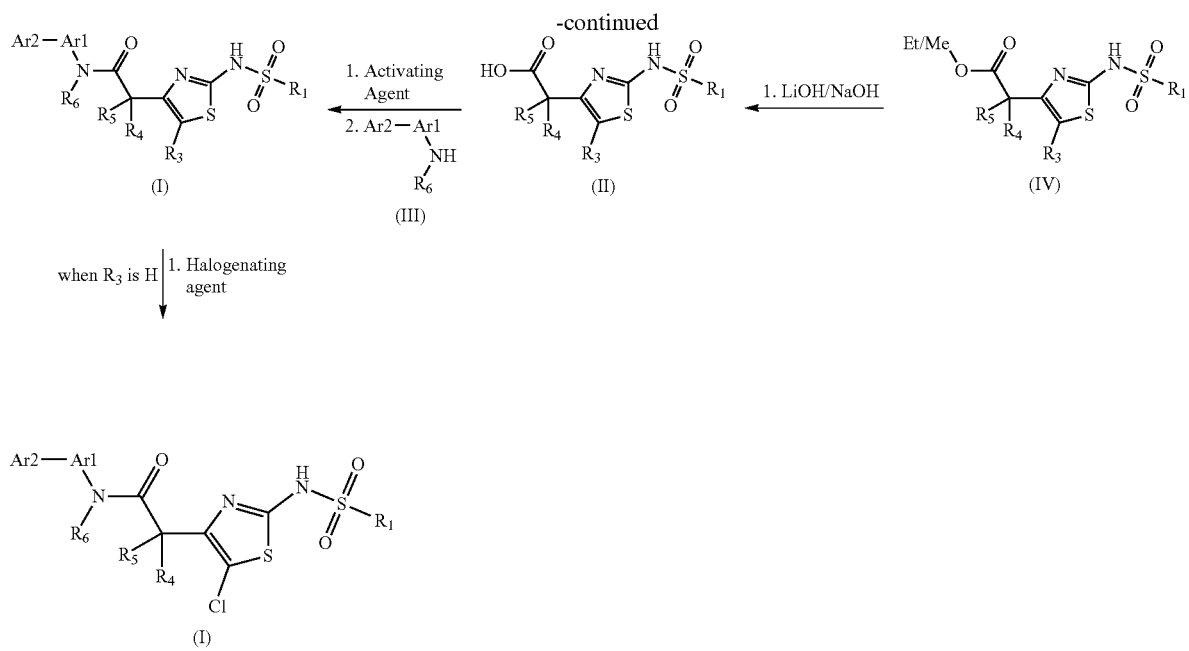

Compounds of general formula (I), where $R_1$, $R_2$, $R_3$, $R_4$, $R_5$, $R_6$, $R_{10}$, $R_{11}$, $R_{12}$, $R_{13}$, Ar1 and Ar2 are defined above, may be synthesised by the general scheme (Scheme 1). Ketoesters of formula (VII) may be prepared by alkylation of an unsubstituted ketoester, which is well established in the literature with many simple derivatives being commercially available.

Intermediates of formula (V) are readily prepared from ketoesters of formula (VII) using a two step procedure. Firstly, bromination using bromine or pyrimidium tribromide can afford the alpha bromoketone ester. This intermediate may be isolated but is routinely used directly without characterisation or purification in the subsequent step. Thiourea (VIII) may be added to form thiazoles of the formula (V) via cyclisation. Such reactions may be subject to gentle heating to, for example, 40° C.

The compound intermediates of formula (IV) can be obtained by sulfonylation of amines of formula (V) with a suitable sulfonyl chloride (VI) in pyridine. Such reactions may be subject to gentle heating to, for example, 30-60° C.

The alkyl esters of formula (IV) may be conveniently hydrolysed by exposure to a suitable inorganic base, for example lithium hydroxide, in an aqueous mixture of aprotic and protic solvents, such as THF:methanol:water. Such reactions may be subject to gentle heating to, for example, 30-50° C.

Compounds of formula (I) may be obtained by a general process whereby a carboxylic acid precursor (II), or a suitably protected derivative thereof, is reacted with an activating agent, to generate a reactive, electrophilic carboxylic acid derivative, followed by subsequent reaction with an amine of formula (III), or a suitably protected derivative thereof. It will be understood by persons skilled in the art that, in some instances, the activated carboxylic acid derivative, such as an acid chloride, may be isolated or in other cases may be a transient intermediate that is not isolated, but generated in situ and used directly. Reagents suitable for the activation of the carboxylate group include carbonyl diimidazole, 1-chloro-N,N,2-trimethylprop-1-en-1-amine (Ghosez reagent) and a wide selection of peptide coupling agents such as 1-[bis(dimethylamino)methylene]-1H-1,2,3-triazolo[4,5-b]pyridinium 3-oxid hexafluorophosphate (HATU) and the like. Such reactions are conveniently carried out in a non-polar, aprotic solvent, such as DCM at or below ambient temperature.

If $R_3$=H in compounds of the general formula (I), substitution can be undertaken using a halogenating reagent, such as N-chlorosuccinimide, in an organic solvent such as MeCN to generate compounds of the general formula (I) wherein $R_3$=Cl.

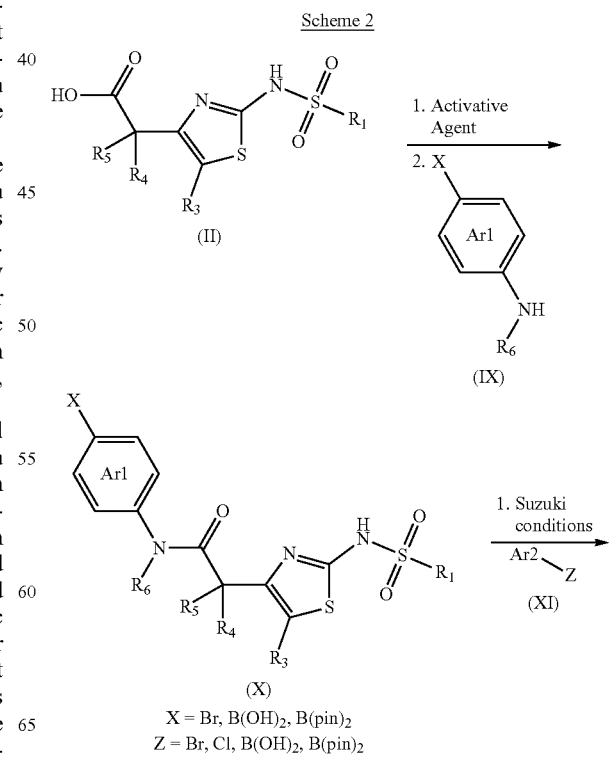

Scheme 2

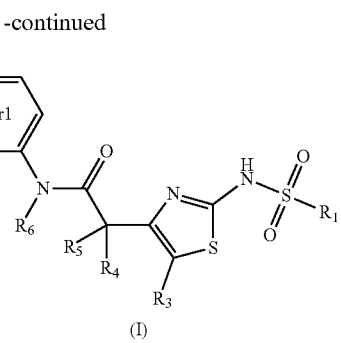

(I)

Compounds of formula (I) may be obtained by a general process whereby a carboxylic acid precursor (II), or a suitably protected derivative thereof, is reacted with an activating agent, to generate a reactive, electrophilic carboxylic acid derivative, followed by subsequent reaction with an amine of formula (IX). Intermediates of formula (X) are then converted to a compound of the invention of general formula (I) by coupling under Suzuki conditions with an aromatic halide or boronate of general formula (XI), of which X is defined above and represents usually a bromide, a dihydroxyboryl or dialkyloxyboryl group, usually a 4,4,5,5-tetramethyl-1,3,3,2-dioxaborolan-2-yl group. The couplings according to the Suzuki method are performed, for example, by heating in the presence of a catalyst such as bis(diphenylphosphino)ferrocene]dichloropalladium(II) and an inorganic base such as potassium carbonate in a solvent mixture of dioxane and water. It will be understood by persons skilled in the art that many catalysts and conditions can be employed for such couplings.

Scheme 3

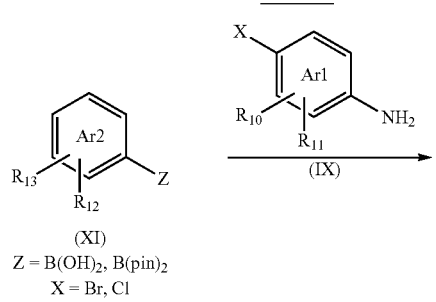

Intermediates of formula (III) where Ar2 is an unsubstituted or substituted 3-pyridyl ring, may be synthesised by coupling under Suzuki conditions of a boronate of general formula (XI), of which $R^{12}$ and $R^{13}$ are defined above and Z represents a dihydroxyboryl or dialkyloxyboryl group, usually a 4,4,5,5-tetramethyl-1,3,3,2-dioxaborolan-2-yl group, to a substituted pyridine of formula (IX) of which $R^{10}$ and $R^{11}$ are defined above and where X denotes a halide. The couplings according to the Suzuki method are performed, for example, by heating in the presence of a catalyst such as [1,1'-bis(diphenylphosphino)ferrocene]dichloropalladium (II) complex with dichloromethane and an inorganic base such as potassium carbonate in a solvent mixture of 1,4-dioxane and water.

Scheme 4

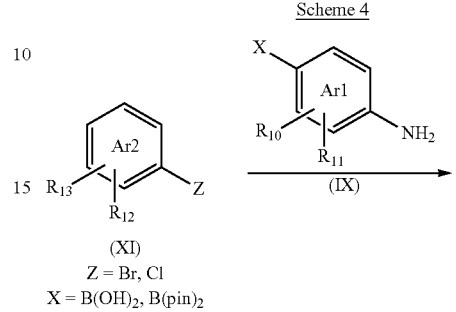

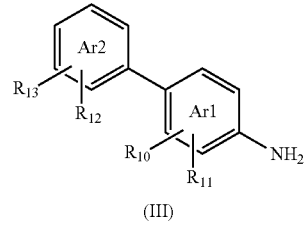

Intermediates of formula (III) where Ar2 is an unsubstituted or substituted 2-pyrazine ring, may be synthesised by coupling under Suzuki conditions of an aromatic halide of general formula (XI), of which $R^{12}$ and $R^{13}$ are defined above and Z represents a halide, to a boronate of general formula (IX) of which $R^{10}$ and $R^{11}$ are defined above and where X denotes a dihydroxyboryl or dialkyloxyboryl group, usually a 4,4,5,5-tetramethyl-1,3,3,2-dioxaborolan-2-yl group. The couplings according to the Suzuki method are performed, for example, by heating in the presence of a catalyst such as tetrakis(triphenylphosphine)palladium or [1,1'-bis(diphenylphosphino) ferrocene]dichloropalladium (II) and an inorganic base such as potassium carbonate in a solvent mixture of dioxane and water.

Scheme 5

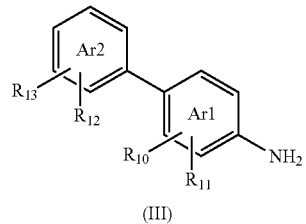

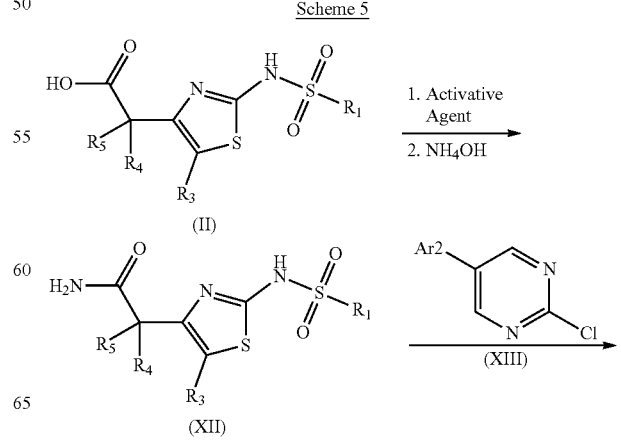

51

-continued

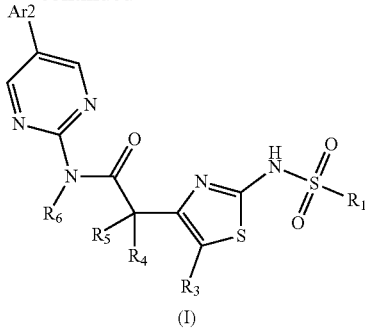

(I)

52

The compound intermediates of formula (I) where Ar1 is a 2-amino pyrimidine, can be obtained by activating the acid (II) with a suitable activating agent, to generate a reactive, electrophilic carboxylic acid derivative, followed by subsequent reaction with an ammonia source such as ammonium hydroxide. The primary amide (XII) can then be coupled with a 2-chloropyrimidine derivative (XIII) using a palladium catalyst such as Pd 177 (Xantphos precatalyst) and inorganic base, for example cesium carbonate in 1,4-dioxane to yield compounds of the general formula (I). It will be understood by persons skilled in the art that traditional coupling conditions directly from an electrophilic carboxylic acid derivative and 2-aminopyrimidine derivative are difficult due to the unreactive nature of the nucleophile.

Scheme 6

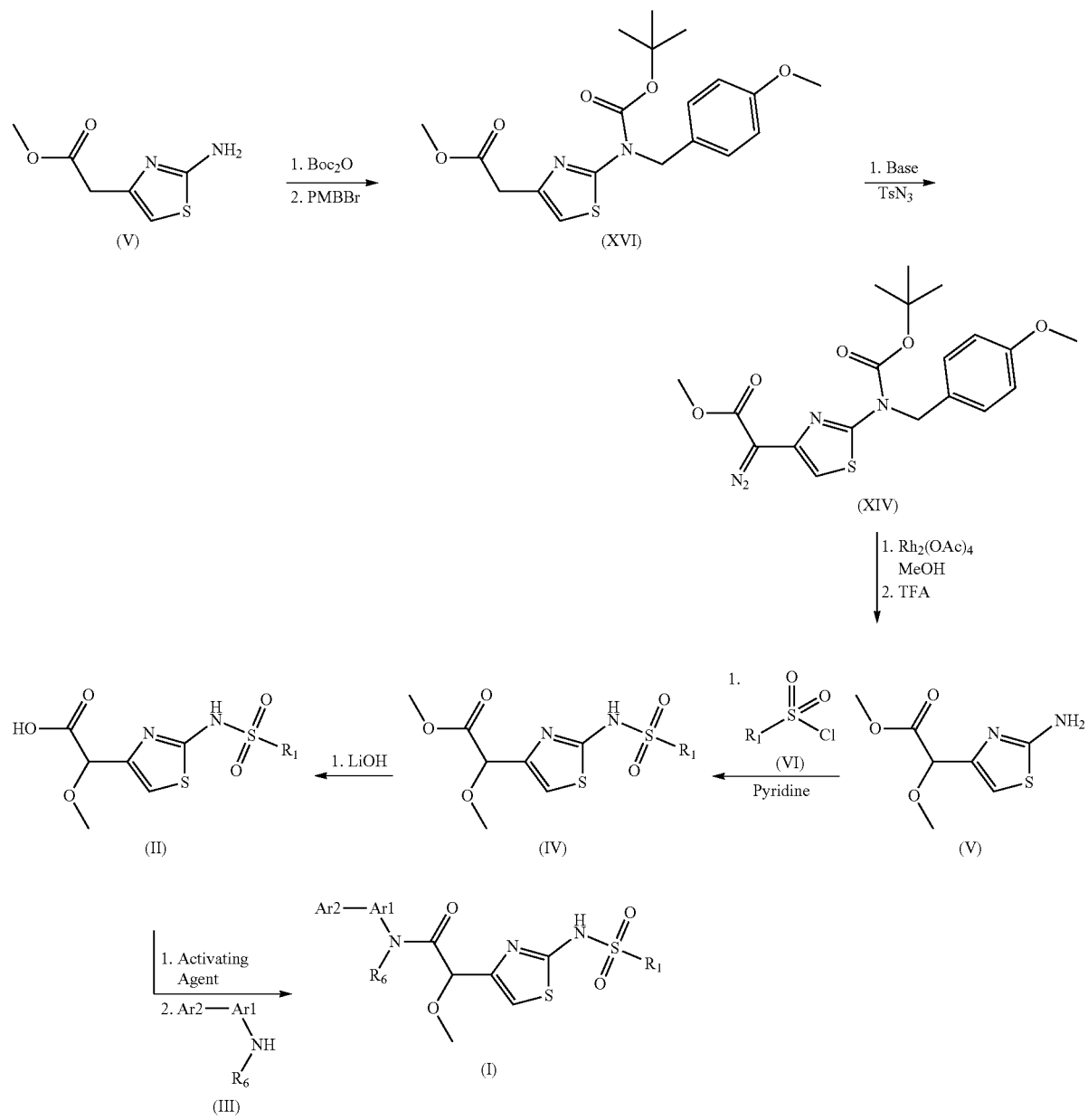

In general and as illustrated in Scheme 6, the 2-(2-(alkylsulfonamido)thiazol-4-yl)amide derivatives of general formula (I) in which $R_1$, $R_6$, Ar1 and Ar2 are defined above may be prepared in several steps, starting from methyl 2-(2-aminothiazol-4-yl)acetate. Intermediates of formula (XVI) can be formed by sequential protection of the amine (V with suitable N-protecting groups such as Boc and PMB protecting groups. Addition of a base, such as 1,8-diazabicyclo[5.4.0]undec-7-ene, and tosyl azide leads to the selective introduction of the diazo functional group on the alpha-position relative to the ester to yield intermediates of formula (XIV). Under rhodium catalysis and in the presence of a nucleophilic source, such as methanol, followed by deprotection of both protecting groups at elevated temperatures, derivatives of formula (V) may be prepared. The compound intermediates of formula (IV) can be obtained by sulfonylation of amines of formula (V) with a suitable sulfonyl chloride (VI) in pyridine. Such reactions may be subject to gentle heating to, for example, 30-50° C. The alkyl esters of formula (IV) may be conveniently converted to compounds of formula (I) according to synthetic steps reported in Scheme 1.

Scheme 7

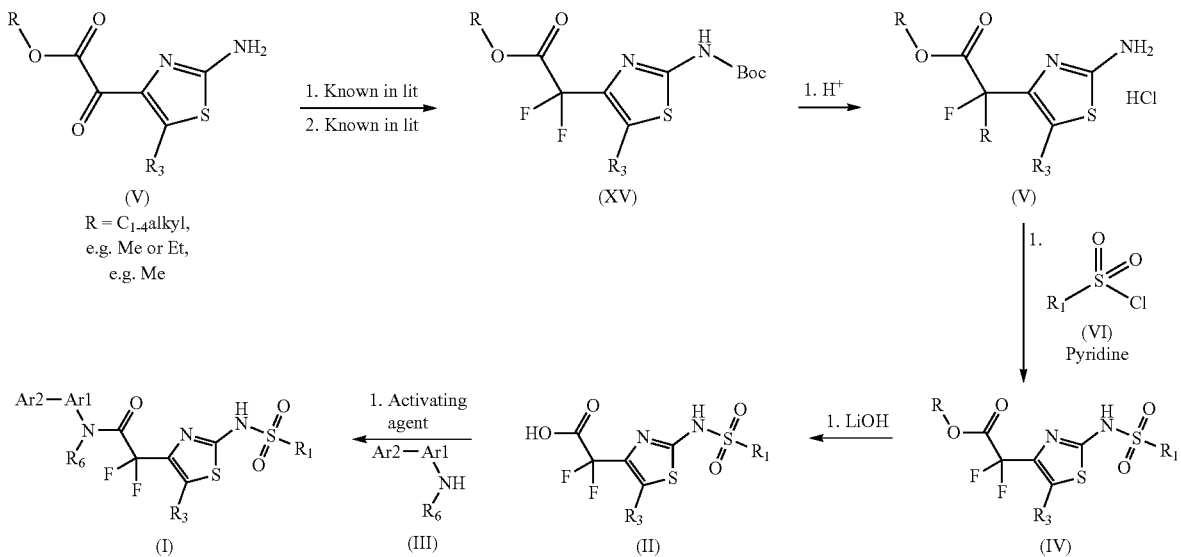

The difluoro intermediate of formula (XV) may be prepared in two steps by firstly Boc protection using Boc-anhydride in a polar solvent such as dichloroethane, followed by utilisation of a fluorinating agent such as bis(2-methoxyethyl)aminosulfur trifluoride. These fluorination reactions are, for example, performed at RT and in a solvent such as toluene. The following deprotection to yield the free aminothiazole (V) is performed, for example, by exposure to acid in an organic solvent, such as HCl in 1,4-dioxane. The compound intermediates of formula (IV) can be obtained by sulfonylation of amines of formula (V) with a suitable sulfonyl chloride (VI) in pyridine. Such reactions may be subject to gentle heating to, for example, 30-50° C. The alkyl esters of formula (IV) may be conveniently converted to compounds of formula (I) according to synthetic steps reported in Scheme 1.

Scheme 8

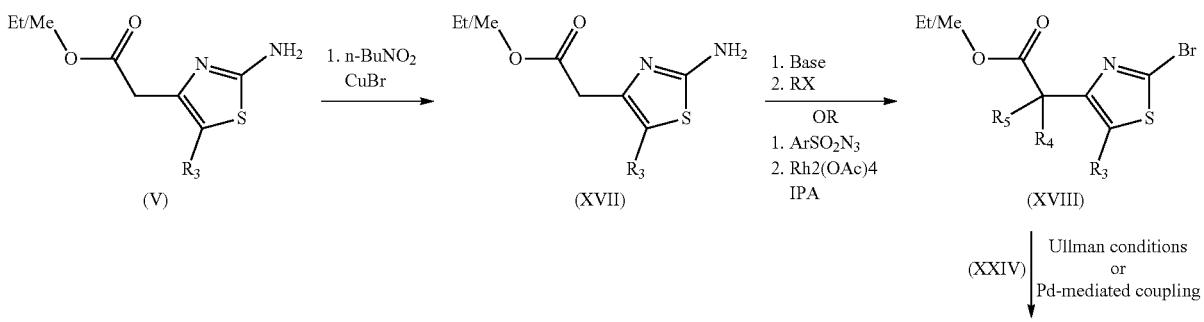

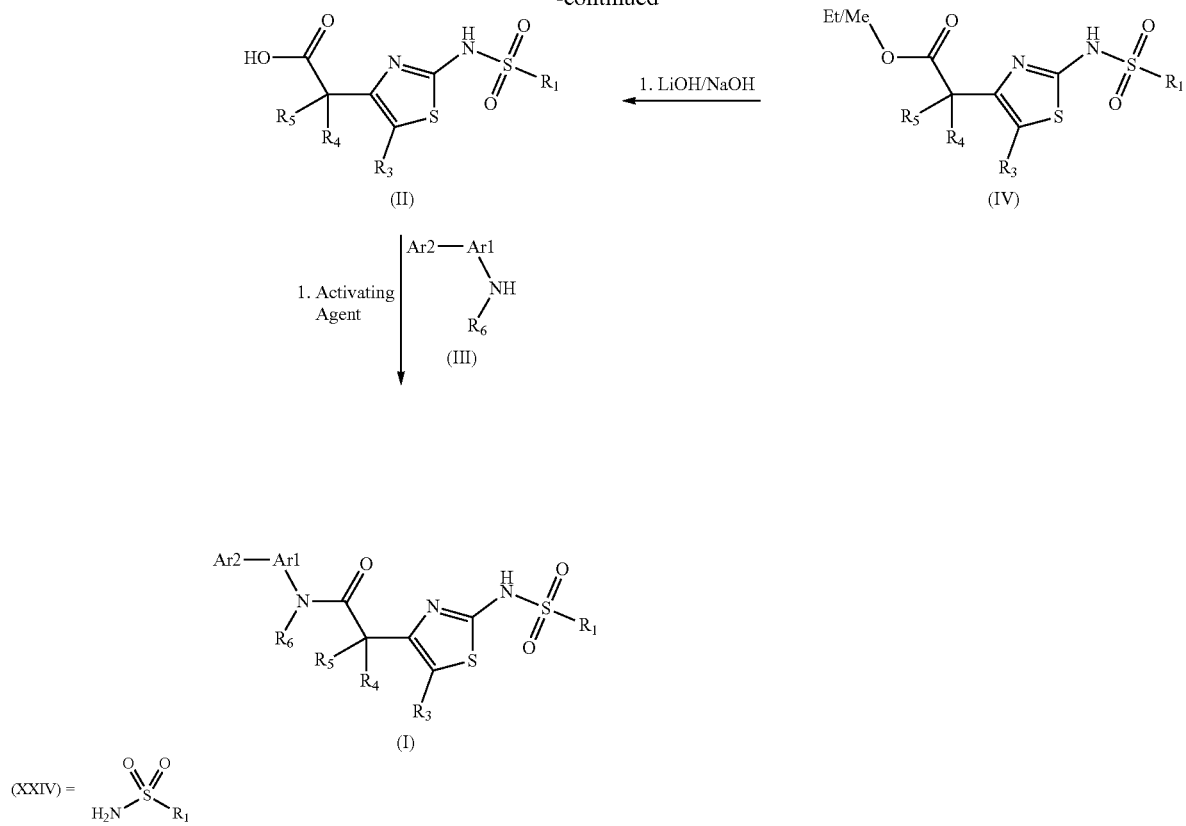

Compound of general formula (XVII) may be prepared by conversion of a suitable 2-(2-aminothiazol-4-yl)acetate derivative, such as a methyl or ethyl derivative, by a Sandmeyer type reaction using an organic nitrite, such as n-butylnitrite, in the presence of a halide source, such as Cu(I)Br in acetonitrile. Such reactions can be undertaken at temperatures of RT to 60° C. Introduction of $R_4/R_5$ can be undertaken by two alternative methods at this stage. Firstly, alkylation of compounds of general formula (XVII) can be undertaken by addition of a suitable base, for example, LiHMDS, together with an alkylating agent, such as iodomethane which results in dialkylation alpha to the ester moiety to yield compounds of formula (XVIII), where $R_4=R_5=$Me. Secondly, diazotisation of compounds of general formula (XVII) with the use of an diazo transfer reagent, such as 4-acetamidobenzenesulfonyl azide, under basic conditions, followed by treatment with rhodium and subsequent insertion of the corresponding nucleophile, such as isopropyl alcohol, gives intermediates of general formula (XVIII) where $R_4=$Oisopropoxy and $R_5 =$H.

Introduction of the sulfonamide group in the preparation of compounds of formula (IV) may be achieved by an Ullmann coupling reaction i.e. Cu mediated coupling conditions using amines of formula (XXIV) and a copper catalyst, such as Cu(I)I, in the presence of an inorganic base, potassium carbonate, and a diamine ligand in dioxane. Such reactions are typically carried out at elevated temperatures such as 80° C. Alternatively, conversion of compounds of formula (XVIII) to (IV) can be achieved via a palladium mediated coupling, for example using a catalyst such as [t-BuXPhos Pd(allyl)]OTf and substituted sulfonamide nucleophile (XXIV), in the presence of an inorganic base, for example potassium carbonate to form compounds of formula (IV). Palladium mediatiated coupling conditions are particularly useful when $R_4$ and $R_5$ together with the carbon atom to which they are attached form a 5- or 6-membered heterocycloalkyl, such as a tetrahydropyranyl. The alkyl esters of formula (IV) may be conveniently converted to compounds of formula (I) according to synthetic steps reported in Scheme 1.

Scheme 9

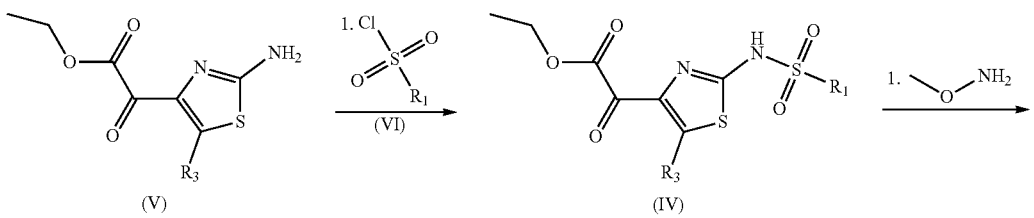

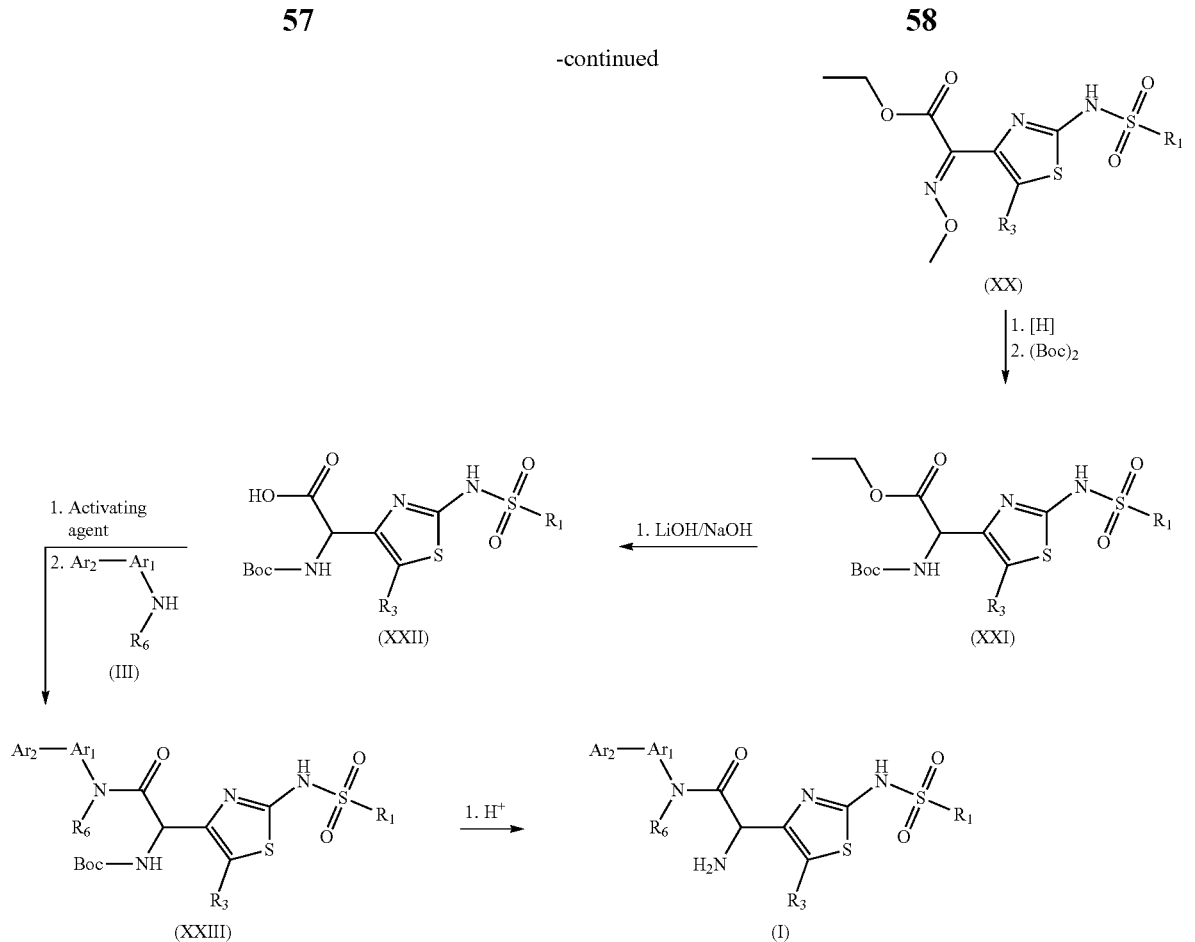

Compounds of general formula (I), where $R_1$, $R_3$, $R_6$, $R_{13}$, Ar1 and Ar2 are defined above, may be synthesised by the general scheme shown above. The compound intermediates of formula (IV) can be obtained by sulfonylation of amines of formula (V) with a suitable sulfonyl chloride (VI) in pyridine. Such reactions may be subject to gentle heating to, for example, 30-60° C. Reaction of ketone (IV) with O-methylhydroxylamine in the presence of trimethylamine yields the methoxyiminoacetate intermediate (XX). This can be reduced by addition of zinc in the presence of formaldehyde at temperatures such as 0° C. Ethyl 2-amino-2-(2-(cyclopropanesulfonamido)thiazol-4-yl)acetate is not formally isolated but after ion exchange chromatography purification may be protected with di-tert-butyl dicarbonate to afford intermediate (XXI). To obtain compound (XXII) intermediate (XXI) can be subjected to hydrolysis using an inorganic base such as LiOH. Compound of formula (XXIII) can be obtained by reaction of acid (XXII) with an activating reagent such as HATU followed by addition in situ of a chosen amine of formula (III). Finally compound (XXIII) can be deprotected using an acid such as TFA to yield final compound (I).

Scheme 10

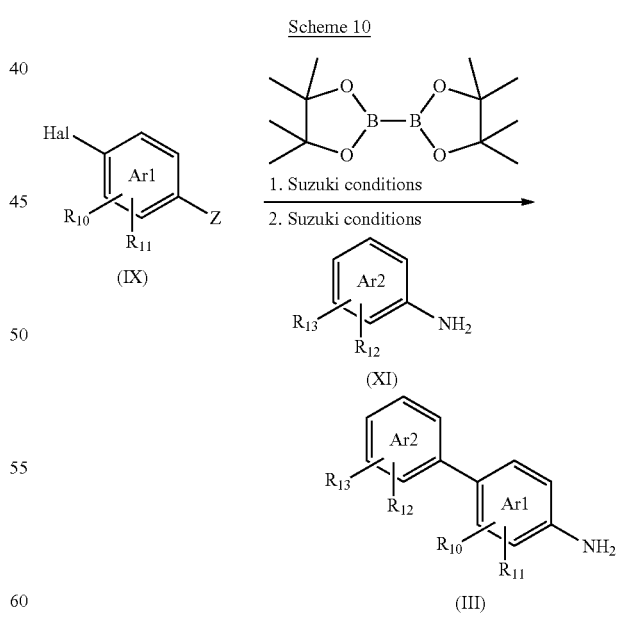

Intermediate compounds of formula (III) may be obtained by a two-step, one pot process whereby an aryl bromide precursor (IX) is reacted with bis(pinacolato)diborane under Suzuki conditions using a catalyst such as bis(diphenylphosphino)ferrocene]dichloropalladium(II) and an inorganic base such as potassium carbonate, in a solvent mixture of dioxane and water. The 4,4,5,5-tetramethyl-1,3,3,2-dioxaborolan-2-yl intermediate is not formally isolated but is then reacted directly by a second Suzuki reaction with an aromatic halide of general formula (XI) using the conditions described above.

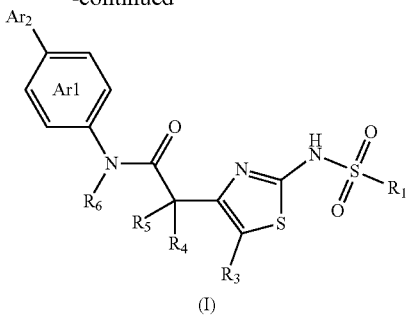

Z = Br, Cl

Compounds of formula (I) may be obtained by a two-step, one pot process whereby an aryl halide precursor (X) is reacted with bis(pinacolato)diborane under Suzuki conditions using a catalyst such as bis(diphenylphosphino)ferrocene]dichloropalladium(II) and an inorganic base such as potassium carbonate, in a solvent mixture of dioxane and water. The 4,4,5,5-tetramethyl-1,3,3,2-dioxaborolan-2-yl intermediate is then reacted directly by a second Suzuki reaction with an aromatic halide of general formula (XI) using the conditions described above.

Scheme 11

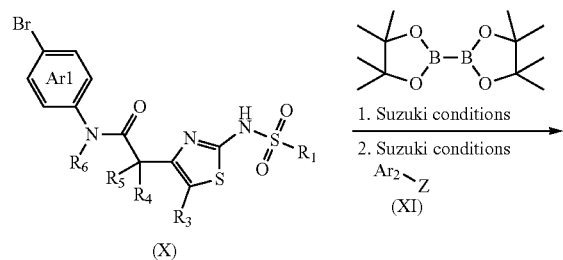

Scheme 12

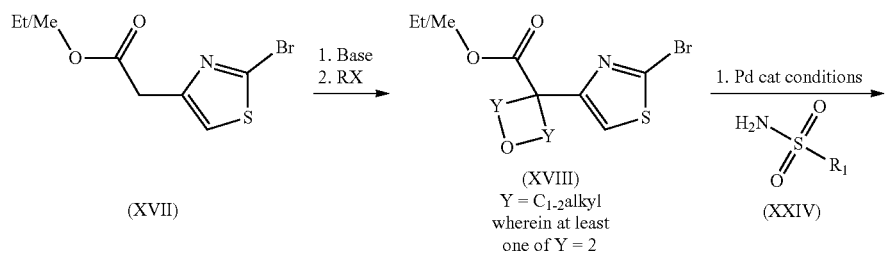

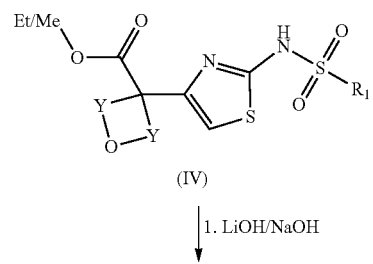

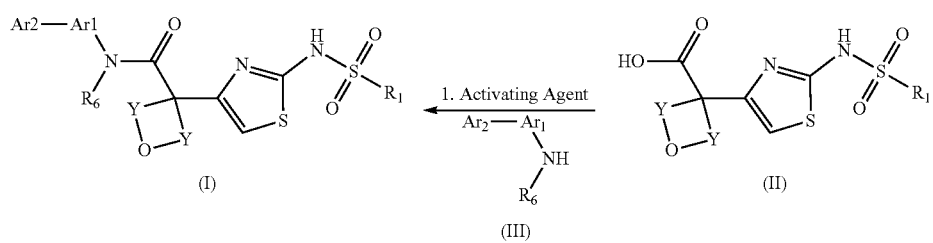

Compounds of general formula (I) when $R_4$ and $R_5$ together with the carbon atom to which they are attached form a $C_{3-6}$heterocycloalkyl ring may be prepared by bis-alkylation of compounds of general formula (XVII) which can be undertaken by the addition of a suitable base, for example, NaOH, together with a bis-alkylating agent, such as 1-bromo-2-(2-bromoethoxy)ethane. Palladium catalysed sulfonamidation of intermediate (XVIII) may be achieved using a catalytic system using [Pd(allyl)Cl]$_2$ and a phosphine mono-dentate ligand such as t-BuXPhos in the presence of a primary sulphonamide (XXIV) to obtain compounds of the formula (IV). Such reactions are typically carried out at elevated temperatures such as 90° C. The alkyl esters of formula (IV) may be conveniently converted to compounds of formula (I) according to synthetic steps reported in Scheme 1.

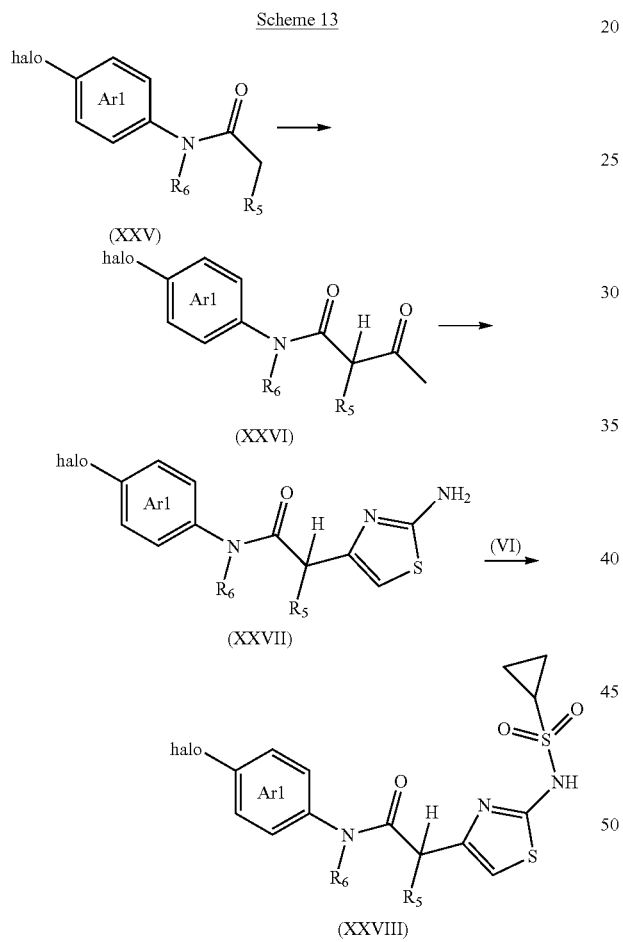

wherein halo is, for example, bromo. Compounds of formula (XXVII), for example, when $R_4$ is H and $R_5$ and $R_6$ are a $C_{2-3}$alkylene chain forming a 5- or 6-membered ring, can be accessed in three steps from compounds of formula (XXV). Acylation of compounds of formula (XXV) in the presence of a strong base such as LDA followed by a quench with an —OAc source such as EtOAc provides compounds of formula (XXVI). Compounds of formula (XXVII) can be made from (XXVI) following addition of bromine and quench with a suitable thiourea, before a coupling with sulfonyl chlorides of formula (VI) to give compounds of formula (XXVIII). Compounds of formula (I) may be accessed using conditions set out in Scheme 2.

INTERMEDIATES OF THE INVENTION

The present invention also relates to novel intermediates in the synthesis of compounds of formula (I) such as compounds of formula (II) to (XXVIII), such as compounds of formula (II) to (XXIII), such as (II)-(XVIII). Particular intermediates of interest are those of the following general formulae, wherein the variable groups and associated preferences are as defined previously for compounds of formula (I):

Compounds of Formula (II)

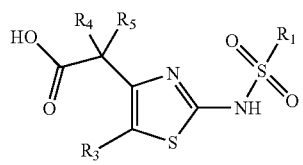

wherein $R_1$, $R_3$, $R_4$ and $R_5$ are as defined herein;
Compounds of Formula (III)

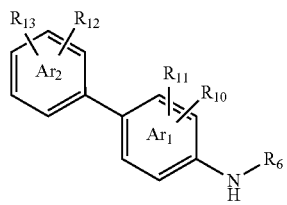

wherein Ar1, Ar2, $R_6$, $R_{10}$, $R_{11}$, $R_{12}$ and $R_{13}$ are as defined herein;
Compounds of Formula (IV)

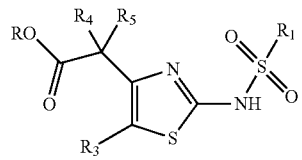

wherein R is $C_{1-6}$alkyl (e.g. methyl, ethyl) or benzyl;
Compounds of Formula (X)

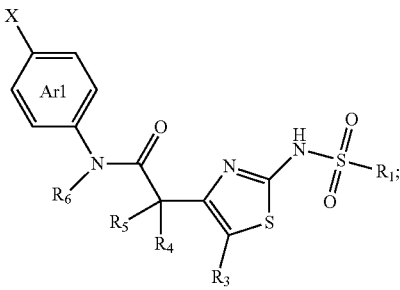

X = Cl, Br, B(OH)$_2$, B(pin)$_2$ wherein Ar1, $R_1$, $R_3$, $R_4$, $R_5$ and $R_6$ are as defined herein;

Compounds of Formula (XII)

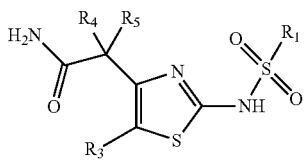

wherein $R_1$, $R_3$, $R_4$ and $R_5$ are as defined herein; and
Compounds of Formula (XIII)

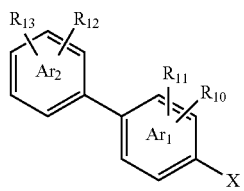

wherein Ar1, Ar2, $R_{10}$, $R_{11}$, $R_{12}$ and $R_{13}$ are as defined herein and X is halo such as Cl.

Suitably, the intermediate is not:

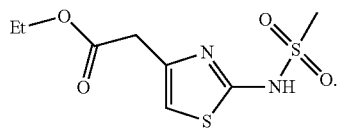 [SMILES: CCOC(=O)Cc1csc(NS(C)(=O)=O)n1]

Suitably, when the compound is a compound of formula (IV), $R_4$ and $R_5$ cannot both be H when $R_1$ is $CH_3$.

Suitably, the intermediate is not:

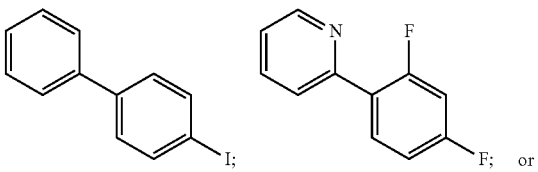

such as

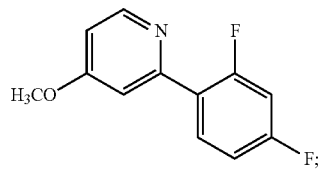

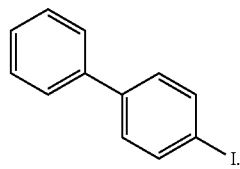 [SMILES: Ic1ccc(-c2ccccc2)cc1]

Included as an aspect of the invention are all novel intermediates described in the examples, including:

Intermediates A1 to A75; and

Intermediates B1 to B73.

Also of interest are intermediates:

A1 to A108, such as A76 to A108; and

B1 to B109, such as B75 to B109.

Also of interest are intermediates:

A109 to A117; and

B110 to B120.

Included as an aspect of the invention are salts such as pharmaceutically acceptable salts of any one of the intermediates disclosed herein, such as any one of compounds of formulae (II)-(XXVIII).

Other intermediates of interest (and compounds of the invention derived therefrom) include:

| | | |
|---|---|---|
| 4-(6-ethoxypyrazin-2-yl)-5-fluoro-2-methylaniline | 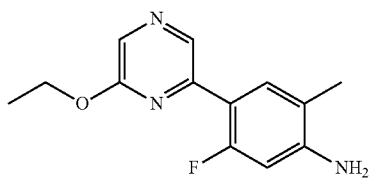 | 8.45 (d, J = 2.2 Hz, 1H), 8.06 (s, 1H), 7.63 (d, J = 8.8 Hz, 1H), 6.47 (d, J = 14.2 Hz, 1H), 5.68 (s, 2H), 4.43 (q, J = 7.0 Hz, 2H), 2.09 (s, 3H), 1.39 (t, J = 7.0 Hz, 3H). |
| 4-(6-ethoxypyrazin-2-yl)-5-fluoro-2-methoxyaniline | 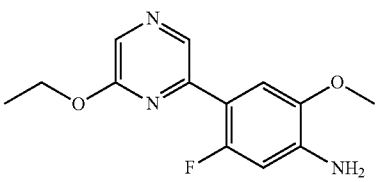 | 8.50 (d, J = 2.0 Hz, 1H), 8.08 (s, 1H), 7.43 (d, J = 7.2 Hz, 1H), 6.51 (d, J = 13.5 Hz, 1H), 5.61 (s, 2H), 4.45 (q, J = 7.1 Hz, 2H), 3.83 (s, 3H), 1.40 (t, J = 7.0 Hz, 3H). |

-continued

| | | |
|---|---|---|
| 4-(6-ethoxypyrazin-2-yl)-2,3-dimethylaniline 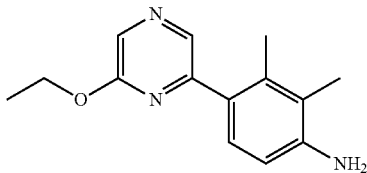 | 8.18 (s, 1H), 8.10 (s, 1H), 7.02 (d, J = 8.3 Hz, 1H), 6.60 (d, J = 8.2 Hz, 1H), 5.11 (s, 2H), 4.36 (q, J = 7.0 Hz, 2H), 2.22 (s, 3H), 2.04 (s, 3H), 1.35 (t, J = 7.0 Hz, 3H). | |
| 4-(6-ethoxypyrazin-2-yl)-2-fluoro-5-methylaniline 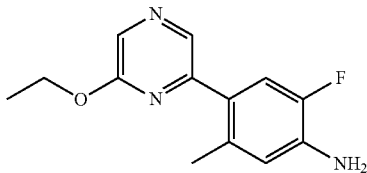 | 8.31 (s, 1H), 8.13 (s, 1H), 7.24 (d, J = 12.5 Hz, 1H), 6.68 (d, J = 9.1 Hz, 1H), 5.44 (s, 2H), 4.38 (q, J = 7.0 Hz, 2H), 2.32 (s, 3H), 1.36 (t, J = 7.0 Hz, 3H). | |
| 4-(6-ethoxypyrazin-2-yl)-2,5-dimethylaniline 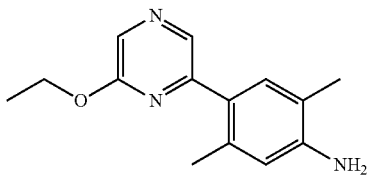 | 8.26 (s, 1H), 8.07 (s, 1H), 7.15 (s, 1H), 6.53 (s, 1H), 5.13 (s, 2H), 4.36 (q, J = 7.0 Hz, 2H), 2.31 (s, 3H), 2.07 (s, 3H), 1.36 (t, J = 7.1 Hz, 3H). | |
| 4-(6-ethoxypyrazin-2-yl)-2,6-difluoroaniline 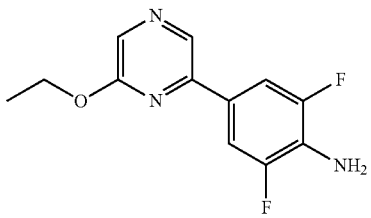 | 8.73 (s, 1H), 8.12 (s, 1H), 7.74 (dd, J = 8.0, 2.5 Hz, 2H), 5.73 (s, 2H), 4.46 (q, J = 7.0 Hz, 2H), 1.39 (t, J = 7.1 Hz, 3H). | |
| 3'-ethoxy-[1,1'-biphenyl]-4-amine 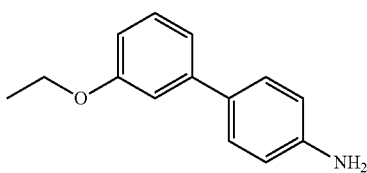 | 7.37-7.32 (m, 2H), 7.29-7.24 (m, 1H), 7.09 (ddd, J = 7.7, 1.7, 0.9 Hz, 1H), 7.06-7.01 (m, 1H), 6.77 (ddd, J = 8.1, 2.5, 1.0 Hz, 1H), 6.63 (d, J = 8.3 Hz, 2H), 5.22 (s, 2H), 4.07 (q, J = 7.0 Hz, 2H), 1.34 (t, J = 6.9 Hz, 3H) | |
| 4-(6-ethoxypyrazin-2-yl)-2-(trifluoromethoxy)aniline 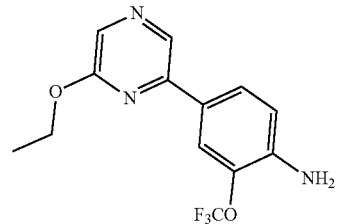 | 8.67 (s, 1H), 8.08 (s, 1H), 7.93-7.78 (m, 2H), 6.91 (d, J = 8.5 Hz, 1H), 5.91 (s, 2H), 4.43 (q, J = 7.0 Hz, 2H), 1.39 (t, J = 7.0 Hz, 3H). | |

-continued

| | |
|---|---|
| 4-(6-ethoxypyrazin-2-yl)-2-methoxyaniline<br>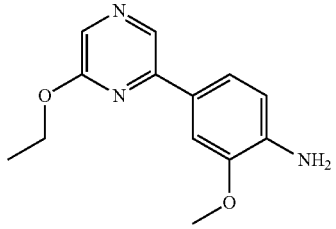 | 8.67 (s, 1H), 8.02 (s, 1H), 7.62-7.46 (m, 2H), 6.72 (d, J = 8.0 Hz, 1H), 5.24 (s, 2H), 4.45 (q, J = 7.0 Hz, 2H), 3.87 (s, 3H), 1.39 (t, J = 7.0 Hz, 3H). |
| 2-chloro-4-(6-ethoxypyrazin-2-yl)aniline<br>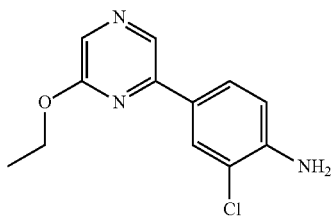 | 8.66 (d, J = 0.5 Hz, 1H), 8.07 (d, J = 0.5 Hz, 1H), 7.99 (d, J = 2.1 Hz, 1H), 7.83 (dd, J = 8.5, 2.1 Hz, 1H), 6.89 (d, J = 8.5 Hz, 1H), 5.85 (s, 2H), 4.44 (q, J = 7.0 Hz, 2H), 1.39 (t, J = 7.0 Hz, 3H). |
| 2-amino-5-(6-ethoxypyrazin-2-yl)-benzonitrile<br>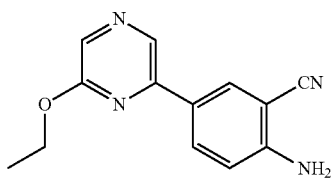 | 8.70 (s, 1H), 8.19 (d, J = 2.2 Hz, 1H), 8.13-8.06 (m, 2H), 6.91 (d, J = 8.9 Hz, 1H), 6.52 (s, 2H), 4.45 (q, J = 7.0 Hz, 2H), 1.39 (t, J = 7.0 Hz, 3H). |

Also of interest are the following intermediates:

| | |
|---|---|
| 5-(6-trifluoromethyl)pyrazin-2-yl)-pyridin-2-amine<br>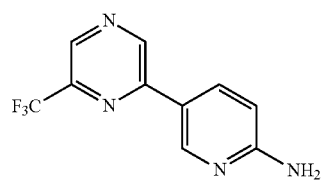 | 9.52-9.41 (m, 1H), 8.95 (t, J = 0.6 Hz, 1H), 8.81 (dd, J = 2.5, 0.8 Hz, 1H), 8.16 (dd, J = 8.8, 2.5 Hz, 1H), 6.66 (s, 2H), 6.59 (dd, J = 8.8, 0.8 Hz, 1H). |
| 4-(6-ethoxypyrazin-2-yl)-2-fluoroaniline<br>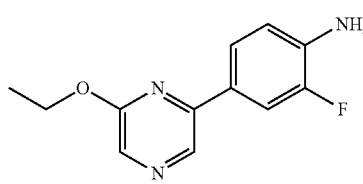 | 8.66 (s, 1H), 8.06 (s, 1H), 7.84-7.63 (m, 2H), 6.93-6.75 (m, 1H), 5.65 (s, 2H), 4.54-4.34 (m, 2H), 1.47-1.29 (m, 3H). |
| 2-fluoro-4-(6-(trifluoromethyl)pyrazin-2-yl)aniline<br>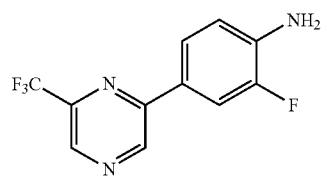 | 9.46 (s, 1H), 8.92 (s, 1H), 7.88 (dd, J = 13.1, 2.1 Hz, 1H), 7.83 (dd, J = 8.4, 2.1 Hz, 1H), 6.90 (t, J = 8.8 Hz, 1H), 5.90 (s, 2H). |

| | |
|---|---|
| 5-(6-ethoxypyrazin-2-yl)pyridin-2-amine | 8.70 (dd, J = 2.5, 0.8 Hz, 1H), 8.64 (s, 1H), 8.10-8.06 (m, 2H), 6.54 (dd, J = 8.7, 0.8 Hz, 1H), 6.41 (s, 2H), 4.43 (q, J = 7.0 Hz, 2H), 1.38 (t, J = 7.0 Hz, 3H). |
| 2-(2-(cyclopropanesulfonamido)thiazol-4-yl)-2-methylpropanoic acid | 12.62 (brs, 2H), 6.51 (s, 1H), 2.66-2.53 (m, 1H), 1.45 (s, 6H), 0.95-0.89 (m, 4H). |
| 2-(2-(cyclopropanesulfonamido)thiazol-4-yl)butanoic acid | 12.58 (br, s, 2H), 6.55 (s, 1H), 3.47 (dd, J = 8.4, 6.7 Hz, 1H), 2.64-2.56 (m, 1H), 1.98-1.73 (m, 2H), 0.95-0.88 (m, 4H), 0.85 (t, J = 7.4 Hz, 3H). |
| 2-(2-(cyclopropanesulfonamido)thiazol-4-yl)-2-methoxyacetic acid | none recorded | and salts, such as pharmaceutically acceptable salts, thereof.

Therapeutic Methods

Compounds of formula (I) of the present invention have utility as inhibitors of CTPS1.

Therefore, the invention also provides a compound of formula (I), or a pharmaceutically acceptable salt and/or solvate (e.g. salt) and/or derivative thereof, for use as a medicament, in particular in the treatment or prophylaxis of a disease or disorder wherein an inhibitor of CTPS1 is beneficial, for example those diseases and disorders mentioned herein below.

The invention provides a method for the treatment or prophylaxis of a disease or disorder wherein an inhibitor of CTPS1 is beneficial, for example those diseases and disorders mentioned herein below, which comprises administering to a subject in need thereof an effective amount of a compound of formula (I) or a pharmaceutically acceptable salt and/or solvate (e.g. salt) and/or derivative thereof.

The invention also provides the use of a compound of formula (I), or a pharmaceutically acceptable salt and/or solvate thereof (e.g. salt) and/or derivative, in the manufacture of a medicament for the treatment or prophylaxis of a disease or disorder wherein an inhibitor of CTPS1 is beneficial, for example those diseases and disorders mentioned herein below.

More suitably, the disease or disorder wherein an inhibitor of CTPS1 is beneficial is a disease or disorder wherein a reduction in T-cell and/or B-cell proliferation would be beneficial.

The invention also provides a compound of formula (I), or a pharmaceutically acceptable salt and/or solvate (e.g. salt) and/or derivative thereof, for use in the inhibition of CTPS1 in a subject.

The invention provides a method for the inhibition of CTPS1 in a subject, which comprises administering to the subject an effective amount of a compound of formula (I) or a pharmaceutically acceptable salt and/or solvate (e.g. salt) and/or derivative thereof.

The invention also provides the use of a compound of formula (I), or a pharmaceutically acceptable salt and/or solvate thereof (e.g. salt) and/or derivative, in the manufacture of a medicament for the inhibition of CTPS1 in a subject.

The invention also provides a compound of formula (I), or a pharmaceutically acceptable salt and/or solvate (e.g. salt) and/or derivative thereof, for use in the reduction of T-cell and/or B-cell proliferation in a subject.

The invention provides a method for the reduction of T-cell and/or B-cell proliferation in a subject, which comprises administering to the subject an effective amount of a compound of formula (I) or a pharmaceutically acceptable salt and/or solvate (e.g. salt) and/or derivative thereof.

The invention also provides the use of a compound of formula (I), or a pharmaceutically acceptable salt and/or solvate thereof (e.g. salt) and/or derivative, in the manufacture of a medicament for the reduction of T-cell and/or B-cell proliferation in a subject.

More suitably, the disease or disorder wherein an inhibitor of CTPS1 is beneficial is a disease or disorder wherein a reduction in T-cell and/or B-cell proliferation would be beneficial.

The term 'treatment' or 'treating' as used herein includes the control, mitigation, reduction, or modulation of the disease state or its symptoms.

The term 'prophylaxis' or 'preventing' is used herein to mean preventing symptoms of a disease or disorder in a subject or preventing recurrence of symptoms of a disease or disorder in an afflicted subject and is not limited to complete prevention of an affliction.

Suitably, the disease or disorder is selected from rejection of transplanted cells and tissues, Graft-related diseases or disorders, allergies and autoimmune diseases.

In one embodiment the disease or disorder is the rejection of transplanted cells and tissues. The subject may have been transplanted with a graft selected from the group consisting of heart, kidney, lung, liver, pancreas, pancreatic islets, brain tissue, stomach, large intestine, small intestine, cornea, skin, trachea, bone, bone marrow (or any other source of hematopoietic precursor cells and stem cells including hematopoietic cells mobilized from bone marrow into peripheral blood or umbilical cord blood cells), muscle, or bladder. The compounds of the invention may be of use in preventing or suppressing an immune response associated with rejection of a donor tissue, cell, graft or organ transplant in a subject.

In a further embodiment the disease or disorder is a Graft-related disease or disorder. Graft-related diseases or disorders include graft versus host disease (GVHD), such as GVHD associated with bone marrow transplantation, and immune disorders resulting from or associated with rejection of organ, tissue, or cell graft transplantation (e.g., tissue or cell allografts or xenografts), including, e.g., grafts of skin, muscle, neurons, islets, organs, parenchymal cells of the liver, etc, and Host-Versus-Graft-Disease (HVGD). The compounds of the invention may be of use in preventing or suppressing acute rejection of such transplant in the recipient and/or for long-term maintenance therapy to prevent rejection of such transplant in the recipient (e.g., inhibiting rejection of insulin-producing islet cell transplant from a donor in the subject recipient suffering from diabetes). Thus the compounds of the invention have utility in preventing Host-Versus-Graft-Disease (HVGD) and Graft-Versus-Host-Disease (GVHD).

A CTPS1 inhibitor may be administered to the subject before, after transplantation and/or during transplantation. In some embodiments, the CTPS1 inhibitor may be administered to the subject on a periodic basis before and/or after transplantation.

In another embodiment, the disease or disorder is an allergy.

In additional embodiments the immune related disease or disorder is an autoimmune disease. As used herein, an "autoimmune disease" is a disease or disorder directed at a subject's own tissues.

Examples of autoimmune diseases include, but are not limited to Addison's Disease, Adult-onset Still's disease, Alopecia Areata, Alzheimer's disease, Anti-neutrophil Cytoplasmic Antibodies (ANCA)-Associated Vasculitis, Ankylosing Spondylitis, Anti-phospholipid Syndrome (Hughes' Syndrome), Aplastic Anemia, Arthritis, Asthma, Atherosclerosis, Atherosclerotic plaque, Atopic Dermatitis, Autoimmune Hemolytic Anemia, Autoimmune Hepatitis, Autoimmune Hypophysitis (Lymphocytic Hypophysitis), Autoimmune Inner Ear Disease, Autoimmune Lymphoproliferative Syndrome, Autoimmune Myocarditis, Autoimmune Neutropenia, Autoimmune Oophoritis, Autoimmune Orchitis, Auto-Inflammatory Diseases requiring an immunosuppressive treatment, Azoospermia, Bechet's Disease, Berger's Disease, Bullous Pemphigoid, Cardiomyopathy, Cardiovascular disease, Celiac disease including Refractory Celiac Disease (type I and type II), Chronic Fatigue Immune Dysfunction Syndrome (CFIDS), Chronic Idiopathic Polyneuritis, Chronic Inflammatory Demyelinating Polyneuropathy (CIPD), Chronic Relapsing Polyneuropathy (Guillain-Barre syndrome), Churg-Strauss Syndrome (CSS), Cicatricial Pemphigoid, Cold Agglutinin Disease (CAD), chronic obstructive pulmonary disease (COPD), CREST Syndrome, Cryoglobulin Syndromes, Cutaneous Lupus, Dermatitis Herpetiformis, Dermatomyositis, Eczema, Epidermolysis Bullosa Acquisita, Essential Mixed Cryoglobulinemia, Evan's Syndrome, Exophthalmos, Fibromyalgia, Goodpasture's Syndrome, Grave's disease, Hemophagocytic Lymphohistiocytosis (HLH) (including Type 1 Hemophagocytic Lymphohistiocytosis), Histiocytosis/Histiocytic Disorders, Hashimoto's Thyroiditis, Idiopathic Pulmonary Fibrosis, Idiopathic Thrombocytopenia Purpura (ITP), IgA Nephropathy, Immunoproliferative Diseases or Disorders, Inflammatory Bowel Disease (IBD), Interstitial Lung Disease, Juvenile Arthritis, Juvenile Idiopathic Arthritis (JIA), Kawasaki's Disease, Lambert-Eaton Myasthenic Syndrome, Lichen Planus, Localized Scleroderma, Lupus Nephritis, Meniere's Disease, Microangiopathic Hemoytic Anemia, Microscopic Polyangitis, Miller Fischer Syndrome/ Acute Disseminated Encephalomyeloradiculopathy, Mixed Connective Tissue Disease, Multiple Sclerosis (MS), Muscular Rheumatism, Myalgic Encephalomyelitis (ME), Myasthenia Gravis, Ocular Inflammation, Pemphigus Foliaceus, Pemphigus Vulgaris, Pernicious Anemia, Polyarteritis Nodosa, Polychondritis, Polyglandular Syndromes (Whitaker's syndrome), Polymyalgia Rheumatica, Polymyositis, Primary Agammaglobulinemia, Primary Biliary Cirrhosis/ Autoimmune Cholangiopathy, Primary Glomerulonephritis, Primary Sclerosing Cholangitis, Psoriasis, Psoriatic Arthritis, Pure Red Cell Anemia, Raynaud's Phenomenon, Reiter's Syndrome/Reactive Arthritis, Relapsing Polychondritis, Restenosis, Rheumatic Fever, Rheumatic Disease, Rheumatoid Arthritis, Sarcoidosis, Schmidt's Syndrome, Scleroderma/Systemic Sclerosis, Sjörgen's Syndrome, Stiff-Man Syndrome, The Sweet Syndrome (Febrile Neutrophilic Dermatosis), Systemic Lupus Erythematosus (SLE), Systemic Scleroderma, Takayasu Arteritis, Temporal Arteritis/Giant Cell Arteritis, Thyroiditis, Type 1 diabetes, Type 2 diabetes, Uveitis, Vasculitis, Vitiligo, Wegener's Granulomatosis, and X-linked lymphoproliferative disease.

Of particular interest are diseases and disorders which are mainly driven by T-cell activation and proliferation, including:

diseases and disorders which are not linked to alloreactivity including:
Alopecia areata, atopic dermatitis, eczema, psoriasis, lichen planus, psoriatic arthritis, vitiligo;
Uveitis;
Ankylosing spondylitis, Reiter's syndrome/reactive arthritis;
Aplastic anemia, autoimmune lymphoproliferative syndrome/disorders, hemophagocytic lymphohistiocytosis;
Type 1 diabetes; and
Refractory celiac disease;

Acute rejection of grafted tissues and transplanted organs; acute graft versus host disease (GVHD) after transplantation of bone marrow cells or any other source of allogenic cells including hematopoietic precursors cells and/or stem cells.

Also of interest are diseases and disorders which are driven by both T- and B-cell activation and proliferation, with an important involvement of B-cells, including:

diseases and disorders for which the involvement of pathogenic auto-antibodies is well characterized, including:

Allergy;

Cicatricial pemphigoid, bullous pemphigoid, epidermolysis bullosa acquisita, pemphigus foliaceus, pemphigus vulgaris, dermatitis herpetiformis;

ANCA-associated vasculitis and microscopic polyangitis, vasculitis, Wegener's granulomatosis; Churg-Strauss syndrome (CSS), polyarteritis nodosa, cryoglobulin syndromes and essential mixed cryglobulinemia;

Systemic lupus erythematosus (SLE), antiphospholipid syndrome (Hughes' syndrome), cutaneous lupus, lupus nephritis, mixed connective tissue disease;

Thyroiditis, Hashimoto thyroiditis, Grave's disease, exophthalmos;

Autoimmune hemolytic anemia, autoimmune neutropenia, ITP, pernicious anaemia, pure red cell anaemia, micro-angiopathic hemolytic anemia;

Primary glomerulonephritis, Berger's disease, Goodpasture's syndrome, IgA nephropathy; and Chronic idiopathic polyneuritis, chronic inflammatory demyelinating polyneuropathy (CIPD), chronic relapsing polyneuropathy (Guillain-Barre syndrome), Miller Fischer syndrome, Stiff man syndrome, Lambert-Eaton myasthenic syndrome, myasthenia gravis.

diseases and disorders for which the involvement of B-cells is less clearly characterized (although sometimes illustrated by the efficacy of anti-CD20 monoclonal antibodies or intravenous immunoglobulin infusions) and may not correspond or be limited to the production of pathogenic antibodies (nevertheless, non-pathogenic antibodies are sometimes described or even often present and used as a diagnosis biomarker), including:

Addison's disease, autoimmune oophoritis and azoospermia, polyglandular syndromes (Whitaker's syndrome), Schmidt's syndrome;

Autoimmune myocarditis, cardiomyopathy, Kawasaki's disease;

Rheumatoid arthritis, Sjögren's syndrome, mixed connective tissue disease, polymyositis and dermatomyositis; polychondritis;

Primary glomerulonephritis;

Multiple sclerosis;

Autoimmune hepatitis, primary biliary cirrhosis/autoimmune cholangiopathy,

Hyper acute rejection of transplanted organs;

Chronic rejection of graft or transplants;

Chronic Graft versus Host reaction/disease after transplantation of bone marrow cells or hematopoietic precursor cells.

Additionally of interest are diseases and disorders for which the mechanism is shared between activation/proliferation of T-cells and activation/proliferation of innate immune cells and other inflammatory cellular subpopulations (including myeloid cells such as macrophages or granulocytes) and resident cells (such as fibroblasts and endothelial cells), including:

COPD, idiopathic pulmonary fibrosis, interstitial lung disease, sarcoidosis;

Adult onset Still's disease, juvenile idiopathic arthritis, Systemic sclerosis, CREST syndrome where B cells and pathogen antibodies may also play a role; the Sweet syndrome; Takayasu arteritis, temporal arteritis/giant cell arteritis;

Ulcerative cholangitis, inflammatory bowel disease (IBD) including Crohn's disease and ulcerative colitis, primary sclerosing cholangitis.

Also of interest are diseases and disorders for which the mechanism remains poorly characterized but involves the activation and proliferation of T-cells, including:

Alzheimer's disease, cardiovascular syndrome, type 2 diabetes, restenosis, chronic fatigue immune dysfuntion syndrome (CFIDS).

Autoimmune Lymphoproliferative disorders, including:

Autoimmune Lymphoproliferative Syndrome and X-linked lymphoproliferative disease.

Suitably the disease or disorder is selected from: inflammatory skin diseases such as psoriasis or lichen planus; acute and/or chronic GVHD such as steroid resistant acute GVHD; acute lymphoproliferative syndrome; systemic lupus erythematosus, lupus nephritis or cutaneous lupus; or transplantation. In addition, the disease or disorder may be selected from myasthenia gravis, multiple sclerosis, and scleroderma/systemic sclerosis.

The compounds of formula (I) may be used in the treatment of cancer.

Thus, in one embodiment there is provided a compound of formula (I), or a pharmaceutically acceptable salt and/or solvate thereof and/or derivative thereof, for use in the treatment of cancer.

Further, there is provided a method for treating cancer in a subject, by administering to a subject in need thereof a compound of formula (I) or a pharmaceutically acceptable salt and/or solvate thereof and/or derivative thereof.

Additionally provided is the use of a compound of formula (I), or a pharmaceutically acceptable salt and/or solvate thereof and/or derivative thereof, in the manufacture of a medicament for the treatment of cancer in a subject.

Suitably the cancer is a haematological cancer, such as Acute myeloid leukemia, Angioimmunoblastic T-cell lymphoma, B-cell acute lymphoblastic leukemia, Sweet Syndrome, T-cell Non-Hodgkins lymphoma (including natural killer/T-cell lymphoma, adult T-cell leukaemia/lymphoma, enteropathy type T-cell lymphoma, hepatosplenic T-cell lymphoma and cutaneous T-cell lymphoma), T-cell acute lymphoblastic leukemia, B-cell Non-Hodgkins lymphoma (including Burkitt lymphoma, diffuse large B-cell lymphoma, Follicular lymphoma, Mantle cell lymphoma, Marginal Zone lymphoma), Hairy Cell Leukemia, Hodgkin lymphoma, Lymphoblastic lymphoma, Lymphoplasmacytic lymphoma, Mucosa-associated lymphoid tissue lymphoma, Multiple myeloma, Myelodysplastic syndrome, Plasma cell myeloma, Primary mediastinal large B-cell lymphoma, chronic myeloproliferative disorders (such as chronic myeloid leukemia, primary myelofibrosis, essential thrombocytemia, polycytemia vera) or chronic lymphocytic leukemia.

Alternatively, the cancer is a non-haematological cancer, such as selected from the group consisting of bladder cancer, breast cancer, melanoma, neuroblastoma, malignant pleural mesothelioma and sarcoma, such as breast cancer and melanoma.

In addition, compounds of formula (I) may be used in enhancing recovery from vascular injury or surgery and reducing morbidity and mortality associated with neointima and restenosis in a subject. Vascular injury may occur in any vessel in the subject, such as a coronary artery, a renal artery, a carotid artery, a dialysis fistulae artery or a peripheral artery.

The compounds of formula (I) may be used in preventing, reducing, or inhibiting neointima formation. The compounds of formula (I) may be used in preventing or reducing the occurrence of restenosis, for example following surgery.

Furthermore, the compounds of formula (I) may be used in conjunction with a medical device. A medical device may be treated prior to insertion or implantation with an effective amount of a compound of formula (I) or a composition comprising a compound of formula (I) in order to prevent, reduce, or inhibit neointima formation following insertion or implantation of the device or graft into the subject. The device can be a device that is inserted into the subject transiently, or a device that is implanted permanently. In some embodiments, the device is a surgical device. Examples of medical devices include, but are not limited to, needles, cannulas, catheters, shunts, balloons, and implants such as stents and valves.

Suitably, the compound of formula (I) may be used in conjunction with angioplasty. The medical device may be a balloon.

Suitably the subject is a mammal, in particular the subject is a human.

Pharmaceutical Compositions

For use in therapy the compounds of the invention are usually administered as a pharmaceutical composition. The invention also provides a pharmaceutical composition comprising a compound of formula (I), or a pharmaceutically acceptable salt and/or solvate (e.g. salt) and/or derivative thereof, and a pharmaceutically acceptable carrier or excipient.

In one embodiment, there is provided a pharmaceutical composition comprising a compound of formula (I), or a pharmaceutically acceptable salt and/or solvate (e.g. salt) and/or derivative thereof, for use in the treatment or prophylaxis of a disease or disorder as described herein.

In a further embodiment, there is provided a method for the prophylaxis or treatment of a disease or disorder as described herein, which comprises administering to a subject in need thereof an effective amount of a pharmaceutical composition comprising a compound of formula (I) or a pharmaceutically acceptable salt and/or solvate (e.g. salt) and/or derivative thereof.

The invention also provides the use of a pharmaceutical composition comprising a compound of formula (I), or a pharmaceutically acceptable salt and/or solvate thereof (e.g. salt) and/or derivative thereof, in the manufacture of a medicament for the treatment or prophylaxis of a disease or disorder as described herein.

The compounds of formula (I) or their pharmaceutically acceptable salts and/or solvates and/or derivatives thereof may be administered by any convenient method, e.g. by oral, parenteral, buccal, sublingual, nasal, rectal or transdermal administration, and the pharmaceutical compositions adapted accordingly.

The compounds of formula (I) or their pharmaceutically acceptable salts and/or solvates and/or derivatives thereof may be administered topically for example to the eye, gut or skin. Thus, in an embodiment there is provided a pharmaceutical composition comprising a compound of the invention optionally in combination with one or more topically acceptable diluents or carriers.

A pharmaceutical composition of the invention may be delivered topically to the skin. Compositions suitable for transdermal administration include ointments, gels and patches. Such a pharmaceutical composition may also suitably be in the form of a cream, lotion, foam, powder, paste or tincture.

The pharmaceutical composition may suitably include vitamin D3 analogues (e.g calcipotriol and maxacalcitol), steroids (e.g. fluticasone propionate, betamethasone valerate and clobetasol propionate), retinoids (e.g. tazarotene), coal tar and dithranol. Topical medicaments are often used in combination with each other (e.g. a vitamin D3 and a steroid) or with further agents such as salicylic acid.

A pharmaceutical composition of the invention may be delivered topically to the eye. Such a pharmaceutical composition may suitably be in the form of eye drops or an ointment.

A pharmaceutical composition of the invention may be delivered topically to the gut. Such a pharmaceutical composition may suitably be delivered orally, such as in the form of a tablet or a capsule, or rectally, such as in the form of a suppository.

Suitably, delayed release formulations are in the form of a capsule.

The compounds of formula (I) or their pharmaceutically acceptable salts and/or solvates and/or derivatives thereof which are active when given orally can be formulated as liquids or solids, e.g. as syrups, suspensions, emulsions, tablets, capsules or lozenges.

A liquid formulation will generally consist of a suspension or solution of the active ingredient (such as a compound of formula (I) or a pharmaceutically acceptable salt and/or solvate (e.g. salt) and/or derivative thereof) in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient (such as a compound of formula (I) or a pharmaceutically acceptable salt and/or solvate (e.g. salt) and/or derivative thereof) can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient (such as a compound of formula (I) or a pharmaceutically acceptable salt and/or solvate (e.g. salt) and/or derivative thereof) in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluoro-chloro-hydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Suitably, the composition is in unit dose form such as a tablet, capsule or ampoule.

The composition may for example contain from 0.1% to 100% by weight, for example from 10 to 60% by weight, of the active material, depending on the method of administration. The composition may contain from 0% to 99% by weight, for example 40% to 90% by weight, of the carrier, depending on the method of administration. The composition may contain from 0.05 mg to 2000 mg, for example from 1.0 mg to 500 mg, of the active material, depending on the method of administration. The composition may contain from 50 mg to 1000 mg, for example from 100 mg to 400 mg of the carrier, depending on the method of administration. The dose of the compound used in the treatment or prophylaxis of the aforementioned disorders will vary in the usual way with the seriousness of the disorders, the weight of the sufferer, and other similar factors. However, as a general guide suitable unit doses may be 0.05 mg to 1000 mg, more suitably 1.0 mg to 500 mg, and such unit doses may be administered more than once a day, for example two or three a day. Such therapy may extend for a number of weeks or months.

The invention provides, in a further aspect, a combination comprising a compound of formula (I) or a pharmaceutically acceptable, salt, solvate and/or derivative thereof (e.g. a combination comprising a compound of formula (I) or a pharmaceutically acceptable derivative thereof) together with a further pharmaceutically acceptable active ingredient or ingredients.

The invention provides a compound of formula (I), for use in combination with a further pharmaceutically acceptable active ingredient or ingredients.

When the compounds are used in combination with other therapeutic agents, the compounds may be administered separately, sequentially or simultaneously by any convenient route.

Optimal combinations may depend on the disease or disorder. Possible combinations include those with one or more active agents selected from the list consisting of: 5-aminosalicylic acid, or a prodrug thereof (such as sulfasalazine, olsalazine or bisalazide); corticosteroids (e.g. prednisolone, methylprednisolone, or budesonide); immunosuppressants (e.g. cyclosporin, tacrolimus, sirolimus, methotrexate, azathioprine mycophenolate mofetil, leflunomide, cyclophosphamide, 6-mercaptopurine or anti-lymphocyte (or thymocyte) globulins); anti-TNF-alpha antibodies (e.g., infliximab, adalimumab, certolizumab pegol or golimumab); anti-IL12/IL23 antibodies (e.g., ustekinumab); anti-IL6 or anti-IL6R antibodies, anti-IL17 antibodies or small molecule IL12/IL23 inhibitors (e.g., apilimod); Anti-alpha-4-beta-7 antibodies (e.g., vedolizumab); MAdCAM-1 blockers (e.g., PF-00547659); antibodies against the cell adhesion molecule alpha-4-integrin (e.g., natalizumab); antibodies against the IL2 receptor alpha subunit (e.g., daclizumab or basiliximab); JAK inhibitors including JAK1 and JAK3 inhibitors (e.g., tofacitinib, baricitinib, R348); Syk inhibitors and prodrugs thereof (e.g., fostamatinib and R-406); Phosphodiesterase-4 inhibitors (e.g., tetomilast); HMPL-004; probiotics; Dersalazine; semapimod/CPSI-2364; and protein kinase C inhibitors (e.g. AEB-071).

For cancer, the further pharmaceutically acceptable active ingredient may be selected from anthracyclins such as doxorubicin; anti-mitotic agents such as vinblastine, paclitaxel and docetaxel; alkylating agents, for example cisplatin, carboplatin, dacarbazine and cyclophosphamide; antimetabolites, for example 5-fluorouracil, cytosine arabinoside and hydroxyurea; intercalating agents for example adriamycin and bleomycin; topoisomerase inhibitors for example etoposide, topotecan and irinotecan; thymidylate synthase inhibitors for example raltitrexed; PI3 kinase inhibitors for example idelalisib; mTor inhibitors for example everolimus and temsirolimus; proteasome inhibitors for example bortezomib; histone deacetylase inhibitors for example panobinostat or vorinostat; and hedgehog pathway blockers such as vismodegib.

The further pharmaceutically acceptable active ingredient may be selected from tyrosine kinase inhibitors such as, for example, axitinib, dasatinib, erlotinib, imatinib, nilotinib, pazopanib and sunitinib.

Anticancer antibodies may be included in a combination therapy and may be selected from the group consisting of olaratumab, daratumumab, necitumumab, dinutuximab, traztuzumab emtansine, pertuzumab, obinutuzumab, brentuximab, ofatumumab, panitumumab, catumaxomab, bevacizumab, cetuximab, tositumomab, traztuzumab, gentuzumab ozogamycin and rituximab.

Compounds or pharmaceutical compositions of the invention may also be used in combination with radiotherapy.

Some of the combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations. The individual components of combinations may also be administered separately, through the same or different routes.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

Medical Devices

In an embodiment, compounds of the invention or pharmaceutical compositions comprising said compounds may be formulated to permit incorporation into the medical device, thus providing application of the compound or composition directly to the site to prevent or treat conditions disclosed herein.

In an embodiment, the compounds of the invention or pharmaceutical composition thereof is formulated by including it within a coating onto the medical device. There are various coatings that can be utilized such as, for example, polymer coatings that can release the compound over a prescribed time period. The compound, or a pharmaceutical composition thereof, can be embedded directly within the medical device. In some embodiments, the compound is coated onto or within the device in a delivery vehicle such as a microparticle or liposome that facilitates its release and delivery. In some embodiments, the compound or pharmaceutical composition is miscible in the coating.

In some embodiments, the medical device is a vascular implant such as a stent. Stents are utilized in medicine to prevent or eliminate vascular restrictions. The implants may be inserted into a restricted vessel whereby the restricted vessel is widened. Excessive growth of the adjacent cells following vascular implantation results in a restriction of the vessel particularly at the ends of the implants which results in reduced effectiveness of the implants. If a vascular implant is inserted into a human artery for the elimination of for example an arteriosclerotic stenosis, intimahyperplasia can occur within a year at the ends of the vascular implant and results in renewed stenosis ("restenosis").

Accordingly, in some embodiments, the stents are coated or loaded with a composition including a compound of the invention or pharmaceutical composition thereof and optionally a targeting signal, a delivery vehicle, or a combination thereof. Many stents are commercially available or otherwise know in the art.

In some embodiments, the stent is a drug-eluting stent. Various drug eluting stents that simultaneously deliver a therapeutic substance to the treatment site while providing artificial radial support to the wall tissue are known in the art. Endoluminal devices including stents are sometimes coated on their outer surfaces with a substance such as a drug releasing agent, growth factor, or the like. Stents have also been developed having a hollow tubular structure with holes or ports cut through the sidewall to allow drug elution from a central lumen. Although the hollow nature of the stent allows the central lumen to be loaded with a drug solution that is delivered via the ports or holes in the sidewall of the stent, the hollow tubular structure may not have suitable mechanical strength to provide adequate scaffolding in the vessel.

In some embodiments, the devices are also coated or impregnated with a compound of the invention, or pharmaceutical composition thereof and one or more additional therapeutic agents, including, but not limited to, antiplatelet agents, anticoagulant agents, anti-inflammatory agents, anti-microbial agents, antimetabolic agents, additional anti-neointima agents, additional antiproliferative agents, immunomodulators, antiproliferative agents, agents that affect migration and extracellular matrix production, agents that affect platelet deposition or formation of thrombis, and agents that promote vascular healing and re-endothelialization, such as those and others described in Sousa et al. (2003) and Salu et al. (2004).

Examples of antithrombin agents include, but are not limited to, Heparin (including low molecular heparin), R-Hirudin, Hirulog, Argatroban, Efegatran, Tick anticoagulant peptide, and Ppack.

Examples of antiproliferative agents include, but are not limited to, Paclitaxel (Taxol), QP-2 Vincristin, Methotrexat, Angiopeptin, Mitomycin, BCP 678, Antisense c-myc, ABT 578, Actinomycin-D, RestenASE, 1-Chlor-deoxyadenosin, PCNA Ribozym, and Celecoxib.

Examples of anti-restenosis agents include, but are not limited to, immunomodulators such as Sirolimus (Rapamycin), Tacrolimus, Biorest, Mizoribin, Cyclosporin, Interferon-γ Ib, Leflunomid, Tranilast, Corticosteroide, Mycophenolic acid and Biphosphonate.

Examples of anti-migratory agents and extracellular matrix modulators include, but are not limited to Halofuginone, Propyl-hydroxylase-Inhibitors, C-Proteinase-Inhibitors, MMP-Inhibitors, Batimastat, Probucol.

Examples of antiplatelet agents include, but are not limited to, heparin.

Examples of wound healing agents and endothelialization promoters include vascular epithelial growth factor ("VEGF"), 17-Estradiol, Tkase-Inhibitors, BCP 671, Statins, nitric oxide ("NO")-Donors, and endothelial progenitor cell ("EPC")-antibodies.

Besides coronary applications, drugs and active agents may be incorporated into the stent or stent coating for other indications. For example, in urological applications, antibiotic agents may be incorporated into the stent or stent coating for the prevention of infection. In gastroenterological and urological applications, active agents may be incorporated into the stent or stent coating for the local treatment of carcinoma. It may also be advantageous to incorporate in or on the stent a contrast agent, radiopaque markers, or other additives to allow the stent to be imaged in vivo for tracking, positioning, and other purposes. Such additives could be added to the absorbable composition used to make the stent or stent coating, or absorbed into, melted onto, or sprayed onto the surface of part or all of the stent. Preferred additives for this purpose include silver, iodine and iodine labelled compounds, barium sulfate, gadolinium oxide, bismuth derivatives, zirconium dioxide, cadmium, tungsten, gold tantalum, bismuth, platinum, iridium, and rhodium. These additives may be, but are not limited to, micro- or nano-sized particles or nano particles. Radio-opacity may be determined by fluoroscopy or by x-ray analysis.

A compound of the invention and one or more additional agents, or pharmaceutical composition thereof, can be incorporated into the stent, either by loading the compound and one or more additional agents, or pharmaceutical composition thereof into the absorbable material prior to processing, and/or coating the surface of the stent with the agent(s). The rate of release of agent may be controlled by a number of methods including varying the following the ratio of the absorbable material to the compound and one or more additional agents, or pharmaceutical composition, the molecular weight of the absorbable material, the composition of the compound and one or more additional agents, or pharmaceutical composition, the composition of the absorbable polymer, the coating thickness, the number of coating layers and their relative thicknesses, and/or the compound and one or more additional agents, or pharmaceutical composition concentration. Top coats of polymers and other materials, including absorbable polymers, may also be applied to active agent coatings to control the rate of release. For example, P4HB can be applied as a top coat on a metallic stent coated with P4HB including an active agent to retard the release of the active agent.

The invention is further exemplified by the following non-limiting examples.

EXAMPLES

Abbreviations used herein are defined below. Any abbreviations not defined are intended to convey their generally accepted meaning.

Table 1: Abbreviations

AcOH glacial acetic acid
AlMe$_3$ trimethylaluminium aq aqueous
Ar Aromatic ring
BEH ethylene bridged hybrid
Bispin Bis(pinacolato)diboron; 4,4,4',4',5,5,5',5'-Octamethyl-2,2'-bi-1,3,2-dioxaborolane
Bz benzyl ($CH_2$-phenyl)
Boc tert-butyloxycarbonyl
br broad
CatCart® catalytic cartridge
$Cs_2CO_3$ cesium carbonate
CSH charged surface hybrid
Cu (I) Copper(I) iodide
d doublet
DBU 1,8-diazabicyclo[5.4.0]undec-7-ene
DCM dichloromethane
DIPEA N,N-diisopropylethylamine
dioxane 1,4-dioxane
DMAP 4-(dimethylamino)pyridine
DMF N,N-dimethylformamide
DMSO (-d6) dimethyl sulfoxide (hexadeuterodimethyl sulfoxide)
dppf 1,1'-bis(diphenylphosphino)ferrocene
ee Enantiomeric excess
($ES^+$) electrospray ionisation, positive mode
($ES^-$) electrospray ionisation, negative mode
ESI electrospray ionisation
Et ethyl
$Et_2NH$ Diethyl amine
EtOAc ethyl acetate
EtOH ethanol
g grams
HATU 1-[bis(dimethylamino)methylene]-1H-1,2,3-triazolo[4,5-b]pyridinium 3-oxid hexafluorophosphate
HCl Hydrogen chloride
HPLC high performance liquid chromatography
hr(s) hour(s)
$IC_{50}$ 50% inhibitory concentration
IPA isopropyl alcohol
iPr isopropyl
$K_2CO_3$ potassium carbonate
KOAc Potassium acetate
LCMS liquid chromatography-mass spectrometry
LDA lithium diisopropylamide
LiOH lithium hydroxide
LiHMDS lithium bis(trimethylsilyl)amide
$(M+H)^+$ protonated molecular ion
$(M-H)^-$ unprotonated molecular ion
M molar concentration
mL millilitre
mmol millimole
$MgSO_4$ magnesium sulfate
Me methyl
MeCN acetonitrile
MeI iodomethane
MeMgBr Methylmagnesium bromide
MeOH methanol
MHz megahertz
min(s) minute(s)
MSD mass selective detector
m/z mass-to-charge ratio
$NaCNBH_4$ Sodium cyanoborohydride
NaH Sodium hydride
$NaHCO_3$ sodium bicarbonate
$Na_2S_2O_3$ sodium thiosulfate
NCS N-chlorosuccinimide
$NH_4OH$ ammonium hydroxide
nm nanometre
nM nanomolar
NMR nuclear magnetic resonance (spectroscopy)
OD optical density
PDA photodiode array
Pd 170 chloro(crotyl)(2-dicyclohexylphosphino-2',4',6'-triisopropybiphenyl)palladium(II) or XPhos Pd(crotyl) Cl
Pd 174 allyl(2-di-tert-butylphosphino-2',4',6'-triisopropyl-1,1'-biphenyl)palladium(II) triflate or [tBuXPhos-Pd(allyl)]OTf
Pd 177 (4,5-bis(diphenylphosphino)-9,9-dimethylxanthene)(allyl)palladium(II) chloride or [XantPhosPd(allyl)]Cl
$PdCl_2$(dppf) [1,1'-bis(diphenylphosphino)ferrocene]dichloropalladium(II)
$Pd(PPh_3)_4$ tetrakis(triphenylphosphine)palladium(0)
$Pd(PPh_3)_2Cl_2$ Bis(triphenylphosphine)palladium(II) dichloride
$Pd(t-Bu_3P)_2$ bis(tri-tert-butylphosphine)palladium(0)
prep HPLC preparative high performance liquid chromatography
Ph phenyl
PMB para-methoxybenzyl
q quartet
RT room temperature
Rt retention time
RP reverse phase
s singlet
sat saturated
SCX solid supported cation exchange (resin)
SDS sodium dodecyl sulphate
t triplet
T3P 2,4,6-tripropyl-1,3,5,2,4,6-trioxatriphosphorinane-2,4,6-trioxide
TBME Tert-butyl methyl ether
tBuXPhos-Pd-G3 [(2-di-tert-butylphosphino-2',4',6'-triisopropyl-1,1'-biphenyl)-2-(2'-amino-1,1'-biphenyl)] palladium(II) methanesulfonate
THF tetrahydrofuran
UPLC ultra performance liquid chromatography
UV ultraviolet
v/v volume/volume
VWD variable wave detector
um micrometre
uM micromolar
uL microlitre
° C. degrees Celsius General Procedures All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated.

Column chromatography was performed on pre-packed silica (230-400 mesh, 40-63 um) cartridges using the amount indicated. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 0.7M $NH_3$ in MeOH.

Preparative Reverse Phase High Performance Liquid Chromatography

Prep HPLC

Acidic Prep

Waters X-Select CSH column C18, 5 um (19×50 mm), flow rate 28 mL min$^{-1}$ eluting with a H$_2$O-MeCN gradient containing 0.1% v/v formic acid over 6.5 min using UV detection at 254 nm.

Basic Prep

Waters X-Bridge Prep column C18, 5 um (19×50 mm), flow rate 28 mL min$^{-1}$ eluting with a 10 mM NH$_4$HCO$_3$-MeCN gradient over 6.5 min using UV detection at 254 nm.

Analytical Methods

Reverse Phase HPLC Conditions for the LCMS Analytical Methods

HPLC acidic: Acidic LCMS 4 minute (5-95%)

Analytical LCMS was carried out using a Waters X-Select CSH C18, 2.5 um, 4.6×30 mm column eluting with a gradient of 0.1% Formic acid in MeCN in 0.1% Formic acid in water. The gradient from 5-95% 0.1% Formic acid in MeCN occurs between 0.00-3.00 minutes at 2.5 mL/min with a flush from 3.01-3.5 minutes at 4.5 mL/min. A column re-equilibration to 5% MeCN is from 3.60-4.00 minutes at 2.5 mL/min. UV spectra of the eluted peaks were measured using an Agilent 1260 Infinity VWD at 254 nm. Mass spectra were measured using an Agilent 6120 MSD running with positive/negative switching.

HPLC basic: Basic LCMS 4 minute (5-95%)

Analytical LCMS was carried out using a Waters X-Select BEH C18, 2.5 um, 4.6×30 mm column eluting with a gradient of MeCN in aqueous 10 mM ammonium bicarbonate. The gradient from 5-95% MeCN occurs between 0.00-3.00 minutes at 2.5 mL/min with a flush from 3.01-3.5 minutes at 4.5 mL/min. A column re-equilibration to 5% MeCN is from 3.60-4.00 minutes at 2.5 mL/min. UV spectra of the eluted peaks were measured using an Agilent 1260 Infinity VWD at 254 nm. Mass spectra were measured using an Agilent 6120 MSD running with positive/negative switching.

Reverse Phase HPLC Conditions for the UPLC Analytical Methods

UPLC acidic: Acidic UPLC 3 minute

Analytical UPLC/MS was carried out using a Waters Acquity CSH C18, 1.7 um, 2.1×30 mm column eluting with a gradient of 0.1% Formic acid in MeCN in 0.1% Formic acid in water. The gradient is structured with a starting point of 5% MeCN held from 0.0-0.11 minutes. The gradient from 5-95% occurs between 0.11-2.15 minutes with a flush from 2.15-2.56 minutes. A column re-equilibration to 5% MeCN is from 2.56-2.83 minutes. UV spectra of the eluted peaks were measured using an Acquity PDA and mass spectra were recorded using an Acquity QDa detector with ESI pos/neg switching.

UPLC Basic: Basic UPLC 3 Minute

Analytical UPLC/MS was carried out using a Waters Acquity BEH C18, 1.7 um, 2.1×30 mm column eluting with a gradient of MeCN in aqueous 10 mM Ammonium Bicarbonate. The gradient is structured with a starting point of 5% MeCN held from 0.0-0.11 minutes. The gradient from 5-95% occurs between 0.11-2.15 minutes with a flush from 2.15-2.56 minutes. A column re-equilibration to 5% MeCN is from 2.56-2.83 minutes. UV spectra of the eluted peaks were measured using an Acquity PDA and mass spectra were recorded using an Acquity QDa detector with ESI pos/neg switching.

Column temperature is 40° C. in all runs. Injection volume is 3 uL and the flow rate is 0.77 mL/min. PDA scan from 210-400 nm on all runs.

Normal Phase HPLC Conditions for the Chiral Analytical Methods

Chiral IA method: Chiral HPLC (Diacel Chiralpak IA, 5 um, 4.6×250 mm, 1.0 mL/min, 30% EtOH in [4:1 isohexane (0.2% TFA): DCM].

Chiral IA2 method: Chiral HPLC (Diacel Chiralpak IA, 5 um, 4.6×250 mm, 1.0 mL/min, 30% EtOH (0.1% formic acid) in DCM (0.1% formic acid).

Chiral IC method: Chiral HPLC (Diacel Chiralpak IC, 5 um, 4.6×250 mm, 1.0 mL/min, 30% EtOH (0.2% TFA) in [4:1 isohexane (0.2% TFA):CHCl$_3$.

Chiral IC2 method: Chiral HPLC (Diacel Chiralpak IC, 5 um, 4.6×250 mm, 1.0 mL/min, gradient 2-50% EtOH (0.2% TFA) in heptane (0.2% TFA)/CHCl$_3$ (4:1).

Chiral IC3 method: Chiral HPLC (Diacel Chiralpak IC, 5 um, 4.6×250 mm, 1.0 mL/min, 40% EtOH (0.2% TFA) in isohexane (0.2% TFA).

$^1$H NMR Spectroscopy $^1$H NMR spectra were acquired on a Bruker Avance III spectrometer at 400 MHz or Bruker Avance III HD spectrometer at 500 MHz using residual undeuterated solvent as reference and unless specified otherwise were run in DMSO-d6.

Preparation of Intermediates

Known synthetic intermediates were procured from commercial sources or were obtained using published literature procedures. Additional intermediates were prepared by the representative synthetic processes described herein.

Thiazole Intermediate Preparation

Ethyl 2-(2-aminothiazol-4-yl)propanoate INTB1

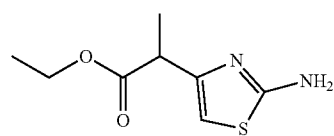

To a solution of ethyl 2-methyl-3-oxobutanoate (3.93 mL, 27.7 mmol) in chloroform (40 mL) protected from light was added pyridinium tribromide (9.34 g, 27.7 mmol). The reaction was heated to 40° C. for 2 hrs. The reaction mixture was concentrated in vacuo. This was then taken up in EtOH (40 mL) and thiourea (2.11 g, 27.7 mmol) was added. The reaction was heated to 70° C. and after 2 hrs the reaction mixture was allowed to cool to RT. This was then concentrated and heated to reflux in EtOAc (10 mL) for 30 min before being allowed to cool to RT. This was then concentrated onto silica. The crude product was purified by chromatography on silica gel (120 g column, 10-70% EtOAc/iso-hexane) to afford ethyl 2-(2-aminothiazol-4-yl)propanoate (2.8 g, 12.58 mmol, 45% yield) as a yellow gum; Rt 0.83 min (UPLC basic); m/z 201 (M+H)$^+$ (ES$^+$); $^1$H NMR (400 MHz, DMSO-d6) δ 6.91 (s, 2H), 6.28 (d, J=0.8 Hz, 1H), 4.13-3.93 (m, 2H), 3.62-3.46 (m, 1H), 1.32 (d, J=7.1 Hz, 3H), 1.16 (t, J=7.1 Hz, 3H).

Methyl 2-(2-aminothiazol-4-yl)-2-methylpropanoate INTB2

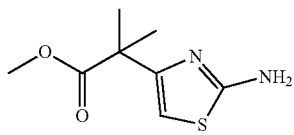

To a solution of methyl 2,2-dimethyl-3-oxobutanoate (9.01 mL, 62.4 mmol) in MeOH (70 mL) at 0° C. was added bromine (4.82 mL, 94 mmol) dropwise over 10 min. The reaction was stirred at 0° C. for 10 min. The reaction mixture was then heated at 30° C. for 2 hrs. After cooling to RT, the reaction mixture was diluted with water (100 mL) was concentrated in vacuo. The product was extracted using EtOAc (3×100 mL). The combined organics were dried (Na$_2$SO$_4$) and concentrated in vacuo. The resulting orange oil was dissolved in MeOH (50 mL) and thiourea (4.75 g, 62.4 mmol) was added. The reaction mixture was heated at 40° C. for 1 hr, then stirred at RT for 18 hrs. The reaction mixture was concentrated vacuo to give a pale yellow solid. The residue was recrystallised from MeOH (40 mL). The resultant solid was filtered, rinsed with MeOH (10 mL), and dried in vacuo to afford methyl 2-(2-aminothiazol-4-yl)-2-methylpropanoate (10.4 g, 50.8 mmol, 81% yield) as a colourless solid; Rt 0.85 min (UPLC basic); m/z 201 (M+H)$^+$ (ES$^+$); $^1$H NMR (400 MHz, DMSO-d6) δ 6.92 (s, 2H), 6.28 (s, 1H), 3.55 (s, 3H), 1.40 (s, 6H).

Ethyl 2-(2-aminothiazol-4-yl)butanoate INTB3

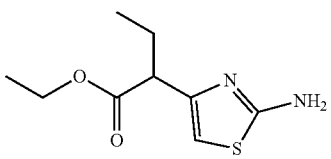

Bromine (5.13 mL, 100 mmol) was added dropwise (over 10 min) to a solution of ethyl 2-ethyl-3-oxobutanoate (10.5 g, 66.4 mmol) in EtOH (70 mL) at 0° C. The reaction was stirred at 0° C. for 10 mins then heated to 30° C. for 2 hrs. The reaction mixture was cooled to RT. The solvent was removed in vacuo and then diluted with water (100 mL) and EtOAc (100 mL). The aqueous phase was extracted further with EtOAc (2×100 mL) and the combined organic phases were passed through a phase separator and solvent removed in vacuo. This was dissolved in EtOH (50 mL) and thiourea (5.05 g, 66.4 mmol) was added. The reaction mixture was heated at 40° C. for 1 hr, then stirred at RT for 18 hrs. The reaction mixture was concentrated in vacuo, then EtOAc (100 mL) was added. The organic phase was washed with a solution of Na$_2$S$_2$O$_3$ (aq. 100 mL), NaHCO$_3$ (aq. 100 mL), passed through a phase separator and solvent removed in vacuo. The crude product was purified by chromatography on silica gel (120 g column, 0-100% EtOAc/iso-hexane) to afford ethyl 2-(2-aminothiazol-4-yl)butanoate (6.18 g, 28.0 mmol, 42% yield) as a pale yellow solid; Rt 0.88 min (HPLC acidic); m/z 215 (M+H)$^+$ (ES$^+$); $^1$H NMR (400 MHz, DMSO-d6) δ 6.91 (s, 2H), 6.28 (s, 1H), 4.15-3.97 (m, 2H), 3.37 (t, J=7.3 Hz, 1H), 1.92-1.70 (m, 2H), 1.16 (t, J=7.1 Hz, 3H), 0.83 (t, J=7.4 Hz, 3H).

Method A: Formation of Thiazole Amines from Ketoesters

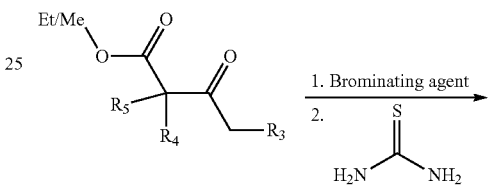

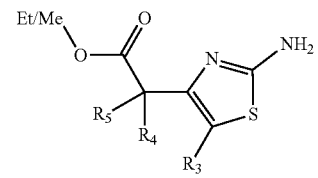

To a solution of ketoester (1 eq) in an alcoholic solvent such as MeOH or EtOH (1 volume) at 0° C. was added bromine (1.5 eq) dropwise over 10 mins. The reaction was stirred at 0° C. for 10 mins. The reaction mixture was then heated at 30° C. for 2 hrs. After cooling to RT the reaction mixture was diluted with water. The product was extracted using an appropriate solvent such as EtOAc. The combined organics were dried (Na$_2$SO$_4$) and concentrated in vacuo. The resulting compound was dissolved in alcoholic solvent such as MeOH or EtOH (1 volume) and thiourea (1 eq) was added. The reaction mixture was heated at 40° C. for 1 hr, then stirred at RT for 18 hrs.

The reaction mixture was concentrated in vacuo and purified by normal phase chromatography or via trituration with an appropriate solvent.

TABLE 2

Additional intermediates made according to Method A.

| INTB# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| INTB4 | ethyl 2-(2-aminothiazol-4-yl)-3-methylbutanoate | Method A, [HPLC basic], 299, (1.77). | 6.91 (s, 2H), 6.31 (s, 1H), 4.14-3.96 (m, 2H), 3.16 (d, J = 9.7 Hz, 1H), 2.25 (dp, J = 9.6, 6.7 Hz, 1H), 1.20-1.11 (m, 3H), 0.91 (d, J = 6.7 Hz, 3H), 0.77 (d, J = 6.7 Hz, 3H). |
| INTB5 | methyl 2-(2-amino-5-methylthiazol-4-yl)-2-methylpropanoate | Method A, [UPLC acidic], 215, (0.46). | 6.60 (s, 2H), 3.61 (s, 3H), 2.00 (s, 3H), 1.41 (s, 6H). |
| INTB6 | ethyl 2-(2-aminothiazol-4-yl)-4-methoxybutanoate | Method A, [UPLC acidic], 245, (0.44). | 6.96 (s, 2H), 6.30 (s, 1H), 4.15-3.90 (m, 2H), 3.57 (t, J = 7.4 Hz, 1H), 3.29-3.23 (m, 2H), 3.19 (s, 3H), 2.17-1.83 (m, 2H), 1.15 (t, J = 7.1 Hz, 3H). |
| INTB61 | ethyl 2-(2-aminothiazol-4-yl)-2-ethylbutanoate | Method A, [UPLC basic], 243, (1.24). | 8.58 (v. br, 2H), 6.73 (s, 1H), 4.20-4.00 (m, 2H), 1.89 (q, J = 7.0, 5.7 Hz, 4H), 1.22-1.13 (m, 3H), 0.71 (t, J = 7.1 Hz, 6H). |

Methyl 2-(2-((tert-butoxycarbonyl)(4-methoxybenzyl)amino)thiazol-4-yl)acetate INTB7

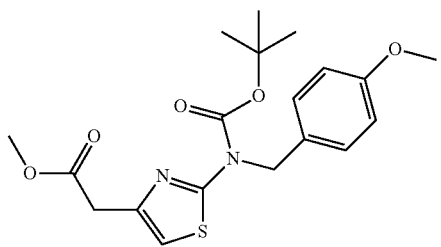

A solution of methyl 2-(2-((tert-butoxycarbonyl)amino)thiazol-4-yl)acetate (7.3 g, 26.8 mmol) in DCM (100 mL) was treated with DBU (7.84 mL, 52.0 mmol) and 1-(bromomethyl)-4-methoxybenzene (3 mL, 20.8 mmol). The solution was then stirred at RT for 18 hrs. 1M HCl (aq, 100 mL) was added and the mixture was passed through a phase separator, further extracting with DCM (50 mL). The organic phases were combined and concentrated on to silica (20 g). The crude product was purified by chromatography on silica gel (80 g column, 0-20% EtOAc/isohexane) to afford methyl 2-(2-((tert-butoxycarbonyl)(4-methoxybenzyl)amino)thiazol-4-yl)acetate (2.5 g, 6.24 mmol, 30.0% yield) as an off-white gum; Rt 1.76 mins (UPLC acidic); m/z 415 (M+Na)+ (ES+); 1H NMR (400 MHz, DMSO-d6) δ 7.31-7.22 (m, 2H), 7.02 (s, 1H), 6.93-6.76 (m, 2H), 5.13 (s, 2H), 3.71 (s, 3H), 3.71-3.70 (m, 2H), 3.62 (s, 3H), 1.47 (s, 9H).

Methyl 2-(2-((tert-butoxycarbonyl)(4-methoxyben-zyl)amino)thiazol-4-yl)-2-diazoacetate INTB8

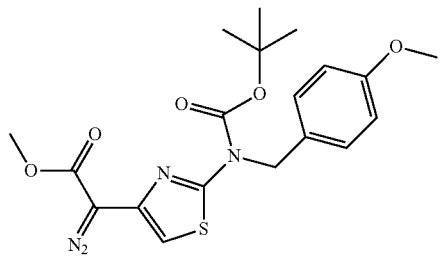

A solution of methyl 2-(2-((tert-butoxycarbonyl)(4-methoxybenzyl)amino)thiazol-4-yl)acetate INTB7 (2.4 g, 6.12 mmol) in MeCN (30 mL) was treated with 4-methyl-benzenesulfonyl azide (30% wt. in toluene) (4.42 mL, 6.73 mmol) followed by dropwise addition of DBU (1.383 mL, 9.17 mmol). The reaction mixture was allowed to stir for 1 hr. The mixture was poured onto ice/water (50 mL) and extracted with EtOAc (3×50 mL). The organic phases were combined, dried (Na$_2$SO$_4$), filtered and concentrated on to silica (10 g). The crude product was purified by chromatography on silica gel (40 g column, 0-15% EtOAc/isohexane) to afford methyl 2-(2-((tert-butoxycarbonyl)(4-methoxybenzyl)amino)thiazol-4-yl)-2-diazoacetate (2.01 g, 4.71 mmol, 77% yield) as a yellow gum; Rt 2.02 mins (UPLC acidic); m/z 441 (M+Na)$^+$ (ES$^+$); $^1$H NMR (400 MHz, DMSO-d6) δ 7.36-7.16 (m, 3H), 6.99-6.76 (m, 2H), 5.10 (s, 2H), 3.81 (s, 3H), 3.72 (s, 3H), 1.51 (s, 9H).

Methyl 2-(2-((tert-butoxycarbonyl)(4-methoxyben-zyl)amino)thiazol-4-yl)-2-methoxyacetate INTB9

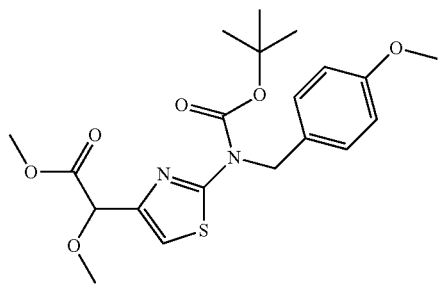

A solution of methyl 2-(2-((tert-butoxycarbonyl)(4-methoxybenzyl)amino)thiazol-4-y)-2-diazoacetate INTB8 (2 g, 4.78 mmol) in DCM (25 mL) was treated with MeOH (0.23 mL, 5.74 mmol), then rhodium(II) acetate dimer (0.042 g, 0.10 mmol) was added resulting in effervescence. After 5 mins the reaction mixture was diluted with DCM (25 mL) and washed with water (50 mL) and brine (50 mL). The organic phase was dried (Na$_2$SO$_4$), filtered and concentrated onto silica (5 g) then the crude product was purified by chromatography on silica gel (24 g column, 0-15% EtOAc/isohexane) to afford methyl 2-(2-((tert-butoxycarbonyl)(4-methoxybenzyl)amino)thiazol-4-yl)-2-methoxyacetate (1.68 g, 3.78 mmol, 79% yield) as a colourless oil; Rt 1.69 mins (UPLC acidic); m/z 445 (M+Na)$^+$ (ES$^+$); $^1$H NMR (400 MHz, DMSO-d6) δ 7.30-7.20 (m, 3H), 6.90-6.83 (m, 2H), 5.17-5.02 (m, 2H), 4.98 (s, 1H), 3.71 (s, 3H), 3.64 (s, 3H), 3.31 (s, 3H), 1.49 (s, 9H).

Methyl 2-(2-aminothiazol-4-yl)-2-methoxyacetate INTB10

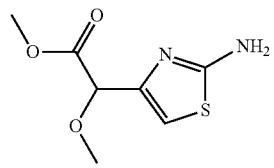

Methyl 2-(2-((tert-butoxycarbonyl)(4-methoxybenzyl)amino)thiazol-4-yl)-2-methoxyacetate INTB9 (1.68 g, 3.78 mmol) was taken up in TFA (7 mL, 91 mmol) and heated to reflux for 5 hrs. The reaction mixture was concentrated in vacuo, then taken up in EtOAc (30 mL) and sat. NaHCO$_3$ (sat. aq, 30 mL), the phases were partitioned and the organic phase was washed with brine (20 mL). The organic phase was then dried (MgSO$_4$), filtered and concentrated on to silica (5 g). The crude product was purified by chromatography on silica gel (24 g column, 0-40% EtOAc/isohexane) to afford methyl 2-(2-aminothiazol-4-yl)-2-methoxyacetate (548 mg, 2.66 mmol, 56% yield) as an off-white solid; Rt 0.31 mins (HPLC acidic); m/z not recorded; $^1$H NMR (400 MHz, DMSO-d6) δ 7.00 (s, 2H), 6.55 (s, 1H), 4.72 (s, 1H), 3.32 (s, 3H), 3.27 (s, 3H).

Methyl 2-(2-bromothiazol-4-yl)-2-diazoacetate INTB11

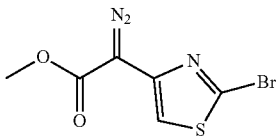

A solution of methyl 2-(2-bromothiazol-4-yl)acetate (2.5 g, 10.6 mmol) in MeCN (80 mL) was treated with 4-acet-amidobenzenesulfonyl azide (2.80 g, 11.7 mmol) followed by dropwise addition of DBU (2.394 mL, 15.88 mmol). The reaction was then allowed to stir at RT for 5 mins. The reaction mixture was then poured onto ice/water (100 mL). The aqueous layer was extracted with EtOAc (3×50 mL), the organic phases were combined, dried (MgSO$_4$), filtered and concentrated in vacuo. The crude product was purified by chromatography on silica gel (24 g column, 0-10% EtOAc/isohexane) to afford methyl 2-(2-bromothiazol-4-yl)-2-diazoacetate (1.85 g, 6.92 mmol, 65% yield) as a yellow solid; Rt 1.46 mins (HPLC acidic); m/z 262 ($^{79}$Br M+H)$^+$ (ES$^+$); $^1$H NMR (400 MHz, DMSO-d6) δ 7.65 (s, 1H), 3.82 (s, 3H).

Methyl 2-(2-bromothiazol-4-yl)-2-isopropoxyacetate INTB12

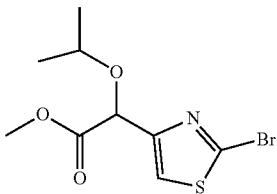

A solution of methyl 2-(2-bromothiazol-4-yl)-2-diazoacetate INTB11 (475 mg, 1.81 mmol) in DCM (25 mL) was treated with IPA (0.140 mL, 1.81 mmol) then rhodium(II) acetate dimer (4 mg, 9.05 umol) was added resulting in effervescence. After 5 mins the reaction mixture was diluted with DCM (25 mL) and washed with water (50 mL) and brine (50 mL). The organic phase was dried ($Na_2SO_4$), filtered and concentrated on to silica (5 g) then the crude product was purified by chromatography onto silica gel (24 g column, 0-15% EtOAc/isohexane) to afford methyl 2-(2-bromothiazol-4-yl)-2-isopropoxyacetate (297 mg, 0.99 mmol, 55% yield) as a colourless oil; Rt 1.22 mins (UPLC acidic); m/z 316 ($^{79}$Br M+Na)$^+$ (ES$^+$); $^1$H NMR (400 MHz, DMSO-d6) δ 7.76 (d, J=0.6 Hz, 1H), 5.26 (s, 1H), 3.73-3.68 (m, 1H), 3.66 (s, 3H), 1.14 (d, J=6.1 Hz, 3H), 1.11 (d, J=6.1 Hz, 3H).

2-(2-(cyclopropanesulfonamido)thiazol-4-yl)-2-isopropoxyacetic acid INTB13

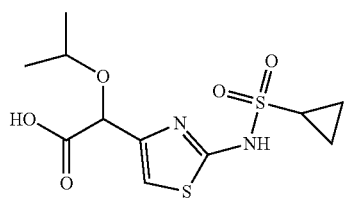 [SMILES: CC(C)OC(C(=O)O)c1csc(NS(=O)(=O)C2CC2)n1]

A suspension of methyl 2-(2-bromothiazol-4-yl)-2-isopropoxyacetate INTB12 (295 mg, 1 mmol), cyclopropanesulfonamide (146 mg, 1.2 mmol) and cesium carbonate (653 mg, 2 mmol) in dioxane (20 mL) at 40° C. was degassed ($N_2$, 5 mins) then Pd 174 (36.2 mg, 0.05 mmol) was added. The mixture was further degassed ($N_2$, 5 mins) before being warmed to 90° C. The reaction was left at 90° C. for 16 hrs. The reaction mixture was allowed to cool to RT then acidified carefully with 1M HCl (aq, 5 mL). This was then extracted with EtOAc (3×40 mL), the organic phases were combined, dried ($Na_2SO_4$), filtered and concentrated on to silica (1 g). The crude product was purified by chromatography on silica gel (24 g column, 0-100% EtOAc (5% MeOH)/iso-hexane) to afford 2-(2-(cyclopropanesulfonamido)thiazol-4-yl)-2-isopropoxyacetic acid (59 mg, 0.19 mmol, 19% yield) as a brown solid; Rt 1.39 mins (HPLC acidic); m/z 321 (M+H)$^+$ (ES$^+$).

Ethyl 2-(2-aminothiazol-4-yl)-2,2-difluoroacetate hydrochloride INTB14

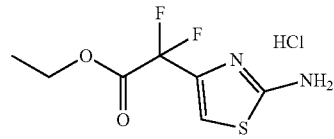

A solution of ethyl 2-(2-((tert-butoxycarbonyl)amino)thiazol-4-yl)-2,2-difluoroacetate (1.6 g, 4.96 mmol) in 4M HCl (dioxane, 12.4 mL, 49.6 mmol) was stirred at RT for 18 hrs. The reaction mixture was concentrated to afford ethyl 2-(2-aminothiazol-4-yl)-2,2-difluoroacetate, HCl (1.3 g, 4.77 mmol, 96% yield) as a colourless solid; Rt 0.95 min (UPLC acidic); m/z 223 (M+H)$^+$ (ES$^+$); $^1$H NMR (400 MHz, DMSO-d6) δ 7.83 (v. br. s, 3H), 7.09 (t, J=1.4 Hz, 1H), 4.30 (q, J=7.1 Hz, 2H), 1.24 (t, J=7.1 Hz, 3H). $^{19}$F NMR (376 MHz, DMSO-d6) 5-101.55 (d, J=1.5 Hz).

Methyl 2-(2-(methylsulfonamido)thiazol-4-yl)acetate INTB15

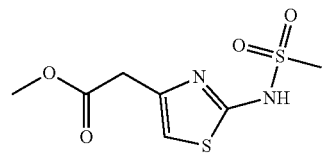

A solution of methyl 2-(2-aminothiazol-4-yl)acetate (3.56 g, 20.7 mmol) and DMAP (0.25 g, 2.07 mmol) in pyridine (16.74 mL, 207 mmol) was cooled to 0° C. whereupon methanesulfonyl chloride (1.61 mL, 20.70 mmol) was added dropwise. The yellow solution was allowed to warm to RT and stirred for 1 hr then added to 1 M HCl (aq, 228 mL) and stirred for 30 min. The resulting precipitate was then filtered and washed with $Et_2O$ (10 mL) to afford a yellow solid. This was slurried in $Et_2O$ (20 mL) and filtered to afford methyl 2-(2-(methylsulfonamido)thiazol-4-yl)acetate (3.56 g, 13.94 mmol, 67% yield) as a colourless solid; Rt 0.83 min (HPLC acidic); m/z 251 (M+H)$^+$ (ES$^+$); 249 (M–H)$^-$ (ES$^-$); $^1$H NMR (400 MHz, DMSO-d6) δ 12.47 (s, 1H), 6.60 (s, 1H), 3.67 (d, J=0.9 Hz, 2H), 3.66 (s, 3H), 2.90 (s, 3H).

Methyl 2-(2-(cyclopropanesulfonamido)thiazol-4-yl)acetate INTB16

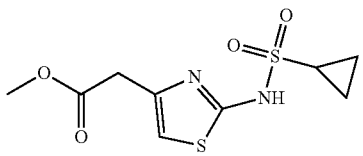 [SMILES: COC(=O)Cc1csc(NS(=O)(=O)C2CC2)n1]

A solution of methyl 2-(2-aminothiazol-4-yl)acetate (6.7 g, 38.9 mmol) and cyclopropanesulfonyl chloride (4.33 mL, 42.8 mmol) in pyridine (19 mL) was warmed to 40° C. and stirred for 18 hrs. The reaction mixture was diluted with pyridine (10 mL) and DMSO (40 mL) and the crude product was purified by chromatography on C18-RP silica gel (330 g column, 10-20% MeCN/10 mM Ammonium bicarbonate) to afford the required product. This was then triturated with MeOH (20 mL) and filtered to afford methyl 2-(2-(cyclopropanesulfonamido)thiazol-4-yl)acetate (2.4 g, 8.51 mmol, 22% yield) as a colourless solid; Rt 0.69 min (UPLC acidic); m/z 277 (M+H)$^+$ (ES$^+$); $^1$H NMR (400 MHz, DMSO-d6) δ 12.52 (s, 1H), 6.57 (s, 1H), 3.67 (s, 2H), 3.66 (s, 3H), 2.62-2.54 (m, 1H), 0.91-0.88 (m, 4H).

Methyl 2-(2-(cyclopropanesulfonamido)thiazol-4-yl)-2-methylpropanoate INTB17

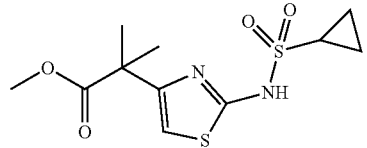 [SMILES: COC(=O)C(C)(C)c1csc(NS(=O)(=O)C2CC2)n1]

A solution of methyl 2-(2-aminothiazol-4-yl)-2-methylpropanoate INTB2 (3.99 g, 19.9 mmol) in pyridine (9.67 mL) was heated to 40° C. Cyclopropanesulfonyl chloride (2.22 mL, 21.9 mmol) was added dropwise. The reaction mixture was cooled to RT after 1 hr. The reaction mixture was poured onto 1M HCl (aq, 120 mL) and diluted with DCM (50 mL), the phases were separated and the aqueous was extracted with DCM (2×50 mL). The combined organics were dried (Na$_2$SO$_4$) and concentrated in vacuo. The crude product was purified by chromatography on silica gel (80 g column, 20-80% EtOAc/iso-hexane). The resulting solid was recrystallised from MeOH (10 mL), filtered, rinsing with MeOH and dried in vacuo to afford methyl 2-(2-(cyclopropanesulfonamido)thiazol-4-yl)-2-methylpropanoate (1.41 g, 4.4 mmol, 22%) as a pale brown crystalline solid; Rt 0.76 min (UPLC basic); m/z 305 (M+H)$^+$ (ES$^+$); $^1$H NMR (400 MHz, DMSO-d6) δ 12.62 (s, 1H), 6.56 (s, 1H), 3.65 (s, 3H), 2.71-2.57 (m, 1H), 1.46 (s, 6H), 1.00-0.81 (m, 4H).

Ethyl 2-(2-(cyclopropanesulfonamido)thiazol-4-yl)butanoate INTB18

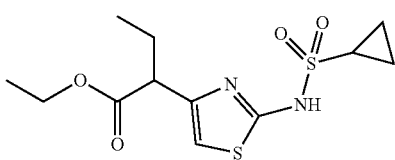 [SMILES: CCOC(=O)C(CC)c1csc(NS(=O)(=O)C2CC2)n1]

Ethyl 2-(2-aminothiazol-4-yl)butanoate INTB3 (3.8 g, 17.7 mmol) in pyridine (7.17 mL) at 40° C. was treated with cyclopropanesulfonyl chloride (1.88 mL, 18.6 mmol) and stirred for 18 hrs. The mixture was cooled to RT then cyclopropanesulfonyl chloride (0.5 mL, 4.94 mmol) was added and the mixture stirred for another 3 hrs. The reaction mixture was then taken up in EtOAc (100 mL) and washed with 1M HCl (aq, 106 mL) and brine (80 mL) before being dried (Na$_2$SO$_4$), filtered and concentrated on to silica. The crude product was purified by chromatography on silica gel (80 g column, 10-40% EtOAc/iso-hexane) to afford ethyl 2-(2-(cyclopropanesulfonamido)thiazol-4-yl)butanoate (2 g, 5.70 mmol, 32% yield) as a red gum; Rt 1.04 min (UPLC acidic); m/z 319 (M+H)$^+$ (ES$^+$); $^1$H NMR (400 MHz, DMSO-d6) δ 12.59 (s, 1H), 6.58 (s, 1H), 4.18-4.07 (m, 2H), 3.61-3.53 (m, 1H), 2.64-2.55 (m, 1H), 1.98-1.76 (m, 2H), 1.22-1.15 (m, 3H), 0.94-0.88 (m, 4H), 0.85 (t, J=7.4 Hz, 3H).

Ethyl 2-(2-(cyclopropanesulfonamido)thiazol-4-yl)-3-methylbutanoate INTB19

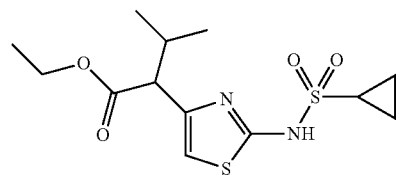 [SMILES: CCOC(=O)C(c1csc(NS(=O)(=O)C2CC2)n1)C(C)C]

Cyclopropanesulfonyl chloride (1.55 mL, 15.3 mmol) was added to a solution of ethyl 2-(2-aminothiazol-4-yl)-3-methylbutanoate INTB4 (3.50 g, 15.3 mmol) in pyridine (6.2 mL). The reaction was stirred at RT for 18 hrs. The reaction was poured onto 1M HCl (aq, 92 mL) and the product was extracted with DCM (3×20 mL). The combined organic phases were passed through a phase separator and solvent removed to give a brown oil. The crude product was purified by chromatography on silica gel (220 g column, 0-100% EtOAc/iso-hexane) to afford ethyl 2-(2-(cyclopropanesulfonamido)thiazol-4-yl)-3-methylbutanoate (1.02 g, 2.91 mmol, 19% yield) as an orange oil; Rt 1.81 min (HPLC acidic); m/z 333 (M+H)$^+$ (ES$^+$); 331 (M−H)$^−$ (ES$^−$); $^1$H NMR (400 MHz, DMSO-d6) δ 12.59 (s, 1H), 6.61 (s, 1H), 4.24-4.05 (m, 2H), 3.33 (d, J=9.4 Hz, 1H, partially obscured by solvent), 2.64-2.54 (m, 1H), 2.36-2.21 (m, 1H), 1.20 (t, J=7.1 Hz, 3H), 0.97-0.87 (m, 7H), 0.82 (d, J=6.7 Hz, 3H).

Method B: Formation of Sulfonamides from Sulfonyl Chlorides

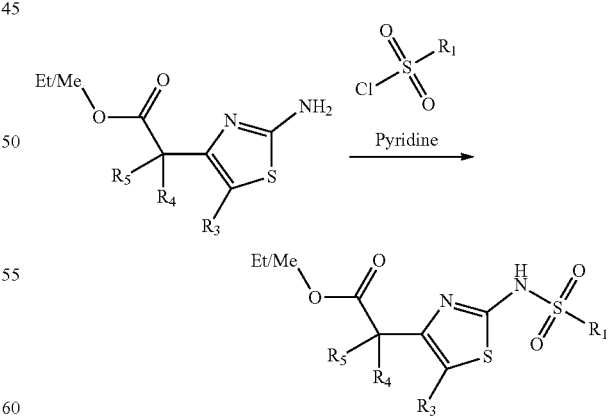

A solution of amine (1.0 eq) and appropriate sulfonyl chloride (1.1 eq) in pyridine (3M volumes) was warmed to 40° C. and stirred for 18 hrs. The reaction mixture was purified by normal or reverse phase chromatography or via trituration with an appropriate solvent.

TABLE 3

| INTB# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| INTB20 | ethyl 2-(2-(cyclopropanesulfonamido)thiazol-4-yl)propanoate | Method B, using INTB1, [HPLC acidic], 305, (1.50). | 12.60 (s, 1H), 6.56 (s, 1H), 4.18-4.00 (m, 2H), 3.83-3.69 (m, 1H), 2.64-2.54 (m, 1H), 1.41 (d, J = 7.3 Hz, 3H), 1.20 (t, J = 7.1 Hz, 3H), 0.96-0.79 (m, 4H). |
| INTB21 | ethyl 2-(2-(cyclopropanesulfonamido)thiazol-4-yl)-2-ethylbutanoate | Method B using INTB61, [UPLC acidic], 347, (1.24). | 12.48 (s, 1H), 6.63 (s, 1H), 4.14 (q, J = 7.1 Hz, 2H), 2.64-2.54 (m, 1H), 1.89 (q, J = 7.4 Hz, 4H), 1.18 (t, J = 7.1, 2.0 Hz, 3H), 0.94-0.87 (m, 4H), 0.70 (t, J = 7.4 Hz, 6H). |
| INTB22 | methyl 2-(2-(cyclopropanesulfonamido)-5-methylthiazol-4-yl)-2-methylpropanoate | Method B using INTB5, [UPLC acidic], 319, (0.92). | 12.07 (s, 1H), 3.68 (s, 3H), 2.63-2.55 (m, 1H), 2.03 (s, 3H), 1.49 (s, 6H), 0.97-0.85 (m, 4H). |
| INTB23 | methyl 2-(2-(cyclopropanesulfonamido)-thiazol-4-yl)-2-methoxyacetate | Method B using INTB10, [UPLC acidic], 307, (0.66). | 12.77 (s, 1H), 6.82 (s, 1H), 4.93 (s, 1H), 3.72 (s, 3H), 3.34 (s, 3H), 2.68-2.56 (m, 1H), 1.00-0.78 (m, 4H). |
| INTB24 | ethyl 2-(2-(cyclopropanesulfonamido)-thiazol-4-yl)-4-methoxybutanoate | Method B using INTB6, [HPLC acidic], 349, (1.53). | 12.61 (s, 1H), 6.60 (s, 1H), 4.10 (qt, J = 7.4, 3.8 Hz, 2H), 3.74 (t, J = 7.6 Hz, 1H), 3.36-3.19 (m, 2H, signal obscured by residual water), 3.19 (s, 3H), 2.64-2.54 (m, 1H), 2.25-1.92 (m, 2H), 1.18 (t, J = 7.1 Hz, 3H), 0.97-0.81 (m, 4H). |

TABLE 3-continued

Additional intermediates were made according to Method B.

| INTB# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| INTB25 | Ethyl 2-(2-(cyclopropanesulfonamido)-thiazol-4-yl)-2,2-difluoroacetate | Method B using INTB14, [UPLC acidic], 327, (1.16). | None recorded |
| INTB62 | ethyl 2-(cyclopropanesulfonamido)-5,6-dihydro-4H-cyclopenta[d]thiazole-4-carboxylate | Method B [UPLC acidic], 317, (0.99). | 12.59 (s, 1H), 4.21-4.04 (m, 2H), 3.97-3.88 (m, 1H), 2.81-2.64 (m, 2H), 2.63-2.58 (m, 1H), 2.49-2.38 (m, 2H), 1.22 (t, J = 7.1 Hz, 3H), 0.94-0.87 (m, 4H). |
| INTB63 | ethyl 2-(cyclopropanesulfonamido)-4,5,6,7-tetrahydrobenzo[d]thiazole-4-carboxylate | Method B [HPLC acidic], 331, (1.71). | None recorded |
| INTB64 | ethyl 2-(2-(cyclopropanesulfonamido)thiazol-4-yl)-2-oxoacetate | Method B [UPLC acidic], 305, (0.88). | 13.11 (s, 1H), 8.32 (s, 1H), 4.35 (q, J = 7.1 Hz, 2H), 2.75-2.64 (m, 1H), 1.32 (t, J = 7.1 Hz, 3H), 1.01-0.87 (m, 4H). |
| INTB110 | methyl 2-methoxy-2-(2-(methylsulfonamido)thiazol-4-yl)acetate | Method B using INTB10, [HPLC basic], 281, (0.65). | 12.75 (s, 1H), 6.84 (s, 1H), 4.94 (s, 1H), 3.71 (s, 3H), 3.34 (s, 3H), 2.93 (v. br s, 3H). |

Methyl 2-(2-bromothiazol-4-yl)propanoate INTB26

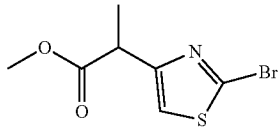

MeI (4.16 mL, 66.5 mmol) was added to a stirred mixture of methyl 2-(2-bromothiazol-4-yl)acetate (3.14 g, 13.3 mmol) and K$_2$CO$_3$ (9.19 g, 66.5 mmol) in acetone (75 mL). The reaction was heated to 60° C. and stirred for 48 hrs. The reaction mixture was cooled with an ice bath then was treated with 1M HCl (aq, 133 mL). This was then extracted with EtOAc (3×100 mL). The organic layers were combined, dried (MgSO$_4$), filtered and concentrated on to silica (20 g). The crude product was purified by chromatography on silica gel (40 g column, 0-20% EtOAc/iso-hexane) to afford methyl 2-(2-bromothiazol-4-yl)propanoate (2.45 g, 9.80 mmol, 74% yield) as an oil; Rt 1.76 mins (HPLC acidic); m/z 250 ($^{79}$Br M+H)$^+$ (ES$^+$).

Methyl 2-(2-bromothiazol-4-yl)-2-methylpropanoate INTB27

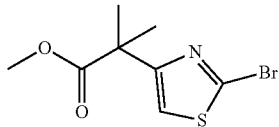

1M LiHMDS (THF, 19 mL, 19 mmol) was added dropwise to a solution of methyl 2-(2-bromothiazol-4-yl)propanoate (3.5 g, 14 mmol) in THF (10 mL) under nitrogen at −78° C. and the mixture was stirred for 20 mins. MeI (1.3 mL, 20.79 mmol) was added and the mixture was allowed to warm to RT and stirred for 2 hrs. The reaction mixture was cooled to 0° C. then quenched with NH$_4$Cl (sat. aq, 50 mL), extracted with EtOAc (2×50 mL), then the organic phases were combined, washed with brine (50 mL), dried (MgSO4), filtered and concentrated on to silica (10 g). The crude product was purified by chromatography on silica gel (24 g column, 0-20% EtOAc/isohexane) to afford methyl 2-(2-bromothiazol-4-yl)-2-methylpropanoate (3.02 g, 11.2 mmol, 80% yield) as a pale tan oil; Rt 1.28 mins (UPLC acidic); m/z 264 ($^{79}$Br M+H)$^+$ (ES$^+$); $^1$H NMR (500 MHz, DMSO-d6) δ 7.57 (s, 1H), 3.60 (s, 3H), 1.50 (s, 6H).

Methyl 2-(2-(cyclobutanesulfonamido)thiazol-4-yl)acetate INTB28

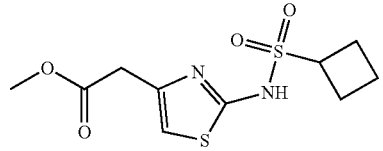 [SMILES: COC(=O)Cc1csc(NS(=O)(=O)C2CCC2)n1]

A suspension of (1R,2R)—N1,N2-dimethylcyclohexane-1,2-diamine (0.012 mL, 0.08 mmol), methyl 2-(2-bromothiazol-4-yl)acetate (87 mg, 0.37 mmol), cyclobutanesulfonamide (50 mg, 0.37 mmol) and K$_2$CO$_3$ (57 mg, 0.41 mmol) in dioxane (1.5 mL) at 40° C. was degassed (N$_2$, 5 mins) then copper(I) iodide (7 mg, 0.04 mmol) was added. The solution was again degassed (N$_2$, 5 mins) before being warmed to 80° C. for 2 hrs before being allowed to cool to RT. 1 M HCl (aq, 5 mL) was added and the aqueous phase was extracted with EtOAc (3×10 mL). The organic phases were combined, dried (Na$_2$SO$_4$), filtered and concentrated on to silica (500 mg). The crude product was purified by chromatography on silica gel (4 g column, 0-100% EtOAc/isohexane) to afford methyl 2-(2-(cyclobutanesulfonamido)thiazol-4-yl)acetate (31 mg, 0.11 mmol, 28% yield) as a red gum; Rt 0.79 mins (UPLC acidic); m/z 291 (M+H)$^+$ (ES$^+$); $^1$H NMR (500 MHz, DMSO-d6) b 12.49 (s, 1H), 6.54 (s, 1H), 3.64 (s, 3H), 3.62 (s, 2H), 2.47-2.44 (m, 1H), 2.33-2.13 (m, 4H), 1.95-1.77 (m, 2H).

Methyl 1-(2-(cyclopropanesulfonamido)thiazol-4-yl) cyclopentane-1-carboxylate INTB65

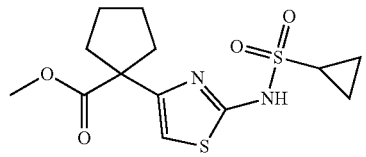 [SMILES: COC(=O)C1(c2csc(NS(=O)(=O)C3CC3)n2)CCCC1]

NaH (60 wt % in mineral oil, 0.13 g, 3.28 mmol) was added to a mixture of methyl 2-(2-bromothiazol-4-yl)acetate INTB16 (0.31 g, 1.31 mmol) and 1,4-dibromobutane (0.17 mL, 1.44 mmol) in DMF (7.5 mL) at 0° C. The mixture was allowed to warm to RT and stirred for 18 hrs. NH$_4$Cl (aq) was added and the crude product extracted with EtOAc. The combined organic extracts were washed with brine, dried (MgSO$_4$) and concentrated onto silica. The crude product was purified by chromatography on silica gel (12 g column, 0-10% iso-hexane/MTBE) to afford methyl 1-(2-bromothiazol-4-yl)cyclopentanecarboxylate (0.22 g, 0.758 mmol, 57.7% yield) as a pale yellow oil. No analysis was undertaken. This material was used as in Method C to afford title compound. Rt 1.76 mins (HPLC acidic); m/z 331 (M+H)$^+$ (ES$^+$).

Methyl 4-(2-bromothiazol-4-yl)tetrahydro-2H-pyran-4-carboxylate INTB115

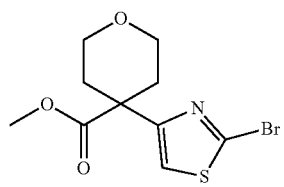 [SMILES: COC(=O)C1(c2csc(Br)n2)CCOCC1]

To a solution of methyl 2-(2-bromothiazol-4-yl)acetate (5 g, 21.18 mmol) in DMF (15 mL) at RT was added NaOH (1.95 g, 48.7 mmol). The reaction mixture was stirred at RT for 20 mins then 1-bromo-2-(2-bromoethoxy)ethane (3.2 mL, 25.4 mmol) was added. The reaction mixture was stirred for 6 hrs then cooled with an ice bath. The reaction mixture was then acidified using 1M HCl (100 mL) before diluting with water (100 mL) and extracting with EtOAc (100 mL). The phases were separated and the organic phase washed with brine (50 mL). The organic phase was dried with MgSO$_4$, filtered and concentrated on to silica (15 g). The crude product was purified by chromatography on silica gel (220 g column, 0-50% EtOAc/iso-hexane) to afford methyl 4-(2-bromothiazol-4-yl)tetrahydro-2H-pyran-4-carboxylate (480 mg, 1.49 mmol, 7% yield) as a yellow oil which solidified on standing. Rt 0.57 (UPLC acidic); m/z 306 (M$^{79}$Br+H)$^+$ (ES$^+$); $^1$H NMR (500 MHz, DMSO-d6) δ 7.66 (s, 1H), 3.71-3.59 (m, 5H), 3.57-3.44 (m, 2H), 2.30-2.20 (m, 2H), 2.07-2.00 (m, 2H).

Method C: Formation of Sulfonamides from Heterocyclic Halides

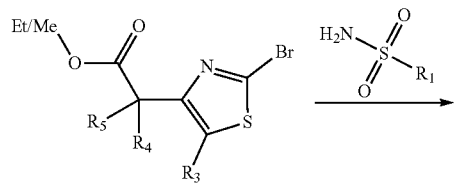

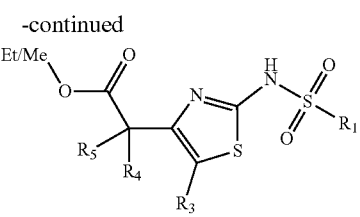

A suspension of (1R,2R)—N1,N2-dimethylcyclohexane-1,2-diamine (0.2 eq), bromothiazole intermediate (1 eq), alkylsulfonamide (1 eq), and K$_2$CO$_3$ (1.1 eq) in dioxane (10 volumes) at 40° C. was degassed (N$_2$, 5 mins) then copper(I) iodide (0.1 equiv.) was added. The solution was again degassed (N$_2$, 5 mins) before being warmed to 80° C. The reaction was progressed for 2 hrs before being allowed to cool to RT. 1M HCl (aq) was added and the aqueous phase was extracted with EtOAc. The organic phases were combined, dried (Na$_2$SO$_4$), filtered and concentrated. The crude material was purified by normal phase chromatography.

TABLE 4

Additional intermediates made according to Method C.

| INTB# | Name/Structure (All examples containing chiral centres are racemates unless stated) | Synthesis Method, [LCMS Method], m/z (M + H)$^+$, (Rt/min) | $^1$H NMR Chemical Shift Data (DMSO-d6 unless stated) |
|---|---|---|---|
| INTB29 | methyl 2-(2-(cyclobutanesulfonamido)thiazol-4-yl)-2-methylpropanoate | Method C, using INTB27, [UPLC acidic], 319, (0.98). | 12.57 (s, 1H), 6.53 (s, 1H), 3.86-3.75 (m, 1H), 3.63 (s, 3H), 2.32-2.11 (m, 4H), 1.95-1.80 (m, 2H), 1.45 (s, 6H). |
| INTB30 | methyl 2-methyl-2-(2-((trifluoromethyl)sulfonamido)thiazol-4-yl)propanoate | Method C, using INTB27, [HPLC acidic], 333, (1.97). | 13.98 (s, 1H), 6.95 (s, 1H), 3.65 (s, 3H), 1.50 (s, 6H). |
| INTB31 | methyl 2-methyl-2-(2-((1-methylethyl)sulfonamido)thiazol-4-yl)propanoate | Method C, using INTB27, [UPLC acidic], 307, (0.95). | None recorded |

TABLE 4-continued

Additional intermediates made according to Method C.

| INTB# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| INTB32 | methyl 2-methyl-2-(2-((1-methylcyclopropane)-1-sulfonamido)thiazol-4-yl)propanoate | Method C, using INTB27, [UPLC acidic], 319, (1.00). | None recorded |
| INTB33 | methyl 2-(2-((1,1-dimethylethyl)sulfonamido)-thiazol-4-yl)-2-methylpropanoate | Method C, using INTB27, [UPLC acidic], 321, (1.04). | None recorded |
| INTB34 | methyl 2-methyl-2-(2-((2-methylpropyl)sulfonamido)thiazol-4-yl)propanoate | Method C, using INTB27, [UPLC acidic], 321, (1.10). | 12.55 (s, 1H), 6.55 (s, 1H), 3.63 (d, J = 2.0 Hz, 3H), 2.89 (br. s, 2H), 2.16-2.02 (m, 1H), 1.46 (s, 6H), 1.06-0.96 (m, 6H). |

2-(2-(methylsulfonamido)thiazol-4-yl)acetic acid INTB35

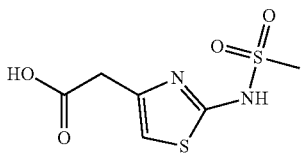

A solution of methyl 2-(2-(methylsulfonamido)thiazol-4-yl)acetate INTB15 (3.61 g, 14.42 mmol) in THF (30 mL), MeOH (15 mL) and 1M LiOH (aq, 28.8 mL, 28.8 mmol) was stirred at RT for 16 hrs. The reaction mixture was partially concentrated (30 mL) then washed with Et₂O (10 mL) then acidified with 1 M HCl (aq, 30 mL). The resulting precipitate was filtered and washed with Et₂O (10 mL) to afford 2-(2-(methylsulfonamido)thiazol-4-yl)acetic acid (2.78 g, 11.53 mmol, 80% yield) as a colourless solid; Rt 0.28 min (UPLC acidic); m/z 237 (M+H)+ (ES+); 1H NMR (400 MHz, DMSO-d6) δ 12.97-12.26 (m, 2H), 6.57 (s, 1H), 3.55 (d, J=0.9 Hz, 2H), 2.89 (s, 3H).

2-(2-(cyclopropanesulfonamido)thiazol-4-yl)acetic acid INTB36

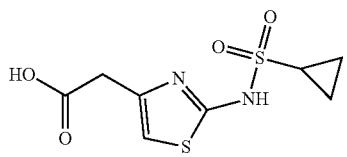 [SMILES: O=C(O)Cc1csc(NS(=O)(=O)C2CC2)n1]

Methyl 2-(2-(cyclopropanesulfonamido)thiazol-4-yl)acetate INTB16 (1.50 g, 5.43 mmol) in THF (13 mL) and MeOH (1 mL) was treated with 1M LiOH (aq, 12.48 mL, 12.48 mmol) and stirred at RT for 1 hr. A further portion of 1 M LiOH (aq, 5.43 mL, 5.43 mmol) was added and the reaction mixture was stirred at RT for 18 hrs. The reaction mixture was part concentrated then acidified with 1 M HCl (20 mL). This was then extracted with EtOAc (3×50 mL). The organic phases were combined, dried (Na₂SO₄), filtered and concentrated in vacuo to afford 2-(2-(cyclopropanesulfonamido)thiazol-4-yl)acetic acid (1.45 g, 5.25 mmol, 97% yield) as a colourless 20 solid; Rt 0.59 min (UPLC acidic); m/z 263 (M+H)+ (ES+); 1H NMR (400 MHz, DMSO-d6) δ 12.75 (br. s, 1H), 12.50 (br. s, 1H), 6.56 (s, 1H), 3.55 (d, J=0.9 Hz, 2H), 2.65-2.54 (m, 1H), 1.03-0.75 (m, 4H).

2-(2-(cyclopropanesulfonamido)thiazol-4-yl)-2-methylpropanoic acid INTB37

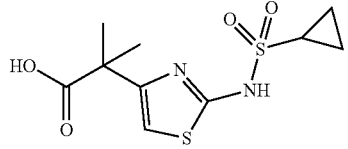 [SMILES: CC(C)(C(=O)O)c1csc(NS(=O)(=O)C2CC2)n1]

To a solution of methyl 2-(2-(cyclopropanesulfonamido)thiazol-4-yl)-2-methylpropanoate INTB17 (1 g, 3.29 mmol) in THF (15 mL) and MeOH (7 mL) was added a solution of LiOH (0.16 g, 6.57 mmol) in water (6.57 mL). The reaction was stirred at RT for 48 hrs. The reaction was concentrated to 10 mL. The pale yellow solution was acidified with 1 M HCl (aq, 30 mL) and diluted with EtOAc (50 mL), the phases were separated and the aqueous extracted with EtOAc (3×50 mL). The combined organics were dried ($Na_2SO_4$), filtered and concentrated in vacuo to give 2-(2-(cyclopropanesulfonamido)thiazol-4-yl)-2-methylpropanoic acid (0.83 g, 2.79 mmol, 85%) as a colourless solid; Rt 0.79 min (HPLC acidic); m/z 291 (M+H)$^+$ (ES$^+$); $^1$H NMR (400 MHz, DMSO-d6) δ 12.62 (brs, 2H), 6.51 (s, 1H), 2.66-2.53 (m, 1H), 1.45 (s, 6H), 0.95-0.89 (m, 4H).

2-(2-(cyclopropanesulfonamido)thiazol-4-yl)butanoic acid INTB38

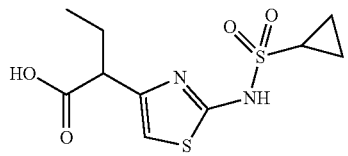 [SMILES: CCC(C(=O)O)c1csc(NS(=O)(=O)C2CC2)n1]

2M LiOH (aq, 3.11 mL, 6.22 mmol) was added to a solution of ethyl 2-(2-(cyclopropanesulfonamido)thiazol-4-yl)butanoate INTB18 (1.8 g, 5.65 mmol) in THF (10 mL) and stirred at RT for 18 hrs. Additional 2M LiOH (aq, 3.11 mL, 6.22 mmol) solution was added and the reaction was heated to 40° C. for 2 hrs. The reaction was allowed to cool to RT and the solvent was removed in vacuo. It was then acidified with 1 M HCl (aq, 40 mL) and extracted with EtOAc (3×50 mL). The combined organic phases were passed through a phase separator and solvent removed in vacuo to give 2-(2-(cyclopropanesulfonamido)thiazol-4-yl)butanoic acid (1.54 g, 5.04 mmol, 89% yield) as a yellow solid; Rt 1.29 min (HPLC acidic); m/z 291 (M+H)$^+$ (ES$^+$); 289 (M−H)$^-$ (ES$^-$); $^1$H NMR (400 MHz, DMSO-d6) δ 12.58 (br. s, 2H), 6.55 (s, 1H), 3.47 (dd, J=8.4, 6.7 Hz, 1H), 2.64-2.56 (m, 1H), 1.98-1.73 (m, 2H), 0.95-0.88 (m, 4H), 0.85 (t, J=7.4 Hz, 3H).

Methyl 4-(2-(cyclopropanesulfonamido)thiazol-4-yl)tetrahydro-2H-pyran-4-carboxylate INTB116

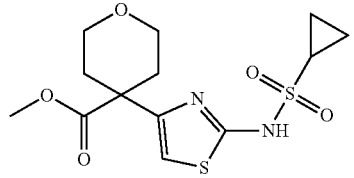 [SMILES: COC(=O)C1(c2csc(NS(=O)(=O)C3CC3)n2)CCOCC1]

A suspension of cyclopropanesulfonamide (250 mg, 2.06 mmol), methyl 4-(2-bromothiazol-4-yl)tetrahydro-2H-pyran-4-carboxylate INTB115 (480 mg, 1.57 mmol) and $Cs_2CO_3$ (800 mg, 2.46 mmol) in dioxane (10 mL) was degassed ($N_2$). A second solution of tBuXPhos (100 mg, 0.235 mmol) and [Pd(allyl)Cl]$_2$ (25 mg, 0.068 mmol) in dioxane (10 mL) was degassed ($N_2$) and stirred 25 at RT for 5 mins before addition of this solution to the reaction mixture. The reaction mixture was stirred at 90° C. for 3 hrs then was allowed to cool to RT. The reaction mixture was diluted with EtOAc (30 mL) and acidified with 1M HCl (20 mL). The phases were separated and the organic phase washed with brine (20 mL). The organic phase was dried with $Na_2SO_4$, filtered and then concentrated onto silica (5 g). The crude product was purified by chromatography on silica gel (24 g column, 0-80% EtOAc/iso-hexane) to afford methyl 4-(2-(cyclopropanesulfonamido)thiazol-4-yl)tetrahydro-2H-pyran-4-carboxylate (178 mg, 0.50 mmol, 32% yield) as a colourless solid. Rt 0.38 (UPLC basic); m/z 347 (M+H)$^+$ (ES$^+$); $^1$H NMR (500 MHz, DMSO-d6) δ 12.57 (s, 1H), 6.70 (s, 1H), 3.68 (s, 3H), 3.65-3.49 (m, 4H), 2.68-2.56 (m, 1H), 2.26-2.18 (m, 2H), 2.05-1.94 (m, 2H), 0.99-0.73 (m, 4H).

3-Acetyl-1-(4-bromophenyl)pyrrolidin-2-one INTB118

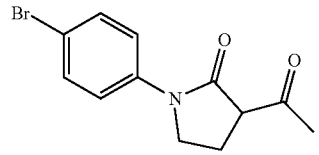 [SMILES: CC(=O)C1CCN(c2ccc(Br)cc2)C1=O]

A solution of 1-(4-bromophenyl)pyrrolidin-2-one (10 g, 41.6 mmol) in THF (100 mL) was cooled to −78° C. whereupon LDA (2M in THF/heptane) (24.99 mL, 50.0 mmol) was added dropwise. The reaction was maintained below −60° C. for 1 hr then EtOAc (8.15 mL, 83 mmol) was added and the reaction mixture was allowed to warm to RT and stirred for 18 hrs. The reaction mixture was cooled to 0° C. then sat. NH$_4$Cl (aq, 10 mL) was added cautiously before the reaction was warmed to RT. The mixture was then diluted with EtOAc (100 mL) and water (100 mL) and the phases were separated. The organic phase was washed with brine (100 mL), dried over MgSO$_4$, filtered and concentrated onto silica (20 g). The crude product was purified by chromatography on silica gel (80 g column, 0-50% EtOAc/iso-hexane) to afford 3-acetyl-1-(4-bromophenyl)pyrrolidin-2-one (8.80 g, 24.95 mmol, 60% yield) as a brown gum. Rt 1.25 (UPLC basic); m/z 282 ($^{79}$Br M+H)$^+$ (ES$^+$). The material was used directly in the next step. 3-(2-Aminothiazol-4-yl)-1-(4-bromophenyl)pyrrolidin-2-one INTB119

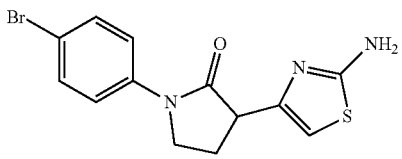 [SMILES: Nc1nc(C2CCN(c3ccc(Br)cc3)C2=O)cs1]

A solution of 3-acetyl-1-(4-bromophenyl)pyrrolidin-2-one INTB118 (8.80 g, 31.2 mmol) in EtOH (70 mL) at 0° C. was treated dropwise with bromine (1.60 mL, 31.2 mmol) over 30 mins. The reaction mixture was maintained at 0° C. for a further 10 mins before warming to RT where it was stirred for a further 4 hrs before thiourea (2.37 g, 31.2 mmol) was added and the reaction mixture was heated at 40° C. for 18 hrs. The reaction mixture was concentrated in vacuo then taken up in sat. NaHCO$_3$ (aq, 200 mL) and EtOAc (200 mL). The phases were partitioned and the organic phase was washed with brine (100 mL), dried over MgSO$_4$, filtered and concentrated onto silica (20 g). The crude product was purified by chromatography on silica gel (120 g column, 0-100% EtOAc/iso-hexane) to afford 3-(2-aminothiazol-4-yl)-1-(4-bromophenyl)pyrrolidin-2-one (650 mg, 1.73 mmol, 6% yield) as a brown solid. Rt 0.80 (UPLC acidic); m/z 338 ($^{79}$Br M+H)$^+$ (ES$^+$). $^1$H NMR (400 MHz, DMSO-d6) δ 7.72-7.66 (m, 2H), 7.63-7.58 (m, 2H), 7.40 (s, 2H), 4.59 (s, 1H), 4.19-4.13 (m, 1H), 4.00-3.94 (m, 1H), 3.85-3.79 (m, 1H), 2.60 (t, J=6.8 Hz, 2H).

N-(4-(1-(4-Bromophenyl)-2-oxopyrrolidin-3-yl)thiazol-2-yl)cyclopropanesulfonamide INTB120

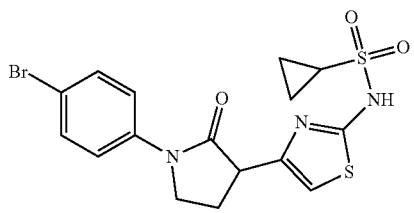 [SMILES: O=C1C(c2csc(NS(=O)(=O)C3CC3)n2)CCN1c1ccc(Br)cc1]

A solution of 3-(2-aminothiazol-4-yl)-1-(4-bromophenyl)pyrrolidin-2-one INTB119 (620 mg, 1.83 mmol) in pyridine (0.741 mL, 9.17 mmol) was treated with cyclopropanesulfonyl chloride (0.223 mL, 2.20 mmol). The reaction mixture was warmed to 40° C. and stirred for 64 hrs. The reaction mixture was diluted with EtOAc (20 mL) and was washed with 1 M HCl (aq, 11 mL) and brine (10 mL). The organic phase was dried over Na$_2$SO$_4$, filtered and concentrated in vacuo. The residue was then taken up in CH$_2$Cl$_2$ (50 mL) and concentrated onto silica (20 g). The crude product was purified by chromatography on silica gel (120 g column, 0-10% MeOH/CH$_2$Cl$_2$) to afford N-(4-(1-(4-bromophenyl)-2-oxopyrrolidin-3-yl)thiazol-2-yl)cyclopropanesulfonamide (382 mg, 0.777 mmol, 42% yield) as a brown solid. Rt 1.23 (UPLC acidic); m/z 442 ($^{79}$Br M+H)$^+$ (ES$^+$). $^1$H NMR (400 MHz, DMSO-d6) δ 12.70 (s, 1H), 7.70-7.64 (m, 2H), 7.62-7.56 (m, 2H), 6.68 (s, 1H), 4.13-3.72 (m, 3H), 2.64-2.55 (m, 1H), 2.33-2.11 (m, 1H), 0.96-0.86 (m, 4H) 1×CH not observed.

Method D: Formation of Acids from Esters

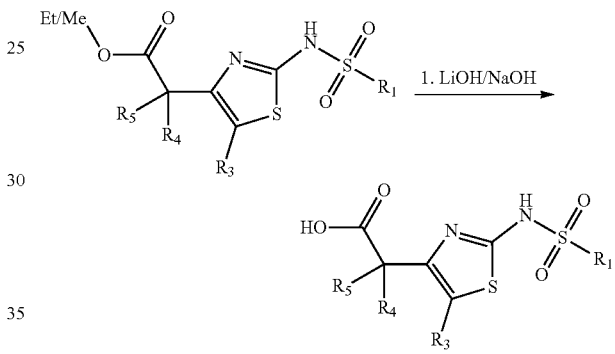

To a solution of ester (1.0 eq.) in THF/MeOH (2:1) was added a solution of appropriate base (2.0 eq. of LiOH or NaOH aq solutions at 1-2M). The reaction was stirred at RT or with heating up to 50° C. The reaction was concentrated in vacuo to half volume and was acidified with 1M HCl. The product was extracted using an appropriate organic solvent (EtOAc). The combined organics were dried (Na$_2$SO$_4$) and concentrated in vacuo to give the desired compound.

TABLE 5

| | | Additional intermediates made according to Method D | | |
|---|---|---|---|---|
| INTB# | Name/Structure (All examples containing chiral centres are racemates unless stated) | | Synthesis Method, [LCMS Method], m/z (M + H)$^+$, (Rt/min) | $^1$H NMR Chemical Shift Data (DMSO-d6 unless stated) |
| INTB39 | 2-(2-(cyclopropanesulfonamido)thiazol-4-yl)propanoic acid 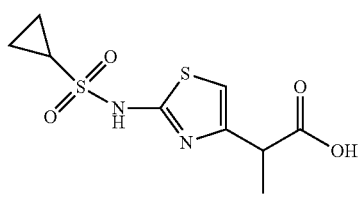 | | Method D using INTB20, [HPLC acidic], 277, (1.09). | 12.92-12.27 (m, 2H), 6.53 (s, 1H), 3.71-3.59 (m, 1H), 2.63-2.55 (m, 1H), 1.40 (d, J = 7.3 Hz, 3H), 0.96-0.78 (m, 4H). |

TABLE 5-continued

Additional intermediates made according to Method D

| INTB# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| INTB40 | 2(2-(cyclopropanesulfonamido)thiazol-4-yl)-3-methylbutanoic acid | Method D using INTB19, [HPLC acidic], 305, (1.41). | None recorded |
| INTB41 | 2(2-(cyclopropanesulfonamido)thiazol-4-yl)-2-ethylbutanoic acid | Method D using INTB21, [HPLC acidic], 319, (1.60). | 12.78 (s, 1H), 12.44 (s, 1H), 6.62 (s, 1H), 2.64-2.56 (m, 1H), 1.94-1.82 (m, 4H), 0.94-0.87 (m, 4H), 0.71 (t, J = 7.4 Hz, 6H). |
| INTB42 | 2-(2-(cyclopropanesulfonamido)-5-methyl-thiazol-4-yl)-2-methylpropanoic acid | Method D using INTB22, [PLC basic], 305, (0.48). | 12.84 (br, 1H), 12.02 (br, 1H), 2.60-2.54 (m, 1H), 2.09 (s, 3H), 1.46 (s, 6H), 0.96-0.86 (m, 4H). |
| INTB43 | 2-(2-(cyclopropanesulfonamido)thiazol-4-yl)-2-methoxyacetic acid | Method D using INTB23, [UPLC acidic], 293, (0.63). | None recorded |
| INTB44 | 2-(2-(cyclopropanesulfonamido)thiazol-4-yl)-4-methoxybutanoic acid | Method D using INTB24, [UPLC acidic], 321, (0.73). | 13.01-12.26 (m, 2H), 6.57 (s, 1H), 3.66 (dd, J = 8.6, 6.5 Hz, 1H), 3.38-3.20 (m, 2H), 3.19 (s, 3H), 2.64-2.54 (m, 1H), 2.22-2.09 (m, 1H), 2.06-1.92 (m, 1H), 0.94-0.79 (m, 4H). |

TABLE 5-continued

Additional intermediates made according to Method D

| INTB# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| INTB45 | 2-(2-(cyclopropanesulfonamido)thiazol-4-yl)-2,2-difluoroacetic acid | Method D using INTB25, [UPLC acidic], 299, (0.79). | None recorded |
| INTB46 | 2-(2-(cyclobutanesulfonamido)thiazol-4-yl)-acetic acid | Method D using INTB28, [HPLC acidic], 277, (1.13). | None recorded |
| INTB47 | 2-(2-cyclobutanesulfonamido)thiazol-4-yl)-2-methylpropanic acid | Method D using INTB29, [HPLC acidic], 305, (1.49). | 12.77 (v, br. s, 1H), 12.55 (v, br. s, 1H), 6.48 (s, 1H), 3.85-3.69 (m, 1H), 2.33-2.09 (m, 4H), 1.97-1.78 (m, 2H), 1.43 (s, 6H). |
| INTB48 | 2-methyl-2-(2-((trifluoromethyl)sulfonamido)thiazol-4-yl)propanoic acid | Method D using INTB30, [HPLC acidic], 319, (1.10). | None recorded |
| INTB49 | 2-methyl-2-(2-((1-methylethyl)sulfonamido)-thiazol-4-yl)propanoic acid | Method D using INTB31, [HPLC acidic], 293, (1.36). | 12.75 (s, 1H), 12.57 (s, 1H), 6.48 (s, 1H), 3.15-3.03 (m, 1H), 1.44 (s, 6H), 1.22 (d, J = 6.8 Hz, 6H). |
| INTB50 | 2-methyl-2-(2-((1-methylcyclopropane)-1-sulfonamido)thiazol-4-yl)propanoic acid | Method D using INTB32, [HPLC acidic], 305, (1.42). | 12.86-12.48 (m, 2H), 6.47 (s, 1H), 1.44 (s, 6H), 1.39 (s, 3H), 1.25-1.08 (m, 2H), 0.82-0.71 (m, 2H). |

TABLE 5-continued

Additional intermediates made according to Method D

| INTB# | Name/Structure (All examples containing chiral centres are racemates unless stated) | Synthesis Method, [LCMS Method], m/z (M + H)+, (Rt/min) | ¹H NMR Chemical Shift Data (DMSO-d6 unless stated) |
|---|---|---|---|
| INTB51 | 2-(2-((1,1-dimethylethyl)sulfonamido)-thiazol-4-yl)-2-methylpropanoic acid 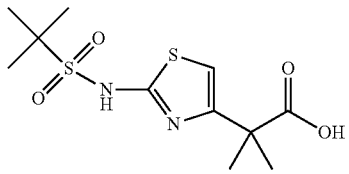 | Method D using INTB33, [HPLC acidic], 307, (1.49). | 12.95-12.19 (m, 2H), 6.46 (s, 1H), 1.44 (s, 6H), 1.28 (s, 9H). |
| INTB52 | 2-methyl-2-(2-((2-methylpropyl)sulfonamido)-thiazol-4-yl)propanoic acid 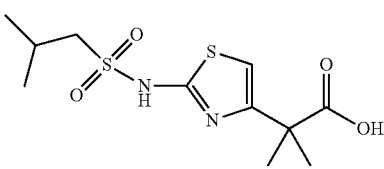 | Method D using INTB34, [UPLC acidic], 307, (0.96). | 12.78 (s, 1H), 12.53 (s, 1H), 6.50 (s, 1H), 2.96-2.82 (m, 2H), 2.15-2.03 (m, 1H), 1.44 (s, 6H), 1.01 (dd, J = 6.7, 2.2 Hz, 6H). |
| INTB66 | 2-(cyclopropanesulfonamido)-5,6-dihydro-4H-cyclopenta[d]thiazole-4-carboxylic acid 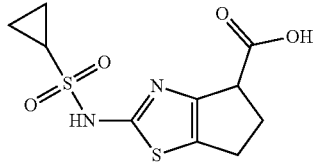 | Method D using INTB62, [UPLC acidic], 289, (0.75). | 12.59-12.52 (m, 2H), 3.85-3.77 (m, 1H), 2.78-2.64 (m, 2H), 2.60 (s, 1H), 2.50-2.38 (m, 2H), 0.94-0.87 (m, 4H). |
| INTB67 | 2-(cyclopropanesulfonamido)-4,5,6,7-tetrahydrobenzo[d]thiazole-4-carboxylic acid 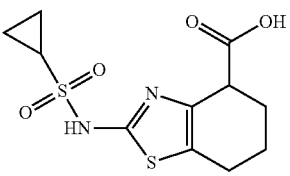 | Method D using INTB63, [UPLC acidic], 303, (0.83). | None recorded |
| INTB68 | 2-(2-(cyclopropanesulfonamido)thiazol-4-yl)-2-oxoacetic acid 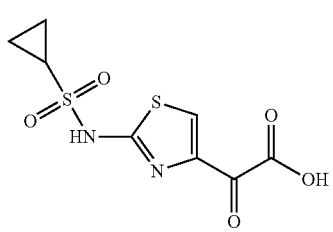 | Method D using INTB64, [UPLC acidic], 277, (0.85). | 13.49-12.80 (v. br s, 2H), 8.22 (s, 1H), 2.77-2.56 (m, 1H), 1.12-0.76 (m, 4H). |

TABLE 5-continued

Additional intermediates made according to Method D

| INTB# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
| --- | --- | --- | --- |
| INTB69 | 1-(2-(cyclopropanesulfonamido)thiazol-4-yl)cyclopentane-1-carboxylic acid | Method D using INTB65, [HPLC acidic], 317, (1.60). | None recorded |
| INTB111 | 2-methoxy-2-(2-(methylsulfonamido)-thiazol-4-yl)acetic acid | Method D using INTB110, [HPLC acidic], 267, (0.77). | 13.26 (v. br. s, 1H), 12.76 (v. br. s, 1H), 6.79 (s, 1H), 4.78 (s, 1H), 3.17 (s, 3H), 2.92 (s, 3H). |
| INTB117 | 4-(2-(cyclopropanesulfonamido)-thiazol-4-yl)tetrahydro-2H-pyran-4-carboxylic acid | Method D using INTB116, [HPLC acidic], 333, (1.17). | 10.96 (s, 1H), 3.57 (t, J = 5.4 Hz, 2H), 3.53 (t, J = 5.5 Hz, 2H), 2.62-2.57 (m, 1H), 2.34-2.29 (m, 2H), 2.14-2.07 (m, 2H), 0.96-0.91 (m, 4H), 2 × H not observed. |

N-(4-bromophenyl)-2-(2-(cyclopropanesulfonamido)thiazol-4-yl)-2-methylpropanamide INTB53

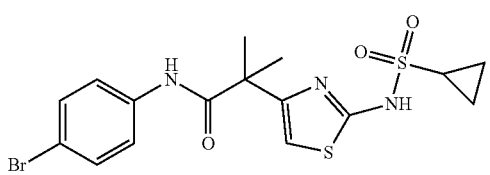 [SMILES: CC(C)(C(=O)Nc1ccc(Br)cc1)c1csc(NS(=O)(=O)C2CC2)n1]

To a suspension of 2-(2-(cyclopropanesulfonamido)thiazol-4-yl)-2-methylpropanoic acid INTB37 (0.75 g, 2.58 mmol) in DCM (10 mL) was added 1-chloro-N,N,2-trimethylprop-1-en-1-amine (0.63 mL, 5.17 mmol). The reaction mixture was stirred at RT for 2 hrs. The reaction mixture was concentrated to dryness. The orange residue was redissolved in pyridine (5 mL) before the addition of 4-bromoaniline (0.49 g, 2.84 mmol). The reaction mixture was stirred at RT for 16 hrs. The reaction mixture was poured onto 1 M HCl (aq, 100 mL) and the product was extracted using DCM (3×75 mL). The combined organics were passed through a phase separator and concentrated in vacuo. The orange residue was triturated with MeOH (2×10 mL) and the resultant solid was filtered, rinsing with MeOH (2×10 mL), and dried in vacuo to afford N-(4-bromophenyl)-2-(2-(cyclopropanesulfonamido)thiazol-4-yl)-2-methylpropanamide (956 mg, 2.09 mmol, 81% yield) as a pale pink solid; Rt 1.26 min (UPLC acidic); m/z 446 (M+H)+ (ES+); 1H NMR (400 MHz, DMSO-d6) δ 12.53 (s, 1H), 9.40 (s, 1H), 7.64-7.54 (m, 2H), 7.55-7.46 (m, 2H), 6.55 (s, 1H), 2.63-2.55 (m, 1H), 1.55 (s, 6H), 1.01-0.84 (m, 4H).

N-(4-bromo-2-methoxyphenyl)-2-(2-(cyclopropane-sulfonamido)thiazol-4-yl)-2-methylpropanamide INTB54

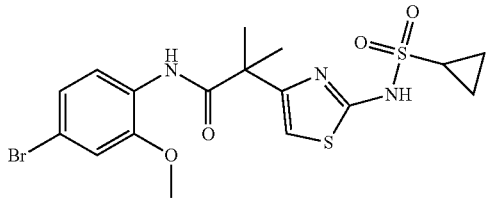 [SMILES: COc1cc(Br)ccc1NC(=O)C(C)(C)c1csc(NS(=O)(=O)C2CC2)n1]

Prepared as Method 1b in preparation of examples section from INTB37. Rt 1.34 min (UPLC acidic); m/z 476 ($^{79}$Br M+H)$^+$ (ES$^+$); 1H NMR (400 MHz, DMSO-d6) δ 12.64 (s, 1H), 8.37 (s, 1H), 7.92-7.72 (m, 1H), 7.24 (s, 1H), 7.14 (d, J=8.5 Hz, 1H), 6.69 (s, 1H), 3.83 (s, 3H), 2.63-2.58 (m, 1H), 1.53 (s, 6H), 0.94-0.89 (m, 4H).

N-(5-bromopyridin-2-yl)-2-(2-(cyclopropanesulfona-mido)thiazol-4-yl)-2-methylpropanamide INTB55

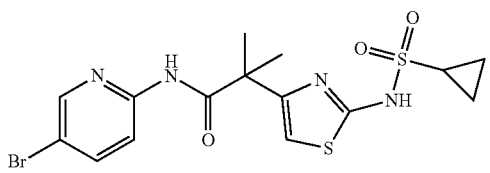 [SMILES: CC(C)(C(=O)Nc1ccc(Br)cn1)c1csc(NS(=O)(=O)C2CC2)n1]

Prepared as Method 1b in preparation of examples section from INTB37. Rt 1.20 mins (UPLC acidic); m/z 445 ($^{79}$Br M+H)$^+$ (ES$^+$); $^1$H NMR (400 MHz, DMSO-d6) δ 12.55 (s, 1H), 10.08 (s, 1H), 8.50-8.45 (m, 1H), 8.09-7.97 (m, 2H), 6.55 (d, J=6.8 Hz, 1H), 2.65-2.54 (m, 1H), 1.58 (s, 6H), 0.94-0.81 (m, 4H).

2-(2-(cyclopropanesulfonamido)thiazol-4-yl)-2-methyl-N-(4-(4,4,5,5-tetramethyl-1,3,2-dioxaboro-lan-2-yl)phenyl)propanamide INTB56

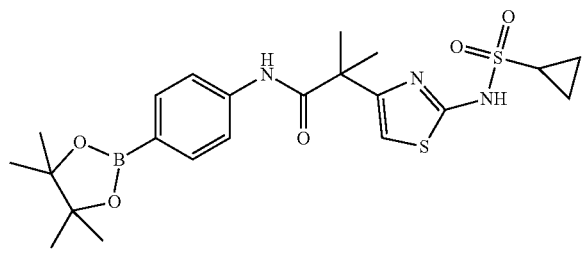 [SMILES: CC(C)(C(=O)Nc1ccc(B2OC(C)(C)C(C)(C)O2)cc1)c1csc(NS(=O)(=O)C2CC2)n1]

HATU (1.26 g, 3.31 mmol) was added to a solution 2-(2-(cyclopropanesulfonamido)thiazol-4-yl)-2-methylpro-panoic acid INTB37 (800 mg, 2.76 mmol), 4-(4,4,5,5-tetramethyl-1,3,2-dioxaborolan-2-yl)aniline (604 mg, 2.76 mmol) and DIPEA (1.44 mL, 8.27 mmol) in DCM (8 mL) at RT. The reaction was stirred at RT for 2 hrs. The solvent was removed to give a brown oil. The crude product was purified by chromatography on silica gel (40 g column, 0-100% EtOAc/iso-hexane) to afford 2-(2-(cyclopropane-sulfonamido)thiazol-4-yl)-2-methyl-N-(4-(4,4,5,5-tetram-ethyl-1,3,2-dioxaborolan-2-yl)phenyl)propanamide (1.36 g, 2.49 mmol, 90% yield) as a colourless solid; Rt 2.22 min (HPLC acidic); m/z 492 (M+H)$^+$ (ES$^+$); 490 (M–H)$^-$ (ES$^-$); $^1$H NMR (400 MHz, DMSO-d6) δ 12.53 (br. s, 1H), 8.18 (br. s, 1H), 7.72-7.55 (m, 4H), 6.46 (s, 1H), 2.63-2.54 (m, 1H), 1.53 (s, 6H), 1.29 (s, 12H), 0.92-0.79 (m, 4H).

2-(2-(cyclopropanesulfonamido)thiazol-4-yl)-N-(2-fluoro-4-(4,4,5,5-tetramethyl-1,3,2-dioxaborolan-2-yl)phenyl)-2-methylpropanamide INTB57

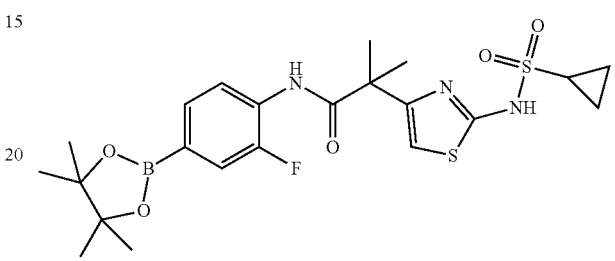

To a solution of 2-(2-(cyclopropanesulfonamido)thiazol-4-yl)-2-methylpropanoic acid INTB37 (0.75 g, 2.58 mmol) in DCM (15 mL) was added 1-chloro-N,N,2-trimethylprop-1-en-1-amine (0.63 mL, 5.17 mmol). The reaction mixture was stirred at RT for 1 hr. The reaction mixture was concentrated to dryness and the resulting brown residue was redissolved in DCM (15 mL). 2-fluoro-4-(4,4,5,5-tetram-ethyl-1,3,2-dioxaborolan-2-yl)aniline (0.67 g, 2.84 mmol) and pyridine (1.67 mL) were added to the reaction mixture. The reaction mixture was stirred at RT for 18 hrs. The reaction mixture was diluted with NH$_4$Cl (sat. aq, 10 mL) and further DCM (10 mL). The phases were separated and the aqueous was extracted with further DCM (2×20 mL). The combined organics were dried (phase separator) and concentrated in vacuo. The crude product was purified by chromatography on silica gel (40 g column, 0-100% EtOAc/iso-hexane) to afford a mixture of 2-(2-(cyclopropanesulfo-namido)thiazol-4-yl)-N-(2-fluoro-4-(4,4,5,5-tetramethyl-1,3,2-dioxaborolan-2-yl)phenyl)-2-methylpropanamide (730 mg, 1.06 mmol, 41% yield) as an orange gum Rt 2.30 min (HPLC acidic); m/z 511 (M+H)$^+$ (ES$^+$), contaminated with boronic acid hydrolysis product; Rt 1.47 min (HPLC acidic); m/z 428 (M+H)$^+$ (ES$^+$).

2-(2-(cyclopropanesulfonamido)thiazol-4-yl)-2-methylpropanamide INTB58

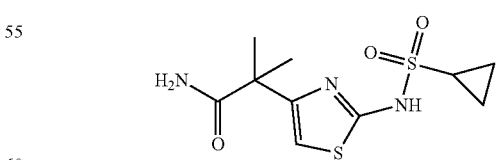

To a suspension of 2-(2-(cyclopropanesulfonamido)thi-azol-4-yl)-2-methylpropanoic acid INTB37 (0.4 g, 1.38 mmol) in DCM (15 mL) was added 1-chloro-N,N,2-trim-ethylprop-1-en-1-amine (0.34 mL, 2.76 mmol). The reaction mixture was stirred at RT for 1 hr. The reaction mixture was concentrated in vacuo and the resulting residue was redissolved in MeCN (10 mL). This solution 10 was added dropwise to NH₄OH (9.58 mL, 68.9 mmol) at 0° C. The reaction mixture was warmed to RT and stirred for at this temperature for 18 hrs. The reaction mixture was concentrated in vacuo and the resulting residue was redissolved in NH₄Cl (sat. aq, 30 mL) and EtOAc (30 mL). The phases were separated and the aqueous was further extracted with EtOAc (2×20 mL). The combined organics were dried (MgSO₄) and concentrated in vacuo to afford 2-(2-(cyclopropanesulfonamido)thiazol-4-yl)-2-methylpropanamide (0.37 g, 1.15 mmol, 83% yield) as a pale brown residue; Rt 1.10 min (HPLC acidic); m/z 290 (M+H)⁺ (ES⁺); ¹H NMR (400 MHz, DMSO-d6) δ 12.39 (s, 1H), 7.09 (s, 2H), 6.45 (s, 1H), 2.61-2.53 (m, 1H), 1.41 (s, 6H), 0.94-0.86 (m, 4H).

N-(4-bromo-3-methylphenyl)-2-(2-(cyclopropanesulfonamido)thiazol-4-yl)-2-methylpropanamide INTB59

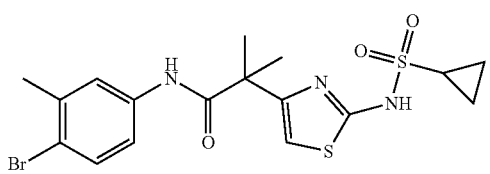 [SMILES: Cc1cc(NC(=O)C(C)(C)c2csc(NS(=O)(=O)C3CC3)n2)ccc1Br]

Prepared as Method 1b from INTB37. Rt 1.36 mins (UPLC acidic); m/z 458/460 (M+H)⁺ (ES⁺); ¹H NMR (500 MHz, DMSO-d6) δ 12.55 (s, 1H), 9.33 (s, 1H), 7.61 (d, J=2.6 Hz, 1H), 7.51 (d, J=8.7 Hz, 1H), 7.42 (dd, J=8.7, 2.6 Hz, 1H), 6.53 (s, 1H), 2.60-2.56 (m, 1H), 2.32 (s, 3H), 1.55 (s, 6H), 0.93-0.83 (m, 4H).

N-(4-bromo-2-methylphenyl)-2-(2-(cyclopropanesulfonamido)thiazol-4-yl)-2-methylpropanamide INTB60

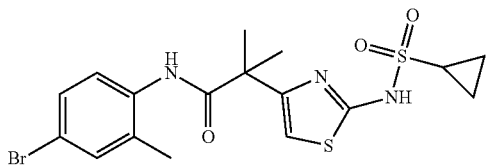 [SMILES: Cc1cc(Br)ccc1NC(=O)C(C)(C)c1csc(NS(=O)(=O)C2CC2)n1]

Prepared as Method 1b from INTB37. Rt 1.71 mins (HPLC acidic); m/z 459 (⁷⁹Br M+H)⁺ (ES⁺); ¹H NMR (400 MHz, DMSO-d6) δ 12.54 (bs, 1H), 8.99 (bs, 1H), 7.44 (s, 1H), 7.42-7.33 (m, 1H), 7.32 (bs, 1H), 6.55 (bs, 1H), 2.59-2.54 (m, 1H), 2.16 (s, 3H), 1.54 (s, 6H), 0.93-0.80 (m, 4H).

N-(4-bromo-2,6-dimethylphenyl)-2-(2-(cyclopropanesulfonamido)thiazol-4-yl)-2-methylpropanamide INTB70

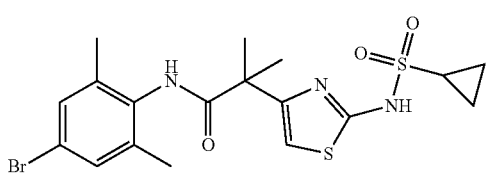 [SMILES: Cc1cc(Br)cc(C)c1NC(=O)C(C)(C)c1csc(NS(=O)(=O)C2CC2)n1]

Prepared as Method 1b from INTB37. Rt 1.28 mins (UPLC acidic); m/z 472/474 (M+H)⁺ (ES⁺); ¹H NMR (500 MHz, DMSO-d6) δ 12.52 (s, 1H), 8.88 (s, 1H), 7.28 (s, 2H), 6.59 (s, 1H), 2.61-2.51 (m, 1H), 2.09 (s, 6H), 1.58 (s, 6H), 0.93-0.83 (m, 4H).

N-(4-bromo-3-ethoxyphenyl)-2-(2-(cyclopropanesulfonamido)thiazol-4-yl)-2-methylpropanamide INTB71

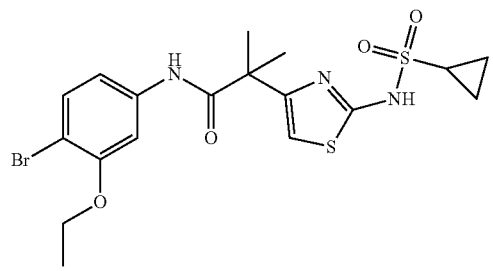 [SMILES: CCOc1cc(NC(=O)C(C)(C)c2csc(NS(=O)(=O)C3CC3)n2)ccc1Br]

Prepared as Method 1b from INTB37. Rt 2.17 mins (HPLC acidic); m/z 488/490 (M+H)⁺ (ES⁺); ¹H NMR (500 MHz, DMSO-d6) δ 12.55 (s, 1H), 9.38 (s, 1H), 7.52-7.45 (m, 2H), 7.21 (dd, J=8.7, 2.3 Hz, 1H), 6.54 (s, 1H), 4.10-3.99 (m, 2H), 2.60-2.56 (m, 1H), 1.56 (s, 6H), 1.37 (t, J=7.0 Hz, 3H), 0.93-0.87 (m, 4H).

N-(5-bromo-3-fluoropyridin-2-yl)-2-(2-(cyclopropanesulfonamido)thiazol-4-yl)-2-methylpropanamide INTB72

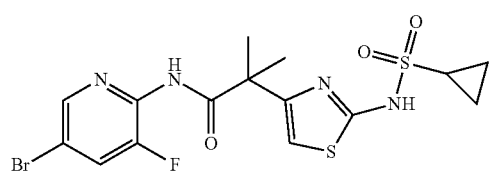 [SMILES: CC(C)(C(=O)Nc1ncc(Br)cc1F)c1csc(NS(=O)(=O)C2CC2)n1]

Prepared as Method 1b from INTB37. Rt 1.00 mins (UPLC acidic); m/z 463/465 (M+H)⁺ (ES⁺); ¹H NMR (400 MHz, DMSO-d6) δ 12.60 (s, 1H), 9.98 (s, 1H), 8.45 (d, J=2.0 Hz, 1H), 8.25 (dd, J=9.3, 2.1 Hz, 1H), 6.57 (s, 1H), 2.61-2.56 (m, 1H), 1.56 (s, 6H), 0.94-0.86 (m, 4H).

N-(4-bromophenyl)-2-(2-(cyclopropanesulfonamido)thiazol-4-yl)acetamide INTB73

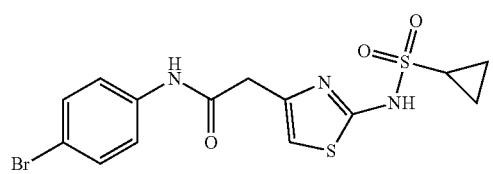 [SMILES: O=C(Cc1csc(NS(=O)(=O)C2CC2)n1)Nc1ccc(Br)cc1]

Prepared as Method 1b from INTB37. Rt 1.61 mins (UPLC acidic); m/z 416 (⁷⁹Br M+H)⁺ (ES⁺); ¹H NMR (400 MHz, DMSO-d6) δ 12.54 (s, 1H), 10.33 (s, 1H), 7.59-7.54

(m, 2H), 7.54-7.48 (m, 2H), 6.55 (s, 1H), 3.64 (s, 2H), 2.63-2.54 (m, 1H), 0.93-0.80 (m, 4H).

Methyl 2-(2-amino-5-chlorothiazol-4-yl)-2-methylpropanoate INTB75

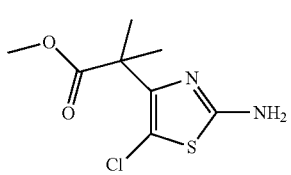

NCS (1.45 g, 10.9 mmol) was added to methyl 2-(2-aminothiazol-4-yl)-2-methylpropanoate INTB2 (1.98 g, 9.89 mmol) in AcOH (15 mL) and the mixture was stirred at RT for 18 hrs. The solvent was evaporated and the residue partitioned between EtOAc (100 mL) and NaHCO$_3$ (aq, 100 mL). The organics were washed with brine (50 mL), dried (MgSO$_4$) and the solvent was evaporated. The crude product was purified by chromatography on silica gel (24 g column, 0-100% EtOAc/iso-hexane) to afford methyl 2-(2-amino-5-chlorothiazol-4-yl)-2-methylpropanoate (1 g, 4.22 mmol, 43% yield) as a yellow solid; 1.70 mins (LCMS basic); m/z 235 (M+H)$^+$ (ES$^+$); $^1$H NMR (500 MHz, DMSO-d6) δ 7.15 (s, 2H), 3.63 (s, 3H), 1.44 (s, 6H).

Methyl 2-(2-amino-5-methoxythiazol-4-yl)-2-methylpropanoate INTB76

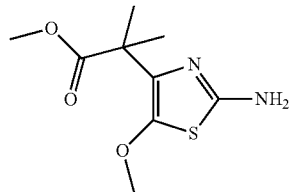

A solution of methyl 2-(2-amino-5-chlorothiazol-4-yl)-2-methylpropanoate INTB75 (300 mg, 1.28 mmol) in MeOH (3 mL) was cooled to 0 °C. in an ice bath, 5.4 M NaOMe (0.24 mL, 1.28 mmol) was added and the resulting mixture was stirred at RT for 18 hrs. The solution was quenched with water (5 mL) and extracted with DCM (2×10 mL). The organics were combined and volatiles evaporated. The crude product was purified by chromatography on silica gel (24 g column, 0-100% EtOAc/iso-hexane) to afford methyl 2-(2-amino-5-methoxythiazol-4-yl)-2-methylpropanoate (187 mg, 0.747 mmol, 43% yield) as a pale yellow solid; Rt 0.99 mins (LCMS acidic); m/z 231 (M+H)$^+$ (ES$^+$); $^1$H NMR (500 MHz, DMSO-d6) δ 6.58 (s, 2H), 3.61 (s, 3H), 3.59 (s, 3H), 1.38 (s, 6H).

TABLE 6

| | | | |
|---|---|---|---|
| | The following intermediates were made according to Method A. | | |
| INT# | Name/Structure (All examples containing chiral centres are racemates unless stated) | Synthesis Method, [LCMS Method], m/z (M + H)$^+$ (Rt/min) | $^1$H NMR Chemical Shift Data (DMSO-d6 unless stated) |
| INTB77 | 3-(2-aminothiazol-4-yl)dihydrofuran-2(3H)-one | Method A, [UPLC basic], 185 (0.44). | 6.98 (s, 2H), 6.42 (s, 1H), 4.40 (td, J = 8.4, 4.1 Hz, 1H), 4.27 (td, J = 8.5, 7.2 Hz, 1H), 3.79 (t, J = 9.1 Hz, 1H), 2.55-2.45 (m, 1H), 2.36 (dq, J = 12.4, 8.5 Hz, 1H). |
| INTB78 | methyl 1-(2-(cyclopropanesulfonamido)thiazol-4-yl)cyclopropane-1-carboxylate | Method A, [HPLC basic], 213 (1.37). | 6.62 (s, 1H), 4.11-4.03 (m, 2H), 1.42-1.37 (m, 2H), 1.33-1.26 (m, 2H), 1.18-1.12 (m, 3H). NH$_2$ not observed. |

Ethyl 2-(2-(cyclopropanesulfonamido)thiazol-4-yl)-2-(methoxyimino)acetate INTB79

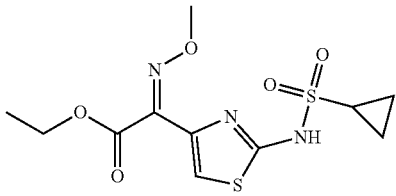 [SMILES: CCOC(=O)/C(=N/OC)c1csc(NS(=O)(=O)C2CC2)n1]

A suspension of ethyl 2-(2-(cyclopropanesulfonamido)thiazol-4-yl)-2-oxoacetate INTB64 (1 g, 3.29 mmol) and O-methylhydroxylamine hydrochloride (0.412 g, 4.93 mmol) in EtOH (40 mL) was treated with Et$_3$N (0.69 mL, 4.95 mmol) to form a solution which was stirred at RT for 72 hrs. The reaction mixture was part concentrated (to approx 5 mL) then taken up in 1M HCl (30 mL) and extracted with EtOAc (3×30 mL). The organic phases were combined, washed with brine (30 mL), dried (Na$_2$SO$_4$), filtered and concentrated on to silica (3 g). The crude product was purified by chromatography on silica gel (24 g column, 0-100% EtOAc/iso-hexane) to afford ethyl 2-(2-(cyclopropanesulfonamido)thiazol-4-yl)-2-(methoxyimino)acetate (950 mg, 2.56 mmol, 78% yield) as an off-white gum. Rt 1.07 min (UPLC, acidic; m/z 334 (M+H)$^+$ (ES$^+$); $^1$H NMR (500 MHz, DMSO-d6) δ 12.84 (s, 1H), 7.38-7.08 (m, 1H), 4.34 (q, J=7.1 Hz, 2H), 3.95 (s, 3H), 2.77-2.59 (m, 1H), 1.28 (t, J=7.1 Hz, 3H), 1.01-0.91 (m, 4H).

Ethyl 2-((tert-butoxycarbonyl)amino)-2-(2-(cyclopropanesulfonamido)thiazol-4-yl)acetate INTB80

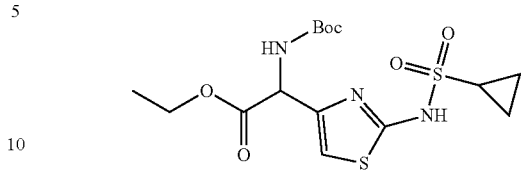

A solution of (E)-ethyl 2-(2-(cyclopropanesulfonamido)thiazol-4-yl)-2-(methoxyimino)acetate INTB79 (950 mg, 2.85 mmol) in EtOH (10 mL) was treated with formic acid (3 mL, 78 mmol) and water (3 mL) then cooled to 0° C. whereupon zinc (560 mg, 8.57 mmol) was added. The reaction mixture was then allowed to warm to RT. After 1 hr the reaction mixture was poured on to SCX (5 g) and washed with MeOH. The intermediate was eluted with 0.1% NH$_3$ in MeOH and concentrated to afford a brown oil. This crude material was then taken up in THF (10 mL) then treated with Di-tert-butyl dicarbonate (1 g, 4.58 mmol). The reaction mixture was stirred at RT for 18 hrs. The reaction mixture was taken up in EtOAc (50 mL) and washed with 1M HCl (50 mL) and sat. NaCl (50 mL). The organic phase was dried (Na$_2$SO$_4$), filtered and concentrated on to silica (3 g). The crude product was purified by chromatography on silica gel (24 g column, 0-100% EtOAc/iso-hexane) to afford ethyl 2-((tert-butoxycarbonyl)amino)-2-(2-(cyclopropanesulfonamido)thiazol-4-yl)acetate (542 mg, 1.07 mmol, 38% yield) as a colourless gum. Rt=1.15 min (UPLC, acidic); m/z 306 (M-Boc+H)$^+$ (ES$^+$); No $^1$H-NMR was recorded.

TABLE 7

The following intermediates were made according to Method B.

| INTB# | Name/Structure (All examples containing chiral centres are racemates unless stated) | Synthesis Method, [LCMS Method], m/z (M + H)$^+$, (Rt/min) | $^1$H NMR Chemical Shift Data (DMSO-d6 unless stated) |
|---|---|---|---|
| INTB81 | N-(4-(2-oxotetrahydrofuran-3-yl)thiazol-2-yl)cyclopropanesulfonamide | Method B using INTB77, [UPLC acidic], 289 (0.46-0.63). | 12.73 (s, 1H), 6.68 (s, 1H), 4.44-4.37 (m, 1H), 4.33-4.23 (m, 1H), 4.11-4.02 (m, 1H), 2.62-2.57 (m, 1H), 2.43-2.35 (m, 2H), 0.96-0.86 (m, 4H). |
| INTB82 | methyl 2-(2-(ethylsulfonamido)thiazol-4-yl)-2-methylpropanoate | Method B using INTB2, [UPLC acidic], 293 (0.86). | 12.57 (s, 1H), 6.56 (s, 1H), 3.64 (s, 3H), 3.12-2.89 (m, 2H), 1.47 (s, 6H), 1.19 (t, J = 10.4 Hz, 3H). |

TABLE 7-continued

The following intermediates were made according to Method B.

| INTB# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| INTB83 | methyl 2-(2-aminothiazol-4-yl)-2-methylpropanoate | Method B using INTB2. [UPLC Basic], 279 (0.67). | (CDCl$_3$) 6.16 (s, 1H), 3.77 (s, 3H), 3.03 (s, 3 H), 1.55 (s, 6 H). exchangeable proton not observed |
| INTB84 | methyl 2-(5-chloro-2-(cyclopropanesulfonamido)thiazol-4-yl)-2-methylpropanoate | Method B using INTB75, [HPLC acidic], 339 (2.15). | 12.46 (s, 1H), 3.68 (s, 3H), 2.79-2.69 (m, 1H), 1.51 (s, 6H), 1.04-0.89 (m, 4H). |
| INTB85 | methyl 2-(2-(cyclopropanesulfonamido)-5-methoxythiazol-4-yl)-2-methylpropanoate | Method B using INTB76, [HPLC acidic], 335 (1.63). | 12.04 (br. s, 1H), 3.71 (s, 3H), 3.65 (s, 3H), 2.69-2.58 (m, 1H), 1.46 (s, 6H), 1.00-0.84 (m, 4H). |
| INTB86 | methyl 2-(2-((2-methoxyethyl)sulfonamido)thiazol-4-yl)-2-methylpropanoate | Method B using INTB2, No LCMS data available. | 12.62 (br. s, 1H), 6.58 (br. s, 1H), 3.68-3.64 (m, 2H), 3.64 (s, 3H), 3.31-3.22 (m, 2H), 3.19 (s, 3H), 1.46 (s, 6H) |

TABLE 7-continued

The following intermediates were made according to Method B.

| INTB# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| INTB87 | methyl 2-(2-((cyclopropylmethyl)sulfonamido)thiazol-4-yl)-2-methylpropanoate | Method B using INTB2, No LCMS data available. | (CDCl3) 6.16 (s, 1H), 3.77 (s, 3H), 3.03 (d, J = 7.2 Hz, 2H), 1.56 (s, 6H), 1.23-1.10 (m, 1H), 0.66-0.58 (m, 2H), 0.43-0.35 (m, 2H) |
| INTB88 | ethyl 1-(2-(cyclopropanesulfonamido)thiazol-4-yl)cyclopropane-1-carboxylate | Method B using INTB78, [HPLC acidic], 317 (0.94). | 12.71 (s, 1H), 6.62 (s, 1H), 4.08 (q, J = 7.1 Hz, 2H), 2.61-2.53 (m, 1H), 1.43-1.34 (m, 2H), 1.32-1.26 (m, 2H), 1.15 (t, J = 7.1 Hz, 3H), 0.95-0.86 (m, 4H). |

TABLE 8

The following intermediates were made according to Method C.

| INTB# | Name/Structure (All examples containing chiral centres are racemates unless stated) | Synthesis Method, [LCMS Method], m/z (M + H)+, (Rt/min) | 1H NMR (Chemical Shift Data (DMSO-d6 unless stated) |
|---|---|---|---|
| INTB89 | methyl 2-(2-(cyclopentanesulfonamido)thiazol-4-yl)-2-methylpropanoate | Method C using INTB27, [UPLC acidic], 333 (1.08). | 12.53 (s, 1H), 6.52 (s, 1H), 3.63 (s, 3H), 3.53-3.41 (m, 1H), 1.91-1.82 (m, 4H), 1.71-1.59 (m, 2H), 1.59-1.48 (m, 2H), 1.46 (s, 6H). |

TABLE 9

| | The following intermediates were made according to Method D. | | |
|---|---|---|---|
| INTB# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
| INTB90 | 2-(2-(cyclopentanesulfonamido)thiazol-4-yl)-2-methylpropanoic acid | Method D using INTB89, [UPLC acidic], 319 (0.96). | No data recorded |
| INTB91 | 2-(2-(ethylsulfonamido)thiazol-4-yl)-2-methylpropanoic acid | Method D using INTB82, [UPLC acidic], 279 (0.47). | 12.77 (s, 1H), 12.55 (s, 1H), 6.52 (s, 1H), 3.11-2.92 (m, 2H), 1.45 (s, 6H), 1.20 (t, J = 7.3 Hz, 3H). |
| INTB92 | methyl 2-(2-aminothiazol-4-yl)-2-methylpropanoate | Method D using INTB83, [UPLC acidic], 265 (0.66). | 12.59 (br, 2 H), 6.54 (s, 1 H), 2.90 (s, 3 H), 1.44 (s, 6 H). |
| INTB93 | 1-(2-(cyclopropanesulfonamido)thiazol-4-yl)cyclopropane-1-carobxylic acid | Method D using INTB88, [UPLC acidic], 289 (0.72). | 12.73-12.69 (m, 2H), 6.60 (s, 1H), 2.62-2.51 (m, 1H), 1.41-1.31 (m, 2H), 1.27-1.21 (m, 2H), 0.95-0.86 (m, 4H). |
| INTB94 | 2-(5-chloro-2-(cyclopropanesulfonamido)thiazol-4-yl)-2-methylpropanoic acid | Method D using INTB84, [HPLC acidic], 325 (1.59). | 13.03-12.26 (m, 2H), 2.75-2.68 (m, 1H), 1.50 (s, 6H), 1.10-0.82 (m, 4H). |

TABLE 9-continued

The following intermediates were made according to Method D.

| INTB# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| INTB95 | 2-(2-(cyclopropanesulfonamido)-5-methoxythiazol-4-yl)-2-methylpropanoic acid | Method D using INTB85, [HPLC acidic], 321 (1.42). | 12.56 (v. br. s, 1H), 12.03 (v. br. s, 1H), 3.73 (s, 3H), 2.66-2.58 (m, 1H), 1.45 (s, 6H), 0.92 (d, J = 6.4 Hz, 4H). |
| INTB96 | 2-(2-(cyclopropylmethylsulfonamido)thiazol-4-yl)-2-methylpropanoic acid | Method D using INTB87, [HPLC acidic], 305 (0.88). | 12.60 (s, 1H), 6.52 (s, 1H), 3.32 (s, 1H), 2.93 (d, J = 7.1 Hz, 2H), 1.45 (s, 6H), 1.03-0.92 (m, 1H), 0.53-0.45 (m, 2H), 0.33-0.25 (m, 2H). |
| INTB97 | 2-(2-(2-methoxyethylsulfonamido)thiazol-4-yl)-2-methylpropanoic acid | Method D using INTB86, [JPLC acidic], 309 (0.73). | 12.76 (s, 1H), 12.61 (s, 1H), 6.54 (s, 1H), 3.66 (t, J = 6.5 Hz, 2H), 3.26 (t, J = 6.5 Hz, 2H), 3.20 (s, 3H), 1.45 (s, 6H). |
| INTB98 | 2-((tert-butoxycarbonyl)amino)-2-(2-(cyclopropanesulfonamido)thiazol-4-yl)acetic acid | Method D using INTB80, [HPLC acidic], 322 (M + H − t-Bu)$^+$ (1.63). | 13.27 (s, 1H), 12.51 (s, 1H), 7.60 (d, J = 8.9 Hz, 1H), 6.66 (s, 1H), 5.11 (d, J = 8.8 Hz, 1H), 2.65-2.55 (m, 1H), 1.41 (s, 9H), 0.95-0.82 (m, 4H). |

Ethyl 2-(2-(cyclopropanesulfonamido)thiazol-4-yl)butanoate INTB38

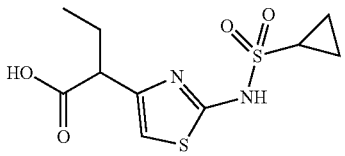 [SMILES: CCC(C(=O)O)c1csc(NS(=O)(=O)C2CC2)n1]

The racemate INTB38 was separated by chiral preparative HPLC using a Diacel Chiralpak IA column (7% EtOH in [60:40 iso-hexane (0.2% TFA): chloroform]) to afford:

Peak A: Stereochemistry of Product was not Assigned

Ethyl 2-(2-(cyclopropanesulfonamido)thiazol-4-yl)butanoate INTB38a; Rt 1.29 min (HPLC acidic); m/z 291 (M+H)$^+$ (ES$^+$); 289 (M–H)$^-$ (ES$^-$); $^1$H NMR (500 MHz, DMSO-d6) δ 12.65 (br, 2H), 6.55 (s, 1H), 3.50-3.44 (m, 1H), 2.64-2.54 (m, 1H), 2.03-1.70 (m, 2H), 1.01-0.76 (m, 7H).

The product was analysed by Chiral HPLC (Diacel Chiralpak IA, 5 um, 4.6×250 mm, 30 min method, 1.0 mL/min, 7% EtOH in [60:40 iso-hexane (0.2% TFA): chloroform]: Rt=21.70 min, >99% ee 254 nm.

Peak B: Stereochemistry of Product was not Assigned

Ethyl 2-(2-(cyclopropanesulfonamido)thiazol-4-yl)butanoate INTB38b; Rt 1.29 min (HPLC acidic); m/z 291 (M+H)$^+$ (ES$^+$); 289 (M–H)$^-$ (ES$^-$); $^1$H NMR (500 MHz, DMSO-d6) δ 12.65 (br, 2H), 6.55 (s, 1H), 3.50-3.44 (m, 1H), 2.64-2.54 (m, 1H), 2.03-1.70 (m, 2H), 1.01-0.76 (m, 7H).

The product was analysed by Chiral HPLC (Diacel Chiralpak IA, 5 um, 4.6×250 mm, 30 min method, 1.0 mL/min, 7% EtOH in [60:40 iso-hexane (0.2% TFA): chloroform]: Rt=30.84 min, >99% ee 254 nm.

TABLE 10

The following intermediates were made according to Method 1b.

| INTB# | Name/Structure (All examples containing chiral centres are racemates unless stated) | Synthesis Method, [LCMS Method], m/z (M + H)$^+$ (Rt/min) | $^1$H NMR Chemical Shift Data (DMSO-d6 unless stated) |
|---|---|---|---|
| INTB99 | N-(4-bromo-3-fluoro-2-methylphenyl)-2-(2-(cyclopropanesulfonamido)thiazol-4-yl)-2-methylpropanamide | Method 1b using INTB37, [UPLC acidic), 476 (1.30). | 12.58 (s, 1H), 9.15 (s, 1H), 7.56-7.49 (m, 1H), 7.06 (d, J = 8.7 Hz, 1H), 6.58 (s, 1H), 2.59-2.55 (m, 1H), 2.10-2.07 (m, 3H), 1.55 (s, 6H), 0.92-0.86 (m, 4H). |
| INTB100 | N-(4-bromo-2-(trifluoromethyl)phenyl)-2-(2-(cyclopropanesulfonamido)thiazol-4-yl)-2-methylpropanamide | Method 1b using INTB37, [UPLC acidic), 512 (1.37). | 12.58 (s, 1H), 0.10 (s, 1H), 7.98-7.90 (m, 2H), 7.49 (d, J = 8.5 Hz, 1H), 6.62 (s, 1H), 2.60-2.56 (m, 1H), 1.53 (s, 6H), 0.93-0.87 (m, 4H). |
| INTB101 | N-(4-bromo-2,6-diethylphenyl)-2-(2-(cyclopropanesulfonamido)thiazol-4-yl)-2-methylpropanamide | Method 1b using INTB37, [UPLC acidic], 500 (1.42). | 12.54 (s, 1H), 8.86 (s, 1H), 7.27 (s, 2H), 6.58 (s, 1H), 2.58-2.52 (m, 1H), 2.44 (q, J = 7.5 Hz, 4H), 1.59 (s, 6H), 1.06 (t, J = 7.5 Hz, 6H), 0.95-0.86 (m, 4H). |

TABLE 10-continued

The following intermediates were made according to Method 1b.

| INTB# | Name/Structure (All examples containing chiral centres are racemates unless stated) | Synthesis Method, [LCMS Method], m/z (M + H)+ (Rt/min) | $^1$H NMR Chemical Shift Data (DMSO-d6 unless stated) |
|---|---|---|---|
| INTB102 | N-(4-bromo-2,3-dimethylphenyl)-2-(2-(cyclopropanesulfonamido)thiazol-4-yl)-2-methylpropanamide 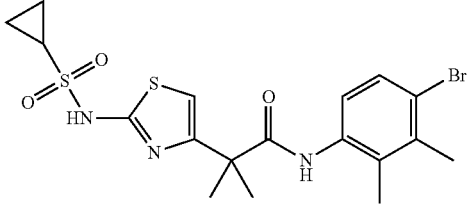 | Method 1b using INTB37, [UPLC acidic], 472 (1.32). | 12.58 (s, 1H), 9.05 (s, 1H), 7.44 (d, J = 8.5 Hz, 1H), 7.00 (d, J = 8.5 Hz, 1H), 6.58 (s, 1H), 2.60-2.56 (m, 1H), 2.36 (s, 3H), 2.10 (s, 3H), 1.56 (s, 6H), 0.94-0.87 (m, 4H). |
| INB103 | N-(4-bromo-2-fluoro-5-methylphenyl)-2-(2-(cyclopropanesulfonamido)thiazol-4-yl)-2-methylpropanamide 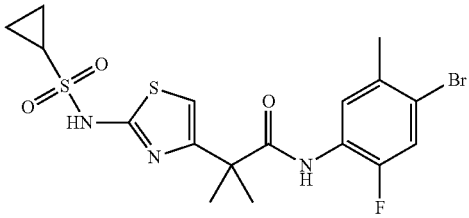 | Method 1b using INTB37, [HPLC acidic], 476 (2.13). | 12.57 (s, 1H), 9.19 (s, 1H), 7.59 (d, J = 9.7 Hz, 1H), 7.48 (d, J = 8.0 Hz, 1H), 6.57 (s, 1H), 2.60-2.56 (m, 1H), 2.31 (s, 3H), 1.55 (s, 6H), 0.94-0.88 (m, 4H). |
| INTB104 | N-(4-bromo-2,5-dimethylphenyl)-2-(2-(cyclopropanesulfonamido)thiazol-4-yl)-2-methylpropanamide 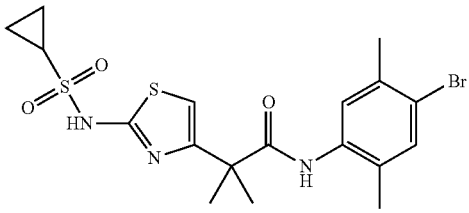 | Method 1b using INTB37, [UPLC acidic], 472 (1.35). | 12.56 (s, 1H), 8.93-8.89 (m, 1H), 7.45 (s, 1H), 7.22 (s, 1H), 6.58 (s, 1H), 2.60-2.56 (m, 1H), 2.30 (s, 3H), 2.10 (s, 3H), 1.56 (s, 6H), 0.93-0.87 (m, 4H). |
| INTB105 | N-(4-bromo-2,6-difluorophenyl)-2-(2-(cyclopropanesulfonamido)thiazol-4-yl)-2-methylpropanamide 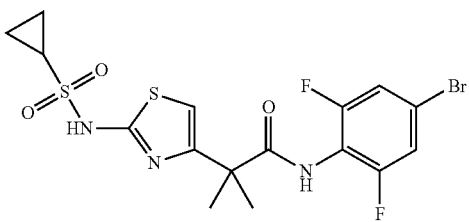 | Method 1b using INTB37, [UPLC acidic], 480 (1.21). | 12.63 (s, 1H), 9.27 (s, 1H), 7.57 (d, J = 7.2 Hz, 2H), 6.56 (s, 1H), 2.60-2.56 (m, 1H), 1.56 (s, 6H), 0.93-0.88 (m, 4H). |

TABLE 10-continued

The following intermediates were made according to Method 1b.

| INTB# | Name/Structure (All examples containing chiral centres are racemates unless stated) | Synthesis Method, [LCMS Method], m/z (M + H)+ (Rt/min) | 1H NMR Chemical Shift Data (DMSO-d6 unless stated) |
|---|---|---|---|
| INTB106 | N-(4-bromo-3-(trifluoromethyl)phenyl)-2-(2-(cyclopropanesulfonamido)thiazol-4-yl)-2-methylpropanamide | Method 1b using INTB37, [UPLC acidic], 512 (1.57). | 12.57 (s, 1H), 9.70 (s, 1H), 8.19 (d, J = 2.4 Hz, 1H), 7.90-7.81 (m, 2H), 6.58 (s, 1H), 2.60-2.56 (m, 1H), 1.56 (s, 6H), 0.93-0.89 (m, 4H). |
| INTB107 | N-(4-bromo-5-fluoro-2-methoxyphenyl)-2-(2-(cyclopropanesulfonamido)thiazol-4-yl)-2-methylpropanamide | Method 1b using INTB37, [UPLC acidic], 492 (1.40). | 12.64 (s, 1H), 8.44 (s, 1H), 7.96-7.92 (m, 1H), 7.37 (d, J = 6.3 Hz, 1H), 6.72 (s, 1H), 3.83 (s, 3H), 2.62-2.58 (m, 1H), 1.55 (s, 6H), 0.94-0.90 (m, 4H). |
| INTB108 | N-(4-bromo-5-fluoro-2-methylphenyl)-2-(2-(cyclopropanesulfonamido)thiazol-4-yl)-2-methylpropanamide | Method 1b using INTB37, [UPLC acidic], 476 (1.32). | 12.56 (s, 1H), 8.97 (s, 1H), 7.59 (d, J = 7.8 Hz, 1H), 7.36-7.31 (m, 1H), 6.61 (s, 1H), 2.60-2.56 (m, 1H), 2.13 (s, 3H), 1.56 (s, 6H), 0.93-0.89 (m, 4H). |
| INTB109 | N-(4-bromo-2-isopropylphenyl)-2-(2-(cyclopropanesulfonamido)thiazol-4-yl)-2-methylpropanamide | Method 1b using INTB37, [UPLC acidic], 486 (1.40). | 12.58 (s, 1H), 8.96 (s, 1H), 7.46-7.36 (m, 2H), 7.15 (d, J = 8.4 Hz, 1H), 6.59 (s, 1H), 3.05-2.95 (m, 1H), 2.63-2.51 (m, 1H), 1.56 (s, 6H), 1.10 (d, J = 6.9 Hz, 6H), 0.94-0.81 (m, 4H). |

Aniline Intermediate Preparation

5-(pyridin-3-yl)pyrimidin-2-amine INTA1

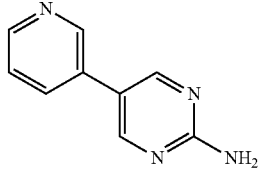 [SMILES: Nc1ncc(-c2cccnc2)cn1]

PdCl$_2$(dppD) (68.3 mg, 0.09 mmol) was added to a degassed (N$_2$, 5 mins) solution of pyridin-3-ylboronic acid (230 mg, 1.87 mmol), 5-bromopyrimidin-2-amine (325 mg, 1.87 mmol) and K$_2$CO$_3$ (774 mg, 5.60 mmol) in dioxane (7 mL) and water (1 mL). The solution was degassed (N$_2$, 5 mins) then heated to 100° C. for 4 hrs and then allowed to cool to RT and stirred for 16 hrs. The reaction mixture was concentrated onto silica. The crude product was purified by chromatography on silica gel (40 g column, 0-10% MeOH/DCM) to afford 5-(pyridin-3-yl)pyrimidin-2-amine (220 mg, 1.25 mmol, 67% yield) as a pale brown solid; Rt 0.79 min (HPLC basic); m/z 173 (M+H)$^+$ (ES$^+$); $^1$H NMR (400 MHz, DMSO-d6) b 8.86 (br. s, 1H), 8.64 (s, 2H), 8.57-8.47 (m, 1H), 8.10-8.00 (m, 1H), 7.45 (dd, J=7.9, 4.7 Hz, 1H), 6.89 (s, 2H).

4-(6-methoxypyrazin-2-yl)aniline INTA2

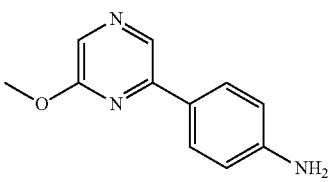

Pd(PPh$_3$)$_4$ (132 mg, 0.11 mmol) was added to a degassed (N$_2$, 5 mins) solution of 4-(4,4,5,5-tetramethyl-1,3,2-dioxaborolan-2-yl)aniline (500 mg, 2.28 mmol), 2-bromo-6-methoxypyrazine (431 mg, 2.28 mmol) and NaHCO$_3$ (575 mg, 6.85 mmol) in MeCN (4 mL) and water (1 mL). The solution was degassed further (N$_2$, 5 mins) and heated to 80° C. for 2 hrs then allowed to cool to RT. The solution was concentrated onto silica. The crude product was purified by chromatography on silica gel (40 g column, 0-10% MeOH/DCM) to afford 4-(6-methoxypyrazin-2-yl)aniline (423 mg, 2.00 mmol, 88% yield) as a pale yellow solid; Rt 1.63 min (HPLC basic); m/z 202 (M+H)+(ES$^+$); $^1$H NMR (400 MHz, DMSO-d6) δ 8.61 (s, 1H), 8.04 (s, 1H), 7.94-7.75 (m, 2H), 6.75-6.54 (m, 2H), 5.59 (s, 2H), 3.98 (s, 3H).

5-(6-(trifluoromethyl)pyrazin-2-yl)pyridin-2-amine INTA3

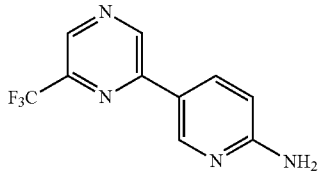

A suspension of 2-chloro-6-(trifluoromethyl)pyrazine (250 mg, 1.37 mmol) and 5-(4,4,5,5-tetramethyl-1,3,2-dioxaborolan-2-yl)pyridin-2-amine (301 mg, 1.37 mmol) in a mixture of 2M NaHCO$_3$ (2.05 mL, 4.11 mmol), EtOH (2 mL) and toluene (10 mL) was degassed (N$_2$, 10 mins) then Pd(PPh$_3$)$_4$ (79 mg, 0.07 mmol) was added and the degassing was continued (N$_2$, 5 mins) before being heated to 85° C. for 18 hrs. The reaction mixture was concentrated in vacuo then taken up in 1 M HCl (7 mL) and washed with DCM (20 mL). The aqueous phase was then brought to pH 12 by careful addition of 2M NaOH (aq). The aqueous layer was extracted with EtOAc (3×15 mL), the organic phases were combined, and concentrated on to silica. The crude product was purified by chromatography on silica gel (12 g column, 20-100% EtOAc/iso-hexane) to afford 5-(6-(trifluoromethyl)pyrazin-2-yl)pyridin-2-amine (227 mg, 0.89 mmol, 66% yield) as a colourless solid; Rt 0.52 min (UPLC acidic); m/z 241 (M+H)$^+$ (ES$^+$); $^1$H NMR (400 MHz, DMSO-d6) b 9.52-9.41 (m, 1H), 8.95 (t, J=0.6 Hz, 1H), 8.81 (dd, J=2.5, 0.8 Hz, 1H), 8.16 (dd, J=8.8, 2.5 Hz, 1H), 6.66 (s, 2H), 6.59 (dd, J=8.8, 0.8 Hz, 1H).

5-(6-propoxypyrazin-2-yl)pyridin-2-amine INTA4

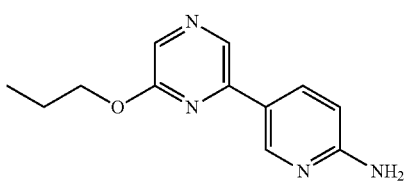 [SMILES: CCCOc1cncc(-c2ccc(N)nc2)n1]

5-(4,4,5,5-tetramethyl-1,3,2-dioxaborolan-2-yl)pyridin-2-amine (319 mg, 1.45 mmol) and 2-chloro-6-propoxypyrazine (250 mg, 1.45 mmol) were dissolved in dioxane (10 mL), 2M NaHCO$_3$ (2.17 mL, 4.35 mmol) was added and the mixture was degassed (N$_2$, 15 mins). Pd(PPh$_3$)$_4$ (84 mg, 0.07 mmol) was then added and the mixture was heated to 80° C. for 18 hrs. The mixture was diluted with H$_2$O (10 mL), the product was extracted with EtOAc (3×10 mL), the combined organic extract was passed through a phase separator and the solvent was removed in vacuo. The crude product was purified by chromatography on silica gel (40 g column, 0-100% EtOAc/iso-hexane) to afford 5-(6-propoxypyrazin-2-yl)pyridin-2-amine (261 mg, 1.00 mmol, 69% yield) as a beige solid; Rt 1.12 min (UPLC basic); m/z 231 (M+H)$^+$ (ES$^+$); $^1$H NMR (400 MHz, DMSO-d6) b 8.71 (dd, J=2.5, 0.8 Hz, 1H), 8.65 (s, 1H), 8.19-8.00 (m, 2H), 6.55 (dd, J=8.7, 0.8 Hz, 1H), 6.42 (s, 2H), 4.35 (t, J=6.6 Hz, 2H), 1.89-1.70 (m, 2H), 1.00 (t, J=7.4 Hz, 3H).

Method E: Suzuki Coupling of Halo Anilines with Heteroaromatic Boronates

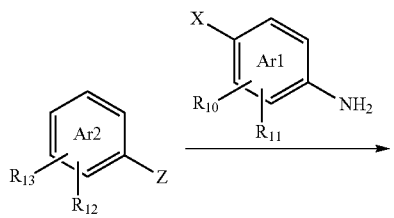

Z = B(OH)$_2$, B(pin)$_2$
X = Br, Cl

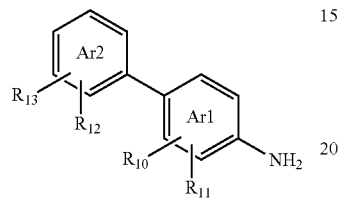

A solution of Ar1-X (1 eq) and Ar2-Z (1 eq) in solvent (3 volumes) and base (2.5 eq) was degassed (N$_2$, 5 min) and heated to 40° C. whereupon Pd catalyst (3 mol %) was added and the reaction mixture further degassed (N$_2$, 5 min) before being heated to 90° C. for 90 mins. The reaction mixture was allowed to cool to RT. In general, the desired compound is purified by column chromatography.

Method F: Suzuki Coupling of Heteroaromatic Halides with Aniline Boronates

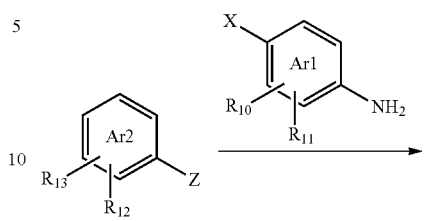

Z = Br, Cl
X = B(OH)$_2$, B(pin)$_2$

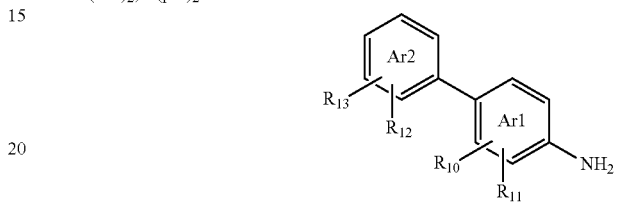

Pd catalyst (5 mol %) was added to a degassed (N$_2$, 5 mins) solution of Ar1-X (1 eq), Ar2-Z (1 eq) and base (3 eq, 6.85 mmol) in solvent (3 volumes). The solution was then degassed further (N$_2$, 5 mins) and then heated to 90° C. for 2 hrs then allowed to cool to RT. In general, the desired compound is purified by column chromatography.

TABLE 11

| | Additional Intermediates were made according to Methods E or F. | | | |
|---|---|---|---|---|
| INTA# | Name/Structure | Synthesis Method, [LCMS Method], m/z (M + H)$^+$, (Rt/min) | $^1$H NMR Chemical Shift Data (DMSO-d6 unless stated) | Catalyst, Base, solvent |
| INTA5 | 5-amino-2-(pyrazin-2-yl)benzonitrile | Method F, [UPLC basic], 197, (0.71) | 8.99 (d, J = 1.6 Hz, 1H), 8.70 (dd, J = 2.5, 1.6 Hz, 1H), 8.59 (d, J = 2.5 Hz, 1H), 7.69 (d, J = 8.6 Hz, 1H), 7.04 (d, J = 2.4 Hz, 1H), 6.96 (dd, J = 8.6, 2.4 Hz, 1H), 6.04 (s, 2H). | PdCl$_2$(dppf), K$_3$PO$_4$, dioxane |
| INTA6 | 2,3-difluoro-4-(pyridin-3-yl)aniline | Method E | 8.76-8.65 (m, 1H), 8.52 (dd, J = 4.8, 1.6 Hz, 1H), 7.94-7.83 (m, 1H), 7.46 (ddd, J = 8.0, 4.8, 0.9 Hz, 1H), 7.10 (td, J = 8.4, 2.0 Hz, 1H), 6.69 (td, J = 8.5, 1.8 Hz, 1H), 5.75 (s, 2H). | Pd(PPh$_3$)$_4$, K$_2$CO$_3$, dioxane |

TABLE 11-continued

Additional Intermediates were made according to Methods E or F.

| INTA# | Name/Structure | Synthesis Method, [LCMS Method], m/z (M + H)+, (Rt/min) | 1H NMR Chemical Shift Data (DMSO-d6 unless stated) | Catalyst, Base, solvent |
|---|---|---|---|---|
| INTA7 | 3-fluoro-4-(pyrazin-2-yl)aniline | Method F, [UPLC basic], 190, (0.79). | 8.88 (dd, J = 2.5, 1.6 Hz, 1H), 8.65 (dd, J = 2.5, 1.6 Hz, 1H), 8.45 (d, J = 2.5 Hz, 1H), 7.72 (t, J = 8.9 Hz, 1H), 6.53 (dd, J = 8.6, 2.2 Hz, 1H), 6.43 (dd, J = 14.6, 2.1 Hz, 1H), 5.95 (s, 2H). | PdCl2(dppf), K3PO4, dioxane |
| INTA8 | 2-chloro-4-(pyridin-3-yl)aniline | Method E, [UPLC basic], 206, (1.04). | 8.81 (d, J = 2.5 Hz, 1H), 8.45 (dd, J = 4.7, 1.6 Hz, 1H), 7.97 (ddd, J = 8.0, 2.4, 1.6 Hz, 1H), 7.60 (d, J = 2.1 Hz, 1H), 7.48-7.28 (m, 2H), 6.89 (d, J = 8.4 Hz, 1H), 5.60 (s, 2H). | Pd(PPh3)4, K2CO3, dioxane |
| INTA9 | 3-methoxy-4-(pyrazin-2-yl)aniline | Method F, [UPLC basic], 202, (0.75). | None recorded | PdCl2(dppf), K3PO4, dioxane |
| INTA11 | 4-(5-ethoxypyridin-3-yl)aniline | Method F, [UPLC basic], 215, (1.05). | 8.36 (d, J = 1.9 Hz, 1H), 8.11 (d, J = 2.7 Hz, 1H), 7.48-7.39 (m, 3H), 6.70-6.62 (m, 2H), 5.34 (s, 2H), 4.17 (q, J = 6.9 Hz, 2H), 1.36 (t, J = 7.0 Hz, 3H). | PdCl2(dppf), K2CO3, dioxane |
| INTA12 | 5-(4-aminophenyl)nicotinonitrile | Method E, [UPLC basic], 196, (0.89). | 9.08 (d, J = 2.4 Hz, 1H), 8.91-8.79 (m, 1H), 8.49-8.43 (m, 1H), 7.58-7.48 (m, 2H), 6.73-6.57 (m, 2H), 5.49 (d, J = 7.0 Hz, 2H). | PdCl2(dppf), K2CO3, dioxane |

TABLE 11-continued

Additional Intermediates were made according to Methods E or F.

| INTA# | Name/Structure | Synthesis Method, [LCMS Method], m/z (M + H)+, (Rt/min) | ¹H NMR Chemical Shift Data (DMSO-d6 unless stated) | Catalyst, Base, solvent |
|---|---|---|---|---|
| INTA13 | 4-(5-fluoropyridin-3-yl)aniline | Method E, [HPLC basic], 189, (1.53). | 8.69 (t, J = 2.0 Hz, 1H), 8.39 (d, J = 2.7 Hz, 1H), 7.87 (ddd, J = 10.9, 2.7, 1.9 Hz, 1H), 7.53-7.45 (m, 2H), 6.71-6.63 (m, 2H), 5.44 (s, 2H). | PdCl$_2$(dppf), K$_2$CO$_3$, dioxane |
| INTA14 | 4-(5-(trifluoromethyl)pyridin-3-yl)aniline | Method E, [UPLC basic], 239, (1.21). | 9.15-9.06 (m, 1H), 8.82-8.72 (m, 1H), 8.30-8.23 (m, 1H), 7.60-7.51 (m, 2H), 6.74-6.64 (m, 2H), 5.50 (s, 2H). | PdCl$_2$(dppf), K$_2$CO$_3$, dioxane |
| INTA15 | 5-amino-2-(pyridin-3-yl)benzonitrile | Method E, [HPLC basic], 196, (1.12). | 8.68 (dd, J = 2.5, 0.9 Hz, 1H), 8.58 (dd, J = 4.8, 1.6 Hz, 1H), 7.91 (ddd, J = 7.9, 2.4, 1.6 Hz, 1H), 7.49 (ddd, J = 7.9, 4.8, 0.9 Hz, 1H), 7.34 (d, J = 8.4 Hz, 1H), 7.02 (d, J = 2.4 Hz, 1H), 6.96 (dd, J = 8.5, 2.5 Hz, 1H), 5.84 (s, 2H). | PdCl$_2$(dppf), K$_2$CO$_3$, dioxane |
| INTA16 | 3-methoxy-4-(pyridin-3-yl)aniline | Method E, [HPLC basic], 201, (1.39). | 8.60 (dd, J = 2.4, 0.9 Hz, 1H), 8.38 (dd, J = 4.7, 1.7 Hz, 1H), 7.78 (ddd, J = 7.9, 2.3, 1.7 Hz, 1H), 7.34 (ddd, J = 7.9, 4.8, 0.9 Hz, 1H), 7.02 (d, J = 8.1 Hz, 1H), 6.34 (d, J = 2.1 Hz, 1H), 6.26 (dd, J = 8.1, 2.0 Hz, 1H), 5.35 (s, 2H), 3.71 (s, 3H). | PdCl$_2$(dppf), K$_3$PO$_4$, dioxane |
| INTA17 | 3-chloro-4-(pyridin-3-yl)aniline | Method E, [UPLC basic], 205, (0.98). | 8.56 (dd, J = 2.4, 0.9 Hz, 1H), 8.54-8.47 (m, 1H), 7.78 (ddd, J = 7.9, 2.3, 1.6 Hz, 1H), 7.42 (ddd, J = 7.9, 4.8, 0.9 Hz, 1H), 7.11 (d, J = 8.3 Hz, 1H), 6.74 (d, J = 2.2 Hz, 1H), 6.62 (dd, J = 8.3, 2.3 Hz, 1H), 5.62 (s, 2H). | PdCl$_2$(dppf), K$_3$PO$_4$, dioxane |

TABLE 11-continued

Additional Intermediates were made according to Methods E or F.

| INTA# | Name/Structure | Synthesis Method, [LCMS Method], m/z (M + H)+, (Rt/min) | ¹H NMR Chemical Shift Data (DMSO-d6 unless stated) | Catalyst, Base, solvent |
|---|---|---|---|---|
| INTA18 | 4-(5-chloropyridin-3-yl)aniline | Method E, [UPLC basic], 205, (1.11). | 8.79-8.74 (m, 1H), 8.49-8.39 (m, 1H), 8.10-7.98 (m, 1H), 7.54-7.42 (m, 2H), 6.72-6.61 (m, 2H), 5.45 (s, 2H). | PdCl$_2$(dppf), K$_2$CO$_3$, dioxane |
| INTA19 | 4-(2-methylpyridin-3-yl)aniline | Method E, [HPLC basic], 185, (1.37). | 8.36 (dd, J = 4.8, 1.8 Hz, 1H), 7.51 (dd, J = 7.7, 1.8 Hz, 1H), 7.22 (dd, J = 7.6, 4.8 Hz, 1H), 7.10-7.00 (m, 2H), 6.70-6.41 (m, 2H), 5.22 (s, 2H), 2.44 (s, 3H). | Pd 170, K$_3$PO$_4$, dioxane |
| INTA20 | 4-(6-methylpyridin-3-yl)aniline | Method E, [HPLC basic], 185, (1.43). | 8.63 (dd, J = 2.5, 0.8 Hz, 1H), 7.80 (dd, J = 8.1, 2.5 Hz, 1H), 7.40-7.32 (m, 2H), 7.23 (dt, J = 8.1, 0.7 Hz, 1H), 6.70-6.58 (m, 2H), 5.27 (s, 2H), 2.46 (s, 3H). | Pd 170, K$_3$PO$_4$, dioxane |
| INTA21 | 4-(5-methylpyridin-3-yl)aniline | Method E, [HPLC basic], 185, (1.47). | 8.57 (d, J = 2.3 Hz, 1H), 8.25 (dd, J = 2.0, 0.8 Hz, 1H), 7.74 (td, J = 2.2, 0.9 Hz, 1H), 7.43-7.30 (m, 2H), 6.72-6.52 (m, 2H), 5.31 (s, 2H), 2.33 (d, J = 0.8 Hz, 3H). | Pd 170, K$_3$PO$_4$, dioxane |
| INTA22 | 4-(5-isopropoxypyridin-3-yl)aniline | Method F, [UPLC basic], 229, (1.15). | 8.41-8.30 (m, 1H), 8.13-8.05 (m, 1H), 7.48-7.35 (m, 3H), 6.72-6.59 (m, 2H), 5.34 (s, 2H), 4.86-4.69 (m, 1H), 1.37-1.23 (m, 6H). | PdCl$_2$(dppf), K$_2$CO$_3$, dioxane |

TABLE 11-continued

Additional Intermediates were made according to Methods E or F.

| INTA# | Name/Structure | Synthesis Method, [LCMS Method], m/z (M + H)+, (Rt/min) | $^1$H NMR Chemical Shift Data (DMSO-d6 unless stated) | Catalyst, Base, solvent |
|---|---|---|---|---|
| INTA23 | 2-fluoro-4-(5-isopropoxypyridin-3-yl)aniline | Method F, [UPLC basic], 247, (1.25). | 8.42-8.34 (m, 1H), 8.17-8.06 (m, 1H), 7.53-7.42 (m, 2H), 7.35-7.28 (m, 1H), 6.89-6.80 (m, 1H), 5.39 (s, 2H), 4.90-4.75 (m, 1H), 1.35-1.26 (m, 6H). | PdCl$_2$(dppf), K$_2$CO$_3$, dioxane |
| INTA24 | 4-(5-(difluoromethoxy)pyridin-3-yl)-2-fluoroaniline | Method F, [UPLC basic], 255, (1.15). | 8.74 (d, J = 1.9 Hz, 1H), 8.35 (d, J = 2.6 Hz, 1H), 7.85 (t, J = 2.3 Hz, 1H), 7.57-7.25 (m, 3H), 6.87 (dd, J = 9.5, 8.3 Hz, 1H), 5.50 (s, 2H). | PdCl$_2$(dppf), K$_2$CO$_3$, dioxane |
| INTA25 | 4-(5-(difluoromethoxy)pyridin-3-yl)aniline | Method F, [UPLC basic], 237, (1.10). | (Methanol-d4) δ 8.60 (d, J = 2.0 Hz, 1H), 8.27 (d, J = 2.3 Hz, 1H), 7.78-7.72 (m, 1H), 7.47-7.40 (m, 2H), 7.18-6.78 (m, 3H), (Exchangable protons not observed). | PdCl$_2$(dppf), K$_2$CO$_3$, dioxane |
| INTA26 | 5-(4-amino-3-fluorophenyl)nicotinonitrile | Method E, [HPLC basic], 214, (1.6). | 9.13 (d, J = 2.3 Hz, 1H), 8.86 (d, J = 1.9 Hz, 1H), 8.54 (t, J = 2.1 Hz, 1H), 7.60 (dd, J = 13.1, 2.1 Hz, 1H), 7.43 (dd, J = 8.3, 2.1 Hz, 1H), 6.87 (dd, J = 9.5, 8.3 Hz, 1H), 5.56 (s, 2H),. | PdCl$_2$(dppf), K$_2$CO$_3$, dioxane |
| INTA27 | 4-(5-chloropyridin-3-yl)-2-fluoroaniline | Method E, [HPLC basic], 223, (1.9). | 8.80 (d, J = 2.0 Hz, 1H), 8.48 (d, J = 2.2 Hz, 1H), 8.14 (t, J = 2.2 Hz, 1H), 7.54 (dd, J = 13.0, 2.1 Hz, 1H), 7.38 (dd, J = 8.3, 2.1 Hz, 1H), 6.86 (dd, J = 9.5, 8.3 Hz, 1H), 5.51 (s, 2H). | PdCl$_2$(dppf), K$_2$CO$_3$, dioxane |

TABLE 11-continued

*Additional Intermediates were made according to Methods E or F.*

| INTA# | Name/Structure | Synthesis Method, [LCMS Method], m/z (M + H)+, (Rt/min) | 1H NMR Chemical Shift Data (DMSO-d6 unless stated) | Catalyst, Base, solvent |
|---|---|---|---|---|
| INTA28 | 4-(5-ethoxypyridin-3-yl)-2-fluoroaniline | Method F, [UPLC basic], 233, (1.16). | 8.40 (d, J = 1.9 Hz, 1H), 8.15 (d, J = 2.7 Hz, 1H), 7.51 (dd, J = 2.7, 1.9 Hz, 1H), 7.47 (dd, J = 13.0, 2.1 Hz, 1H), 7.33 (dd, J = 8.3, 2.1 Hz, 1H), 6.85 (dd, J = 9.5, 8.3 Hz, 1H), 5.40 (s, 2H), 4.18 (q, J = 7.0 Hz, 2H), 1.37 (t, J = 7.0 Hz, 3H). | PdCl2(dppf), K3PO4, dioxane |
| INTA29 | 2-fluoro-4-(5-fluoropyridin-3-yl)aniline | Method F, [UPLC basic], 207, (1.07). | 8.74 (t, J = 1.9 Hz, 1H), 8.43 (d, J = 2.7 Hz, 1H), 8.00-7.89 (m, 1H), 7.54 (dd, J = 13.0, 2.1 Hz, 1H), 7.39 (dd, J = 8.3, 2.1 Hz, 1H), 6.86 (dd, J = 9.5, 8.3 Hz, 1H), 5.50 (s, 2H). | PdCl2(dppf), K3PO4, dioxane |
| INTA30 | 2-fluoro-4-(5-(2,2,2-trifluoro ethoxy)pyridin-3-yl)aniline | Method F, [UPLC basic], 287, (1.26). | 8.61-8.50 (m, 1H), 8.31-8.22 (m, 1H), 7.77-7.64 (m, 1H), 7.59-7.47 (m, 1H), 7.42-7.33 (m, 1H), 6.93-6.75 (m, 1H), 5.44 (s, 2H), 5.01-4.88 (m, 2H). | PdCl2(dppf), K3PO4, dioxane |
| INTA31 | 4-(5-(2,2,2-trifluoro-ethoxy)pyridin-3-yl)aniline | Method F, [UPLC basic], 269, (1.18). | 8.55-8.41 (m, 1H), 8.29-8.13 (m, 1H), 7.69-7.61 (m, 1H), 7.53-7.43 (m, 2H), 6.73-6.61 (m, 2H), 5.38 (s, 2H), 5.02-4.82 (m, 2H). | PdCl2(dppf), K3PO4, dioxane |
| INTA32 | 5'-ethoxy-[3,3'-bipyridin]-6-amine | Method F, [UPLC basic], 216, (0.88). | 8.39 (d, J = 1.9 Hz, 1H), 8.32 (d, J = 2.5 Hz, 1H), 8.17 (d, J = 2.7 Hz, 1H), 7.78 (dd, J = 8.6, 2.6 Hz, 1H), 7.51 (dd, J = 2.7, 1.9 Hz, 1H), 6.54 (dd, J = 8.6, 0.8 Hz, 1H), 6.18 (s, 2H), 4.18 (q, J = 7.0 Hz, 2H), 1.37 (t, J = 7.0 Hz, 3H). | PdCl2(dppf), K2CO3, dioxane |

TABLE 11-continued

*Additional Intermediates were made according to Methods E or F.*

| INTA# | Name/Structure | Synthesis Method, [LCMS Method], m/z (M + H)+, (Rt/min) | ¹H NMR Chemical Shift Data (DMSO-d6 unless stated) | Catalyst, Base, solvent |
|---|---|---|---|---|
| INTA33 | 6'-amino-[3,3'-bipyridine]-5-carbonitrile | Method E, [UPLC basic], 197, (0.72). | 9.12 (d, J = 2.3 Hz, 1H), 8.88 (d, J = 1.9 Hz, 1H), 8.55 (t, J = 2.1 Hz, 1H), 8.41 (dd, J = 2.6, 0.7 Hz, 1H), 7.86 (dd, J = 8.7, 2.6 Hz, 1H), 6.56 (dd, J = 8.7, 0.8 Hz, 1H), 6.33 (s, 2H). | PdCl$_2$(dppf), K$_2$CO$_3$, dioxane |
| INTA34 | 5'-methyl-[3,3'-bipyridin]-6-amine | Method F, [UPLC basic], 186, (1.22). | 8.60 (d, J = 2.2 Hz, 1H), 8.39-8.23 (m, 2H), 7.86-7.70 (m, 2H), 6.54 (dd, J = 8.7, 0.9 Hz, 1H), 6.15 (s, 2H), 2.34 (s, 3H). | Pd(PPh$_3$)$_4$, NaHCO$_3$, MeCN |
| INTA35 | 5'-(difluoromethoxy)-[3,3'-bipyridin]-6-amine | Method F, [UPLC basic], 238, (0.88). | 8.73 (d, J = 1.9 Hz, 1H), 8.37 (d, J = 2.6 Hz, 2H), 7.88-7.79 (m, 2H), 7.41 (t, J = 73.6 Hz, 1H), 6.55 (dd, J = 8.6, 0.8 Hz, 1H), 6.28 (s, 2H). | PdCl$_2$(dppf), K$_2$CO$_3$, dioxane |
| INTA36 | 5'-(2,2,2-trifluoroethoxy)-[3,3'-bipyridin]-6-amine | Method F, [UPLC basic], 270, (1.00). | 8.57-8.46 (m, 1H), 8.41-8.34 (m, 1H), 8.32-8.23 (m, 1H), 7.88-7.78 (m, 1H), 7.76-7.68 (m, 1H), 6.60-6.50 (m, 1H), 6.22 (s, 2H), 5.03-4.87 (m, 2H). | PdCl$_2$(dppf), K$_3$PO$_4$, dioxane |
| INTA37 | 5'-fluoro-[3,3'-bipyridin]-6-amine | Method F, [UPLC basic], 190, (0.76). | 8.72 (t, J = 1.9 Hz, 1H), 8.45 (d, J = 2.7 Hz, 1H), 8.38 (dd, J = 2.6, 0.8 Hz, 1H), 7.97 (ddd, J = 10.7, 2.7, 1.8 Hz, 1H), 7.83 (dd, J = 8.6, 2.6 Hz, 1H), 6.55 (dd, J = 8.6, 0.8 Hz, 1H), 6.28 (s, 2H). | PdCl$_2$(dppf), Cs$_2$CO$_3$, dioxane |

TABLE 11-continued

*Additional Intermediates were made according to Methods E or F.*

| INTA# | Name/Structure | Synthesis Method, [LCMS Method], m/z (M + H)+, (Rt/min) | ¹H NMR Chemical Shift Data (DMSO-d6 unless stated) | Catalyst, Base, solvent |
|---|---|---|---|---|
| INTA38 | 4-(6-ethoxypyrazin-2-yl)aniline | Method F, [HPLC basic], 216, (1.78). | 8.59 (s, 1H), 8.00 (s, 1H), 7.86-7.75 (m, 2H), 6.69-6.59 (m, 2H), 5.59 (s, 2H), 4.43 (q, J = 7.0 Hz, 2H), 1.38 (t, J = 7.0 Hz, 3H). | Pd(PPh$_3$)$_4$, NaHCO$_3$, MeCN |
| INTA39 | 4-(6-(trifluoromethyl)pyrazin-2-yl)aniline | Method F, [HPLC acidic], 240, (1.92). | 9.40 (s, 1H), 8.86 (s, 1H), 7.99-7.89 (m, 2H), 6.74-6.66 (m, 2H), 5.83 (s, 2H). | Pd(PPh$_3$)$_4$, NaHCO$_3$, MeCN |
| INTA40 | 4-(6-isopropoxypyrazin-2-yl)aniline | Method F, [UPLC basic], 230, (1.31). | 8.57 (s, 1H), 7.95 (s, 1H), 7.87-7.73 (m, 2H), 6.73-6.56 (m, 2H), 5.59 (s, 2H), 5.45-5.27 (m, 1H), 1.47-1.25 (m, 6H). | PdCl$_2$(dppf), K$_3$PO$_4$, dioxane |
| INTA41 | 4-(6-cyclopropoxypyrazin-2-yl)aniline | Method F, [HPLC basic], 228, (1.83). | 8.19-8.02 (m, 1H), 7.58-7.41 (m, 1H), 7.40-7.22 (m, 2H), 6.21-5.99 (m, 2H), 5.09-4.99 (m, 2H), 3.86-3.73 (m, 1H), 0.37-0.09 (m, 4H). | PdCl$_2$(dppf), K$_3$PO$_4$, dioxane |
| INTA42 | 4-(6-propoxypyrazin-2-yl)aniline | Method F, [HPLC basic], 230, (2.07). | 8.59 (s, 1H), 8.01 (s, 1H), 7.90-7.76 (m, 2H), 6.72-6.59 (m, 2H), 5.59 (s, 2H), 4.34 (t, J = 6.6 Hz, 2H), 1.86-1.72 (m, 2H), 1.00 (t, J = 7.4 Hz, 3H). | PdCl$_2$(dppf), K$_3$PO$_4$, dioxane |

TABLE 11-continued

*Additional Intermediates were made according to Methods E or F.*

| INTA# | Name/Structure | Synthesis Method, [LCMS Method], m/z (M + H)+, (Rt/min) | ¹H NMR Chemical Shift Data (DMSO-d6 unless stated) | Catalyst, Base, solvent |
|---|---|---|---|---|
| INTA43 | 4-(6-chloropyrazin-2-yl)aniline | Method F, [HPLC basic], 206, (1.75). | 9.06 (d, J = 0.6 Hz, 1H), 8.47 (d, J = 0.6 Hz, 1H), 7.89-7.81 (m, 2H), 6.73-6.62 (m, 2H), 5.79 (s, 2H). | PdCl$_2$(dppf), K$_3$PO$_4$, dioxane |
| INTA44 | 6-(4-aminophenyl)pyrazine-2-carbonitrile | Method F, [HPLC basic], 197, (1.54). | 9.36 (d, J = 0.5 Hz, 1H), 8.90 (d, J = 0.5 Hz, 1H), 7.95-7.86 (m, 2H), 6.74-6.64 (m, 2H), 5.86 (s, 2H). | PdCl$_2$(dppf), K$_3$PO$_4$, dioxane |
| INTA45 | 2-fluoro-4-(pyrazin-2-yl)aniline | Method F, [UPLC basic], 190, (0.84). | 9.12 (d, J = 1.6 Hz, 1H), 8.58 (dd, J = 2.6, 1.5 Hz, 1H), 8.44 (d, J = 2.5 Hz, 1H), 7.86-7.71 (m, 2H), 6.87 (dd, J = 9.3, 8.4 Hz, 1H), 5.67 (s, 2H). | PdCl$_2$(dppf), K$_2$CO$_3$, dioxane |
| INTA47 | 4-(6-ethoxypyrazin-2-yl)-2-fluoroaniline | Method F, [UPLC basic], 234, (1.31). | 8.66 (s, 1H), 8.06 (s, 1H), 7.84-7.63 (m, 2H), 6.93-6.75 (m, 1H), 5.65 (s, 2H), 4.54-4.34 (m, 2H), 1.47-1.29 (m, 3H). | PdCl$_2$(dppf), K$_2$CO$_3$, dioxane |
| INTA48 | 2-fluoro-4-(6-(trifluoromethyl)pyrazin-2-yl)aniline | Method F, [HPLC basic], 258, (2.13). | 9.46 (s, 1H), 8.92 (s, 1H), 7.88 (dd, J = 13.1, 2.1 Hz, 1H), 7.83 (dd, J = 8.4, 2.1 Hz, 1H), 6.90 (t, J = 8.8 Hz, 1H), 5.90 (s, 2H). | PdCl$_2$(dppf), K$_3$PO$_4$, dioxane |

TABLE 11-continued

Additional Intermediates were made according to Methods E or F.

| INTA# | Name/Structure | Synthesis Method, [LCMS Method], m/z (M + H)+, (Rt/min) | $^1$H NMR Chemical Shift Data (DMSO-d6 unless stated) | Catalyst, Base, solvent |
|---|---|---|---|---|
| INTA49 | 4-(6-chloropyrazin-2-yl)-2-methylaniline | Method F, [UPLC basic], 220, (1.24). | 9.06 (s, 1H), 8.46 (s, 1H), 7.84-7.65 (m, 2H), 6.78-6.63 (m, 1H), 5.55 (s, 2H), 2.14 (s, 3H). | PdCl$_2$(dppf), K$_3$PO$_4$, dioxane |
| INTA50 | 6-(4-amino-3-methylphenyl)pyrazine-2-carbonitrile | Method F, [HPLC basic], 211, (1.67). | 9.36 (s, 1H), 8.89 (s, 1H), 7.88-7.72 (m, 2H), 6.78-6.67 (m, 1H), 5.62 (s, 2H), 2.14 (s, 3H). | PdCl$_2$(dppf), K$_3$PO$_4$, dioxane |
| INTA51 | 4-(6-ethoxypyrazin-2-yl)-2-methylaniline | Method F, [UPLC basic], 230, (1.27). | 8.60 (s, 1H), 8.00 (s, 1H), 7.80-7.63 (m, 2H), 6.75-6.61 (m, 1H), 5.35 (s, 2H), 4.51-4.33 (m, 2H), 2.13 (s, 3H), 1.45-1.31 (m, 3H). | PdCl$_2$(dppf), K$_3$PO$_4$, dioxane |
| INTA52 | 2-fluoro-4-(6-(2,2,2-trifluoroethoxy)pyrazin-2-yl)aniline | Method F, [UPLC basic], 288, (1.38). | 8.82 (s, 1H), 8.24 (s, 1H), 7.94-7.85 (m, 1H), 7.81-7.74 (m, 1H), 6.92-6.82 (m, 1H), 5.72 (s, 2H), 5.23-5.09 (m, 2H). | PdCl$_2$(dppf), K$_3$PO$_4$, dioxane |
| INTA53 | 4-(6-(2,2,2-trifluoroethoxy)pyrazin-2-yl)aniline | Method F, [UPLC basic], 270, (1.31). | 8.76 (s, 1H), 8.18 (s, 1H), 7.95-7.84 (m, 2H), 6.73-6.58 (m, 2H), 5.67 (s, 2H), 5.22-5.04 (m, 2H). | PdCl$_2$(dppf), K$_3$PO$_4$, dioxane |

TABLE 11-continued

Additional Intermediates were made according to Methods E or F.

| INTA# | Name/Structure | Synthesis Method, [LCMS Method], m/z (M + H)+, (Rt/min) | 1H NMR Chemical Shift Data (DMSO-d6 unless stated) | Catalyst, Base, solvent |
|---|---|---|---|---|
| INTA55 | 5-(6-cyclobutoxypyrazin-2-yl)pyridin-2-amine | Method F, [UPLC basic], 243, (1.16). | 8.70 (dd, J = 2.5, 0.8 Hz, 1H), 8.66 (s, 1H), 8.12-8.03 (m, 2H), 6.55 (dd, J = 8.8, 0.8 Hz, 1H), 6.42 (s, 2H), 5.31-5.14 (m, 1H), 2.49-2.43 (m, 2H), 2.21-2.04 (m, 2H), 1.90-1.64 (m, 2H). | Pd(PPh3)4, Na2CO3, Toluene, EtOH |
| INTA56 | 5-(6-cyclopropoxypyrazin-2-yl)pyridin-2-amine | Method F, [UPLC basic], 229, (0.98). | 8.81-8.64 (m, 2H), 8.18-8.00 (m, 2H), 6.55 (dd, J = 8.8, 0.8 Hz, 1H), 6.44 (s, 2H), 4.37 (tt, J = 6.2, 3.0 Hz, 1H), 0.94-0.69 (m, 4H). | Pd(PPh3)4, Na2CO3, Toluene, EtOH |
| INTA57 | 5-(6-ethoxypyrazin-2-yl)-3-fluoropyridin-2-amine | Method F, [HPLC basic], 235, (1.73). | 8.72 (s, 1H), 8.62-8.57 (m, 1H), 8.12 (s, 1H), 8.04 (dd, J = 12.6, 1.9 Hz, 1H), 6.73 (s, 2H), 4.46 (q, J = 7.0 Hz, 2H), 1.39 (t, J = 7.0 Hz, 3H). | PdCl2(dppf), K2CO3, dioxane |
| INTA58 | 3-fluoro-5-(6-(trifluoromethyl)pyrazin-2-yl)pyridin-2-amine | Method F, [HPLC basic], 259, (1.82). | 9.53 (s, 1H), 9.00 (s, 1H), 8.72-8.66 (m, 1H), 8.09 (dd, J = 12.4, 2.0 Hz, 1H), 6.98 (s, 2H). | PdCl2(dppf), K2CO3, dioxane |
| INTA59 | 6-(6-amino-5-fluoropyridin-3-yl)pyrazine-2-carbonitrile | Method F, [UPLC acidic], 216, (0.87). | 9.48 (s, 1H), 9.03 (s, 1H), 8.70-8.64 (m, 1H), 8.09 (dd, J = 12.5, 2.0 Hz, 1H), 6.99 (s, 2H). | PdCl2(dppf), K2CO3, dioxane |

TABLE 11-continued

Additional Intermediates were made according to Methods E or F.

| INTA# | Name/Structure | Synthesis Method, [LCMS Method], m/z (M + H)+, (Rt/min) | 1H NMR Chemical Shift Data (DMSO-d6 unless stated) | Catalyst, Base, solvent |
|---|---|---|---|---|
| INTA60 | 3-fluoro-5-(pyrazin-2-yl)pyridin-2-amine | Method F, [UPLC basic], 191, (0.7). | 9.18 (d, J = 1.5 Hz, 1H), 8.65-8.59 (m, 2H), 8.50 (d, J = 2.5 Hz, 1H), 8.06 (dd, J = 12.6, 1.9 Hz, 1H), 6.75 (s, 2H). | PdCl$_2$(dppf), K$_2$CO$_3$, dioxane |
| INTA61 | 5-(6-methoxypyrazin-2-yl)pyridin-2-amine | Method F, [UPLC basic], 203, (0.85). | 8.76-8.71 (m, 1H), 8.67 (s, 1H), 8.14-8.08 (m, 2H), 6.56 (dd, J = 8.7, 0.8 Hz, 1H), 6.43 (s, 2H), 3.98 (s, 3H). | PdCl$_2$(dppf), K$_3$PO$_4$, dioxane |
| INTA62 | 5-(6-(2,2,2-trifluoroethoxy)pyrazin-2-yl)pyridin-2-amine | Method F, [UPLC basic], 271, (1.11). | 8.84-8.80 (m, 1H), 8.79-8.75 (m, 1H), 8.30-8.23 (m, 1H), 8.19-8.12 (m, 1H), 6.62-6.52 (m, 1H), 6.49 (s, 2H), 5.23-5.06 (m, 2H). | PdCl$_2$(dppf), K$_3$PO$_4$, dioxane |
| INTA63 | 6-(6-aminopyridin-3-yl)pyrazine-2-carbonitrile | Method F, [UPLC basic], 198, (0.76). | 9.44 (s, 1H), 8.98 (s, 1H), 8.79 (dd, J = 2.6, 0.7 Hz, 1H), 8.14 (dd, J = 8.8, 2.6 Hz, 1H), 6.68 (s, 2H), 6.58 (dd, J = 8.8, 0.7 Hz, 1H). | PdCl$_2$(dppf), K$_3$PO$_4$, dioxane |
| INTA64 | 5-(6-chloropyrazin-2-yl)pyridin-2-amine | Method F, [HPLC basic], 207, (0.41). | 9.12 (s, 1H), 8.73 (dd, J = 2.6, 0.7 Hz, 1H), 8.55 (s, 1H), 8.08 (dd, J = 8.8, 2.6 Hz, 1H), 6.60 (s, 2H), 6.55 (dd, J = 8.8, 0.8 Hz, 1H). | PdCl$_2$(dppf), Cs$_2$CO$_3$, dioxane |

TABLE 11-continued

Additional Intermediates were made according to Methods E or F.

| INTA# | Name/Structure | Synthesis Method, [LCMS Method], m/z (M + H)+, (Rt/min) | 1H NMR Chemical Shift Data (DMSO-d6 unless stated) | Catalyst, Base, solvent |
|---|---|---|---|---|
| INTA65 | N-methyl-4-(6-(trifluoromethyl)pyrazin-2-yl)aniline | Method F, [UPLC basic], 254, (1.47). | 9.42 (s, 1H), 8.86 (s, 1H), 8.03-7.97 (m, 2H), 6.72-6.65 (m, 2H), 6.41 (q, J = 5.0 Hz, 1H), 2.76 (d, J = 5.0 Hz, 3H). | PdCl$_2$(dppf), K$_2$CO$_3$, dioxane |
| INTA66 | 4-(5-chloropyridin-3-yl)-N-methylaniline | Method E, [UPLC basic], 219, (1.34). | 8.77 (d, J = 2.0 Hz, 1H), 8.44 (d, J = 2.3 Hz, 1H), 8.10-8.05 (m, 1H), 7.60-7.53 (m, 2H), 6.68-6.61 (m, 2H), 6.06-6.00 (m, 1H), 2.73 (d, J = 5.0 Hz, 3H). | PdCl$_2$(dppf), K$_2$CO$_3$, dioxane |
| INTA67 | 5-(4-(methylamino)phenyl)nicotinonitrile | Method E, [UPLC basic], 210, (1.14). | 9.10 (d, J = 2.4 Hz, 1H), 8.82 (d, J = 1.9 Hz, 1H), 8.51-8.44 (m, 1H), 7.65-7.56 (m, 2H), 6.71-6.62 (m, 2H), 6.12-6.05 (m, 1H), 2.73 (d, J = 5.0 Hz, 3H). | PdCl$_2$(dppf), K$_2$CO$_3$, dioxane |
| INTA68 | N-methyl-4-(pyridin-3-yl)aniline | Method E, [UPLC basic], 185, (1.04). | 8.80 (dd, J = 2.4, 0.9 Hz, 1H), 8.42 (dd, J = 4.7, 1.6 Hz, 1H), 7.97-7.90 (m, 1H), 7.55-7.46 (m, 2H), 7.42-7.35 (m, 1H), 6.70-6.61 (m, 2H), 5.96-5.89 (m, 1H), 2.72 (d, J = 5.0 Hz, 3H). | PdCl$_2$(dppf), K$_2$CO$_3$, dioxane |
| INTA70 | 2-fluoro-4-(5-(trifluoromethyl)pyridin-2-yl)aniline | Method F, [HPLC basic], 257, (2.06). | 9.14 (d, J = 2.2 Hz, 1H), 8.82 (dd, J = 2.1, 1.0 Hz, 1H), 8.35 (td, J = 2.3, 0.8 Hz, 1H), 7.63 (dd, J = 13.1, 2.1 Hz, 1H), 7.45 (dd, J = 8.3, 2.1 Hz, 1H), 6.88 (dd, J = 9.5, 8.3 Hz, 1H), 5.54 (s, 2H). | PdCl$_2$(dppf), K$_2$CO$_3$, dioxane |

TABLE 11-continued

Additional Intermediates were made according to Methods E or F.

| INTA# | Name/Structure | Synthesis Method, [LCMS Method], m/z (M + H)+, (Rt/min) | $^1$H NMR Chemical Shift Data (DMSO-d6 unless stated) | Catalyst, Base, solvent |
|---|---|---|---|---|
| INTA71 | 5-(6-isopropoxypyrazin-2-yl)pyridin-2-amine | Method F, [UPLC basic], 232, (1.09). | 8.69 (d, J = 2.4 Hz, 1H), 8.62 (s, 1H), 8.07 (dd, J = 8.7, 2.5 Hz, 1H), 8.02 (s, 1H), 6.55 (dd, J = 8.7, 0.8 Hz, 1H), 6.42 (s, 2H), 5.44-5.28 (m, 1H), 1.37 (d, J = 6.1 Hz, 6H). | Pd(PPhd$_3$)$_4$, Na$_2$CO$_3$, dioxane |
| INTA72 | 5-(6-ethoxypyrazin-2-yl)pyridin-2-amine | Method F, [UPLC, basic], 217, (0.98). | 8.70 (dd, J = 2.5, 0.8 Hz, 1H), 8.64 (s, 1H), 8.10-8.06 (m, 2H), 6.54 (dd, J = 8.7, 0.8 Hz, 1H), 6.41 (s, 2H), 4.43 (q, J = 7.0 Hz, 2H), 1.38 (t, J = 7.0 Hz, 3H). | PdCl$_2$(dppf), Cs$_2$CO$_3$, dioxane |
| INTA109 | 4-(5-chloro-4-methylpyridin-3-yl)aniline | Method F, [UPLC basic], 219/221, (1.18). | 8.47 (s, 1H), 8.27 (s, 1H), 7.10-7.03 (m, 2H), 6.70-6.63 (m, 2H), 5.33 (s, 2H), 2.31 (s, 3H). | PdCl$_2$(dppf), K$_2$CO$_3$, dioxane |
| INTA110 | 4-(6-ethoxypyrazin-2-yl)-2-(trifluoromethyl)aniline | Method F, [UPLC basic], 284, (1.49). | 8.70 (s, 1H), 8.12-8.09 (m, 2H), 8.08-8.04 (m, 1H), 6.95 (d, J = 8.7 Hz, 1H), 6.08 (s, 2H), 4.44 (q, J = 7.0 Hz, 2H), 1.39 (t,d J = 7.0 Hz, 3H). | PdCl$_2$(dppf), K$_3$PO$_4$, dioxane |
| INTA112 | 5′-propoxy-[3,3′-bipyridin]-6-amine | Method F [HPLC basic], 230, (1.63). | 8.39 (d, J = 1.9 Hz, 1H), 8.32 (d, J = 2.5 Hz, 1H), 8.17 (d, J = 2.7 Hz, 1H), 7.79-7.77 (m, 1H), 7.54-7.51 (m, 1H), 6.55-6.56 (m, 1H), 6.17 (s, 2H), 4.08 (t, J = 6.6 Hz, 2H), 1.86-1.65 (m, 2H), 1.00 (t, J = 7.4 Hz, 3H). | PdCl$_2$(dppf), K$_3$PO$_4$, dioxane |

TABLE 11-continued

Additional Intermediates were made according to Methods E or F.

| INTA# | Name/Structure | Synthesis Method, [LCMS Method], m/z (M + H)+, (Rt/min) | 1H NMR Chemical Shift Data (DMSO-d6 unless stated) | Catalyst, Base, solvent |
|---|---|---|---|---|
| INTA113 | 5'-methoxy-[3,3'-bipyridin]-6-amine 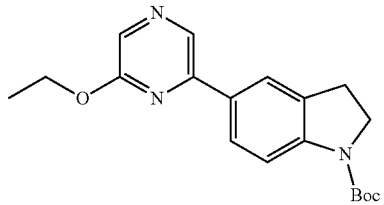 [SMILES: CCOc1cncc(-c2ccc3c(c2)CCN3C(=O)OC(C)(C)C)n1] | Method F [HPLC basic], 202 (1.24). | 8.40 (d, J = 1.9 Hz, 1H), 8.33 (dd, J = 2.5, 0.8 Hz, 1H), 8.19 (d, J = 2.8 Hz, 1H), 7.79 (dd, J = 8.6, 2.6 Hz, 1H), 7.53 (dd, J = 2.8, 1.9 Hz, 1H), 6.55 (dd, J = 8.6, 0.8 Hz, 1H), 6.18 (s, 2H), 3.89 (s, 3H). | Pd(PPh3)4, NaHCO3, MeCN | tert-butyl
5-(6-ethoxypyrazin-2-yl)indoline-1-carboxylate
INTA73

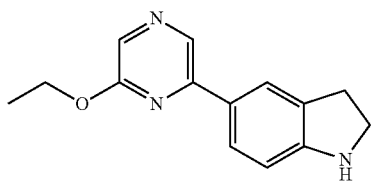 [SMILES: CCOc1cncc(-c2ccc3c(c2)CCN3)n1]

Tert-butyl 5-(4,4,5,5-tetramethyl-1,3,2-dioxaborolan-2-yl)indoline-1-carboxylate (1 g, 2.9 mmol), 2-chloro-6-ethoxypyrazine (0.418 g, 2.63 mmol) and K$_2$CO$_3$ (1.09 g, 7.9 mmol) were suspended in dioxane (10 mL) and water (3 mL). The mixture was degassed (N$_2$, mins), PdCl$_2$(dppf) (0.215 g, 0.26 mmol) was added and the resulting mixture was heated under N$_2$ at 90° C. for 18 hrs. The mixture was allowed to cool to RT, diluted with water (50 mL) and extracted with DCM (3×40 mL). The organics were combined, dried (phase separator) and concentrated in vacuo. The crude product was purified by chromatography on silica gel (40 g column, 0-100% EtOAc/isohexane) to afford tert-butyl 5-(6-ethoxypyrazin-2-yl)indoline-1-carboxylate (0.65 g, 1.71 mmol, 65% yield) as a white solid; Rt 1.90 mins (UPLC acidic); m/z 342 (M+H)$^+$ (ES$^+$); $^1$H NMR (400 MHz, DMSO-d6) δ 8.82-8.66 (m, 1H), 8.15 (s, 1H), 8.03-7.87 (m, 2H), 7.87-7.30 (m, 1H), 4.53-4.39 (m, 2H), 4.03-3.90 (m, 2H), 3.22-3.03 (m, 2H), 1.53 (s, 9H), 1.44-1.35 (m, 3H).

5-(6-ethoxypyrazin-2-yl)indoline INTA74

4M HCl (dioxane, 2.4 mL, 9.52 mmol) was added to tert-butyl 5-(6-ethoxypyrazin-2-yl)indoline-1-carboxylate INTA73 (0.65 g, 1.9 mmol) in MeOH (20 mL). The resulting mixture was stirred under N$_2$ at 60° C. for 18 hrs. The mixture was allowed to cool to RT and concentrated in vacuo. The crude material was diluted in NaHCO$_3$ (sat. aq, 50 mL) and extracted with DCM (3×40 mL). The organics were combined, dried (phase separator) and concentrated in vacuo. The crude product was purified by chromatography on silica gel (24 g column, 0-100% EtOAc/isohexane) to afford 5-(6-ethoxypyrazin-2-yl)indoline (0.41 g, 1.36 mmol, 71% yield) as a dark red solid; 1.35 mins (UPLC basic); m/z 242 (M+H)$^+$ (ES$^+$); $^1$H NMR (400 MHz, DMSO-d6) b 8.62 (s, 1H), 8.03 (s, 1H), 7.87-7.82 (m, 1H), 7.81-7.73 (m, 1H), 6.69-6.62 (m, 1H), 4.49-4.37 (m, 2H), 3.59-3.49 (m, 2H), 3.07-2.97 (m, 2H), 1.42-1.31 (m, 3H), 1 exchangeable proton not observed.

4-(6-((trimethylsilyl)ethynyl)pyrazin-2-yl)aniline
INTA46

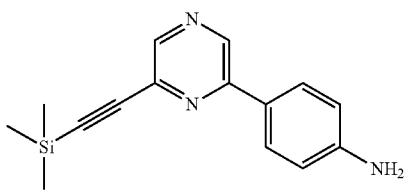 [SMILES: C[Si](C)(C)C#Cc1cncc(-c2ccc(N)cc2)n1]

A solution of 4-(6-chloropyrazin-2-yl)aniline (150 mg, 0.73 mmol), ethynyltrimethylsilane (0.15 mL, 1.09 mmol) and DIPEA (0.19 mL, 1.09 mmol) in DMF (1 mL) was degassed (N$_2$, 5 mins). To this, Cu(I)I (28 mg, 0.15 mmol) and Pd(PPh)$_2$Cl$_2$ (51 mg, 0.07 mmol) were added and the mixture degassed (N$_2$, 5 mins) with sonication. The mixture was stirred at RT for 18 hrs. Solvent was evaporated and the mixture partitioned between EtOAc (20 mL) and water (20 mL). The phases were separated and the organics loaded onto silica. The crude product was purified by chromatography on silica gel (12 g column, 0-100% EtOAc/isohexane) to afford 4-(6-((trimethylsilyl)ethynyl)pyrazin-2-yl)aniline (200 mg, 0.73 mmol, 99% yield) as a pale orange solid; Rt 2.44 mins (HPLC acidic); 268 (M+H)⁺ (ES⁺); ¹H NMR (400 MHz, DMSO-d₆) b 9.01 (s, 1H), 8.46 (s, 1H), 7.97-7.69 (m, 2H), 6.74-6.56 (m, 2H), 5.68 (s, 2H), 0.28 (s, 9H).

4-(6-ethynylpyrazin-2-yl)aniline INTA75

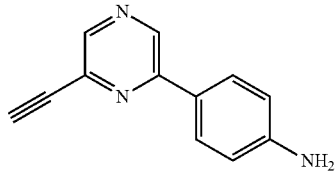

To a solution of 4-(6-((trimethylsilyl)ethynyl)pyrazin-2-yl)aniline INTA46 (190 mg, 0.71 mmol) in MeOH (10 mL), Na₂CO₃ (565 mg, 5.33 mmol) was added and the mixture stirred at RT for 1 hr. Solvent was evaporated and the mixture was partitioned between water (20 mL) and EtOAc (20 mL). The organics were concentrated onto silica. The crude product was purified by chromatography on silica gel (12 g column, 0-100% EtOAc/iso-hexane) to afford 4-(6-ethynylpyrazin-2-yl)aniline (107 mg, 0.54 mmol, 77% yield) as a yellow solid; Rt 1.46 mins (HPLC acidic); ¹H NMR (400 MHz, DMSO-d6) b 9.05 (s, 1H), 8.51 (s, 1H), 8.01-7.75 (m, 2H), 6.86-6.50 (m, 2H), 5.70 (s, 2H), 4.60 (s, 1H).

2-(6-Chloropyrazin-2-yl)propan-2-ol INTA76

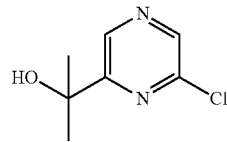

A suspension of methyl 6-chloropyrazine-2-carboxylate (3.4 g, 19.7 mmol) in THF (100 mL) was cooled to below 10° C. and treated dropwise with 3M MeMgBr (Et₂O, 13.13 mL, 39.4 mmol), maintaining the reaction temperature below 10° C. The reaction mixture was then allowed to warm to RT. After 1 hr, the reaction mixture was concentrated then taken up in 1M HCl (aq, 150 mL) and extracted with EtOAc (3×70 mL). The organic layers were combined, dried (MgSO₄), filtered and concentrated on to silica (4 g). The crude product was purified by chromatography on silica gel (40 g column, 20-70% EtOAc/iso-hexane) to afford 2-(6-chloropyrazin-2-yl)propan-2-ol (1.4 g, 7.71 mmol, 39% yield) as an orange oil; Rt 1.30 mins (HPLC acidic); m/z 173 (M+H)⁺ (ES⁺); ¹H NMR (500 MHz, DMSO-d6) b 8.87 (d, J=0.5 Hz, 1H), 8.67 (d, J=0.5 Hz, 1H), 5.61 (s, 1H), 1.46 (s, 6H).

2-Chloro-6-(2-methoxypropan-2-yl)pyrazine INTA77

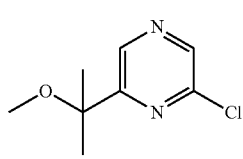

A solution of 2-(6-chloropyrazin-2-yl)propan-2-ol INTA76 (1.41 g, 8.17 mmol) in THF (15 mL) was cooled to 0° C. and treated with portion wise addition of NaH (60% wt. on mineral oil, 327 mg, 8.17 mmol). The reaction was allowed to warm to RT then treated with MeI (1.53 mL, 24.5 mmol) and heated to 50° C. for 18 hrs. The reaction mixture was allowed to cool to RT then treated with 1M HCl (aq, 100 mL) and extracted with EtOAc (3×80 mL). The organic phases were combined, dried (MgSO₄), filtered and concentrated onto silica (10 g). The crude product was purified by chromatography on silica gel (40 g column, 0-30% EtOAc/iso-hexane) to afford 2-chloro-6-(2-methoxypropan-2-yl)pyrazine (750 mg, 3.94 mmol, 48% yield) as a yellow oil; Rt 1.21 mins (UPLC acidic); m/z 187 (M+H)⁺ (ES⁺); ¹H NMR (500 MHz, DMSO-d6) b 8.78 (d, J=0.5 Hz, 1H), 8.72 (d, J=0.5 Hz, 1H), 3.13 (s, 3H), 1.49 (s, 6H).

2-Chloro-6-(prop-1-en-2-yl)pyrazine INTA78

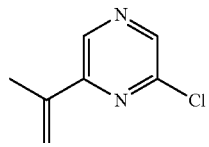

A solution of 2,6-dichloropyrazine (1.0 g, 6.71 mmol) and 4,4,5,5-tetramethyl-2-(prop-1-en-2-yl)-1,3,2-dioxaborolane (1.13 g, 6.72 mmol) in dioxane (60 mL) was treated with 2M K₂CO₃ (aq, 8.4 mL, 16.8 mmol) then degassed (N₂, 5 mins) and heated to 40° C. PdCl₂(dppf)-DCM adduct (274 mg, 0.336 mmol) was added and the mixture further degassed (N₂, 5 mins) before the reaction was heated to 70° C. for 1 hr. The reaction was allowed to cool to RT then treated with 1M HCl (aq, 40 mL) and EtOAc (40 mL). This was passed through celite, the phases were separated and the aqueous phase was further extracted with EtOAc (2×20 mL). The organic phases were combined, dried (MgSO₄), filtered and concentrated on to silica (4 g). The crude product was purified by chromatography on silica gel (24 g column, 0-15% EtOAc/iso-hexane) to afford 2-chloro-6-(prop-1-en-2-yl)pyrazine (1.0 g, 3.75 mmol, 56% yield) as a brown gum; Rt 1.96 mins (HPLC acidic); m/z none observed.

5-(6-(Prop-1-en-2-yl)pyrazin-2-yl)pyridin-2-amine INTA79

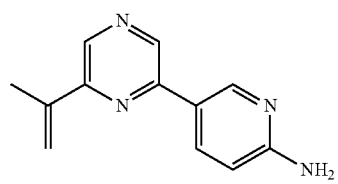 [SMILES: C=C(C)c1cncc(-c2ccc(N)nc2)n1]

A solution of 2-chloro-6-(prop-1-en-2-yl)pyrazine INTA78 (1 g, 3.75 mmol) and 5-(4,4,5,5-tetramethyl-1,3,2-dioxaborolan-2-yl)pyridin-2-amine (1.65 g, 7.50 mmol) in dioxane (60 mL) was treated with 2M K₂CO₃ (7.5 mL, 15.00 mmol) then degassed (N₂, 5 mins) and heated to 40° C. PdCl₂(dppf)-DCM adduct (0.306 g, 0.375 mmol) was added and the mixture degassed further (N₂, 5 mins) and the reaction was heated to 70° C. for 1 hr. The reaction was allowed to cool to RT then concentrated (to approx. 10 mL). This was then treated with 1 M HCl (aq, 37.5 mL) and EtOAc (40 mL) and filtered over celite eluting with EtOAc (50 mL). The phases were partitioned and the organic phase was discarded. The aqueous phase was then brought to pH 10 by addition of solid Na$_2$CO$_3$ and then extracted with EtOAc (3×50 mL). The organic phases were combined, dried (MgSO$_4$), filtered and concentrated on to silica (5 g) and the crude product was purified by chromatography on silica gel (24 g column, 30-100% EtOAc/iso-hexane) to afford 5-(6-(prop-1-en-2-yl)pyrazin-2-yl)pyridin-2-amine (320 mg, 1.43 mmol, 38% yield) as an off-white solid; Rt 0.98 mins (HPLC acidic); m/z 213 (M+H)$^+$ (ES$^+$); $^1$H NMR (500 MHz, DMSO-d6) b 9.00 (s, 1H), 8.78-8.75 (m, 1H), 8.74 (s, 1H), 8.16 (dd, J=8.7, 2.5 Hz, 1H), 6.57 (dd, J=8.7, 0.7 Hz, 1H), 6.43 (s, 2H), 6.10 (t, J=1.2 Hz, 1H), 5.47 (t, J=1.6 Hz, 1H), 2.23 (s, 3H).

5-(6-Isopropylpyrazin-2-yl)pyridin-2-amine INTA80

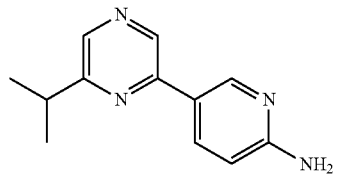 [SMILES: CC(C)c1cncc(-c2ccc(N)nc2)n1]

A solution of 5-(6-(prop-1-en-2-yl)pyrazin-2-yl)pyridin-2-amine INTA79 (320 mg, 1.51 mmol) in EtOH (20 mL) was prepared. The reaction mixture was hydrogenated in the H-Cube (10% Pd/C, 30×4 mm, full hydrogen, 40° C., 1.5 mL/min). The reaction mixture was concentrated to afford 5-(6-isopropylpyrazin-2-yl)pyridin-2-amine as a colourless solid; Rt 0.98 mins (HPLC acidic); m/z 215 (M+H)$^+$ (ES$^+$); $^1$H NMR (500 MHz, DMSO-d6) b 8.92 (s, 1H), 8.72 (dd, J=2.5, 0.8 Hz, 1H), 8.39 (s, 1H), 8.12 (dd, J=8.7, 2.5 Hz, 1H), 6.56 (dd, J=8.7, 0.8 Hz, 1H), 6.40 (s, 2H), 3.18-3.00 (m, 1H), 1.30 (d, J=6.9 Hz, 6H).

Method G: Telescoped Boronate Formation and Suzuki Coupling

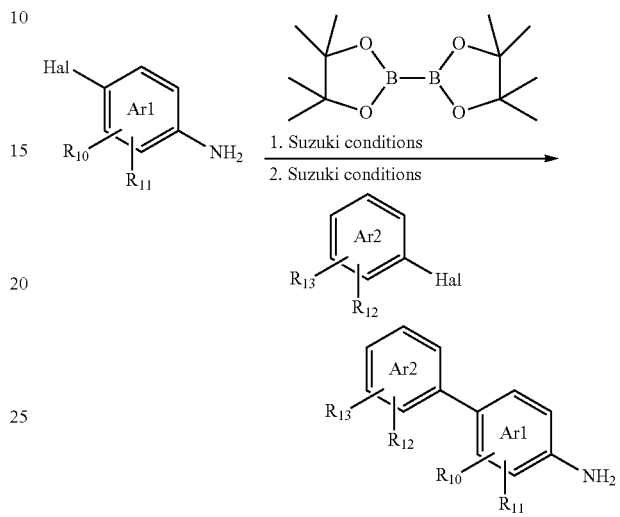

Bispin (1.1 eq) and KOAc (4 eq) were added to Ar1-Hal (1 eq) in dioxane (5 volumes). The reaction was heated to 60° C. and degassed (N$_2$, 5 mins). PdCl$_2$(dpp)-DCM adduct (5 mol %) was added to the reaction mixture and the temperature was increased to 90° C. for 1 hr. The reaction mixture was then cooled to RT and a solution of Ar2-Hal (1 eq) in dioxane (3 volumes) was added followed by a solution of K$_2$CO$_3$ (4 eq) in water (2 volumes). The temperature was then increased to 90 (C for 18 hrs. The reaction was cooled to RT, an aqueous work up was performed and the crude compound was purified by normal phase chromatography.

TABLE 12

| | The following intermediates were made according to Methods E, F and G. | | | |
|---|---|---|---|---|
| INTA# | Name/Structure | Synthesis Method, [LCMS Method], m/z (M + H)$^+$, (Rt/min) | $^1$H NMR Chemical Shift Data (DMSO-d6 unless stated) | Catalyst, Base, solvent |
| INTA81 | 5'-chloro-[3,3'-bipyridin]-6-amine<br>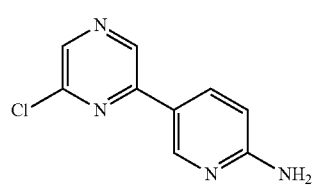 | Method E, [UPLC basic], 206 (0.88). | 8.79 (d, J = 2.0 Hz, 1H), 8.52-8.47 (m, 1H), 8.37 (d, J = 2.6 Hz, 1H), 8.17-8.12 (m, 1H), 7.82 (dd, J = 8.7, 2.6 Hz, 1H), 6.54 (d, J = 8.7 Hz, 1H), 6.28 (s, 2H). | PdCl$_2$(dppf)-DCM adduct, K$_2$CO$_3$, dioxane |

TABLE 12-continued

The following intermediates were made according to Methods E, F and G.

| INTA# | Name/Structure | Synthesis Method, [LCMS Method], m/z (M + H)+, (Rt/min) | 1H NMR Chemical Shift Data (DMSO-d6 unless stated) | Catalyst, Base, solvent |
|---|---|---|---|---|
| INTA82 | 4-(6-ethylpyrazin-2-yl)-2-fluoroaniline | Method F, [UPLC basic], 218 (1.18). | 8.92 (s, 1H), 8.35 (s, 1H), 7.81 (dd, J = 13.2, 2.0 Hz, 1H), 7.75 (dd, J = 8.4, 2.0 Hz, 1H), 6.90-6.81 (m, 1H), 5.63 (s, 2H), 2.80 (q, J = 7.6 Hz, 2H), 1.29 (t, J = 7.6 Hz, 3H). | PdCl$_2$(dppf)-DCM adduct, K$_2$CO$_3$, dioxane |
| INTA83 | 2-(6-(6-aminopyridin-3-yl)pyrazin-2-yl)propan-2-ol | Method F, [HPLC acidic], 231 (0.38). | 8.94 (s, 1H), 8.73 (dd, J = 2.5, 0.8 Hz, 1H), 8.69 (s, 1H), 8.12 (dd, J = 8.7, 2.5 Hz, 1H), 6.55 (dd, J = 8.8, 0.8 Hz, 1H), 6.40 (s, 2H), 5.40 (s, 1H), 1.50 (s, 6H). | PdCl$_2$(dppf)-DCM adduct, K$_3$PO$_4$, dioxane |
| INTA84 | 5-(6-(2-methoxypropan-2-yl)pyrazin-2-yl)pyridin-2-amine | Method F, [UPLC acidic], 245 (0.52). | 9.00 (s, 1H), 8.74 (dd, J = 2.5, 0.8 Hz, 1H), 8.58 (s, 1H), 8.14 (dd, J = 8.7, 2.5 Hz, 1H), 6.57 (dd, J = 8.7, 0.8 Hz, 1H), 6.43 (s, 2H), 3.15 (s, 3H), 1.54 (s, 6H). | PdCl$_2$(dppf)-DCM adduct, K$_3$PO$_4$, dioxane |
| INTA85 | 4-(6-(2-methoxypropan-2-yl)pyrazin-2-yl)aniline | Method F, [UPLC acidic], 244 (0.99). | 8.93 (s, 1H), 8.51 (s, 1H), 7.94-7.81 (m, 2H), 6.72-6.61 (m, 2H), 5.59 (s, 2H), 3.14 (s, 3H), 1.54 (s, 6H). | PdCl$_2$(dppf)-DCM adduct, K$_3$PO$_4$, dioxane |
| INTA86 | 2-fluoro-4-(6-(2-methoxypropan-2-yl)pyrazin-2-yl)aniline | Method F, [UPLC acidic], 262 (1.24). | 9.00 (s, 1H), 8.57 (s, 1H), 7.83 (dd, J = 13.1, 2.0 Hz, 1H), 7.77 (dd, J = 8.3, 2.0 Hz, 1H), 6.87 (dd, J = 9.3, 8.3 Hz, 1H), 5.66 (s, 2H), 3.15 (s, 3H), 1.54 (s, 6H). | PdCl$_2$(dppf)-DCM adduct, K$_3$PO$_4$, dioxane |

TABLE 12-continued

The following intermediates were made according to Methods E, F and G.

| INTA# | Name/Structure | Synthesis Method, [LCMS Method], m/z (M + H)+, (Rt/min) | $^1$H NMR Chemical Shift Data (DMSO-d6 unless stated) | Catalyst, Base, solvent |
|---|---|---|---|---|
| INTA87 | 6-(4-amino-3-fluorophenyl)pyrazine-2-carbonitrile | Method F, [HPLC acidic], 215 (.176). | 9.42 (d, J = 0.6 Hz, 1H), 8.96 (s, 1H), 7.86 (dd, J = 13.0, 2.1 Hz, 1H), 7.80 (dd, J = 8.4, 2.1 Hz, 1H), 6.89 (dd, J = 9.3, 8.4 Hz, 1H), 5.92 (s, 2H). | PdCl$_2$(dppf)-DCM adduct, K$_3$PO$_4$, dioxane |
| INTA88 | 2-methyl-4-(6-(trfluoromethyl)pyrazin-2-yl)aniline | Method F, [HPLC acidic], 254 (2.14). | 9.40 (s, 1H), 8.85 (s, 1H), 7.89-7.78 (m, 2H), 6.73 (d, J = 8.3 Hz, 1H), 5.60 (s, 2H), 2.15 (s, 3H). | PdCl$_2$(dppf)-DCM adduct, K$_3$PO$_4$, dioxane |
| INTA89 | 2-fluoro-4-(6-isopropoxypyrazin-2-yl)aniline | Method F, [UPLC basic], 248 (1.41). | 8.64 (s, 1H), 8.01 (s, 1H), 7.82-7.63 (m, 2H), 6.92-6.80 (m, 1H), 5.67 (s, 2H), 5.45-5.28 (m, 1H), 1.46-1.24 (m, 6H). | PdCl$_2$(dppf)-DCM adduct, K$_2$CO$_3$, dioxane |
| INTA90 | 5-(6-methylpyrazin-2-yl)pyridin-2-amine | Method F, [HPLC acidic], 187 (0.29). | 8.90 (s, 1H), 8.70 (d, J = 2.4 Hz, 1H), 8.35 (s, 1H), 8.10 (dd, J = 8.7, 2.5 Hz, 1H), 6.55 (d, J = 8.7 Hz, 1H), 6.40 (s, 2H), 2.50 (s, 3H, obscured by DMSO). | PdCl$_2$(dppf)-DCM adduct, K$_2$CO$_3$, dioxane |
| INTA91 | 4-(5-fluoropyridin-3-yl)-2-(trifluoromethyl)aniline | Method E, [HPLC basic], 257 (2.77) | 8.74 (t, J = 1.9 Hz, 1H), 8.46 (d, J = 2.7 Hz, 1H), 8.00 (ddd, J = 10.7, 2.7, 1.9 Hz, 1H), 7.79-7.70 (m, 2H), 6.96 (d, J = 8.5 Hz, 1H), 5.94 (s, 2H). | PdCl$_2$(dppf)-DCM adduct, K$_3$PO$_4$, dioxane |

TABLE 12-continued

The following intermediates were made according to Methods E, F and G.

| INTA# | Name/Structure | Synthesis Method, [LCMS Method], m/z (M + H)+, (Rt/min) | ¹H NMR Chemical Shift Data (DMSO-d6 unless stated) | Catalyst, Base, solvent |
|---|---|---|---|---|
| INTA92 | 4-(6-ethoxypyrazin-2-yl)-5-fluoro-2-methylaniline | Method G, [UPLC basic], 248 (1.36). | 8.45 (d, J = 2.2 Hz, 1H), 8.06 (s, 1H), 7.63 (d, J = 8.8 Hz, 1H), 6.47 (d, J = 14.2 Hz, 1H), 5.68 (s, 2H), 4.43 (q, J = 7.0 Hz, 2H), 2.09 (s, 3H), 1.39 (t, J = 7.0 Hz, 3H). | (i)PdCl$_2$(dppf)-DCM adduct, KOAc, dioxane, then (ii)PdCl2(dppf)-DCM adduct, K$_2$CO$_3$, dioxane |
| INTA93 | 4-(6-ethoxypyrazin-2-yl)-5-fluoro-2-methoxyaniline | Method G, [UPLC basic], 264 (1.37). | 8.50 (d, J = 2.0 Hz, 1H), 8.08 (s, 1H), 7.43 (d, J = 7.2 Hz, 1H), 6.51 (d, J = 13.5 Hz, 1H), 5.61 (s, 2H), 4.45 (q, J = 7.1 Hz, 2H), 3.83 (s, 3H), 1.40 (t, J = 7.0 Hz, 3H). | (i)PdCl$_2$(dppf)-DCM adduct, KOAc, dioxane, then (ii)PdCl2(dppf)-DCM adduct, K$_2$CO$_3$, dioxane |
| INTA94 | 4-(6-ethoxypyrazin-2-yl)-2,3-dimethylaniline | Method G, [UPLC basic], 244 (1.28). | 8.18 (s, 1H), 8.10 (s, 1H), 7.02 (d, J = 8.3 Hz, 1H), 6.60 (d, J = 8.2 Hz, 1H), 5.11 (s, 2H), 4.36 (q, J = 7.0 Hz, 2H), 2.22 (s, 3H), 2.04 (s, 3H), 1.35 (t, J = 7.0 Hz, 3H). | (i)PdCl$_2$(dppf)-DCM adduct, KOAc, dioxane, then (ii)PdCl2(dppf)-DCM adduct, K$_2$CO$_3$, dioxane |
| INTA95 | 4-(6-ethoxypyrazin-2-yl)-2-fluoro-5-methylaniline | Method G, [HPLC acidic], 248 (2.41). | 8.31 (s, 1H), 8.13 (s, 1H), 7.24 (d, J = 12.5 Hz, 1H), 6.68 (d, J = 9.1 Hz, 1H), 5.44 (s, 2H), 4.38 (q, J = 7.0 Hz, 2H), 2.32 (s, 3H), 1.36 (t, J = 7.0 Hz, 3H). | (i)PdCl$_2$(dppf)-DCM adduct, KOAc, dioxane, then (ii)PdCl2(dppf)-DCM adduct, K$_2$CO$_3$, dioxane |
| INTA96 | 4-(6-ethoxypyrazin-2-yl)-2,5-dimethylaniline | Method G, [HPLC acidic], 244 (2.22). | 8.26 (s, 1H), 8.07 (s, 1H), 7.15 (s, 1H), 6.53 (s, 1H), 5.13 (s, 2H), 4.36 (q, J = 7.0 Hz, 2H), 2.31 (s, 3H), 2.07 (s, 3H), 1.36 (t, J = 7.1 Hz, 3H). | (i)PdCl$_2$(dppf)-DCM adduct, KOAc, dioxane, then (ii)PdCl2(dppf)-DCM adduct, K$_2$CO$_3$, dioxane |

TABLE 12-continued

The following intermediates were made according to Methods E, F and G.

| INTA# | Name/Structure | Synthesis Method, [LCMS Method], m/z (M + H)+, (Rt/min) | ¹H NMR Chemical Shift Data (DMSO-d6 unless stated) | Catalyst, Base, solvent |
|---|---|---|---|---|
| INTA97 | 4-(6-ethoxypyrazin-2-yl)-2,6-difluoroaniline | Method G, [HPLC acidic], 252 (2.41). | 8.73 (s, 1H), 8.12 (s, 1H), 7.74 (dd, J = 8.0, 2.5 Hz, 2H), 5.7 (s, 2H), 4.46 (q, J = 7.0 Hz, 2H), 1.39 (t, J = 7.1 Hz, 3H). | (i)PdCl$_2$(dppf)-DCM adduct, KOAc, dioxane, then (ii)PdCl2(dppf)-DCM adduct, K$_2$CO$_3$, dioxane |
| INTA98 | 3'-ethoxy-[1,1'-biphenyl]-4-amine | Method F, [UPLC basic], 214 (1.39). | 7.37-7.32 (m, 2H), 7.29-7.24 (m, 1H), 7.09 (ddd, J = 7.7, 1.7, 0.9 Hz, 1H), 7.06-7.01 (m, 1H), 6.77 (ddd, J = 8.1, 2.5, 1.0 Hz, 1H), 6.63 (d, J = 8.3 Hz, 2H), 5.22 (s, 2H), 4.07 (q, J = 7.0 Hz, 2H), 1.34 (t, J = 6.9 Hz, 3H) | PdCl$_2$(dppf)-DCM adduct, K$_2$CO$_3$, dioxane |
| INTA99 | 4-(pyrazin-2-yl)aniline | Method F, [UPLC acidic], 172 (0.56). | 9.05 (d, J = 1.6 Hz, 1H), 8.54 (dd, J = 2.5, 1.6 Hz, 1H), 8.38 (d, J = 2.5 Hz, 1H), 7.93-7.77 (m, 2H), 6.72-6.62 (m, 2H), 5.61 (s, 2H). | PdCl$_2$(dppf)-DCM adduct, K$_2$CO$_3$, dioxane |
| INTA100 | 5'-(trifluoromethyl)-[3,3'-bipyridin]-6-amine | Method F, [HPLC basic], 240 (1.59). | 9.13 (d, J = 2.2 Hz, 1H), 8.84 (dd, J = 2.1, 1.0 Hz, 1H), 8.44 (dd, J = 2.6, 0.8 Hz, 1H), 8.40-8.33 (m, 1H), 7.90 (dd, J = 8.7, 2.6 Hz, 1H), 6.57 (dd, J = 8.7, 0.8 Hz, 1H), 6.32 (s, 2H). | PdCl$_2$(dppf)-DCM adduct, K$_3$PO$_4$, dioxane |
| INTA101 | 4-(5-methoxypyridin-3-yl)aniline | Method E [UPLC acidic], 201 (0.91). | 8.38 (d, J = 1.9 Hz, 1H), 8.13 (d, J = 2.8 Hz, 1H), 7.49-7.40 (m, 3H), 6.71-6.62 (m, 2H), 5.35 (s, 2H), 3.88 (s, 3H). | PdCl$_2$(dppf)-DCM adduct, K$_2$CO$_3$, dioxane |

TABLE 12-continued

The following intermediates were made according to Methods E, F and G.

| INTA# | Name/Structure | Synthesis Method, [LCMS Method], m/z (M + H)+, (Rt/min) | 1H NMR Chemical Shift Data (DMSO-d6 unless stated) | Catalyst, Base, solvent |
|---|---|---|---|---|
| INTA102 | 2-fluoro-4-(6-methoxypyrazin-2-yl)aniline | Method F, [UPLC basic], 220 (1.20). | 8.68 (s, 1H), 8.09 (s, 1H), 7.81 (dd, J = 13.1, 2.0 Hz, 1H), 7.74 (dd, J = 8.4, 2.0 Hz, 1H), 6.90-6.82 (m, 1H), 5.66 (s, 2H), 3.99 (s, 3H). | PdCl$_2$(dppf)-DCM adduct, K$_2$CO$_3$, dioxane |
| INTA103 | 4-(6-ethoxypyrazin-2-yl)-2-(trifluoromethoxy)aniline | Method F, [HPLC basic], 300 (2.38). | 8.67 (s, 1H), 8.08 (s, 1H), 7.93-7.78 (m, 2H), 6.91 (d, J = 8.5 Hz, 1H), 5.91 (s, 2H), 4.43 (q, J = 7.0 Hz, 2H), 1.39 (t, J = 7.0 Hz, 3H). | PdCl$_2$(dppf)-DCM adduct, K$_3$PO$_4$, dioxane |
| INTA104 | 4-(6-ethoxypyrazin-2-yl)-2-methoxyaniline | Method F, [HPLC basic], 246 (1.99). | 8.67 (s, 1H), 8.02 (s, 1H), 7.62-7.46 (m, 2H), 6.72 (d, J = 8.0 Hz, 1H), 5.24 (s, 2H), 4.45 (q, J = 7.0 Hz, 2H), 3.87 (s, 3H), 1.39 (t, J = 7.0 Hz, 3H). | PdCl$_2$(dppf)-DCM adduct, K$_3$PO$_4$, dioxane |
| INTA105 | 2-chloro-4-(6-ethoxypyrazin-2-yl)aniline | Method F, [HPLC basic], 250 (2.26). | 8.66 (d, J = 0.5 Hz, 1H), 8.07 (d, J = 0.5 Hz, 1H), 7.99 (d, J = 2.1 Hz, 1H), 7.83 (dd, J = 8.5, 2.1 Hz, 1H), 6.89 (d, J = 8.5 Hz, 1H), 5.85 (s, 2H), 4.44 (q, J = 7.0 Hz, 2H), 1.39 (t, J = 7.0 Hz, 3H). | PdCl$_2$(dppf)-DCM adduct, K$_3$PO$_4$, dioxane |

TABLE 12-continued

The following intermediates were made according to Methods E, F and G.

| INTA# | Name/Structure | Synthesis Method, [LCMS Method], m/z (M + H)+, (Rt/min) | $^1$H NMR Chemical Shift Data (DMSO-d6 unless stated) | Catalyst, Base, solvent |
|---|---|---|---|---|
| INTA106 | 2-fluoro-4-(pyridin-3-yl)aniline | Method E, [UPLC basic], 189 (0.90). | 8.82 (dd, J = 2.5, 0.9 Hz, 1H), 8.45 (dd, J = 4.7, 1.6 Hz, 1H), 7.97 (ddd, J = 8.0, 2.5, 1.6 Hz, 1H), 7.45 (dd, J = 13.0, 2.1 Hz, 1H), 7.40 (ddd, J = 8.0, 4.7, 0.9 Hz, 1H), 7.31 (dd, J = 8.2, 2.1 Hz, 1H), 6.86 (dd, J = 9.5, 8.3 Hz, 1H), 5.39 (s, 2H). | PdCl$_2$(dppf)-DCM adduct, K$_2$CO$_3$, dioxane |
| INTA107 | 2-amino-5-(6-ethoxypyrazin-2-yl)benzonitrile | Method G, [HPLC basic], 241 (1.99). | 8.70 (s, 1H), 8.19 (d, J = 2.2 Hz, 1H), 8.13-8.06 (m, 2H), 6.91 (d, J = 8.9 Hz, 1H), 6.52 (s, 2H), 4.45 (q, J = 7.0 Hz, 2H), 1.39 (t, J = 7.0 Hz, 3H). | (i)PdCl$_2$(dppf)-DCM adduct, KOAc, dioxane, then (ii)PdCl2(dppf)-DCM adduct, K$_2$CO$_3$, dioxane |
| INTA111 | 5-(6-ethoxypyrazin-2-yl)-3-methylpyridin-2-amine | Method G, [UPLC basic], 231, (1.07). | 8.64 (s, 1H), 8.59 (d, J = 2.3 Hz, 1H), 8.06 (s, 1H), 7.94 (dd, J = 2.4, 1.0 Hz, 1H), 6.21 (s, 2H), 4.44 (q, J = 7.0 Hz, 2H), 2.12 (s, 3H), 1.38 (t, J = 7.1 Hz, 3H). | (i)PdCl$_2$(dppf), KOAc, dioxane, then (ii)PdCl$_2$(dppf), K$_2$CO$_3$, dioxane |

Method H: Suzuki Coupling of Halo Pyrimidines with Heteroaromatic Boronates

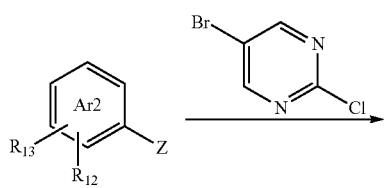

Z = B(OH)$_2$, B(pin)$_2$

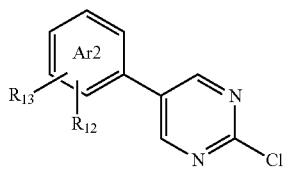

A solution of 5-bromo-2-chloropyrimidine (1.2 eq) and Ar2-Z (1 eq) in solvent (3 volumes) and base (4 eq) was degassed (N$_2$, 5 min) and heated to 40° C. whereupon Pd catalyst (5 mol %) was added and the reaction mixture further degassed (N$_2$, 5 min) before being heated to 90° C. for up to 24 hrs. The reaction mixture was allowed to cool to RT and an aqueous work-up was performed. In general, the desired compound is purified by column chromatography.

TABLE 13

The following intermediates were made according to Method H.

| INTA# | Name/Structure | Synthesis Method, [LCMS Method], m/z (M + H)⁺, (Rt/min) | ¹H NMR Chemical Shift Data (DMSO-d6 unless stated) | Catalyst, Base, solvent |
|---|---|---|---|---|
| INTA115 | 2-chloro-5-(5-methoxypyridin-3-yl)pyrimidine | 1882-86 Method H [UPLC basic], 222 $^{35}$Cl isotope (0.91) | 9.23 (s, 2H), 8.63 (d, J = 1.9 Hz, 1H), 8.41 (d, J = 2.8 Hz, 1H), 7.86 (dd, J = 2.8, 1.9 Hz, 1H), 3.93 (s, 3H) | PdCl$_2$(dppf), K$_2$CO$_3$, dioxane |
| INTA116 | 2-chloro-5-(5-fluoropyridin-3-yl)pyrimidine | 1882-95-1 Method H [HPLC acidic], 210 $^{35}$Cl isotope (1.37) | 9.26 (s, 2H), 8.96-8.94 (m, 1H), 8.72 (d, J = 2.8 Hz, 1H), 8.31 (dd, J = 10.1, 2.8, 1.8 Hz, 1H). | PdCl$_2$(dppf), K$_2$CO$_3$, dioxane |
| INTA117 | 2-chloro-5-(5-(trifluoromethyl)pyridin-3-yl)pyrimidine | 1882-94 Method H [HPLC acidic], 260 $^{35}$Cl isotope (1.81) | 9.35 (d, J = 2.1 Hz, 1H), 9.31 (s, 2H), 9.11-9.09 (m, 1H), 8.74-8.72 (m, 1H). | PdCl$_2$(dppf), K$_2$CO$_3$, dioxane |

Method I: Amide Coupling to Form Intermediates

TABLE 14

The following intermediates were made using amide coupling methods described below

| INTB# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| INTB112 | tert-butyl (1-(2-(cyclopropanesulfonamido)thiazol-4-yl)-2-oxo-2-((5-(6-(trifluoromethyl)pyrazin-2-yl)pyridin-2-yl)amino)ethyl)carbamate | Method 1c using INTB98 and INTA3, [HPLC acidic], 600, (2.26). | None recorded |
| INTB113 | tert-butyl (1-(2-(cyclopropanesulfonamido)-thiazol-4-yl)-2-((2-fluoro-4-(6-(trifluoromethyl)-pyrazin-2-yl)phenyl)amino)-2-oxoethyl)carbamate | Method 1 using INTB98 and INTA48, [HPLC acidic], 639 [M + Na]+, (2.39). | 12.66-12.53 (m, 1H), 10.37-10.33 (m, 1H), 9.65 (s, 1H), 9.15 (s, 1H), 8.27-8.20 (m, 1H), 8.18-8.11 (m, 1H), 8.12-8.07 (m, 1H), 7.70 (s, 1H), 6.65 (s, 1H), 5.48 (s, 1H), 2.64-2.51 (m, 1H), 1.42 (s, 9H), 0.93-0.89 (m, 4H). |
| INTB114 | tert-butyl (1-(2-(cyclopropanesulfonamido)-thiazol-4-yl)-2-((4-(6-ethoxypyrazin-2-yl)-2-fluorophenyl)amino)-2-oxoethyl)carbamate | Method 1c using INTB98 and INTA47, [HPLC acidic], 537 [M − t-Bu + H]+, (2.35). | 12.62 (s, 1H), 10.26 (s, 1H), 8.84 (s, 1H), 8.25 (s, 1H), 8.14 (t, J = 8.3 Hz, 1H), 8.05 (d, J = 12.2 Hz, 1H), 8.00 (d, J = 8.6 Hz, 1H), 7.66 (s, 1H), 6.65 (s, 1H), 5.46 (s, 1H), 4.49 (q, J = 7.0 Hz, 2H), 2.63-2.55 (m, 1H), 1.42 (s, 9H), 1.40 (t, J = 7.0 Hz, 3H), 1.08-0.77 (m, 4H). |

Preparation of Examples

Amide Couplings

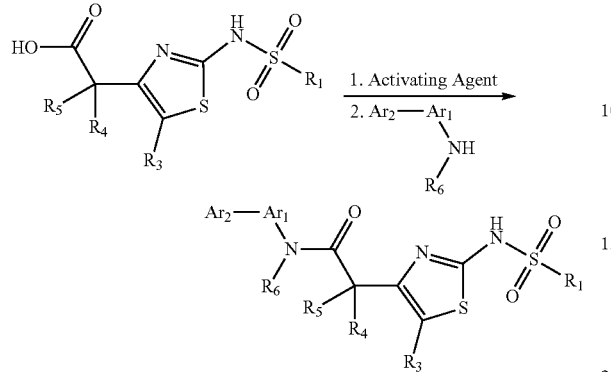

Method 1: HATU (1.2 eq) was added to a solution of appropriate acid (1 eq), amine (1 eq) and DIPEA (3 eq) in DCM (10 volumes) at RT. The reaction was stirred at RT for 18 hrs. The solvent was removed and the crude product was purified by normal phase chromatography, reverse phase chromatography or trituration from an appropriate solvent.

Method 1b: 1-chloro-N,N,2-trimethylprop-1-en-1-amine (2 eq) was added to a solution of 2-(2-(cyclopropanesulfonamido)thiazol-4-yl)-2-methylpropanoic acid (1 eq) in DCM (20 volumes). The reaction mixture was stirred at RT for 2 hrs. The reaction mixture was concentrated in vacuo and the residue redissolved in pyridine (2 mL) before addition of the appropriate amine (1.1 eq). The reaction mixture was stirred at RT for 2 hrs. An aqueous work up was performed and the crude product was purified by normal phase chromatography, reverse phase chromatography or trituration from an appropriate solvent.

Method 1c: T3P (50% in EtOAc, 2.5 eq) was added to a solution of appropriate acid (1 eq), amine (1 eq) and pyridine (3 eq) in a mixture of EtOAc (20 volumes) and DMF (10 volumes). The reaction was stirred for 1 hr at RT. An aqueous work up was performed and the crude product was purified by normal phase chromatography, reverse phase chromatography or trituration from an appropriate solvent.

Method 1e: Thionyl chloride (2 eq) was added to a solution of an appropriate acid (1 eq) in toluene (20 volumes) at 70° C. The reaction mixture was stirred at 70° C. for 1 hr. The reaction mixture was cooled to RT and concentrated to dryness. The resulting intermediate was redissolved in EtOAc (10 volumes) and a solution of amine (1.1 eq) in EtOAc (20 volumes) was added followed by triethylamine (2 eq). The reaction mixture was stirred at 40° C. for 16 hrs. An aqueous work up was performed and the crude product was purified by normal phase chromatography, reverse phase chromatography or trituration from an appropriate solvent.

Suzuki Couplings
Method 2: Suzuki Coupling of Ar1-Bromide with Heteroaromatic Boronates

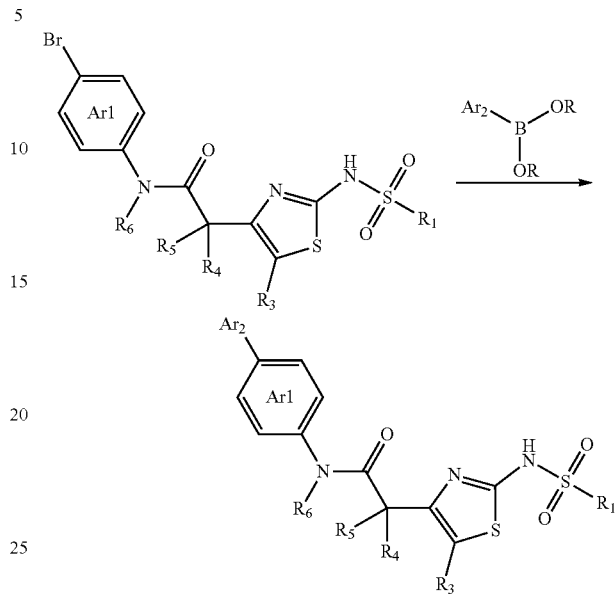

To a suspension of Ar1-Br (1 eq) in dioxane (10 volumes) was added arylboronic acid or ester (1 eq) and 2M $K_2PO_4$ (2 eq). The resulting suspension was heated to 60° C. and degassed ($N_2$, 5 mins). Pd 170 or other appropriate catalyst (5 mol %) was added and the reaction mixtures were stirred at 60° C. for 16 hrs. The reaction mixture was then cooled to RT. An aqueous work up was performed and the crude product was purified by normal phase chromatography, reverse phase chromatography or trituration from an appropriate solvent.

Method 2b: Suzuki Coupling of Ar1-B(OR)$_2$ with Heteroaromatic Halides

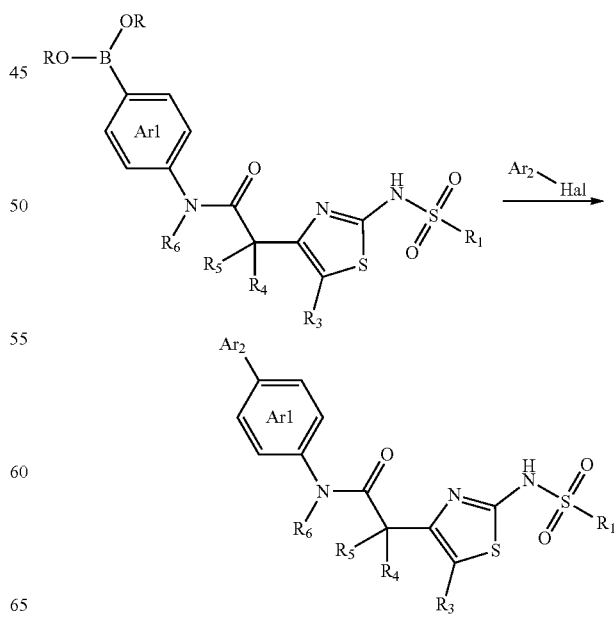

PdCl$_2$(dppf)-CH$_2$Cl$_2$ (10 mol %) or other appropriate catalyst was added to a degassed (N$_2$, 5 mins) solution of Ar1-B(OR)$_2$ (1 eq), Ar2-halide (1.2 eq) and K$_2$CO$_3$ (5 eq) in dioxane (10 volumes) and water (15 volumes). The solution was then degassed further (N$_2$, 5 mins) and then heated to 90° C. for 1-2 hrs. The reaction mixture was allowed to cool to RT. An aqueous work up was performed and the crude product was purified by normal phase chromatography, reverse phase chromatography or trituration from an appropriate solvent.

Method 3: Coupling of Primary Amides with 2-Chloropyrimidines

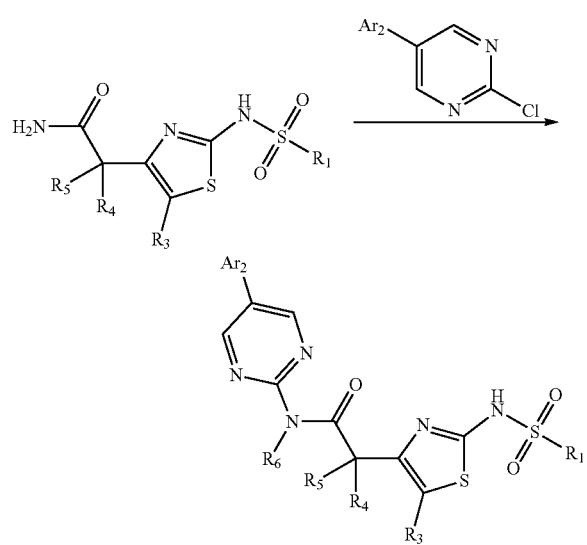

To a solution of amide (1 eq) and 2-chloropyrimidine (1 eq) in dioxane (30 volumes) was added Cs$_2$CO$_3$ (1.5 eq). The reaction mixture was heated to 60° C. and degassed (N$_2$, 5 mins). Pd 177 (10 mol %) was added to the reaction mixture and the temperature was increased to 90° C. After 2 hrs, the reaction was stirred for 16 hrs at 60° C. The reaction mixture was cooled to RT and an aqueous work up was performed. The crude product was purified by normal phase chromatography, reverse phase chromatography or trituration from an appropriate solvent.

N-([1,1'-biphenyl]-4-yl)-2-(2-(methylsulfonamido) thiazol-4-yl)acetamide T1

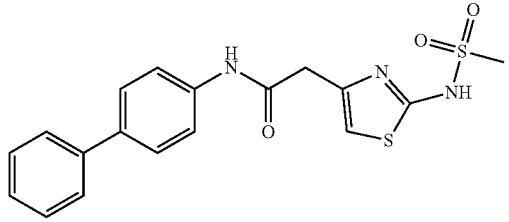 [SMILES: CS(=O)(=O)Nc1nc(CC(=O)Nc2ccc(-c3ccccc3)cc2)cs1]

HATU (133 mg, 0.35 mmol) was added to a solution of 2-(2-(cyclopropanesulfonamido)thiazol-4-yl)acetic acid INTB35 (75 mg, 0.32 mmol), [1,1'-biphenyl]-4-amine (53 mg, 0.32 mmol) and DIPEA (166 uL, 0.95 mmol) in DMF (1 mL) at RT. The reaction was stirred at RT for 18 hrs. The reaction mixture was acidified with addition of formic acid (100 uL), shaken for 5 min then filtered. The crude product was purified by preparative HPLC (Waters, Acidic (0.1% Formic acid), Acidic, Waters X-Select Prep-C18, 5 um, 19×50 mm column, 25-55% MeCN in Water) to afford N-([1,1'-biphenyl]-4-yl)-2-(2-(methylsulfonamido)thiazol-4-yl)acetamide; Rt 1.26 min (UPLC acidic); m/z 388 (M+H)$^+$ (ES$^+$); $^1$H NMR (400 MHz, DMSO-d6) δ 12.51 (s, 1H), 10.27 (s, 1H), 7.77-7.58 (m, 5H), 7.53-7.39 (m, 2H), 7.39-7.26 (m, 2H), 6.59 (s, 1H), 3.67 (s, 2H), 2.90 (s, 3H).

N-([1,1'-biphenyl]-4-yl)-2-(2-(cyclopropanesulfonamido)thiazol-4-yl)acetamide T2

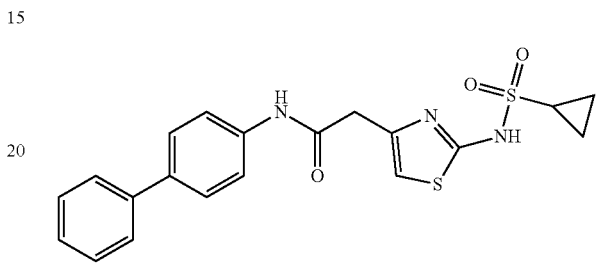

HATU (80 mg, 0.21 mmol) was added to a solution of 2-(2-(cyclopropanesulfonamido)thiazol-4-yl)acetic acid INTB36 (50 mg, 0.19 mmol), [1,1'-biphenyl]-4-amine (35.5 mg, 0.21 mmol) and DIPEA (1.0 mL, 0.57 mmol) in DMF (0.5 mL) at RT. The reaction was stirred at RT for 18 hrs. The reaction mixture was acidified with addition of formic acid (50 uL), shaken for 5 mins then filtered. The crude product was purified by preparative HPLC (Waters, Acidic (0.1% Formic acid), Acidic, Waters X-Select Prep-C18, 5 um, 19×50 mm column, 35-65% MeCN in Water) to afford N-([1,1'-biphenyl]-4-yl)-2-(2-(cyclopropanesulfonamido) thiazol-4-yl)acetamide (32 mg, 0.077 mmol, 40% yield) as an off-white solid; Rt 2.01 min (HPLC acidic); m/z 414 (M+H)$^+$ (ES$^+$); 412 (M−H)$^-$ (ES$^-$); $^1$H NMR (400 MHz, DMSO-d6) δ 12.54 (s, 1H), 10.27 (s, 1H), 7.72-7.61 (m, 6H), 7.45 (dd, J=8.4, 7.0 Hz, 2H), 7.38-7.29 (m, 1H), 6.57 (s, 1H), 3.71-3.65 (m, 2H), 2.62-2.56 (m, 6.0, 4.6 Hz, 1H), 0.93-0.88 (m, 4H).

2-(2-(cyclopropanesulfonamido)thiazol-4-yl)-2-ethyl-N-(5-(pyrazin-2-yl)pyridin-2-yl)butanamide

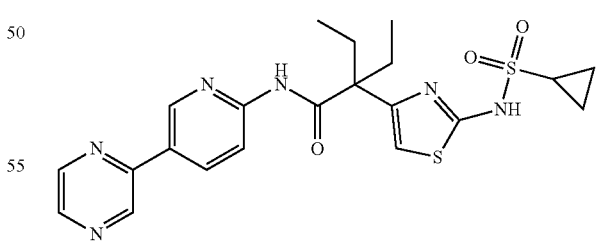

Prepared as Method 1b from INTB41 and 5-(pyrazin-2-yl)pyridin-2-amine (Cheng et al., 2016). Rt 1.17 min (UPLC acidic); m/z 473 (M+H)$^+$ (ES$^+$); $^1$H NMR (400 MHz, DMSO-d6) δ 12.49 (s, 1H), 10.02 (s, 1H), 9.32 (s, 1H), 9.11 (s, 1H), 8.74 (t, J=2.0 Hz, 1H), 8.64 (d, J=2.5 Hz, 1H), 8.60-8.52 (m, 1H), 8.23 (d, J=8.7 Hz, 1H), 6.66 (s, 1H), 2.57 (s, 1H), 2.17-1.97 (m, 4H), 0.94-0.87 (m, 4H), 0.74 (t, J=7.3 Hz, 6H).

2-(2-(cyclopropanesulfonamido)thiazol-4-yl)-2-methyl-N-(4-(pyrimidin-2-yl)phenyl)propanamide

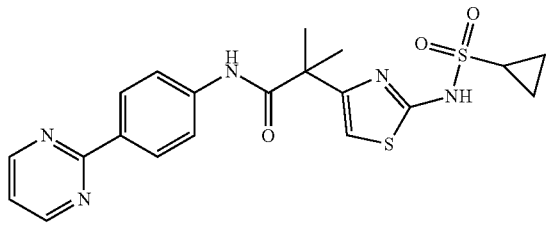 [SMILES: CC(C)(C(=O)Nc1ccc(-c2ncccn2)cc1)c1csc(NS(=O)(=O)C2CC2)n1]

HATU (118 mg, 0.31 mmol) was added to a solution 2-(2-(cyclopropanesulfonamido)thiazol-4-yl)-2-methylpropanoic acid INTB37 (75 mg, 0.26 mmol), 4-(pyrimidin-2-yl)aniline (44 mg, 0.26 mmol) and DIPEA (135 uL, 0.78 mmol) in DCM (1 mL) at RT. The reaction was stirred at RT for 18 hrs. The solvent was removed to give a yellow oil. The crude product was purified by chromatography on silica gel (24 g column, 0-100% EtOAc/iso-hexane) to afford 2-(2-(cyclopropanesulfonamido)thiazol-4-yl)-2-methyl-N-(4-(pyrimidin-2-yl)phenyl)propanamide (102 mg, 0.22 mmol, 85% yield) as a white solid; Rt 1.72 min (HPLC acidic); m/z 444 (M+H)$^+$ (ES$^+$); $^1$H NMR (400 MHz, DMSO-d6) δ 12.60 (s, 1H), 9.51 (s, 1H), 8.92 (d, J=4.8 Hz, 2H), 8.68 (t, J=1.9 Hz, 1H), 8.13 (dt, J=7.8, 1.4 Hz, 1H), 7.82 (ddd, J=8.1, 2.3, 1.1 Hz, 1H), 7.52-7.41 (m, 2H), 6.56 (s, 1H), 2.65-2.53 (m, 1H), 1.59 (s, 6H), 1.00-0.85 (m, 4H).

2-(2-(cyclopropanesulfonamido)thiazol-4-yl)-N-(4-(pyridin-3-yl)phenyl)butanamide T5

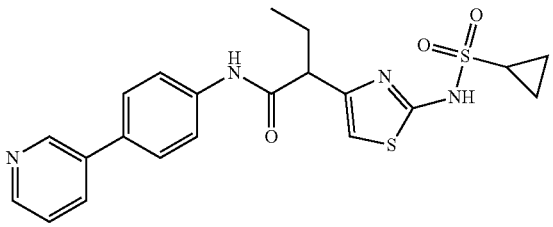 [SMILES: CCC(C(=O)Nc1ccc(-c2cccnc2)cc1)c1csc(NS(=O)(=O)C2CC2)n1]

HATU (314 mg, 0.83 mmol) was added to a solution of 2-(2-(cyclopropanesulfonamido)thiazol-4-yl)butanoic acid INTB38 (200 mg, 0.69 mmol), 4-(pyridin-3-yl)aniline (Xing-Li et al., 2009) (117 mg, 0.69 mmol) and DIPEA (3.6 mL, 2.07 mmol) in DCM (2 mL) at RT. The reaction was stirred at RT for 2 hrs. Water (10 mL) was added and the phases were separated. The solvent was removed to give a brown oil. The crude product was purified by chromatography on silica gel (24 g column, 0-10% MeOH/DCM) to afford 2-(2-(cyclopropanesulfonamido)thiazol-4-yl)-N-(4-(pyridin-3-yl)phenyl)butanamide (207 mg, 0.458 mmol, 66.5% yield) as a pale orange solid; Rt 1.29 min (HPLC acidic); m/z 443 (M+H)$^+$ (ES$^+$); $^1$H NMR (400 MHz, DMSO-d6) δ 12.59 (s, 1H), 10.29 (s, 1H), 8.89 (dd, J=2.4, 0.9 Hz, 1H), 8.54 (dd, J=4.7, 1.6 Hz, 1H), 8.06 (ddd, J=8.0, 2.5, 1.6 Hz, 1H), 7.78-7.65 (m, 4H), 7.47 (ddd, J=7.9, 4.7, 0.8 Hz, 1H), 6.59-6.52 (m, 1H), 3.60 (t, J=7.4 Hz, 1H), 2.65-2.55 (m, 1H), 2.03-1.83 (m, 2H), 0.97-0.83 (m, 7H).

The racemate T5 (180 mg) was separated by chiral preparative HPLC (Gilson, iso-hexane+0.2% TFA: DCM, 4:1 with EtOH 30%). A salt exchange (TFA to HCl) was undertaken by adding 1.25M HCl (EtOH, 2 mL×5) and removing solvent to afford:

Peak A: Stereochemistry of Product was not Assigned
2-(2-(cyclopropanesulfonamido)thiazol-4-yl)-N-(4-(pyridin-3-yl)phenyl)butanamide.HCl T6 (98 mg, 0.20 mmol, 29% yield); Rt 1.28 mins (HPLC acidic); m/z 443 (M+H)$^+$ (ES$^+$); 441 (M−H)$^-$ (ES-); $^1$H NMR (400 MHz, DMSO-d6) δ 12.63 (s, 1H), 10.53 (s, 1H), 9.13 (s, 1H), 8.82-8.71 (m, 1H), 8.62 (d, J=8.3 Hz, 1H), 7.91 (dd, J=8.2, 5.3 Hz, 1H), 7.86-7.77 (m, 4H), 6.57 (s, 1H), 3.68 (t, J=7.5 Hz, 1H), 2.63-2.57 (m, 1H), 1.94 (dtt, J=27.6, 13.7, 7.3 Hz, 2H), 0.97-0.85 (m, 7H).

The product was analysed by Chiral IA method HPLC; Rt=4.58 mins, 99% ee at 254 nm.

Peak B: Stereochemistry of Product was not Assigned
2-(2-(cyclopropanesulfonamido)thiazol-4-yl)-N-(4-(pyridin-3-yl)phenyl)butanamide.HCl T7 (92 mg, 0.19 mmol, 28% yield); Rt 1.28 min (HPLC acidic); m/z 443 (M+H)$^+$ (ES$^+$); 441 (M−H)$^-$ (ES$^-$); $^1$H NMR (400 MHz, DMSO-d6) δ 12.64 (s, 1H), 10.55 (s, 1H), 9.14 (d, J=2.2 Hz, 1H), 8.84-8.73 (m, 1H), 8.64 (d, J=8.3 Hz, 1H), 7.93 (dd, J=8.2, 5.4 Hz, 1H), 7.88-7.76 (m, 4H), 6.57 (s, 1H), 3.68 (t, J=7.5 Hz, 1H), 2.65-2.56 (m, 1H), 1.94 (dtt, J=27.7, 13.6, 7.3 Hz, 2H), 0.97-0.85 (m, 7H).

The product was analysed by Chiral IA method HPLC Rt=11.04 mins, >99% ee at 254 nm.

N-(4-(5-chloropyridin-3-yl)phenyl)-2-(2-(cyclopropanesulfonamido)thiazol-4-yl)butanamide T8

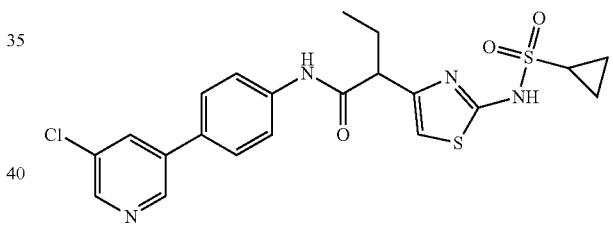

Prepared as Method 1 from INTB38. Rt 1.11 mins (UPLC basic); m/z 477 (M+H)$^+$ (ES$^+$); $^1$H NMR (400 MHz, DMSO-d6) δ 12.63 (s, 1H), 10.34 (s, 1H), 8.87 (d, J=2.0 Hz, 1H), 8.59 (d, J=2.3 Hz, 1H), 8.23 (t, J=2.2 Hz, 1H), 7.84-7.70 (m, 4H), 6.55 (s, 1H), 3.60 (t, J=7.4 Hz, 1H), 2.60 (d, J=5.4 Hz, 1H), 1.92 (dtt, J=20.6, 13.9, 7.2 Hz, 2H), 0.96-0.80 (m, 7H).

The racemate T8 was separated by chiral preparative HPLC (30% EtOH vs 4:1 isoehexanes+0.2% TFA:DCM IA column). A salt exchange (TFA to HCl) was undertaken by adding 1.25M HCl (EtOH, 2 mL×5) and removing solvent to afford:

Peak A: Stereochemistry of Product was not Assigned
N-(4-(5-chloropyridin-3-yl)phenyl)-2-(2-(cyclopropanesulfonamido)thiazol-4-yl)butanamide.HCl T9; Rt 1.1 mins (UPLC basic); m/z 477 (M+H)$^+$ (ES$^+$); $^1$H NMR (400 MHz, DMSO-d6) δ 12.57 (s, 1H), 10.43 (s, 1H), 8.81 (d, J=2.0 Hz, 1H), 8.53 (d, J=2.3 Hz, 1H), 8.18 (t, J=2.1 Hz, 1H), 7.75-7.62 (m, 4H), 6.49 (s, 1H), 3.64-3.56 (m, 1H), 2.57-2.48 (m, 1H), 1.94-1.74 (m, 2H), 0.93-0.75 (m, 7H).

Peak B: Stereochemistry of Product was not Assigned
N-(4-(5-chloropyridin-3-yl)phenyl)-2-(2-(cyclopropanesulfonamido)thiazol-4-yl)butanamide.HCl T10; Rt 1.1 mins (UPLC basic); m/z 477 (M+H)$^+$ (ES$^+$); $^1$H NMR (400 MHz, DMSO-d6) δ 12.64 (s, 1H), 10.47 (s, 1H), 8.88 (d, J=1.9 Hz, 1H), 8.60 (d, J=2.3 Hz, 1H), 8.25 (t, J=2.1 Hz, 1H), 7.82-7.75 (m, 4H), 6.56 (s, 1H), 3.76-3.61 (m, 1H), 2.70-2.58 (m, 1H), 2.04-1.84 (m, 2H), 0.96-0.81 (m, 7H).

2-(2-(cyclopropanesulfonamido)thiazol-4-yl)-3-methyl-N-(4-(pyrimidin-5-yl)phenyl)butanamide T11

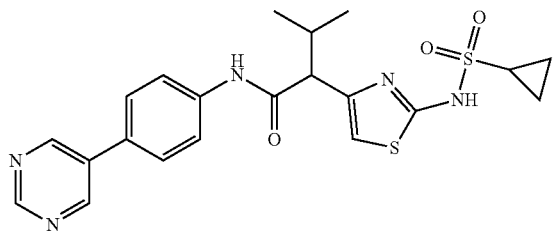 [SMILES: CC(C)C(C(=O)Nc1ccc(-c2cncnc2)cc1)c1csc(NS(=O)(=O)C2CC2)n1]

Prepared as Method 1 from INTB40. Rt 1.71 min (HPLC acidic); m/z 458 (M+H)$^+$ (ES$^+$); 456 (M–H)$^-$ (ES$^-$); $^1$H NMR (400 MHz, DMSO-d6) δ 12.59 (s, 1H), 10.37 (s, 1H), 9.15 (s, 1H), 9.12 (s, 2H), 7.83-7.73 (m, 4H), 6.60 (s, 1H), 3.37 (d, J=9.9 Hz, 1H), 2.64-2.54 (m, 1H), 2.46-2.37 (m, 1H), 0.98 (d, J=6.6 Hz, 3H), 0.94-0.83 (m, 7H).

2-(2-(cyclopropanesulfonamido)thiazol-4-yl)-3-methyl-N-(4-(pyridin-3-yl)phenyl)butanamide T12

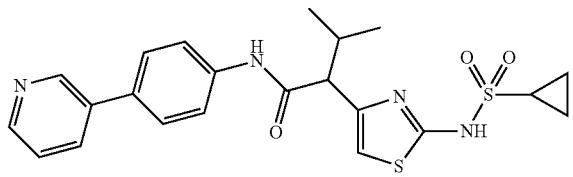 [SMILES: CC(C)C(C(=O)Nc1ccc(-c2cccnc2)cc1)c1csc(NS(=O)(=O)C2CC2)n1]

Prepared as Method 1 from INTB40 and 4-(pyridin-3-yl)aniline (Xing-Li et al, 2009) Rt 1.39 mins (HPLC acidic); m/z 457 (M+H)$^+$ (ES$^+$); 455 (M–H)$^-$ (ES$^-$); $^1$H NMR (400 MHz, DMSO-d6) δ 12.56 (s, 1H), 10.32 (s, 1H), 8.88 (dd, J=2.5, 0.9 Hz, 1H), 8.54 (dd, J=4.8, 1.6 Hz, 1H), 8.05 (ddd, J=8.0, 2.5, 1.6 Hz, 1H), 7.83-7.67 (m, 4H), 7.47 (ddd, J=8.0, 4.8, 0.9 Hz, 1H), 6.60 (s, 1H), 3.36 (d, J=9.9 Hz, 1H), 2.64-2.57 (m, 1H), 2.47-2.33 (m, 1H), 0.98 (d, J=6.5 Hz, 3H), 0.93-0.83 (m, 7H).

The racemate T12 was separated by chiral preparative HPLC (Gilson, iso-hexane+0.2% TFA:DCM, 4:1 with EtOH 30%). A salt exchange (TFA to HCl) was undertaken by adding 1.25M HCl (EtOH, 2 mL×5) and removing solvent to afford:

Peak A: Stereochemistry of Product was not Assigned
2-(2-(cyclopropanesulfonamido)thiazol-4-yl)-3-methyl-N-(4-(pyridin-3-yl)phenyl)butanamide.HCl T13 (97 mg, 0.20 mmol, 30% yield); Rt 1.36 min (HPLC acidic); m/z 457 (M+H)$^+$ (ES$^+$); 455 (M–H)$^-$ (ES$^-$); $^1$H NMR (400 MHz, DMSO-d6) δ 12.59 (s, 1H), 10.59 (s, 1H), 9.22-9.11 (m, 1H), 8.77 (d, J=5.4 Hz, 1H), 8.66 (d, J=8.3 Hz, 1H), 7.95 (dd, J=8.3, 5.4 Hz, 1H), 7.89-7.77 (m, 4H), 6.62 (s, 1H), 3.46 (d, J=10.0 Hz, 1H), 2.64-2.56 (m, 1H), 2.46-2.39 (m, 1H), 0.98 (d, J=6.5 Hz, 3H), 0.94-0.80 (m, 7H).

The product was analysed by Chiral IA method HPLC; Rt=4.66 min, >99% ee at 254 nm.

Peak B: Stereochemistry of product was not assigned
2-(2-(cyclopropanesulfonamido)thiazol-4-yl)-3-methyl-N-(4-(pyridin-3-yl)phenyl)butanamide.HCl T14 (95 mg, 0.19 mmol, 29% yield); Rt 1.36 mins (HPLC acidic); m/z 457 (M+H)$^+$ (ES$^+$); 455 (M–H)$^-$ (ES$^-$); $^1$H NMR (400 MHz, DMSO-d6) δ 12.60 (s, 1H), 10.62 (s, 1H), 9.24-9.12 (m, 1H), 8.78 (d, J=5.4 Hz, 1H), 8.68 (d, J=8.2, 1.6 Hz, 1H), 7.97 (dd, J=8.2, 5.4 Hz, 1H), 7.92-7.77 (m, 4H), 6.63 (s, 1H), 3.47 (d, J=10.0 Hz, 1H), 2.64-2.57 (m, 1H), 2.47-2.39 (m, 1H), 0.98 (d, J=6.5 Hz, 3H), 0.94-0.83 (m, 7H).

The product was analysed by Chiral IA method HPLC; Rt=10.84 min, >99% ee at 254 nm.

2-(2-(cyclopropanesulfonamido)thiazol-4-yl)-N-(4-(5-methoxypyridin-3-yl)phenyl)-2-methylpropanamide T15

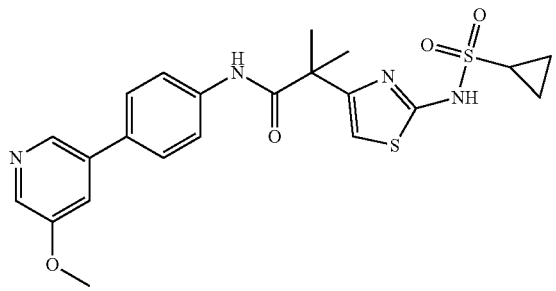 [SMILES: COc1cncc(-c2ccc(NC(=O)C(C)(C)c3csc(NS(=O)(=O)C4CC4)n3)cc2)c1]

To a solution of 2-(2-(cyclopropanesulfonamido)thiazol-4-yl)-2-methylpropanoic acid INTB37 (50 mg, 0.17 mmol) in DCM (2 mL) was added 1-chloro-N,N,2-trimethylprop-1-en-1-amine (0.04 mL, 0.34 mmol). The reaction mixture was stirred at RT for 2 hrs. The reaction mixture was concentrated in vacuo and the residue redissolved in pyridine (2 mL) before addition of 4-(5-methoxypyridin-3-yl)aniline INTA101 (38 mg, 0.19 mmol). The reaction mixture was poured into NH$_4$Cl (sat. aq, 10 mL) and the products were extracted using EtOAc (3×10 mL). The combined extracts were dried (MgSO$_4$), filtered and concentrated in vacuo. The crude product was purified by chromatography on silica gel (12 g column, 0-100% EtOAc/iso-hexane) to afford 2-(2-(cyclopropanesulfonamido)thiazol-4-yl)-N-(4-(5-methoxypyridin-3-yl)phenyl)-2-methylpropanamide (6 mg, 0.01 mmol, 7% yield) as a colourless solid; Rt 0.90 min (UPLC acidic); m/z 473 (M+H)$^+$ (ES$^+$); $^1$H NMR (400 MHz, DMSO-d6) δ 12.56 (s, 1H), 9.43 (s, 1H), 8.49 (d, J=1.8 Hz, 1H), 8.25 (d, J=2.7 Hz, 1H), 7.75 (s, 4H), 7.61 (t, J=2.3 Hz, 1H), 6.55 (s, 1H), 3.91 (s, 3H), 2.63-2.58 (m, 1H), 1.58 (s, 6H), 0.93-0.88 (m, 4H).

N-(2-chloro-4-(pyridin-3-yl)phenyl)-2-(2-(cyclopropanesulfonamido)thiazol-4-yl)acetamide T16

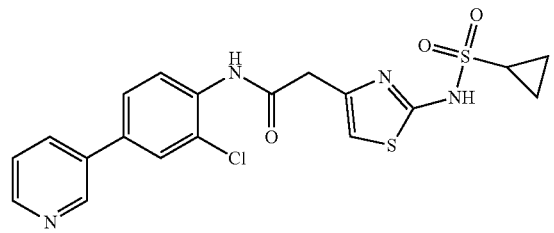 [SMILES: O=C(Cc1csc(NS(=O)(=O)C2CC2)n1)Nc1ccc(-c2cccnc2)cc1Cl]

2-(2-(cyclopropanesulfonamido)thiazol-4-yl)acetic acid INTB36 (75 mg, 0.29 mmol), 2-chloro-4-(pyridin-3-yl)aniline INTA8 (58.5 mg, 0.29 mmol) and T3P (50% in EtOAc, 0.4 mL, 0.72 mmol) were dissolved in a mixture of EtOAc (2 mL) and DMF (1 mL). Triethylamine (1.2 mL, 0.86 mmol) was added and the mixture was stirred for 1 hr at RT. The mixture was partitioned between EtOAc (10 mL) and H$_2$O (10 mL), the two phases were separated, the aqueous phase was re-extracted with EtOAc (2×10 mL), the combined organic extracts were passed through a phase separator and the solvent was removed in vacuo. The crude product was purified by chromatography on silica gel (24 g column, 0-10% MeOH/DCM) and the sample was dried under vacuum at 50° C. to give N-(2-chloro-4-(pyridin-3-yl)phenyl)-2-(2-(cyclopropanesulfonamido)thiazol-4-yl)acetamide (10 mg, 0.02 mmol, 7% yield) as a pale brown solid; Rt 1.47 min (HPLC basic); m/z 449 (M+H)+(ES$^+$); $^1$H NMR (400 MHz, DMSO-d6) δ 12.53 (s, 1H), 9.91 (s, 1H), 8.98-8.88 (m, 1H), 8.64-8.52 (m, 1H), 8.12 (ddd, J=8.0, 2.5, 1.6 Hz, 1H), 7.96 (d, J=8.6 Hz, 1H), 7.91 (d, J=2.1 Hz, 1H), 7.73 (dd, J=8.5, 2.2 Hz, 1H), 7.52-7.46 (m, 1H), 6.56 (s, 1H), 3.74 (s, 2H), 2.61-2.51 (m, 1H), 0.93-0.82 (m, 4H).

2-(2-(cyclopropanesulfonamido)-5-methylthiazol-4-yl)-2-methyl-N-(4-(6-(trifluoromethyl)pyrazin-2-yl)phenyl)propanamide T17

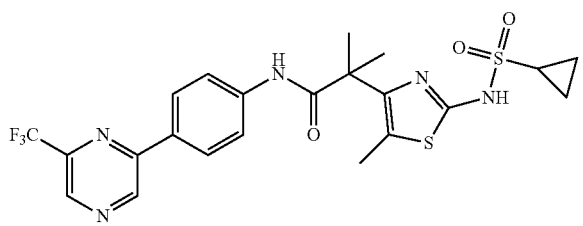 [SMILES: Cc1sc(NS(=O)(=O)C2CC2)nc1C(C)(C)C(=O)Nc1ccc(-c2cncc(C(F)(F)F)n2)cc1]

To a solution of 2-(2-(cyclopropanesulfonamido)-5-methylthiazol-4-yl)-2-methylpropanoic acid INTB42 (100 mg, 0.33 mmol) in toluene (20 mL) at 70° C. was added thionyl chloride (0.8 mL, 10.91 mmol). The reaction mixture was stirred at 70° C. for 1 hr. The reaction mixture was cooled to RT and concentrated in vacuo. The resulting oil was redissolved in EtOAc (10 mL) and a solution of 4-(6-(trifluoromethyl)pyrazin-2-yl)aniline INTA39 (86 mg, 0.36 mmol) in EtOAc (20 mL) was added followed by triethylamine (0.8 mL, 5.74 mmol). The reaction mixture was stirred at 40° C. for 16 hrs. The reaction mixture was diluted with NH$_4$Cl (sat. aq, 30 mL) and EtOAc (30 mL). The phases were separated and the aqueous was extracted with further EtOAc (2×40 mL). The combined organic phases were dried (MgSO$_4$) and concentrated onto silica. The crude product was purified by chromatography on silica gel (40 g cartridge, 0-100% EtOAc/isohexane) to afford 2-(2-(cyclopropanesulfonamido)-5-methylthiazol-4-yl)-2-methyl-N-(4-(6-(trifluoromethyl)pyrazin-2-yl)phenyl)propanamide as a pale yellow solid; Rt 2.30 mins (HPLC acidic); m/z 526 (M+H)+(ES$^+$); $^1$H NMR (500 MHz, DMSO-d6) δ 12.05 (s, 1H), 9.99 (s, 1H), 9.58 (s, 1H), 9.08 (s, 1H), 8.23-8.13 (m, 2H), 7.92-7.81 (m, 2H), 2.62-1.54 (m, 1H), 1.95 (s, 3H), 1.53 (s, 6H), 0.97-0.86 (m, 4H).

2-(2-(cyclopropanesulfonamido)thiazol-4-yl)-2-methyl-N-(4-(pyrimidin-5-yl)phenyl)propanamide T18

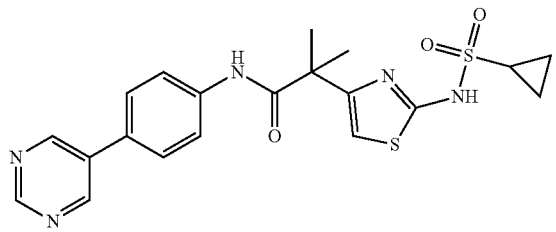 [SMILES: CC(C)(C(=O)Nc1ccc(-c2cncnc2)cc1)c1csc(NS(=O)(=O)C2CC2)n1]

To a suspension of N-(4-bromophenyl)-2-(2-(cyclopropanesulfonamido)thiazol-4-yl)-2-methylpropanamide INTB37 (58 mg, 0.13 mmol) in dioxane (3 mL) was added pyrimidin-5-ylboronic acid (16 mg, 0.13 mmol) and 2M K$_2$PO$_4$ (aq, 131 uL, 0.26 mmol). The resulting suspension was heated to 60° C. and degassed (N$_2$, 5 mins). Pd 170 (4.40 mg, 6.53 umol) was added and the reaction mixtures were stirred at 60° C. for 16 hrs. The reaction mixture was cooled to RT, diluted with NH$_4$Cl (aq, 20 mL) and EtOAc (20 mL). The phases were separated, and the aqueous phase extracted with further EtOAc (3×20 mL). The combined organics were washed with brine, dried (Na$_2$SO$_4$) and concentrated to dryness. The crude product was purified by chromatography on silica gel (4 g column, 0-80% EtOAc/isohexane) to afford 2-(2-(cyclopropanesulfonamido)thiazol-4-yl)-2-methyl-N-(4-(pyrimidin-5-yl)phenyl)propanamide (15 mg, 0.03 mmol, 25% yield) as a pale yellow solid; Rt 0.98 min (UPLC acidic); m/z 444 (M+H)+(ES$^+$); $^1$H NMR (400 MHz, DMSO-d6) δ 12.58 (s, 1H), 9.47 (s, 1H), 9.18-9.12 (m, 3H), 7.81 (s, 4H), 6.55 (s, 1H), 2.62-2.57 (m, 1H), 1.58 (s, 6H), 0.94-0.87 (m, 4H).

6-(4-(2-(2-(cyclopropanesulfonamido)thiazol-4-yl)-2-methylpropanamido)phenyl)-N,N-dimethylpyrazine-2-carboxamide T19

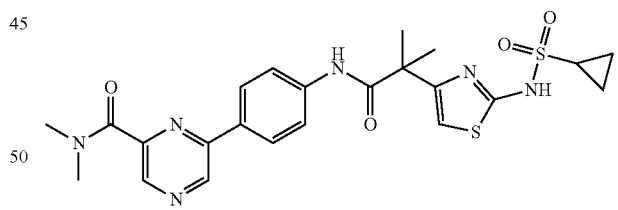

Pd(PPh$_3$)$_4$ (8.8 mg, 0.008 mmol) was added to a degassed (N$_2$, 5 mins) solution of 2-(2-(cyclopropanesulfonamido)thiazol-4-yl)-2-methyl-N-(4-(4,4,5,5-tetramethyl-1,3,2-dioxaborolan-2-yl)phenyl)propanamide INTB56 (75 mg, 0.15 mmol), 6-chloro-N,N-dimethylpyrazine-2-carboxamide (34.0 mg, 0.18 mmol) and NaHCO$_3$ (38.5 mg, 0.46 mmol) in MeCN (4 mL) and water (1 mL). The solution was then degassed (N$_2$, 5 mins) and then heated to 90° C. for 1 hr. The reaction mixture was allowed to cool to RT for 18 hrs. The solution was concentrated onto silica. The crude product was purified by chromatography on silica gel (24 g column, 0-10% MeOH/DCM) to afford 6-(4-(2-(2-(cyclopropanesulfonamido)thiazol-4-yl)-2-methylpropanamido)phenyl)-N,N-dimethylpyrazine-2-carboxamide (35 mg, 0.07 mmol, 44% yield) as a colourless solid; Rt 1.57 min (HPLC acidic); m/z 515 (M+H)+ (ES+); 513 (M−H)− (ES−); 1H NMR (400 MHz, DMSO-d6) δ 12.61 (s, 1H), 9.55 (s, 1H), 9.31 (s, 1H), 8.72 (s, 1H), 8.24-8.06 (m, 2H), 7.91-7.75 (m, 2H), 6.56 (s, 1H), 3.07 (s, 3H), 3.05 (s, 3H), 2.64-2.54 (m, 1H), 1.59 (s, 6H), 0.98-0.84 (m, 4H).

N-(5-(5-cyanopyridin-3-yl)pyrimidin-2-yl)-2-(2-(cyclopropanesulfonamido)thiazol-4-yl)-2-methyl-propanamide T20

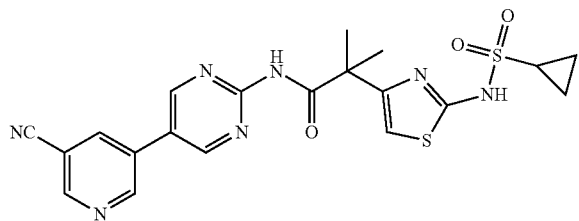 [SMILES: CC(C)(C(=O)Nc1ncc(-c2cncc(C#N)c2)cn1)c1csc(NS(=O)(=O)C2CC2)n1]

To a solution of 2-(2-(cyclopropanesulfonamido)thiazol-4-yl)-2-methylpropanamide INTB58 (82 mg, 0.28 mmol) and 5-(2-chloropyrimidin-5-yl)nicotinonitrile INTA114 (56 mg, 0.26 mmol) in dioxane (3 mL) was added Cs2CO3 (118 mg, 0.36 mmol). The reaction mixture was heated to 60° C. and degassed (N2, 5 mins). Pd 177 (20 mg, 0.03 mmol) was added to the reaction mixture and the temperature was increased to 90° C. After 2 hrs, the reaction was stirred for 16 hrs at 60° C. The reaction mixture was cooled to RT and diluted with NH4Cl (sat. aq, 10 mL) and EtOAc (10 mL). The phases were separated and the aqueous was extracted with EtOAc (2×10 mL) and DCM (1×10 mL). The combined organics were dried (MgSO4) and concentrated onto silica. The crude product was purified by chromatography on silica gel (12 g column, 0-100% EtOAc/iso-hexane, then 5% MeOH/EtOAc) and then by chromatography on C18-RP silica gel (12 g column, 5-40% MeCN/Water 0.1% Formic Acid) to afford N-(5-(5-cyanopyridin-3-yl)pyrimidin-2-yl)-2-(2-(cyclopropanesulfonamido)thiazol-4-yl)-2-methylpropanamide (5 mg, 0.01 mmol, 4% yield) as a yellow solid; Rt 0.90 min (UPLC acidic); m/z 470 (M+H)+ (ES+); 1H NMR (400 MHz, DMSO-d6) δ 12.64 (s, 1H), 10.39 (s, 1H), 9.32 (s, 1H), 9.18 (s, 2H), 9.08 (s, 1H), 8.83 (s, 1H), 6.55 (s, 1H), 2.70-2.38 (m, 1H), 1.59 (s, 6H), 0.98-0.78 (m, 4H).

N-([1,1'-biphenyl]-4-yl)-2-(5-chloro-2-(cyclopropanesulfonamido)thiazol-4-yl)acetamide T21

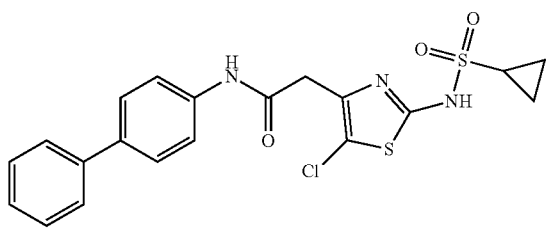 [SMILES: O=C(Cc1nc(NS(=O)(=O)C2CC2)sc1Cl)Nc1ccc(-c2ccccc2)cc1]

A solution of N-([1,1'-biphenyl]-4-yl)-2-(2-(cyclopropanesulfonamido)thiazol-4-yl)acetamide T2 (27 mg, 0.07 mmol) in MeCN (0.5 mL) was treated with NCS (9.2 mg, 0.07 mmol) and stirred for 2 hrs. The reaction mixture was diluted with water (3 mL) and DCM (5 mL) and partitioned with a phase separator. The organic phase was concentrated and the crude product was purified by preparative HPLC (Gilson, Acidic (0.1% Formic acid), Acidic, Waters X-Select Prep-C18, 5 um, 19×50 mm column, 20-60% MeCN in Water) to afford N-([1,1'-biphenyl]-4-yl)-2-(5-chloro-2-(cyclopropanesulfonamido)thiazol-4-yl)acetamide (3 mg, 6.03 umol, 9% yield) as a yellow solid; Rt 2.26 min (HPLC acidic); m/z 448 (35Cl M+H)+ (ES+); 1H NMR (400 MHz, DMSO-d6) δ 12.82 (s, 1H), 10.35 (s, 1H), 7.74-7.61 (m, 6H), 7.44 (dd, J=8.4, 7.0 Hz, 2H), 7.37-7.28 (m, 1H), 3.69 (s, 2H), 2.67-2.58 (m, 1H), 0.96-0.81 (m, 4H).

2-(2-(cyclopropanesulfonamido)thiazol-4-yl)-N-(4-(6-ethynylpyrazin-2-yl)phenyl)butanamide T22

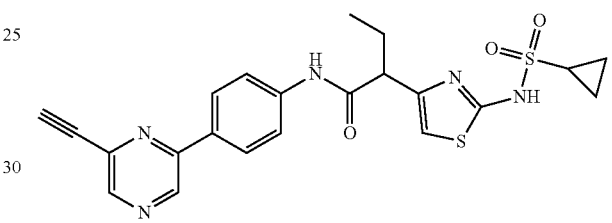

A solution of N-(4-(6-chloropyrazin-2-yl)phenyl)-2-(2-(cyclopropanesulfonamido)thiazol-4-yl)butanamide T78 (94 mg, 0.2 mmol), ethynyltrimethylsilane (0.04 mL, 0.3 mmol) and DIPEA (0.05 mL, 0.3 mmol) in DMF (1 mL) was degassed (N2, 5 mins). To this Cu(I)I (7.5 mg, 0.04 mmol) and Pd(PPh3)2Cl2 (13.8 mg, 0.02 mmol) were added and the mixture degassed (N2, 5 mins) with sonication. The mixture was stirred at RT for 16 hrs. The solvent was removed in vacuo and the mixture partitioned between EtOAc (20 mL) and water (20 mL). The phases were separated and the organic phase concentrated onto silica. The crude product was purified by chromatography on silica gel (24 g cartridge, 0-100% EtOAc/iso-hexane) to afford 2-(2-(cyclopropanesulfonamido)thiazol-4-yl)-N-(4-(6-((trimethylsilyl)ethynyl)pyrazin-2-yl)phenyl)butanamide. The material was taken up in MeOH (2 mL) and Na2CO3 (aq, 208 mg, 1.97 mmol) was added. The mixture was stirred at RT for 1 hr. The solvent was evaporated and water (10 mL) was added. The pH was neutralised to pH 7 and extracted with EtOAc (2×20 mL). The organic phases were combined, dried (MgSO4), filtered and solvent removed. The crude product was purified by chromatography on silica gel (24 g cartridge, 0-100% EtOAc/iso-hexane) and then on C18-RP silica gel (12 g cartridge, 0-80% MeCN/Water 0.1% Formic Acid) to afford 2-(2-(cyclopropanesulfonamido)thiazol-4-yl)-N-(4-(6-ethynylpyrazin-2-yl)phenyl)butanamide (21 mg, 0.044 mmol, 23% yield) as a white solid; 1.89 mins (HPLC acidic); m/z 468 (M+H)+ (ES+); 1H NMR (500 MHz, DMSO-d6) δ 12.62 (s, 1H), 10.42 (s, 1H), 9.23 (s, 1H), 8.70 (s, 1H), 8.19-8.07 (m, 2H), 7.85-7.74 (m, 2H), 6.54 (s, 1H), 4.69 (s, 1H), 3.61 (t, J=7.4 Hz, 1H), 2.63-2.56 (m, 1H), 2.03-1.83 (m, 2H), 1.00-0.78 (m, 7H).

TABLE 15

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T23 | 2-(2-(cyclopropanesulfonamido)thiazol-4-yl)-N-(6-(pyrimidin-5-yl)pyridin-3-yl)acetamide | Method 1 using INTB36, [HPLC acidic], 417, (1.24) | 12.53 (s, 1H), 10.61 (s, 1H), 9.41 (s, 2H), 9.21 (s, 1H), 8.89 (d, J = 2.5 Hz, 1H), 8.21 (dd, J = 8.7, 2.5 Hz, 1H), 8.14 (d, J = 8.5 Hz, 1H), 6.59 (s, 1H), 3.72 (s, 2H), 2.61-2.53 (m, 1H), 0.94-0.81 (m, 4H). |
| T24 | 2-(2-(cyclopropanesulfonamido)thiazol-4-yl)-N-(5-phenylpyridin-2-yl)acetamide | Method 1 using INTB36, [UPLC acidic], 415, (1.18) | 12.63-12.38 (m, 1H), 10.85 (s, 1H), 8.68 (t, J = 1.7 Hz, 1H), 8.14 (br. s, J = 1.9 Hz, 2H), 7.76-7.70 (m, 2H), 7.49 (dd, J = 8.4, 6.9 Hz, 2H), 7.42-7.36 (m, 1H), 6.58 (s, 1H), 3.75 (s, 2H), 2.63-2.55 (m, 1H), 0.95-0.85 (m, 4H). |
| T25 | 2-(2-(cyclopropanesulfonamido)thiazol-4-yl)-N-(4′-fluoro-[1,1′-biphenyl]-4-yl)acetamide | Method 1 using INTB36, [HPLC acidic], 432, (2.04) | 12.56 (s, 1H), 10.29 (s, 1H), 7.77-7.58 (m, 6H), 7.36-7.19 (m, 2H), 6.57 (s, 1H), 3.67 (s, 2H), 2.63-2.55 (m, 1H), 0.94-0.81 (m, 4H). |
| T26 | 2-(2-(cyclopropanesulfonamido)thiazol-4-yl)-N-methyl-N-(4-(pyridin-3-yl)phenyl)acetamide | Method 1 using INTB36 and INTA68, [UPLC acidic], 429, 0.69) | 12.33 (s, 1H), 8.93 (d, J = 2.3 Hz, 1H), 8.59 (dd, J = 4.8, 1.6 Hz, 1H), 8.11 (dt, J = 8.1, 1.8 Hz, 1H), 7.84 (d, J = 8.0 Hz, 2H), 7.54-7.46 (m, 3H), 6.42 (s, 1H), 3.38 (s, 2H), 3.23 (s, 3H), 2.60-2.50 (m, 1H), 0.90-0.80 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T27 | 2-([2,3'-bipyridin]-5-yl)-2-(2-(cyclopropanesulfonamido)thiazol-4-yl)propanamide | Method 1 using INTB39, [HPLC acidic], 430, (1.07) | (Methanol-d4) 9.16 (dd, J = 2.3, 0.9 Hz, 1H), 8.88 (dd, J = 2.6, 0.7 Hz, 1H), 8.58 (dd, J = 4.9, 1.6 Hz, 1H), 8.42 (ddd, J = 8.0, 2.3, 1.6 Hz, 1H), 8.28 (dd, J = 8.7, 2.6 Hz, 1H), 7.95 (dd, J = 8.6, 0.8 Hz, 1H), 7.56 (ddd, J = 8.0, 4.9, 0.9 Hz, 1H), 6.55 (d, J = 0.9 Hz, 1H), 3.92-3.77 (m, 1H), 2.67-2.56 (m, 1H), 1.61 (d, J = 7.1 Hz, 3H), 1.20-1.05 (m, 2H), 1.07-0.87 (m, 2H), 2 exchangeable protons observed. |
| T28 | 2-(2-(cyclopropanesulfonamido)thiazol-4-yl)-N-(3'-methoxy-[1,1'-biphenyl]-4-yl)-2-methylpropanamide | Method 1 using INTB37, [HPLC basic], 472, (1.94) | 12.57 (s, 1H), 9.38 (s, 1H), 7.74-7.67 (m, 2H), 7.67-7.61 (m, 2H), 7.35 (t, J = 7.9 Hz, 1H), 7.22 (ddd, J = 7.7, 1.8, 1.0 Hz, 1H), 7.17 (dd, J = 2.6, 1.7 Hz, 1H), 6.90 (ddd, J = 8.2, 2.6, 0.9 Hz, 1H), 6.54 (s, 1H), 3.82 (s, 3H), 2.64-2.54 (m, 1H), 1.57 (s, 6H), 0.96-0.84 (m, 4H). |
| T29 | 2-(2-(cyclopropanesulfonamido)thiazol-4-yl)-2-methyl-N-(4-(pyridin-3-yl)phenyl)propanamide | Method 1 using INTB37, [UPLC acidic], 443, (0.73) | 12.58 (s, 1H), 9.47 (s, 1H), 8.95 (d, J = 2.7 Hz, 1H), 8.62-8.56 (m, 1H), 8.21 (s, 1H), 7.82-7.71 (m, 4H), 7.57 (s, 1H), 6.57 (s, 1H), 2.60 (dd, J = 7.4, 4.7 Hz, 1H), 1.58 (s, 6H), 0.94-0.85 (m, 4H). |
| T30 | 2-(2-(cyclopropanesulfonamido)thiazol-4-yl)-2-methyl-N-(4-(5-methylpyridin-3-yl)phenyl)propanamide | Method 1 using INTB37 and INTA21, [HPLC acidic], 457, (1.25) | 12.55 (s, 1H), 9.42 (s, 1H), 8.71 (d, J = 2.2 Hz, 1H), 8.40 (d, J = 2.0 Hz, 1H), 7.93 (s, 1H), 7.80-7.67 (m, 4H), 6.57 (s, 1H), 2.66-2.52 (m, 1H), 2.38 (s, 3H), 1.58 (s, 6H), 0.98-0.85 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T31 | 2-(2-(cyclopropanesulfonamido)thiazol-4-yl)-2-methyl-N-(4-(pyridazin-4-yl)phenyl)propanamide | Method 1 using INTB37, [HPLC acidic], 444, (1.50) | 12.56 (s, 1H), 9.71-9.49 (m, 2H), 9.23 (dd, J = 5.5, 1.2 Hz, 1H), 8.00 (dd, J = 5.5, 2.6 Hz, 1H), 7.97-7.92 (m, 2H), 7.87-7.81 (m, 2H), 6.57 (s, 1H), 2.66-2.56 (m, 1H), 1.59 (s, 6H), 0.96-0.87 (m, 4H). |
| T32 | 2-(2-(cyclopropanesulfonamido)thiazol-4-yl)-2-methyl-N-(4-(pyazin-2-yl)phenyl)propanamide | Method 1 using INTB37, [HPLC acidic], 444, (1.66) | 12.59 (s, 1H), 9.50 (s, 1H), 9.24 (d, J = 1.5 Hz, 1H), 8.68 (dd, J = 2.5, 1.5 Hz, 1H), 8.57 (d, J = 2.5 Hz, 1H), 8.18-8.09 (m, 2H), 7.85-7.77 (m, 2H), 6.56 (s, 1H), 2.64-2.54 (m, 1H), 1.59 (s, 6H), 0.98-0.83 (m, 4H). |
| T33 | 2-(2-(cyclopropanesulfonamido)thiazol-4-yl)-N-(4-(6-methoxypyrazin-2-yl)phenyl)butanamide | Method 1 using INTB38 and INTA2, [HPLC acidic], 474, (1956) | 12.62 (s, 1H), 10.37 (s, 1H), 8.79 (s, 1H), 8.22 (s, 1H), 8.19-8.09 (m, 2H), 7.83-7.71 (m, 2H), 6.55 (s, 1H), 4.02 (s, 3H), 3.62 (t, J = 7.6 Hz, 1H), 2.63-2.55 (m, 1H), 2.02-1.84 (m, 2H), 0.96-0.87 (m, 7H). |
| T34 | N-(3-cyano-4-(pyrazin-2-yl)phenyl)-2-(2-(cyclopropanesulfonamido)thiazol-4-yl)-2-methylpropanamide | Method 1b using INTB37 and INTA5, [UPLC basic], 469, (0.95) | 12.62 (s, 1H), 9.80 (s, 1H), 9.13 (d, J = 1.5 Hz, 1H), 8.81 (dd, J = 2.5, 1.5 Hz, 1H), 8.74 (d, J = 2.5 Hz, 1H), 8.29 (d, J = 2.2 Hz, 1H), 8.08 (dd, J = 8.7, 2.2 Hz, 1H), 8.02 (d, J = 8.6 Hz, 1H), 6.61 (s, 1H), 2.65-2.55 (m, 1H), 1.59 (s, 6H), 0.97-0.84 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T35 | 2-(2-(cyclopropanesulfonamido)thiazol-4-yl)-2-methyl-N-(5-(6-(trifluoromethyl)pyrazin-2-yl)pyridin-2-yl)propanamide | Method 1b using INTB37 and INTA3, [UPLC acidic], 513, (1.35) | 12.58 (s, 1H), 10.26 (s, 1H), 9.68 (s, 1H), 9.16 (br. s, 2H), 8.60 (d, J = 8.6 Hz, 1H), 8.26 (dd, J = 8.8, 0.8 Hz, 1H), 6.58 (s, 1H), 2.65-2.54 (m, 1H), 1.61 (s, 6H), 0.91 (s, 4H). |
| T36 | 2-(2-(cyclopropanesulfonamido)thiazol-4-yl)-N-(2,3-difluoro-4-(pyridin-3-yl)phenyl)-2-methylpropanamide | Method 1b using INTB37 and INTA6, [HPLC basic], 479, (1.63) | 12.59 (s, 1H), 9.48 (s, 1H), 8.87-8.72 (m, 1H), 8.64 (dd, J = 4.8, 1.6 Hz, 1H), 8.08-7.96 (m, 1H), 7.55 (ddd, J = 8.0, 4.8, 0.9 Hz, 1H), 7.44 (d, J = 4.9 Hz, 2H), 6.62 (s, 1H), 2.63-2.53 (m, 1H), 1.59 (s, 6H), 0.99-0.86 (m, 4H). |
| T37 | 2-(2-(cyclopropanesulfonamido)thiazol-4-yl)-2-methyl-N-(5-(pyridin-3-yl)pyrimidin-2-yl)propanamide | Method 1b using INTB37 and INTA1, [HPLC acidic], 445, (1.12) | 12.60 (s, 1H), 10.26 (s, 1H), 9.11 (s, 2H), 9.05-8.99 (m, 1H), 8.65 (dd, J = 4.8, 1.6 Hz, 1H), 8.23 (ddd, J = 8.0, 2.4, 1.6 Hz, 1H), 7.60-7.51 (m, 1H), 6.58 (s, 1H), 2.64-2.55 (m, 1H), 1.60 (s, 6H), 0.98-0.83 (m, 4H). |
| T38 | 2-(2-(cyclopropanesulfonamido)thiazol-4-yl)-2-methyl-N-(5-(6-propoxypyrazin-2-yl)pyridin-2-yl)propanamide | Method 1b using INTB37 and INTA4, [HPLC basic], 503, (1.90) | 12.58 (s, 1H), 10.11 (s, 1H), 9.09 (d, J = 2.4 Hz, 1H), 8.87 (s, 1H), 8.53 (dd, J = 8.8, 2.5 Hz, 1H), 8.27 (s, 1H), 8.19 (dd, J = 8.8, 0.8 Hz, 1H), 6.59 (s, 1H), 4.40 (t, J = 6.6 Hz 2H), 2.65-2.56 (m, 1H), 1.88-1.76 (m, 2H), 1.62 (s, 6H), 1.02 (t, J = 7.4 Hz, 3H), 0.95-0.87 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | ¹H NMR Chemical Shift Data (DMSO-d6 unless stated) |
|---|---|---|---|
| T39 | 2-(2-(cyclopropanesulfonamido)thiazol-4-yl)-N-(3-fluoro-4-(pyrazin-2-yl)phenyl)-2-methylpropanamide | Method 1b using INTB37 and INTA7, [UPLC basic], 463, (0.96) | 12.61 (s, 1H), 9.72 (s, 1H), 9.03 (dd, J = 2.5, 1.6 Hz, 1H), 8.78 (dd, J = 2.5, 1.6 Hz, 1H), 8.63 (d, J = 2.5 Hz, 1H), 7.97 (t, J = 8.8 Hz, 1H), 7.82 (dd, J = 14.2, 2.0 Hz, 1H), 7.62 (dd, J = 8.6, 2.1 Hz, 1H), 6.58 (s, 1H), 2.66-2.54 (m, 1H), 1.58 (s, 6H), 0.95-0.87 (m, 4H). |
| T40 | 2-(2-(cyclopropanesulfonamido)thiazol-4-yl)-2-methyl-N-(4-(pyridin-3-yl)-2-(trifluoromethoxy)phenyl)propanamide | Method 1b using INTB37, [UPLC basic], 527, (1.07) | 12.57 (s, 1H), 9.18 (s, 1H), 8.95 (d, J = 2.4 Hz, 1H), 8.61 (dd, J = 4.8, 1.7 Hz, 1H), 8.18-8.10 (m, 1H), 7.85-7.77 (m, 3H), 7.55-7.47 (m, 1H), 6.66 (s, 1H), 2.64-2.54 (m, 1H), 1.57 (s, 6H), 0.96-0.86 (m, 4H). |
| T41 | N-(2-chloro-4-(pyridin-3-yl)phenyl)-2-(2-(cyclopropanesulfonamido)thiazol-4-yl)-2-methylpropanamide | Method 1b using INTB37 and INTA8, [HPLC basic], 477, (1.67) | 12.59 (s, 1H), 9.01 (s, 1H), 8.94 (dd, J = 2.4, 0.8 Hz, 1H), 8.59 (dd, J = 4.8, 1.6 Hz, 1H), 8.13 (ddd, J = 8.0, 2.5, 1.6 Hz, 1H), 7.95-7.89 (m, 1H), 7.80-7.73 (m, 2H), 7.49 (ddd, J = 7.9, 4.8, 0.9 Hz, 1H), 6.70 (s, 1H), 2.63-2.55 (m, 1H), 1.59 (s, 6H), 0.99-0.84 (m, 4H). |
| T42 | 2-(2-(cyclopropanesulfonamido)thiazol-4-yl)-N-(2-fluoro-4-(pyridin-3-yl)phenyl)-2-methylpropanamide | Method 1b using INTB37 and INTA106, [HPLC basic], 461, (1.60) | 12.58 (s, 1H), 9.24 (s, 1H), 8.95 (d, J = 2.1 Hz, 1H), 8.59 (dd, J = 4.8, 1.6 Hz, 1H), 8.14 (dt, J = 8.2, 1.9 Hz, 1H), 7.76-7.63 (m, 2H), 7.63-7.58 (m, 1H), 7.50 (dd, J = 8.0, 4.8 Hz, 1H), 6.61 (s, 1H), 2.64-2.55 (m, 1H), 1.58 (s, 6H), 0.94-0.87 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T43 | 2-(2-(cyclopropanesulfonamido)thiazol-4-yl)-N-(3-methoxy-4-(pyrazin-2-yl)phenyl)-2-methylpropanamide | Method 1b using INTB37 and INTA9, [UPLC basic], 474, (0.94) | 12.59 (s, 1H), 9.65 (s, 1H), 9.11 (d, J = 1.6 Hz, 1H), 8.70 (dd, J = 2.5, 1.6 Hz, 1H), 8.51 (d, J = 2.5 Hz, 1H), 7.79 (d, J = 8.5 Hz, 1H), 7.63 (d, J = 1.9 Hz, 1H), 7.46 (dd, J = 8.5, 1.9 Hz, 1H), 6.53 (s, 1H), 3.88 (s, 3H), 2.68-2.57 (m, 1H), 1.58 (s, 6H), 0.99-0.82 (m, 4H). |
| T44 | 2-(2-(cyclopropanesulfonamido)thiazol-4-yl)-N-(4-(2-methoxypyridin-3-yl)phenyl)-2-methylpropanamide | Method 2 using INTB53, [UPLC acidic], 487, (1.30) | 12.56 (s, 1H), 9.33 (s, 1H), 8.00 (d, J = 5.2 Hz, 1H), 7.69-7.61 (m, 2H), 7.15 (d, J = 8.5 Hz, 2H), 6.96-6.90 (m, 1H), 6.52 (d, J = 12.8 Hz, 1H), 3.73 (s, 3H), 2.61-2.56 (m, 1H), 2.05 (s, 3H), 1.56 (s, 6H), 0.93-0.74 (m, 4H). |
| T45 | 2-(2-(cyclopropaneulfonamido)thiazol-4-yl)-N-(4-(5-(hydroxymethyl)pyridin-3-yl)phenyl)acetamide | Method 2 using INTB36, [HPLC acidic], 445, (0.97) | 12.53 (s, 1H), 10.32 (s, 1H), 8.76 (d, J = 2.3 Hz, 1H), 8.49 (d, J = 2.0 Hz, 1H), 7.97 (t, J = 2.2 Hz, 1H), 7.72 (d, J = 2.1 Hz, 4H), 6.56 (s, 1H), 5.36 (t, J = 5.7 Hz, 1H), 4.61 (d, J = 5.7 Hz, 2H), 3.67 (s, 2H), 2.64-2.55 (m, 1H), 0.95-0.83 (m, 4H). |
| T46 | 2-(2-(cyclopropaneulfonamido)thiazol-4-yl)-N-(4-(6-methoxypyridin-3-yl)phenyl)-2-methylpropanamide | Method 2 using INTB53, [UPLC acidic], 473, (1.24) | 12.56 (s, 1H), 9.36 (s, 1H), 8.46 (dd, J = 2.6, 0.8 Hz, 1H), 7.99 (dd, J = 8.7, 2.6 Hz, 1H), 7.74-7.65 (m, 2H), 7.66-7.58 (m, 2H), 6.88 (dd, J = 8.7, 0.7 Hz, 1H), 6.52 (s, 1H), 3.88 (s, 3H), 2.60-2.55 (m, 1H), 1.56 (s, 6H), 0.94-0.87 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T47 | N-(4-(5-cyanopyridin-3-yl)phenyl)-2-(2-(cyclopropanesulfonamido)thiazol-4-yl)-2-methylpropanamide | Method 2 using INTB53, [UPLC acidic], 468, (1.20) | 12.58 (s, 1H), 9.47 (s, 1H), 9.20 (d, J = 2.3 Hz, 1H), 8.97 (d, J = 1.9 Hz, 1H), 8.65 (t, J = 2.1 Hz, 1H), 7.81 (q, J = 8.7 Hz, 4H), 6.55 (s, 1H), 2.65-2.51 (m, 1H), 1.58 (s, 6H), 0.92 (s, 4H). |
| T48 | 2-(2-(cyclopropaneulfonamido)thiazol-4-yl)-2-methyl-N-(4-(5-(trifluoromethyl)pyridin-3-yl)phenyl)propanamide | Method 2 using INTB53, [UPLC acidic], 511, (1.36) | 12.58 (s, 1H), 9.47 (s, 1H), 9.22 (d, J = 2.3 Hz, 1H), 8.93 (d, J = 2.0 Hz, 1H), 8.45 (d, J = 2.2 Hz, 1H), 7.90-7.76 (m, 4H), 6.55 (s, 1H), 2.63-2.56 (m, 1H), 1.58 (s, 6H), 0.94-0.87 (m, 4H). |
| T49 | 2-(2-(cyclopropaneulfonamido)thiazol-4-yl)-2-methyl-N-(4-(5-(methylsulfonyl)pyridin-3-yl)phenyl)propanamide | Method 2 using INTB53, [UPLC acidic], 521, (1.06) | 12.58 (s, 1H), 9.48 (s, 1H), 9.24 (d, J = 2.2 Hz, 1H), 9.00 (d, J = 2.1 Hz, 1H), 8.56-8.50 (m, 1H), 7.90-7.77 (m, 4H), 6.55 (s, 1H), 3.40 (s, 3H), 2.62-2.56 (m, 1H), 1.58 (s, 6H), 1.04-0.87 (m, 4H). |
| T50 | 2-(2-(cyclopropaneulfonamido)thiazol-4-yl)-N-(2-methoxy-4-(5-methoxypyridin-3-yl)phenyl)-2-methylpropanamide | Method 2 using INTB54, [UPLC acidic], 503, (1.02) | 12.65 (s, 1H), 8.54 (d, J = 1.9 Hz, 1H), 8.41 (s, 1H), 8.28 (d, J = 2.7 Hz, 1H), 8.03 (d, J = 8.3 Hz, 1H), 7.65 (t, J = 2.3 Hz, 1H), 7.43-7.32 (m, 2H), 6.77 (s, 1H), 3.92 (s, 6H), 2.66-2.58 (m, 1H), 1.57 (s, 6H), 0.96-0.88 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T51 | 2-(2-(cyclopropaneulfonamido)thiazol-4-yl)-2-methyl-N-(6-(trifluoromethyl)-[2,3'-bipyridin]-6'-yl)propanamide | Method 2 using INTB55, [HPLC acidic], 512, (1.93) | 12.51 (s, 1H), 10.00 (s, 1H), 9.28 (d, J = 2.1 Hz, 1H), 9.01-8.95 (m, 1H), 8.87 (d, J = 2.5 Hz, 1H), 8.56 (s, 1H), 8.35 (dd, J = 8.8, 2.6 Hz, 1H), 8.22-8.14 (m, 1H), 6.61 (s, 1H), 2.61 (s, 1H), 1.62 (s, 6H), 0.97-0.86 (m, 4H). |
| T52 | 2-(2-(cyclopropaneulfonamido)thiazol-4-yl)-N-(4-(6-ethoxypyrazin-2-yl)phenyl)-2-methylpropanamide | Method 2b using INTB56, [HPLC acidic], 488, (2.10) | 12.59 (s, 1H), 9.50 (s, 1H), 8.78 (s, 1H), 8.19 (s, 1H), 8.15-8.05 (m, 2H), 7.85-7.74 (m, 2H), 6.55 (s, 1H), 4.48 (q, J = 7.1 Hz, 2H), 2.63-2.56 (m, 1H), 1.59 (s, 6H), 1.41 (t, J = 7.0 Hz, 3H), 0.99-0.84 (m, 4H). |
| T53 | 2-(2-(cyclopropaneulfonamido)thiazol-4-yl)-2-methyl-N-(4-(6-morpholinopyrazin-2-yl)phenyl)propanamide | Method 2b using INTB56, [HPLC acidic], 529, (1.96) | 12.59 (s, 1H), 9.47 (s, 1H), 8.49 (s, 1H), 8.24 (s, 1H), 8.07 (d, J = 8.5 Hz, 2H), 7.83-7.68 (m, 2H), 6.55 (s, 1H), 3.79-3.72 (m, 4H), 3.66-3.58 (m, 4H), 2.63-2.55 (m, 1H), 1.58 (s, 6H), 0.97-0.82 (m, 4H). |
| T54 | N-(4-(6-cyclobutoxypyrazin-2-yl)phenyl)-2-(2-(cyclopropanesulfonamido)thiazol-4-yl)-2-methylpropanamide | Method 2b using INTB56, [HPLC basic], 514, (2.00) | 12.58 (s, 1H), 9.50 (s, 1H), 8.79 (s, 1H), 8.17 (s, 1H), 8.14-8.04 (m, 2H), 7.86-7.74 (m, 2H), 6.55 (s, 1H), 5.34-5.18 (m, 1H), 2.65-2.56 (m, 1H), 2.57-2.50 (m, 1H), 2.51-2.43 (m, 1H), 2.22-2.09 (m, 2H), 1.90-1.67 (m, 2H), 1.59 (s, 6H), 0.95-0.86 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T55 | 2-(2-(cyclopropaneulfonamido)thiazol-4-yl)-2-methyl-N-(4-(6-propoxypyrazin-2-yl)phenyl)propanamide | Method 2b using INTB56, [HPLC basic], 502, (2.00) | 12.59 (s, 1H), 9.50 (s, 1H), 8.78 (s, 1H), 8.20 (s, 1H), 8.17-8.06 (m, 2H), 7.83-7.77 (m, 2H), 6.55 (s, 1H), 4.39 (t, J = 6.6 Hz, 2H), 2.65-2.54 (m, 1H), 1.87-1.76 (m, 2H), 1.59 (s, 6H), 1.02 (t, J = 7.4 Hz, 3H), 0.94-0.85 (m, 4H). |
| T56 | 2-(2-(cyclopropanesulfonamido)thiazol-4-yl)-N-(2-fluoro-4-(5-methoxypyridin-3-yl)phenyl)-2-methylpropanamide | Method 2b using INTB56, [UPLC acidic], 491, (0.99) | 12.57 (s, 1H), 9.21 (s, 1H), 8.52 (d, J = 1.9 Hz, 1H), 8.28 (d, J = 2.8 Hz, 1H), 7.80-7.72 (m, 1H), 7.70-7.60 (m, 3H), 6.60 (s, 1H), 3.91 (s, 3H), 2.61-2.56 (m, 1H), 1.57 (s, 6H), 0.93-0.88 (m, 4H). |
| T57 | 2-(2-(cyclopropaneulfonamido)thiazol-4-yl)-2-methoxy-N-(4-(6-methoxypyrazin-2-yl)phenyl)acetamide | Method 1 using INTB43 and INTA2, [HPLC acidic], 476, (1.53) | 12.77 (v. br. s, 1H), 10.12 (s, 1H), 8.80 (s, 1H), 8.22 (s, 1H), 8.14 (d, J = 8.8 Hz, 2H), 7.87 (d, J = 8.8 Hz, 2H), 6.74 (v. br. s, 1H), 4.81 (s, 1H), 4.02 (s, 3H), 3.38 (s, 3H), 2.54-2.50 (m, 1H), 0.91-0.76 (m, 4H). |
| T58 | N-(4-(5-chloropyridin-3-yl)phenyl)-2-(2-(cyclopropanesulfonamido)thiazol-4-yl)-2-isopropoxyacetamide | Method 1c using INTB13 and INTA18, [UPLC acidic], 507, (1.78) | 12.78 (s, 1H), 9.89 (s, 1H), 8.88 (d, J = 2.0 Hz, 1H), 8.59 (d, J = 2.3 Hz, 1H), 8.25 (t, J = 2.2 Hz, 1H), 7.86-7.67 (m, 4H), 6.79 (s, 1H), 5.02 (s, 1H), 3.83-3.67 (m, 1H), 2.60-2.50 (m, 1H), 1.24-1.18 (m, 6H), 0.93-0.84 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T59 | 2-(2-(cyclopropanesulfonamido)thiazol-4-yl)-4-methoxy-N-(5-(6-(trifluoromethyl)pyrazin-2-yl)pyridin-2-yl)butanamide | Method 1c using INTB44 and INTA3, [UPLC acidic], 543, (1.30) | 12.60 (s, 1H), 11.01 (s, 1H), 9.66 (s, 1H), 9.16 (d, J = 4.7 Hz, 2H), 8.59 (dd, J = 8.8, 2.5 Hz, 1H), 8.27 (d, J = 8.8 Hz, 1H), 6.57 (s, 1H), 4.09-3.97 (m, 1H), 3.38-3.26 (m, 2H obscured by residual water), 3.20 (s, 3H), 2.64-2.55 (m, 1H), 2.30-2.18 (m, 1H), 2.14-1.99 (m, 1H), 0.95-0.72 (m, 4H). |
| T60 | N-([1,1'-biphenyl]-4-yl)-2-(2-(cyclopropanesulfonamido)thiazol-4-yl)-2,2-difluoroacetamide | Method 1 using INTB45, [UPLC acidic], 450, (1.54) | 10.90 (s, 1H), 7.86-7.80 (m, 2H), 7.74-7.66 (m, 4H), 7.65-7.54 (m, 1H), 7.47 (dd, J = 8.3, 6.9 Hz, 2H), 7.42-7.32 (m, 1H), 2.87-2.74 (m, 1H), 1.10-0.88 (m, 4H), N—H not observed. |
| T61 | 2-(2-(cyclobutanesulfonamido)thiazol-4-yl)-N-(4-(6-methoxypyrazin-2-yl)phenyl)acetamide | Method 1 using INTB46 and INTA2, [UPLC acidic], 460, (1.89) | (Methanol-d4) δ 8.66 (s, 1H), 8.18-8.02 (m, 3H), 7.81-7.72 (m, 2H), 6.54 (s, 1H), 4.09 (s, 3H), 3.96-3.86 (m, 1H), 3.74 (d, J = 1.0 Hz, 2H), 2.56-2.41 (m, 2H), 2.32 2.41-2.23 (m, 2H), 2.15-1.94 (m, 2H), 2 x exchnagable protons not observed. |
| T62 | N-([3,3'-bipyridin]-6-yl)-2-(2-(cyclopropanesulfonamido)thiazol-4-yl)butanamide | Method 1c using INTB38, [HPLC acidic] 444, (1.23) | 12.57 (s, 1H), 10.86 (s, 1H), 8.95 (dd, J = 2.4, 0.9 Hz, 1H), 8.75 (t, J = 1.7 Hz, 1H), 8.63-8.55 (m, 1H), 8.21 (d, J = 1.7 Hz, 2H), 8.19-8.10 (m, 1H), 7.51 (ddd, J = 8.0, 4.8, 0.9 Hz, 1H), 6.57 (s, 1H), 3.80 (t, J = 7.4 Hz, 1H), 2.64-2.55 (m, 1H), 2.02-1.84 (m, 2H), 0.96-0.83 (m, 7H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | ¹H NMR Chemical Shift Data (DMSO-d6 unless stated) |
|---|---|---|---|
| T63 | 2-(2-(cyclopropanesulfonamido)thiazol-4-yl)-2-methyl-N-(5-phenylpyridin-2-yl)propanamide | Method 1 using INTB37, [UPLC acidic], 443, (1.34) | 12.60 (s, 1H), 9.98 (s, 1H), 8.67 (s, 1H), 8.18-8.07 (m, 2H), 7.76-7.68 (m, 2H), 7.53-7.44 (m, 2H), 7.44-7.34 (m, 1H), 6.57 (s, 1H), 2.62-2.56 (m, 1H), 1.60 (s, 6H), 0.93-0.86 (m, 4H). |
| T64 | 2-(2-(cyclopropaneulfonamido)thiazol-4-yl)-N-(5-(pyrimidin-5-yl)pyridin-2-yl)acetamide | Method 1 using INTB36, [HPLC acidic], 417, (1.25) | 12.52 (s, 1H), 10.94 (s, 1H), 9.22 (s, 2H), 9.21 (s, 1H), 8.83 (dd, J = 2.5, 0.9 Hz, 1H), 8.30 (dd, J = 8.6, 2.5 Hz, 1H), 8.19 (d, J = 8.6 Hz, 1H), 6.58 (s, 1H), 3.77 (s, 2H), 2.64-2.56 (m, 1H), 0.97-0.79 (m, 4H). |
| T65 | N-([3,3'-bipyridin]-6-yl)-2-(2-(cyclopropanesulfonamido)thiazol-4-yl)acetamide | Method 1 using INTB36, [HPLC acidic], 416, (1.04) | 12.51 (s, 1H), 10.89 (s, 1H), 9.01 (d, J = 2.4 Hz, 1H), 8.77 (dd, J = 2.4, 0.9 Hz, 1H), 8.63 (dd, J = 4.9, 1.5 Hz, 1H), 8.29-8.19 (m, 2H), 8.17 (d, J = 8.8 Hz, 1H), 7.60 (dd, J = 8.0, 5.0 Hz, 1H), 6.58 (s, 1H), 3.57 (s, 2H), 2.63-2.56 (m, 1H), 0.93-0.85 (m, 4H). |
| T66 | 2-(2-(cyclopropanesulfonamido)thiazol-4-yl)-N-(6-phenylpyridin-3-yl)acetamide | Method 1 using INTB36, [UPLC acidic], 415, (1.03) | 12.56 (s, 1H), 10.52 (s, 1H), 8.88-8.78 (m, 1H), 8.14 (dd, J = 8.7, 2.6 Hz, 1H), 8.08-8.03 (m, 2H), 7.98 (d, J = 8.7 Hz, 1H), 7.51-7.45 (m, 2H), 7.44-7.36 (m, 1H), 6.60 (s, 1H), 3.75-3.66 (m, 2H), 2.65-2.56 (m, 1H), 0.96-0.85 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T67 | N-([2,3'-bipyridin]-5-yl)-2-(2-(cyclopropanesulfonamido)thiazol-4-yl)acetamide | Method 1 using INTB36, [HPLC acidic], 416, (1.05) | 12.53 (s, 1H), 10.56 (s, 1H), 9.25 (dd, J = 2.3, 0.9 Hz, 1H), 8.87 (d, J = 2.4 Hz, 1H), 8.62 (dd, J = 4.8, 1.6 Hz, 1H), 8.44 (dt, J = 8.1, 2.0 Hz, 1H), 8.19 (dd, J = 8.7, 2.6 Hz, 1H), 8.07 (d, J = 8.7 Hz, 1H), 7.54 (dd, J = 8.0, 4.8 Hz, 1H), 6.60 (s, 1H), 3.72 (s, 2H), 2.64-2.56 (m, 1H), 0.94-0.84 (m, 4H). |
| T68 | 2-(2-(cyclopropaneulfonamido)thiazol-4-yl)-2-methyl-N-(4-(pyridazin-3-yl)phenyl)propanamide | Method 1 using INTB37, [HPLC basic], 444, (1.44) | 12.58 (s, 1H), 9.52 (s, 1H), 9.17 (dd, J = 4.9, 1.6 Hz, 1H), 8.21 (dd, J = 8.7, 1.6 Hz, 1H), 8.16 (d, J = 8.8 Hz, 2H), 7.83 (d, J = 8.8 Hz, 2H), 7.76 (dd, J = 8.7, 4.9 Hz, 1H), 6.57 (s, 1H), 2.65-2.56 (m, 1H), 1.59 (s, 6H), 0.96-0.84 (m, 4H). |
| T69 | 2-(2-(cyclopropaneulfonamido)thiazol-4-yl)-N-(4-(pyridazin-4-yl)phenyl)butanamide | Method 1 using INTB38, [HPLC acidc], 444, (1.91) | 12.61 (s, 1H), 10.41 (s, 1H), 9.64 (dd, J = 2.6, 1.2 Hz, 1H), 9.24 (dd, J = 5.5, 1.2 Hz, 1H), 8.05-7.87 (m, 3H), 7.85-7.73 (m, 2H), 6.56 (s, 1H), 3.61 (t, J = 7.4 Hz, 1H), 2.65-2.56 (m, 1H), 1.98-1.87 (m, 2H), 0.98-0.82 (m, 7H). |
| T70 | 2-(2-(cyclopropanesulfonamido)thiazol-4-yl)-N-(4-(pyrazin-2-yl)phenyl)butanamide | Method 1 using INTB38, [HPLC acidic], 444, (1.71) | 12.62 (s, 1H), 10.38 (s, 1H), 9.23 (d, J = 1.5 Hz, 1H), 8.69 (dd, J = 2.5, 1.5 Hz, 1H), 8.57 (d, J = 2.5 Hz, 1H), 8.21-8.09 (m, 2H), 7.85-7.72 (m, 2H), 6.56 (s, 1H), 3.62 (t, J = 7.4 Hz, 1H), 2.65-2.56 (m, 1H), 2.02-1.84 (m, 2H), 0.97-0.83 (m, 7H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | ¹H NMR Chemical Shift Data (DMSO-d6 unless stated) |
|---|---|---|---|
| T71 | N-(4-(5-chloropyridin-3-yl)phenyl)-2-(2-(cyclopropanesulfonamido)thiazol-4-yl)-4-methoxybutanamide | Method 1 using INTB44 and INTA18, [HPLC acidic], 507, (1.92) | 12.63 (1H, s), 10.34 (1H, s), 8.87 (1H, d), 8.59 (1H, d), 8.23 (1H, t), 7.82-7.71 (4H, m), 6.52 (1H, s), 3.86-3.77 (1H, m), 3.23 (3H, s), 2.64-2.56 (1H, m), 2.27-2.01 (2H, m), 0.95-0.84 (4H, m) CH2 obscured at 3.3 ppm |
| T72 | Single enantiomer - stereochemistry unassigned 2-(2-(cyclopropanesulfonamido)thiazol-4-yl)-N-(4-(5-fluoropyridin-3-yl)phenyl)butanamide | Method 1 using INTB38 and INTA13, Chiral IA [UPLC basic], 461, (1) | 12.65 (s, 1H), 10.46 (s, 1H), 8.82 (t, J = 1.8 Hz, 1H), 8.57 (d, J = 2.7 Hz, 1H), 8.09 (ddd, J = 10.5, 2.7, 1.8 Hz, 1H), 7.86-7.59 (m, 4H), 6.56 (s, 1H), 3.74-3.61 (m, 1H), 2.66-2.56 (m, 1H), 2.09-1.80 (m, 2H), 1.02-0.84 (m, 7H). |
| T73 | 2-(2-(cyclopropanesulfonamido)thiazol-4-yl)-N-(4-(6-(trifluoromethyl)pyrazin-2-yl)phenyl)butanamide | Method 1 using INTB38 and INTA39, [HPLC acidic], 512, (2.16) | 12.62 (s, 1H), 10.46 (s, 1H), 9.59 (s, 1H), 9.09 (s, 1H), 8.26-8.15 (m, 2H), 7.90-7.76 (m, 2H), 6.56 (s, 1H), 3.63 (t, J = 7.1 Hz, 1H), 2.63-2.55 (m, 1H), 2.04-1.85 (m, 2H), 0.97-0.83 (m, 7H). |
| T74 | 2-(2-(cyclopropanesulfonamido)thiazol-4-yl)-3-methyl-N-(4-(pyrazin-2-yl)phenyl)butanamide | Method 1 using INTB40, [HPLC basic], 458, (1.6) | 12.59 (s, 1H), 10.40 (s, 1H), 9.23 (d, J = 1.6 Hz, 1H), 8.68 (dd, J = 2.5, 1.6 Hz, 1H), 8.57 (d, J = 2.5 Hz, 1H), 8.18-8.09 (m, 2H), 7.82-7.73 (m, 2H), 6.60 (s, 1H), 3.38 (d, J = 9.8 Hz, 1H), 2.64-2.55 (m, 1H), 2.47-2.32 (m, 1H), 0.98 (d, J = 6.6 Hz, 3H), 0.94-0.84 (m, 7H). |

TABLE 15-continued

*Preparation methods and characterisation of Examples T23-T322, T422-T443 and T445-T465. Where no INTA number is given, the aniline is commercially available.*

| T# | Name/Structure (All examples containing chiral centres are racemates unless stated) | Synthesis Method, [LCMS Method], m/z (M + H)+, (Rt/min) | ¹H NMR Chemical Shift Data (DMSO-d6 unless stated) |
|---|---|---|---|
| T75 | 2-(2-(cyclopropanesulfonamido)thiazol-4-yl)-N-(4-(6-propoxypyrazin-2-yl)phenyl)butanamide | Method 1 using INTB38 and INTA42, [HPLC acidic], 502, (2.29) | 12.45 (s, 1H), 10.36 (s, 1H), 8.76 (s, 1H), 8.19 (s, 1H), 8.15-8.06 (m, 2H), 7.82-7.71 (m, 2H), 6.55 (s, 1H), 4.38 (t, J = 6.6 Hz, 2H), 3.61 (t, J = 7.5 Hz, 1H), 2.65-2.53 (m, 1H), 2.04-1.83 (m, 2H), 1.86-1.73 (m, 2H), 1.01 (t, J = 7.4 Hz, 3H), 0.95-0.83 (m, 7H). |
| T76 | 2-(2-(cyclopropanesulfonamido)thiazol-4-yl)-N-(4-(6-isopropoxypyrazin-2-yl)phenyl)butanamide | Method 1 using INTB38 and INTA40, [HPLC acidic], 502, (2.26) | 12.60 (s, 1H), 10.36 (s, 1H), 8.74 s, 1H), 8.12 (s, 1H), 8.11-8.06 (m, 2H), 7.87-7.63 (m, 2H), 6.54 (s, 1H), 5.47-5.34 (m, 1H), 3.61 (t, J = 7.5 Hz, 1H), 2.65-2.53 (m, 1H), 2.03-1.82 (m, 2H), 1.38 (d, J = 6.2 Hz, 6H), 0.96-0.84 (m, 7H). |
| T77 | 2-(2-(cyclopropanesulfonamido)thiazol-4-yl)-N-(4-(6-cyclopropoxypyrazin-2-yl)phenyl)butanamide | Method 1 using INTB38 and INTA41, [HPLC basic], 500, (1.8) | 12.62 (s, 1H), 10.37 (s, 1H), 8.84 (s, 1H), 8.24 (s, 1H), 8.18-8.10 (m, 2H), 7.77 (d, J = 8.8 Hz, 2H), 6.56 (s, 1H), 4.42 (tt, J = 6.2, 3.1 Hz, 1H), 3.62 (t, J = 7.5 Hz, 1H), 2.65-2.55 (m, 1H), 2.04-1.83 (m, 2H), 0.97-0.80 (m, 11H). |
| T78 | N-(4-(6-chloropyrazin-2-yl)phenyl)-2-(2-(cyclopropanesulfonamido)thiazol-4-yl)butanamide | Method 1 using INTB38 and INTA43, [HPLC basic], 478, (1.8) | 12.62 (s, 1H), 10.43 (s, 1H), 9.25 (s, 1H), 8.70 (s, 1H), 8.17-8.10 (m, 2H), 7.85-7.75 (m, 2H), 6.56 (s, 1H), 3.62 (t, J = 7.4 Hz, 1H), 2.65-2.55 (m, 1H), 2.04-1.85 (m, 2H), 0.96-0.88 (m, 7H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T79 | N-(4-(6-cyanopyrazin-2-yl)phenyl)-2-(2-(cyclopropanesulfonamido)thiazol-4-yl)butanamide | Method 1 using INTB38 and INTA44, [HPLC basic], 469, (1.7) | 12.62 (s, 1H), 10.45 (s, 1H), 9.54 (s, 1H), 9.12 (s, 1H), 8.27-8.13 (m, 2H), 7.87-7.75 (m, 2H), 6.56 (s, 1H), 3.63 (t, J = 7.4 Hz, 1H), 2.64-2.55 (m, 1H), 2.04-1.82 (m, 2H), 0.95-0.80 (m, 7H). |
| T80 | Single enantiomer - stereochemistry unassigned 2-(2-(cyclopropanesulfonamido)thiazol-4-yl)-N-(4-(6-(trifluoromethyl)pyrazin-2-yl)phenyl)butanamide | Method 1 using INTB38 and INTA39, Chiral IA (5.8), [HPLC acidic], 512, (2.2) | 12.63 (s, 1H), 10.50 (s, 1H), 9.59 (s, 1H), 9.09 (s, 1H), 8.29-8.13 (m, 2H), 7.93-7.78 (m, 2H), 6.54 (s, 1H), 3.61 (t, J = 7.4 Hz, 1H), 2.65-2.56 (m, 1H), 2.03-1.81 (m, 2H), 1.00-0.72 (m, 7H). |
| T81 | 2-(2-(cyclopropanesulfonamido)thiazol-4-yl)-N-(4-(6-methoxypyrazin-2-yl)phenyl)acetamide | Method 1 using INTB36 and INTA2, [HPLC acidic], 446, (1.78) | 12.53 (s, 1H), 10.39 (s, 1H), 8.78 (s, 1H), 8.21 (s, 1H), 8.19-8.08 (m, 2H), 7.75 (d, J = 8.7 Hz, 2H), 6.57 (s, 1H), 4.01 (s, 3H), 3.68 (s, 2H), 2.63-2.54 (m, 1H), 0.97-0.82 (m, 4H). |
| T82 | 2-(2-(cyclopropanesulfonamido)thiazol-4-yl)-N-(4-(pyrazin-2-yl)phenyl)acetamide | Method 1 using INTB36 and INTA99, [HPLC acidic], 416, (1.44) | 12.54 (s, 1H), 10.40 (s, 1H), 9.23 (d, J = 1.6 Hz, 1H), 8.69 (dd, J = 2.5, 1.5 Hz, 1H), 8.57 (d, J = 2.5 Hz, 1H), 8.24-8.01 (m, 2H), 7.86-7.65 (m, 2H), 6.58 (s, 1H), 3.74-3.63 (m, 2H), 2.64-2.55 (m, 1H), 0.96-0.85 (m, 4H). |

TABLE 15-continued

*Preparation methods and characterisation of Examples T23-T322, T422-T443 and T445-T465. Where no INTA number is given, the aniline is commercially available.*

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T83 | N-([1,1'-biphenyl]-4-yl)-2-(cyclopropanesulfonamido)-4,5,6,7-tetrahydrobenzo[d]thiazole-4-carboxamide | Method 1 using INTB67, [HPLC acidic], 454, (2.23) | 12.35 (s, 1H), 10.32 (s, 1H), 7.72 (d, J = 8.7 Hz, 2H), 7.69-7.61 (m, 4H), 7.45 (t, J = 7.7 Hz, 2H), 7.36-7.30 (m, 1H), 3.71-3.62 (m, 1H), 3.30 (s, 2H), 2.62-2.53 (m, 1H), 2.19-1.66 (m, 4H), 0.98-0.74 (m, 4H). |
| T84 | 2-(cyclopropanesulfonamido)-N-(4-(pyridin-3-yl)phenyl)-4,5,6,7-tetrahydrobenzo[d]thiazole-4-carboxamide | Method 1 using INTB67, [HPLC acidic], 455, (1.27) | 12.32 (s, 1H), 10.28 (s, 1H), 8.89 (dd, J = 2.4, 0.8 Hz, 1H), 8.53 (dd, J = 4.7, 1.6 Hz, 1H), 8.06 (ddd, J = 8.0, 2.5, 1.6 Hz, 1H), 7.78-7.68 (m, 4H), 7.46 (ddd, J = 8.0, 4.7, 0.9 Hz, 1H), 3.66 (t, J = 6.0 Hz, 1H), 2.62-2.51 (m, 1H), 2.14-2.07 (m, 1H), 2.00-1.95 (m, 1H), 1.89-1.84 (m, 1H), 1.78-1.73 (m, 1H), 1.30-1.22 (m, 2H), 0.93-0.85 (m, 4H). |
| T85 | N-([1,1'-biphenyl]-4-yl)-2-(2-(cyclopropanesulfonamido)thiazol-4-yl)butanamide | Method 1 using INTB38, [HPLC basic], 442, (2) | 12.59 (s, 1H), 10.24 (s, 1H), 7.75-7.66 (m, 2H), 7.68-7.60 (m, 4H), 7.44 (dd, J = 8.4, 7.0 Hz, 2H), 7.37-7.28 (m, 1H), 6.53 (s, 1H), 3.58 (t, J = 7.4 Hz, 1H), 2.62-2.54 (m, 1H), 2.02-1.81 (m, 2H), 0.95-0.78 (m, 7H). |
| T86 | N-([1,1'-biphenyl]-4-yl)-2-(2-(cyclopropanesulfonamido)thiazol-4-yl)butanamide | Method 1 using INTB40, [HPLC acidic], 456, (2.35) | 12.58 (s, 1H), 10.27 (s, 1H), 7.76-7.60 (m, 6H), 7.45 (dd, J = 8.4, 7.0 Hz, 2H), 7.39-7.28 (m, 1H), 6.57 (s, 1H), 3.36 (d, J = 9.9 Hz, 1H), 2.66-2.56 (m, 1H), 2.47-2.35 (m, 1H), 1.04-0.81 (m, 10H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T87 | N-(3'-chloro-[1,1'-biphenyl]-4-yl)-2-(2-(cyclopropanesulfonamido)thiazol-4-yl)-2-methylpropanamide | Method 1 using INTB37, [HPLC acidic], 477, (2.36) | 12.58 (s, 1H), 9.41 (s, 1H), 7.77-7.67 (m, 5H), 7.67-7.63 (m, 1H), 7.48 (t, J = 7.9 Hz, 1H), 7.42-7.37 (m, 1H), 6.55 (s, 1H), 2.64-2.55 (m, 1H), 1.58 (s, 6H), 0.96-0.86 (m, 4H). |
| T88 | N-(3'-chloro-[1,1'-biphenyl]-4-yl)-2-(2-(cyclopropanesulfonamido)thiazol-4-yl)-2-methylpropanamide | Method 1 using INTB37, [HPLC acidic], 467, (2.110 | 12.57 (s, 1H), 9.42 (s, 1H), 8.17-8.13 (m, 1H), 8.05-8.00 (m, 1H), 7.81-7.76 (m, 1H), 7.75 (s, 4H), 7.64 (t, J = 7.8 Hz, 1H), 6.54 (s, 1H), 2.62-2.54 (m, 1H), 1.57 (s, 6H), 0.96-0.83 (m, 4H). |
| T89 | 2-(2-(cyclopropanesulfonamido)thiazol-4-yl)-2,2-difluoro-N-(4-(pyridin-3-yl)phenyl)acetamide | Method 1 using INTB45, [UPLC acidic], 451, (0.84) | 10.95 (s, 1H), 8.92 (d, J = 2.5 Hz, 1H), 8.57 (dd, J = 4.8, 1.6 Hz, 1H), 8.10 (dt, J = 7.9, 1.9 Hz, 1H), 7.91-7.82 (m, 2H), 7.82-7.76 (m, 2H), 7.63-7.57 (m, 1H), 7.49 (dd, J = 8.1, 4.9 Hz, 1H), 2.86-2.76 (m, 1H), 1.01 (s, 4H). N—H not observed. |
| T90 | N-(4-(5-fluoropyridin-3-yl)phenyl)-2-(2-(cyclopropanesulfonamido)thiazol-4-yl)butanamide | Method 1 using INTB38 and INTA13, [UPLC basic], 477, (1.11) | 12.62 (s, 1H), 10.34 (s, 1H), 8.80 (t, J = 1.9 Hz, 1H), 8.54 (d, J = 2.7 Hz, 1H), 8.05 (ddd, J = 10.5, 2.7, 1.8 Hz, 1H), 7.83-7.67 (m, 4H), 6.55 (s, 1H), 3.60 (t, J = 7.4 Hz, 1H), 2.55-2.66 (m, 1H), 2.01-1.84 (m, 2H), 0.97-0.84 (m, 7H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T91 | Single enantiomer - stereochemistry unassigned N-(4-(5-fluoropyridin-3-yl)phenyl)-2-(2-(cyclopropanesulfonamido)thiazol-4-yl)butanamide•HCl | Method 1 using INTB38 and INTA13, Chiral IA [UPLC basic], 475, (1.1) | 12.57 (s, 1H), 10.43 (s, 1H), 8.81 (d, J = 2.0 Hz, 1H), 8.53 (d, J = 2.3 Hz, 1H), 8.18 (dd, J = 2.1 Hz, 1H), 7.75-7.62 (m, 4H), 6.49 (s, 1H), 3.60 (dd, J = 7.5 Hz, 1H), 2.57-2.48 (m, 1H), 1.94-1.74 (m, 2H), 0.93-0.75 (m, 7H). |
| T92 | 2-(2-(cyclopropanesulfonamido)thiazol-4-yl)-2-ethyl-N-(4-(pyridin-3-yl)phenyl)butanamide | Method 1 using INTB41, [UPLC acidic], 471.1, (0.88) | 12.44 (s, 1H), 9.33 (s, 1H), 8.87 (d, J = 2.4 Hz, 1H), 8.52 (dd, J = 4.7, 1.6 Hz, 1H), 8.04 (ddd, J = 8.0, 2.5, 1.6 Hz, 1H), 7.78-7.65 (m, 4H), 7.57 (ddd, J = 7.9, 4.8, 0.9 Hz, 1H), 6.63 (s, 1H), 2.56-2.63 (m, 1H), 2.08-1.90 (m, 4H), 0.93-0.82 (m, 4H), 0.73 (t, J = 7.3 Hz, 6H). |
| T93 | N-(4-(5-cyanopyridin-3-yl)phenyl)-2-(2-(cyclopropanesulfonamido)thiazol-4-yl)-2-ethylbutanamide | Method 1 using INTB41 and INTA12, [UPLC acidic], 496.4, (1.3) | 12.48 (s, 1H), 9.38 (s, 1H), 9.18 (d, J = 2.3 Hz, 1H), 8.96 (d, J = 1.9 Hz, 1H), 8.63 (dd, J = 2.1 Hz, 1H), 7.84-7.73 (m, 4H), 6.61 (s, 1H), 2.54-2.62 (m, 1H), 2.08-1.92 (m, 4H), 0.92-0.85 (m, 4H), 0.72 (t, J = 7.3 Hz, 6H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T94 | 2-(2-(cyclopropanesulfonamido)thiazol-4-yl)-N-(4-(5-ethoxypyridin-3-yl)phenyl)propanamide | Method 1 using INTB39 and INTA11, [UPLC acidic], 473, (0.94) | (Methanol-d4) 8.38 (s, 1H), 8.19 (d, J = 2.7 Hz, 1H), 7.82-7.72 (m, 2H), 7.72-7.63 (m, 2H), 7.60 (dd, J = 2.7, 1.8 Hz, 1H), 6.54 (d, J = 0.9 Hz, 1H), 4.21 (q, J = 7.0 Hz, 2H), 3.84 (q, J = 7.2 Hz, 1H), 2.66-2.58 (m, 1H), 1.60 (d, J = 7.1 Hz, 3H), 1.47 (t, J = 7.0 Hz, 3H), 1.16-1.05 (m, 2H), 1.00-0.89 (m, 2H), 2 exchangeable N—H not observed). |
| T95 | N-(4-(5-chloropyridin-3-yl)phenyl)-2-(2-(cyclopropanesulfonamido)thiazol-4-yl)propanamide | Method 1 using INTB39 and INTA18, [UPLC acidic], 464, (1.23) | 12.63 (s, 1H), 10.31 (s, 1H), 8.86 (d, J = 2.0 Hz, 1H), 8.58 (d, J = 2.3 Hz, 1H), 8.22 (dd, J = 2.2 Hz, 1H), 7.82-7.65 (m, 4H), 6.49 (s, 1H), 3.76 (q, J = 7.1 Hz, 1H), 2.62-2.53 (m, 1H), 1.46 (d, J = 7.1 Hz, 3H), 0.96-0.80 (m, 4H). |
| T96 | 2-(2-(cyclopropanesulfonamido)thiazol-4-yl)-N-(4-(5-ethoxypyridin-3-yl)phenyl)butanamide | Method 1 using INTB38 and INTA11, [HPLC basic], 487, (1.7) | 12.59 (s, 1H), 10.29 (s, 1H), 8.47 (d, J = 1.9 Hz, 1H), 8.24 (d, J = 2.7 Hz, 1H), 7.74 (s, 4H), 7.66-7.52 (m, 1H), 6.56 (s, 1H), 4.20 (q, J = 7.0 Hz, 2H), 3.60 (t, J = 7.4 Hz, 1H), 2.64-2.55 (m, 1H), 2.02-1.83 (m, 2H), 1.38 (t, J = 7.0 Hz, 3H), 0.96-0.86 (m, 7H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T97 | N-([1,1'-biphenyl]-4-yl)-2-(2-(cyclopropanesulfonamido)thiazol-4-yl)-2-methylpropanamide | Method 1 using INTB37, [HPLC acidic], 442, (1.43) | 12.60 (s, 1H), 9.40 (s, 1H), 7.76-7.68 (m, 2H), 7.70-7.60 (m, 4H), 7.49-7.41 (m, 2H), 7.38-7.29 (m, 1H), 6.55 (s, 1H), 2.63-2.56 (m, 1H), 1.58 (s, 6H), 0.94-0.87 (m, 4H). |
| T98 | 2-(2-(cyclopropanesulfonamido)thiazol-4-yl)-N-(4-(4-methylpyridin-3-yl)phenyl)acetamide | Method 1 using INTB36 and INTA, [HPLC acidic], 429, (0.99) | 12.54 (s, 1H), 10.37 (s, 1H), 8.63 (d, J = 5.7 Hz, 2H), 7.86-7.65 (m, 3H), 7.54-7.40 (m, 2H), 6.58 (s, 1H), 3.68 (d, J = 1.0 Hz, 2H), 2.63-2.55 (m, 1H), 2.44 (s, 3H), 0.94-0.86 (m, 4H). |
| T99 | 2-(2-(cyclopropanesulfonamido)thiazol-4-yl)-N-(4-(5-methylpyridin-3-yl)phenyl)acetamide | Method 1 using INTB36 and INTA21, [HPLC acidic], 429, (1.07) | 12.53 (s, 1H), 10.31 (s, 1H), 8.70 (d, J = 2.2 Hz, 1H), 8.39 (dd, J = 2.0, 0.8 Hz, 1H), 7.91 (d, J = 2.3 Hz, 1H), 7.83-7.58 (m, 4H), 6.58 (s, 1H), 3.76-3.56 (m, 2H), 2.62-2.56 (m, 1H), 2.37 (s, 3H), 0.95-0.86 (m, 4H). |
| T100 | 2-(2-(cyclopropanesulfonamido)thiazol-4-yl)-N-(4-(2-methylpyridin-3-yl)phenyl)acetamide | Method 1 using INTB36 and INTA19, [HPLC acidic], 429, (0.94) | 12.54 (s, 1H), 10.35 (s, 1H), 8.61 (s, 1H), 7.99 (s, 1H), 7.78-7.72 (m, 2H), 7.61 (s, 1H), 7.52-7.31 (m, 2H), 6.58 (s, 1H), 3.68 (s, 2H), 2.62-2.56 (m, 1H), 0.98-0.76 (m, 4H), 1 proton obscured by solvent |
| T101 | 2-(2-(cyclopropanesulfonamido)thiazol-4-yl)-N-(4-(6-methylpyridin-3-yl)phenyl)acetamide | Method 1 using INTB36 and INTA20, [HPLC acidic], 429, (1) | 12.53 (s, 1H), 10.30 (s, 1H), 8.78 (d, J = 2.4 Hz, 1H), 8.03 (d, J = 8.2 Hz, 1H), 7.77-7.63 (m, 4H), 7.38 (d, J = 8.2 Hz, 1H), 6.58 (s, 1H), 3.72-3.62 (m, 2H), 2.63-2.56 (m, 1H), 0.96-0.84 (m, 4H), 1 proton obscured by solvent |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T102 | 2-(2-(cyclopropanesulfonamido)thiazol-4-yl)-N-(4-(pyridin-3-yl)phenyl)propanamide | Method 1 using INTB39, [HPLC acidic], 429, (2.11) | 12.60 (s, 1H), 10.27 (s, 1H), 8.88 (dd, J = 2.5, 0.9 Hz, 1H), 8.53 (dd, J = 4.8, 1.6 Hz, 1H), 8.05 (ddd, J = 8.0, 2.5, 1.6 Hz, 1H), 7.78-7.67 (m, 4H), 7.46 (ddd, J = 8.0, 4.8, 0.9 Hz, 1H), 6.50 (s, 1H), 3.77 (q, J = 7.1 Hz, 1H), 2.60-2.50 (m, 1H), 1.46 (d, J = 7.1 Hz, 3H), 0.92-0.84 (m, 4H). |
| T103 | 2-(2-(cyclopropanesulfonamido)thiazol-4-yl)-2-methyl-N-(4-(2-methylpyridin-3-yl)phenyl)propanamide | Method 1 using INTB37 and INTA19, [HPLC acidic], 457, (1.1) | 12.63 (s, 2H), 9.45 (s, 1H), 8.44 (dd, J = 4.8, 1.8 Hz, 1H), 8.13 (s, 1H), 7.76-7.67 (m, 2H), 7.58 (dd, J = 7.7, 1.8 Hz, 1H), 7.39-7.30 (m, 2H), 7.28 (dd, J = 7.7, 4.9 Hz, 1H), 6.55 (s, 1H), 2.63-2.51 (m, 1H), 2.43 (s, 3H), 1.57 (s, 6H), 0.95-0.83 (m, 4H). |
| T104 | 2-(2-(cyclopropanesulfonamido)thiazol-4-yl)-2-oxo-N-(4-(pyridin-3-yl)phenyl)acetamide | Method 1 using INTB68, [UPLC acidic], 429, (0.8) | 13.19 (s, 1H), 11.01 (s, 1H), 8.93 (dd, J = 2.4, 0.9 Hz, 1H), 8.57 (dd, J = 4.7, 1.6 Hz, 1H), 8.50 (s, 1H), 8.16-8.07 (m, 1H), 7.98-7.85 (m, 2H), 7.81-7.74 (m, 2H), 7.50 (ddd, J = 8.0, 4.8, 0.9 Hz, 1H), 2.76-2.56 (m, 1H), 1.00-0.87 (m, 4H). |
| T105 | 2-(2-(cyclopropanesulfonamido)thiazol-4-yl)-2-methyl-N-(4-(6-methylpyridin-3-yl)phenyl)propanamide | Method 1 using INTB37 and INTA20, [UPLC acidic], 457, (0.7) | 12.55 (s, 1H), 9.41 (s, 1H), 8.78-8.72 (m, 1H), 7.95 (dd, J = 8.0, 2.5 Hz, 1H), 7.78-7.64 (m, 4H), 7.32 (d, J = 8.1 Hz, 1H), 6.56 (s, 1H), 3.32 (s, 3H), 2.64-2.54 (m, 1H), 1.58 (s, 6H), 0.95-0.85 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T106 | Single enantiomer - stereochemistry unassigned 2-(2-(cyclopropanesulfonamido)thiazol-4-yl)-N-(4-(6-(trifluoromethyl)pyrazin-2-yl)phenyl)butanamide | Method 1 using INTB38 and INTA39, Chiral IA (7.8), [HPLC acidic], 512, (2.19) | 12.64 (s, 1H), 10.50 (s, 1H), 9.59 (s, 1H), 9.09 (s, 1H), 8.21 (d, J = 8.8 Hz, 2H), 7.84 (d, J = 8.9 Hz, 2H), 6.52 (s, 1H), 3.60 (t, J = 7.5 Hz, 1H), 2.66-2.55 (m, 1H), 2.02-1.81 (m, 2H), 0.973-0.785 (m, 7H). 1968-02B |
| T107 | Single enantiomer - stereochemistry unassigned 2-(2-(cyclopropanesulfonamido)thiazol-4-yl)-2-methoxy-N-(4-(6-methoxypyrazin-2-yl)phenyl)acetamide | Method 1 using INTB43 and INTA2 Chiral IC (10.2), [UPLC acidic], 476, (1.31) | 12.80 (s, 1H), 10.09 (s, 1H), 8.80 (s, 1H), 8.23 (s, 1H), 8.17-8.11 (m, 2H), 7.88-7.83 (m, 3H), 6.84 (s, 1H), 4.90 (s, 1H), 4.02 (s, 4H), 3.40 (s, 4H), 2.55-2.51 (m, 1H), 0.90 (d, J = 7.5 Hz, 6H). |
| T108 | Single enantiomer - stereochemistry unassigned 2-(2-(cyclopropanesulfonamido)thiazol-4-yl)-2-methoxy-N-(4-(6-methoxypyrazin-2-yl)phenyl)acetamide | Method 1 using INTB43 and INTA2 Chiral IC (25.2), [UPLC acidic], 476, (1.31) | 12.80 (s, 1H), 10.09 (s, 1H), 8.80 (s, 1H), 8.23 (s, 1H), 8.17-8.11 (m, 2H), 7.88-7.83 (m, 3H), 6.84 (s, 1H), 4.90 (s, 1H), 4.02 (s, 4H), 3.40 (s, 4H), 2.55-2.51 (m, 1H), 0.90 (d, J = 7.5 Hz, 6H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T109 | 2-(2-(cyclopropanesulfonamido)thiazol-4-yl)-2-methyl-N-(5-(6-(2,2,2-trifluoroethoxy)pyrazin-2-yl)pyridin-2-yl)propanamide | Method 1b using INTB37 and INTA62, [HPLC basic], 543, (1.91) | 12.59 (s, 1H), 10.15 (s, 1H), 9.16 (d, J = 2.4 Hz, 1H), 9.04 (s, 1H), 8.62 (dd, J = 8.8, 2.5 Hz, 1H), 8.46 (s, 1H), 8.20 (d, J = 8.8 Hz, 1H), 6.58 (s, 1H), 5.22 (q, J = 9.0 Hz, 2H), 2.60 (s, 1H), 1.62 (s, 6H), 1.01-0.82 (m, 4H). |
| T110 | 2-(2-(cyclopropanesulfonamido)thiazol-4-yl)-N-(3-fluoro-5-(pyrazin-2-yl)pyridin-2-yl)-2-methylpropanamide | Method 1b using INTB37 and INTA60, [UPLC acidic], 463, (0.93) | 12.64 (s, 1H), 10.10 (s, 1H), 9.39 (d, J = 1.5 Hz, 1H), 9.07-9.03 (m, 1H), 8.79-8.75 (m, 1H), 8.70 (d, J = 2.5 Hz, 1H), 8.51-8.45 (m, 1H), 6.57 (s, 1H), 2.60-2.56 (m, 1H), 1.59 (s, 6H), 0.93-0.87 (m, 4H). |
| T111 | 2-(2-(cyclopropanesulfonamido)thiazol-4-yl)-N-(5-(6-ethoxypyrazin-2-yl)-3-fluoropyridin-2-yl)-2-methylpropanamide | Method 1b using INTB37 and INTA57, [HPLC acidic], 507, (1.22) | 12.64 (s, 1H), 10.08 (s, 1H), 9.05-9.00 (m, 1H), 8.93 (s, 1H), 8.44 (dd, J = 11.0, 1.9 Hz, 1H), 8.32 (s, 1H), 6.56 (s, 1H), 4.49 (q, J = 7.1 Hz, 2H), 2.60-2.56 (m, 1H), 1.59 (s, 6H), 1.39 (t, J = 7.0 Hz, 3H), 0.90 (s, 4H). |
| T112 | 2-(2-(cyclopropanesulfonamido)thiazol-4-yl)-N-(3-fluoro-5-(6-(trifluoromethyl)pyrazin-2-yl)pyridin-2-yl)-2-methylpropanamide | Method 1b using INTB37 and INTA58, [UPLC acidic], 531, (1.25) | 12.66 (s, 1H), 10.20 (s, 1H), 9.73 (s, 1H), 9.24 (s, 1H), 9.11-9.07 (m, 1H), 8.57-8.50 (m, 1H), 6.59 (s, 1H), 2.61-2.57 (m, 1H), 1.61 (s, 6H), 0.94-0.90 (m, 4H). |

… TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T113 | N-(5-(6-cyanopyrazin-2-yl)-3-fluoropyridin-2-yl)-2-(2-(cyclopropanesulfonamido)thiazol-4-yl)-2-methylpropanamide | Method 1b using INTB37 and INTA59, [UPLC acidic], 488, (1.07) | 12.66 (s, 1H), 10.19 (s, 1H), 9.68 (s, 1H), 9.26 (s, 1H), 9.08 (s, 1H), 8.58-8.51 (m, 1H), 6.59 (s, 1H), 2.61-2.57 (m, 1H), 1.61 (s, 6H), 0.94-0.90 (m, 4H). |
| T114 | 2-(2-(cyclopropanesulfonamido)thiazol-4-yl)-2-methyl-N-(5'-(2,2,2-trifluroethoxy)-[3,3'-bipyridin]-6-yl)propanamide | Method 1b using INTB37 and INTA36, [HPLC acidic], 542, (1.94) | 12.56 (s, 1H), 10.05 (s, 1H), 8.81 (dd, J = 2.5, 0.8 Hz, 1H), 8.68 (d, J = 1.8 Hz, 1H) 8.42 (d, J = 2.8 Hz, 1H), 8.27 (dd, J = 8.8, 2.5 Hz, 1H), 8.16 (dd, J = 8.8, 0.8 Hz, 1H), 7.92 (dd, J = 2.8, 1.8 Hz, 1H), 6.60 (s, 1H), 4.99 (q, J = 8.9 Hz, 2H), 2.66-2.54 (m, 1H), 1.62 (s, 6H), 0.98-0.81 (m, 4H). |
| T115 | 2-(2-(cyclopropanesulfonamido)thiazol-4-yl)-N-(5'-(difluoromethoxy)-[3,3'-bipyridin]-6-yl)-2-methylpropanamide | Method 1b using INTB37 and INTA35, [UPLC acidic], 510, (1.2) | 12.57 (s, 1H), 10.08 (s, 1H), 8.87 (d, J = 1.9 Hz, 1H), 8.80 (d, J = 2.5 Hz, 1H), 8.50 (d, J = 2.6 Hz, 1H), 8.27 (dd, J = 8.7, 2.6 Hz, 1H), 8.15 (dd, J = 8.8, 0.8 Hz, 1H), 8.07-8.03 (m, 1H), 7.42 (t, J = 73.4 Hz, 1H), 6.57 (s, 1H), 2.60-2.56 (m, 1H), 1.60 (s, 6H), 0.92-0.87 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T116 | N-([2,3'-bipyridin]-5-yl)-2-(2-(cyclopropanesulfonamido)thiazol-4-yl)-2-methylpropanamide | Method 1b using INTB37, [UPLC acidic], 444, (0.7) | 12.57 (s, 1H), 9.67 (s, 1H), 9.24 (dd, J = 2.5, 0.9 Hz, 1H), 8.92 (d, J = 2.5 Hz, 1H), 8.60 (dd, J = 4.8, 1.6 Hz, 1H), 8.41 (dt, J = 8.0, 1.9 Hz, 1H), 8.18 (dd, J = 8.7, 2.5 Hz, 1H), 8.06 (d, J = 8.7 Hz, 1H), 7.50 (ddd, J = 8.0, 4.8, 0.9 Hz, 1H), 6.60 (s, 1H), 2.66-2.55 (m, 1H), 1.59 (s, 6H), 0.96-0.85 (m, 4H). |
| T117 | 2-(2-(cyclopropanesulfonamido)thiazol-4-yl)-2-methyl-N-(6-(pyrimidin-5-yl)pyridin-3-yl)propanamide | Method 1b using INTB37, [UPLC acidic], 445, (0.89) | 12.58 (s, 1H), 9.71 (s, 1H), 9.40 (s, 2H), 9.20 (s, 1H), 8.95 (d, J = 2.5 Hz, 1H), 8.20 (dd, J = 8.6, 2.5 Hz, 1H), 8.13 (d, J = 8.6 Hz, 1H), 6.58 (s, 1H), 2.59 (s, 1H), 1.58 (s, 6H), 0.93-0.85 (m, 4H). |
| T118 | 2-(2-(cyclopropanesulfonamido)thiazol-4-yl)-N-(4-(5-(difluoromethoxy)pyridin-3-yl)phenyl)-2-methylpropanamide | Method 1b using INTB37 and INTA25, [UPLC acidic], 509.3, (1.24) | 12.58 (s, 1H), 9.45 (s, 1H), 8.81 (d, J = 1.9 Hz, 1H), 8.45 (d, J = 2.6 Hz, 1H), 7.94 (dd, J = 2.3 Hz, 1H), 7.78 (s, 4H), 7.43 (t, J = 73.5 Hz, 1H), 6.55 (s, 1H), 2.62-2.57 (m, 1H), 1.58 (s, 6H), 0.94-0.87 (m, 4H). |
| T119 | 2-(2-(cyclopropanesulfonamido)thiazol-4-yl)-2-ethyl-N-(4-(6-methoxypyrazin-2-yl)phenyl)butanamide | Method 1b using INTB41 and INTA2, [UPLC acidic], 502, (1.4) | 12.50 (s, 1H), 9.42 (s, 1H), 8.79 (s, 1H), 8.22 (s, 1H), 8.16-8.08 (m, 2H), 7.84-7.75 (m, 2H), 6.63 (s, 1H), 4.02 (s, 3H), 2.61-2.56 (m, 1H), 2.11-1.92 (m, 4H), 0.94-0.86 (m, 4H), 0.74 (t, J = 7.3 Hz, 6H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T120 | N-(4-(5-chloropyridin-3-yl)phenyl)-2-(2-(cyclopropanesulfonamido)thiazol-4-yl)-2-ethylbutanamide | Method 1b using INTB41 and INTA18, [HPLC basic], 506, (1.9) | 12.49 (s, 1H), 9.38 (s, 1H), 8.87 (d, J = 2.0 Hz, 1H), 8.59 (d, J = 2.3 Hz, 1H), 8.24 (dd, J = 2.2 Hz, 1H), 7.78 (s, 4H), 6.63 (s, 1H), 2.63-2.54 (m, 1H), 2.11-1.91 (m, 4H), 0.97-0.86 (m, 4H), 0.74 (t, J = 7.4 Hz, 6H). |
| T121 | 2-(2-(cyclopropanesulfonamido)thiazol-4-yl)-2-ethyl-N-(2-fluoro-4-(pyridiin-3-yl)phenyl)butanamide | Method 1b using INTB41, [HPLC basic], 489, (1.7) | 12.46 (s, 1H), 9.21 (s (br), 1H), 8.95 (d, J = 2.4 Hz, 1H), 8.64-8.56 (m, 1H), 8.13 (d, J = 8.1 Hz, 1H), 7.71 (d, J = 11.7 Hz, 1H), 7.66-7.56 (m, 2H), 7.50 (dd, J = 8.0, 4.8 Hz, 1H), 6.68 (s, 1H), 2.64-2.54 (m, 1H), 2.07-1.94 (m, 4H), 0.96-0.84 (m, 4H), 0.77 (t, J = 7.3 Hz, 6H). |
| T122 | 2-(2-(cyclopropanesulfonamido)thiazol-4-yl)-2-ethyl-N-(4-(pyrazin-2-yl)phenyl)butanamide | Method 1b using INTB41, [HPLC acidic], 472, (1.88) | 12.50 (s, 1H), 9.42 (s, 1H), 9.23 (d, J = 1.5 Hz, 1H), 8.68 (dd, J = 2.5, 1.5 Hz, 1H), 8.57 (d, J = 2.5 Hz, 1H), 8.18-8.08 (m, 2H), 7.86-7.76 (m, 2H), 6.64 (s, 1H), 2.64-2.54 (m, 1H), 2.11-1.93 (m, 4H), 0.96-0.85 (m, 4H), 0.74 (t, J = 7.3 Hz, 6H). |
| T123 | 2-(2-(cyclopropanesulfonamido)thiazol-4-yl)-2-ethyl-N-(4-(6-propoxypyrazin-2-yl)phenyl)butanamide | Method 1b using INTB41 and INTA42, [HPLC acidic], 530, (2.44) | 12.49 (s, 1H), 9.41 (s, 1H), 8.77 (s, 1H), 8.19 (s, 1H), 8.17-8.02 (m, 2H), 7.84-7.70 (m, 2H), 6.62 (s, 1H), 4.38 (t, J = 6.6 Hz, 2H), 2.62-2.54 (m, 1H), 2.01 (hept, J = 7.2 Hz, 4H), 1.80 (h, J = 7.1 Hz, 2H), 1.01 (t, J = 7.4 Hz, 3H), 0.89 (d, J = 8.2 Hz, 4H), 0.73 (t, J = 7.4 Hz, 6H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | ¹H NMR Chemical Shift Data (DMSO-d6 unless stated) |
|---|---|---|---|
| T124 | 2-(2-(cyclopropanesulfonamido)thiazol-4-yl)-N-(2-fluoro-4-(6-(trifluoromethyl)pyrazin-2-yl)phenyl)-2-methylpropanamide | Method 1b using INTB37 and INTA48, [HPLC basic], 530, (1.93) | 12.60 (s, 1H), 9.66 (s, 1H), 9.39 (s, 1H), 9.16 (s, 1H), 8.13 (dd, J = 11.7, 2.0 Hz, 1H), 8.08 (dd, J = 8.4, 2.0 Hz, 1H), 7.86 (s, 1H), 6.60 (s, 1H), 2.64-2.54 (m, 1H), 1.59 (s, 6H), 0.99-0.77 (m, 4H). |
| T125 | 2-(2-(cyclopropanesulfonamido)thiazol-4-yl)-N-(4-(5-ethoxypyridin-3-yl)-2-fluorophenyl)-2-methylpropanamide | Method 1b using INTB37 and INTA28, [HPLC basic], 505, (1.75) | 12.57 (s, 1H), 9.29 (s, 1H), 8.52 (d, J = 1.9 Hz, 1H), 8.28 (d, J = 2.7 Hz, 1H), 7.82-7.51 (m, 4H), 6.57 (s, 1H), 4.21 (q, J = 7.0 Hz, 2H), 2.61-2.53 (m, 1H), 1.57 (s, 6H), 1.38 (t, J = 7.0 Hz, 3H), 0.95-0.86 (m, 4H). |
| T126 | 2-(2-(cyclopropanesulfonamido)thiazol-4-yl)-N-(2-fluoro-4-(5-fluoropyridin-3-yl)phenyl)-2-methylpropanamide | Method 1b using INTB37 and INTA29, [HPLC basic], 479, (1.65) | 12.59 (s, 1H), 9.27 (s, 1H), 8.87 (t, J = 1.9 Hz, 1H), 8.59 (d, J = 2.7 Hz, 1H), 8.18-8.12 (m, 1H), 7.85-7.78 (m, 1H), 7.68 (s, 2H), 6.61 (s, 1H), 2.66-2.55 (m, 1H), 1.58 (s, 6H), 0.94-0.88 (m, 4H). |
| T127 | 2-(2-(cyclopropanesulfonamido)thiazol-4-yl)-2-methyl-N-(4-(6-(2,2,2-trifluoroethoxy)pyrazin-2-yl)phenyl)propanamide | Method 1b using INTB37 and INTA53, [HPLC basic], 542, (1.93) | 12.59 (s, 1H), 9.52 (s, 1H), 8.95 (s, 1H), 8.39 (s, 1H), 8.25-8.11 (m, 2H), 7.88-7.74 (m, 2H), 6.55 (s, 1H), 5.20 (q, J = 9.0 Hz, 2H), 2.64-2.55 (m, 1H), 1.59 (s, 6H), 0.94-0.83 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | ¹H NMR Chemical Shift Data (DMSO-d6 unless stated) |
|---|---|---|---|
| T128 | N-(4-(5-chloropyridin-3-yl)-2-fluorophenyl)-2-(2-(cyclopropanesulfonamido)thiazol-4-yl)-2-methylpropanamide | Method 1b using INTB37 and INTA27, [HPLC acidic], 495, (2.03) | 12.60 (s, 1H), 9.25 (s, 1H), 8.93 (d, J = 2.0 Hz, 1H), 8.64 (d, J = 2.3 Hz, 1H), 8.33 (t, J = 2.2 Hz, 1H), 7.89-7.76 (m, 1H), 7.68 (s, 2H), 6.60 (s, 1H), 2.63-2.56 (m, 1H), 1.58 (s, 6H), 1.01-0.81 (m, 4H). |
| T129 | N-(4-(5-cyanopyridin-3-yl)-2-fluorophenyl)-2-(2-(cyclopropanesulfonamido)thiazol-4-yl)-2-methylpropanamide | Method 1b using INTB37 and INTA26, [HPLC acidic], 486, (1.85) | 12.60 (s, 1H), 9.28 (s, 1H), 9.26 (d, J = 2.3 Hz, 1H), 9.02 (d, J = 1.9 Hz, 1H), 8.73 (t, J = 2.1 Hz, 1H), 7.91-7.82 (m, 1H), 7.71 (s, 2H), 6.60 (s, 1H), 2.65-2.57 (m, 1H), 1.58 (s, 6H), 1.06-0.86 (m, 4H). |
| T130 | 1-(2-(cyclopropanesulfonamido)thiazol-4-yl)-N-(4-(6-methoxypyrazin-2-yl)phenyl)cyclopentane-1-carboxamide | Method 1b using INTB69 and INTA2, [HPLC acidic], 500, (2.32) | 12.57 (s, 1H), 9.51 (s, 1H), 8.79 (s, 1H), 8.22 (s, 1H), 8.16-8.09 (m, 2H), 7.82-7.75 (m, 2H), 6.64 (s, 1H), 4.02 (s, 3H), 2.64-2.54 (m, 1H), 2.45-2.35 (m, 2H), 2.13-2.04 (m, 2H), 1.75-1.61 (m, 4H), 0.96-0.84 (m, 4H). |
| T131 | 1-(2-(cyclopropanesulfonamido)thiazol-4-yl)-N-(2-fluoro-4-(6-(2,2,2-trifluoroethoxy)pyrazin-2-yl)phenyl)-2-methylpropanamide | Method 1b using INTB37 and INTA52, [UPLC basic], 560, (1.27) | 12.60 (s, 1H), 9.30 (s, 1H), 9.02 (s, 1H), 8.45 (s, 1H), 8.15 (dd, J = 12.0, 1.9 Hz, 1H), 8.06 (dd, J = 8.5, 1.9 Hz, 1H), 7.75 (s, 1H), 6.60 (s, 1H), 5.23 (q, J = 9.0 Hz, 2H), 2.64-2.54 (m, 1H), 1.59 (s, 6H), 0.96-0.83 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
| --- | --- | --- | --- |
| T132 | 2-(2-(cyclopropanesulfonamido)thiazol-4-yl)-N-(2-fluoro-4-(5-(2,2,2-trifluoroethoxy)pyridin-3-yl)phenyl)-2-methylpropanamide | Method 1b using INTB37 and INTA30, [HPLC acidic], 559, (2.03) | 12.58 (s, 1H), 9.24 (s, 1H), 8.66 (d, J = 1.8 Hz, 1H), 8.40 (d, J = 2.8 Hz, 1H), 7.88 (dd, J = 2.8, 1.9 Hz, 1H), 7.83-7.76 (m, 1H), 7.66 (s, 2H), 6.60 (s, 1H), 4.98 (q, J = 8.9 Hz, 2H), 2.65-2.54 (m, 1H), 1.58 (s, 6H), 0.95-0.84 (m, 4H). |
| T133 | 2-(2-(cyclopropanesulfonamido)thiazol-4-yl)-N-(2-fluoro-4-(5-(trifluoromethyl)pyridin-3-yl)phenyl)-2-methylpropanamide | Method 1b using INTB37 and INTA70, [HPLC acidic], 529, (2.08) | 12.61 (s, 1H), 9.27 (d, J = 2.2 Hz, 2H), 9.05-8.90 (m, 1H), 8.59-8.49 (m, 1H), 7.91 (dd, J = 12.0, 1.8 Hz, 1H), 7.75 (dd, J = 8.4, 2.0 Hz, 1H), 7.73-7.64 (m, 1H), 6.61 (s, 1H), 2.65-2.55 (m, 1H), 1.59 (s, 6H), 0.96-0.82 (m, 4H). |
| T134 | 2-(2-(cyclopropanesulfonamido)thiazol-4-yl)-N-(4-(6-ethoxypyrazin-2-yl)-2-fluorophenyl)-2-methylpropanamide | Method 1b using INTB37 and INTA47, [HPLC acidic], 506, (2.11) | 12.61 (s, 1H), 9.28 (s, 1H), 8.86 (s, 1H), 8.26 (s, 1H), 8.12-7.94 (m, 2H), 7.72 (s, 1H), 6.61 (s, 1H), 4.49 (q, J = 7.1 Hz, 2H), 2.59 (s, 1H), 1.59 (s, 6H), 1.41 (t, J = 7.0 Hz, 3H), 0.99-0.84 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T135 | 2-(2-(cyclopropanesulfonamido)thiazol-4-yl)-2-methyl-N-(4-(5-(2,2,2-trifluoroethoxy)pyridin-3-yl)phenyl)propanamide | Method 1b using INTB37 and INTA31, [HPLC acidic], 541, (1.97) | 12.56 (s, 1H), 9.45 (s, 1H), 8.61 (d, J = 1.8 Hz, 1H), 8.36 (d, J = 2.7 Hz, 1H), 7.81 (dd, J = 2.8, 1.9 Hz, 1H), 7.78 (d, J = 1.0 Hz, 4H), 6.57 (s, 1H), 4.98 (q, J = 8.9 Hz, 2H), 2.66-2.55 (m, 1H), 1.59 (s, 6H), 0.96-0.82 (m, 4H). |
| T136 | 2-(2-(cyclopropanesulfonamido)thiazol-4-yl)-N-(4-(6-ethynylpyrazin-2-yl)phenyl)-2-methylpropanamide | Method 1b using INTB37 and INTA75, [UPLC acidic], 468, (1.85) | 12.59 (s, 1H), 9.53 (s, 1H), 9.24 (s, 1H), 8.70 (s, 1H), 8.19-8.06 (m, 2H), 7.90-7.75 (m, 2H), 6.56 (s, 1H), 4.69 (s, 1H), 2.59 (s, 1H), 1.59 (s, 6H), 1.01-0.81 (m, 4H). |
| T137 | 2-(2-(cyclopropanesulfonamido)thiazol-4-yl)-N-(4-(6-ethoxypyrazin-2-yl)-2-methylphenyl)-2-methylpropanamide | Method 1b using INTB37 and INTA51, [HPLC acidic], 502, (1.8) | 12.62 (s, 1H), 8.96 (s, 1H), 8.80 (s, 1H), 8.21 (s, 1H), 8.01 (d, J = 2.1 Hz, 1H), 7.96 (dd, J = 8.3, 2.1 Hz, 1H), 7.44 (d, J = 8.3 Hz, 1H), 6.62 (s, 1H), 4.49 (q, J = 7.0 Hz, 2H), 2.63-2.54 (m, 1H), 2.25 (s, 3H), 1.60 (s, 6H), 1.41 (t, J = 7.0 Hz, 3H), 0.96-0.87 (m, 4H). |
| T138 | N-(4-(6-chloropyrazin-2-yl)-2-methylphenyl)-2-(2-(cyclopropanesulfonamido)thiazol-4-yl)-2-methylpropanamide | Method 1b using INTB37 and INTA49, [HPLC acidic], 493, (1.99) | 12.61 (s, 1H), 9.28 (s, 1H), 8.99 (s, 1H), 8.73 (s, 1H), 8.05-8.01 (m, 1H), 7.98 (dd, J = 8.4, 2.2 Hz, 1H), 7.51 (s, 1H), 6.62 (s, 1H), 2.63-2.54 (m, 1H), 2.26 (s, 3H), 1.59 (s, 6H), 0.96-0.88 (m, 4H). |

TABLE 15-continued

*Preparation methods and characterisation of Examples T23-T322, T422-T443 and T445-T465. Where no INTA number is given, the aniline is commercially available.*

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T139 | 2-(2-(cyclopropanesulfonamido)thiazol-4-yl)-N-(4-(5-(difluoromethoxy)pyridin-3-yl)-2-fluorophenyl)-2-methylpropanamide | Method 1b using INTB37 and INTA24, [UPLC acidic], 527, (1.27) | 12.60 (s, 1H), 9.24 (s, 1H), 8.86 (d, J = 1.9 Hz, 1H), 8.49 (d, J = 2.6 Hz, 1H), 8.04-7.99 (m, 1H), 7.83-7.76 (m, 1H), 7.68-7.64 (m, 2H), 7.43 (t, J = 73.4 Hz, 1H), 6.59 (s, 1H), 2.60-2.56 (m, 1H), 1.57 (s, 6H), 0.93-0.87 (m, 4H). |
| T140 | 2-(2-(cyclopropanesulfonamido)thiazol-4-yl)-2-methyl-N-(5-(pyrazin-2-yl)pyridin-2-yl)propanamide | Method 1b using INTB37, [UPLC acidic], 445, (1) | 12.58 (s, 1H), 10.14 (s, 1H), 9.33 (d, J = 1.6 Hz, 1H), 9.12 (d, J = 2.3 Hz, 1H), 8.74 (dd, J = 2.5, 1.5 Hz, 1H), 8.64 (d, J = 2.5 Hz, 1H), 8.56 (dd, J = 8.8, 2.5 Hz, 1H), 8.21 (dd, J = 8.8, 0.8 Hz, 1H), 6.59 (s, 1H), 2.66-2.56 (m, 1H), 1.62 (s, 6H), 1.05-0.79 (m, 4H). |
| T141 | N-(5-(6-cyclobutoxypyrazin-2-yl)pyridin-2-yl)-2-(2-(cyclopropanesulfonamido)thiazol-4-yl)-2-methylpropanamide | Method 1b using INTB37 and INTA55, [HPLC basic], 515, (2) | 12.59 (s, 1H), 10.09 (s, 1H), 9.07 (d, J = 2.4 Hz, 1H), 8.87 (s, 1H), 8.51 (dd, J = 8.8, 2.4 Hz, 1H), 8.24 (s, 1H), 8.19 (dd, J = 8.8, 0.8 Hz, 1H), 6.59 (s, 1H), 5.32-5.22 (m, 1H), 2.66-2.50 (m, 1H), 2.23-2.10 (m, 2H), 1.92-1.66 (m, 2H), 1.62 (s, 6H), 0.95-0.80 (m, 6H). |
| T142 | 2-(2-(cyclopropanesulfonamido)thiazol-4-yl)-N-(5-(6-cyclopropoxypyrazin-2-yl)pyridin-2-yl)-2-methylpropanamide | Method 1b using INTB37 and INTA56, [HPLC basic], 501, (1.8) | 12.59 (s, 1H), 10.11 (s, 1H), 9.12 (d, J = 2.4 Hz, 1H), 8.94 (s, 1H), 8.55 (dd, J = 8.8, 2.5 Hz, 1H), 8.32 (s, 1H), 8.19 (dd, J = 8.8, 0.8 Hz, 1H), 6.59 (s, 1H), 4.43 (tt, J = 6.3, 3.0 Hz, 1H), 2.65-2.54 (m, 1H), 1.62 (s, 6H), 0.95-0.87 (m, 9H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T143 | 2-(2-(cyclopropanesulfonamido)thiazol-4-yl)-N-(5-(6-isopropoxypyrazin-2-yl)pyridin-2-yl)-2-methylpropanamide | Method 1b using INTB37 and INTA71, [HPLC basic], 503, (1.9) | 12.59 (s, 1H), 10.10 (s, 1H), 9.07 (t, J = 1.5 Hz, 1H), 8.84 (s, 1H), 8.51 (dd, J = 8.8, 2.5 Hz, 1H), 8.21 (d, J = 0.5 Hz, 1H), 8.19 (dd, J = 8.8, 0.8 Hz, 1H), 6.59 (s, 1H), 5.41 (hept, J = 6.2 Hz, 1H), 2.60 (s, 1H), 1.62 (s, 6H), 1.39 (d, J = 6.1 Hz, 6H), 0.96-0.85 (m, 4H). |
| T144 | N-([3,3'-bipyridin]-6-yl)-2-(2-(cyclopropanesulfonamido)thiazol-4-yl)-2-ethylbutanamide | Method 1b using INTB41, [HPLC basic], 472, (1.69) | 12.45 (s, 1H), 9.88 (s, 1H), 8.95 (dd, J = 2.4, 0.9 Hz, 1H), 8.73 (dd, J = 2.4, 0.9 Hz, 1H), 8.60 (dd, J = 4.8, 1.6 Hz, 1H), 8.29-8.06 (m, 3H), 7.51 (ddd, J = 8.0, 4.8, 0.9 Hz, 1H), 6.67 (s, 1H), 2.65-2.56 (m, 1H), 2.18-1.95 (m, 4H), 0.94-0.87 (m, 4H), 0.74 (t, J = 7.4 Hz, 6H). |
| T145 | 2-(2-(cyclopropanesulfonamido)thiazol-4-yl)-N-(5'-ethoxy-[3,3'-bipyridin]-6-yl)-2-ethylbutanamide | Method 1b using INTB41 and INTA32, [HPLC basic], 516, (1.85) | 12.47 (s, 1H), 9.93 (s, 1H), 8.75 (dd, J = 2.5, 0.8 Hz, 1H), 8.55 (d, J = 1.9 Hz, 1H), 8.32 (d, J= 2.7 Hz, 1H), 8.24 (dd, J = 8.7, 2.5 Hz, 1H), 8.16 (dd, J = 8.7, 0.8 Hz, 1H), 7.73 (t, J = 2.3 Hz, 1H), 6.67 (s, 1H), 4.22 (q, J = 7.0 Hz, 2H), 2.65-2.56 (m, 1H), 2.17-1.95 (m, 4H), 1.38 (t, J = 7.0 Hz, 3H), 0.95-0.85 (m, 4H), 0.73 (t, J = 7.4 Hz, 6H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T146 | 2-(2-(cyclopropanesulfonamido)thiazol-4-yl)-2-methyl-N-(5'-propoxy-[3,3'-bipyridin]-6-yl)propanamide | Method 1b using INTB37 and INTA112, [HPLC basic], 502, (1.81) | 12.57 (s, 1H), 10.06 (s, 1H), 8.77 (dd, J = 2.5, 0.8 Hz, 1H), 8.54 (d, J = 1.8 Hz, 1H), 8.30 (d, J = 2.7 Hz, 1H), 8.24 (d, J = 2.6 Hz, 1H), 8.14 (dd, J = 8.7, 0.8 Hz, 1H), 7.71 (dd, J = 2.8, 1.9 Hz, 1H), 6.60 (s, 1H), 4.12 (t, J = 6.5 Hz, 2H), 2.67-2.55 (m, 1H), 1.86-1.71 (m, 2H), 1.61 (s, 6H), 1.01 (t, J= 7.4 Hz, 3H), 0.96-0.89 (m, 4H). |
| T147 | 2-(2-(cyclopropanesulfonamido)thiazol-4-yl)-2-ethyl-N-(5-(6-(trifluoromethyl)pyrazin-2-yl)pyridin-2-yl)butanamide | Method 1b using INTB41 and INTA3, [HPLC basic], 541, (2.05) | 12.50 (s, 1H), 10.14 (s, 1H), 9.68 (s, 1H), 9.21-9.11 (m, 2H), 8.60 (dd, J = 8.9, 2.5 Hz, 1H), 8.30-8.24 (m, 1H), 6.66 (s, 1H), 2.63-2.55 (m, 1H), 2.19-1.92 (m, 4H), 0.95-0.87 (m, 4H), 0.74 (t, J = 7.4 Hz, 6H). |
| T148 | N-([3,3'-bipyridin]-6-yl)-2-(2-(cyclopropanesulfonamido)thiazol-4-yl)-2-methylpropanamide | Method 1b using INTB37, [HPLC acidic], 444, (0.76) | 12.55 (s, 1H), 10.00 (s, 1H), 8.98-8.92 (m, 1H), 8.77-8.71 (m, 1H), 8.59 (dd, J = 4.8, 1.6 Hz, 1H), 8.22 (dd, J = 8.8, 2.5 Hz, 1H), 8.19-8.11 (m, 2H), 7.51 (ddd, J = 8.0, 4.8, 0.9 Hz, 1H), 6.60 (s, 1H), 2.66-2.54 (m, 1H), 1.61 (s, 6H), 0.95-0.84 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T149 | 2-(2-(cyclopropanesulfonamido)thiazol-4-yl)-N-(2-methoxy-4-(pyridin-3-yl)phenyl)-2-methylpropanamide | Method 1b using INTB37 and INTA, [HPLC basic], 473, (1.6) | 12.64 (s, 1H), 8.94 (dd, J = 2.4, 0.9 Hz, 1H), 8.56 (dd, J = 4.8, 1.6 Hz, 1H), 8.42 (s, 1H), 8.11 (ddd, J = 8.0, 2.5, 1.6 Hz, 1H), 8.05 (d, J = 8.3 Hz, 1H), 7.48 (ddd, J = 8.0, 4.7, 0.9 Hz, 1H), 7.40 (d, J = 2.0 Hz, 1H), 7.33 (dd, J = 8.3, 2.0 Hz, 1H), 6.76 (s, 1H), 3.92 (s, 3H), 2.67-2.56 (m, 1H), 1.57 (s, 6H), 0.96-0.89 (m, 4H). |
| T150 | 2-(2-(cyclopropanesulfonamido)thiazol-4-yl)-N-(3-methoxy-4-(pyridin-3-yl)phenyl)-2-methylpropanamide | Method 1b using INTB37 and INTA16, [HPLC basic], 473, (1.79) | 12.58 (s, 1H), 9.45 (s, 1H), 8.67 (d, J = 2.1 Hz, 1H), 8.49 (d, J = 6.7 Hz, 1H), 7.88 (ddd, J = 7.9, 1.9 Hz, 1H), 7.55 (d, J = 1.9 Hz, 1H), 7.45-7.37 (m, 2H), 7.32 (d, J = 8.3 Hz, 1H), 6.57 (s, 1H), 3.78 (s, 3H), 2.68-2.55 (m, 1H), 1.59 (s, 6H), 0.91 (m, 4H). |
| T151 | 2-(2-(cyclopropanesulfonamido)thiazol-4-yl)-N-(3-fluoro-4-(pyridin-3-yl)phenyl)-2-methylpropanamide | Method 1b using INTB37, [HPLC basic], 461, (1.9) | 12.55 (s (br), 1H), 9.66 (s (br), 1H), 8.75 (m, 1H), 8.58 (dd, J = 4.8, 1.6 Hz, 1H), 7.96 (m, 1H), 7.80-7.74 (m, 1H), 7.61-7.55 (m, 2H), 7.50 (ddd, J = 8.0, 4.8, 0.9 Hz, 1H), 6.56 (s, 1H), 2.66-2.55 (m, 1H), 1.57 (s, 6H), 0.95-0.86 (m, 4H). |
| T152 | N-(3-cyano-4-(pyridin-3-yl)phenyl)-2-(2-(cyclopropanesulfonamido)thiazol-4-yl)-2-methylpropanamide | Method 1b using INTB37 and INTA15, [HPLC basic], 468, (1.88) | 12.56 (s (br), 1H), 9.74 (s (br), 1H), 8.78 (dd, J = 2.4, 0.9 Hz, 1H), 8.68 (dd, J = 4.8, 1.6 Hz, 1H), 8.25 (d, J = 2.2 Hz, 1H), 8.07-7.99 (m, 2H), 7.69 (d, J = 8.6 Hz, 1H), 7.57 (ddd, J = 7.9, 4.8, 0.9 Hz, 1H), 6.61 (s, 1H), 2.66-2.55 (m, 1H), 1.58 (s, 6H), 0.96-0.86 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T153 | N-(3-chloro-4-(pyridin-3-yl)phenyl)-2-(2-(cyclopropanesulfonamido)thiazol-4-yl)-2-methylpropanamide | Method 1b using INTB37 and INTA17, [HPLC basic], 477, (1.04) | 10.87 (s (br), 1H), 8.62 (dd, J = 2.4, 0.9 Hz, 1H), 8.59 (dd, J = 4.8, 1.6 Hz, 1H), 8.08 (m, 1H), 7.87 (ddd, J = 7.9, 2.4, 1.6 Hz, 1H), 7.77 (dd, J = 8.4, 2.1 Hz, 1H), 7.49 (ddd, J = 7.9, 4.8, 0.9 Hz, 1H), 7.41 (d, J = 8.4, 1H), 6.32 (s, 1H), 2.64-2.59 (m, 1H), 1.50 (s, 6H), 0.94-0.85 (m, 2H), 0.81-0.70 (m, 2H). |
| T154 | N-(4-(6-cyanopyrazin-2-yl)phenyl)-2-(2-(cyclopropanesulfonamido)thiazol-4-yl)-2-methylpropanamide | Method 1b using INTB37 and INTA44, [HPLC basic], 469, (1.7) | 12.56 (s, 1H), 10.07-9.57 (bs, 1H), 9.55 (s, H), 9.11 (s, 1H), 8.28-8.10 (m, 2H), 8.01-7.77 (m, 2H), 6.52 (s, 1H), 2.65-2.57 (m, 1H), 1.56 (s, 6H), 0.98-0.65 (m, 4H). |
| T155 | N-(4-(6-chloropyrazin-2-yl)phenyl)-2-(2-(cyclopropanesulfonamido)thiazol-4-yl)-2-methylpropanamide | Method 1b using INTB37 and INTA43, [HPLC basic], 478, (1.8) | 12.56 (s, 1H), 9.26 (s, 1H), 8.69 (s, 1H), 8.22-8.04 (m, 2H), 7.94-7.75 (m, 2H), 6.53 (s, 1H), 2.71-2.55 (m, 1H), 1.57 (s, 7H), 0.98-0.79 (m, 4H). |
| T156 | 2-(2-(cyclopropanesulfonamido)thiazol-4-yl)-2-ethyl-N-(4-(5-fluoropyridin-3-yl)phenyl)butanamide | Method 1b using INTB41 and INTA13, [HPLC basic], 489, (1.8) | 12.49 (s, 1H), 9.38 (s, 1H), 8.81 (dd, J = 1.9 Hz, 1H), 8.54 (d, J = 2.7 Hz, 1H), 8.05 (ddd, J = 10.5, 2.8, 1.8 Hz, 1H), 7.78 (s, 4H), 6.63 (s (br), 1H), 2.64-2.65 (m, 1H), 2.11-1.93 (m, 4H), 0.95-0.85 (m, 4H), 0.74 (t, J = 7.4 Hz, 6H) |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T157 | 2-(2-(cyclopropanesulfonamido)thiazol-4-yl)-2-methyl-N-(4-(5-propoxypyridin-3-yl)phenyl)propanamide | Method 1b using INTB37, [HPLC basic], 501, (1.85) | 12.58 (s, 1H), 9.45 (s, 1H), 8.48 (d, J = 1.8 Hz, 1H), 8.24 (d, J = 2.7 Hz, 1H), 7.75 (s, 4H), 7.61 (dd, J = 2.7, 1.9 Hz, 1H), 6.56 (s, 1H), 4.10 (t, J = 6.5 Hz, 2H), 2.65-2.54 (m, 1H), 1.85-1.71 (m, 2H), 1.58 (s, 6H), 1.01 (t, J = 7.4 Hz, 3H), 0.95-0.86 (m, 4H). |
| T158 | 2-(2-(cyclopropanesulfonamido)thiazol-4-yl)-N-(4-(5-isopropoxypyridin-3-yl)phenyl)-2-methylpropanamide | Method 1b using INTB37 and INTA22, [HPLC basic], 501, (1.79) | 12.55 (s, 1H), 9.42 (s, 1H), 8.46 (d, J = 1.9 Hz, 1H), 8.21 (d, J = 2.7 Hz, 1H), 7.84-7.67 (m, 4H), 7.59 (dd, J = 2.3 Hz, 1H), 6.56 (s, 1H), 4.92-4.78 (m, 1H), 2.65-2.56 (m, 1H), 1.58 (s, 6H), 1.32 (d, J = 6.0 Hz, 6H), 0.96-0.87 (m, 4H). |
| T159 | 2-(2-(cyclopropanesulfonamido)thiazol-4-yl)-N-(2-fluoro-4-(5-isopropoxypyridin-3-yl)phenyl)-2-methylpropanamide | Method 1b using INTB37 and INTA23, [HPLC basic], 519, (1.82) | 12.58 (s, 1H), 9.22 (s, 1H), 8.51 (d, J = 1.9 Hz, 1H), 8.26 (d, J = 2.7 Hz, 1H), 7.81-7.71 (m, 1H), 7.69-7.66 (m, 1H), 7.65-7.59 (m, 2H), 6.62 (s, 1H), 4.93-4.82 (m, 1H), 2.64-2.56 (m, 1H), 1.59 (s, 6H), 1.32 (d, J = 6.0 Hz, 6H), 0.96-0.87 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T160 | N-(4-(6-chloropyrazin-2-yl)phenyl)-2-(2-(cyclopropanesulfonamido)thiazol-4-yl)-2-ethylbutanamide | Method 1b using INTB41 and INTA43, [HPLC basic], 507, (1.94) | 12.51 (s, 1H), 9.47 (s, 1H), 9.25 (s, 1H), 870 (s, 1H), 8.13 (d, J = 8.8 Hz, 2H), 7.88-7.76 (m, 2H), 6.64 (s, 1H), 2.64-2.54 (m, 1H), 2.15-1.90 (m, 4H), 0.95-0.84 (m, 4H), 0.74 (t, J= 7.4 Hz, 6H). |
| T161 | N-(4-(6-cyanopyrazin-2-yl)phenyl)-2-(2-(cyclopropanesulfonamido)thiazol-4-yl)-2-ethylbutanamide | Method 1b using INTB41 and INTA44, [HPLC basic], 497, (1.87) | 12.51 (s, 1H), 9.55 (s, 1H), 9.4 (s, 1H), 9.12 (s, 1H), 8.27-8.11 (m, 2H), 7.93-7.75 (m, 2H), 6.64 (s, 1H), 2.65-2.54 (m, 1H), 2.16-1.87 (m, 4H), 0.96-0.87 (m, 4H), 0.74 (t, J = 7.3 Hz, 6H). |
| T163 | 2-methyl-2-(2-(methylsulfonamido)thiazol-4-yl)-N-(4-(pyridin-3-yl)phenyl)propanamide | Method 1b using INTB37, [HPLC acidic], 417, (1.06) | 12.52 (s, 1H), 9.43 (s, 1H), 8.89 (dd, J = 2.4, 0.9 Hz, 1H), 8.53 (dd, J = 4.8, 1.6 Hz, 1H), 8.06 (ddd, J = 8.0, 2.4, 1.6 Hz, 1H), 7.80-7.67 (m, 4H), 7.46 (ddd, J = 8.1, 4.8, 0.9 Hz, 1H), 6.58 (s, 1H), 2.91 (s, 3H), 1.57 (s, 6H). |
| T164 | 2-(2-(cyclopropanesulfonamido)thiazol-4-yl)-N,2-dimethyl-N-(4-(pyridin-3-yl)phenyl)propanamide | Method 1b using INTB37 and INTA68, [HPLC acidic], 457, (0.74) | 12.53 (s, 1H), 8.85 (dd, J = 2.5, 0.8 Hz, 1H), 8.60 (dd, J = 4.8, 1.6 Hz, 1H), 8.03 (ddd, J = 8.0, 2.4, 1.6 Hz, 1H), 7.62-7.54 (m, 2H), 7.51 (ddd, J = 7.9, 4.8, 0.9 Hz, 1H), 7.23-7.15 (m, 2H), 5.77 (s, 1H), 3.15 (s, 3H), 2.66-2.55 (m, 1H), 1.42 (s, 6H), 0.92 (d, J = 6.3 Hz, 4H). |

| T# | Name/Structure (All examples containing chiral centres are racemates unless stated) | Synthesis Method, [LCMS Method], m/z (M + H)+, (Rt/min) | ¹H NMR Chemical Shift Data (DMSO-d6 unless stated) |
|---|---|---|---|
| T169 | 2-(cyclopropanesulfonamido)-N-(5-(6-(trifluoromethyl)pyrazin-2-yl)pyridin-2-yl)-5,6-dihydro-4H-cyclopenta[d]thiazole-4-carboxamide | Method 1c using INTB66 and INTA3, [HPLC acidic], 511, (1.3) | 12.52 (s, 1H), 11.08 (s, 1H), 9.67 (s, 1H), 9.21-9.14 (m, 2H), 8.60 (dd, J = 8.8, 2.5 Hz, 1H), 8.28 (d, J = 8.8 Hz, 1H), 4.18 (s, 1H), 2.86-2.64 (m, 3H), 2.60 (s, 2H), 0.94-0.89 (m, 4H). |
| T170 | 2-(2-(cyclopropanesulfonamido)thiazol-4-yl)-4-methoxy-N-(5-(pyrazin-2-yl)pyridin-2-yl)butanamide | Method 1c using INTB44 and comercially available aniline, [HPLC acidic], 475, (1.55) | 12.63 (s, 1H), 10.95 (s, 1H), 9.32 (d, J = 1.6 Hz, 1H), 9.12 (d, J = 2.4 Hz, 1H), 8.74 (dd, J = 2.6, 1.5 Hz, 1H), 8.64 (d, J = 2.5 Hz, 1H), 8.55 (dd, J = 8.8, 2.5 Hz, 1H), 8.24 (d, J = 8.8 Hz, 1H), 6.58 (s, 1H), 4.05-3.97 (m, 1H), 3.21 (s, 3H), 2.64-2.56 (m, 1H), 2.32-2.19 (m, 1H), 2.14-2.01 (m, 1H), 0.95-0.79 (m, 4H), CH2 at 3.3 obscured by residual water |
| T171 | 2-(2-(cyclopropanesulfonamido)thiazol-4-yl)-4-methoxy-N-(5'-methoxy-[3,3'-bipyridin]-6-yl)butanamide | Method 1c using INTB44 and INTA113, [HPLC acidic], 504, (1.45) | (Chloroform-d) 9.69 (s, 1H), 8.52 (d, J = 2.4 Hz, 1H), 8.45 (s, 1H), 8.39-8.33 (m, 1H), 8.26 (d, J = 8.7 Hz, 1H), 7.90 (dd, J = 8.7, 2.5 Hz, 1H), 7.41-7.35 (m, 1H), 6.42 (s, 1H), 4.21 (t, J = 7.5 Hz, 1H), 3.94 (s, 3H), 3.43 (tt, J = 6.4, 5.2, 2.4 Hz, 2H), 3.29 (s, 3H), 2.62 (tt, J = 8.1, 4.9 Hz, 1H), 2.44-2.31 (m, 1H), 2.09 (ddd, J = 14.4, 6.8, 5.3 Hz, 1H), 1.32-119 (m, 2H), 1.00-0.88 (m, 2H), N—H sulfonamide not observed. |

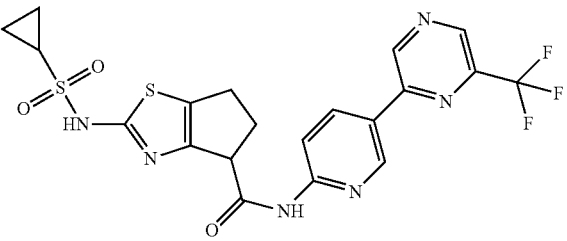

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T172 | 2-(2-(cyclopropanesulfonamido)thiazol-4-yl)-2-isopropoxy-N-(5-(6-(trifluoromethyl)pyrazin-2-yl)pyridin-2-yl)acetamide | Method 1c using INTB13 and INTA3, [UPLC acidic], 543, (1.43) | 9.29 (s, 1H), 9.25 (s, 1H), 9.04 (d, J = 2.3 Hz, 1H), 8.92 (s, 1H), 8.46 (dd, J = 8.8, 2.4 Hz, 1H), 8.36 (d, J = 8.7 Hz, 1H), 6.50 (d, J = 1.2 Hz, 1H), 5.13 (d, J = 1.3 Hz, 1H), 4.01-3.88 (m, 1H), 2.69-2.57 (m, 1H), 1.38 (d, J = 6.1 Hz, 3H), 1.35 (d, J = 6.1 Hz, 3H), 1.29-1.20 (m, 2H), 1.00-0.85 (m, 2H), N—H not observed. |
| T173 | 2-(2-(cyclopropanesulfonamido)thiazol-4-yl)-N-(5-(6-propoxypyrazin-2-yl)pyridin-2-yl)butanamide | Method 1c using INTB38 and INTA4, [HPLC basic], 503, (1.92) | 12.59 (s, 1H), 10.95 (s, 1H), 9.09 (dd, J = 2.4, 0.8 Hz, 1H), 8.86 (s, 1H), 8.52 (dd, J = 8.7, 2.4 Hz, 1H), 8.27 (s, 1H), 8.24 (d, J = 8.8 Hz, 1H), 6.56 (s, 1H), 4.40 (t, J = 6.6 Hz, 2H), 3.87-3.77 (m, 1H), 2.64-2.55 (m, 1H), 2.05-1.85 (m, 2H), 1.85-1.75 (m, 2H), 1.02 (t, J = 7.4 Hz, 3H), 0.94-0.86 (m, 7H). |
| T174 | 2-(2-(cyclopropanesulfonamido)thiazol-4-yl)-N-(5-(6-isopropoxypyrazin-2-yl)pyridin-2-yl)butanamide | Method 1c using INTB38 and INTA71, [HPLC acidic], 503, (1.41) | 12.59 (s, 1H), 10.93 (s, 1H), 9.07 (d, J = 2.4 Hz, 1H), 8.82 (s, 1H), 8.49 (dd, J = 8.8, 2.5 Hz, 1H), 8.23 (d, J = 8.9 Hz, 1H), 8.20 (s, 1H), 6.55 (s, 1H), 5.49-5.36 (m, 1H), 3.89-3.74 (m, 1H), 2.60 2.50 (m, 1H), 2.05-1.81 (m, 2H), 1.38 (d, J = 6.2 Hz, 6H), 0.95-0.80 (m, 7H). |
| T175 | 2-(2-(cyclopropanesulfonamido)thiazol-4-yl)-N-(5-(6-(trifluoromethyl)pyrazin-2-yl)pyridin-2-yl)butanamide | Method 1c using INTB38 and INTA3, [HPLC acidic], 513, (1.35) | 12.59 (s, 1H), 11.06 (s, 1H), 9.66 (s, 1H), 9.29-9.10 (m, 2H), 8.59 (dd, J = 8.8, 2.5 Hz, 1H), 8.29 (d, J = 8.8 Hz, 1H), 6.56 (s, 1H), 3.82 (s, 1H), 2.62-2.55 (m, 1H), 2.05-1.82 (m, 2H), 0.96-0.76 (m, 7H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | ¹H NMR Chemical Shift Data (DMSO-d6 unless stated) |
|---|---|---|---|
| T176 | 2-(2-(cyclopropanesulfonamido)thiazol-4-yl)-N-(5-(6-methoxypyrazin-2-yl)pyridin-2-yl)butanamide | Method 1c using INTB38 and INTA61, [HPLC acidic], 475, (1.21) | 12.60 (s, 1H), 10.95 (s, 1H), 9.12 (d, J = 2.4 Hz, 1H), 8.88 (s, 1H), 8.55 (dd, J = 8.8, 2.5 Hz, 1H), 8.29 (s, 1H), 8.24 (d, J = 8.8 Hz, 1H), 6.56 (s, 1H), 4.04 (s, 3H), 3.82 (s, 1H), 2.60-2.52 (m, 1H), 2.05-1.80 (m, 2H), 0.98-0.82 (m, 7H). |
| T177 | 2-(2-(cyclopropanesulfonamido)thiazol-4-yl)-N-(5-(6-ethoxypyrazin-2-yl)pyridin-2-yl)butanamide | Method 1c using INTB38 and INTA72, [UPLC acidic], 489, (1.32) | 12.59 (s, 1H), 10.94 (s, 1H), 9.13-9.04 (m, 1H), 8.85 (s, 1H), 8.51 (dd, J = 8.7, 2.4 Hz, 1H), 8.25 (s, 1H), 8.23 (d, J = 8.8 Hz, 1H), 6.55 (s, 1H), 4.49 (q, J = 7.0 Hz, 2H), 3.87-3.74 (m, 1H), 2.63-2.54 (m, 1H), 2.02-1.82 (m, 2H), 1.40 (t, J = 7.1 Hz, 3H), 0.96-0.75 (m, 7H). |
| T178 | N-(5-(6-cyanopyrazin-2-yl)pyridin-2-yl)-2-(2-(cyclopropanesulfonamido)thiazol-4-yl)butanamide | Method 1c using INTB38 and INTA63, [UPLC acidic], 470, (1.17) | 12.59 (s, 1H), 11.06 (s, 1H), 9.62 (s, 1H), 9.18 (s, 1H), 9.15 (dd, J = 2.5, 0.8 Hz, 1H), 8.58 (dd, J = 8.8, 2.5 Hz, 1H), 8.27 (d, J = 8.8 Hz, 1H), 6.56 (s, 1H), 3.81 (t, J = 7.8 Hz, 1H), 2.62-2.54 (m, 1H), 2.04-1.79 (m, 2H), 0.94-0.78 (m, 7H). |
| T179 | 2-(2-(cyclopropanesulfonamido)thiazol-4-yl)-N-(5'-fluoro-[3,3'-bipyridin]-6-yl)butanamide | Method 1c using INTB38 and INTA37, [HPLC acidic], 462, (1.78) | 12.58 (s, 1H), 10.90 (s, 1H), 8.87 (t, J = 1.9 Hz, 1H), 8.81 (dd, J = 2.5, 0.9 Hz, 1H), 8.59 (d, J = 2.7 Hz, 1H), 8.27 (dd, J = 8.7, 2.6 Hz, 1H), 8.23-8.12 (m, 2H), 6.55 (s, 1H), 3.80 (s, 1H), 2.64-2.54 (m, 1H), 2.04-1.82 (m, 2H), 0.96-0.79 (m, 7H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T180 | N-(5'-cyano-[3,3'-bipyridin]-6-yl)-2-(2-(cyclopropanesulfonamido)thiazol-4-yl)butanamide | Method 1c using INTB38 and INTA33, [HPLC acidic], 469, (1.75) | 12.60 (s, 1H), 10.94 (s, 1H), 9.26 (d, J = 2.3 Hz, 1H), 9.03 (d, J = 1.9 Hz, 1H), 8.85 (d, J = 2.5 Hz, 1H), 8.75 (t, J = 2.1 Hz, 1H), 8.31 (dd, J = 8.7, 2.6 Hz, 1H), 8.22 (d, J = 8.8 Hz, 1H), 6.55 (s, 1H), 3.80 (s, 1H), 2.64-2.55 (m, 1H), 2.06-1.85 (m, 2H), 0.96-0.71 (m, 7H). |
| T181 | 2-(2-(cyclopropanesulfonamido)thiazol-4-yl)-N-(5-phenylpyridin-2-yl)butanamide | Method 1c using INTB38, [UPLC acidic], 443, (1.36) | 12.58 (s, 1H), 10.80 (s, 1H), 8.67 (dd, J = 2.4, 0.9 Hz, 1H), 8.21-8.09 (m, 2H), 7.75-7.69 (m, 2H), 7.54-7.44 (m, 2H), 7.43-7.33 (m, 1H), 6.55 (s, 1H), 3.79 (t, J = 7.4 Hz, 1H), 2.63-2.53 (m, 1H), 2.05-1.79 (m, 2H), 0.95-0.79 (m, 7H). |
| T182 | 2-(2-(cyclopropanesulfonamido)thiazol-4-yl)-N-(5-(6-(2,2,2-trifluoroethoxy)pyrazin-2-yl)pyridin-2-yl)butanamide | Method 1c using INTB38 and INTA62, [UPLC acidic], 543, (1.39) | 12.60 (s, 1H), 10.,98 (s, 1H), 9.17 (dd, J = 2.4, 0.9 Hz, 1H), 9.03 (d, 1H), 8.61 (dd, J = 8.8, 2.4 Hz, 1H), 8.46 (d, J = 0.5 Hz, 1H), 8.25 (d, J = 8.7 Hz, 1H), 6.57 (s, 1H), 5.23 (q, J = 9.0 Hz, 2H), 3.87-3.80 (m, 1H), 2.64-2.56 (m, 1H), 2.03-1.86 (m, 2H), 095-0.88 (m, 7H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)$^+$, (Rt/min) | $^1$H NMR Chemical Shift Data (DMSO-d6 unless stated) |
|---|---|---|---|
| T183 | 2-(2-(cyclopropanesulfonamido)thiazol-4-yl)-N-(5-(6-ethoxypyrazin-2-yl)-3-fluoropyridin-2-yl)butanamide | Method 1c using INTB38 and INTA57, [UPLC acidic], 507, (1.24) | 12.63 (s, 1H), 10.72 (s, 1H), 9.04-9.00 (m, 1H), 8.93 (s, 1H), 8.46 (dd, J = 11.1, 2.0 Hz, 1H), 8.33 (s, 1H), 6.54 (s, 1H), 4.51 (q, J = 7.0 Hz, 2H), 3.79-3.72 (m, 1H), 2.63-2.56 (m, 1H), 2.03-1.83 (m, 2H), 1.41 (t, J = 7.0 Hz, 3H), 0.98-0.87 (m, 7H). |
| T184 | N-(5-(6-cyanopyrazin-2-yl)-3-fluoropyridin-2-yl)-2-(2-(cyclopropanesulfonamido)thiazol-4-yl)butanamide | Method 1c using INTB38 and INTA59, [UPLC acidic], 488, (1.09) | 12.63 (s, 1H), 10.82 (s, 1H), 9.67 (s, 1H), 9.25 (s, 1H), 9.08-9.04 (m, 1H), 8.54 (dd, J = 11.0, 2.0 Hz, 1H), 6.55 (s, 1H), 3.80-3.73 (m, 1H), 2.62-2.58 (m, 1H), 2.05-1.84 (m, 2H), 0.98-0.80 (m, 7H). |
| T185 | 2-(2-(cyclopropanesulfonamido)thiazol-4-yl)-N-(5'-(2,2,2-trifluoroethoxy)-[3,3'-bipyridin]-6-yl)butanamide | Method 1c using INTB38 and INTA36, [UPLC acidic], 542, (1.27) | 12.59 (s, 1H), 10.90 (s, 1H), 8.81 (d, J = 2.4 Hz, 1H), 8.67 (d, J = 1.8 Hz, 1H), 8.42 (d, J = 2.8 Hz, 1H), 8.30-8.23 (m, 1H), 8.24-8.18 (m, 1H), 7.94-7.89 (m, 1H), 6.56 (s, 1H), 4.99 (q, J = 8.9 Hz, 2H), 3.83-3.79 (m, 1H), 2.61-2.57 (m, 1H), 2.03-1.84 (m, 2H), 0.94-0.83 (m, 7H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T186 | 2-(2-(cyclopropanesulfonamido)thiazol-4-yl)-N-(5'-(difluoromethoxy)-[3,3'-bipyridin]-6-yl)butanamide | Method 1c using INTB38 and INTA35, [HPLC acidic], 510, (1.2) | 12.59 (s, 1H), 10.92 (s, 1H), 8.87 (d, J = 1.9 Hz, 1H), 8.81 (d, J = 2.5 Hz, 1H), 8.51 (d, J = 2.6 Hz, 1H), 8.30-8.24 (m, 1H), 8.24-8.19 (m, 1H), 8.08-8.03 (m, 1H), 7.44 (t, J = 73.4 Hz, 1H), 6.56 (s, 1H), 3.84-3.77 (m, 1H), 2.61-2.57 (m, 1H), 2.03-1.84 (m, 2H), 0.94-0.87 (m, 7H). |
| T187 | N-(5-(6-chloropyrazin-2-yl)pyridin-2-yl)-2-(2-(cyclopropanesulfonamido)thiazol-4-yl)butanamide | Method 1c using INTB38 and INTA64, [UPLC acidic], 479, (1.27) | 12.59 (s, 1H), 11.03 (s, 1H), 9.33 (s, 1H), 9.10 (dd, J = 2.4, 0.8 Hz, 1H), 8.77 (s, 1H), 8.53 (dd, J = 8.8, 2.5 Hz, 1H), 8.26 (d, J = 8.8 Hz, 1H), 6.55 (s, 1H), 3.86-3.74 (m, 1H), 2.61-2.55 (m, 1H), 2.04-1.81 (m, 2H), 0.94-0.81 (m, 7H). |
| T188 | 2-(2-(cyclopropanesulfonamido)thiazol-4-yl)-N-(2,3-difluoro-4-(pyridin-3-yl)phenyl)acetamide | Method 1c using INTB36 and INTA6, [HPLC basic], 451, (1.4) | 12.53 (s, 1H), 10.34 (s, 1H), 8.79 (q, J = 1.5, 0.9 Hz, 1H), 8.63 (dd, J = 4.8, 1.6 Hz, 1H), 8.02 (dq, J = 8.0, 1.7 Hz, 1H), 7.93-7.83 (m, 1H), 7.54 (ddd, J = 8.0, 4.8, 0.9 Hz, 1H), 7.43 (td, J = 8.5, 2.2 Hz, 1H), 6.58 (s, 1H), 3.77 (s, 2H), 2.64-2.54 (m, 1H), 0.98-0.86 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T189 | 2-(2-(cyclopropanesulfonamido)thiazol-4-yl)-N-(4-(6-ethoxypyrazin-2-yl)phenyl)butanamide | Method 1c using INTB38 and INTA38, [HPLC basic], 488, (1.83) | 12.64 (s, 1H), 10.40 (s, 1H), 8.78 (s, 1H), 8.19 (s, 1H), 8.16-8.08 (m, 2H), 7.80-7.74 (m, 2H), 6.56 (s, 1H), 4.48 (q, J = 7.1 Hz, 2H), 3.61 (t, J = 7.4 Hz, 1H), 2.65-2.55 (m, 1H), 2.01-1.85 (m, 2H), 1.40 (t, J = 7.0 Hz, 3H), 0.95-0.84 (m, 7H). |
| T190 | 2-(2-(cyclopropanesulfonamido)thiazol-4-yl)-4-methoxy-N-(4-(6-methoxypyrazin-2-yl)phenyl)butanamide | Method 1c using INTB44 and INTA2, [HPLC acidic], 504, (1.92) | 12.65 (s, 1H), 10.40 (s, 1H), 8.79 (s, 1H), 8.22 (s, 1H), 8.13 (d, J = 8.8 Hz, 2H), 7.79-7.64 (m, 2H), 6.55 (s, 1H), 4.01 (s, 3H), 3.83 (s, 1H), 3.22 (s, 3H), 2.62-2.50 (m, 1H), 2.27-2.00 (m, 2H), 0.97-0.79 (m, 4H), CH2 at 3.3 obscured by residual water. |
| T191 | 2-(2-(cyclopropanesulfonamido)thiazol-4-yl)-N-4-(5-fluoropyridin-3-yl)phenyl)-4-methoxybutanamide | Method 1c using INTB44 and INTA13, [HPLC acidic], 491, (1.82) | 12.65 (s, 1H), 10.36 (s, 1H), 8.80 (t, J = 1.8 Hz, 1H), 8.54 (d, J = 2.7 Hz, 1H), 8.10-8.00 (m, 1H), 7.86-7.66 (m, 4H), 6.55 (s, 1H), 3.82 (t, J = 7.6 Hz, 1H), 3.22 (s, 3H), 2.64-2.54 (m, 1H), 2.26-2.03 (m, 2H), 0.94-0.84 (m, 4H), CH2 at 3.3 obscured by residual water. |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T192 | 2-(2-(cyclopropanesulfonamido)thiazol-4-yl)-N-(4-(6-ethoxypyrazin-2-yl)phenyl)propanamide | Method 1c using INTB39 and INTA38, [HPLC acidic], 474, (1.73) | 12.62 (s, 1H), 10.34 (s, 1H), 8.77 (s, 1H), 8.18 (s, 1H), 8.14-8.05 (m, 2H), 7.82-7.71 (m, 2H), 6.52 (s, 1H), 4.47 (q, J = 7.0 Hz, 2H), 3.78 (q, J = 7.1 Hz, 1H), 2.62-2.54 (m, 1H), 1.46 (d, J = 7.1 Hz, 3H), 1.40 (t, J = 7.0 Hz, 3H), 0.95-0.81 (m, 4H). |
| T193 | 2-(2-(cyclopropanesulfonamido)thiazol-4-yl)-N-(4-(5-(trifluoromethyl)pyridin-3-yl)phenyl)butanamide | Method 1c using INTB38 and INTA14, [HPLC acidic], 511, (1.38) | 12.62 (s, 1H), 10.35 (s, 1H), 9.21 (d, J = 2.2 Hz, 1H), 8.93 (dd, J = 2.1, 1.0 Hz, 1H), 8.44 (d, J = 2.4 Hz, 1H), 7.90-7.83 (m, 2H), 7.83-7.73 (m, 2H), 6.55 (s, 1H), 3.61 (t, J = 7.5 Hz, 1H), 2.64-2.53 (m, 1H), 2.03-1.73 (m, 2H), 0.96-0.84 (m, 7H). |
| T194 | N-(4-(5-cyanopyridin-3-yl)phenyl)-2-(2-(cyclopropanesulfonamido)thiazol-4-yl)butanamide | Method 1c using INTB38 and INTA12, [HPLC acidic], 468, (1.19) | 12.62 (s, 1H), 10.36 (s, 1H), 9.19 (d, J = 2.3 Hz, 1H), 8.97 (d, J = 2.0 Hz, 1H), 8.64 (t, J = 2.1 Hz, 1H), 7.87-7.81 (m, 2H), 7.80-7.75 (m, 2H), 6.54 (s, 1H), 3.60 (t, J = 7.4 Hz, 1H), 2.63-2.55 (m, 1H), 2.04-1.79 (m, 2H), 0.97-0.81 (m, 7H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T195 | 2-(2-(cyclopropanesulfonamido)thiazol-4-yl)-N-(4-(6-(2,2,2-trifluoroethoxy)pyrazin-2-yl)phenyl)butanamide | Method 1c using INTB38 and INTA53, [HPLC acidic], 542, (2.25) | 12.60 (s, 1H), 10.95 (s, 1H), 9.12 (d, J = 2.4 Hz, 1H), 8.88 (s, 1H), 8.55 (dd, J = 8.8, 2.5 Hz, 1H), 8.29 (s, 1H), 8.24 (d, J = 8.8 Hz, 1H), 6.56 (s, 1H), 4.04 (s, 3H), 3.82 (s, 1H), 2.60-2.52 (m, 1H), 2.05-1.80 (m, 2H), 0.98-0.82 (m, 7H). |
| T196 | 2-(2-(cyclopropanesulfonamido)thiazol-4-yl)-N-(2-fluoro-4-(6-(pyrazin-2-yl)phenyl)butanamide | Method 1c using INTB38 and INTA45, [HPLC acidic], 462, (1.75) | 12.56 (s, 1H), 10.17 (s, 1H), 9.30 (d, J = 1.5 Hz, 1H), 8.75-8.69 (m, 1H), 8.62 (d, J = 2.5 Hz, 1H), 8.19-8.10 (m, 1H), 8.11-7.98 (m, 2H), 6.55 (s, 1H), 3.82 (t, J = 7.4 Hz, 1H), 2.65-2.50 (m, 1H), 1.98-1.83 (m, 2H), 0.97-0.79 (m, 7H). |
| T197 | 2-(2-(cyclopropanesulfonamido)thiazol-4-yl)-N-(2-fluoro-4-(6-(trifluoromethyl)pyrazin-2-yl)phenyl)butanamide | Method 1c using INTB38 and INTA48, [HPLC acidic], 530, (2.23) | 12.59 (s, 1H), 10.22 (s, 1H), 9.63 (s, 1H), 9.13 (s, 1H), 8.21 (t, J = 8.3 Hz, 1H), 8.16-8.08 (m, 1H), 8.10-8.02 (m, 1H), 6.54 (s, 1H), 3.83 (t, J = 7.4 Hz, 1H), 2.63-2.54 (m, 1H), 2.02-1.82 (m, 2H), 0.95-0.85 (m, 7H). |
| T198 | 2-(2-(cyclopropanesulfonamido)thiazol-4-yl)-N-(4-(6-ethoxypyrazin-2-yl)-2-fluorophenyl)butanamide | Method 1c using INTB38 and INTA47, [HPLC acidic], 506, (2.19) | 12.59 (s, 1H), 10.14 (s, 1H), 8.83 (s, 1H), 8.23 (s, 1H), 8.11 (t, J = 8.3 Hz, 1H), 8.07-7.93 (m, 2H), 6.53 (s, 1H), 4.47 (q, J = 7.0 Hz, 2H), 3.81 (t, J = 7.4 Hz, 1H), 2.62-2.54 (m, 1H), 2.02-1.82 (m, 2H), 1.39 (t, J = 7.0 Hz, 3H), 0.95-0.85 (m, 7H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T199 | 2-(2-(cyclopropanesulfonamido)thiazol-4-yl)-N-(4-(5-ethoxypyridin-3-yl)-2-fluorophenyl)butanamide | Method 1c using INTB38 and INTA28, [HPLC acidic], 505, (1.77) | 12.56 (s, 1H), 10.06 (s, 1H), 8.50 (d, J = 1.9 Hz, 1H), 8.26 (d, J = 2.7 Hz, 1H), 8.01 (t, J = 8.4 Hz, 1H), 7.79-7.71 (m, 1H), 7.67-7.56 (m, 2H), 6.54 (s, 1H), 4.19 (q, J = 7.0 Hz, 2H), 3.79 (t, J = 7.4 Hz, 1H), 2.64-2.54 (m, 1H), 2.00-1.81 (m, 2H), 1.36 (t, J = 7.0 Hz, 3H), 0.95-0.83 (m, 7H). |
| T200 | 2-(2-(cyclopropanesulfonamido)thiazol-4-yl)-N-(2-fluoro-4-(5-fluoropyridin-3-yl)phenyl)butanamide | Method 1c using INTB38 and INTA29, [HPLC acidic], 479, (1.93) | 12.60 (s, 1H), 10.12 (s, 1H), 8.89-8.83 (m, 1H), 8.59 (d, J = 2.7 Hz, 1H), 8.18-8.09 (m, 1H), 8.12-8.03 (m, 1H), 7.87-7.79 (m, 1H), 7.71-7.63 (m, 1H), 6.55 (s, 1H), 3.81 (t, J = 7.5 Hz, 1H), 2.66-2.56 (m, 1H), 2.02-1.83 (m, 2H), 0.97-0.87 (m, 7H). |
| T201 | 2-(2-(cyclopropanesulfonamido)thiazol-4-yl)-N-(2-fluoro-4-(pyridin-3-yl)phenyl)butanamide | Method 1c using INTB38, [HPLC acidic], 461, (1.37) | 12.58 (s, 1H), 10.08 (s, 1H), 8.94 (d, J = 2.4 Hz, 1H), 8.61-8.54 (m, 1H), 8.16-8.08 (m, 1H), 8.04 (t, J = 8.4 Hz, 1H), 7.78-7.70 (m, 1H), 7.63-7.56 (m, 1H), 7.53-7.45 (m, 1H), 6.56 (s, 1H), 3.85-3.76 (m, 1H), 2.65-2.54 (m, 1H), 2.04-1.81 (m, 2H), 0.97-0.84 (m, 7H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T202 | N-(4-(5-cyanopyridin-3-yl)-2-fluorophenyl)-2-(2-(cyclopropanesulfonamido)thiazol-4-yl)butanamide | Method 1c using INTB38 and INTA26, [UPLC acidic], 486.1, (1.2) | 12.59 (s, 1H), 10.13 (s, 1H), 9.23 (d, J = 2.3 Hz, 1H), 9.00 (d, J = 1.9 Hz, 1H), 8.73-8.67 (m, 1H), 8.13-8.03 (m, 1H), 7.91-7.82 (m, 1H), 7.73-7.66 (m, 1H), 6.54 (s, 1H), 3.80 (t, J = 7.5 Hz, 1H), 2.63-2.53 (m, 1H), 2.01-1.82 (m, 2H), 0.96-0.85 (m, 7H). |
| T203 | N-(4-(5-chloropyridin-3-yl)-2-fluorophenyl)-2-(2-(cyclopropanesulfonamido)thiazol-4-yl)butanamide | Method 1c using INTB38 and INTA27, [HPLC acidic], 495.3, (1.34) | 12.60 (s, 1H), 10.12 (s, 1H), 8.92 (d, J = 2.0 Hz, 1H), 8.63 (d, J = 2.3 Hz, 1H), 8.35-8.28 (m, 1H), 8.11-8.02 (m, 1H), 7.88-7.79 (m, 1H), 7.71-7.63 (m, 1H), 6.55 (s, 1H), 3.81 (t, J = 7.4 Hz 1H), 2.64-2.52 (m, 1H), 2.02-1.83 (m, 2H), 0.97-0.79 (m, 7H). |
| T204 | Single enantiomer - stereochemistry unassigned 2-(2-(cyclopropanesulfonamido)thiazol-4-yl)-N-(4-(6-ethoxypyrazin-2-yl)phenyl)butanamide | Method 1c using INTB38 and INTA38, Chiral IA (28.0), [HPLC basic], 488, (1.85) | 12.63 (s, 1H), 10.41 (s, 1H), 8.77 (s, 1H), 8.19 (s, 1H), 8.16-8.07 (m, 2H), 7.82-7.73 (m, 2H), 6.56 (s, 1H), 4.48 (q, J = 7.0 Hz, 2H), 3.66-3.59 (m, 1H), 2.60 (d, J = 6.1 Hz, 1H), 2.01-1.85 (m, 2H), 1.40 (t, J = 7.0 Hz, 3H), 0.95-0.84 (m, 7H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | ¹H NMR Chemical Shift Data (DMSO-d6 unless stated) |
|---|---|---|---|
| T205 | Single enantiomer - stereochemistry unassigned 2-(2-(cyclopropanesulfonamido)thiazol-4-yl)-N-(4-(6-ethoxypyrazin-2-yl)phenyl)butanamide | Method 1c using INTB38 and INTA38, Chiral IA (30.6), [HPLC basic], 488, (1.85) | 12.63 (s, 1H), 10.41 (s, 1H), 8.77 (s, 1H), 8.19 (s, 1H), 8.16-8.07 (m, 2H), 7.84-7.71 (m, 2H), 6.56 (s, 1H), 4.48 (q, J = 7.0 Hz, 2H), 3.63 (t, J = 7.4 Hz, 1H), 2.59 (d, J = 6.5 Hz, 1H), 2.03-1.81 (m, 2H), 1.40 (t, J = 7.0 Hz, 3H), 0.97-0.81 (m, 7H). |
| T206 | N-(4-(1-(5-(6-ethoxypyrazin-2-yl)indolin-1-yl)-1-oxobutan-2-yl)thiazol-2-yl)cyclopropanesulfonamide | Method 1 using INTB38 and INTA74, [UPLC acidic], 514.4, (1.47) | 12.60 (s, 1H), 8.77 (s, 1H), 8.32-8.11 (m, 2H), 8.09-7.89 (m, 2H), 6.58 (s, 1H), 4.55-4.41 (m, 2H), 4.35-4.18 (m, 2H), 3.98-3.82 (m, 1H), 3.30-3.23 (m, 2H), 2.64-2.54 (m, 1H), 2.08-1.81 (m, 2H), 1.49-1.34 (m, 3H), 1.00-0.79 (m, 7H). |
| T207 | 2-(2-(cyclopropanesulfonamido)thiazol-4-yl)-N-(2-fluoro-4-(6-(2,2,2-trifluoroethoxy)pyrazin-2-yl)phenyl)butanamide | Method 1c using INTB38 and INTA52, [UPLC acidic], 560, (1.48) | 12.61 (s, 1H), 10.18 (s, 1H), 9.01 (s, 1H), 8.44 (s, 1H), 8.20-8.12 (m, 2H), 8.05 (dd, J = 8.6, 2.0 Hz, 1H), 6.56 (s, 1H), 5.22 (q, J = 9.0 Hz, 2H), 3.88-3.81 (m, 1H), 2.61-2.52 (m, 1H), 2.01-1.85 (m, 2H), 0.96-0.87 (m, 7H). |
| T208 | 2-(2-(cyclopropanesulfonamido)thiazol-4-yl)-N-(2-fluoro-4-(6-methoxypyrazin-2-yl)phenyl)butanamide | Method 1c using INTB38 and INTA102, [UPLC acidic], 492, (1.32) | 12.61 (s, 1H), 10.16 (s, 1H), 8.86 (s, 1H), 8.28 (s, 1H), 8.17-8.10 (m, 1H), 8.07 (dd, J = 12.3, 2.0 Hz, 1H), 8.01 (dd, J = 8.5, 2.0 Hz, 1H), 6.56 (s, 1H), 4.03 (s, 3H), 3.87-3.80 (m, 1H), 2.63-2.55 (m, 1H), 2.03-1.83 (m, 2H), 0.96-0.87 (m, 7H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T209 | 2-(2-(cyclopropanesulfonamido)thiazol-4-yl)-N-(4-(5-(difluoromethoxy)pyridin-3-yl)-2-fluorophenyl)butanamide | Method 1c using INTB38 and INTA24, [UPLC acidic], 527, (1.29) | 12.61 (s, 1H), 10.12 (s, 1H), 8.86 (d, J = 1.9 Hz, 1H), 8.49 (d, J = 2.6 Hz, 1H), 8.11-8.04 (m, 1H), 8.04-7.99 (m, 1H), 7.82 (dd, J = 12.2, 2.1 Hz, 1H), 7.66 (dd, J = 8.5, 2.0 Hz, 1H), 7.44 (t, J = 73.4 Hz, 1H), 6.55 (s, 1H), 3.85-3.75 (m, 1H), 2.61-2.57 (m, 1H), 2.03-1.84 (m, 2H), 0.96-0.87 (m, 7H). |
| T210 | 2-(2-(cyclopropanesulfonamido)thiazol-4-yl)-N-(4-(5-(difluoromethoxy)pyridin-3-yl)phenyl)butanamide | Method 1c using INTB38 and INTA25, [UPLC acidic], 509, (1.26) | 12.61 (s, 1H), 10.33 (s, 1H), 8.80 (d, J = 1.9 Hz, 1H), 8.45 (d, J = 2.6 Hz, 1H), 7.97-7.90 (m, 1H), 7.81-7.72 (m, 4H), 7.43 (t, J = 73.5 Hz, 1H), 6.55 (s, 1H), 3.64-3.57 (m, 1H), 2.62-2.56 (m, 1H), 2.03-1.83 (m, 2H), 0.95-0.86 (m, 7H). |
| T211 | 2-(2-(cyclopropanesulfonamido)thiazol-4-yl)-N-(4-(5-(2,2,2-trifluoroethoxy)pyridin-3-yl)phenyl)butanamide | Method 1c using INTB38 and INTA31, [UPLC acidic], 541, (1.3) | 12.59 (s, 1H), 10.31 (s, 1H), 8.59 (d, J = 1.8 Hz, 1H), 8.36 (d, J = 2.8 Hz, 1H), 7.82-7.71 (m, 5H), 6.56 (s, 1H), 4.98 (q, J = 8.9 Hz, 2H), 3.60 (s, 1H), 2.64-2.55 (m, 1H), 2.03-1.83 (m, 2H), 0.95-0.85 (m, 7H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T212 | 2-(2-(cyclopropanesulfonamido)thiazol-4-yl)-N-(2-fluoro-4-(5-(2,2,2-trifluoroethoxy)pyridin-3-yl)phenyl)butanamide | Method 1c using INTB38 and INTA30, [UPLC acidic], 559, (1.34) | 12.58 (s, 1H), 10.09 (s, 1H), 8.64 (d, J = 1.8 Hz, 1H), 8.38 (d, J = 2.8 Hz, 1H), 8.08-8.00 (m, 1H), 7.86 (dd, J = 2.8, 1.9 Hz, 1H), 7.84-7.77 (m, 1H), 7.65 (dd, J = 8.5, 2.1 Hz, 1H), 6.54 (s, 1H), 4.97 (q, J = 8.8 Hz, 2H), 3.83-3.76 (m, 1H), 2.60-2.56 (m, 1H), 2.00-1.83 (m, 2H), 0.95-0.86 (m, 7H). |
| T213 | 2-(cyclopropanesulfonamido)-N-(4-(pyridin-3-yl)phenyl)-5,6-dihydro-4H-cyclopenta[d]thiazole-4-carboxamide | Method 1c using INTB66, [HPLC acidic], 441, (1.15) | 12.56 (s, 1H), 10.31 (s, 1H), 8.90 (dd, J = 2.4, 0.9 Hz, 1H), 8.54 (dd, J = 4.8, 1.6 Hz, 1H), 8.07 (ddd, J = 8.0, 2.4, 1.6 Hz, 1H), 7.80-7.71 (m, 4H), 7.47 (ddd, J = 8.0, 4.7, 0.9 Hz, 1H), 4.06-3.97 (m, 1H), 2.85-2.71 (m, 3H), 2.67-2.56 (m, 1H), 2.50-2.44 (m, 1H, partially obscured by solvent), 0.97-0.87 (m, 4H). |
| T214 | 2-(2-(cyclopropanesulfonamido)thiazol-4-yl)-2-methoxy-N-(5-(6-(trifluoromethyl)pyrazin-2-yl)pyridin-2-yl)acetamide | Method 1c using INTB43 and INTA3, [UPLC acidic], 515, (1.27) | 12.85 (s, 1H), 10.44 (s, 1H), 9.68 (s, 1H), 9.20 (d, J = 2.4 Hz, 1H), 9.17 (s, 1H), 8.63 (dd, J = 8.8, 2.5 Hz, 1H), 8.27 (d, J = 8.8 Hz, 1H), 6.89 (s, 1H), 5.02 s, 1H), 3.40 (s, 3H), 2.65-2.53 (m, 1H), 0.94-0.82 (m, 4H). |
| T215 | 2-(2-(cyclopropanesulfonamido)thiazol-4-yl)-N-(2-methoxy-4-(pyridin-3-yl)phenyl)acetamide | Method 1c using INTB36 and INTA, [HPLC basic], 445, (1.4) | 12.52 (s, 1H), 9.51 (s, 1H), 8.95 (dd, J = 2.4, 0.9 Hz, 1H), 8.56 (dd, J = 4.8, 1.6 Hz, 1H), 8.18-8.07 (m, 2H), 7.48 (ddd, J = 8.0, 4.8, 0.9 Hz, 1H), 7.41 (d, J = 2.0 Hz, 1H), 7.31 (dd, J = 8.4, 2.0 Hz, 1H), 6.56 (s, 1H), 3.98 (s, 3H), 3.75 (s, 2H), 2.64-2.53 (m, 1H), 0.90 (dt, J = 8.1, 2.5 Hz, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | ¹H NMR Chemical Shift Data (DMSO-d6 unless stated) |
|---|---|---|---|
| T216 | 2-(2-(cyclopropanesulfonamido)thiazol-4-yl)-N-(2-fluoro-4-(pyridin-3-yl)phenyl)acetamide | Method 1c using INTB36, [HPLC basic], 433, (1.36) | 12.52 (s, 1H), 10.11 (s, 1H), 8.94 (d, J = 2.4 Hz, 1H), 8.57 (dd, J = 4.8, 1.6 Hz, 1H), 8.15-8.04 (m, 2H), 7.74 (dd, J = 12.3, 2.1 Hz, 1H), 7.59 (dd, J = 8.4, 1.9 Hz, 1H), 7.51-7.46 (m, 1H), 6.57 (s, 1H), 3.75 (s, 2H), 2.63-2.52 (m, 1H), 0.93-0.86 (m, 4H). |
| T217 | N-(4-(5-cyanopyridin-3-yl)phenyl)-2-(cyclopropanesulfonamido)-5,6-dihydro-4H-cyclopenta[d]thiazole-4-carboxamide | Method 1c using INTB66 and INTA12, [UPLC acidic], 466, (1.14) | 12.59 (s (br), 1H), 10.38 (s, 1H), 9.19 (d, J = 2.3 Hz, 1H), 8.97 (d, J = 1.9 Hz, 1H), 8.63 (dd, J = 2.1 Hz, 1H), 7.84 (d, J = 8.9 Hz, 1H), 7.77 (d, J = 8.9 Hz, 1H), 4.06-3.99 (m, 1H), 2.86-2.68 (m, 3H), 2.60 (s, 1H), 0.90 (dd, J = 6.9, 4.5 Hz, 4H). 1 proton under DMSO peak |
| T218 | 2-(cyclopropanesulfonamido)-N-(4-(5-fluoropyridin-3-yl)phenyl)-5,6-dihydro-4H-cyclopenta[d]thiazole-4-carboxamide | Method 1c using INTB66 and INTA13, [UPLC acidic], 459.3, (1.14) | 12.59 (s, 1H), 10.34 (s, 1H), 8.81 (dd, J = 1.9 Hz, 1H), 8.54 (d, J = 2.7 Hz, 1H), 8.06 (ddd, J = 10.6, 2.8, 1.9 Hz, 1H), 7.84-7.73 (m, 4H), 4.04-3.97 (m, 1H), 2.84-2.70 (m, 3H), 2.63-2.58 (m, 1H), 0.94-0.87 (m, 5H). |
| T219 | 2-(2-(cyclopropanesulfonamido)thiazol-4-yl)-2-methoxy-N-(4-(pyridin-3-yl)phenyl)acetamide | Method 1c using INTB43, [HPLC basic], 445, (1.35) | 12.76 (s, 1H), 10.05 (s, 1H), 8.97-8.84 (m, 1H), 8.55 (dd, J = 4.8, 1.6 Hz, 1H), 8.12-8.04 (m, 1H), 7.84 (d, J = 8.7 Hz, 2H), 7.74 (d, J = 8.7 Hz, 2H), 7.53-7.44 (m, 1H), 6.82 (s, 1H), 4.86 (s, 1H), 3.40 (s, 3H), 2.65-2.54 (m, 1H), 0.88 0.97-0.74 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T220 | 2-(2-(cyclopropanesulfonamido)thiazol-4-yl)-N-(2-fluoro-4-(pyridin-3-yl)phenyl)-2-methoxyacetamide | Method 1c using INTB43, [HPLC basic], 463, (1.41) | 9.71 (s, 1H), 8.99-8.92 (m, 1H), 8.57 (dd, J = 4.8, 1.6 Hz, 1H), 8.16-8.04 (m, 2H), 7.76 (dd, J = 12.2, 2.1 Hz, 1H), 7.61 (dd, J = 8.4, 2.0 Hz, 1H), 7.48 (dd, J = 8.0, 4.9 Hz, 1H), 6.66 (s, 1H), 4.81 (s, 1H), 3.37 (s, 3H), 2.56-2.52 (m, 1H), 0.91-0.62 (m, 4H) 1 x N—H not observed. |
| T221 | N-(2-chloro-4-(pyridin-3-yl)phenyl)-2-(2-(cyclopropanesulfonamido)thiazol-4-yl)butanamide | Method 1c using INTB38 and INTA8, [HPLC basic], 477, (1.59) | 12.62 (s, 1H), 9.87 (s, 1H), 8.94 (d, J = 2.3 Hz, 1H), 8.60 (dd, J = 4.8, 1.6 Hz, 1H), 8.17-8.11 (m, 1H), 7.93 (d, J = 2.1 Hz, 1H), 7.85 (d, J = 8.4 Hz, 1H), 7.74 (dd, J = 8.4, 2.2 Hz, 1H), 7.50 (dd, J = 8.0, 4.7 Hz, 1H), 6.59 (s, 1H), 3.80 (t, J = 7.4 Hz, 1H), 2.66-2.55 (m, 1H), 2.04-1.82 (m, 2H), 0.99-0.85 (m, 7H). |
| T222 | Single enantiomer - stereochemistry unassigned 2-(2-(cyclopropanesulfonamido)thiazol-4-yl)-N-(4-(6-(2,2,2-trifluoroethoxy)pyrazin-2-yl)phenyl)butanamide | Method 1c using INTB38 and INTA53 Chiral IC (20.6), [UPLC acidic], 542, (1.44) | 12.62 (s, 1H), 10.39 (s, 1H), 8.94 (s, 1H), 8.39 (s, 1H), 8.23-8.13 (m, 2H), 7.80-7.73 (m, 2H), 6.56 (s, 1H), 5.20 (q, J = 9.0 Hz, 2H), 2.63-2.56 (m, 1H), 2.03-1.83 (m, 2H), 0.96-0.79 (m, 7H), 1 proton obscured by solvent |
| T223 | Single enantiomer - stereochemistry unassigned 2-(2-(cyclopropanesulfonamido)thiazol-4-yl)-N-(4-(6-(2,2,2-trifluoroethoxy)pyrazin-2-yl)phenyl)butanamide | Method 1c using INTB38 and INTA53 Chiral IC (26.1), [UPLC acidic], 542, (1.44) | 12.62 (s, 1H), 10.39 (s, 1H), 8.93 (s, 1H), 8.38 (s, 1H), 8.22-8.16 (m, 2H), 7.81-7.74 (m, 2H), 6.55 (s, 1H), 5.19 (q, J = 9.0 Hz, 2H), 3.60 (d, J = 7.5 Hz, 1H), 2.61-2.53 (m, 1H), 2.04-1.82 (m, 2H), 0.96-0.86 (m, 7H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T224 | 2-(2-(cyclopropanesulfonamido)thiazol-4-yl)-N-(5'-methoxy-[3,3'-bipyridin]-6-yl)-2-methylpropanamide | Method 2 using INTB55, [UPLC acidic], 474, (0.94) | 12.54 (s, 1H), 10.01 (s, 1H), 8.76 (d, J = 2.4 Hz, 1H), 8.54 (d, J = 1.9 Hz, 1H), 8.30 (d, J = 2.8 Hz, 1H), 8.23 (dd, J = 8.7, 2.6 Hz, 1H), 8.13 (d, J = 8.7 Hz, 1H), 7.70 (t, J = 2.3 Hz, 1H), 6.58 (s, 1H), 3.91 (s, 3H), 2.61-2.56 (m, 1H), 1.60 (s, 6H), 0.93-0.86 (m, 4H). |
| T225 | N-(5'-chloro-[3,3'-bipyridin]-6-yl)-2-(2-(cyclopropanesulfonamido)thiazol-4-yl)-2-methylpropanamide | Method 2 using INTB55, [UPLC basic], 478, (1.07) | 12.58 (s, 1H), 10.09 (s, 1H), 8.95 (d, J = 2.0 Hz, 1H), 8.82 (d, J = 2.5 Hz, 1H), 8.65 (d, J = 2.3 Hz, 1H), 8.37 (t, J = 2.2 Hz, 1H), 8.29 (dd, J = 8.7, 2.6 Hz, 1H), 8.19-8.10 (m, 1H), 6.58 (s, 1H), 2.65-2.55 (m, 1H), 1.61 (s, 6H), 1.01-0.88 (m, 4H). |
| T226 | N-(5'-cyano-[3,3'-bipyridin]-6-yl)-2-(2-(cyclopropanesulfonamido)thiazol-4-yl)-2-methylpropanamide | Method 2 using INTB55, [UPLC acidic], 469, (1.1) | 12.57 (s, 1H), 10.11 (s, 1H), 9.26 (d, J = 2.3 Hz, 1H), 9.02 (d, J = 1.9 Hz, 1H), 8.85 (s, 1H), 8.75 (t, J = 2.1 Hz, 1H), 8.31 (dd, J = 8.7, 2.6 Hz, 1H), 8.16 (d, J = 8.8 Hz, 1H), 6.57 (s, 1H), 2.63-2.53 (m, 1H), 1.60 (s, 6H), 0.93-0.78 (m, 4H). |
| T227 | 2-(2-(cyclopropanesulfonamido)thiazol-4-yl)-N-(5-fluoro-[3,3'-bipyridin]-6-yl)-2-methylpropanamide | Method 2 using INTB72, [UPLC acidic], 462, (0.76) | 12.60 (s, 1H), 9.98 (s, 1H), 9.01 (d, J = 2.3 Hz, 1H), 8.72-8.67 (m, 1H), 8.66-8.60 (m, 1H), 8.29-8.18 (m, 2H), 7.57-7.49 (m, 1H), 6.58 (s, 1H), 2.63-2.55 (m, 1H), 1.58 (s, 6H), 0.94-0.84 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T228 | N-(5'-cyano-4-fluoro-[3,3'-bipyridin]-6-yl)-2-(2-(cyclopropanesulfonamido)thiazol-4-yl)-2-methylpropanamide | Method 2, using INTB72 [UPLC acidic], 487.3, (1.01) | 12.64 (s, 1H), 10.06 (s, 1H), 9.33 (d, J = 2.3 Hz, 1H), 9.08 (d, J = 1.9 Hz, 1H), 8.86-8.77 (m, 2H), 8.40-8.32 (m, 1H), 6.57 (s, 1H), 2.61-2.56 (m, 1H), 1.59 (s, 6H), 0.94-0.87 (m, 4H). |
| T229 | N-(5'-chloro-5-fluoro-[3,3'-bipyridin]-6-yl)-2-(2-(cyclopropanesulfonamido)thiazol-4-yl)-2-methylpropanamide | Method 2, using INTB72 [UPLC acidic], 496.3, (1.14) | 12.63 (s, 1H), 10.03 (s, 1H), 9.00 (d, J = 2.0 Hz, 1H), 8.75 (s, 1H), 8.68 (d, J = 2.3 Hz, 1H), 8.47-8.41 (m, 1H), 8.36-8.27 (m, 1H), 6.56 (s, 1H), 2.60-2.55 (m, 1H), 1.58 (s, 6H), 0.93-0.86 (m, 4H). |
| T230 | 2-(2-(cyclopropanesulfonamido)thiazol-4-yl)-N-(5,5'-difluoro-[3,3'-bipyridin]-6-yl)-2-methylpropanamide | Method 2, using INTB72 [UPLC acidic], 480.1, (1.02) | 12.65 (s, 1H), 10.05 (s, 1H), 8.98-8.92 (m, 1H), 8.80-8.75 (m, 1H), 8.66 (d, J = 2.7 Hz, 1H), 8.37-8.24 (m, 2H), 6.58 (s, 1H), 2.62-2.57 (m, 1H), 1.60 (s, 6H), 0.95-0.90 (m, 4H). |
| T231 | N-(5-(3-chloro-5-methylphenyl)pyridin-2-yl)-2-(2-(cyclopropanesulfonamido)thiazol-4-yl)-2-methylpropanamide | Method 2 using INTB55, [UPLC acidic], 492, (1.6) | 12.57 (s, 1H), 10.00 (s, 1H), 8.70 (d, J = 2.1 Hz, 1H), 8.20-8.06 (m, 2H), 7.63-7.57 (m, 1H), 7.56-7.50 (m, 1H), 7.29 (s, 1H), 6.57 (s, 1H), 2.64-2.53 (m, 1H), 2.38 (s, 3H), 1.60 (s, 6H), 0.93-0.87 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | ¹H NMR Chemical Shift Data (DMSO-d6 unless stated) |
|---|---|---|---|
| T232 | 2-(2-(cyclopropanesulfonamido)thiazol-4-yl)-N-(5-(3-methoxyphenyl)pyridin-3-yl)-2-methylpropanamide | Method 2 using INTB55, [UPLC acidic], 473, (1.36) | 12.58 (s, 1H), 9.94 (s, 1H), 8.67 (s, 1H), 8.20-8.00 (m, 2H), 7.39 (t, J = 7.9 Hz, 1H), 7.33-7.19 (m, 2H), 6.99-6.90 (m, 1H), 6.57 (s, 1H), 3.83 (s, 3H), 2.65-2.53 (m, 1H), 1.60 (s, 6H), 0.96-0.80 (m, 4H). |
| T233 | 2-(2-(cyclopropanesulfonamido)thiazol-4-yl)-N-(5-(3-fluoro-5-methoxyphenyl)pyridin-2-yl)-2-methylpropanamide | Method 2 using INTB55, [UPLC acidic], 491, (1.43) | 12.57 (s, 1H), 10.02 (s, 1H), 8.70 (s, 1H), 8.21-8.09 (m, 2H), 7.22-7.11 (m, 2H), 6.85 (d, J = 10.8 Hz, 1H), 6.56 (s, 1H), 3.85 (s, 3H), 2.63-2.51 (m, 1H), 1.56 (s, 6H), 0.97-0.69 (m, 4H). |
| T234 | 2-(2-(cyclopropanesulfonamido)thiazol-4-yl)-N-(5-(3,5-dimethoxyphenyl)pyridin-2-yl)-2-methylpropanamide | Method 2 using INTB55, [UPLC acidic], 503, (1.38) | 12.59 (s, 1H), 9.95 (s, 1H), 8.68 (s, 1H), 8.18-8.06 (m, 2H), 6.85 (d, J = 2.2 Hz, 2H), 6.58 (s, 1H), 6.53 (t, J = 2.2 Hz, 1H), 3.82 (s, 6H), 2.65-2.53 (m, 1H), 1.61 (s, 6H), 0.96-0.82 (m, 4H). |
| T235 | 2-(2-(cyclopropanesulfonamido)thiazol-4-yl)-2-methyl-N-(5-(3-(trifluoromethyl)phenyl)pyridin-2-yl)propanamide | Method 2 using INTB55, [UPLC acidic], 511, (1.54) | 12.58 (s, 1H), 10.04 (s, 1H), 8.77 (s, 1H), 8.25 (dd, J = 8.6, 2.6 Hz, 1H), 8.15 (d, J = 8.8 Hz, 1H), 8.09-8.02 (m, 2H), 7.80-7.66 (m, 2H), 6.57 (s, 1H), 2.63-2.54 (m, 1H), 1.61 (s, 6H), 0.95-0.83 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T236 | 2-(2-(cyclopropanesulfonamido)thiazol-4-yl)-2-methyl-N-(5-(3-(trifluoromethoxy)phenyl)pyridin-2-yl)propanamide | Method 2 using INTB55, [UPLC acidic], 527, (1.57) | 12.56 (s, 1H), 10.01 (s, 1H), 8.73 (d, J = 2.5 Hz, 1H), 8.22-8.16 (m, 1H), 8.13 (dd, J = 8.7, 0.8 Hz, 1H), 7.82-7.76 (m, 1H), 7.75 (s, 1H), 7.62 (t, J = 8.0 Hz, 1H), 7.42-7.36 (m, 1H), 6.59 (s, 1H), 2.65-2.54 (m, 1H), 1.60 (s, 6H), 0.94-0.74 (m, 4H). |
| T237 | 2-(2-(cyclopropanesulfonamido)thiazol-4-yl)-N-(5-(3-(2-hydroxypropan-2-yl)phenyl)pyridin-2-yl)-2-methylpropanamide | Method 2 using INTB55, [UPLC acidic], 501, (1.22) | 12.59 (s, 1H), 9.95 (s, 1H), 8.65 (s, 1H), 8.15-8.09 (m, 2H), 7.78 (t, J = 1.8 Hz, 1H), 7.56-7.50 (m, 1H), 7.50-7.47 (m, 1H), 7.45-7.39 (m, 1H), 6.59 (s, 1H), 2.64-2.55 (m, 1H), 1.61 (s, 6H), 1.48 (s, 6H), 0.97-0.83 (m, 4H), O—H not observed. |
| T238 | 2-(2-(cyclopropanesulfonamido)thiazol-4-yl)-2-methyl-N-(5-(3-morpholinophenyl)pyridin-2-yl)propanamide | Method 2 using INTB55, [UPLC acidic], 528, (1.3) | 12.59 (s, 1H), 9.93 (s, 1H), 8.65 (s, 1H), 8.16-8.03 (m, 2H), 7.34 (t, J = 7.9 Hz, 1H), 7.22 (d, J = 2.1 Hz, 1H), 7.14 (d, J = 7.6 Hz, 1H), 7.01-6.93 (m, 1H), 6.58 (s, 1H), 3.80-3.73 (m, 4H), 3.23-3.16 (m, 4H), 2.63-2.56 (m, 1H), 1.61 (s, 6H), 0.98-0.80 (m, 4H). |
| T239 | 2-(2-(cyclopropanesulfonamido)thiazol-4-yl)-2-methyl-N-(6-phenylpyridin-3-yl)propanamide | Method 1, using INTB37, [UPLC acidic], 443, (1.14) | 12.61 (s, 1H), 9.64 (s, 1H), 8.88 (d, J = 2.5 Hz, 1H), 8.14 (dd, J = 8.7, 2.5 Hz, 1H), 8.09-8.02 (m, 2H), 7.98 (d, J = 8.7 Hz, 1H), 7.53-7.37 (m, 3H), 6.60 (s, 1H), 2.60 (s, 1H), 1.59 (s, 6H), 0.95-0.85 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T240 | 2-(2-(cyclopropanesulfonamido)thiazol-4-yl)-N-(4-(2-fluoropyridin-3-yl)phenyl)-2-methylpropanamide | Method 2 using INTB53, [UPLC acidic], 461, (1.2) | 12.58 (s, 1H), 9.46 (s, 1H), 8.24-8.19 (m, 1H), 8.15-8.08 (m, 1H), 7.81-7.73 (m, 2H), 7.59 (d, J = 8.0 Hz, 2H), 7.49-7.43 (m, 1H), 6.55 (s, 1H), 2.48-2.42 (m, 1H), 1.58 (s, 6H), 0.94-0.87 (m, 4H). |
| T241 | 2-(2-(cyclopropanesulfonamido)thiazol-4-yl)-N-(4-(5-(hydroxymethyl)pyridin-3-yl)phenyl)-2-methylpropanamide | Method2 using INTB53, [UPLC acidic], 473, (0.69) | 12.51 (s, 1H), 9.37 (s, 1H), 8.72 (d, J = 2.3 Hz, 1H) 8.44 (d, J = 1.9 Hz, 1H), 7.95-7.90 (m, 1H), 7.74-7.69 (m, 2H), 7.69-7.63 (m, 2H), 6.50 (s, 1H), 5.32 (t, J = 5.7 Hz, 1H), 4.56 (d, J = 5.7 Hz, 2H), 2.52-2.47 (m, 1H), 1.53 (s, 6H), 0.88-0.84 (m, 4H). |
| T242 | 2-(2-(cyclopropanesulfonamido)thiazol-4-yl)-N-(4-(2-methoxypyrimidin-5-yl)phenyl)acetamide | Method 2 using INTB73, [HPLC acidic], 446, (1.53) | 12.56 (s, 1H), 10.34 (s, 1H), 8.93 (s, 2H), 7.72 (s, 4H), 6.57 (s, 1H), 3.96 (s, 3H), 3.67 (s, 2H), 2.63-2.55 (m, 1H), 0.95-0.69 (m, 4H). |
| T243 | N-(4'-(tert-butyl)-[1,1'-biphenyyl]-4-yl)-2-(2-(cyclopropanesulfonamido)thiazol-4-yl)acetamide | Method 2, using INTB73 [HPLC acidic], 470, (2.48) | 12.56 (s, 1H), 10.27 (s, 1H), 7.71-7.65 (m, 2H), 7.65-7.60 (m, 2H), 7.60-7.55 (m, 1H), 7.49-7.43 (m, 2H), 6.56 (s, 1H), 3.66 (s, 2H), 2.63-2.54 (m, 1H), 1.31 (s, 9H), 0.94-0.82 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T244 | 2-(2-(cyclopropanesulfonamido)thiazol-4-yl)-N-(4-(pyridin-3-yl)phenyl)acetamide | Method 2, using INTB73 [HPLC acidic], 415, (1.02) | (Methanol-d4) 8.81 (dd, J = 2.4, 0.9 Hz, 1H), 8.51 (dd, J = 4.9, 1.6 Hz, 1H), 8.11 (ddd, J = 8.0, 2.4, 1.6 Hz, 1H), 7.80-7.74 (m, 2H), 7.72-7.65 (m, 2H), 7.56-7.51 (m, 1H), 6.53 (d, J = 1.0 Hz, 1H), 3.73 (d, J = 1.0 Hz, 2H), 2.63 tt, J = 8.1, 4.8 Hz, 1H), 1.13-1.07 (m, 2H), 0.99-0.92 (m, 2H). |
| T245 | 2-(2-(cyclopropanesulfonamido)thiazol-4-yl)-N-(4-(pyridin-3-yl)phenyl)acetamide | Method 2, using INTB73 [HPLC acidic], 415, (0.94) | (Methanol-d4) 8.60-8.52 (m, 2H), 7.86-7.71 (m, 6H), 6.47 (d, J = 1.0 Hz, 1H), 3.66 (d, J = 1.0 Hz, 2H), 2.74-2.63 (m, 1H), 1.14-1.04 (m, 2H), 0.93-0.78 (m, 2H). |
| T246 | 2-(2-(cyclopropanesulfonamido)thiazol-4-yl)-N-(2'-methoxy-[1,1'-biphenyl]-4-yl)acetamide | Method 2, using INTB73 [HPLC acidic], 444, (2.02) | 12.57 (s, 1H), 10.25 (s, 1H), 7.65-7.59 (m, 2H), 7.47-7.40 (m, 2H), 7.36-7.23 (m, 2H), 7.10 (dd, J = 8.3, 1.1 Hz, 1H), 7.02 (td, J = 7.5, 1.1 Hz, 1H), 6.56 (s, 1H), 3.76 (s, 3H), 3.65 (s, 2H), 2.63-2.54 (m, 1H), 0.94-0.83 (m, 4H). |
| T247 | 2-(2-(cyclopropanesulfonamido)thiazol-4-yl)-N-(4-(pyrimidin-5-yl)phenyl)acetamide | Method 2, using INTB73 [UPLC acidic], 416, (0.86) | 12.56 (s, 1H), 10.40 (s, 1H), 9.16 (s, 1H), 9.14 (s, 2H), 7.84-7.80 (m, 2H), 7.79-7.73 (m, 2H), 6.57 (s, 1H), 3.68 (s, 2H), 2.63-2.54 (m, 1H), 0.96-0.82 (m, 4H). |
| T248 | 2-(2-(cyclopropanesulfonamido)thiazol-4-yl)-2-methyl-N-(4-(2-(trifluoromethyl)pyridin-3-yl)phenyl)propanamide | Method 2 using INTB53, [UPLC acidic], 511, (1.3) | 12.56 (s, 1H), 9.43 (s, 1H), 8.78-8.71 (m, 1H), 7.93-7.86 (m, 1H), 7.80-7.67 (m, 3H), 7.30 (d, J = 8.4 Hz, 2H), 6.54 (s, 1H), 2.60-2.55 (m, 1H), 1.57 (s, 6H), 0.92-0.85 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T249 | 2-(2-(cyclopropanesulfonamido)thiazol-4-yl)-2-methyl-N-(5'-methyl-[3,3'-bipyridin]-6-yl)propanamide | Method 2 using INTB55, [UPLC acidic], 458, (0.77) | 12.54 (s, 1H), 9.99 (s, 1H), 8.73 (dd, J = 7.8, 2.3 Hz, 2H), 8.43 (d, J = 2.0 Hz, 1H), 8.20 (dd, J = 8.8, 2.5 Hz, 1H), 8.13 (d, J = 8.7 Hz, 1H), 7.97 (d, J = 2.5 Hz, 1H), 6.59 (s, 1H), 2.62-2.57 (m, 1H), 2.37 (s, 3H), 1.60 (s, 6H), 0.94-0.86 (m, 4H). |
| T250 | 2-(2-(cyclopropanesulfonamido)thiazol-4-yl)-N-(4-(2-methoxy-4-methylpyridin-3-yl)phenyl)-2-methylpropanamide | Method 2 using INTB53, [UPLC acidic], 487, (1.3) | 12.56 (s, 1H), 9.33 (s, 1H), 8.00 (d, J = 5.2 Hz, 1H), 7.69-7.61 (m, 2H), 7.15 (d, J = 8.5 Hz, 2H), 6.96-6.90 (m, 1H), 6.52 (d, J = 12.8 Hz, 1H), 3.73 (s, 3H), 2.61-2.56 (m, 1H), 2.05 (s, 3H), 1.56 (s, 6H), 0.93-0.74 (m, 4H). |
| T251 | 2-(2-(cyclopropanesulfonamido)thiazol-4-yl)-N-(4-(6-methoxy-5-methylpyridin-3-yl)phenyl)-2-methylpropanamide | Method 2 using INTB53, [UPLC acidic], 487, (1.4) | 12.57 (s, 1H), 9.37 (s, 1H), 8.30 (d, J = 2.4 Hz, 1H), 7.87 (d, J = 2.4 Hz, 1H), 7.71 (d, J = 8.6 Hz, 2H), 7.62 (d, J = 8.6 Hz, 2H), 6.54 (s, 1H), 3.92 (s, 3H), 2.52 (s, 1H), 2.21 (s, 3H), 1.58 (s, 6H), 0.91 (s, 4H). |
| T252 | N-(4-(5-chloropyridin-3-yl)phenyl)-2-(2-(cyclopropanesulfonamido)thiazol-4-yl)-2-methylpropanamide | Method 2 using INTB53, [UPLC acidic], 477, (1.3) | (Methanol-d4) 8.76 (d, J = 2.0 Hz, 1H), 8.52 (d, J = 2.3 Hz, 1H), 8.15 (d, J = 2.2 Hz, 1H), 7.77 (d, J = 8.4 Hz, 2H), 7.68 (d, J = 8.5 Hz, 2H), 6.61 (s, 1H), 3.37 (s, 1H), 1.67 (s, 6H), 1.11 (s, 2H), 0.96 (d, J = 6.4 Hz, 2H). 2 exchangable protons not observed |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | ¹H NMR Chemical Shift Data (DMSO-d6 unless stated) |
|---|---|---|---|
| T253 | 2-(2-(cyclopropanesulfonamido)thiazol-4-yl)-N-(4-(5-fluoropyridin-3-yl)phenyl)-2-methylpropanamide | Method 2 using INTB53, [UPLC acidic], 461, (1.2) | 12.56 (s, 1H), 9.44 (s, 1H), 8.80 (d, J = 2.0 Hz, 1H), 8.52 (d, J = 2.7 Hz, 1H), 8.05 (dt, J = 10.5, 2.3 Hz, 1H), 7.77 (d, J = 1.8 Hz, 4H), 6.53 (s, 1H), 2.58 (s, 1H), 1.57 (s, 6H), 0.92-0.85 (m, 4H). |
| T254 | 2-(2-(cyclopropanesulfonamido)thiazol-4-yl)-2-methyl-N-(4-(4-methylpyridin-3-yl)phenyl)propanamide | Method 2 using INTB53, [UPLC acidic], 457, (0.7 | 12.56 (s, 1H), 9.42 (s, 1H), 8.44-8.33 (m, 2H), 7.78-7.69 (m, 2H), 7.40-7.29 (m, 3H), 6.57 (s, 1H), 2.66-2.54 (m, 1H), 2.28 (s, 3H), 1.59 (s, 6H), 0.96-0.85 (m, 4H). |
| T255 | 2-(2-(cyclopropanesulfonamido)thiazol-4-yl)-2-methyl-N-(4-(4-trifluoromethyl)pyridin-3-yl)phenyl)propanamide | Method 2 using INTB53, [UPLC acidic], 511, (1.3) | (Methanol-d4) δ 8.78 (s, 1H), 8.62 (s, 1H), 7.79 (d, J = 5.2 Hz, 1H), 7.74-7.67 (m, 2H), 7.33 (d, J = 8.3 Hz, 2H), 6.60 (s, 1H), 2.79-2.44 (m, 1H), 1.66 (s, 6H), 1.14-1.05 (m, 2H), 1.00-0.83 (m, 2H). |
| T256 | N-(4-(-chloropyridin-3-yl)-2-methoxyphenyl)-2-(2-(cyclopropanesulfonamido)thiazol-4-yl)-2-methylpropanamide | Method 2 using INTB54, [HPLC acidic], 507, (2.04) | 12.65 (s, 1H), 8.92 (d, J = 2.0 Hz, 1H), 8.60 (d, J = 2.3 Hz, 1H), 8.39 (s, 1H), 8.31 (t, J = 2.2 Hz, 1H), 8.07 (d, J = 8.4 Hz, 1H), 7.49-7.37 (m, 2H), 6.76 (s, 1H), 3.93 (s, 3H), 2.64-2.59 (m, 1H), 1.57 (s, 6H), 0.96-0.88 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T257 | 2-(2-(cyclopropanesulfonamido)thiazol-4-yl)-N-(4-(5-(dimethylamino)pyridin-3-yl)phenyl)-2-methylpropanamide | Method 2 using INTB53, [UPLC acidic], 486, (0.76) | 12.55 (s, 1H), 9.41 (s, 1H), 8.16 (d, J = 1.8 Hz, 1H), 8.07 (d, J = 2.8 Hz, 1H), 7.76-7.66 (m, 4H), 7.23 (t, J = 2.3 Hz, 1H), 6.54 (s, 1H), 2.99 (s, 6H), 2.63-2.54 (m, 1H), 1.56 (s, 6H), 0.93-0.83 (m, 4H). |
| T258 | 2-(2-(cyclopropanesulfonamido)thiazol-4-yl)-N-(2-methoxy-4-(5-methylpyridin-3-yl)phenyl)-2-methylpropanamide | Method 2 using INTB54, [UPLC acidic], 487, (0.86) | (Methanol-d4) 8.59 (d, J = 2.1 Hz, 1H), 8.37-8.31 (m, 1H), 8.13 (d, J = 8.2 Hz, 1H), 7.92 (m, 1H), 7.29-7.20 (m, 2H), 6.75 (s, 1H), 3.95 (s, 3H), 2.69-2.58 (m, 1H), 2.43 (d, J = 0.7 Hz, 3H), 1.65 (s, 6H), 1.17-1.02 (m, 2H), 1.05-0.90 (m, 2H). 2 exchangable protons not observed |
| T259 | 2-(2-(cyclopropanesulfonamido)thiazol-4-yl)-N-(2-methoxy-4-(5-(trifluoromethyl)pyridin-3-yl)phenyl)-2-methylpropanamide | Method 2 using INTB54, [UPLC acidic], 541, (1.43) | 12.69 (s, 1H), 9.26 (d, J = 2.1 Hz, 1H), 8.94 (d, J = 1.0 Hz, 1H), 8.51 (m, 1H), 8.40 (s (br), 1H), 8.07 (s, (br), 1H), 7.55-7.43 (m, 2H), 6.74 (s (br), 1H), 3.94 (s, 3H), 2.71-2.55 (m, 1H), 1.56 (s, 6H), 0.92 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T260 | 2-(2-(cyclopropanesulfonamido)thiazol-4-yl)-N-(4-(6-methoxypyridin-3-yl)phenyl)acetamide | Method 2, using INTB73 [UPLC acidic], 445, (1.13) | 12.52 (s, 1H), 10.27 (s, 1H), 8.46 (dd, J = 2.6, 0.8 Hz, 1H), 7.99 (dd, J = 8.7, 2.6 Hz, 1H), 7.70-7.66 (m, 2H), 7.63 (d, J = 6.9 Hz, 1H), 6.89 (dd, J = 8.6, 0.7 Hz, 1H), 6.54 (s, 1H), 3.88 (s, 3H), 3.65 (s, 2H), 2.60-2.55 (m, 1H), 0.92-0.83 (m, 4H). |
| T261 | 2-(2-(cyclopropanesulfonamido)thiazol-4-yl)-N-(5'-fluoro-[3,3'-bipyridin]-6-yl)-2-methylpropanamide | Method 2 using INTB55, [UPLC acidic], 462, (1.1) | 12.57 (s, 1H), 10.07 (s, 1H), 8.87 (d, J = 1.9 Hz, 1H), 8.81 (d, J = 2.5 Hz, 1H), 8.60 (d, J = 2.7 Hz, 1H), 8.28 (dd, J = 8.7, 2.6 Hz, 1H), 8.22-8.11 (m, 2H), 6.57 (s, 1H), 2.62-2.57 (m, 1H), 1.61 (s, 6H), 0.94-0.87 (m, 4H). |
| T262 | N-(5-(6-chloropyrazin-2-yl)pyridin-2-yl)-2-(2-(cyclopropanesulfonamido)thiazol-4-yl)-2-methylpropanamide | Method 1b using INTB37 and INTA64, [HPLC basic], 479, (1.8) | 12.56 (s, 1H), 10.42 (s, 1H), 9.33 (s, 1H), 9.10 (s, 1H), 8.77 (s, 1H), 8.53 (dd, J = 8.7, 2.4 Hz, 1H), 8.23 (dd, J = 8.9, 0.8 Hz, 1H), 6.55 (s, 1H), 2.62-2.55 (m, 1H), 1.59 (s, 6H), 0.94-0.79 (m, 4H). |
| T263 | N-(5-(6-cyanopyrazin-2-yl)pyridin-2-yl)-2-(2-(cyclopropanesulfonamido)thiazol-4-yl)-2-methylpropanamide | Method 1b using INTB37 and INTA63, [HPLC basic], 470, (1.7) | 12.59 (s, 1H), 10.27 (s, 1H), 9.64 (s, 1H), 9.19 (s, 1H), 9.16 (d, J = 2.5 Hz, 1H), 8.60 (dd, J = 8.8, 2.5 Hz, 1H), 8.24 (d, J = 8.8 Hz, 1H), 6.59 (s, 1H), 2.64-2.55 (m, 1H), 1.62 (s, 6H), 0.96-0.84 (m, 4H) |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)$^+$, (Rt/min) | $^1$H NMR Chemical Shift Data (DMSO-d6 unless stated) |
|---|---|---|---|
| T264 | 2-(2-(cyclopropanesulfonamido)thiazol-4-yl)-2-methyl-N-(5-(pyrimidin-5-yl)pyridin-2-yl)propanamide | Method 1b using INTB37, [UPLC acidic], 445, (0.92) | (Methanol-d4) 9.18 (s, 1H), 9.13 (s, 2H), 8.69 (d, J = 2.5 Hz, 1H), 8.32 (d, J = 8.7 Hz, 1H), 8.21 (dd, J = 8.7, 2.5 Hz, 1H), 6.72 (s, 1H), 2.68 (s, 1H), 1.69 (s, 6H), 1.16-1.08 (m, 2H), 1.03-0.93 (m, 2H), 2 exchangable protons not observed |
| T265 | 2-(2-(cyclopropanesulfonamido)thiazol-4-yl)-N-(4-(6-methoxypyrazin-2-yl)phenyl)-2-methylpropanamide | Method 2b using INTB56, [HPLC acidic], 474, (1.93) | 12.60 (s, 1H), 9.52 (s, 1H), 8.80 (s, 1H), 8.22 (s, 1H), 8.17-8.08 (m, 2H), 7.87-7.72 (m, 2H), 6.55 (s, 1H), 4.02 (s, 3H), 2.66-2.54 (m, 1H), 1.59 (s, 6H), 0.97-0.82 (m, 4H). |
| T266 | 2-(2-(cyclopropanesulfonamido)thiazol-4-yl)-2-methyl-N-(4-(6-methylpyrazin-2-yl)phenyl)propanamide | Method 2b using INTB56, [HPLC acidic], 458, (2.13) | 12.65 (s, 1H), 9.56 (s, 1H), 9.09 (s, 1H), 8.52 (s, 1H), 8.24-8.12 (m, 2H), 7.91-7.78 (m, 2H), 6.62 (s, 1H), 2.69-2.63 (m, 1H), 2.62 (s, 3H), 1.65 (s, 6H), 1.02-0.90 (m, 4H). |
| T267 | 2-(2-(cyclopropanesulfonamido)thiazol-4-yl)-2-methyl-N-(4-(6-trifluoromethyl)pyrazin-2-yl)phenyl)propanamide | Method 2b using INTB56, [HPLC acidic], 512, (2.65) | 12.60 (s, 1H), 9.60 (s, 2H), 9.09 (s, 1H), 8.28-8.15 (m, 2H), 7.94-7.81 (m, 2H), 6.57 (s, 1H), 2.64-2.55 (m, 1H), 1.59 (s, 6H), 0.97-0.86 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T268 | N-(4-(6-chloropyridin-2-yl)phenyl)-2-(2-(cyclopropanesulfonamido)thiazol-4-yl)-2-methylpropanamide | Method 2b using INTB56, [HPLC acidic], 477, (2.1) | (Methanol-d4) 8.05-7.98 (m, 2H), 7.87-7.78 (m, 2H), 7.75-7.70 (m, 2H), 7.33 (dd, J = 6.6, 2.0 Hz, 1H), 6.62 (s, 1H), 2.70-2.59 (m, 1H), 1.67 (s, 6H), 1.14-1.07 (m, 2H), 1.02-0.92 (m, 2H), 2 exchangable protons not observed |
| T269 | 2-(2-(cyclopropanesulfonamido)thiazol-4-yl)-N-(4-(6-methoxypyridin-2-yl)phenyl)-2-methylpropanamide | Method 2b using INTB56, [HPLC acidic], 473, (2.11) | 12.57 (s, 1H), 9.44 (s, 1H), 8.13-8.05 (m, 2H), 7.80-7.71 (m, 3H), 7.56-7.49 (m, 1H), 6.78-6.70 (m, 1H), 6.54 (s, 1H), 3.96 (s, 3H), 2.65-2.56 (m, 1H), 1.58 (s, 6H), 0.95-0.83 (m, 4H) |
| T270 | 2-(2-(cyclopropanesulfonamido)thiazol-4-yl)-2-methyl-N-(4-(6-(trifluoromethyl)pyridin-2-yl)phenyl)propanamide | Method 2b using INTB56, [HPLC acidic], 511, (2.24) | 12.58 (s, 1H), 9.51 (s, 1H), 8.27 (d, J = 8.1 Hz, 1H), 8.18-8.08 (m, 3H), 7.87-7.77 (m, 3H), 6.55 (s, 1H), 2.64-2.56 (m, 1H), 1.59 (s, 6H), 0.97-0.84 (m, 4H). |
| T271 | 2-(2-(cyclopropanesulfonamido)thiazol-4-yl)-N-(4-(4-methoxypyridin-2-yl)phenyl)-2-methylpropanamide | Method 2b using INTB56, [HPLC acidic], 473, (1.15) | 12.55 (s, 1H), 9.42 (s, 1H), 8.44 (d, J = 5.6 Hz, 1H), 8.12-8.06 (m, 2H), 7.80-7.69 (m, 2H), 7.46 (d, J = 2.4 Hz, 1H), 6.91 (dd, J = 5.7, 2.3 Hz, 1H), 6.56 (s, 1H), 3.91 (s, 3H), 2.65-2.54 (m, 1H), 1.58 (s, 6H), 0.97-0.85 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T272 | 2-(2-(cyclopropanesulfonamido)thiazol-4-yl)-N-(4-(6-isopropoxypyrazin-2-yl)phenyl)-2-methylpropanamide | Method 2b using INTB56, [HPLC basic], 502, (1.9) | 12.58 (s, 1H), 9.50 (s, 1H), 8.75 (s, 1H), 8.13 (s, 1H), 8.11-8.06 (m, 2H), 7.85-7.73 (m, 2H), 6.55 (s, 1H), 5.49-5.35 (m, 1H), 2.64-2.55 (m, 1H), 1.59 (s, 6H), 1.39 (d, J = 6.2 Hz, 6H), 0.97-0.84 (m, 4H). |
| T273 | 2-(2-(cyclopropanesulfonamido)thiazol-4-yl)-N-(4-(6-cyclopropoxypyrazin-2-yl)phenyl)-2-methylpropanamide | Method 2b, using INTB56, [UPLC basic], 500, (1.2) | 12.58 (s, 1H), 9.50 (s, 1H), 8.85 (s, 1H), 8.24 (s, 1H), 8.15-8.11 (m, 2H), 7.83-7.78 (m, 2H), 6.55 (s, 1H), 4.45-4.39 (m, 1H), 2.65-2.54 (m, 1H), 1.59 (s, 6H), 0.95-0.75 (m, 8H). |
| T274 | 2-(2-(cyclopropanesulfonamido)thiazol-4-yl)-N-(2-fluoro-4-(pyrazin-2-yl)phenyl)-2-methylpropanamide | Method 2b using INTB57, [UPLC acidic], 462, (1.1) | (Methanol-d4) 10.68 (d, J = 1.5 Hz, 1H), 10.23 (dd, J = 2.6, 1.5 Hz, 1H), 10.09 (d, J = 2.5 Hz, 1H), 9.55-9.40 (m, 3H), 8.23 (s, 1H), 4.26-4.11 (m, 1H), 3.22 (s, 6H), 2.68-2.61 (m, 2H), 2.58-2.46 (m, 2H). v |
| T275 | 2-(2-(cyclopropanesulfonamido)thiazol-4-yl)-N-(2-fluoro-4-(6-methoxypyrazin-2-yl)phenyl)-2-methylpropanamide | Method 2b using INTB57, [UPLC acidic], 492, (1.3) | 12.62 (s, 1H), 9.28 (s, 1H), 8.88 (s, 1H), 8.29 (s, 1H), 8.10-7.98 (m, 2H), 7.72 (s, 1H), 6.61 (s, 1H), 4.04 (s, 3H), 2.62-2.57 (m, 1H), 1.59 (s, 6H), 1.07-0.73 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T276 | N-(4-(6-chloro-3-methylpyrazin-2-yl)phenyl)-2-(2-(cyclopropanesulfonamido)thiazol-4-yl)-2-methylpropanamide | Method 2b using INTB56, [HPLC basic], 493, (1.73) | 12.59 (s, 1H), 8.62 (s, 1H), 7.90-7.75 (m, 2H), 7.71-7.54 (m, 2H), 6.44 (s, 1H), 2.60 (s, 4H), 1.54 (s, 6H), 0.99-0.74 (m, 4H) 1 exchangable protons not observed |
| T277 | N-(4-(6-chloro-5-methylpyrazin-2-yl)phenyl)-2-(2-(cyclopropanesulfonamido)thiazol-4-yl)-2-methylpropanamide | Method 2b using INTB56, [HPLC basic], 493, (1.85) | 12.57 (s, 1H), 9.55 (s, 1H), 9.12 (s, 1H), 8.15-8.04 (m, 2H), 7.91-7.72 (m, 2H), 6.63-6.42 (m, 1H), 2.66-2.56 (m, 4H), 1.58 (s, 6H), 0.97-0.82 (m, 4H) |
| T278 | 2-(2-(cyclopropanesulfonamido)thiazol-4-yl)-2-methyl-N-(4-(6-(pyrrolidin-1-yl)pyrazin-2-yl)phenyl)propanamide | Method 2b using INTB56, [HPLC basic], 513, (1.86) | 12.56 (s, 1H), 9.45 (s, 1H), 8.34 (s, 1H), 8.10-8.00 (m, 2H), 7.88 (s, 1H), 7.79-7.70 (m, 2H), 6.56 (s, 1H), 3.62-3.42 (m, 4H), 2.59 (d, J = 6.0 Hz, 1H), 2.06-1.93 (m, 4H), 1.59 (s, 6H), 0.99-0.82 (m, 4H). |
| T279 | 2-(2-(cyclopropanesulfonamido)thiazol-4-yl)-N-(4-(6-(2-(dimethylamino)ethoxy)pyrazin-2-yl)phenyl)-2-methylpropanamide | Method 2b using INTB56, [HPLC basic], 531, (1.57) | 11.6 (s, 1H), 10.07 (s, 1H), 8.81 (s, 1H), 8.20 (s, 1H), 8.17-8.07 (m, 2H), 7.88-7.79 (m, 2H), 6.46 (s, 1H), 4.60 (t, J = 5.5 Hz, 2H), 3.01-2.93 (m, 2H), 2.65-2.57 (m, 1H), 2.46 (s, 6H), 1.55 (s, 6H), 0.96-0.75 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T280 | 2-(2-(cyclopropanesulfonamido)thiazol-4-yl)-2-methyl-N-(4-(3-methylpyrazin-2-yl)phenyl)propanamide | Method 2b using INTB56, [HPLC basic], 458, (1.46) | 12.59 (s, 1H), 9.47 (s, 1H), 8.54 (d, J = 2.5 Hz, 1H), 8.50 (d, J = 2.5 Hz, 1H), 7.80-7.75 (m, 2H), 7.66-7.61 (m, 2H), 6.56 (s, 1H), 2.64-2.57 (m, 4H), 1.59 (s, 6H), 0.91 (s, 4H). |
| T281 | N-(4-(6-acetamidopyrazin-2-yl)phenyl)-2-(2-(cyclopropanesulfonamido)thiazol-4-yl)-2-methylpropanamide | Method 2b using INTB56, [HPLC acidic], 501, (1.65) | 12.57 (s, 1H), 10.78 (s, 1H), 9.54-9.43 (m, 1H), 9.21 (s, 1H), 8.91 (s, 1H), 8.12-8.06 (m, 2H), 7.84-7.77 (m, 2H), 6.55 (s, 1H), 2.65-2.53 (m, 1H), 2.16 (s, 3H), 1.58 (s, 6H), 0.96-0.84 (m, 4H). |
| T282 | 2-(2-(cyclopropanesulfonamido)thiazol-4-yl)-N-(4-(5,6-dimethylpyrazin-2-yl)phenyl)-2-methylpropanamide | Method 2b using INTB56, [HPLC acidic], 473, (1.86) | 12.57 (s, 1H), 9.46 (s, 1H), 8.87 (s, 1H), 8.10-8.03 (m, 2H), 7.80-7.73 (m, 2H), 6.54 (s, 1H), 2.65-2.56 (m, 1H), 2.54 (s, 3H), 1.57 (s, 6H), 0.96-0.83 (m, 4H). |
| T283 | 2-(2-(cyclopropanesulfonamido)thiazol-4-yl)-N-(4-(6-(hydroxymethyl)pyrazin-2-yl)phenyl)-2-methylpropanamide | Method 2b using INTB56, [HPLC acidic], 474, (1.54) | 12.58 (s, 1H), 9.50 (s, 1H), 9.11 (s, 1H), 8.62 (s, 1H), 8.17-8.10 (m, 2H), 7.84-7.78 (m, 2H), 6.56 (s, 1H), 5.62 (t, J = 5.9 Hz, 1H), 4.70 (d, J = 5.8 Hz, 2H), 2.59 (s, 1H), 1.58 (s, 6H), 1.00-0.83 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | ¹H NMR Chemical Shift Data (DMSO-d6 unless stated) |
|---|---|---|---|
| T284 | 2-(2-(cyclopropanesulfonamido)thiazol-4-yl)-N-(4-(3,6-dimethylpyrazin-2-yl)phenyl)-2-methylpropanamide | Method 2b using INTB56, [HPLC acidic], 472, (1.72) | 12.58 (s, 1H), 9.45 (s, 1H), 8.37 (s, 1H), 7.78-7.72 (m, 2H), 7.62-7.56 (m, 2H), 6.55 (s, 1H), 2.63-2.54 (m, 1H), 2.52 (s, 3H), 1.58 (s, 6H), 0.95-0.85 (m, 4H). |
| T285 | 2-(2-(cyclopropanesulfonamido)thiazol-4-yl)-N-(4-(5-methoxypyridin-3-yl)-2-methylphenyl)-2-methylpropanamide | Method 2b using INTB60, [HPLC acidic], 487, (1.58) | 12.58 (s, 1H), 8.95 (s, 1H), 8.49 (d, J = 1.8 Hz, 1H), 8.27 (d, J = 2.7 Hz, 1H), 7.67-7.61 (m, 2H), 7.59 (dd, J = 8.2, 2.2 Hz, 1H), 7.45-7.34 (m, 1H), 6.63 (s, 1H), 3.92 (s, 3H), 2.64-2.54 (m, 1H), 2.23 (s, 3H), 1.59 (s, 6H), 0.97-0.86 (m, 4H). |
| T286 | N-(4-(5-cyanopyridin-3-yl)-2-methylphenyl)-2-(2-(cyclopropanesulfonamido)thiazol-4-yl)-2-methylpropanamide | Method 2b using INTB60, [HPLC acidic], 482, (1.6) | 12.60 (s, 1H), 9.21 (d, J = 2.3 Hz, 1H), 9.03-8.91 (m, 2H), 8.67 (t, J = 2.1 Hz, 1H), 7.78-7.72 (m, 1H), 7.68 (dd, J = 8.3, 2.3 Hz, 1H), 7.47-7.37 (m, 1H), 6.62 (s, 1H), 2.64-2.54 (m, 1H), 2.24 (s, 3H), 1.59 (s, 6H), 0.99-0.83 (m, 4H). |
| T287 | 2-(2-(cyclopropanesulfonamido)thiazol-4-yl)-N-(4-(5-fluoropyridin-3-yl)-2-methylphenyl)-2-methylpropanamide | Method 2b using INTB60, [UPLC acidic], 475, (1.18) | 12.60 (s, 1H), 8.96 (s, 1H), 8.82 (t, J = 1.9 Hz, 1H), 8.56 (d, J = 2.7 Hz, 1H), 8.08 (ddd, J = 10.5, 2.7, 1.8 Hz, 1H), 7.70 (d, J = 2.2 Hz, 1H), 7.64 (dd, J = 8.2, 2.3 Hz, 1H), 7.42 (d, J = 8.2 Hz, 1H), 6.62 (s, 1H), 2.59 (s, 1H), 2.23 (s, 3H), 1.59 (s, 6H), 0.91 (d, J = 8.1 Hz, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T288 | N-(4-(5-chloropyridin-3-yl)-3-methylphenyl)-2-(2-(cyclopropanesulfonamido)thiazol-4-yl)-2-methylpropanamide | Method 2 using INTB59, [UPLC acidic], 491, (1.33) | 12.57 (s, 1H), 9.36 (s, 1H), 8.62 (d, J = 2.3 Hz, 1H), 8.52 (d, J = 1.9 Hz, 1H), 7.98-7.93 (m, 1H), 7.61-7.55 (m, 2H), 7.27-7.21 (m, 1H), 6.53 (s, 1H), 2.63-2.54 (m, 1H), 2.24 (s, 3H), 1.57 (s, 6H), 0.95-0.85 (m, 4H). |
| T289 | N-(4-(5-cyanopyridin-3-yl)-3-ethoxyphenyl)-2-(2-(cyclopropanesulfonamido)thiazol-4-yl)-2-methylpropanamide | Method 2, using INTB71 [UPLC acidic], 512, (1.29) | 12.58 (s, 1H), 9.44 (s, 1H), 9.03-8.99 (m, 1H), 8.94-8.90 (m, 1H), 8.44-8.39 (m, 1H), 7.56 (s, 1H), 7.46-7.36 (m, 2H), 6.54 (s, 1H), 4.10-3.98 (m, 2H), 2.61-2.57 (m, 1H), 1.58 (s, 6H), 1.31 (t, J = 6.9, 1.1 Hz, 3H), 0.93-0.89 (m, 4H). |
| T290 | 2-(2-(cyclopropanesulfonamido)thiazol-4-yl)-N-(4-(5-ethoxypyridin-3-yl)phenyl)-2-methylpropanamide | Method 2b using INTB56, [HPLC acidic], 487, (1.6) | 12.55 (s, 1H), 9.43 (s, 1H), 8.49 (d, J = 1.8 Hz, 1H), 8.25 (d, J = 2.7 Hz, 1H), 7.75 (s, 4H), 7.62 (m, 1H), 6.57 (s, 1H), 4.21 (q, J = 7.0 Hz, 2H), 2.59 (m, |
| T291 | 2-(2-(cyclopropanesulfonamido)thiazol--4yl)-N-(4-(6-cyclopropylpyrazin-2-yl)phenyl)butanamide | Method 2c, using INTB38 [UPLC acidic], 484, (1.37) | 12.62 (s, 1H), 10.36 (s, 1H), 8.94 (s, 1H), 8.52 (s, 1H), 8.10-8.04 (m, 2H), 7.80-7.71 (m, 2H), 6.55 (s, 1H), 3.61 (t, J = 7.4 Hz, 1H), 2.64-2.56 (m, 1H), 2.29-2.18 (m, 1H), 2.03-1.82 (m, 2H), 1.11-1.03 (m, 4H), 0.94-0.85 (m, 7H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T292 | 2-(2-(cyclopropanesulfonamido)thiazol-4-yl)-N-(5-(5-methoxypyridin-3-yl)pyrimidin-2-yl)-2-methylpropanamide | Method 3 using INTB58 and INTA115, [UPLC acidic], 475, (0.82) | 12.58 (s, 1H), 10.25 (s, 1H), 9.11 (s, 2H), 8.59 (d, J = 1.8 Hz, 1H), 8.35 (d, J = 2.8 Hz, 1H), 7.80 (t, J = 2.3 Hz, 1H), 6.57 (s, 1H), 3.91 (s, 3H), 2.59 (td, J = 7.3, 3.4 Hz, 1H), 1.59 (s, 6H), 0.90 (dd, J = 6.3, 3.3 Hz, 4H). |
| T293 | 2-(2-(cyclopropanesulfonamido)thiazol-4-yl)-N-(5-(5-fluoropyridin-3-yl)pyrimidin-2-yl)-2-methylpropanamide | Method 3 using INTB58 and INTA116, [UPLC acidic], 463, (0.9) | 12.63 (s, 1H), 10.34 (s, 1H), 9.15 (s, 2H), 8.93 (t, J = 1.8 Hz, 1H), 8.64 (d, J = 2.7 Hz, 1H), 8.27 (dt, J = 10.3, 2.3 Hz, 1H), 6.55 (s, 1H), 2.61-2.56 (m, 1H), 1.59 (s, 6H), 0.93-0.86 (m, 4H). |
| T294 | 2-(2-(cyclopropanesulfonamido)thiazol-4-yl)-2-methyl-N-(5-(5-(trifluoromethyl)pyridin-3-yl)pyrimidin-2-yl)propanamide | Method 3 using INTB58 and INTA117, [UPLC acidic], 513, (1.1) | 12.62 (s, 1H), 10.34 (s, 1H), 9.32 (d, J = 2.1 Hz, 1H), 9.20 (s, 2H), 9.03 (d, J = 2.1 Hz, 1H), 8.70-8.62 (m, 1H), 6.56 (s, 1H), 2.61-2.56 (m, 1H), 1.59 (s, 6H), 0.93-0.88 (m, 4H). |
| T295 | N-(5-(6-ethoxypyrazin-2-yl)pyridin-2-yl)-2-methyl-2-(2-((2-methylpropyl)sulfonamido)thiazol-4-yl)propanamide | Method 1b using INTB52 and INTA72, [UPLC acidic], 506, (1.45) | 12.51 (s, 1H), 10.08 (s, 1H), 9.07 (s, 1H), 8.85 (s, 1H), 8.51 (d, J = 9.3 Hz, 1H), 8.25 (s, 1H), 8.18 (dd, J = 8.8, 0.8 Hz, 1H), 6.65-6.49 (m, 1H), 4.48 (q, J = 7.1 Hz, 2H), 2.95-2.83 (m, 2H), 2.16-2.00 (m, 1H), 1.59 (s, 6H), 1.40 (t, J = 7.0 Hz, 3H), 1.05-0.95 (m, 6H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | ¹H NMR Chemical Shift Data (DMSO-d6 unless stated) |
|---|---|---|---|
| T296 | N-(4-(6-ethoxypyrazin-2-yl)phenyl)-2-methyl-2-(2-((trifluoromethyl)sulfonamido)thiazol-4-yl)propanamide | Method 1b using INTB48 and INTA38, [UPLC acidic], 516, (1.59) | 13.93 (v. br. s, 1H), 9.69 (b. br. s, 1H), 8.77 (s, 1H), 8.17 (s, 1H), 8.13-8.04 (m, 2H), 7.82-7.67 (m, 2H), 6.83 (s, 1H), 4.47 (q, J = 7.1 Hz, 2H), 1.57 (s, 6H), 1.40 (t, J = 7.0 Hz, 3H). |
| T297 | 2-methyl-2-(2-((1-methylethyl)sulfonamido)thiazol-4-yl)-N-(4-(pyridin-3-yl)phenyl)propanamide | Method 1b using INTB49, [HPLC acidic], 445, (1.22) | 12.51 (s, 1H), 9.41 (s, 1H), 8.89 (d, J = 2.4 Hz, 1H), 8.59-8.41 (m, 1H), 8.10-8.00 (m, 1H), 7.78-7.73 (m, 2H), 7.73-7.69 (m, 2H), 7.46 (dd, J = 8.0, 4.7 Hz, 1H), 6.54 (s, 1H), 3.15-3.07 (m, 1H), 1.57 (s, 6H), 1.23 (d, J = 6.8 Hz, 6H). |
| T298 | N-(4-(6-ethoxypyrazin-2-yl)phenyl)-2-methyl-2-(2-((1-methylethyl)sulfonamido)thiazol-4-yl)propanamide | Method 1b using INTB49 and INTA38, [HPLC acidic], 490, (2.1) | 12.54 (s, 1H), 9.48 (s, 1H), 8.77 (s, 1H), 8.18 (s, 1H), 8.14-8.07 (m, 2H), 7.81-7.75 (m, 2H), 6.52 (s, 1H), 4.47 (q, J = 7.1 Hz, 2H), 3.16-3.04 (m, 1H), 1.57 (s, 6H), 1.40 (t, J = 7.0 Hz, 3H), 1.22 (d, J = 6.8 Hz, 6H). |
| T299 | 2-methyl-2-(2-((1-methylcyclopropane)-1-sulfonamido)thiazol-4-yl)-N-(4-(pyridin-3-yl)phenyl)propanamide | Method 1b using INTB50, [HPLC acidic], 457, (1.26) | 12.56 (s, 1H), 9.42 (s, 1H), 8.89 (dd, J = 2.4, 0.9 Hz, 1H), 8.53 (dd, J = 4.8, 1.6 Hz, 1H), 8.06 (ddd, J = 8.0, 2.4, 1.6 Hz, 1H), 7.77-.74 (m, 2H), 7.74-7.68 (m, 2H), 7.46 (ddd, J = 7.9, 4.8, 0.9 Hz, 1H), 6.53 (s, 1H), 1.57 (s, 6H), 1.40 (s, 3H), 1.20-1.11 (m, 2H), 0.81-0.67 (m, 2H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | ¹H NMR Chemical Shift Data (DMSO-d6 unless stated) |
| --- | --- | --- | --- |
| T300 | N-(4-(5-chloropyridin-3-yl)phenyl)-2-methyl-2-(2-((1-methylcyclopropane)-1-sulfonamido)thiazol-4-yl)propanamide | Method 1b using INTB50 and INTA18, [HPLC acidic], 491, (2.05) | 12.59 (s, 1H), 9.45 (s, 1H), 8.87 (d, J = 2.1 Hz, 1H), 8.58 (d, J = 2.3 Hz, 1H), 8.24 (t, J = 2.2 Hz, 1H), 7.86-7.72 (m, 4H), 6.51 (s, 1H), 1.66-1.49 (m, 6H), 1.40 (s, 3H), 1.23-1.07 (m, 2H), 0.77-0.66 (m, 2H). |
| T301 | N-(4-(6-ethoxypyrazin-2-yl)phenyl)-2-methyl-2-(2-((1-methylcyclopropane)-1-sulfonamido)thiazol-4-yl)propanamide | Method 1b using INTB50 and INTA38, [HPLC acidic], 502, (2.16) | 12.59 (s, 1H), 9.49 (s, 1H), 8.77 (s, 1H), 8.18 (s, 1H), 8.11-8.03 (m, 2H), 7.79 (d, J = 8.7 Hz, 2H), 6.52 (s, 1H), 4.47 (q, J = 7.1 Hz, 2H), 1.58 (s, 6H), 1.51-1.36 (m, 6H), 1.22-1.13 (m, 2H), 0.81-0.70 (m, 2H). |
| T302 | 2-methyl-2-(2-((1-methylcyclopropane)-1-sulfonamido)thiazol-4-yl)-N-(4-(6-(trifluoromethl)pyrazin-2-yl)phenyl)propanamide | Method 1b using INTB50 and INTA39, [HPLC acidic], 526, (2.22) | 12.60 (s, 1H), 9.59 (s, 1H), 9.58 (s, 1H), 9.08 (s, 1H), 8.23-8.17 (m, 2H), 7.89-7.84 (m, 2H), 6.53 (s, 1H), 1.58 (s, 6H), 1.40 (s, 3H), 1.23-1.10 (m, 2H), 0.81-0.70 (m, 2H). |
| T303 | 2-(2-(((1,1-dimethylethyl)sulfonamido)thiazol-4-yl)-2-methyl-N-(4-(pyridin-3-yl)phenyl)propanamide | Method 1b using INTB51, [HPLC acidic], 459, (1.31) | 12.51 (s, 1H), 9.45 (s, 1H), 8.89 (dd, J = 2.5, 0.9 Hz, 1H), 8.53 (dd, J = 4.7, 1.6 Hz, 1H), 8.06 (dd, J = 8.0, 2.5, 1.6 Hz, 1H), 7.77-7.73 (m, 2H), 7.73-7.69 (m, 2H), 7.46 (ddd, J = 8.0, 4.7, 0.9 Hz, 1H), 6.50 (s, 1H), 1.57 (s, 6H), 1.28 (s, 9H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | ¹H NMR Chemical Shift Data (DMSO-d6 unless stated) |
|---|---|---|---|
| T304 | 2-(2-((1,1-dimethylethyl)sulfonamido)thiazol-4-yl)-N-(4-(6-ethoxypyrazin-2-yl)phenyl)-2-methylpropanamide | Method 1b using INTB51 and INTA38, [HPLC acidic], 504, (2.2) | 12.51 (s, 1H), 9.48 (s, 1H), 8.77 (d, J = 0.6 Hz, 1H), 8.18 (d, J = 0.5 Hz, 1H), 8.14-8.07 (m, 2H), 7.81-7.73 (m, 2H), 6.51 (s, 1H), 4.47 (q, J = 7.1 Hz, 2H), 1.58 (s, 6H), 1.40 (t, J = 7.0 Hz, 3H), 1.28 (s, 9H). |
| T305 | 2-(2-((1,1-dimethylethyl)sulfonamido)thiazol-4-yl)-2-methyl-N-(4-(6-(trifluoromethyl)pyrazin-2-yl)phenyl)propanamide | Method 1b using INTB51 and INTA39, [HPLC acidic], 528, (2.26) | 12.52 (s, 1H), 9.59 (s, 1H), 9.57 (s, 1H), 9.08 (s, 1H), 8.22-8.17 (m, 2H), 7.89-7.85 (m, 2H), 6.52 (s, 1H), 1.58 (s, 6H), 1.28 (s, 9H). |
| T306 | 2-(2-(cyclobutanesulfonamido)thiazol-4-yl)-2-methyl-N-(4-(pyridin-3-yl)phenyl)propanamide | Method 1b using INTB47, [HPLC acidic], 457, (1.26) | 12.53 (s, 1H), 9.40 (s, 1H), 8.89 (dd, J = 2.4, 0.9 Hz, 1H), 8.53 (dd, J = 4.8, 1.6 Hz, 1H), 8.06 (ddd, J = 8.0, 2.5, 1.6 Hz, 1H), 7.77-7.73 (m, 2H), 7.73-7.69 (m, 2H), 7.48-7.44 (m, 1H), 6.54 (s, 1H), 3.90-3.71 (m, 1H), 2.33-2.11 (m, 4H), 1.94-1.78 (m, 2H), 1.57 (s, 6H). |
| T307 | 2-(2-(cyclobutanesulfonamido)thiazol-4-yl)-N-(4-(6-ethoxypyrazin-2-yl)phenyl)-2-methylpropanamide | Method 1b using INTB47 and INTA38, [HPLC acidic], 502, (2.14) | 12.56 (s, 1H), 9.48 (s, 1H), 8.77 (d, J = 0.6 Hz, 1H), 8.22-8.14 (m, 1H), 8.14-8.04 (m, 2H), 7.83-7.73 (m, 2H), 6.53 (s, 1H), 4.47 (q, J = 7.1 Hz, 2H), 3.84-3.76 (m, 1H), 2.39-2.13 (m, 4H), 1.96-1.77 (m, 2H), 1.57 (s, 6H), 1.40 (t, J = 7.0 Hz, 3H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T308 | 2-(2-(cyclobutanesulfonamido)thiazol-4-yl)-2-methyl-N-(4-(6-(trifluoromethyl)pyrazin-2-yl)phenyl)propanamide | Method 1b using INTB47 and INTA39, [HPLC acidic], 526, (2.21) | 12.58 (s, 1H), 9.60 (s, 1H), 9.57 (s, 1H), 9.09 (s, 1H), 8.22-8.13 (m, 2H), 7.92-7.80 (m, 2H), 6.55 (s, 1H), 3.85-3.70 (m, 1H), 2.37-2.11 (m, 4H), 1.98-1.75 (m, 2H), 1.58 (s, 6H). |
| T309 | N-(4-(5-cyanopyridin-3-yl)phenyl)-2-(2-(cyclopropanesulfonamido)thiazol-4-yl)-N,2-dimethylpropanamide | Method 1b using INTB37 and INTA67, [HPLC acidic], 482, (1.72) | 12.55 (s, 1H), 9.14 (d, J = 2.3 Hz, 1H), 9.04 (d, J = 1.9 Hz, 1H), 8.61-8.56 (m, 1H), 7.70-7.64 (m, 2H), 7.23 (d, J = 7.9 Hz, 2H), 5.76 (s, 1H), 3.15 (s, 3H), 2.61-2.57 (m, 1H), 1.42 (s, 6H), 0.95-0.89 (m, 4H). |
| T310 | 2-(2-(cyclopropanesulfonamido)thiazol-4-yl)-N,2-dimethyl-N-(4-(6-(trifluoromethyl)pyrazin-2-yl)phenyl)propanamide | Method 1b using INTB37 and INTA65, [UPLC acidic], 526, (1.31) | 12.59 (s, 1H), 9.57 (s, 1H), 9.17 (s, 1H), 8.13-8.07 (m, 2H), 7.30 (d, J = 8.1 Hz, 2H), 5.83 (s, 1H), 3.15 (s, 3H), 2.64-2.60 (m, 1H), 1.42 (s, 6H), 1.02-0.92 (m, 4H). |
| T311 | 2-methyl-2-(2-((2-methylpropyl)sulfonamido)thiazol-4-yl)-N-(4-(pyridin-3-yl)phenyl)propanamide | Method 1b using INTB52, [UPLC acidic], 459, (0.88) | 12.50 (s, 1H), 9.40 (s, 1H), 8.88 (dd, J = 2.4, 0.9 Hz, 1H), 8.53 (dd, J = 4.8, 1.6 Hz, 1H), 8.06 (ddd, J = 8.0, 2.5, 1.6 Hz, 1H), 7.80-7.73 (m, 2H), 7.73-7.67 (m, 2H), 7.46 (ddd, J = 8.0, 4.7, 0.9 Hz, 1H), 6.57 (s, 1H), 2.91 (d, J = 6.5 Hz, 2H), 2.17-2.01 (m, 1H), 1.57 (s, 6H), 1.01 (d, J = 6.7 Hz, 6H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T312 | N-(4-(6-ethoxypyrazin-2-yl)phenyl)-2-methyl-2-(2-((2-methylpropyl)sulfonamido)thiazol-4-yl)propanamide | Method 1b using INTB52 and INTA38, [UPLC acidic], 504, (1.48) | 12.53 (s, 1H), 9.48 (s, 1H), 8.77 (s, 1H), 8.17 (s, 1H), 8.14-8.04 (m, 2H), 7.81-7.63 (m, 2H), 6.54 (s, 1H), 4.47 (q, J = 7.0 Hz, 2H), 2.95-2.85 (m, 2H), 2.16-2.04 (m, 1H), 1.56 (s, 6H), 1.40 (d, J = 7.1 Hz, 3H), 1.00 (d, J = 6.7 Hz, 6H). |
| T313 | 2-methyl-2-(2-((2-methylpropyl)sulfonamido)thiazol-4-yl)-N-(4-(6-(trifluoromethyl)pyrazin-2-yl)phenyl)propanamide | Method 1b using INTB52 and INTA39, [HPLC acidic], 528, (1.52) | 12.52 (s, 1H), 9.58 (s, 1H), 9.07 (s, 1H), 8.27-8.13 (m, 2H), 7.95-7.78 (m, 2H), 6.52 (s, 1H), 2.98-2.86 (m, 2H), 2.16-1.99 (m, 1H), 1.55 (s, 6H), 1.00 (d, J = 6.7 Hz, 6H), 1 × N—H not observed. |
| T314 | N-(4-(5-chloropyridin-3-yl)phenyl)-2-(2-(cyclopropanesulfonamido)-5-methylthiazol-4-yl)-2-methylpropanamide | Method 1e using INTB42 and INTA18, [HPLC acidic], 491 $^{35}$Cl isotope, (2.16) | 12.04 (s, 1H), 9.86 (s, 1H), 8.86 (d, J = 2.0 Hz, 1H), 8.58 (d, J = 2.3 Hz, 1H), 8.23 (t, J = 2.2 Hz, 1H), 7.81-7.73 (m, 4H), 2.62-2.53 (m, 1H), 1.95 (s, 3H), 1.52 (s, 6H), 0.98-0.87 (m, 4H). |
| T315 | 2-(2-(cyclopropanesulfonamido)thiazol-4-yl)-N-methyl-N-(4-(pyridin-3-yl)phenyl)butanamide | Method 1c using INTB38 and INTA68, [UPLC acidic], 457, (0.85) | 12.23 (s, 1H), 8.97-8.92 (m, 1H), 8.59 (dd, J = 4.8, 1.6 Hz, 1H), 8.13 (d, J = 8.0 Hz, 1H), 7.85 (d, J = 8.0 Hz, 2H), 7.50 (dd, J = 8.0, 4.7 Hz, 1H), 7.41-7.36 (m, 2H), 6.37 (s, 1H), 3.47-3.43 (m, 1H), 3.22 (s, 3H), 2.59-2.51 (m, 1H), 1.85-1.78 (m, 1H), 1.72-1.66 (m, 1H), 0.89-0.82 (m, 4H), 0.73 (t, J = 7.3 Hz, 3H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T316 | N-(4-(5-cyanopyridin-3-yl)phenyl)-2-(2-(cyclopropanesulfonamido)thiazol-4-yl)-N-methylbutanamide | Method 1c using INTB38 and INTA67, [UPLC acidic], 482, (1.17) | 12.25 (s, 1H), 9.26 (d, J = 2.3 Hz, 1H), 9.05 (d, J = 1.9 Hz, 1H), 8.74-8.69 (m, 1H), 7.96 (d, J = 7.8 Hz, 2H), 7.45 (d, J = 8.2 Hz, 2H), 6.37 (s, 1H), 3.47-3.43 (m, 1H), 3.24 (s, 3H), 2.58-2.52 (m, 1H), 1.85-1.81 (m, 1H), 1.73-1.69 (m, 1H), 0.91-0.86 (m, 4H), 0.74 (s, 3H). |
| T317 | 2-(2-(cyclopropanesulfonamido)-5-methylthiazol-4-yl)-N-(4-(6-ethoxypyrazin-2-yl)phenyl)-2-methylpropanamide | Method 1e using INTB42 and INTA38, [HPLC acidic], 502, (2.25) | 12.04 (s, 1H), 9.90 (s, 1H), 8.76 (s, 1H), 8.19 (s, 1H), 8.13-8.04 (m, 2H), 7.84-7.73 (m, 2H), 4.48 (q, J = 7.0 Hz, 2H), 2.62-2.55 (m, 1H), 1.95 (s, 3H), 1.53 (s, 6H), 1.40 (t, J = 7.0 Hz, 3H), 0.95-0.85 (m, 4H). |
| T318 | N-(4-(5-chloropyridin-3-yl)phenyl)-2-(2-(cyclopropanesulfonamido)thiazol-4-yl)-N,2-dimethylpropanamide | Method 1b using INTB37 and INTA66, [HPLC acidic], 492 35Cl isotope, (1.20) | 12.54 (s, 1H), 8.81 (d, J = 1.9 Hz, 1H), 8.64 (d, J = 2.3 Hz, 1H), 8.20-8.15 (m, 1H), 7.64-7.59 (m, 2H), 7.19 (d, J = 7.9 Hz, 2H), 5.74 (s, 1H), 3.13 (s, 3H), 2.60-2.56 (m, 1H), 1.40 (s, 6H), 0.92-0.88 (m, 4H). |
| T319 | 2-(2-(cyclopropanesulfonamido)-5-methylthiazol-4-yl)-2-methyl-N-(4-(pyridin-3-yl)phenyl)propanamide | Method 1e using INTB42, [HPLC acidic], 457, (1.377) | 12.02 (s, 1H), 9.83 (s, 1H), 8.88 (dd, J = 2.4, 0.9 Hz, 1H), 8.54 (dd, J = 4.7, 1.6 Hz, 1H), 8.09-8.00 (m, 1H), 7.79-7.65 (m, 4H), 7.49-7.42 (m, 1H), 2.63-2.54 (m, 1H), 1.96 (s, 3H), 1.52 (s, 6H), 0.95-0.90 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T320 | N-(4-(5-cyanopyridin-3yl)-2,6-dimethylphenyl)-2-(2-(cyclopropanesulfonamido)thiazol-4-yl)-2-methylpropanamide | Method 2 using INTB70, [UPLC acidic], 496, (1.16) | 12.57 (s, 1H), 9.19 (d, J = 2.3 Hz, 1H), 8.98 (d, J = 1.9 Hz, 1H), 8.67-8.62 (m, 1H), 7.56 (s, 2H), 6.59 (s, 1H), 2.58-2.54 (m, 1H), 2.19 (s, 6H), 1.61 (s, 6H), 0.92-0.88 (m, 4H). 1 exchangeable proton not observed. |
| T321 | N-(4-(5-chloropyridin-3-yl)-2,6-dimethylphenyl)-2-(2-(cyclopropanesulfonamido)thiazol-4-yl)-2-methylpropanamide | Method 2 using INTB70, [UPLC acidic], 505, (1.28) | 12.56 (s, 1H), 8.95 (s, 1H), 8.86 (d, J = 2.0 Hz, 1H), 8.59 (d, J = 2.3 Hz, 1H), 8.26-8.21 (m, 1H), 7.52 (s, 2H), 6.59 (s, 1H), 2.61-2.48 (m, 1H), 2.18 (s, 6H), 1.60 (s, 6H), 0.91-0.87 (m, 4H). |
| T322 | N-(4-(5-cyanopyridin-3-yl)-3-methylphenyl)-2-(2-(cyclopropanesulfonamido)thiazol-4-yl)-2-methylpropanamide | Method 2 using INTB60, [UPLC acidic], 482, (1.2) | 12.56 (s, 1H), 9.37 (s, 1H), 9.00 (d, J = 2.0 Hz, 1H), 8.84 (d, J = 2.2 Hz, 1H), 8.38-8.33 (m, 1H), 7.62-7.56 (m, 2H), 7.29-7.23 (m, 1H), 6.52 (s, 1H), 2.59-2.55 (m, 1H), 2.23 (s, 3H), 1.56 (s, 6H), 0.92-0.87 (m, 4H). |
| T422 | 2-(2-(cyclopropanesulfonamido)thiazol-4-yl)-N-(5-(6-ethoxypyrazin-2-yl)pyridin-2-yl)-2,2-difluoroacetamide | Method 1c using INTB45 and INTA72, [HPLC Acidic], 497, (2.24) | 9.10 (d, J = 2.4 Hz, 1H), 8.70 (s, 1H), 8.54 (dd, J = 8.7, 2.4 Hz, 1H), 8.26 (d, J = 8.7 Hz, 1H), 8.17 (s, 1H), 7.53 (s, 1H), 4.56 (q, J = 7.1 Hz, 2H), 2.86-2.69 (m, 1H), 1.48 (t, J = 7.1 Hz, 3H), 1.23-1.13 (m, 2H), 1.09-0.97 (m, 2H), 2 x exchangeable N—H not observed. |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T423 | 2-(2-(cyclopropanesulfonamido)thiazol-4-yl)-N-(4-(6-ethoxypyraizn-2-yl)-2-fluorophenyl)acetamide | Method 1c using INTB36 and INTA47, [HPLC Acidic], 478, (1.98) | 12.53 (s, 1H), 10.19 (s, 1H), 8.83 (s, 1H), 8.32-7.87 (m, 4H), 6.57 (s, 1H), 4.49 (q, J = 7.1 Hz, 2H), 3.77 (s, 2H), 2.66-2.53 (m, 1H), 1.40 (t, J = 7.1 Hz, 3H), 0.98-0.88 (m, 4H). |
| T424 | 2-(2-(cyclopropanesulfonamido)thiazol-4-yl)-N-(4-(6-ethoxypyrazin-2-yl)phenyl)acetamide | Method 1 using INTB36 and INTA38, [UPLC Acidic], 460, (1.21) | 12.53 (s, 1H), 10.40 (s, 1H), 8.77 (s, 1H), 8.18 (s, 1H), 8.13-8.05 (m, 2H), 7.79-7.67 (m, 2H), 6.56 (s, 1H), 4.47 (q, J = 7.0 Hz, 2H), 3.67 (s, 2H), 2.63-2.53 (m, 1H), 1.40 (t, J = 7.0 Hz, 3H), 0.94-0.80 (m, 4H). |
| T425 | 2-methyl-2-(2-(methylsulfonamido)thiazol-4-yl)-N-(5-(6-(trilfuoromethyl)pyrazin-2-yl)pyridin-2-yl)propanamide | Method 1b using INTB92 and INTA3, [UPLC Acidic], 487, (1.25) | 12.55 (s, 1H), 10.50 (s, 1H), 9.66 (s, 1H), 9.45-9.05 (m, 1H), 8.58 (dd, J = 8.8, 2.5 Hz, 1H), 8.25 (d, J = 8.8 Hz, 1H), 6.54 (s, 1H), 2.85 (s, 3H), 1.58 (s, 6H). |
| T426 | N-(2-fluoro-4-(5-(trifluoromethyl)pyridin-3-yl)phenyl)-2-methyl-2-(2-(methylsulfonamido)thiaozl-4-yl)propanamide | Method 1b using INTB92 and INTA70, [UPLC Acidic], 503, (1.27) | 12.57 (s, 1H), 9.36-9.20 (m, 2H) 9.03-8.90 (m, 1H), 8.54 (d, J = 2.3 Hz, 1H), 7.90 (dd, J = 11.8, 2.0 Hz, 1H), 7.79-7.56 (m, 2H), 6.64 (s, 1H), 2.91 (s, 3H), 1.58 (s, 6H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T427 | 2-(2-((cyclopropylmethyl)sulfonamido)thiazol-4-yl)-N-(2-fluoro-4-(5-(trifluoromethyl)pyridin-3-yl)phenyl)-2-methylpropanamide | Method 1b using INTB96 and INTA70, [UPLC Acidic], 543, (1.4) | 12.61 (s, 1H), 9.27 (d, J = 2.2 Hz, 1H), 9.24 (s, 1H), 8.98 (d, J = 2.1 Hz, 1H), 8.55 (d, J = 2.4 Hz, 1H), 7.90 (dd, J = 11.8, 2.0 Hz, 1H), 7.75 (dd, J = 8.3, 2.1 Hz, 1H), 7.70 (s, 1H), 6.62 (s, 1H), 2.96-2.90 (m, 2H), 1.59 (s, 6H), 1.03-0.95 (m, 1H), 0.55-0.46 (m, 2H), 0.34-0.26 (m, 2H). |
| T428 | N-(4-(5-chloro-4-methylpyridin-3-yl)phenyl)-2-(2-(cyclopropanesulfonamido)thiazol-4-yl)-2-methylpropanamide | Method 1b using INTB37 and INTA109, [UPLC Acidic], 491, (1.9) | 12.56 (s, 1H), 9.43 (s, 1H), 8.56 (s, 1H), 8.32 (s, 1H), 7.78-7.71 (m, 2H), 7.39-7.34 (m, 1H), 6.54 (s, 1H), 2.60-2.56 (m, 1H), 2.29 (s, 3H), 1.57 (s, 6H), 0.93-0.86 (m, 4H). |
| T429 | N-(4-(6-ethoxypyrazin-2-yl)-2-(trifluoromethyl)phenyl)-2-methyl-2-(2-(methylsulfonamido)thiazol-4-yl)propanamide | Method 1b using INTB92 and INTA110, [UPLC Acidic], 530, (1.38) | 12.59 (s, 1H), 9.10 (s, 1H), 8.93 (s, 1H), 8.50-8.37 (m, 2H), 8.31 (s, 1H), 7.73 (d, J = 8.5 Hz, 1H), 6.70 (s, 1H), 4.49 (q, J = 7.1 Hz, 2H), 2.91 (s, 3H), 1.56 (s, 6H), 1.41 (t, J = 7.0 Hz, 3H). |
| T430 | 2-(2-((cyclopropylmethyl)sulfonamido)thiazol-4-yl)-N-(2-fluoro-4-(6-(trifluoromethyl)pyrazin-2-yl)phenyl)-2-methylpropanamide | Method 1b using INTB96 and INTA48, [UPLC Acidic], 544, (1.47) | 12.62 (s, 1H), 9.66 (s, 1H), 9.31 (s, 1H), 9.16 (s, 1H), 8.16-8.06 (m, 2H), 7.81 (s, 1H), 6.62 (s, 1H), 2.98-2.87 (m, 2H), 1.59 (s, 6H), 1.02-0.95 (m, 1H), 0,.53-0.46 (m, 2H), 0.33-0.28 (m, 2H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T431 | N-(4-(6-ethoxypyrazin-2-yl)-2-fluorophenyl)-2-methyl-2-(2-(methylsulfonamido)thiazol-4-yl)propanamide | Method 1b using INTB92 and INTA47, [UPLC Acidic], 480, (1.27) | 12.58 (s, 1H), 9.27 (s, 1H), 8.85 (s, 1H), 8.25 (s, 1H), 8.07-7.91 (m, 2H), 7.71 (s, 1H), 6.63 (s, 1H), 4.49 (q, J = 7.1 Hz, 2H), 2.91 (s, 3H), 1.58 (s, 6H), 1.40 (t, J = 7.1 Hz, 3H). |
| T432 | N-(4-(6-ethoxypyrazin-2-yl)-2-fluorophenyl)-2-(2-((2-methoxyethyl)sulfonamido)thiazol-4-yl)-2-methylpropanamide | Method 1b using INTB97 and INTA47, [UPLC Acidic], 524, (1.3) | 12.66 (s, 1H), 9.26 (s, 1H), 8.86 (s, 1H), 8.26 (s, 1H), 8.06-7.96 (m, 2H), 7.71 (s, 1H), 6.64 (s, 1H), 4.49 (q, J = 7.0 Hz, 2H), 3.66 (t, J = 6.6 Hz, 2H), 3.29-3.24 (m, 2H), 3.20 (s, 3H), 1.59 (s, 6H), 1.41 (t, J = 7.1 Hz, 3H). |
| T433 | 2-(2-((cyclopropylmethyl)sulfonamido)thiazol-4-yl)-N-(4-(6-ethoxypyrazin-2-yl)-2-fluorophenyl)-2-methylpropanamide | Method 1b using INTB96 and INTA47, [UPLC Acidic], 520, (1.42) | 12.61 (s, 1H), 9.24 (s, 1H), 8.86 (s, 1H), 8.26 (s, 1H), 8.07-7.96 (m, 2H), 7.71 (s, 1H), 6.61 (s, 1H), 4.49 (q, J = 7.0 Hz, 2H), 2.92 (s, 2H), 1.59 (s, 6H), 1.41 (t, J = 7.1 Hz, 3H), 1.02-0.95 (m, 1H), 0.53-0.47 (m, 2H), 0.33-0.26 (m, 2H). |
| T434 | N-(4-(6-ethoxypyrazin-2-yl)phenyl)-2-methyl-2-(2-(methylsulfonamido)thiazol-4-yl)propanamide | Method 1b using INTB92 and INTA38, [UPLC Acidic], 462, (1.26) | 12.55 (s, 1H), 9.49 (s, 1H), 8.77 (s, 1H), 8.18 (s, 1H), 8.15-8.03 (m, 2H), 7.86-7.36 (m, 2H), 6.59 (s, 1H), 4.47 (q, J = 7.0 Hz, 2H), 2.91 (s, 3H), 1.58 (s, 6H), 1.40 (t, J = 7.0 Hz, 3H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T435 | 2-(2-(cyclopropanesulfonamido)thiazol-4-yl)-N-(5-(6-ethoxypyrazin-2-yl)-3-fluoropyridin-2-yl)-4-methoxybutanamide | Method 1c using INTB44 and INTA57, [UPLC Acidic], 537, (1.18) | 12.64 (s, 1H), 10.70 (s, 1H), 9.02 (d, J = 1.9 Hz, 1H), 8.93 (s, 1H), 8.46 (dd, J = 11.1, 2.0 Hz, 1H), 8.32 (s, 1H), 6.55 (s, 1H), 4.51 (q, J = 7.0 Hz, 2H), 4.01-3.93 (m, 1H), 3.42-3.33 (m, 2H), 3.24 (s, 3H), 2.62-2.56 (m, 1H), 2.27-2.16 (m, 1H), 2.15-2.06 (m, 1H), 1.41 (t, J = 7.0 Hz, 3H), 0.93-0.88 (m, 4H). |
| T436 | 2-(2-(cyclopropanesulfonamido)thiazol-4-yl)-N-(5-(6-ethoxypyrazin-2-yl)pyridin-2-yl)-4-methoxybutanamide | Method 1c using INTB44 and INTA72, [UPLC Acidic], 519, (1.26) | 12.60 (s, 1H), 10.88 (s, 1H), 9.08 (d, J = 2.4 Hz, 1H), 8.84 (s, 1H), 8.51 (dd, J = 8.9, 2.4 Hz, 1H), 8.27-8.18 (m, 2H), 6.55 (s, 1H), 4.48 (q, J = 7.0 Hz, 2H), 4.07-3.99 (m, 1H), 3.33 (d, J = 2.5 Hz, 2H), 3.20 (s, 3H), 2.59-2.50 (m, 1H), 2.25-2.20 (m, 1H), 2.11-2.03 (m, 1H), 1.40 (t, J = 7.0 Hz, 3H), 0.90-0.86 (m, 4H). |
| T437 | 2-(2-(cyclopropanesulfonamido)thiazol-4-yl)-4-methoxy-N-(4-(6-(trifluoromethyl)pyrazin-2-yl)phenyl)butanamide | Method 1c using INTB44 and INTA39, [UPLC Acidic], 542, (1.37) | 12.64 (s, 1H), 10.47 (s, 1H), 9.59 (s, 1H), 9.09 (s, 1H), 8.24-8.18 (m, 2H), 7.86-7.80 (m, 2H), 6.56 (s, 1H), 3.88-3.81 (m, 2H), 3.41-3.28 (m, 1H), 3.22 (s, 3H), 2.61-2.57 (m, 1H), 2.27-2.16 (m, 1H), 2.16-2.05 (m, 1H), 0.92-0.87 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T438 | 2-(2-(cyclopropanesulfonamido)thiazol-4-yl)-N-(5-(6-ethoxypyrazin-2-yl)-3-methylpyridin-2-yl)butanamide | Method 1c using INTB38 and INTA111, [UPLC Acidic], 503, (1.2) | 12.61 (s, 1H), 10.40 (s, 1H), 8.98 (d, J = 2.3 Hz, 1H), 8.87 (s, 1H), 8.38 (d, J = 2.2 Hz, 1H), 8.29 (s, 1H), 6.55 (s, 1H), 4.50 (q, J = 7.0 Hz, 2H), 3.77-3.69 (m, 1H), 2.63-2.57 (m, 1H), 2.25 (s, 3H), 2.05-1.94 (m, 1H), 1.94-1.84 (m, 1H), 1.41 (t, J = 7.0 Hz, 3H), 0.95 (t, J = 7.3 Hz, 3H), 0.93-0.86 (m, 4H). |
| T439 | N-(2-chloro-4-(6-ethoxypyrazin-2-yl)phenyl)-2-(2-(cyclopropanesulfonamido)thiazol-4-yl)butanamide | Method 1c using INTB38 and INTA105, [UPLC Acidic], 524, (1.45) | 12.61 (s, 1H), 9.87 (s, 1H), 8.85 (s, 1H), 8.26 (s, 1H), 8.24 (d, J = 2.0 Hz, 1H), 8.11 (dd, J = 8.5, 2.1 Hz, 1H), 7.91 (d, J = 8.5 Hz, 1H), 6.58 (s, 1H), 4.48 (q, J = 7.1 Hz, 2H), 3.81 (t, J = 7.5 Hz, 1H), 2.59 (s, 1H), 2.03-1.85 (m, 2H), 1.40 (t, J = 7.0 Hz, 3H), 0.99-0.84 (m, 7H). |
| T440 | N-(2-cyano-4-(6-ethoxypyrazin-2-yl)phenyl)-2-(2-(cyclopropanesulfonamido)thiazol-4-yl)butanamide | Method 1c using INTB38 and INTA107, [UPLC Acidic], 513, (1.35) | 12.64 (s, 1H), 10.55 (s, 1H), 8.90 (s, 1H), 8.57 (d, J = 2.1 Hz, 1H), 8.44 (dd, J = 8.7, 2.2 Hz, 1H), 8.29 (s, 1H), 7.77 (d, J = 8.7 Hz, 1H), 6.58 (s, 1H), 4.50 (q, J = 7.1 Hz, 2H), 3.72 (t, J = 7.4 Hz, 1H), 2.59 (s, 1H), 2.04-1.85 (m, 2H), 1.40 (t, J = 7.0 Hz, 3H), 0.96 (t, J = 7.3 Hz, 3H), 0.93-0.86 (m, 4H). |
| T441 | 2-(2-(cyclopropanesulfonamido)thiazol-4-yl)-N-(4-(6-ethoxypyrazin-2-yl)-2-methylphenyl)butanamide | Method 1c using INTB38 and INTA51, [UPLC Acidic], 502, (1.37) | 12.60 (s, 1H), 9.62 (s, 1H), 8.78 (s, 1H), 8.20 (s, 1H), 7.99 (d, J = 2.1 Hz, 1H), 7.93 (dd, J = 8.3, 2.1 Hz, 1H), 7.61 (d, J = 8.3 Hz, 1H), 6.57 (s, 1H), 4.47 (q, J = 7.1 Hz, 2H), 3.71 (t, J = 7.5 Hz, 1H), 2.58 (d, J = 5.6 Hz, 1H), 2.30 (s, 3H), 2.02-1.84 (m, 2H), 1.40 (t, J = 7.1 Hz, 3H), 0.98-0.85 (m, 7H) |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T442 | 2-(2-(cyclopropanesulfonamido)thiazol-4-yl)-N-(4-(6-ethoxypyrazin-2-yl)-2-(trifluoromethoxy)phenyl)butanamide | Method 1c using INTB38 and INTA103, [UPLC Acidic], 572, (1.53) | 12.59 (s, 1H), 10.12 (s, 1H), 8.87 (s, 1H), 8.27 (s, 1H), 8.19-8.12 (m, 2H), 8.08 (d, J = 8.5 Hz, 1H), 6.54 (s, 1H), 4.47 (q, J = 7.0 Hz, 2H), 3.83 (t, J = 7.4 Hz, 1H), 2.58 (s, 1H), 2.02-1.82 (m, 2H), 1.40 (t, J = 7.0 Hz, 3H), 1.00-0.76 (m, 7H). |
| T443 | 2-(2-(cyclopropanesulfonamido)thiazol-4-yl)-N-(4-(6-ethoxypyrazin-2-yl)-2-methoxyphenyl)butanamide | Method 1c using INTB38 and INTA104, [UPLC Acidic], 518, (1.42) | 12.58 (s, 1H), 9.51 (s, 1H), 8.84 (s, 1H), 8.20 (s, 1H), 8.17 (d, J = 8.4 Hz, 1H), 7.76 (d, J = 1.9 Hz, 1H), 7.72 (dd, J = 8.4, 1.9 Hz, 1H), 6.54 (s, 1H), 4.48 (q, J = 7.1 Hz, 2H), 3.97 (s, 3H), 3.85 (s,1H), 2.58 (s, 1H), 1.98-1.80 (m, 2H), 1.40 (t, J = 7.0 Hz, 3H), 1.00-0.76 (m, 7H). |
| T445 | 2-(2-(cyclopropanesulfonamido)thiazol-4-yl)-N-(5-(6-ethoxypyrazin-2-yl)-3-fluoropyridin-2-yl)-2-methoxyacetamide | Method 1c using INTB43 and INTA57, [HPLC Basic], 509, (1.52) | 12.86 (s, 1H), 10.51 (s, 1H), 9.05 (d, J = 1.8 Hz, 1H), 8.95 (s, 1H), 8.49 (dd, J = 11.0, 1.9 Hz, 1H), 8.33 (s, 1H), 6.81 (s, 1H), 4.99 (s, 1H), 4.51 (q, J = 7.0 Hz, 2H), 3.42 (s, 3H), 2.66-2.57 (m, 1H), 1.41 (t, J = 7.0 Hz, 3H), 0.97-0.79 (m, 4H). |
| T446 | 2-(2-(cyclopropanesulfonamido)thiazol-4-yl)-N-(5-(6-ethoxypyrazin-2-yl)pyridin-2-yl)-2-methoxyacetamide | Method 1c using INTB43 and INTA72, [HPLC Basic], 491, (1.61) | 12.84 (s, 1H), 10.32 (s, 1H), 9.12 (d, J = 2.4 Hz, 1H), 8.87 (s, 1H), 8.56 (dd, J = 8.8, 2.4 Hz, 1H), 8.27 (s, 1H), 8.22 (d, J = 8.8 Hz, 1H), 6.90 (s, 1H), 5.02 (s, 1H), 4.50 (q, J = 7.0 Hz, 2H), 3.40 (s, 3H), 2.64-2.57 (m, 1H), 1.41 (t, J = 7.0 Hz, 3H), 0.97-0.86 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | ¹H NMR Chemical Shift Data (DMSO-d6 unless stated) |
|---|---|---|---|
| T447 | 2-(2-(cyclopropanesulfonamido)thiazol-4-yl)-N-(4-(5-fluoropyridin-3-yl)-2-(trifluoromethyl)phenyl)-2-methoxyacetamide | Method 1c using INTB43 and INTA91, [HPLC Acidic], 531, (2.02) | 12.86 (s, 1H),9.68 (s, 1H), 8.90 (d, J = 1.8 Hz, 1H), 8.63 (d, J = 2.7 Hz, 1H), 8.23 (dt, J = 10.3, 2.3 Hz, 1H), 8.20-8.13 (m, 2H), 8.09-7.92 (m, 1H), 6.90 (s, 1H), 4.96 (s, 1H), 3.44 (s, 3H), 2.67-2.56 (m, 1H), 1.09-0.75 (m, 4H). |
| T448 | 2-(2-(cyclopropanesulfonamido)thiazol-4-yl)-N-(2-fluoro-4-(5-(trifluoromethyl)pyridin-3-yl)phenyl)-2-methoxyacetamide | Method 1c using INTB43 and INTA70, [HPLC Acidic], 531 (2.08) | 12.84 (s, 1H), 9.77 (s, 1H), 9.31-9.21 (m, 1H), 9.02-8.88 (m, 1H), 8.56-8.53 (m, 1H), 8.07 (t, J = 8.4 Hz, 1H), 7.96 (dd, J = 12.1, 2.1 Hz, 1H), 7.77 (dd, J = 8.6, 2.0 Hz, 1H), 6.89 (s, 1H), 5.00 (s, 1H), 3.42 (s, 3H), 2.63-2.57 (m, 1H), 0.94-0.85 (m, 4H). |
| T449 | 2-(2-(cyclopropanesulfonamido)thiazol-4-yl)-N-(4-(6-ethoxypyrazin-2-yl)-2-(trifluoromethyl)phenyl)-2-methoxyacetamide | Method 1c using INTB43 and INTA110, [HPLC Acidic], 558, (2.29) | 12.87 (s, 1H), 9.67 (s, 1H), 8.94 (s, 1H), 8.49-8.40 (m, 2H), 8.31 (s, 1H), 8.07 (d, J = 8.4 Hz, 1H), 6.90 (s, 1H), 4.98 (s, 1H), 4.49 (q, J = 7.0 Hz, 2H), 3.44 (s ,3H), 2.68-2.54 (m, 1H), 1.41 (t, J = 7.0 Hz, 3H), 0.99-0.70 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| T450 | N-(2-choro-4-(6-ethoxypyrazin-2-yl)phenyl)-2-(2-(cyclopropanesulfonamido)thiazol-4-yl)-2-methoxyacetamide | Method 1c using INTB43 and INTA105, [HPLC Acidic], 524, (2.25) | 12.88 (s, 1H), 9.63 (s, 1H), 8.87 (s, 1H), 8.31 (d, J = 2.0 Hz, 1H), 8.27 (s, 1H), 8.23 (d, J = 8.7 Hz, 1H), 8.16 (dd, J = 8.6, 2.0 Hz, 1H), 6.95 (s, 1H), 5.02 (s, 1H), 4.49 (q, J = 7.0 Hz, 2H), 3.45 (s, 3H), 2.63-2.57 (m, 1H), 1.41 (t, J = 7.0 Hz, 3H), 1.00-0.76 (m, 4H). |
| T451 | N-(2-cyano-4-(6-ethoxypyrazin-2-yl)phenyl)-2-(2-(cyclopropanesulfonamido)thiazol-4-yl)-2-methoxyacetamide | Method 1c using INTB43 and INTA107, [HPLC Acidic], 515 (2.05) | 12.85 (s, 1H), 10.19 (s, 1H), 8.91 (s, 1H), 8.61 (d, J = 2.1 Hz, 1H), 8.47 (dd, J = 8.7, 2.2 Hz, 1H), 8.29 (s, 1H), 8.01 (d, J = 8.8 Hz, 1H), 6.93 (s, 1H), 5.00 (s, 1H), 4.51 (q, J = 7.0 Hz, 2H), 3.46 (s, 3H), 2.66-2.53 (m, 1H), 1.41 (t, J = 7.0 Hz, 3H), 0.96-0.80 (m, 4H). |
| T452 | N-(2-fluoro-4-(6-(trifluoromethyl)pyraizn-2-yl)phenyl)-2-methoxy-2-(2-(methylsulfonamido)thiazol-4-yl)acetamide | Method 1c using INTB111 and INTA48, [UPLC Acidic], 506, (1.27) | 12.81 (s, 1H), 9.82 (s, 1H), 9.65 (s, 1H), 9.16 (s, 1H), 8.24-8.05 (m, 3H), 6.92 (s, 1H), 5.02 (s, 1H), 3.41 (s, 3H), 2.92 (s, 3H). |
| T453 | 2-(2-(cyclopropanesulfonamido)thiazol-4-yl)-N-(4-(6-ethoxypyrazin-2-yl)-2,6-difluorophenyl)-2-methoxyacetamide | Method 1c using INTB43 and INTA97, [HPLC Acidic], 526, (2.01) | 12.86 (s, 1H), 10.05 (s, 1H), 8.92 (s, 1H), 8.31 (s, 1H), 7.97 (d, J = 9.0 Hz, 2H), 6.76 (s, 1H), 4.94 (s, 1H), 4.50 (q, J = 7.0 Hz, 2H), 3.44 (s, 3H), 2.68-2.54 (m, 1H), 1.40 (t, J = 7.0 Hz, 3H), 1.00-0.78 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T454 | 2-(2-(cyclopropanesulfonamido)thiazol-4-yl)-N-(4-(6-ethoxypyrazin-2-yl)-2-(trifluoromethoxy)phenyl)-2-methoxyacetamide | Method 1c using INTB43 and INTA103, [HPLC Acidic], 574, (2.37) | 12.85 (s, 1H), 9.75 (s, 1H), 8.88 (s, 1H), 8.28 (s, 1H), 8.25-8.01 (m, 3H), 6.88 (s, 1H), 5.01 (d, J = 3.0 Hz, 1H), 4.48 (q, J = 7.0 Hz, 2H), 3.42 (s, 3H), 2.66-2.54 (m, 1H), 1.41 (t, J = 7.0 Hz, 3H), 0.96-0.82 (m, 4H). |
| T455 | N-(4-(6-ethoxypyrazin-2-yl)phenyl)-2-methoxy-2-(2-(methylsulfonamido)thiazol-4-yl)acetamide | Method 1c using INTB111 and INTA38, [UPLC Acidic], 464, (1.17) | 12.77 (s, 1H), 10.10 (s, 1H), 8.79 (s, 1H), 8.20 (s, 1H), 8.16-8.11 (m, 2H), 7.89-7.84 (m, 2H), 6.88 (s, 1H), 4.91 (s, 1H), 4.49 (q, J = 7.0 Hz, 2H), 3.41 (s, 3H), 2.92 (s, 3H), 1.41 (t, J = 7.0 Hz, 3H). |
| T456 | Single enantiomer - stereochemistry unassigned 2-(2-(cyclopropanesulfonamido)thiazol-4-yl)-N-(5-(6-ethoxypyrazin-2-yl)-3-fluoropyridin-2-yl)butanamide | Method 1c using INTB38 and INTA57, Chiral IC3 (13.36), [HPLC Acidic], 507, (1.94) | 12.63 (s, 1H), 10.72 (s, 1H), 9.07-8.99 (m, 1H), 8.93 (s, 1H), 8.46 (dd, J = 11.1, 1.9 Hz, 1H), 8.32 (s, 1H), 6.54 (s, 1H), 4.51 (q, J = 7.0 Hz, 2H), 3.75 (t, J = 7.5 Hz, 1H), 2.67-2.56 (m, 1H), 2.05-1.83 (m, 2H), 1.41 (t, J = 7.0 Hz, 3H), 0.99-0.85 (m, 7H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T457 | Single enantiomer - stereochemistry unassigned 2-(2-(cyclopropanesulfonamido)thiazol-4-yl)-N-(5-(6-ethoxypyrazin-2-yl)-3-fluoropyridin-2-yl)butanamide | Method 1c using INTB38 and INTA57, Chiral IC3 (19.91), [HPLC Acidic], 507 (1.94) | 12.63 (s, 1H), 10.72 (s, 1H), 9.02 (d, J = 1.8 Hz, 1H), 8.93 (s, 1H), 8.46 (dd, J = 11.1, 1.9 Hz, 1H), 8.32 (s, 1H), 6.54 (s, 1H), 4.50 (q, J = 7.0 Hz, 2H), 3.75 (t, J = 7.5 Hz, 1H), 2.69-2.55 (m, 1H), 2.05-1.84 (m, 2H), 1.41 (t, J = 7.0 Hz, 3H), 1.04-0.80 (m, 8H). |
| T458 | 2-(2-(cyclopropanesulfonamido)thiazol-4-yl)-N-(2-fluoro-4-(6-(trifluoromethyl)pyrazin-2-yl)phenyl)-2-methoxyacetamide | Method 1c using INTB43 and INTA48, Chiral IA2 (15.9), [UPLC Acidic], 532, (1.37) | 12.85 (s, 1H), 9.82 (s, 1H), 9.66 (s, 1H), 9.16 (s, 1H), 8.25-8.05 (m, 3H), 6.90 (s, 1H), 5.02 (s, 1H), 3.42 (s, 3H), 2.63-2.57 (m, 1H), 0.97-0.82 (m, 4H). |
| T459 | Single enantiomer - stereochemistry unassigned 2-(2-(cyclopropanesulfonamido)thiazol-4-yl)-N-(2-fluoro-4-(6-(trifluoromethyl)pyrazin-2-yl)phenyl)-2-methoxyacetamide | Method 1c using INTB43 and INTA48, Chiral IA2 (13.0), [UPLC Acidic], 532, (1.37) | 12.84 (s, 1H), 9.82 (s, 1H), 9.66 (s, 1H), 9.16 (s, 1H), 8.25-8.07 (m, 3H), 6.90 (s, 1H), 5.02 (s, 1H), 3.42 (s, 3H), 2.64-2.57 (m, 1H), 0.97-0.82 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T460 | 4-(2-(cyclopropanesulfonamido)thiazol-4-yl)-N-(4-(6-ethoxypyrazin-2-yl)-2-fluorophenyl)tetrahydro-2H-pyrazin-4-carboxamide | Method 1b using INTB117 and INTA47, [Agilent Acidic], 548, (2.06) | 12.58 (s, 1H), 9.46-9.28 (m, 1H), 8.86 (s, 1H), 8.26 (s, 1H), 8.08-7.90 (m, 2H), 7.76-7.62 (m, 1H), 6.78-6.60 (m, 1H), 4.49 (q, J = 7.0 Hz, 2H), 3.71-3.57 (m, 4H), 2.64-2.58 (m, 1H), 2.41-2.31 (m, 2H), 2.18-2.06 (m, 2H), 1.41 (t, J = 7.0 Hz, 3H), 0.99-0.82 (m, 4H). |
| T461 | 4-(2-(cyclopropanesulfonamido)thiazol-4-yl)-N-(5-(6-(trifluoromethyl)pyrazin-2-yl)pyridin-2-yl)tetrahydro-2H-pyran-4-carboxamide | Method 1b: using INTB117 and INTA3, [Agilent Acidic], 555, (2.03) | 12.64 (s, 1H), 10.18 (s, 1H), 9.68 (s, 1H), 9.28-9.05 (m, 2H), 8.61 (d, J = 8.8 Hz, 1H), 8.28 (d, J = 8.8 Hz, 1H), 6.77 (s, 1H), 3.69-3.55 (m, 4H), 2.66-2.56 (m, 1H), 2.48-2.39 (m, 2H), 2.24-2.04 (m, 2H), 0.97-0.78 (m, 4H). |
| T462 | 4-(2-(cyclopropanesulfonamido)thiazol-4-yl)-N-(5-(6-ethoxypyrazin-2-yl)pyridin-2-yl)tetrahydro-2H-pyran-4-carboxamide | Method 1b using INTB117 and INTA72, [UPLC Acidic], 531, (1.25) | 12.62 (s, 1H), 10.03 (s, 1H), 9.08 (d, J = 2.2 Hz, 1H), 8.86 (s, 1H), 8.53 (dd, J = 8.8, 2.5 Hz, 1H), 8.27 (s, 1H), 8.21 (d, J = 8.7 Hz, 1H), 6.78 (s, 1H), 4.49 (q, J = 7.0 Hz, 2H), 3.68-3.54 (m, 4H), 2.68-2.57 (m, 1H), 2.46-2.37 (m, 2H), 2.25-2.10 (m, 2H), 1.40 (t, J = 7.0 Hz, 3H), 0.98-0.85 (m, 4H). |

TABLE 15-continued

Preparation methods and characterisation of Examples T23-T322, T422-T443 and T445-T465. Where no INTA number is given, the aniline is commercially available.

| T# | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| T463 | N-(4-(1-(4-(5-methoxypyridin-3-yl)phenyl)-2-oxopyrrolidin-3-yl)thiazol-2-yl)cyclopropanesulfonamide | Method 2 Using INTB120 [HPLC acidic] 471, (1.44) | 12.72 (s, 1H), 8.52 (d, J = 1.8 Hz, 1H), 8.28 (d, J = 2.7 Hz, 1H), 7.86-7.76 (m, 4H), 7.66 (s, 1H), 6.70 (s, 1H), 4.08-4.00 (m, 1H), 3.99-3.86 (m, 5H), 2.65-2.57 (m, 1H), 2.31-2.21 (m, 1H), 0.96-0.83 (m, 4H) 1 x CH obscured by residual solvent. |
| T464 | 2-(2-(cyclopropanesulfonamido)thiazol-4-yl)-2-methyl-N-(5-(6-methylpyrazin-2-yl)pyridin-2-yl)propanamide | Method 1e Using INTB37 and INTA90 [HPLC acidic] 459, (1.73) | 12.57 (s, 1H), 10.17 (s, 1H), 9.19-9.02 (m, 2H), 8.60-8.48 (m, 2H), 8.20 (d, J = 8.7 Hz, 1H), 6.58 (s, 1H), 2.67-2.55 (m, 4H), 1.61 (s, 6H), 1.01-0.72 (m, 4H). |
| T465 | N-(4-(6-cyanopyrazin-2-yl)-2-methylphenyl)-2-(2-(cyclopropanesulfonamido)thiazol-4-yl)-2-methylpropanamide | Method 1b, using INTB37 and INTA50 [HPLC acidic] 483, 1.68) | 12.62 (s, 1H), 9.57 (s, 1H), 9.14 (s, 1H), 9.00 (s, 1H), 8.10-8.07 (m, 1H), 8.04 (dd, J = 8.3, 2.2 Hz, 1H), 7.58-7.49 (m, 1H), 6.63 (s, 1H), 2.63-2.55 (m, 1H), 2.27 (s, 3H), 1.60 (s, 6H), 0.96-0.87 (m, 4H). |

Method 2c: Telescoped Boronate Formation and Suzuki Coupling on Sulfonamide Scaffold

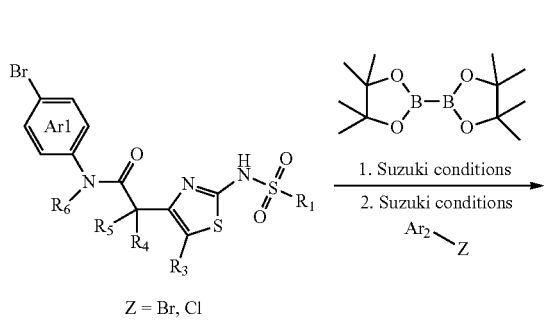

Z = Br, Cl

1. Suzuki conditions
2. Suzuki conditions

Ar2—Z

-continued

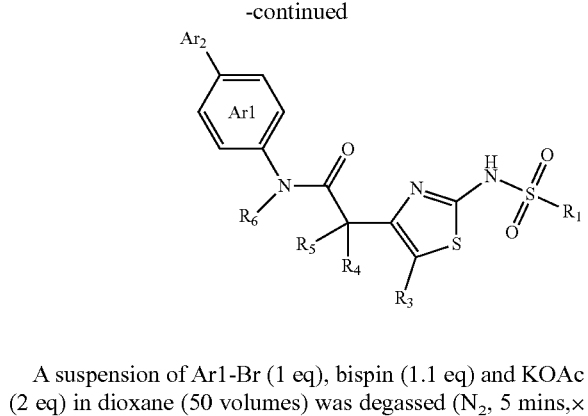

A suspension of Ar1-Br (1 eq), bispin (1.1 eq) and KOAc (2 eq) in dioxane (50 volumes) was degassed ($N_2$, 5 mins,×

3) then charged with PdCl₂(dppf)-DCM adduct (5 mol %) and again degassed (N₂, 5 mins,×3). The reaction mixture was heated to 90° C. for 1 hr and then the reaction was allowed to cool to RT. Ar2-Z (1 eq) and 2M K₂CO₃ (aq, 2 eq) were added and the reaction was then heated to 90° C. for 18 hrs. The reaction was allowed to cool to RT, an aqueous work up was performed and the crude compound was purified by normal phase chromatography.

2-Amino-2-(2-(cyclopropanesulfonamido)thiazol-4-yl)-N-(4-(6-ethoxypyrazin-2-yl)phenyl)acetamide T325

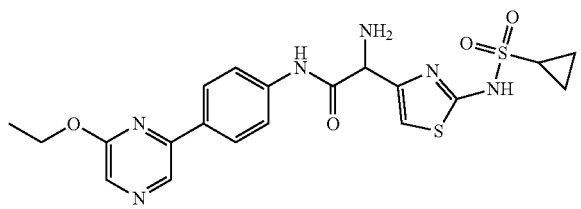 [SMILES: CCOc1cncc(-c2ccc(NC(=O)C(N)c3csc(NS(=O)(=O)C4CC4)n3)cc2)n1]

A solution of tert-butyl (1-(2-(cyclopropanesulfonamido)thiazol-4-yl)-2-((4-(6-ethoxypyrazin-2-yl)phenyl)amino)-2-oxoethyl)carbamate T407 (60 mg, 0.104 mmol) in DCM (2 mL) was treated with TFA (0.30 mL, 3.89 mmol) and stirred at RT for 30 mins. The reaction mixture was diluted with MeOH (2 mL) then loaded on to SCX (500 mg), washed with MeOH and the product eluted with 0.1% NH₃ in MeOH then concentrated to afford 2-amino-2-(2-(cyclopropanesulfonamido)thiazol-4-yl)-N-(4-(6-ethoxypyrazin-2-yl)phenyl)acetamide (37 mg, 0.076 mmol, 73% yield) as an orange solid; Rt 0.87 mins (UPLC acidic); m/z 475.0 (M+H)⁺ (ES⁺); ¹H NMR (500 MHz, DMSO-d6) δ 10.55 (s, 1H), 8.78 (s, 1H), 8.19 (s, 1H), 8.16-8.10 (m, 2H), 7.82-7.77 (m, 2H), 6.57 (s, 1H), 4.73 (s, 1H), 4.48 (q, J=7.0 Hz, 2H), 2.49-2.43 (m, 1H), 1.40 (t, J=7.0 Hz, 3H), 0.89-0.80 (m, 2H), 0.78-0.66 (m, 2H), 3 exchangeable N—H not observed.

2-acetamido-2-(2-(cyclopropanesulfonamido)thiazol-4-yl)-N-(4-(6-ethoxypyrazin-2-yl)phenyl)acetamide T326

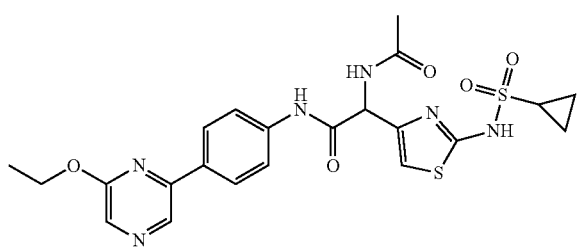 [SMILES: CCOc1cncc(-c2ccc(NC(=O)C(NC(C)=O)c3csc(NS(=O)(=O)C4CC4)n3)cc2)n1]

A suspension of 2-amino-2-(2-(cyclopropanesulfonamido)thiazol-4-yl)-N-(4-(6-ethoxypyrazin-2-yl)phenyl)acetamide T325 (20 mg, 0.042 mmol) in DCM (2 mL) was treated with DIPEA (10 uL, 0.057 mmol) followed by acetic anydride (5 uL, 0.053 mmol). The reaction mixture was left to stir at RT for 72 hrs. The mixture was then treated with sat. NH4Cl (aq., 5 mL) and extracted with DCM (3×5 mL) partitioning with a phase separator. The organic phases were combined and concentrated onto silica (~200 mg). The crude product was purified by chromatography on silica gel (4 g cartridge, 0-10% MeOH/DCM) followed by chromatography on RP Flash C₁₈ (4 g column, 15-70% MeCN/10 mM Ammonium Bicarbonate) to afford 2-acetamido-2-(2-(cyclopropanesulfonamido)thiazol-4-yl)-N-(4-(6-ethoxypyrazin-2-yl)phenyl)acetamide (18 mg, 0.032 mmol, 76% yield) as a colourless solid. Rt 1.17 min (UPLC, acidic); m/z 517 (M+H)⁺ (ES⁺); ¹H NMR (500 MHz, DMSO-d6) δ 10.55 (s, 1H), 8.77 (s, 1H), 8.64 (s, 1H), 8.18 (s, 1H), 8.14-8.09 (m, 2H), 7.78 (d, J=8.5 Hz, 2H), 6.57 (s, 1H), 5.50 (d, J=7.0 Hz, 1H), 4.48 (q, J=7.0 Hz, 2H), 2.61-2.53 (m, 1H), 1.94 (s, 3H), 1.40 (t, J=7.0 Hz, 3H), 0.94-0.75 (m, 4H)N—H not observed.

methyl (1-(2-(cyclopropanesulfonamido)thiazol-4-yl)-2-((4-(6-ethoxypyrazin-2-yl)phenyl)amino)-2-oxoethyl)carbamate T327

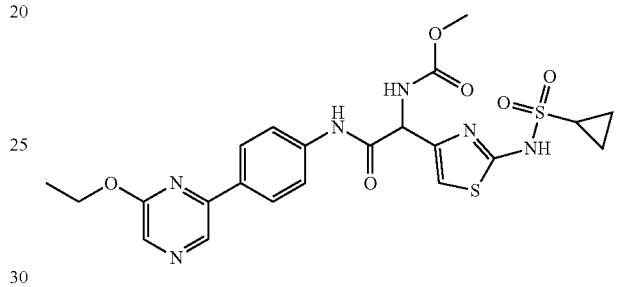

A suspension of 2-amino-2-(2-(cyclopropanesulfonamido)thiazol-4-yl)-N-(4-(6-ethoxypyrazin-2-yl)phenyl)acetamide T325 (20 mg, 0.042 mmol) in DCM (2 mL) was treated with DIPEA (10 ul, 0.057 mmol) followed by methyl chloroformate (5 uL, 0.065 mmol). The reaction mixture was left to stir at RT for 72 hrs. The mixture was then treated with sat. NH₄Cl (aq., 5 mL) and extracted with DCM (3×5 mL), partitioning with a phase separator. The organic phases were combined and concentrated onto silica (200 mg). The crude product was purified by chromatography on silica gel (4 g column, 0-10% MeOH/DCM) to afford methyl (1-(2-(cyclopropanesulfonamido)thiazol-4-yl)-2-((4-(6-ethoxypyrazin-2-yl)phenyl)amino)-2-oxoethyl)carbamate (12 mg, 0.022 mmol, 52% yield) was isolated as a colourless solid. Rt 1.24 (UPLC, acidic); m/z 533 (M+H)⁺ (ES⁺). ¹H NMR (500 MHz, DMSO-d6) δ 12.66 (s, 1H), 10.55 (s, 1H), 8.77 (s, 1H), 8.19 (s, 1H), 8.16-8.10 (m, 2H), 8.09-7.98 (m, 1H), 7.80-7.72 (m, 2H), 6.58 (s, 1H), 5.32 (s, 1H), 4.48 (q, J=7.0 Hz, 2H), 3.60 (s, 3H), 2.63-2.55 (m, 1H), 1.40 (t, J=7.1 Hz, 3H), 0.94-0.83 (m, 4H).

2-(2-(cyclopropanesulfonamido)thiazol-4-yl)-2-(dimethylamino)-N-(4-(6-ethoxypyrazin-2-yl)phenyl)acetamide T328

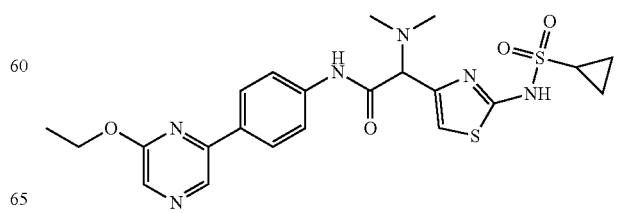

A suspension 2-amino-2-(2-(cyclopropanesulfonamido)thiazol-4-yl)-N-(4-(6-ethoxypyrazin-2-yl)phenyl)acetamide T325 (35 mg, 0.074 mmol) in MeOH (2 mL) was treated with formaldehyde (37% in water) (10 uL, 0.37 mmol), stirred for 5 mins then NaCNBH$_4$ (13.90 mg, 0.221 mmol) was added. After 1 hr the reaction mixture was loaded on to SCX (1 g), then washed with MeOH and the required product eluted with 1% NH$_3$ in MeOH, this was then concentrated onto silica (500 mg). The crude product was purified by chromatography on silica gel (4 g column, 0-10% (0.7 M NH$_3$/MeOH in DCM) to afford 2-(2-(cyclopropanesulfonamido)thiazol-4-yl)-2-(dimethylamino)-N-(4-(6-ethoxypyrazin-2-yl)phenyl)acetamide (18 mg, 0.034 mmol, 46% yield) as a brown solid. Rt 1.73 min (HPLC, basic); m/z 503 (M+H)$^+$ (ES$^+$); $^1$H NMR (500 MHz, DMSO-d6) δ 12.62 (v. br. s, 1H), 10.19 (s, 1H), 8.78 (s, 1H), 8.19 (s, 1H), 8.15-8.06 (m, 2H), 7.90-7.66 (m, 2H), 6.75 (s, 1H), 4.48 (q, J=7.0 Hz, 2H), 4.28 (s, 1H), 2.63-2.56 (m, 1H), 2.30 (s, 6H), 1.40 (t, J=7.0 Hz, 3H), 0.94-0.82 (m, 4H).

2-(2-(cyclopropanesulfonamido)thiazol-4-yl)-N-(4-(6-ethoxypyrazin-2-yl)phenyl)-4-hydroxybutanamide T329

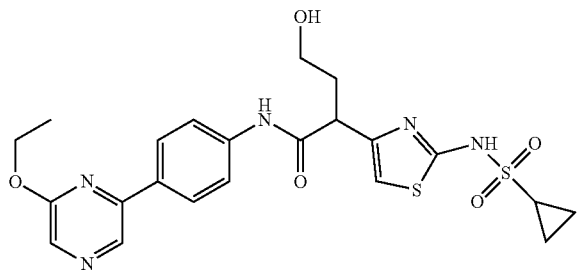 [SMILES: CCOc1cncc(-c2ccc(NC(=O)C(CCO)c3csc(NS(=O)(=O)C4CC4)n3)cc2)n1]

A suspension of 4-(6-ethoxypyrazin-2-yl)aniline INTA38 (258 mg, 1.200 mmol) in DCM (2 mL) at 0° C. was treated with AlMe$_3$ (2M in heptane) (600 uL, 1.200 mmol) dropwise, the reaction mixture was stirred for 15 mins before a solution of N-(4-(2-oxotetrahydrofuran-3-yl)thiazol-2-yl)cyclopropanesulfonamide INTB81 (255 mg, 0.884 mmol) in DCM (2 mL) was added dropwise resulting in effervescence. The reaction mixture was left stirring at RT for 18 hrs.

The reaction mixture was quenched by dropwise addition of 1M HCl aq. (10 mL). The product was extracted using DCM (3×10 mL) separating with a phase separator. The organic phase was concentrated onto silica (3 g) and the crude product was purified by chromatography on silica gel (12 g column, 0-10% MeOH/DCM) to afford 2-(2-(cyclopropanesulfonamido)thiazol-4-yl)-N-(4-(6-ethoxypyrazin-2-yl)phenyl)-4-hydroxybutanamide (77 mg, 0.150 mmol, 12% yield) as a brown gum which was triturated from DCM and TBME to afford a colourless solid. Rt 1.18 min (UPLC, acidic); m/z 504 (M+H)$^+$ (ES$^+$). $^1$H NMR (500 MHz, DMSO-d6) δ 12.60 (s, 1H), 10.35 (s, 1H), 8.77 (s, 1H), 8.19 (s, 1H), 8.15-8.07 (m, 2H), 7.79-7.72 (m, 2H), 6.54 (s, 1H), 4.71-4.61 (m, 1H), 4.48 (q, J=7.1 Hz, 2H), 3.90-3.81 (m, 1H), 3.48-3.38 (m, 2H), 2.62-2.53 (m, 1H), 2.20-2.08 (m, 1H), 2.06-1.94 (m, 1H), 1.40 (t, J=7.0 Hz, 3H), 0.95-0.85 (m, 4H).

The racemate T410 was separated by chiral preparative HPLC [Chiralpak® IB (Daicel Ltd.) column (4.6 mm×25 mm), flow rate 0.5 mL min$^{-1}$ eluting with a mixture of (30% of ethanol) ethanol in heptane+0.2% Et$_2$NH, UV detection at 254 nm followed by SCX (300 mg) purification (elution with MeOH) to afford:

2-(2-(cyclopropanesulfonamido)thiazol-4-yl)-N-(4-(6-ethoxypyrazin-2-yl)phenyl)-2-methoxyacetamide T410

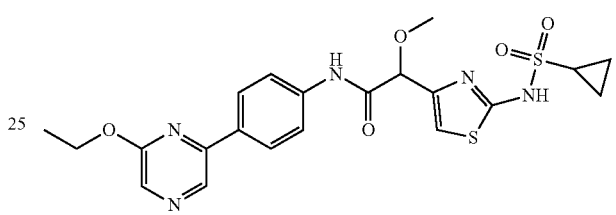

The racemate T410 was prepared using Method 1b was separated by chiral preparative HPLC using a Diacel Chiralpak IB column (30% EtOH (0.1% DEA) in iso-hexane (0.2% DEA) to afford:

Peak 1: Stereochemistry of Product was Unassigned
2-(2-(cyclopropanesulfonamido)thiazol-4-yl)-N-(4-(6-ethoxypyrazin-2-yl)phenyl)-2-methoxyacetamide T330 (10 mg, 0.020 mmol, 15% yield) was isolated as a colourless solid. Rt 10=1.27 min (UPLC, acidic); m/z 490 (M+H)$^+$ (ES$^+$). $^1$H NMR (500 MHz, DMSO-d6) δ 12.81 (s, 1H), 10.09 (s, 1H), 8.78 (s, 1H), 8.19 (s, 1H), 8.16-8.06 (m, 2H), 7.91-7.82 (m, 2H), 6.84 (s, 1H), 4.90 (s, 1H), 4.48 (q, J=7.0 Hz, 2H), 3.40 (s, 3H), 2.63-2.54 (m, 1H), 1.40 (t, J=7.1 Hz, 3H), 0.96-0.84 (m, 4H).

The product was analysed by chiral HPLC [Diacel Chiralpak IB, 5 um, 4.6×250 mm, 30 min method, 0.5 mL/min, 30% EtOH (0.1% DEA) in iso-hexane (0.2% DEA)]; Rt=12.1 min, 98% ee.

Peak 2: Stereochemistry of Product was Unassigned
2-(2-(cyclopropanesulfonamido)thiazol-4-yl)-N-(4-(6-ethoxypyrazin-2-yl)phenyl)-2-methoxyacetamide T331 (13 mg, 0.026 mmol, 19% yield) was isolated as a colourless solid. Rt=1.27 min (UPLC, acidic); m/z 490 (M+H)$^+$ (ES$^+$). $^1$H NMR (500 MHz, DMSO-d6) δ 12.81 (s, 1H), 10.09 (s, 1H), 8.78 (s, 1H), 8.19 (s, 1H), 8.16-8.06 (m, 2H), 7.91-7.82 (m, 2H), 6.84 (s, 1H), 4.90 (s, 1H), 4.48 (q, J=7.0 Hz, 2H), 3.40 (s, 3H), 2.63-2.54 (m, 1H), 1.40 (t, J=7.1 Hz, 3H), 0.96-0.84 (m, 4H).

The product was analysed by Chiral HPLC [Diacel Chiralpak IB, 5 um, 4.6×250 mm, 30 min method, 0.5 mL/min, 30% EtOH (0.1% DEA) in iso-hexane (0.2% DEA)]; Rt=20.7 min. 94% ee.

TABLE 16

Preparation methods and characterisation data of examples T332-T416

| T # | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| T332 | 2-(2-((2-methoxyethyl)sulfonamido)thiazol-4-yl)-2-methyl-N-(5-(6-(trifluoromethyl)pyrazin-2-yl)pyridin-2-yl)propanamide | Method 1b using INTB97 and INTA3, [UPLC Acidic], 531, (1.27) | 12.61 (s, 1H), 10.23 (s, 1H), 9.68 (s, 1H), 9.19-9.15 (m, 2H), 8.61 (dd, J = 8.9, 2.5 Hz, 1H), 8.26 (dd, J = 8.8, 0.8 Hz, 1H), 6.72-6.54 (m, 2H), 3.66 (t, J = 6.6 Hz, 2H), 3.31-3.27 (m, 1H), 3.19 (s, 3H), 1.62 (s, 6H). |
| T333 | 2-(2-(cyclopentanesulfonamido)thiazol-4-yl)-2-methyl-N-(4-(pyridin-3-yl)phenyl)propanamide | Method 1b using INTB90, [UPLC Acidic], 471, (0.88) | 12.49 (s, 1H), 9.41 (s, 1H), 8.90 (d, J = 2.4 Hz, 1H), 8.54 (dd, J = 4.7, 1.6 Hz, 1H), 8.07 (dt, J = 8.0, 2.1 Hz, 1H), 7.78-7.74 (m, 2H), 7.74-7.70 (m, 2H), 7.47 (dd, J = 8.0, 4.7 Hz, 1H), 6.55 (s, 1H), 3.54-3.41 (m, 1H), 1.93-1.84 (m, 4H), 1.74-1.61 (m, 2H), 1.61-1.44 (m, 8H). |
| T334 | 2-(2-(cyclopentanesulfonamido)thiazol-4-yl)-2-methyl-N-(4-(6-(trifluoromethyl)pyrazin-2-yl)phenyl)propanamide | Method 1b using INTB90 and INTA39, [UPLC Acidic], 540, (1.50) | 12.53 (s, 1H), 9.59 (s, 1H), 9.56 (s, 1H), 9.08 (s, 1H), 8.23-8.14 (m, 2H), 7.91-7.80 (m, 2H), 6.53 (s, 1H), 3.53-3.41 (m, 1H), 1.93-1.79 (m, 4H), 1.74-1.61 (m, 2H), 1.61-1.47 (m, 8H). |
| T335 | 2-(2-(cyclopentanesulfonamido)thiazol-4-yl)-N-(4-(6-ethoxypyrazin-2-yl)phenyl)-2-methylpropanamide | Method 1b using INTB90 and INTA38, [UPLC Acidic], 516, (1.46) | 12.52 (s, 1H), 9.49 (s, 1H), 8.78 (s, 1H), 8.19 (s, 1H), 8.15-8.07 (m, 2H), 7.84-7.71 (m, 2H), 6.52 (s, 1H), 4.48 (q, J = 7.0 Hz, 2H), 3.47 (s, 1H), 1.94-1.81 (m, 4H), 1.70-1.62 (m, 2H), 1.62-1.49 (m, 8H), 1.41 (t, J = 7.0 Hz, 3H). |
| T336 | 2-(2-(cyclopropanesulfonamido)thiazol-4-yl)-N-(5-(6-isopropylpyrazin-2-yl)pyridin-2-yl)-2-methylpropanamide | Method 1b using INTB37 and INTA80, [HPLC Acidic], 487, (2.11) | 12.59 (s, 1H), 10.13 (s, 1H), 9.13 (s, 1H), 9.12-9.10 (m, 1H), 8.58 (s, 1H), 8.55 (dd, J = 8.8, 2.4 Hz, 1H), 8.20 (dd, J = 8.8, 0.8 Hz, 1H), 6.58 (s, 1H), 3.24-3.13 (m, 1H), 2.63-2.54 (m, 1H), 1.62 (s, 6H), 1.34 (d, J = 6.9 Hz, 6H), 0.97-0.82 (m, 4H). |

TABLE 16-continued

Preparation methods and characterisation data of examples T332-T416

| T # | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| T337 | 2-(2-(cyclopropanesulfonamido)thiazol-4-yl)-N-(5'-ethoxy-[3,3'-bipyridin]-6-yl)-2-methylpropanamide | Method 1b using INTB37 and INTA32, [HPLC Acidic], 488.1, (1.70) | 12.55 (s, 1H), 10.01 (s, 1H), 8.77 (dd, J = 2.6, 0.8 Hz, 1H), 8.54 (d, J = 1.8 Hz, 1H), 8.30 (d, J = 2.7 Hz, 1H), 8.24 (dd, J = 8.7, 2.6 Hz, 1H), 8.14 (dd, J = 8.7, 0.8 Hz, 1H), 7.70 (dd, J = 2.8, 1.9 Hz, 1H), 6.60 (s, 1H), 4.22 (q, J = 7.0 Hz, 2H), 2.56-2.26 (m, 1H), 1.61 (s, 6H), 1.38 (t, J = 7.0 Hz, 3H), 0.96-0.87 (m, 4H) |
| T338 | 2-(2-(cyclopropanesulfonamido)thiazol-4-yl)-N-(5-(6-(2-hydroxypropan-2-yl)pyrazin-2-yl)pyridin-2-yl)-2-methylpropanamide | Method 1b using INTB37 and INTA83, [UPLC Acidic], 503, (1.06) | 12.58 (s, 1H), 10.12 (s, 1H), 9.16 (s, 1H), 9.12 (s, 1H), 8.86 (s, 1H), 8.56 (dd, J = 8.8, 2.5 Hz, 1H), 8.19 (dd, J = 8.8, 0.8 Hz, 1H), 6.57 (s, 1H), 5.50 (s, 1H), 2.62-2.54 (m, 1H), 1.61 (s, 6H), 1.54 (s, 6H), 0.97-0.81 (m, 4H). |
| T339 | 2-(2-(cyclopropanesulfonamido)thiazol-4-yl)-N-(5-(6-(2-methoxypropan-2-yl)pyrazin-2-yl)pyridin-2-yl)-2-methylpropanamide | Method 1b using INTB37 and INTA84, [UPLC Acidic], 517, (1.26) | 12.58 (s, 1H), 10.12 (s, 1H), 9.21 (s, 1H), 9.12 (s, 1H), 8.75 (s, 1H), 8.60-8.49 (m, 1H), 8.20 (dd, J = 8.7, 0.8 Hz, 1H), 6.56 (s, 1H), 3.16 (s, 3H), 2.63-2.55 (m, 1H), 1.61 (s, 6H), 1.57 (s, 6H), 0.99-0.75 (m, 4H). |
| T340 | 2-(2-(cyclopropanesulfonamido)-5-methylthiazol-4-yl)-2-methyl-N-(5-(6-(trifluoromethyl)pyrazin-2-yl)pyridin-2-yl)propanamide | Method 1e using INTB42 and INTA3, [HPLC Acidic], 527, (2.20) | 11.95 (s, 1H), 10.88 (s, 1H), 9.67 (s, 1H), 9.21-9.11 (m, 2H), 8.59 (dd, J = 8.8, 2.5 Hz, 1H), 8.28 (d, J = 8.7 Hz, 1H), 2.63-2.53 (m, 1H), 1.94 (s, 3H), 1.54 (s, 6H), 0.98-0.85 (m, 4H). |
| T341 | 2-(2-(cyclopropanesulfonamido)thiazol-4-yl)-N-(5-(6-ethoxypyrazin-2-yl)pyridin-2-yl)-2-methylpropanamide | Method 1b using INTB 37 and INTA72, [HPLC Acidic], 489, (1.93) | 12.59 (s, 1H), 10.12 (s, 1H), 9.09 (d, J = 2.3 Hz, 1H), 8.87 (s, 1H), 8.53 (dd, J = 8.8, 2.5 Hz, 1H), 8.26 (s, 1H), 8.23-8.15 (m, 1H), 6.58 (s, 1H), 4.49 (q, J = 7.0 Hz, 2H), 2.63-2.56 (m, 1H), 1.62 (s, 6H), 1.41 (t, J = 7.0 Hz, 3H), 0.97-0.84 (m, 4H). |

TABLE 16-continued

Preparation methods and characterisation data of examples T332-T416

| T # | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| T342 | 2-(2-(cyclopropanesulfonamido)-5-methylthiazol-4-yl)-N-(5-(6-ethoxypyrazin-2-yl)pyridin-2-yl)-2-methylpropanamide | Method 1e using INTB42 and INTA72, [HPLC Acidic], 503, (2.14) | 11.95 (s, 1H), 10.75 (s, 1H), 9.07 (d, J = 2.4 Hz, 1H), 8.86 (s, 1H), 8.51 (dd, J = 8.8, 2.5 Hz, 1H), 8.26 (s, 1H), 8.21 (d, J = 8.8 Hz, 1H), 4.48 (q, J = 7.0 Hz, 2H), 2.61-2.55 (m, 1H), 1.94 (s, 3H), 1.54 (s, 6H), 1.40 (t, J = 7.0 Hz, 3H), 0.96-0.88 (m, 4H). |
| T343 | N-(4-(5-chloropyridin-3-yl)-2-(trifluoromethyl)phenyl)-2-(2-(cyclopropanesulfonamido)thiazol-4-yl)-2-methylpropanamide | Method 2 using INTB100, [UPLC Acidic], 545, (1.38) | 12.60 (s, 1H), 9.09 (s, 1H), 8.96 (d, J = 2.0 Hz, 1H), 8.67 (d, J = 2.3 Hz, 1H), 8.43-8.39 (m, 1H), 8.17-8.09 (m, 2H), 7.69 (d, J = 8.3 Hz, 1H), 6.64 (s, 1H), 2.59-2.55 (m, 1H), 1.55 (s, 6H), 0.91 (s, 4H). |
| T344 | N-(4-(5-cyanopyridin-3-yl)-2-(trifluoromethyl)phenyl)-2-(2-(cyclopropanesulfonamido)thiazol-4-yl)-2-methylpropanamide | Method 2 using INTB100, [UPLC Acidic], 536, (1.26) | 12.60 (s, 1H), 9.29 (d, J = 2.3 Hz, 1H), 9.11 (s, 1H), 9.06 (d, J = 1.9 Hz, 1H), 8.83-8.79 (m, 1H), 8.21-8.15 (m, 2H), 7.74-7.70 (m, 1H), 6.65 (s, 1H), 2.60-2.56 (m, 1H), 1.56 (s, 6H), 0.94-0.89 (m, 4H). |
| T345 | 2-(2-(cyclopropanesulfonamido)thiazol-4-yl)-N-(4-(5-fluoropyridin-3-yl)-2-(trifluoromethyl)phenyl)-2-methylpropanamide | Method 1b using INTB37 and INTA91, [HPLC Acidic], 529, (2.04) | 12.61 (s, 1H), 9.10 (s, 1H), 8.93-8.88 (m, 1H), 8.64 (d, J = 2.7 Hz, 1H), 8.27-8.22 (m, 1H), 8.18-8.13 (m, 1H), 8.13-8.09 (m, 1H), 7.71 (d, J = 8.3 Hz, 1H), 6.66 (s, 1H), 2.63-2.54 (m, 1H), 1.57 (s, 6H), 1.00-0.82 (m, 4H). |

TABLE 16-continued

Preparation methods and characterisation data of examples T332-T416

| T # | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| T346 | 2-(2-(cyclopropanesulfonamido)thiazol-4-yl)-2-methyl-N-(2-(trifluoromethyl)-4-(6-(trifluoromethyl)pyrazin-2-yl)phenyl)propanamide | Method 2 using INTB100, [UPLC Acidic], 580, (1.49) | 12.64 (s, 1H), 9.75 (s, 1H), 9.22 (s, 1H), 9.15 (s, 1H), 8.57-8.47 (m, 2H), 7.83 (d, J = 8.3 Hz, 1H), 6.67 (s, 1H), 2.61-2.57 (m, 1H), 1.58 (s, 6H), 0.94-0.90 (m, 4H). |
| T347 | 2-(2-(cyclopropanesulfonamido)thiazol-4-yl)-N-(4-(6-ethoxypyrazin-2-yl)-2-(trifluoromethyl)phenyl)-2-methylpropanamide | Method 2 using INTB100, [UPLC Acidic], 556, (1.47) | 12.63 (s, 1H), 9.10 (s, 1H), 8.94 (s, 1H), 8.49-8.40 (m, 2H), 8.31 (s, 1H), 7.75 (d, J = 8.5 Hz, 1H), 6.66 (s, 1H), 4.49 (q, J = 7.1 Hz, 2H), 2.61-2.57 (m, 1H), 1.57 (s, 6H), 1.42 (t, J = 7.0 Hz, 3H), 0.95-0.87 (m, 4H). |
| T348 | N-(4-(5-chloropyridin-3-yl)-2,6-diethylphenyl)-2-(2-(cyclopropanesulfonamido)thiazol-4-yl)-2-methylpropanamide | Method 2 using INTB101, [UPLC Acidic], 533, (1.40) | (Methanol-d4) 8.73 (d, J = 2.0 Hz, 1H), 8.53 (d, J = 2.3 Hz, 1H), 8.15-8.10 (m, 1H), 7.42 (s, 2H), 6.67 (s, 1H), 2.68-2.53 (m, 5H), 1.70 (s, 6H), 1.19 (t, J = 7.6 Hz, 6H), 1.13-1.08 (m, 2H), 1.00-0.93 (m, 2H). 2 exchangeable protons not observed. |
| T349 | N-(4-(5-cyanopyridin-3-yl)-2,6-diethylphenyl)-2-(2-(cyclopropanesulfonamido)thiazol-4-yl)-2-methylpropanamide | Method 2 using INTB101, [UPLC Acidic], 524, (1.28) | 12.55 (s, 1H), 9.21 (d, J = 2.3 Hz, 1H), 8.98 (d, J = 1.9 Hz, 1H), 8.93 (s, 1H), 8.72-8.67 (m, 1H), 7.53 (s, 2H), 6.59 (s, 1H), 2.59-2.47 (m, 5H), 1.61 (s, 6H), 1.12 (t, J = 7.5 Hz, 6H), 0.94-0.84 (m, 4H). |

TABLE 16-continued

Preparation methods and characterisation data of examples T332-T416

| T # | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| T350 | 2-(2-(cyclopropanesulfonamido)-5-methylthiazol-4-yl)-N-(2-fluoro-4-(5-(trifluoromethyl)pyridin-3-yl)phenyl)-2-methylpropanamide | Method 1e using INTB42 and INTA70, [HPLC Acidic], 543, (2.22) | 12.02 (s, 1H), 9.76 (s, 1H), 9.26 (d, J = 2.2 Hz, 1H), 8.98 (d, J = 2.0 Hz, 1H), 8.54 (d, J = 2.3 Hz, 1H), 7.89 (dd, J = 11.8, 2.1 Hz, 1H), 7.73 (dd, J = 8.4, 2.0 Hz, 1H), 7.67-7.60 (m, 1H), 2.63-2.55 (m, 1H), 2.05 (s, 3H), 1.53 (s, 6H), 0.97-0.86 (m, 4H). |
| T351 | N-(4-(5-chloropyridin-3-yl)-2,6-difluorophenyl)-2-(2-(cyclopropanesulfonamido)thiazol-4-yl)-2-methylpropanamide | Method 2 using INTB105, [UPLC Acidic], 513, (1.25) | 12.64 (s, 1H), 9.35 (s, 1H), 8.97 (d, J = 2.0 Hz, 1H), 8.67 (d, J = 2.3 Hz, 1H), 8.42-8.37 (m, 1H), 7.78-7.70 (m, 2H), 6.58 (s, 1H), 2.61-2.57 (m, 1H), 1.58 (s, 6H), 0.94-0.88 (m, 4H). |
| T352 | N-(4-(5-chloropyridin-3-yl)-2-fluoro-5-methylphenyl)-2-(2-(cyclopropanesulfonamido)thiazol-4-yl)-2-methylpropanamide | Method 2 using INTB103, [UPLC Acidic], 509, (1.34) | 12.59 (s, 1H), 9.21 (s, 1H), 8.66 (d, J = 2.3 Hz, 1H), 8.56 (d, J = 1.9 Hz, 1H), 8.05-8.00 (m, 1H), 7.47 (d, J = 7.7 Hz, 1H), 7.26 (d, J = 10.9 Hz, 1H), 6.58 (s, 1H), 2.60-2.56 (m, 1H), 2.21 (s, 3H), 1.57 (s, 6H), 0.93-0.87 (m, 4H). |
| T353 | 2-(2-(cyclopropanesulfonamido)thiazol-4-yl)-N-(2-fluoro-4-(6-(2-methoxypropan-2-yl)pyrazin-2-yl)phenyl)-2-methylpropanamide | Method 1b using INTB37 and INTA86, [UPLC Acidic], 534, (1.33) | 12.62 (s, 1H), 9.29 (s, 1H), 9.20 (s, 1H), 8.75 (s, 1H), 8.13-7.98 (m, 3H), 6.60 (s, 1H), 3.17 (s, 3H), 2.62-2.55 (m, 1H), 1.59 (s, 6H), 1.58 (s, 6H), 0.95-0.76 (m, 4H). |

TABLE 16-continued

Preparation methods and characterisation data of examples T332-T416

| T # | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| T354 | 2-(2-(cyclopropanesulfonamido)-5-methylthiazol-4-yl)-N-(2-fluoro-4-(6-(trifluoromethyl)pyrazin-2-yl)phenyl)-2-methylpropanamide | Method 1e using INTB42 and INTA48, [HPLC Acidic], 544, (2.29) | 12.03 (s, 1H), 9.86 (s, 1H), 9.66 (s, 1H), 9.17 (s, 1H), 8.18-8.02 (m, 2H), 7.76 (t, J = 8.1 Hz, 1H), 2.64-2.53 (m, 1H), 2.05 (s, 3H), 1.54 (s, 6H), 0.92 (t, J = 6.8 Hz, 4H). |
| T355 | N-(4-(6-cyanopyrazin-2-yl)-2-fluorophenyl)-2-(2-(cyclopropanesulfonamido)thiazol-4-yl)-2-methylpropanamide | Method 1b using INTB37 and INTA87, [UPLC Acidic], 487, (1.22) | 12.62 (s, 1H), 9.61 (s, 1H), 9.33 (s, 1H), 9.18 (s, 1H), 8.12 (dd, J = 11.7, 2.0 Hz, 1H), 8.07 (d, J = 8.3 Hz, 1H), 7.80 (s, 1H), 6.61 (s, 1H), 2.62-2.54 (m, 1H), 1.59 (s, 6H), 0.97-0.74 (m, 4H). |
| T356 | 2-(2-(cyclopropanesulfonamido)thiazol-4-yl)-N-(4-(6-ethylpyrazin-2-yl)-2-fluorophenyl)-2-methylpropanamide | Method 1b using INTB37 and INTA82, [HPLC Acidic], 490, (2.04) | 12.61 (s, 1H), 9.27 (s, 1H), 9.11 (s, 1H), 8.54 (s, 1H), 8.11-7.92 (m, 2H), 7.71 (s, 1H), 6.60 (s, 1H), 2.87 (q, J = 7.6 Hz, 2H), 2.61-2.54 (m, 1H), 1.58 (s, 6H), 1.31 (t, J = 7.6 Hz, 3H), 0.94-0.86 (m, 4H). |
| T357 | 2-(2-(cyclopropanesulfonamido)thiazol-4-yl)-N-(2-fluoro-4-(6-isopropoxypyrazin-2-yl)phenyl)-2-methylpropanamide | Method 1e using INTB37 and INTA89, [HPLC Acidic], 520, (2.28) | 12.62 (s, 1H), 9.28 (s, 1H), 8.83 (s, 1H), 8.20 (s, 1H), 8.08-7.94 (m, 2H), 7.78-7.64 (m, 1H), 6.60 (s, 1H), 5.43 (hept, J = 6.2 Hz, 1H), 2.66-2.55 (m, 1H), 1.59 (s, 6H), 1.39 (d, J = 6.2 Hz, 6H), 0.91 (d, J = 8.3 Hz, 4H). |

TABLE 16-continued

Preparation methods and characterisation data of examples T332-T416

| T # | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| T358 | 2-(2-(cyclopropanesulfonamido)-5-methylthiazol-4-yl)-N-(4-(6-ethoxypyrazin-2-yl)-2-fluorophenyl)-2-methylpropanamide | Method 1e using INTB42 and INTA47, [HPLC Acidic], 520, (2.25) | 12.00 (s, 1H), 9.75 (s, 1H), 8.85 (s, 1H), 8.26 (s, 1H), 8.06-7.95 (m, 2H), 7.71-7.62 (m, 1H), 4.49 (q, J = 7.0 Hz, 2H), 2.63-2.54 (m, 1H), 2.06 (s, 3H), 1.54 (s, 6H), 1.41 (t, J = 7.0 Hz, 3H), 0.96-0.85 (m, 4H). |
| T359 | N-(4-(5-chloropyridin-3-yl)-2-isopropylphenyl)-2-(2-(cyclopropanesulfonamido)thiazol-4-yl)-2-methylpropanamide | Method 2 using INTB109, [UPLC Acidic], 519, (1.38) | 12.60 (s, 1H), 8.98 (s, 1H), 8.88 (d, J = 2.0 Hz, 1H), 8.61 (d, J = 2.3 Hz, 1H), 8.31-8.26 (m, 1H), 7.67 (d, J = 2.2 Hz, 1H), 7.61 (dd, J = 8.2, 2.2 Hz, 1H), 7.36-7.32 (m, 1H), 6.61 (s, 1H), 3.12-3.03 (m, 1H), 2.59-2.55 (m, 1H), 1.57 (s, 6H), 1.17 (d, J = 6.8 Hz, 6H), 0.93-0.84 (m, 4H). |
| T360 | N-(4-(5-cyanopyridin-3-yl)-2-isopropylphenyl)-2-(2-(cyclopropanesulfonamido)thiazol-4-yl)-2-methylpropanamide | Method 2, [UPLC using INTB109 Acidic], 510, (1.27) | 12.60 (s, 1H), 9.22 (d, J = 2.3 Hz, 1H), 8.99 (d, J = 1.9 Hz, 1H), 8.74-8.69 (m, 1H), 7.73 (d, J = 2.2 Hz, 1H), 7.66 (dd, J = 8.2, 2.2 Hz, 1H), 7.36 (d, J = 8.0 Hz, 1H), 6.61 (s, 1H), 3.13-3.03 (m, 1H), 2.59-2.52 (m, 1H), 1.58 (s, 6H), 1.18 (d, J = 6.9 Hz, 6H), 0.95-0.87 (m, 4H). 1 exchangeable proton missing. |
| T361 | 2-(2-(cyclopropanesulfonamido)thiazol-4-yl)-N-(2-isopropyl-4-(6-(trifluoromethyl)pyrazin-2-yl)phenyl)-2-methylpropanamide | Method 2c using INTB109, [UPLC Acidic], 554, (1.48) | 12.63 (s, 1H), 9.66 (s, 1H), 9.13 (s, 1H), 9.05 (s, 1H), 8.11 (d, J = 2.1 Hz, 1H), 8.03 (dd, J = 8.3, 2.1 Hz, 1H), 7.46 (d, J = 8.2 Hz, 1H), 6.63 (s, 1H), 3.15-3.09 (m, 1H), 2.60-2.56 (m, 1H), 1.60 (s, 6H), 1.20 (d, J = 6.9 Hz, 6H), 0.95-0.87 (m, 4H). |

TABLE 16-continued

Preparation methods and characterisation data of examples T332-T416

| T # | Name/Structure (All examples containing chiral centres are racemates unless stated) | Synthesis Method, [LCMS Method], m/z (M + H)+, (RT/Min) | ¹H NMR Chemical Shift Data (DMSO-d6 unless stated) |
| --- | --- | --- | --- |
| T362 | 2-(2-(cyclopropanesulfonamido)thiazol-4-yl)-N-(4-(6-ethoxypyrazin-2-yl)-2-isopropylphenyl)-2-methylpropanamide | Method 2c using INTB109, [UPLC Acidic], 530, (1.45) | 12.62 (s, 1H), 9.00 (s, 1H), 8.83 (s, 1H), 8.22 (s, 1H), 8.04 (d, J = 2.0 Hz, 1H), 7.94 (dd, J = 8.2, 2.0 Hz, 1H), 7.37 (d, J = 8.2 Hz, 1H), 6.61 (s, 1H), 4.48 (q, J = 7.0 Hz, 2H), 3.12-3.06 (m, 1H), 2.60-2.56 (m, 1H), 1.59 (s, 6H), 1.41 (t, J = 7.0 Hz, 3H), 1.18 (d, J = 6.8 Hz, 6H), 0.93-0.87 (m, 4H). |
| T363 | N-(4-(5-chloropyridin-3-yl)-3-fluoro-2-methylphenyl)-2-(2-(cyclopropanesulfonamido)thiazol-4-yl)-2-methylpropanamide | Method 2 using INTB99, [UPLC Acidic], 509, (1.32) | 12.61 (s, 1H), 9.19 (s, 1H), 8.74-8.69 (m, 1H), 8.65 (d, J = 2.3 Hz, 1H), 8.16-8.11 (m, 1H), 7.47 (t, J = 8.4 Hz, 1H), 7.24 (d, J = 8.2 Hz, 1H), 6.60 (s, 1H), 2.59-2.55 (m, 1H), 2.11 (s, 3H), 1.58 (s, 6H), 0.92-0.88 (m, 4H). |
| T364 | N-(4-(5-chloropyridin-3-yl)-5-fluoro-2-methylphenyl)-2-(2-(cyclopropanesulfonamido)thiazol-4-yl)-2-methylpropanamide | Method 2 using INTB108, [UPLC Acidic], 509, (1.35) | (Methanol-d4) 8.67- 8.62 (m, 1H), 8.55 (d, J = 2.3 Hz, 1H), 8.08-8.03 (m, 1H), 7.48-7.40 (m, 2H), 6.70 (s, 1H), 2.68-2.59 (m, 1H), 2.22 (s, 3H), 1.67 (s, 6H), 1.19-1.05 (m, 2H), 1.02-0.93 (m, 2H). 2 exchangeable protons unobserved. |
| T365 | N-(4-(5-chloropyridin-3-yl)-2,3-dimethylphenyl)-2-(2-(cyclopropanesulfonamido)thiazol-4-yl)-2-methylpropanamide | Method 2 using INTB102, [UPLC Acidic], 505, (1.30) | 12.60 (s, 1H), 9.07 (s, 1H), 8.64 (d, J = 2.3 Hz, 1H), 8.47 (d, J = 1.9 Hz, 1H), 7.94-7.89 (m, 1H), 7.19-7.13 (m, 1H), 7.11 (d, J = 8.1 Hz, 1H), 6.58 (s, 1H), 2.59-2.55 (m, 1H), 2.14 (s, 3H), 2.09 (s, 3H), 1.58 (s, 6H), 0.93-0.87 (m, 4H). |

TABLE 16-continued

Preparation methods and characterisation data of examples T332-T416

| T # | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| T366 | N-(4-(5-chloropyridin-3-yl)-2,5-dimethylphenyl)-2-(2-(cyclopropanesulfonamido)thiazol-4-yl)-2-methylpropanamide | Method 2 using INTB104, [UPLC Acidic], 505, (1.33) | 12.59 (s, 1H), 8.93 (s, 1H), 8.63 (d, J = 2.3 Hz, 1H), 8.53 (d, J = 1.9 Hz, 1H), 7.99-7.95 (m, 1H), 7.23 (s, 1H), 7.16 (s, 1H), 6.60 (s, 1H), 2.61-2.57 (m, 1H), 2.21 (s, 3H), 2.14 (s, 3H), 1.58 (s, 6H), 0.94-0.88 (m, 4H). |
| T367 | N-(4-(5-cyanopyridin-3-yl)-3-fluoro-2-methylphenyl)-2-(2-(cyclopropanesulfonamido) thiazol-4-yl)-2-methylpropanamide | Method 2 using INTB99, [UPLC Acidic], 500, (1.19) | (Methanol-d4) 9.00-8.96 (m, 1H), 8.91 (d, J = 2.0 Hz, 1H), 8.41-8.36 (m, 1H), 7.46-7.39 (m, 1H), 7.34 (d, J = 8.3 Hz, 1H), 6.69 (s, 1H), 2.67-2.59 (m, 1H), 2.17 (d, J = 2.4 Hz, 3H), 1.68 (s, 6H), 1.15-1.05 (m, 2H), 1.03-0.94 (m, 2H). 2 exchangeable protons unobserved. |
| T368 | 2-(2-(cyclopropanesulfonamido)thiazol-4-yl)-2-methyl-N-(2-methyl-4-(6-(trifluoromethyl)pyrazin-2-yl)phenyl)propanamide | Method 1e using INTB37 and INTA88, [HPLC Acidic], 526, (2.18) | 12.61 (s, 1H), 9.61 (s, 1H), 9.23-8.94 (m, 2H), 8.22-7.98 (m, 2H), 7.56 (d, J = 8.2 Hz, 1H), 6.64 (s, 1H), 2.63-2.54 (m, 1H), 2.28 (s, 3H), 1.60 (s, 6H), 1.03-0.77 (m, 4H). |
| T369 | N-(4-(5-chloropyridin-3-yl)-5-fluoro-2-methoxyphenyl)-2-(2-(cyclopropanesulfonamido) thiazol-4-yl)-2-methylpropanamide | Method 2 using INTB107, [UPLC Acidic], 525, (1.44) | 12.68 (s, 1H), 8.79-8.74 (m, 1H), 8.65 (d, J = 2.3 Hz, 1H), 8.46 (s, 1H), 8.20-8.16 (m, 1H), 8.00-7.96 (m, 1H), 7.31 (d, J = 7.0 Hz, 1H), 6.75 (s, 1H), 3.89 (s, 3H), 2.62-2.58 (m, 1H), 1.56 (s, 6H), 0.94-0.90 (m, 4H). |

TABLE 16-continued

Preparation methods and characterisation data of examples T332-T416

| T # | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| T370 | N-(4-(5-chloropyridin-3-yl)-3-(trifluoromethyl)phenyl)-2-(2-(cyclopropanesulfonamido)thiazol-4-yl)-2-methylpropanamide | Method 2 using INTB106, [UPLC Acidic], 544, (1.45) | 12.60 (s, 1H), 9.75 (s, 1H), 8.70 (d, J = 2.3 Hz, 1H), 8.47 (d, J = 1.8 Hz, 1H), 8.24-8.20 (m, 1H), 8.04-7.98 (m, 1H), 7.96-7.92 (m, 1H), 7.48 (d, J = 8.4 Hz, 1H), 6.58 (s, 1H), 2.61-2.57 (m, 1H), 1.58 (s, 6H), 0.93-0.89 (m, 4H). |
| T371 | 2-(2-(cyclopropanesulfonamido)thiazol-4-yl)-N-(4-(6-ethoxypyrazin-2-yl)-3-methylphenyl)-2-methylpropanamide | Method 2c using INTB59, [UPLC Acidic], 502, (1.36) | 12.57 (s, 1H), 9.39 (s, 1H), 8.35 (s, 1H), 8.22 (s, 1H), 7.65-7.59 (m, 2H), 7.48 (d, J = 8.2 Hz, 1H), 6.56-6.50 (m, 1H), 4.39 (q, J = 7.0 Hz, 2H), 2.62-2.52 (m, 1H), 2.41 (s, 3H), 1.57 (s, 6H), 1.37 (t, J = 7.0 Hz, 3H), 0.93-0.89 (m, 4H). |
| T372 | N-(4-(5-chloropyridin-3-yl)-3-ethoxyphenyl)-2-(2-(cyclopropanesulfonamido)thiazol-4-yl)-2-methylpropanamide | Method 2 using INTB71, [UPLC Acidic], 521, (1.41) | 12.58 (s, 1H), 9.43 (s, 1H), 8.68 (d, J = 1.9 Hz, 1H), 8.54 (d, J = 2.3 Hz, 1H), 8.06-8.02 (m, 1H), 7.55 (d, J = 1.9 Hz, 1H), 7.43-7.34 (m, 2H), 6.55 (s, 1H), 4.06 (q, J = 6.9 Hz, 2H), 2.61-2.57 (m, 1H), 1.58 (s, 6H), 1.31 (t, J = 6.9 Hz, 3H), 0.94-0.87 (m, 4H). |
| T373 | N-(4-(5-chloropyridin-3-yl)phenyl)-1-(2-(cyclopropanesulfonamido)thiazol-4-yl)cyclopropane-1-carboxamide | Method 1b using INTB93 and INTA18, [UPLC Acidic], 475, (1.25) | 12.73 (s, 1H), 9.39 (s, 1H), 8.87 (d, J = 2.0 Hz, 1H), 8.58 (d, J = 2.3 Hz, 1H), 8.26-8.22 (m, 1H), 7.81-7.75 (m, 2H), 7.78-7.69 (m, 2H), 6.75 (s, 1H), 2.60-2.56 (m, 1H), 1.51-1.45 (m, 2H), 1.27-1.21 (m, 2H), 0.94-0.88 (m, 4H). |

TABLE 16-continued

Preparation methods and characterisation data of examples T332-T416

| T # | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| T374 | N-(4-(5-cyanopyridin-3-yl)phenyl)-2-(2-(cyclopropanesulfonamido)-5-methylthiazol-4-yl)-2-methylpropanamide | Method 1e using INTB42 and INTA12, [UPLC Acidic], 482, (1.24) | 12.04 (s, 1H), 9.88 (s, 1H), 9.19 (d, J = 2.3 Hz, 1H), 8.97 (d, J = 1.9 Hz, 1H), 8.63 (t, J = 2.1 Hz, 1H), 7.86-(m, 4H), 2.62-2.55 (m, 1H), 1.95 (s, 3H), 1.52 (s, 6H), 0.97-0.87 (m, 4H). |
| T375 | 2-(2-(cyclopropanesulfonamido)thiazol-4-yl)-N-(4-(6-(2-methoxypropan-2-yl)pyrazin-2-yl)phenyl)-2-methylpropanamide | Method 1b using INTB37 and INTA85, [UPLC Acidic], 516, (1.29) | 12.59 (s, 1H), 9.51 (s, 1H), 9.12 (s, 1H), 8.69 (s, 1H), 8.19-8.04 (m, 2H), 7.87-7.77 (m, 2H), 6.55 (s, 1H), 3.16 (s, 3H), 2.64-2.55 (m, 1H), 1.70-1.42 (m, 12H), 1.05-0.78 (m, 4H). |
| T376 | 2-(5-chloro-2-(cyclopropanesulfonamido)thiazol-4-yl)-N-(4-(6-ethoxypyrazin-2-yl)phenyl)-2-methylpropanamide | Method 1b using INTB94 and INTA38, [HPLC Acidic], 522, (2.39) | 12.50 (s, 1H), 9.87 (s, 1H), 8.76 (s, 1H), 8.18 (s, 1H), 8.13-8.04 (m, 2H), 7.80-7.71 (m, 2H), 4.48 (q, J = 7.0 Hz, 2H), 2.73-2.65 (m, 1H), 1.55 (s, 6H), 1.40 (t, J = 7.0 Hz, 3H), 1.03-0.91 (m, 4H). |
| T377 | 2-(2-(cyclopropanesulfonamido)-5-methoxythiazol-4-yl)-N-(4-(6-ethoxypyrazin-2-yl)phenyl)-2-methylpropanamide | Method 1b using INTB95 and INTA38, [HPLC Acidic], 518.3, (2.22) | 12.01 (s, 1H), 9.73 (s, 1H), 8.76 (s, 1H), 8.18 (s, 1H), 8.11-8.07 (m, 2H), 7.83-7.75 (m, 2H), 4.48 (q, J = 7.0 Hz, 2H), 3.61 (s, 3H), 2.61 (m, 1H), 1.52 (s, 6H), 1.40 (t, J = 7.0 Hz, 3H), 0.96-0.89 (m, 4H). |

TABLE 16-continued

Preparation methods and characterisation data of examples T332-T416

| T # | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| T378 | N-(4-(6-(cyclopentylmethoxy)pyrazin-2-yl)phenyl)-2-(2-(cyclopropanesulfonamido)thiazol-4-yl)-2-methylpropanamide | Method 2b using INTB56, [HPLC acidic], 542, (3.22) | 12.59 (s, 1H), 9.51 (s, 1H), 8.78 (s, 1H), 8.20 (s, 1H), 8.14-8.02 (m, 2H), 7.87-7.75 (m, 2H), 6.55 (s, 1H), 4.31 (d, J = 7.1 Hz, 2H), 2.64-2.56 (m, 1H), 2.43-2.32 (m, 2H), 1.87-1.75 (m, 2H), 1.68-1.54 (m, 9H), 1.45-1.31 (m, 2H), 0.96-0.85 (m, 4H) |
| T379 | 2-(2-(cyclopropanesulfonamido)thiazol-4-yl)-N-(4-(6-hydroxypyrazin-2-yl)phenyl)-2-methylpropanamide | Method 2b using INTB56, [HPLC Acidic], 460, (1.46) | 12.58 (s, 1H), 9.49 (s, 1H), 8.08-7.85 (m, 3H), 7.81-7.73 (m, 2H), 6.55 (s, 1H), 2.63-2.55 (m, 1H), 1.58 (s, 6H), 0.96-0.86 (m, 4H). Two exchangeable protons are not observed |
| T380 | 2-(2-(ethylsulfonamido)thiazol-4-yl)-2-methyl-N-(5'-(trifluoromethyl)-[3,3'-bipyridin]-6-yl)propanamide | Method 1b using INTB91 and INTA100, [UPLC Acidic], 500, (1.25) | 12.55 (s, 1H), 10.10 (s, 1H), 9.28 (d, J = 2.2 Hz, 1H), 8.98 (d, J = 2.0 Hz, 1H), 8.87 (d, J = 2.6 Hz, 1H), 8.58 (s, 1H), 8.35 (dd, J = 8.8, 2.6 Hz, 1H), 8.17 (d, J = 8.7 Hz, 1H), 6.57 (s, 1H), 3.01-2.97 (m, 2H), 1.60 (s, 6H), 1.20 (t, J = 7.3 Hz, 3H). |
| T381 | 2-(2-(ethylsulfonamido)thiazol-4-yl)-2-methyl-N-(5-(6-(trifluoromethyl)pyrazin-2-yl)pyridin-2-yl)propanamide | Method 1b using INTB91 and INTA3, [UPLC Acidic], 501, (1.29) | 12.56 (s, 1H), 10.25 (s, 1H), 9.68 (s, 1H), 9.19-9.14 (m, 2H), 8.60 (dd, J = 8.8, 2.5 Hz, 1H), 8.25 (d, J = 8.8 Hz, 1H), 6.59 (s, 1H), 3.00 (s, 2H), 1.61 (s, 6H), 1.20 (t, J = 7.4 Hz, 3H). |
| T382 | N-(5-(6-ethoxypyrazin-2-yl)pyridin-2-yl)-2-(2-(ethylsulfonamido)thiazol-4-yl)-2-methylpropanamide | Method 1b using INTB91 and INTA72, [UPLC Acidic], 477, (1.26) | 12.56 (s, 1H), 10.10 (s, 1H), 9.10-9.06 (m, 1H), 8.86 (s, 1H), 8.52 (dd, J = 8.9, 2.3 Hz, 1H), 8.28-8.24 (m, 1H), 8.18 (d, J = 8.8 Hz, 1H), 6.58 (s, 1H), 4.52-4.44 (m, 2H), 3.02-2.98 (m, 2H), 1.61 (s, 6H), 1.40 (t, J = 7.0, 1.6 Hz, 3H), 1.20 (t, J = 7.3 Hz, 3H). |

TABLE 16-continued

Preparation methods and characterisation data of examples T332-T416

| T # | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| T383 | 2-(2-(ethylsulfonamido)thiazol-4-yl)-N-(2-fluoro-4-(6-isopropoxypyrazin-2-yl)phenyl)-2-methylpropanamide | Method 1b using INTB91 and INTA89, [UPLC Acidic], 508, (1.42) | 12.59 (s, 1H), 9.25 (s, 1H), 8.82 (s, 1H), 8.19 (s, 1H), 8.03-7.94 (m, 2H), 7.72-7.68 (m, 1H), 6.61 (s, 1H), 5.46-5.37 (m, 1H), 3.01-2.97 (m, 2H), 1.58 (s, 6H), 1.38 (d, J = 6.2, 1.9 Hz, 6H), 1.20 (t, J = 7.3 Hz, 3H). |
| T384 | N-(4-(5-cyanopyridin-3-yl)phenyl)-2-(2-(ethylsulfonamido)thiazol-4-yl)-2-methylpropanamide | Method 1b using INTB91 and INTA12, [UPLC Acidic], 456, (1.13) | 12.57 (s, 1H), 9.47 (s, 1H), 9.20 (d, J = 2.3 Hz, 1H), 8.97 (d, J = 1.9 Hz, 1H), 8.70-8.61 (m, 1H), 7.89-7.75 (m, 4H), 6.56 (s, 1H), 3.07-2.93 (m, 2H), 1.58 (s, 6H), 1.21 (t, J = 7.3 Hz, 3H). |
| T385 | 2-(2-(ethylsulfonamido)thiazol-4-yl)-N-(4-(5-fluoropyridin-3-yl)phenyl)-2-methylpropanamide | Method 1b using INTB91 and INTA13, [UPLC Acidic], 449, (1.13) | 12.55 (s, 1H), 9.44 (s, 1H), 8.83-8.78 (m, 1H), 8.53 (d, J = 2.7 Hz, 1H), 8.09-8.02 (m, 1H), 7.82-7.74 (m, 4H), 6.56 (s, 1H), 3.01-2.97 (m, 2H), 1.57 (d, J = 4.9 Hz, 6H), 1.20 (t, J = 7.3 Hz, 3H). |
| T386 | 2-(2-(ethylsulfonamido)thiazol-4-yl)-2-methyl-N-(4-(pyridin-3-yl)phenyl)propanamide | Method 1b using INTB91, [UPLC Acidic], 431, (0.7) | 12.53 (s, 1H), 9.42 (s, 1H), 8.89 (dd, J = 2.4, 0.9 Hz, 1H), 8.54 (dd, J = 4.8, 1.6 Hz, 1H), 8.07 (ddd, J = 8.0, 2.5, 1.6 Hz, 1H), 7.81-7.68 (m, 4H), 7.47 (ddd, J = 7.9, 4.7, 0.8 Hz, 1H), 6.57 (s, 1H), 3.01 (q, J = 7.3 Hz, 2H), 1.58 (s, 6H), 1.21 (t, J = 7.3 Hz, 3H). |
| T387 | 2-(2-(ethylsulfonamido)thiazol-4-yl)-2-methyl-N-(4-(6-(trifluoromethyl)pyrazin-2-yl)phenyl)propanamide | Method 1b using INTB91 and INTA39, [UPLC Acidic], 500, (1.35) | 12.58 (s, 1H), 9.62-9.55 (m, 2H), 9.09 (s, 1H), 8.24-8.18 (m, 2H), 7.90-7.84 (m, 2H), 6.57 (s, 1H), 3.02-2.97 (m, 2H), 1.59 (s, 6H), 1.26-1.13 (m, 3H). |

TABLE 16-continued

Preparation methods and characterisation data of examples T332-T416

| T # | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| T388 | 2-(2-(ethylsulfonamido)thiazol-4-yl)-N-(4-(6-isopropoxypyrazin-2-yl)phenyl)-2-methylpropanamide | Method 1b using INTB91 and INTA40, [UPLC Acidic], 490, (1.39) | 12.56 (s, 1H), 9.48 (s, 1H), 8.74 (s, 1H), 8.14-8.05 (m, 3H), 7.81-7.74 (m, 2H), 6.55 (s, 1H), 5.45-5.36 (m, 1H), 3.00-2.96 (m, 2H), 1.57 (s, 6H), 1.37 (d, J = 6.2 Hz, 6H), 1.23-1.14 (m, 3H). |
| T389 | 2-methyl-2-(2-(methylsulfonamido)thiazol-4-yl)-N-(5'-(trifluoromethyl)-[3,3'-bipyridin]-6-yl)propanamide | Method 1b using INTB92 and INTA100, [UPLC Acidic], 486, (1.17) | 12.56 (s, 1H), 10.15 (s, 1H), 9.28 (d, J = 2.1 Hz, 1H), 8.99 (d, J = 2.1 Hz, 1H), 8.88 (d, J = 2.5 Hz, 1H), 8.59 (d, J = 2.3 Hz, 1H), 8.36 (dd, J = 8.7, 2.6 Hz, 1H), 8.17 (d, J = 8.7 Hz, 1H), 6.61 (s, 1H), 2.91 (s, 3H), 1.61 (s, 6H). |
| T390 | N-(5-(6-ethoxypyrazin-2-yl)pyridin-2-yl)-2-methyl-2-(2-(methylsulfonamido)thiazol-4-yl)propanamide | Method 1b using INTB92 and INTA72, [UPLC Acidic], 463, (1.19) | 12.57 (s, 1H), 10.16 (s, 1H), 9.09 (d, J = 2.4 Hz, 1H), 8.87 (s, 1H), 8.53 (dd, J = 8.8, 2.5 Hz, 1H), 8.26 (s, 1H), 8.19 (d, J = 8.8 Hz, 1H), 6.61 (s, 1H), 4.49 (q, J = 7.1 Hz, 2H), 2.91 (s, 3H), 1.61 (s, 6H), 1.40 (t, J = 7.0 Hz, 3H). |
| T391 | N-(2-fluoro-4-(6-(trifluoromethyl)pyrazin-2-yl)phenyl)-2-methyl-2-(2-(methylsulfonamido) thiazol-4-yl)propanamide | Method 1b using INTB92 and NTA48, [UPLC Acidic], 504, (1.31) | 12.60 (s, 1H), 9.66 (s, 1H), 9.36 (s, 1H), 9.16 (s, 1H), 8.18-8.04 (m, 2H), 7.79 (s, 1H), 6.65 (s, 1H), 2.91 (s, 3H), 1.59 (s, 6H). |

TABLE 16-continued

Preparation methods and characterisation data of examples T332-T416

| T # | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| T392 | N-(2-fluoro-4-(6-isopropoxypyrazin-2-yl)phenyl)-2-methyl-2-(2-(methylsulfonamido)thiazol-4-yl)propanamide 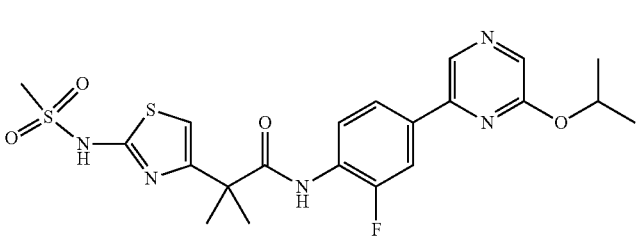 [SMILES: CC(C)Oc1cncc(-c2ccc(NC(=O)C(C)(C)c3csc(NS(C)(=O)=O)n3)c(F)c2)n1] | Method 1b using INTB92 and INTA89, [UPLC Acidic], 494, (1.36) | 12.58 (s, 1H), 9.27 (s, 1H), 8.82 (s, 1H), 8.19 (s, 1H), 8.03-7.94 (m, 2H), 7.70 (s, 1H), 6.63 (s, 1H), 5.42 (p, J = 6.2 Hz, 1H), 2.91 (s, 3H), 1.58 (s, 6H), 1.39 (s, 3H), 1.38 (s, 3H). |
| T393 | N-(4-(5-chloropyridin-3-yl)phenyl)-2-methyl-2-(2-(methylsulfonamido)thiazol-4-yl)propanamide 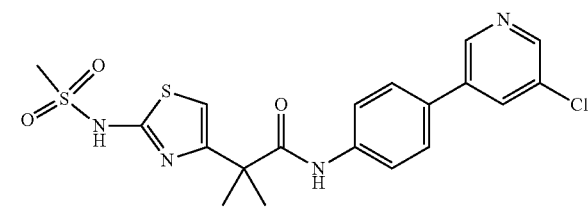 [SMILES: CC(C)(C(=O)Nc1ccc(-c2cncc(Cl)c2)cc1)c1csc(NS(C)(=O)=O)n1] | Method 1b using INTB92 and INTA18, [UPLC Basic], 451, (1.05) | 12.55 (s, 1H), 9.45 (s, 1H), 8.88 (d, J = 2.0 Hz, 1H), 8.59 (d, J = 2.3 Hz, 1H), 8.27-8.22 (m, 1H), 7.82-7.74 (m, 4H), 6.59 (s, 1H), 2.92 (s, 3H), 1.58 (s, 6H). |
| T394 | 2-methyl-2-(2-(methylsulfonamido)thiazol-4-yl)-N-(4-(6-(trifluoromethyl)pyrazin-2-yl)phenyl)propanamide 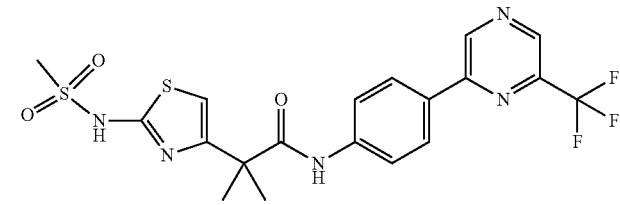 [SMILES: CC(C)(C(=O)Nc1ccc(-c2cncc(C(F)(F)F)n2)cc1)c1csc(NS(C)(=O)=O)n1] | Method 1b using INTB92 and INTA39, [UPLC Basic], 486, (1.14) | 12.56 (s, 1H), 9.59 (s, 2H), 9.08 (s, 1H), 8.23-8.17 (m, 2H), 7.90-7.83 (m, 2H), 6.59 (s, 1H), 2.91 (s, 3H), 1.59 (s, 6H). |
| T395 | N-(4-(6-isopropoxypyrazin-2-yl)phenyl)-2-methyl-2-(2-(methylsulfonamido)thiazol-4-yl)propanamide 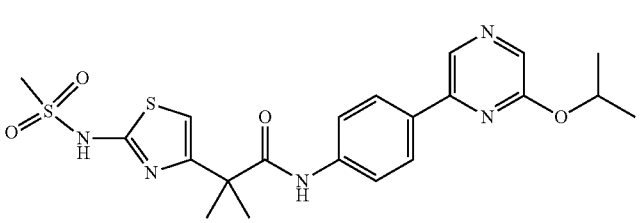 [SMILES: CC(C)Oc1cncc(-c2ccc(NC(=O)C(C)(C)c3csc(NS(C)(=O)=O)n3)cc2)n1] | Method 1b using INTB92 and INTA40, [UPLC Basic], 476, (1.17) | 12.56 (s, 1H), 9.49 (s, 1H), 8.75 (s, 1H), 8.13 (s, 1H), 8.09 (d, J = 8.8 Hz, 2H), 7.79 (d, J = 8.8 Hz, 2H), 6.58 (s, 1H), 5.46-5.37 (m, 1H), 2.91 (s, 3H), 1.59 (s, 6H), 1.39 (s, 3H), 1.38 (s, 3H). |

TABLE 16-continued

Preparation methods and characterisation data of examples T332-T416

| T # | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| T396 | 2-(2-((cyclopropylmethyl)sulfonamido)thiazol-4-yl)-2-methyl-N-(5-(6-(trifluoromethyl)pyrazin-2-yl)pyridin-2-yl)propanamide | Method 1b using INTB96 and INTA3, [UPLC Acidic], 527, (1.39) | 12.58 (s, 1H), 10.22 (s, 1H), 9.68 (s, 1H), 9.20-9.14 (m, 2H), 8.61 (dd, J = 8.8, 2.5 Hz, 1H), 8.25 (d, J = 8.8 Hz, 1H), 6.59 (s, 1H), 2.97-2.88 (m, 2H), 1.62 (s, 6H), 1.01-0.95 (m, 1H), 0.53-0.46 (m, 2H), 0.32-0.26 (m, 2H). |
| T397 | 1-(2-(cyclopropanesulfonamido)thiazol-4-yl)-N-(4-(6-(trifluoromethyl)pyrazin-2-yl)phenyl)cyclopropane-1-carboxamide | Method 1c using INTB93 and INTA39, [UPLC Acidic], 510, (1.37) | 12.74 (s, 1H), 9.59 (s, 1H), 9.51 (s, 1H), 9.08 (s, 1H), 8.22-8.15 (m, 2H), 7.85-7.78 (m, 2H), 6.76 (s, 1H), 2.59-2.54 (m, 1H), 1.53-1.47 (m, 2H), 1.28-1.22 (m, 2H), 0.94-0.88 (m, 4H). |
| T398 | 1-(2-(cyclopropanesulfonamido)thiazol-4-yl)-N-(4-(6-ethoxypyrazin-2-yl)phenyl)cyclopropane-1-carboxamide | Method 1c using INTB93 and INTA38, [UPLC Acidic], 486, (1.32) | 12.73 (s, 1H), 9.42 (s, 1H), 8.77 (s, 1H), 8.18 (s, 1H), 8.09 (d, J = 8.4 Hz, 2H), 7.73 (d, J = 8.4 Hz, 2H), 6.74 (s, 1H), 4.47 (q, J = 7.0 Hz, 2H), 2.53-2.49 (m, 1H), 1.52-1.45 (m, 2H), 1.39 (t, J = 7.0 Hz, 3H), 1.28-1.20 (m, 2H), 0.94-0.86 (m, 4H). |
| T399 | 2-(2-(cyclopropanesulfonamido)thiazol-4-yl)-N-(2-fluoro-4-(6-(trifluoromethyl)pyrazin-2-yl)phenyl)-4-methoxybutanamide | Method 1c using INTB44 and INTA48, [HPLC Acidic], 560, (2.11) | 12.61 (s, 1H), 10.22 (s, 1H), 9.65 (s, 1H), 9.15 (s, 1H), 8.25-8.11 (m, 1H), 8.13 (dd, J = 12.1, 2.0 Hz, 1H), 8.07 (dd, J = 8.5, 2.0 Hz, 1H), 6.57 (s, 1H), 4.09-4.02 (m, 1H), 3.40-3.33 (m, 2H), 3.24 (s, 3H), 2.64-2.54 (m, 1H), 2.27-2.17 (m, 1H), 2.13-2.06 (m, 1H), 0.95-0.85 (m, 4H). |

TABLE 16-continued

Preparation methods and characterisation data of examples T332-T416

| T # | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| T400 | 2-(2-(cyclopropanesulfonamido)thiazol-4-yl)-N-(2-fluoro-4-(6-isopropoxypyrazin-2-yl)phenyl)-4-methoxybutanamide | Method 1c using INTB44 and INTA89, [HPLC Acidic], 550, (2.24) | 12.60 (s, 1H), 10.14 (s, 1H), 8.81 (s, 1H), 8.19 (s, 1H), 8.15-8.08 (m, 1H), 8.05-7.95 (m, 2H), 6.56 (s, 1H), 5.42 (hept, J = 6.1 Hz, 1H), 4.06-4.01 (m, 1H), 3.39-3.33 (m, 2H), 3.22 (s, 3H), 2.63-2.54 (m, 1H) 2.25-2.18 (m, 1H), 2.13-2.04 (m, 1H), 1.39 (d, J = 6.2 Hz, 6H), 0.95-0.84 (m, 4H). |
| T401 | 2-(2-(cyclopropanesulfonamido)thiazol-4-yl)-N-(5-(6-isopropylpyrazin-2-yl)pyridin-2-yl)butanamide | Method 1c using INTB38 and INTA80, [HPLC Acidic], 487, (2.19) | 12.60 (s, 1H), 10.94 (s, 1H), 9.12 (s, 1H), 9.11 (d, J = 2.4 Hz, 1H), 8.58 (s, 1H), 8.54 (dd, J = 8.8, 2.4 Hz, 1H), 8.25 (d, J = 8.8 Hz, 1H), 6.55 (s, 1H), 3.86-3.72 (m, 1H), 3.24-3.09 (m, 1H), 2.62-2.54 (m, 1H), 2.07-1.81 (m, 2H), 1.34 (d, J = 6.9 Hz, 6H), 0.95-0.80 (m, 7H). |
| T402 | 2-(2-(cyclopropanesulfonamido)thiazol-4-yl)-N-(5-(6-(2-methoxypropan-2-yl)pyrazin-2-yl)pyridin-2-yl)butanamide | Method 1c using INTB38 and INTA84, [UPLC Acidic], 517, (1.26) | 12.59 (s, 1H), 10.95 (s, 1H), 9.19 (s, 1H), 9.17-9.08 (m, 1H), 8.75 (s, 1H), 8.56 (dd, J = 8.7, 2.4 Hz, 1H), 8.25 (d, J = 8.9 Hz, 1H), 6.56 (s, 1H), 3.85-3.74 (m, 1H), 3.16 (s, 3H), 2.61-2.54 (m, 1H), 2.03-1.81 (m, 2H), 1.57 (s, 6H), 0.94-0.83 (m, 7H). |
| T403 | 2-(2-(cyclopropanesulfonamido)thiazol-4-yl)-N-(2-fluoro-4-(6-(2-methoxypropan-2-yl)pyrazin-2-yl)phenyl)butanamide | Method 1c using INTB38 and INTA86, [UPLC Acidic], 534, (1.35) | 12.60 (s, 1H), 10.16 (s, 1H), 9.18 (s, 1H), 8.74 (s, 1H), 8.17-7.99 (m, 3H), 6.55 (s, 1H), 3.83 (t, J = 7.4 Hz, 1H), 3.16 (s, 3H), 2.62-2.55 (m, 1H), 2.00-1.85 (m, 2H), 1.57 (s, 6H), 0.94-0.87 (m, 7H). |

TABLE 16-continued

Preparation methods and characterisation data of examples T332-T416

| T # | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| T404 | N-(4-(6-cyanopyrazin-2-yl)-2-fluorophenyl)-2-(2-(cyclopropanesulfonamido)thiazol-4-yl)butanamide | Method 1c using INTB38 and INTA87, [UPLC Acidic], 487, (1.25) | 12.60 (s, 1H), 10.23 (s, 1H), 9.59 (s, 1H), 9.17 (s, 1H), 8.21 (t, J = 8.3 Hz, 1H), 8.12 (dd, J = 12.2, 2.1 Hz, 1H), 8.05 (dd, J = 8.5, 2.0 Hz, 1H), 6.55 (s, 1H), 3.85 (t, J = 7.5 Hz, 1H), 2.63-2.55 (m, 1H), 2.02-1.84 (m, 2H), 0.96-0.85 (m, 7H). |
| T405 | 2-(2-(cyclopropanesulfonamido)thiazol-4-yl)-N-(4-(6-ethylpyrazin-2-yl)-2-fluorophenyl)butanamide | Method 1c using INTB38 and INTA82, [HPLC Acidic], 490, (2.08) | 12.60 (s, 1H), 10.14 (s, 1H), 9.10 (s, 1H), 8.53 (s, 1H), 8.12 (t, J = 8.3 Hz, 1H), 8.08-7.98 (m, 2H), 6.55 (s, 1H), 3.82 (s, 1H), 2.86 (q, J = 7.6 Hz, 2H), 2.62-2.54 (m, 1H), 2.01-1.84 (m, 2H), 1.31 (t, J = 7.6 Hz, 3H), 0.95-0.82 (m, 7H). |
| T406 | 2-(2-(cyclopropanesulfonamido)thiazol-4-yl)-N-(4-(6-(2-methoxypropan-2-yl)pyrazin-2-yl)phenyl)butanamide | Method 1c using INTB38 and INTA85, [UPLC Acidic], 516, (1.31) | 12.61 (s, 1H), 10.37 (s, 1H), 9.11 (s, 1H), 8.68 (s, 1H), 8.19-8.08 (m, 2H), 7.83-7.70 (m, 2H), 6.55 (s, 1H), 3.61 (t, J = 7.5 Hz, 1H), 3.16 (s, 3H), 2.61-2.53 (m, 1H), 2.05-1.82 (m, 2H), 1.56 (s, 6H), 0.95-0.79 (m, 7H). |
| T407 | tert-butyl (1-(2-(cyclopropanesulfonamido)thiazol-4-yl)-2((4-(6-ethoxypyrazin-2-yl)phenyl)amino)-2-oxoethyl)carbamate | Method 1 using INTB98 and INTA38, [HPLC Basic], 575, (1.92) | 12.63 (s, 1H), 10.52 (s, 1H), 8.78 (s, 1H), 8.19 (s, 1H), 8.15-8.09 (m, 2H), 7.79-7.73 (m, 2H), 7.65 (s, 1H), 6.60 (s, 1H), 5.28 (d, J = 8.3 Hz, 1H), 4.48 (q, J = 7.0 Hz, 2H), 2.65-2.53 (m, 1H), 1.50-1.22 (m, 12H), 0.96-0.83 (m, 4H). |

TABLE 16-continued

Preparation methods and characterisation data of examples T332-T416

| T # | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
| --- | --- | --- | --- |
| T408 | 2-(2-(cyclopropanesulfonamido)thiazol-4-yl)-N-(2-fluoro-4-(6-(trifluoromethyl)pyrazin-2-yl)phenyl)-2-methoxyacetamide | Method 1c using INTB43 and INTA48, [HPLC Acidic], 532, (2.15) | 12.85 (s, 1H), 9.82 (d, J = 1.5 Hz, 1H), 9.66 (s, 1H), 9.16 (s, 1H), 8.25-8.05 (m, 3H), 6.90 (s, 1H), 5.02 (s, 1H), 3.42 (s, 3H), 2.62-2.56 (m, 1H), 0.95-0.81 (m, 4H). |
| T409 | 2-(2-(cyclopropanesulfonamido)thiazol-4-yl)-N-(4-(6-ethoxypyrazin-2-yl)-2-fluorophenyl)-2-methoxyacetamide | Method 1c using INTB43 and INTA47, [HPLC Acidic], 508, (2.10) | 12.84 (s, 1H), 9.76 (d, J = 1.6 Hz, 1H), 8.86 (s, 1H), 8.26 (s, 1H), 8.17-7.97 (m, 3H), 6.89 (s, 1H), 5.01 (s, 1H), 4.50 (q, J = 7.0 Hz, 2H), 3.42 (s, 3H), 2.63-2.56 (m, 1H), 1.41 (t, J = 7.0 Hz, 3H), 0.96-0.82 (m, 4H). |
| T410 | 2-(2-(cyclopropanesulfonamido)thiazol-4-yl)-N-(4-(6-ethoxypyrazin-2-yl)phenyl)-2-methoxyacetamide | Method 1c using INTB43 and INTA38, [UPLC Acidic], 490, (1.27) | 12.80 (s, 1H), 10.09 (s, 1H), 8.78 (s, 1H), 8.19 (s, 1H), 8.18-8.10 (m, 2H), 7.88-7.82 (m, 2H), 6.83 (s, 1H), 4.88 (s, 1H), 4.48 (q, J = 7.0 Hz, 2H), 3.40 (s, 3H), 2.62-2.56 (m, 1H), 1.40 (t, J = 7.0 Hz, 3H), 0.93-0.83 (m, 4H). |
| T411 | 2-(2-(cyclopropanesulfonamido)thiazol-4-yl)-N-(4-(6-isopropoxypyrazin-2-yl)phenyl)-2-methoxyacetamide | Method 1c using INTB43 and INTA40, [HPLC Acidic], 504, (2.14) | 12.81 (s, 1H), 10.10 (s, 1H), 8.76 (s, 1H), 8.16-8.07 (m, 3H), 7.89-7.80 (m, 2H), 6.84 (s, 1H), 5.48-5.35 (m, 1H), 4.90 (s, 1H), 3.41 (s, 3H), 2.63-2.57 (m, 1H), 1.39 (d, J = 6.2 Hz, 6H), 0.93-0.86 (m, 4H). |

TABLE 16-continued

Preparation methods and characterisation data of examples T332-T416

| T # | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
| --- | --- | --- | --- |
| T412 | Single enantiomer—stereochemistry unassigned 2-(2-(cyclopropanesulfonamido)thiazol-4-yl)-N-(4-(6-ethoxypyrazin-2-yl)-2-fluorophenyl)butanamide | Method 1c using INTB38a and INTA47, Chiral IA (6.71), [HPLC Acidic], 506, (2.19) | 12.60 (s, 1H), 10.15 (s, 1H), 8.84 (s, 1H), 8.24 (s, 1H), 8.12 (t, J = 8.3 Hz, 1H), 8.04 (dd, J = 12.3, 2.0 Hz, 1H), 7.98 (dd, J = 8.5, 2.0 Hz, 1H), 6.56 (s, 1H), 4.49 (q, J = 7.0 Hz, 2H), 3.83 (t, J = 7.5 Hz, 1H), 2.64-2.56 (m, 1H), 2.03-1.85 (m, 2H), 1.40 (t, J = 7.0 Hz, 3H), 0.97-0.85 (m, 7H). |
| T413 | Single enantiomer—stereochemistry unassigned 2-(2-(cyclopropanesulfonamido)thiazol-4-yl) N-(4-(6-ethoxypyrazin-2-yl)-2-fluorophenyl)butanamide | Method 1c using INTB38b and INTA47, Chiral IA (9.33) [HPLC Acidic], 506, (2.20) | 12.60 (s, 1H), 10.15 (s, 1H), 8.84 (s, 1H), 8.25 (s, 1H), 8.12 (t, J = 8.3 Hz, 1H), 8.05 (dd, J = 12.3, 2.0 Hz, 1H), 7.99 (dd, J = 8.5, 2.0 Hz, 1H), 6.55 (s, 1H), 4.49 (q, J = 7.0 Hz, 2H), 3.83 (t, J = 7.4 Hz, 1H), 2.60-2.55 (m, 1H), 2.01-1.84 (m, 2H), 1.41 (t, J = 7.1 Hz, 3H), 0.99-0.83 (m, 7H). |
| T414 | Single enantiomer—stereochemistry unassigned 2-(2-(cyclopropanesulfonamido)thiazol-4-yl) N-(5-(6-(trifluoromethyl)pyrazin-2-yl)pyridin-2-yl)butanamide | Method 1c using INTB38b and INTA3, Chiral IC2 (42.70) [HPLC Acidic], 513, (2.11) | 12.60 (s, 1H), 11.07 (s, 1H), 9.67 (s, 1H), 9.25-9.10 (m, 2H), 8.60 (dd, J = 8.8, 2.5 Hz, 1H), 8.29 (d, J = 8.8 Hz, 1H), 6.57 (s, 1H), 3.83 (t, J = 7.5 Hz, 1H), 2.03-1.85 (m, 2H), 2.62-2.56 (m, 1H), 1.02-0.83 (m, 7H). |

TABLE 16-continued

Preparation methods and characterisation data of examples T332-T416

| T # | Name/Structure (All examples containing chiral centres are racemates unless stated) | Synthesis Method, [LCMS Method], m/z (M + H)+, (RT/Min) | ¹H NMR Chemical Shift Data (DMSO-d6 unless stated) |
|---|---|---|---|
| T415 | Single enantiomer—stereochemistry unassigned 2-(2-(cyclopropanesulfonamido)thiazol-4-yl)-N-(2-fluoro-4-(5-(trifluoromethyl)pyridin-3-yl)phenyl)butanamide | Method 1c using INTB38a and INTA70, Chiral IA (6.64) [HPLC Acidic], 529, (2.18) | 12.63 (s, 1H), 10.16 (s, 1H), 9.26 (d, J = 2.1 Hz, 1H), 8.97 (d, J = 2.1 Hz, 1H), 8.57-8.50 (m, 1H), 8.10 (t, J = 8.3 Hz, 1H), 7.93 (dd, J = 12.2, 2.1 Hz, 1H), 7.74 (dd, J = 8.5, 2.1 Hz, 1H), 6.56 (s, 1H), 3.82 (t, J = 7.4 Hz, 1H), 2.64-2.55 (m, 1H), 2.03-1.83 (m, 2H), 0.92 (q, J = 8.5, 7.9 Hz, 7H). |
| T416 | Single enantiomer—stereochemistry unassigned 2-(2-(cyclopropanesulfonamido)thiazol-4-yl)-N-(2-fluoro-4-(5-(trifluoromethyl)pyridin-3-yl)phenyl)butanamide | Method 1c using INTB38b and INTA70, Chiral IA (8.31) [HPLC Acidic], 529, (2.18) | δ 12.61 (s, 1H), 10.14 (s, 1H), 9.26 (d, J = 2.2 Hz, 1H), 8.97 (dd, J = 2.1, 0.9 Hz, 1H), 8.56-8.45 (m, 1H), 8.10 (q, J = 8.0 Hz, 1H), 7.92 (dd, J = 12.2, , 2.1 Hz, 1H), 7.74 (dd, J = 8.5, 2.0 Hz, 1H), 6.55 (s, 1H), 3.82 (t, J = 7.6 Hz, 1H), 2.65-2.55 (m, 1H), 2.04-1.84 (m, 2H), 0.98-0.83 (m, 7H). |

2-(2-(Cyclopropanesulfonamido)thiazol-4-yl)-N-(4-(6-(ethylamino)pyrazin-2-yl)phenyl)butanamide T444

A solution of N-(4-(6-chloropyrazin-2-yl)phenyl)-2-(2-(cyclopropanesulfonamido)thiazol-4-yl)butanamide T78 (0.19 g, 0.397 mmol) in DMSO (2 mL) was added 2M ethanamine in THF (2 mL, 4 mmol). The mixture was stirred at 120° C. for 5 hrs in a sealed vessel. The reaction mixture was concentrated in vacuo. The crude product was purified by chromatography on RP Flash $C_{18}$ (24 g cartridge, 5-50% MeCN/Water 0.1% Formic Acid) followed by chromatography on silica gel (24 g column, 0-10% MeOH/DCM) followed by trituration in EtOH (10 mL) to afford 2-(2-(cyclopropanesulfonamido)thiazol-4-yl)-N-(4-(6-(ethylamino)pyrazin-2-yl)phenyl)butanamide (0.033 g, 0.064 mmol, 16% yield) as a white solid. Rt 1.17 (UPLC acidic); m/z 487 (M+H)⁺ (ES⁺); ¹H NMR (500 MHz, DMSO-d6) δ 12.60 (s, 1H), 10.31 (s, 1H), 8.22 (s, 1H), 8.07-7.98 (m, 2H), 7.82 (s, 1H), 7.76-7.64 (m, 2H), 7.07 (t, J=5.4 Hz, 1H), 6.55 (s, 1H), 3.61 (t, J=7.5 Hz, 1H), 3.38 (qd, J=7.1, 5.2 Hz, 2H), 2.62-2.55 (m, 1H), 2.02-1.80 (m, 2H), 1.20 (t, J=7.2 Hz, 3H), 0.96-0.85 (m, 7H).

2-Amino-2-(2-(cyclopropanesulfonamido)thiazol-4-yl)-N-(5-(6-(trifluoromethyl)pyrazin-2-yl)pyridin-2-yl)acetamide hydrochloride T417 tert-Butyl (1-(2-(cyclopropanesulfonamido)thiazol-4-yl)-2-oxo-2-((5-(6-(trifluoromethyl)pyrazin-2-yl)pyridin-2-yl)

amino)ethyl)carbamate INTB112 (13 mg, 0.022 mmol) was treated with 4M HCl in dioxane (1 mL, 4.00 mmol) to give a suspension. After 5 mins MeOH (0.1 mL) was added to afford a solution. The reaction mixture was stirred for 1 hr before being concentrated in vacuo. This was then evaporated from MeCN (2 mL) to afford 2-amino-2-(2-(cyclopropanesulfonamido)thiazol-4-yl)-N-(5-(6-(trifluoromethyl)pyrazin-2-yl)pyridin-2-yl)acetamide, HCl (10 mg, 0.018 mmol, 82% yield) as a yellow solid. Rt 1.52 (HPLC basic); m/z 500 (M+H)$^+$ (ES$^+$); $^1$H NMR (500 MHz, DMSO-d6) δ 11.54 (s, 1H), 9.68 (s, 1H), 9.26-8.97 (m, 2H), 8.97-8.79 (m, 3H), 8.69-8.55 (m, 1H), 8.31-8.19 (m, 1H), 7.18 (br s, 1H), 5.32 (s, 1H), 2.86-2.72 (m, 1H), 1.12-0.83 (m, 4H) 1×N—H not observed.

2-Amino-2-(2-(cyclopropanesulfonamido)thiazol-4-yl)-N-(4-(6-ethoxypyrazin-2-yl)-2-fluorophenyl)acetamide hydrochloride T419

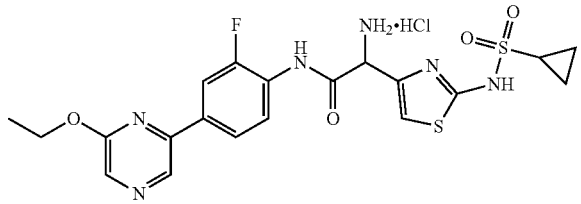

Prepared as for INT417 using tert-butyl (1-(2-(cyclopropanesulfonamido)thiazol-4-yl)-2-((4-(6-ethoxypyrazin-2-yl)-2-fluorophenyl)amino)-2-oxoethyl)carbamate INTB114 to afford 2-amino-2-(2-(cyclopropanesulfonamido)thiazol-4-yl)-N-(4-(6-ethoxypyrazin-2-yl)-2-fluorophenyl)acetamide hydrochloride (160 mg, 0.296 mmol, 89% yield) as a yellow solid. Rt 1.60 min (HPLC, basic); m/z 493 (M+H)$^+$ (ES$^+$); $^1$H NMR (500 MHz, DMSO-d6) δ 12.65 (v. br. s, 1H), 10.77 (s, 1H), 8.91 (br. s, 3H), 8.86 (s, 1H), 8.27 (s, 1H), 8.14-8.00 (m, 3H), 7.15 (v. br. s, 1H), 5.40 (s, 1H), 4.49 (q, J=7.0 Hz, 2H), 2.94-2.70 (m, 1H), 1.41 (t, J=7.0 Hz, 3H), 1.11-0.76 (m, 4H).

2-Amino-2-(2-(cyclopropanesulfonamido)thiazol-4-yl)-N-(2-fluoro-4-(6-(trifluoromethyl)pyrazin-2-yl)phenyl)acetamide T418

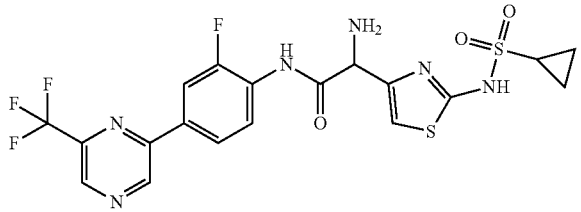 [SMILES: NC(C(=O)Nc1ccc(-c2cncc(C(F)(F)F)n2)cc1F)c1csc(NS(=O)(=O)C2CC2)n1]

A solution of tert-butyl (1-(2-(cyclopropanesulfonamido)thiazol-4-yl)-2-((2-fluoro-4-(6-(trifluoromethyl)pyrazin-2-yl)phenyl)amino)-2-oxoethyl)carbamate INTA113 (199 mg, 0.323 mmol) in DCM (3 mL) was treated with TFA (0.3 mL, 3.89 mmol) and stirred at RT for 18 hrs. The reaction mixture was concentrated in vacuo then taken up in DMSO (1 mL) and the crude mixture was purified by chromatography on RP Flash C$_{18}$ (12 g column, 10-50% MeCN/Water 0.1% Formic Acid), the product fractions were basified with 1% NH$_3$ in MeOH then concentrated to afford a brown solid. The crude product was purified by chromatography on RP Flash C$_{18}$ (12 g column, 10-45% MeCN/10 mM Ammonium Bicarbonate) to afford 2-amino-2-(2-(cyclopropanesulfonamido)thiazol-4-yl)-N-(2-fluoro-4-(6-(trifluoromethyl)pyrazin-2-yl)phenyl)acetamide (12 mg, 0.023 mmol, 7% yield) as a brown solid. Rt 1.66 (HPLC basic); m/z 517 (M+H)$^+$ (ES$^+$); $^1$H NMR (500 MHz, DMSO-d6) δ 9.65 (s, 1H), 9.15 (s, 1H), 8.33 (t, J=8.3 Hz, 1H), 8.21-8.04 (m, 2H), 6.63 (s, 1H), 4.87 (s, 1H), 0.89-0.73 (m, 4H), C—H obscured by residual DMSO, 4×N—H not observed, zwitterion.

2-(2-(Cyclopropanesulfonamido)thiazol-4-yl)-2-(dimethylamino)-N-(2-fluoro-4-(6-(trifluoromethyl)pyrazin-2-yl)phenyl)acetamide T420

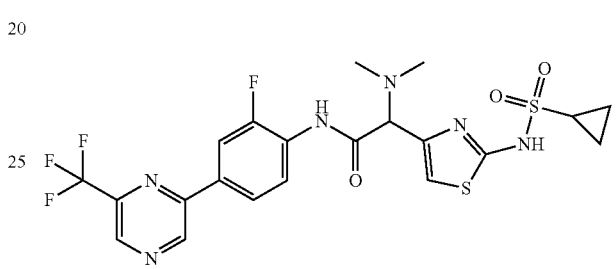

Prepared as for T328 using 2-amino-2-(2-(cyclopropanesulfonamido)thiazol-4-yl)-N-(2-fluoro-4-(6-(trifluoromethyl)pyrazin-2-yl)phenyl)acetamide T418 as the HCl salt, to afford (2-(cyclopropanesulfonamido)thiazol-4-yl)-2-(dimethylamino)-N-(2-fluoro-4-(6-(trifluoromethyl)pyrazin-2-yl)phenyl)acetamide (30% yield) as a yellow solid. Rt 1.65 (HPLC 10 acidic); m/z 545 (M+H)$^+$ (ES$^+$); $^1$H NMR (500 MHz, DMSO-d6) δ 12.68 (s, 1H), 10.09 (s, 1H), 9.66 (s, 1H), 9.16 (s, 1H), 8.27 (t, J=8.3 Hz, 1H), 8.18 (dd, J=12.1, 2.0 Hz, 1H), 8.11 (dd, J=8.5, 2.0 Hz, 1H), 6.75 (s, 1H), 4.41 (s, 1H), 2.63-2.55 (m, 1H), 2.31 (s, 6H), 0.98-0.78 (m, 4H).

2-(2-(Cyclopropanesulfonamido)thiazol-4-yl)-2-(dimethylamino)-N-(4-(6-ethoxypyrazin-2-yl)-2-fluorophenyl)acetamide T421

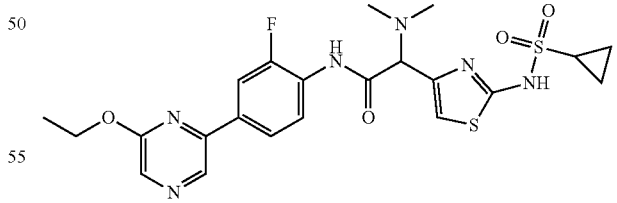

Prepared as for T328 using 2-amino-2-(2-(cyclopropanesulfonamido)thiazol-4-yl)-N-(4-(6-ethoxypyrazin-2-yl)-2-fluorophenyl)acetamide hydrochloride T419 to afford 2-(2-(cyclopropanesulfonamido)thiazol-4-yl)-2-(dimethylamino)-N-(4-(6-ethoxypyrazin-2-yl)-2-fluorophenyl)acetamide (40% yield) as a yellow solid. Rt 1.61 (HPLC acidic); m/z 521 (M+H)+(ES$^+$); $^1$H NMR (500 MHz, DMSO-d6) δ 12.64 (s, 1H), 10.01 (s, 1H), 8.86 (s, 1H), 8.25 (s, 1H), 8.22-7.97 (m, 3H), 6.77 (s, 1H), 4.50 (q, J=7.0 Hz, 2H), 4.44 (s, 1H), 2.63-2.57 (m, 1H), 2.31 (s, 6H), 1.41 (t, J=7.0 Hz, 3H), 0.95-0.80 (m, 4H).

Biological Examples

Biological Example 1—Human CTPS1 Enzyme Inhibition

The enzyme inhibitory activities of compounds invented against the target of interest were determined using the ADP-Glo™ Max assay (Promega, UK). Assays for human CTPS1 were performed in 1× assay buffer containing 50 mM Tris, 10 mM MgCl$_2$, 0.01% Tween-20, pH to 8.0 accordingly. Finally, immediately before use, L-cysteine was added to the 1× assay buffer to a final concentration of 2 mM. All reagents are from Sigma-Aldrich unless specified otherwise. Human full length active C-terminal FLAG-Hisstag CTPS1 (UniProtKB—P17812, CTPS[1-591]-GGDYKDDDDKGGHHHHHHHH (SEQ ID NO: 1)) was obtained from Proteros biostructures GmbH.

Assay Procedure

3× human CTPS1 protein was prepared in 1× assay buffer to the final working protein concentration required for the reaction. A 2 uL volume per well of 3× human CTPS1 protein was mixed with 2 uL per well of 3× test compound (compound prepared in 1× assay buffer to an appropriate final 3× compound concentration respective to the concentration response curve designed for the compounds under test) for 10 minutes at 25° C. The enzymatic reaction was then initiated by addition of a 2 uL per well volume of a pre-mixed substrate mix (UltraPure ATP from ADP-Glo™ Max kit (0.31 mM), GTP (0.034 mM), UTP (0.48 mM) and L-glutamine (0.186 mM)) and the mixture was incubated for an appropriate amount of time within the determined linear phase of the reaction at 25° C. under sealed plate conditions with constant agitation at 500 revolutions per minute (rpm). ADP-Glo™ Max reagent was added for 60 minutes (6 uL per well) and subsequently ADP-Glo™ Max development reagent was added for 60 minutes (12 uL per well) prior to signal detection in a microplate reader (EnVision® Multi-label Reader, Perkin Elmer). Following each reagent addition over the course of the assay, assay plates were pulse centrifuged for 30 seconds at 500 rpm.

In all cases, the enzyme converts ATP to ADP and the ADP-Glo™ Max reagent subsequently depletes any remaining endogenous ATP in the reaction system. The ADP-Glo™ Max detection reagent converts the ADP that has been enzymatically produced back into ATP and using ATP as a substrate together with luciferin for the enzyme luciferase, light is generated which produces a detectable luminescence. The luminescent signal measured is directly proportional to the amount of ADP produced by the enzyme reaction and a reduction in this signal upon compound treatment demonstrates enzyme inhibition. The percentage inhibition produced by each concentration of compound was calculated using the equation shown below:

$$\% \text{ Inhibition} = 1 - \frac{(Mean_{Min} - Mean_{Inh})}{(Mean_{Min} - Mean_{Max})} \times 100$$

Percentage inhibition was then plotted against compound concentration, and the 50% inhibitory concentration (IC$_{50}$) was determined from the resultant concentration-response curve.

The data for all compounds tested are presented below.

TABLE 17

Human CTPS1 Enzyme Inhibition data grouped by potency range
(+ indicates IC$_{50}$ in the range >1 to 10 micromolar,
++ indicates IC$_{50}$ in the range >0.1 to 1 micromolar,
+++ indicates IC$_{50}$ of ≤0.1 micromolar)

| T # | CTPS1 |
|---|---|
| T1 | + |
| T2 | ++ |
| T3 | ++ |
| T4 | + |
| T5 | +++ |
| T6 | ++ |
| T7 | +++ |
| T8 | +++ |
| T9 | +++ |
| T10 | +++ |
| T11 | ++ |
| T12 | ++ |
| T13 | ++ |
| T14 | ++ |
| T15 | ++ |
| T16 | ++ |
| T17 | ++ |
| T18 | +++ |
| T19 | ++ |
| T20 | ++ |
| T21 | + |
| T22 | +++ |
| T23 | ++ |
| T24 | ++ |
| T25 | + |
| T26 | ++ |
| T27 | ++ |
| T28 | ++ |
| T29 | +++ |
| T30 | +++ |
| T31 | + |
| T32 | +++ |
| T33 | +++ |
| T34 | ++ |
| T35 | +++ |
| T36 | ++ |
| T37 | ++ |
| T38 | +++ |
| T39 | ++ |
| T40 | +++ |
| T41 | ++ |
| T42 | +++ |
| T43 | ++ |
| T44 | ++ |
| T45 | ++ |
| T46 | + |
| T47 | +++ |
| T48 | +++ |
| T49 | ++ |
| T50 | +++ |
| T51 | +++ |
| T52 | +++ |
| T53 | + |
| T54 | ++ |
| T55 | +++ |
| T56 | +++ |
| T57 | +++ |
| T58 | +++ |
| T59 | +++ |
| T60 | ++ |
| T61 | +++ |
| T62 | ++ |
| T63 | ++ |
| T64 | ++ |
| T65 | ++ |
| T66 | ++ |
| T67 | ++ |

TABLE 17-continued

Human CTPS1 Enzyme Inhibition
data grouped by potency range
(+ indicates IC$_{50}$ in the range >1 to 10 micromolar,
++ indicates IC$_{50}$ in the range >0.1 to 1 micromolar,
+++ indicates IC$_{50}$ of ≤0.1 micromolar)

| T # | CTPS1 |
|---|---|
| T68 | ++ |
| T69 | + |
| T70 | ++ |
| T71 | +++ |
| T72 | +++ |
| T73 | +++ |
| T74 | ++ |
| T75 | +++ |
| T76 | +++ |
| T77 | +++ |
| T78 | +++ |
| T79 | ++ |
| T80 | +++ |
| T81 | +++ |
| T82 | +++ |
| T83 | + |
| T84 | ++ |
| T85 | ++ |
| T86 | + |
| T87 | ++ |
| T88 | ++ |
| T89 | +++ |
| T90 | +++ |
| T91 | +++ |
| T92 | +++ |
| T93 | +++ |
| T94 | +++ |
| T95 | +++ |
| T96 | +++ |
| T97 | ++ |
| T98 | ++ |
| T99 | +++ |
| T100 | ++ |
| T101 | + |
| T102 | +++ |
| T103 | ++ |
| T104 | ++ |
| T105 | + |
| T106 | +++ |
| T107 | +++ |
| T108 | +++ |
| T109 | +++ |
| T110 | ++ |
| T111 | +++ |
| T112 | +++ |
| T113 | + |
| T114 | ++ |
| T115 | +++ |
| T116 | ++ |
| T117 | ++ |
| T118 | +++ |
| T119 | +++ |
| T120 | +++ |
| T121 | +++ |
| T122 | +++ |
| T123 | +++ |
| T124 | +++ |
| T125 | +++ |
| T126 | +++ |
| T127 | +++ |
| T128 | +++ |
| T129 | +++ |
| T130 | +++ |
| T131 | +++ |
| T132 | ++ |
| T133 | +++ |
| T134 | +++ |
| T135 | ++ |
| T136 | +++ |
| T137 | +++ |
| T138 | +++ |
| T139 | +++ |
| T140 | ++ |
| T141 | ++ |
| T142 | +++ |
| T143 | +++ |
| T144 | ++ |
| T145 | +++ |
| T146 | ++ |
| T147 | +++ |
| T148 | ++ |
| T149 | +++ |
| T150 | ++ |
| T151 | ++ |
| T152 | ++ |
| T153 | ++ |
| T154 | ++ |
| T155 | +++ |
| T156 | +++ |
| T157 | +++ |
| T158 | +++ |
| T159 | +++ |
| T160 | +++ |
| T161 | ++ (n = 2) + (n = 6) |
| T163 | ++ |
| T164 | + |
| T169 | ++ |
| T170 | ++ |
| T171 | +++ |
| T172 | +++ |
| T173 | +++ |
| T174 | +++ |
| T175 | +++ |
| T176 | +++ |
| T177 | +++ |
| T178 | + |
| T179 | +++ |
| T180 | +++ |
| T181 | ++ |
| T182 | +++ |
| T183 | +++ |
| T184 | + |
| T185 | +++ (n = 1) ++ (n = 2) |
| T186 | +++ |
| T187 | +++ |
| T188 | ++ |
| T189 | +++ |
| T190 | +++ |
| T191 | +++ |
| T192 | +++ |
| T193 | +++ |
| T194 | +++ |
| T195 | +++ |
| T196 | +++ |
| T197 | +++ |
| T198 | +++ |
| T199 | +++ |
| T200 | +++ |
| T201 | +++ |
| T202 | +++ |
| T203 | +++ |
| T204 | +++ |
| T205 | +++ |
| T206 | +++ |
| T207 | +++ |
| T208 | +++ |
| T209 | +++ |
| T210 | +++ |

TABLE 17-continued

Human CTPS1 Enzyme Inhibition
data grouped by potency range
(+ indicates IC$_{50}$ in the range >1 to 10 micromolar,
++ indicates IC$_{50}$ in the range >0.1 to 1 micromolar,
+++ indicates IC$_{50}$ of ≤0.1 micromolar)

| T # | CTPS1 |
|---|---|
| T211 | +++ |
|  | (n = 1) |
|  | ++ |
|  | (n = 2) |
| T212 | +++ |
| T213 | ++ |
| T214 | +++ |
| T215 | +++ |
| T216 | ++ |
| T217 | +++ |
| T218 | ++ |
| T219 | +++ |
| T220 | +++ |
| T221 | +++ |
| T222 | ++ |
| T223 | +++ |
| T224 | +++ |
| T225 | +++ |
| T226 | +++ |
| T227 | ++ |
| T228 | +++ |
| T229 | +++ |
| T230 | +++ |
| T231 | + |
| T232 | ++ |
| T233 | + |
| T234 | + |
| T235 | ++ |
| T236 | ++ |
| T237 | + |
| T238 | + |
| T239 | ++ |
| T240 | ++ |
| T241 | ++ |
| T242 | + |
| T243 | + |
| T244 | ++ |
| T245 | + |
| T246 | ++ |
| T247 | ++ |
| T248 | + |
| T249 | +++ |
| T250 | + |
| T251 | + |
| T252 | +++ |
| T253 | +++ |
| T254 | ++ |
| T255 | + |
| T256 | +++ |
| T257 | ++ |
| T258 | ++ |
| T259 | +++ |
| T260 | + |
| T261 | +++ |
| T262 | +++ |
| T263 | + |
| T264 | ++ |
| T265 | +++ |
| T266 | +++ |
| T267 | +++ |
| T268 | ++ |
| T269 | ++ |
| T270 | ++ |
| T271 | + |
| T272 | +++ |
| T273 | +++ |
| T274 | +++ |
| T275 | +++ |
| T276 | ++ |
| T277 | ++ |
| T278 | +++ |
| T279 | + |
| T280 | + |
| T281 | ++ |
| T282 | ++ |
| T283 | ++ |
| T284 | + |
| T285 | +++ |
| T286 | +++ |
| T287 | +++ |
| T288 | ++ |
| T289 | ++ |
| T290 | +++ |
| T291 | +++ |
| T292 | ++ |
| T293 | ++ |
| T294 | ++ |
| T295 | ++ |
| T296 | ++ |
| T297 | + |
| T298 | +++ |
| T299 | ++ |
| T300 | ++ |
| T301 | +++ |
| T302 | ++ |
| T303 | + |
| T304 | ++ |
| T305 | ++ |
| T306 | ++ |
| T307 | +++ |
| T308 | ++ |
| T309 | + |
| T310 | + |
| T311 | + |
| T312 | ++ |
| T313 | ++ |
| T314 | ++ |
| T315 | ++ |
| T316 | ++ |
| T317 | ++ |
| T318 | + |
| T319 | + |
| T320 | ++ |
| T321 | +++ |
| T322 | ++ |

Additional Potency Data:

TABLE 18

Human CTPS1 Enzyme Inhibition
data grouped by potency range
(+ indicates IC$_{50}$ in the range >1 to 10 micromolar,
++ indicates IC$_{50}$ in the range >0.1 to 1 micromolar,
+++ indicates IC$_{50}$ of ≤0.1 micromolar)

| Cpd # | CTPS1 |
|---|---|
| T326 | +++ |
| T327 | +++ |
| T328 | +++ |
| T329 | +++ |
| T330 | +++ |
| T331 | +++ |
| T332 | ++ |
| T333 | + |
| T334 | ++ |
| T335 | ++ |
| T336 | ++ |
| T337 | +++ |
| T338 | + |
| T339 | + |

TABLE 18-continued

Human CTPS1 Enzyme Inhibition
data grouped by potency range
(+ indicates IC$_{50}$ in the range >1 to 10 micromolar,
++ indicates IC$_{50}$ in the range >0.1 to 1 micromolar,
+++ indicates IC$_{50}$ of ≤0.1 micromolar)

| Cpd # | CTPS1 |
|---|---|
| T340 | ++ |
| T341 | +++ |
| T342 | +++ |
| T343 | +++ |
| T344 | +++ |
| T345 | +++ |
| T346 | ++ |
| T347 | +++ |
| T348 | ++ |
| T349 | ++ |
| T350 | ++ |
| T351 | ++ (n = 1) |
|  | +++ (n = 2) |
| T352 | ++ |
| T353 | ++ |
| T354 | ++ |
| T355 | + |
| T356 | +++ |
| T357 | +++ |
| T358 | +++ |
| T359 | +++ |
| T360 | ++ |
| T361 | ++ |
| T362 | +++ |
| T363 | +++ |
| T364 | ++ |
| T365 | +++ |
| T366 | ++ |
| T367 | +++ |
| T368 | +++ |
| T369 | ++ |
| T370 | + |
| T371 | +++ |
| T372 | ++ |
| T373 | +++ |
| T374 | + |
| T375 | ++ |
| T376 | ++ |
| T377 | ++ |
| T378 | + |
| T379 | + |
| T380 | +++ |
| T381 | +++ |
| T382 | +++ |
| T383 | +++ |
| T384 | ++ |
| T385 | +++ |
| T386 | ++ |
| T387 | +++ |
| T388 | +++ |
| T389 | ++ |
| T390 | +++ |
| T391 | +++ |
| T392 | +++ |
| T393 | ++ |
| T394 | +++ |
| T395 | +++ |
| T396 | ++ |
| T397 | ++ |
| T398 | +++ |
| T399 | +++ |
| T400 | +++ |
| T401 | ++ |
| T402 | + |
| T403 | ++ |
| T404 | ++ |
| T405 | +++ |
| T406 | ++ |
| T407 | +++ |
| T408 | +++ |
| T409 | +++ |
| T410 | +++ |
| T411 | +++ |
| T412 | +++ |
| T413 | +++ |
| T414 | +++ |
| T415 | ++ |
| T416 | +++ |
| T417 | ++ |
| T418 | ++ |
| T419 | +++ |
| T420 | +++ |
| T421 | +++ |
| T422 | ++ |
| T423 | +++ |
| T424 | +++ |
| T425 | +++ |
| T426 | ++ |
| T427 | ++ |
| T428 | ++ |
| T429 | +++ |
| T430 | ++ |
| T431 | +++ |
| T432 | ++ |
| T433 | +++ |
| T434 | +++ |
| T435 | +++ |
| T436 | +++ |
| T437 | +++ |
| T438 | +++ |
| T439 | +++ |
| T440 | +++ |
| T441 | +++ |
| T442 | +++ |
| T443 | +++ |
| T444 | +++ |
| T445 | +++ |
| T446 | +++ |
| T447 | +++ |
| T448 | +++ |
| T449 | +++ |
| T450 | +++ |
| T451 | +++ |
| T452 | +++ |
| T453 | +++ |
| T454 | +++ |
| T455 | +++ |
| T456 | +++ |
| T457 | +++ |
| T458 | +++ |
| T459 | +++ |
| T463 | ++ |
| T464 | +++ |
| T465 | + |

All compounds of the invention which have been tested were found to demonstrate inhibition of CTPS1 enzyme in this assay. Consequently, these compounds may be expected to have utility in the inhibition of CTPS1. The compounds of the invention are also expected to have utility as research tools, for example, for use in CTPS assays.

Biological Example 2—RapidFire/MS-Based Enzyme Selectivity Assays

Human CTPS1 Versus CTPS2 Selectivity Assessment by RapidFire/MS Analysis.

The enzyme inhibitory activities against each target isoform of interest may be determined for the compounds of the invention using an optimised RapidFire high-throughput mass spectrometry (RF/MS) assay format. RF/MS assays for both human CTPS1 and CTPS2 may be performed in assay buffer consisting of 50 mM HEPES (Merck), 20 mM $MgCl_2$, 5 mM KCl, 1 mM DTT, 0.01% Tween-20, pH to 8.0 accordingly. Human full-length active C-terminal FLAG-His-tag CTPS1 (UniProtKB—P17812, CTPS[1-591]-GGDYKDDDDKGGHHHHHHHH (SEQ ID NO: 1)) may be obtained from Proteros biostructures GmbH. Human full length active C-terminal FLAG-His-Avi tagged CTPS2 (UniProtKB—Q9NRF8, CTPS2 [1-586]-DYKDDDDKHHHHHHGLNDIFEAQKIEWHE (SEQ ID NO: 2)) may be obtained from Harker Bio.

Assay Procedure

Human CTPS (1 or 2) protein may be prepared in 1× assay buffer to the final working protein concentration required for the reaction. A 2 uL volume per well of 2×CTPS (1 or 2) protein may be mixed with 40 nL of compound using acoustic (ECHO) delivery and incubated for 10 minutes at 25° C. Each isoform enzymatic reaction may be subsequently initiated by addition of 2 uL per well of a 2× substrate mix in assay buffer. For hCTPS1: ATP (0.3 mM), UTP (0.2 mM), GTP (0.07 mM) and L-glutamine (0.1 mM). For hCTPS2: ATP (0.1 mM), UTP (0.04 mM), GTP (0.03 mM) and L-glutamine (0.1 mM). Each mixture may be incubated for an appropriate amount of time per isoform within the determined linear phase of the reaction at 25° C. A 60 uL volume of stop solution (1% formic acid with 0.5 uM $^{13}C_a$-$^{15}N3$-CTP in $H_2O$) may be added and the plate immediately heat-sealed and centrifuged for 10 minutes at 4,000 rpm. Following centrifugation, plates may be loaded onto the Agilent RapidFire microfluidic solid phase extraction system coupled to an API4000 triple quadrupole mass spectrometer (RF/MS) for analysis.

In all cases, the enzyme converts UTP to CTP. Highly specific and sensitive multiple reaction monitoring (MRM) MS methods may be optimised for the detection of the enzymatic reaction product, CTP, and the stable isotope labelled product standard $^{13}C_9$-$^{15}N_3$-CTP. Readout for data analysis may be calculated as the ratio between the peak area of the product CTP and the internal standard $^{13}C_9$-$^{15}N_3$-CTP. For data reporting, the following equation may be used:

$$R = \frac{P}{IS}$$

(R=ratio/readout, P=product signal area, IS=internal standard signal area)

For each screening plate, the means of the negative (DMSO) and positive control values may be used for the calculation of the respective assay window (S/B) and Z' values. The median of the respective control values may be used for calculation of percent inhibition according to the following equation:

$$1 = \frac{R_{neg} - R_{sample}}{[R_{neg} - R_{pos}]} \%$$

(I=Inhibition, $R_{neg}$=median of negative control readout values, $R_{pos}$=median of positive control readout values, $R_{sample}$=sample readout value)

Percentage inhibition may be then plotted against compound concentration, and the 50% inhibitory concentration ($IC_{50}$) may be determined from the resultant concentration-response curve.

Fold selectivity between CTPS1 and CTPS2 may be subsequently calculated according to the following equation:

$$\text{Fold selectivity} = \frac{CTPS2\ IC_{50}}{CTPS1\ IC_{50}}$$

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims which follow.

All publications, including but not limited to patents and patent applications, cited in this specification are herein incorporated by reference as if each individual publication were specifically and individually indicated to be incorporated by reference herein as though fully set forth.

Clauses of the Invention:

Clause 1—A compound of formula (I):

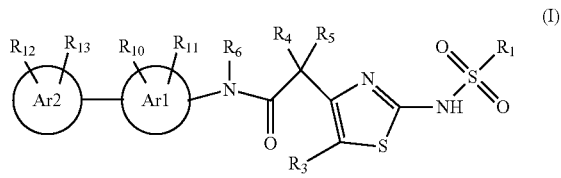

wherein $R_1$ is $C_{1-5}$alkyl, $C_{0-2}$alkylene$C_{3-5}$cycloalkyl which cycloalkyl is optionally substituted by $CH_3$, $C_{1-3}$alkyleneO$C_{1-2}$alkyl, or $CF_3$;

$R_3$ is H, halo, $CH_3$, $OC_{1-2}$alkyl or $CF_3$;

or $R_3$ together with $R_5$ forms a 5- or 6-membered cycloalkyl or 5 or 6 membered oxygen-containing heterocycloalkyl;

$R_4$ and $R_5$ are each independently H, halo, $C_{1-6}$alkyl, $C_{0-2}$alkylene$C_{3-6}$cycloalkyl, $C_{0-2}$alkylene$C_{3-6}$heterocycloalkyl, $OC_{1-6}$alkyl, $OC_{0-2}$alkylene$C_{3-6}$cycloalkyl, $C_{1-3}$alkyleneO$C_{1-3}$alkyl, $C_{1-6}$alkylOH, $C_{1-6}$haloalkyl, $OC_{1-6}$haloalkyl or $NR_{21}R_{22}$, or $R_4$ is H and $R_5$ together with $R_3$ form a 5- or 6-membered cycloalkyl or 5 or 6 membered oxygen-containing heterocycloalkyl, or $R_4$ and $R_5$ together with the carbon atom to which they are attached form a $C_{3-6}$cycloalkyl or $C_{3-6}$heterocycloalkyl, or $R_4$ is H and $R_5$ and $R_6$ are a $C_{2-3}$alkylene chain forming a 5- or 6-membered ring;

or $R_4$ is O and $R_5$ is absent;

$R_6$ is H or $C_{1-3}$alkyl, or $R_6$ together with $R_{11}$ when in the ortho-position to the amide are a $C_2$alkylene chain forming a 5-membered ring, or $R_5$ and $R_6$ are a $C_{2-3}$alkylene chain forming a 5- or 6-membered ring and $R_4$ is H;

Ar1 is 6-membered aryl or heteroaryl;

Ar2 is a 6-membered aryl or heteroaryl and is attached to Ar1 in the para position relative to the amide;

$R_{10}$ is H, halo, $C_{1-3}$alkyl, $OC_{1-2}$alkyl, $C_{1-2}$haloalkyl, $OC_{1-2}$haloalkyl or CN;

$R_{11}$ is H, F, Cl, $CH_3$, ethyl, $OCH_3$, $CF_3$, $OCF_3$ or CN, or $R_{11}$, when in the ortho-position to the amide, together with $R_6$ are a $C_2$alkylene chain forming a 5-membered ring;

$R_{12}$ is attached to Ar2 in the ortho or meta position relative to Ar1 and $R_{12}$ is H, halo, $C_{1-4}$alkyl, $C_{2-4}$alkynyl, $C_{0-2}$alkylene$C_{3-5}$cycloalkyl, $OC_{1-4}$alkyl, $OC_{0-2}$alkylene$C_{3-5}$cycloalkyl, $OCH_2CH_2N(CH_3)_2$, OH, $C_{1-4}$alkylOH, CN, $C_{1-3}$alkyleneOC$_{1-3}$alkyl, $C_{1-4}$haloalkyl, $OC_{1-4}$ haloalkyl, C(=O)$C_{1-2}$alkyl, $NR_{23}R_{24}$, $SO_2$$C_{1-4}$alkyl, $SOC_{1-4}$alkyl, $SC_{1-4}$alkyl, SH, C(O)N(CH$_3$)$_2$, NHC(O)$C_{1-3}$alkyl, $C_{3-6}$heterocycloalkyl comprising one nitrogen located at the point of attachment to Ar2, or $R_{12}$ together with a nitrogen atom to which it is attached forms an N-oxide ($N^+$—$O^-$);

$R_{13}$ is H, halo, $CH_3$ or $OCH_3$;

$R_{21}$ is H, $C_{1-5}$alkyl, C(O)$C_{1-5}$alkyl, C(O)O$C_{1-5}$alkyl;

$R_{22}$ is H or $CH_3$;

$R_{23}$ is H or $C_{1-2}$alkyl; and $R_{24}$ is H or $C_{1-2}$alkyl;

or a salt and/or solvate thereof and/or derivative thereof.

Clause 2—The compound according to clause 1 which is a compound of formula (I):

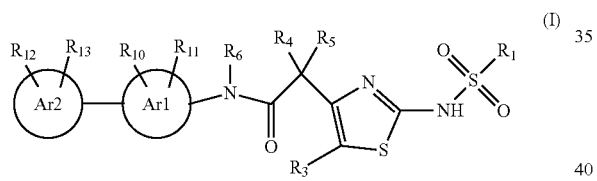

(I)

wherein $R_1$ is $C_{1-5}$alkyl, $C_{1-2}$alkyleneOC$_{1-2}$alkyl, $C_{0-2}$alkylene$C_{3-5}$cycloalkyl which cycloalkyl is optionally substituted by $CH_3$, or $CF_3$;

$R_3$ is H, halo, $CH_3$, $CF_3$ or $OCH_3$;

or $R_3$ together with $R_5$ forms a 5- or 6-membered cycloalkyl;

$R_4$ and $R_5$ are each independently H, F, $C_{1-6}$alkyl, $C_{0-2}$alkylene$C_3$s-cycloalkyl, $OC_{1-6}$alkyl, $OC_{0-2}$alkylene$C_{3-6}$cycloalkyl, $C_{1-3}$alkyleneOC$_{1-3}$alkyl, $C_{1-6}$alkylOH, $C_{1-6}$haloalkyl, $OC_{1-6}$ haloalkyl or $NR_{21}R_{22}$, or $R_4$ is H and $R_5$ together with $R_3$ form a 5- or 6-membered cycloalkyl, or $R_4$ and $R_5$ together with the carbon atom to which they are attached form a $C_{3-6}$cycloalkyl, or $R_4$ is O and $R_5$ is absent;

$R_6$ is H or $C_{1-3}$alkyl, or $R_6$ together with $R_{11}$ in the ortho-position to the amide are a $C_2$alkylene chain forming a 5-membered ring;

Ar1 is 6-membered aryl or heteroaryl;

Ar2 is a 6-membered aryl or heteroaryl and is attached to Ar1 in the para position relative to the amide;

$R_{10}$ is H, halo, $C_{1-3}$alkyl, $OC_{1-2}$alkyl, $C_{1-2}$haloalkyl, $OC_{1-2}$haloalkyl or CN;

$R_{11}$ is H, F, Cl, $CH_3$, $OCH_3$, $CF_3$, $OCF_3$ or CN, or $R_{11}$, when in the ortho-position to the amide, together with $R_6$ are a $C_2$alkylene chain forming a 5-membered ring;

$R_{12}$ is attached to Ar2 in the ortho or meta position relative to Ar1 and $R_{12}$ is H, halo, $C_{1-4}$ alkyl, $C_{2-4}$alkynyl, $C_{0-2}$alkylene$C_{3-5}$cycloalkyl, $OC_{1-4}$alkyl, $OC_{0-2}$alkylene$C_{3-5}$cycloalkyl, $OCH_2CH_2N(CH_3)_2$, OH, $C_{1-4}$alkylOH, CN, $C_{1-3}$alkyleneOC$_{1-3}$alkyl, $C_{1-4}$haloalkyl, $OC_{1-4}$ haloalkyl, $N(CH_3)_2$, $SO_2CH_3$, C(O)N(CH$_3$)$_2$, NHC(O)$C_{1-3}$alkyl or a $C_{3-6}$heterocycloalkyl comprising one nitrogen located at the point of attachment to Ar2;

$R_{13}$ is H, F, $CH_3$ or $OCH_3$;

$R_{21}$ is H, $C_{1-5}$alkyl, C(O)$C_{1-5}$alkyl, C(O)O$C_{1-5}$alkyl; and $R_{22}$ is H or $CH_3$;

or a salt and/or solvate thereof and/or derivative thereof.

Clause 3—The compound according to clause 1 which is a compound of formula (I):

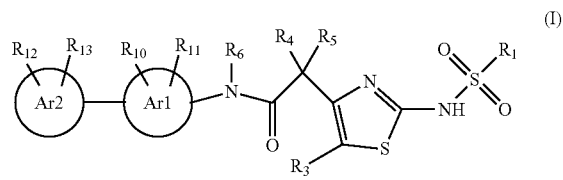

(I)

wherein $R_1$ is $C_{1-5}$alkyl, $C_{0-2}$alkylene$C_{3-5}$cycloalkyl which cycloalkyl is optionally substituted by $CH_3$, or $CF_3$;

$R_3$ is H, halo, $CH_3$ or $CF_3$, or $R_3$ together with $R_5$ forms a 5- or 6-membered cycloalkyl;

$R_4$ and $R_5$ are each independently H, F, $C_{1-6}$alkyl, $C_{0-2}$alkylene$C_{3-6}$cycloalkyl, $OC_{1-6}$alkyl, $OC_{0-2}$alkylene$C_{3-6}$cycloalkyl, $C_{1-3}$alkyleneOC$_{1-3}$alkyl, $C_{1-6}$haloalkyl or $OC_{1-6}$haloalkyl, or $R_4$ is H and $R_5$ together with $R_3$ form a 5- or 6-membered cycloalkyl, or $R_4$ and $R_5$ together with the carbon atom to which they are attached form a $C_{3-6}$cycloalkyl, or $R_4$ is O and $R_5$ is absent;

$R_6$ is H or $C_{1-3}$alkyl, or $R_6$ together with $R_{11}$ in the ortho-position to the amide are a $C_2$alkylene chain forming a 5-membered ring;

Ar1 is 6-membered aryl or heteroaryl;

Ar2 is a 6-membered aryl or heteroaryl and is attached to Ar1 in the para position relative to the amide;

$R_{10}$ is H, halo, $C_{1-2}$alkyl, $OC_{1-2}$alkyl, $C_{1-2}$haloalkyl, $OC_{1-2}$haloalkyl or CN;

$R_{11}$ is H, F, C, $CH_3$, $OCH_3$, $CF_3$, $OCF_3$ or CN, or $R_{11}$, when in the ortho-position to the amide, together with $R_6$ are a $C_2$alkylene chain forming a 5-membered ring;

$R_{12}$ is attached to Ar2 in the ortho or meta position relative to Ar1 and $R_{12}$ is H, halo, $C_{1-4}$ alkyl, $C_{2-4}$alkynyl, $C_{0-2}$alkylene$C_{3-5}$cycloalkyl, $OC_{1-4}$alkyl, $OC_{0-2}$alkylene$C_{3-5}$cycloalkyl, $OCH_2CH_2N(CH_3)_2$, $C_{1-4}$alkylOH, CN, $C_{1-3}$alkyleneOC$_{1-3}$alkyl, $C_{1-4}$haloalkyl, $OC_{1-4}$ haloalkyl, $N(CH_3)_2$, $SO_2CH_3$, C(O)N(CH$_3$)$_2$, NHC(O)$C_{1-3}$alkyl or a $C_{3-6}$heterocycloalkyl comprising one nitrogen located at the point of attachment to Ar2; and $R_{13}$ is H, F, $CH_3$ or $OCH_3$;

or a salt and/or solvate thereof and/or derivative thereof.

Clause 4—The compound according to any one of clauses 1 to 3 wherein $R_1$ is $C_{1-5}$alkyl such as $CH_3$ or ethyl.

Clause 5—The compound according to clause 4 wherein $R_1$ is $CH_3$.

Clause 6—The compound according to any one of clauses 1 to 3 wherein $R_1$ is $C_{0-2}$alkylene$C_{3-5}$cycloalkyl which cycloalkyl is optionally substituted by $CH_3$.

Clause 7—The compound according to clause 6, wherein $R_1$ is $C_{0-2}$alkylene$C_{3-5}$cycloalkyl.

Clause 8—The compound according to clause 6, wherein $R_1$ is $C_{0-2}$alkylene$C_{3-5}$cycloalkyl which cycloalkyl is substituted by $CH_3$.

Clause 9—The compound according to any one of clauses 6 to 8, wherein $R_1$ is $C_{3-5}$cycloalkyl, optionally substituted by $CH_3$.

Clause 10—The compound according to any one of clauses 6 to 8, wherein $R_1$ is $C_1$alkylene$C_{3-5}$cycloalkyl which cycloalkyl is optionally substituted by $CH_3$.

Clause 11—The compound according to any one of clauses 6 to 8, wherein $R_1$ is $C_2$alkylene$C_{3-5}$cycloalkyl which cycloalkyl is optionally substituted by $CH_3$.

Clause 12—The compound according to any one of clauses 6 to 11, wherein $R_1$ is $C_{0-2}$alkylene$C_3$cycloalkyl which cycloalkyl is optionally substituted by $CH_3$.

Clause 13—The compound according to any one of clauses 6 to 11 wherein $R_1$ is $C_{0-2}$alkylene$C_4$cycloalkyl which cycloalkyl is optionally substituted by $CH_3$.

Clause 14—The compound according to any one of clauses 6 to 11 wherein $R_1$ is $C_{0-2}$alkylene$C_5$cycloalkyl which cycloalkyl is optionally substituted by $CH_3$.

Clause 15—The compound according to any one of clauses 1 to 14 wherein $R_1$ is cyclopropyl, cyclopropyl substituted by $CH_3$ at the point of attachment, cyclopropylmethylene, cyclobutyl, cyclopentyl, $CH_3$, ethyl, isopropyl, sec-butyl or tert-butyl, especially cyclopropyl, cyclopropyl substituted by $CH_3$ at the point of attachment, cyclobutyl, $CH_3$, ethyl or isopropyl.

Clause 16—The compound according to any one of clauses 1 to 15 wherein $R_1$ is cyclopropyl, cyclopropyl substituted by $CH_3$ at the point of attachment, cyclobutyl, $CH_3$, isopropyl, sec-butyl or tert-butyl.

Clause 17—The compound according to any clause 16 wherein $R_1$ is cyclopropyl, cyclopropyl substituted by $CH_3$ at the point of attachment, cyclobutyl or isopropyl.

Clause 18—The compound according to any one of clauses 1 to 17 wherein $R_3$ is H.

Clause 19—The compound according to any one of clauses 1 to 17 wherein $R_3$ is chloro or fluoro.

Clause 20—The compound according to any one of clauses 1 to 17 wherein $R_3$ is $CH_3$.

Clause 21—The compound according to any one of clauses 1 to 17 wherein $R_3$ is $OCH_3$.

Clause 22—The compound according to any one of clauses 1 to 17 wherein $R_3$ is $CF_3$.

Clause 23—The compound according to any one of clauses 1 to 17 wherein $R_3$ together with $R_5$ forms a 5- or 6-membered cycloalkyl.

Clause 24—The compound according to clause 23 wherein $R_3$ together with $R_5$ forms a 5-membered cycloalkyl.

Clause 25—The compound according to any one of clauses 1 to 17 wherein $R_4$ is H and $R_3$ together with $R_5$ forms a 5- or 6-membered oxygen-containing heterocycloalkyl such as tetrahydrofuranyl or tetrahydropyranyl.

Clause 26—The compound according to any one of clauses 1 to 22 wherein $R_4$ together with $R_5$ form a $C_{3-6}$cycloalkyl.

Clause 27—The compound according to clause 26 wherein $R_4$ together with $R_5$ form cyclopropyl or cyclopentyl.

Clause 28—The compound according to any one of clauses 1 to 22 wherein $R_4$ together with $R_5$ form a $C_{3-6}$heterocycloalkyl.

Clause 29—The compound according to clause 28 wherein $R_4$ together with $R_5$ form heterocyclopentyl or heterocyclohexyl, such as tetrahydrofuranyl, pyrrolidinyl, tetrahydropyranyl or piperidinyl such as tetrahydropyranyl or piperidinyl.

Clause 30—The compound according to any one of clauses 1 to 24, wherein $R_4$ is $C_{1-6}$alkyl, in particular $C_{1-4}$alkyl such as methyl, ethyl or propyl (n-propyl or isopropyl).

Clause 31—The compound according to any one of clauses 1 to 24, wherein $R_4$ is $C_{0-2}$alkylene$C_{3-6}$cycloalkyl, such as $C_{3-6}$cycloalkyl, $C_1$alkylene$C_{3-6}$cycloalkyl or $C_2$alkylene$C_{3-6}$cycloalkyl.

Clause 32—The compound according to any one of clauses 1 to 24, wherein $R_4$ is $OC_{1-6}$alkyl, in particular $OC_{1-4}$alkyl, such as methoxy or isopropoxy.

Clause 33—The compound according to any one of clauses 1 to 24, wherein $R_4$ is $OC_{0-2}$alkylene$C_{3-6}$cycloalkyl such as $OC_{3-6}$cycloalkyl, $OC_1$alkylene$C_{3-6}$cycloalkyl or $OC_2$alkylene$C_{3-6}$cycloalkyl.

Clause 34—The compound according to any one of clauses 1 to 24, wherein $R_4$ is $C_{1-3}$ alkylene$OC_{1-3}$alkyl, in particular $C_{1-2}$alkylene$OC_{1-2}$alkyl, such as $CH_2CH_2OCH_3$.

Clause 35—The compound according to any one of clauses 1 to 24, wherein $R_4$ is $C_{1-6}$ haloalkyl, in particular $C_{1-4}$haloalkyl.

Clause 36—The compound according to any one of clauses 1 to 24, wherein $R_4$ is $OC_{1-6}$ haloalkyl, in particular $OC_{1-4}$haloalkyl.

Clause 37—The compound according to clause 1 to 24 wherein $R_4$ is H.

Clause 38—The compound according to clause 1 to 24 wherein $R_4$ is halo such as F.

Clause 39—The compound according to clause 1 to 24 wherein $R_4$ is $C_{1-6}$alkylOH, such as $CH_2CH_2OH$.

Clause 40—The compound according to clause 1 to 24 wherein $R_4$ is $NR_{21}R_{22}$.

Clause 41—The compound according to clause 40 wherein $R_{21}$ is H.

Clause 42—The compound according to clause 40 wherein $R_{21}$ is $C_{1-5}$alkyl, such as methyl, ethyl or propyl.

Clause 43—The compound according to clause 40 wherein $R_{21}$ is $C(O)C_{1-5}$alkyl, such as $C(O)CH_3$.

Clause 44—The compound according to clause 40 wherein $R_{21}$ is $C(O)OC_{1-5}$alkyl, such as $C(O)OCH_3$ or $C(O)O$tert-butyl.

Clause 45—The compound according to clause 40 to 44 wherein $R_{22}$ is H.

Clause 46—The compound according to clause 40 to 44 wherein $R_{22}$ is $CH_3$.

Clause 47. The compound according to any one of clauses 1 to 24 wherein $R_4$ is $C_{0-2}$alkylene$C_{3-6}$heterocycloalkyl.

Clause 48—The compound according to any one of clauses 1 to 47 wherein any nitrogen atom in the $C_{3-6}$heterocycloalkyl ring is substituted, for example by $C_{1-4}$alkyl, $C(O)H$, $C(O)C_{1-4}$alkyl, $C(O)OC_{1-4}$alkyl, $C(O)OC_{1-4}$alkylaryl such as $C(O)OBz$, $C(O)NHC_{1-4}$alkyl, $C(O)NHC_{1-4}$alkylaryl such as $C(O)NHBz$, an Fmoc group, $C(O)C_{1-4}$haloalkyl, $C(O)OC_{1-4}$haloalkyl or $C(O)NHC_{1-4}$ haloalkyl such as $C(O)O$tBu.

Clause 49—The compound according to any one of clauses 1 to 47 wherein any nitrogen atom in the $C_{3-6}$heterocycloalkyl ring is not substituted.

Clause 50—The compound according to any one of clauses 1 to 49 wherein any sulphur atom in the $C_{3-6}$heterocycloalkyl ring is substituted, for example by one oxygen atom to form S=O or by two oxygen atoms to form $S(O)_2$.

Clause 51—The compound according to any one of clauses 1 to 49 wherein any sulphur atom in the $C_{3-6}$heterocycloalkyl ring is not substituted.

Clause 52—The compound according to any one of clauses 1 to 22 and 30 to 51, wherein $R_5$ is H, methyl, ethyl or fluoro e.g. H, methyl or ethyl.

Clause 53—The compound according to clause 52, wherein $R_5$ is H.

Clause 54—The compound according to any one of clauses 1 to 52 wherein $R_4$ and $R_5$ are methyl.

Clause 55—The compound according to any one of clauses 1 to 52 wherein $R_4$ and $R_5$ are ethyl.

Clause 56—The compound according to any one of clauses 1 to 22 wherein $R_4$ is H and $R_5$ and $R_6$ are a $C_{2-3}$alkylene chain forming a 5- or 6-membered ring, such as a 5-membered ring.

Clause 57—The compound according to any one of clauses 1 to 22 wherein $R_4$ is O and $R_5$ is absent.

Clause 58—The compound according to any one of clauses 1 to 52 wherein $R_4$ is ethyl and $R_5$ is H and the groups are arranged in the S configuration.

Clause 59—The compound according to any one of clauses 1 to 58 wherein $R_6$ is H.

Clause 60—The compound according to any one of clauses 1 to 58 wherein $R_6$ is $C_{1-3}$alkyl such as $CH_3$.

Clause 61—The compound according to any one of clauses 1 to 58 wherein $R_6$ together with $R_{11}$ in the ortho-position to the amide are a $C_2$alkylene chain forming a 5-membered ring.

Clause 62—The compound according to any one of clauses 1 to 61 wherein Ar1 is phenyl.

Clause 63—The compound according to any one of clauses 1 to 61 wherein Ar1 is pyridyl.

Clause 64—The compound according to clause 63 wherein Ar1 is 2-pyridyl.

Clause 65—The compound according to any one of clauses 1 to 61 wherein Ar1 is pyridazinyl.

Clause 66—The compound according to any one of clauses 1 to 61 wherein Ar1 is pyrimidinyl.

Clause 67—The compound according to any one of clauses 1 to 61 wherein Ar1 is pyrazinyl.

Clause 68—The compound according to any one of clauses 1 to 67 wherein $R_{10}$ is H.

Clause 69—The compound according to any one of clauses 1 to 67 wherein $R_{10}$ is chloro or fluoro, such as fluoro.

Clause 70—The compound according to any one of clauses 1 to 67 wherein $R_{10}$ is methoxy or ethoxy such as methoxy.

Clause 71—The compound according to any one of clauses 1 to 67 wherein $R_{10}$ is $C_{1-3}$alkyl.

Clause 72—The compound according to clause 65 wherein $R_{10}$ is methyl.

Clause 73—The compound according to any one of clauses 1 to 67 wherein $R_{10}$ is $OCF_3$.

Clause 74—The compound according to any one of clauses 1 to 67 wherein $R_{10}$ is $CF_3$.

Clause 75—The compound according to any one of clauses 1 to 67 wherein $R_{10}$ is CN.

Clause 76—The compound according to any one of clauses 69 to 75 wherein $R_{10}$ is in the ortho or meta position with respect to the amide, such as the ortho position with respect to the amide.

Clause 77—The compound according to any one of clauses 1 to 76 wherein $R_{11}$ is H.

Clause 78—The compound according to any one of clauses 1 to 76 wherein $R_{11}$ is fluoro.

Clause 79—The compound according to any one of clauses 1 to 76 wherein $R_{11}$ is methyl.

Clause 80—The compound according to any one of clauses 78 to 79 wherein $R_{11}$ is in the ortho or meta position with respect to the amide, such as the ortho position with respect to the amide.

Clause 81—The compound according to any one of clauses 1 to 80 wherein Ar2 is phenyl.

Clause 82—The compound according to any one of clauses 1 to 80 wherein Ar2 is pyridyl.

Clause 83—The compound according to clause 82 wherein Ar2 is 3-pyridyl.

Clause 84—The compound according to any one of clauses 1 to 80 wherein Ar2 is pyridazinyl.

Clause 85—The compound according to any one of clauses 1 to 80 wherein Ar2 is pyrimidinyl.

Clause 86—The compound according to any one of clauses 1 to 80 wherein Ar2 is pyrazinyl.

Clause 87—The compound according to any one of clauses 1 to 86 wherein $R_{12}$ is H.

Clause 88—The compound according to any one of clauses 1 to 86 wherein $R_{12}$ is halo, such as F or Cl.

Clause 89—The compound according to any one of clauses 1 to 86 wherein $R_{12}$ is $C_{1-4}$alkyl, such as ethyl or methyl, especially methyl.

Clause 90—The compound according to any one of clauses 1 to 86 wherein $R_{12}$ is $C_{2-4}$alkynyl, such as C≡CH.

Clause 91—The compound according to any one of clauses 1 to 86 wherein $R_{12}$ is $C_{0-2}$alkylene$C_{3-5}$cycloalkyl, such as cyclopropyl.

Clause 92—The compound according to any one of clauses 1 to 86 wherein $R_{12}$ is $OC_{1-4}$alkyl such as methoxy, ethoxy, isopropoxy or n-propoxy.

Clause 93—The compound according to any one of clauses 1 to 86 wherein $R_{12}$ is $OC_{0-2}$alkylene$C_{3-5}$cycloalkyl, such as cyclopropoxyl or cyclobutoxy.

Clause 94—The compound according to any one of clauses 1 to 86 wherein $R_{12}$ is $OCH_2CH_2N(CH_3)_2$ Clause 95—The compound according to any one of clauses 1 to 86 wherein $R_{12}$ is $C_{1-4}$alkylOH, such as $CH_2OH$ or $C(CH_3)_2OH$.

Clause 96—The compound according to any one of clauses 1 to 86 wherein $R_{12}$ is CN.

Clause 97—The compound according to any one of clauses 1 to 86 wherein $R_{12}$ is $C_{1-3}$ alkyleneO$C_{1-3}$alkyl.

Clause 98—The compound according to any one of clauses 1 to 86 wherein $R_{12}$ is $C_{1-4}$ haloalkyl, such as $CF_3$.

Clause 99—The compound according to any one of clauses 1 to 86 wherein $R_{12}$ is $OC_{1-4}$ haloalkyl, such as $OCF_s$, $OCHF_2$ or $OCH_2CF_3$.

Clause 100—The compound according to any one of clauses 1 to 86 wherein $R_{12}$ is $C(=O)C_{1-2}$ alkyl, such as $C(=O)CH_3$.

Clause 101—The compound according to any one of clauses 1 to 86 wherein $R_{12}$ is $NR_{23}R_{24}$.

Clause 102—The compound according to clause 101 wherein $R_{12}$ is $N(CH_3)_2$.

Clause 103—The compound according to clause 101 wherein $R_{12}$ is N(H)Et.

Clause 104—The compound according to any one of clauses 1 to 86 wherein $R_{12}$ is $SO_2C_{1-4}$alkyl.

Clause 105—The compound according to clause 104 wherein $R_{12}$ is $SO_2CH_3$.

Clause 106—The compound according to any one of clauses 1 to 86 wherein $R_{12}$ is $C(O)N(CH_3)_2$.

Clause 107—The compound according to any one of clauses 1 to 86 wherein $R_{12}$ is $NHC(O)C_{1-3}$ alkyl such as $NHC(O)CH_3$.

Clause 108—The compound according to any one of clauses 1 to 86 wherein $R_{12}$ is OH.

Clause 109—The compound according to any one of clauses 1 to 86 wherein $R_{12}$ is $C_{3-6}$heterocycloalkyl comprising one nitrogen located at the point of attachment to Ar2 such as a $C_5$heterocycloalkyl or $C_6$heterocycloalkyl, and in particular pyrrolidinyl.

Clause 110—The compound according to any one of clauses 1 to 86 wherein $R_{12}$ together with a nitrogen atom to which it is attached forms an N-oxide ($N^+$—$O^-$).

Clause 111—The compound according to any one of clauses 1 to 110 wherein $R_{12}$ is in the meta position of Ar2.

Clause 112—The compound according to any one of clauses 1 to 110 wherein $R_{12}$ is in the ortho position of Ar2.

Clause 113—The compound according to any one of clauses 1 to 104 wherein $R_{13}$ is H.

Clause 114—The compound according to any one of clauses 1 to 104 wherein $R_{13}$ is methyl.

Clause 115—The compound according to clause 114 wherein $R_{13}$ is in the ortho position with respect to Ar1.

Clause 116—The compound according to clause 114 wherein $R_{13}$ is in the para position with respect to Ar1.

Clause 117—A compound of the examples T1 to T416.

Clause 118—A compound of the examples T417 to T465.

Clause 119—A compound of the formula:

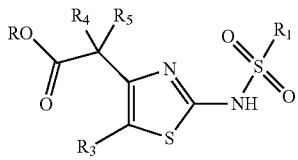

wherein $R_1$, $R_3$, $R_4$ and $R_5$ are as defined in any preceding clause and R is H, $C_{1-6}$alkyl (e.g. methyl and ethyl) or benzyl.

Clause 120—A compound of formula (III):

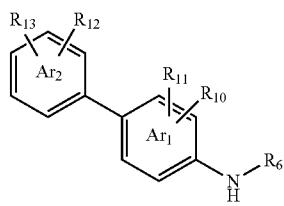

(III)

wherein Ar1, Ar2, $R_6$, $R_{10}$, $R_{11}$, $R_{12}$ and $R_{13}$ are as defined in any preceding clause.

Clause 121—A compound of formula (X):

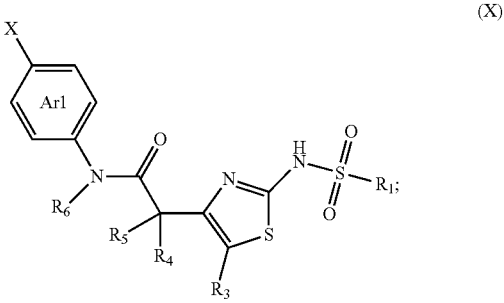

(X)

X = Cl, Br, B(OH)$_2$, B(pin)$_2$ wherein Ar1, $R_1$, $R_3$, $R_4$, $R_5$ and $R_6$ are as defined in any preceding clause.

Clause 122—A compound of formula (XII):

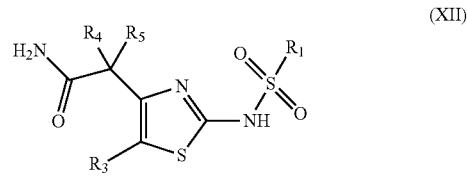

(XII)

wherein $R_1$, $R_3$, $R_4$ and $R_5$ are as defined in any preceding clause.

Clause 123—A compound of formula (XIII):

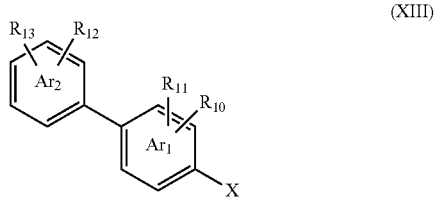

(XIII)

wherein Ar1, Ar2, $R_{10}$, $R_{11}$, $R_{12}$ and $R_{13}$ are as defined in any preceding clause and X is halo such as Cl.

Clause 124—A compound of INTA1 to INTA113, or salt such as pharmaceutically acceptable salt thereof.

Clause 125—A compound of INTB1 to INTB120, or salt such as pharmaceutically acceptable salt thereof.

Clause 126—The compound according to any one of clauses 1 to 123 wherein each heterocycloalkyl is a fully saturated hydrocarbon ring containing the specified number of carbon atoms wherein at least one of the carbon atoms is replaced by a heteroatom such as N, S or O.

Clause 127—A compound according to any one of clauses 1 to 118, for use as a medicament.

Clause 128—The compound according to clause 127, for use in the inhibition of CTPS1 in a subject.

Clause 129—The compound according to clause 127, for use in the reduction of T-cell and/or B-cell proliferation in a subject.

Clause 130—The compound according to clause 127, for use in the treatment or prophylaxis of: inflammatory skin diseases such as psoriasis or lichen planus; acute and/or chronic GVHD such as steroid resistant acute GVHD; acute lymphoproliferative syndrome (ALPS); systemic lupus erythematosus, lupus nephritis or cutaneous lupus; or transplantation.

Clause 131. The compound according to clause 127, for use in the treatment or prophylaxis of myasthenia gravis, multiple sclerosis or scleroderma/systemic sclerosis.

Clause 132—A method for the inhibition of CTPS1 in a subject, which comprises administering to the subject an effective amount of a compound according to any one of clauses 1 to 118.

Clause 133—Use of a compound according to any one of clauses 1 to 118, in the manufacture of a medicament for the inhibition of CTPS1 in a subject.

Clause 134. A compound according to clause 127, for use in the treatment of cancer.

Clause 135. A method for treating cancer in a subject, by administering to a subject in need thereof a compound according to any one of clauses 1 to 118.

Clause 136. Use of a compound according to any one of clauses 1 to 118, in the manufacture of a medicament for the treatment of cancer in a subject.

Clause 137. The compound according to clause 134, the method according to clause 135 or the use according to clause 136 wherein the cancer is a haematological cancer.

Clause 138. The compound, method or use according to clause 137 wherein the haematological cancer is selected from the group consisting of Acute myeloid leukemia, Angioimmunoblastic T-cell lymphoma, B-cell acute lymphoblastic leukemia, Sweet Syndrome, T-cell Non-Hodgkins lymphoma (including natural killer/T-cell lymphoma, adult T-cell leukaemia/lymphoma, enteropathy type T-cell lymphoma, hepatosplenic T-cell lymphoma and cutaneous T-cell lymphoma), T-cell acute lymphoblastic leukemia, B-cell Non-Hodgkins lymphoma (including Burkitt lymphoma, diffuse large B-cell lymphoma, Follicular lymphoma, Mantle cell lymphoma, Marginal Zone lymphoma), Hairy Cell Leukemia, Hodgkin lymphoma, Lymphoblastic lymphoma, Lymphoplasmacytic lymphoma, Mucosa-associated lymphoid tissue lymphoma, Multiple myeloma, Myelodysplastic syndrome, Plasma cell myeloma, Primary mediastinal large B-cell lymphoma, chronic myeloproliferative disorders (such as chronic myeloid leukemia, primary myelofibrosis, essential thrombocytemia, polycytemia vera) and chronic lymphocytic leukemia.

Clause 139. The compound according to clause 134, the method according to clause 135 or the use according to clause 136 wherein the cancer is a non-haematological cancer such as bladder cancer, breast cancer, melanoma, neuroblastoma, malignant pleural mesothelioma and sarcoma, such as breast cancer and melanoma.

Clause 140. The compound according to clause 127, for use in enhancing recovery from vascular injury or surgery and reducing morbidity and mortality associated with neointima and restenosis in a subject.

Clause 141. A method for enhancing recovery from vascular injury or surgery and reducing morbidity and mortality associated with neointima and restenosis in a subject, by administering to a subject in need thereof a compound according to any one of clauses 1 to 118.

Clause 142. Use of a compound according to any one of clauses 1 to 118, in the manufacture of a medicament for enhancing recovery from vascular injury or surgery and reducing morbidity and mortality associated with neointima and restenosis in a subject.

Clause 143—A pharmaceutical composition comprising a compound according to any one of clauses 1 to 118.

Clause 144—The compound, method or use according to any one of clauses 127 to 142, for administration to a human subject.

Clause 145—The compound, method, use or composition according to any one of clauses 127 to 144, for administration in conjunction with a further pharmaceutically acceptable active ingredient or ingredients.

Clause 146. The compound, method, use or composition according to any one of clauses 127 to 145, for topical administration to the skin, eye or gut.

Clause 147—The compound according to any one of clauses 1 to 146, which is in natural isotopic form.

REFERENCES

Cheng, D. et al. Discovery of Pyridinyl Acetamide Derivatives as Potent, Selective, and Orally Bioavailable Porcupine Inhibitors. Medicinal Chemistry Letters, 7(7), 676-680; 2016

Evans, D. R. & Guy, H. I. Mammalian pyrimidine biosynthesis: fresh insights into an ancient pathway. J. Biol. Chem. 279, 33035-33038 (2004).

Fairbanks, L. D., Bofill, M., Ruckemann, K. & Simmonds, H. A. Importance of ribonucleotide availability to proliferating T-lymphocytes from healthy humans. Disproportionate expansion of pyrimidine pools and contrasting effects of de novo synthesis inhibitors. J. Biol. Chem. 270, 29682-29689 (1995).

Higgins, M. J., Graves, P. R. & Graves, L. M. Regulation of human cytidine triphosphate synthetase 1 by glycogen synthase kinase 3. J. Biol. Chem. 282, 29493-29503 (2007).

Kursula, P., Flodin, S., Ehn, M., Hammarstrom, M., Schuler, H., Nordlund, P. and Stenmarka, P. Structure of the synthetase domain of human CTP synthetase, a target for anticancer therapy. Acta Crystallogr Sect F Struct Biol Cryst Commun. 62 (Pt7): 613-617 (2006).

Lieberman I. Enzymatic amination of uridine triphosphate to cytidine triphosphate. The J. Biol. Chem. 222 (2): 765-75 (1956).

Lubbers, T et al. Aminothiazoles as γ-secretase modulators. Bioorganic & Medicinal Chemistry Letters, 21(21), 6554-6558; 2011

Martin E. et al.; CTP synthase 1 deficiency in humans reveals its central role in lymphocytes proliferation. Nature. June 12; 510(7504):288-92 (2014). Erratum in: Nature. July 17; 511(7509):370 (2014).

McCluskey G D et al., Exploring the Potent Inhibition of CTP Synthase by Gemcitabine-5'-Triphosphate. Chembiochem. 17, 2240-2249 (2016).

Ostrander, D. B., O'Brien, D. J., Gorman, J. A. & Carman, G. M. Effect of CTP synthetase regulation by CTP on phospholipid synthesis in *Saccharomyces cerevisiae*. J. Biol. Chem. 273, 18992-19001 (1998).

Sakamoto K, Ishibashi Y, Adachi R, et al. Identification of cytidine-5-triphosphate synthase1-selective inhibitory peptide from random peptide library displayed on T7 phage. Peptides. 2017; 94:56-63 (2017).

Salu et al. Drug-eluting stents: a new treatment in the prevention of restenosis Part I: experimental studies. Acta Cardiol, 59, 51-61 (2004).

Sousa J. E. et al. Drug-Eluting Stents. Circulation, 107 (2003) 2274 (Part I), 2283 (Part II).

van den Berg, A. A. et al. Cytidine triphosphate (CTP) synthetase activity during cell cycle progression in normal and malignant T-lymphocytic cells. Eur. J. Cancer 31, 108-112 (1995).

van Kuilenburg, A. B. P, Meinsma, R., Vreken, P., Waterham, H. R., van Gennip, A. H. Identification of a cDNA encoding an isoform of human CTP synthetase. Biochimica et Biophysica Acta 1492548-552 (2000).

Xing-Li F. et al. Efficient Diphosphane-Based Catalyst for the Palladium-Catalyzed Suzuki Cross-Coupling Reaction of 3-Pyridylboronic Acids. European Journal of Organic Chemistry, (13), 2051-2054; 2009.

The invention claimed is:

1. A compound of formula (I):

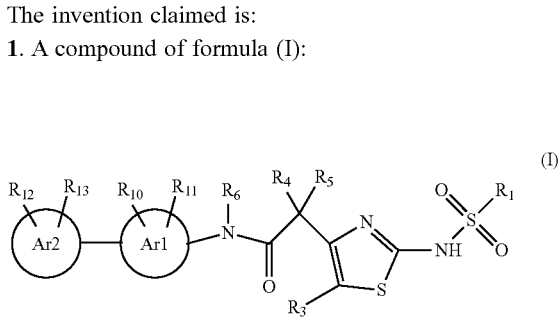

wherein $R_1$ is $C_{1-5}$alkyl, $C_{0-2}$alkylene$C_{3-5}$cycloalkyl which cycloalkyl is optionally substituted by $CH_3$, $C_{1-3}$alkyleneOC$_{1-2}$alkyl, or $CF_3$;

$R_3$ is H, halo, $CH_3$, $OC_{1-2}$alkyl or $CF_3$;

or $R_3$ together with $R_5$ forms a 5- or 6-membered cycloalkyl or 5 or 6 membered oxygen-containing heterocycloalkyl;

$R_4$ and $R_5$ are each independently H, halo, $C_{1-6}$alkyl, $C_{0-2}$alkylene$C_{3-6}$cycloalkyl, $C_{0-2}$alkylene$C_{3-6}$heterocycloalkyl, $OC_{1-6}$alkyl, $OC_{0-2}$alkylene$C_{3-6}$cycloalkyl, $C_{1-3}$alkyleneOC$_{1-3}$alkyl, $C_{1-6}$alkylOH, $C_{1-6}$haloalkyl, $OC_{1-6}$haloalkyl or $NR_{21}R_{22}$, or $R_4$ is H and $R_5$ together with $R_3$ form a 5- or 6-membered cycloalkyl or 5 or 6 membered oxygen-containing heterocycloalkyl, or $R_4$ and $R_5$ together with the carbon atom to which they are attached form a $C_{3-6}$cycloalkyl or $C_{3-6}$heterocycloalkyl, or $R_4$ is H and $R_5$ and $R_6$ are a $C_{2-3}$alkylene chain forming a 5- or 6-membered ring;

or $R_4$ is O and $R_5$ is absent;

$R_6$ is H or $C_{1-3}$alkyl, or $R_6$ together with Rn when in the ortho-position to the amide are a $C_2$alkylene chain forming a 5-membered ring, or $R_5$ and $R_6$ are a $C_{2-3}$alkylene chain forming a 5- or 6-membered ring and $R_4$ is H;

Ar1 is 6-membered aryl or 6-membered heteroaryl;

Ar2 is a 6-membered aryl or 6-membered heteroaryl and is attached to Ar1 in the para position relative to the amide;

$R_{10}$ is H, halo, $C_{1-3}$alkyl, $OC_{1-2}$alkyl, $C_{1-2}$haloalkyl, $OC_{1-2}$haloalkyl or CN;

$R_{11}$ is H, F, Cl, $CH_3$, ethyl, $OCH_3$, $CF_3$, $OCF_3$ or CN, or $R_{11}$, when in the ortho-position to the amide, together with $R_6$ are a $C_2$alkylene chain forming a 5-membered ring;

$R_{12}$ is attached to Ar2 in the ortho or meta position relative to Ar1 and $R_{12}$ is H, halo, $C_{1-4}$alkyl, $C_{2-4}$alkynyl, $C_{0-2}$alkylene$C_{3-5}$cycloalkyl, $OC_{1-4}$alkyl, $OC_{0-2}$alkylene$C_{3-5}$cycloalkyl, $OCH_2CH_2N(CH_3)_2$, OH, $C_{1-4}$alkylOH, CN, $C_{1-3}$alkyleneOC$_{1-3}$alkyl, $C_{1-4}$haloalkyl, $OC_{1-4}$haloalkyl, C(=O)$C_{1-2}$alkyl, $NR_{23}R_{24}$, $SO_2C_{1-4}$alkyl, $SOC_{1-4}$alkyl, $SC_{1-4}$alkyl, SH, $C(O)N(CH_3)_2$, $NHC(O)C_{1-3}$alkyl, $C_{3-6}$heterocycloalkyl comprising one nitrogen located at the point of attachment to Ar2, or $R_{12}$ together with a nitrogen atom to which it is attached forms an N-oxide ($N^+$—$O^-$);

$R_{13}$ is H, halo, $CH_3$ or $OCH_3$;

$R_{21}$ is H, $C_{1-5}$alkyl, $C(O)C_{1-5}$alkyl, $C(O)OC_{1-5}$alkyl;

$R_{22}$ is H or $CH_3$;

$R_{23}$ is H or $C_{1-2}$alkyl; and $R_{24}$ is H or $C_{1-2}$alkyl;

or a salt, solvate, or salt and solvate thereof.

2. The compound, salt, solvate, or salt and solvate thereof according to claim 1:

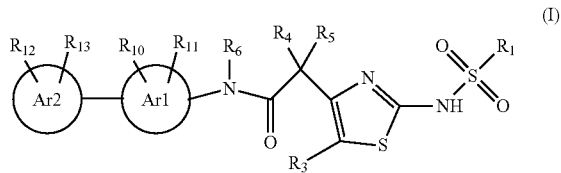

(I)

wherein $R_1$ is $C_{1-5}$alkyl, $C_{1-2}$alkyleneOC$_{1-2}$alkyl, $C_{0-2}$alkyleneC$_{3-5}$cycloalkyl which cycloalkyl is optionally substituted by $CH_3$, or $CF_3$;

$R_3$ is H, halo, $CH_3$, $CF_3$ or $OCH_3$;

or $R_3$ together with $R_5$ forms a 5- or 6-membered cycloalkyl;

$R_4$ and $R_5$ are each independently H, F, $C_{1-6}$alkyl, $C_{0-2}$alkyleneC$_{3-6}$cycloalkyl, $OC_{1-6}$alkyl, $OC_{0-2}$alkyleneC$_{3-6}$cycloalkyl, $C_{1-3}$alkyleneOC$_{1-3}$alkyl, $C_{1-6}$alkylOH, $C_{1-6}$haloalkyl, $OC_{1-6}$haloalkyl or $NR_{21}R_{22}$, or $R_4$ is H and $R_5$ together with $R_3$ form a 5- or 6-membered cycloalkyl, or $R_4$ and $R_5$ together with the carbon atom to which they are attached form a $C_{3-6}$cycloalkyl, or $R_4$ is O and $R_5$ is absent;

$R_6$ is H or $C_{1-3}$alkyl, or $R_6$ together with $R_{11}$ in the ortho-position to the amide are a $C_2$alkylene chain forming a 5-membered ring;

Ar1 is 6-membered aryl or 6-membered heteroaryl;

Ar2 is a 6-membered aryl or 6-membered heteroaryl and is attached to Ar1 in the para position relative to the amide;

$R_{10}$ is H, halo, $C_{1-3}$alkyl, $OC_{1-2}$alkyl, $C_{1-2}$haloalkyl, $OC_{1-2}$haloalkyl or CN;

$R_{11}$ is H, F, Cl, $CH_3$, ethyl, $OCH_3$, $CF_3$, $OCF_3$ or CN, or $R_{11}$, when in the ortho-position to the amide, together with $R_6$ are a $C_2$alkylene chain forming a 5-membered ring;

$R_{12}$ is attached to Ar2 in the ortho or meta position relative to Ar1 and $R_{12}$ is H, halo, $C_{1-4}$alkyl, $C_{2-4}$alkynyl, $C_{0-2}$alkyleneC$_{3-5}$cycloalkyl, $OC_{1-4}$alkyl, $OC_{0-2}$alkyleneC$_{3-5}$cycloalkyl, $OCH_2CH_2N(CH_3)_2$, OH, $C_{1-4}$alkylOH, CN, $C_{1-3}$alkyleneOC$_{1-3}$alkyl, $C_{1-4}$haloalkyl, $OC_{1-4}$haloalkyl, $N(CH_3)_2$, $SO_2CH_3$, $C(O)N(CH_3)_2$, $NHC(O)C_{1-3}$alkyl or a $C_{3-6}$heterocycloalkyl comprising one nitrogen located at the point of attachment to Ar2;

$R_{13}$ is H, F, $CH_3$ or $OCH_3$;

$R_{21}$ is H, $C_{1-5}$alkyl, $C(O)C_{1-5}$alkyl, $C(O)OC_{1-5}$alkyl; and $R_{22}$ is H or $CH_3$;

or a salt, solvate, or salt and solvate thereof.

3. The compound, salt, solvate, or salt and solvate thereof according to claim 1:

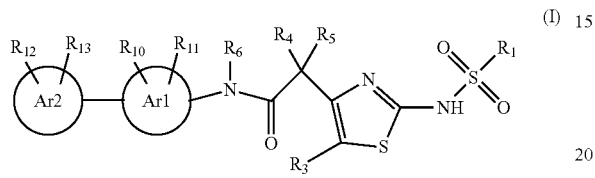

(I)

wherein $R_1$ is $C_{1-5}$alkyl, $C_{0-2}$alkyleneC$_{3-5}$cycloalkyl which cycloalkyl is optionally substituted by $CH_3$, or $CF_3$;

$R_3$ is H, halo, $CH_3$ or $CF_3$, or $R_3$ together with $R_5$ forms a 5- or 6-membered cycloalkyl;

$R_4$ and $R_5$ are each independently H, F, $C_{1-6}$alkyl, $C_{0-2}$alkyleneC$_{3-6}$cycloalkyl, $OC_{1-6}$alkyl, $OC_{0-2}$alkyleneC$_{3-6}$cycloalkyl, $C_{1-3}$alkyleneOC$_{1-3}$alkyl, $C_{1-6}$haloalkyl or $OC_{1-6}$haloalkyl, or $R_4$ is H and $R_5$ together with $R_3$ form a 5- or 6-membered cycloalkyl, or $R_4$ and $R_5$ together with the carbon atom to which they are attached form a $C_{3-6}$cycloalkyl, or $R_4$ is O and $R_5$ is absent;

$R_6$ is H or $C_{1-3}$alkyl, or $R_6$ together with $R_{11}$ in the ortho-position to the amide are a $C_2$alkylene chain forming a 5-membered ring;

Ar1 is 6-membered aryl or 6-membered heteroaryl;

Ar2 is a 6-membered aryl or 6-membered heteroaryl and is attached to Ar1 in the para position relative to the amide;

$R_{10}$ is H, halo, $C_{1-2}$alkyl, $OC_{1-2}$alkyl, $C_{1-2}$haloalkyl, $OC_{1-2}$haloalkyl or CN;

$R_{11}$ is H, F, Cl, $CH_3$, $OCH_3$, $CF_3$, $OCF_3$ or CN, or $R_{11}$, when in the ortho-position to the amide, together with $R_6$ are a $C_2$alkylene chain forming a 5-membered ring;

$R_{12}$ is attached to Ar2 in the ortho or meta position relative to Ar1 and $R_{12}$ is H, halo, $C_{1-4}$alkyl, $C_{2-4}$alkynyl, $C_{0-2}$alkyleneC$_{3-5}$cycloalkyl, $OC_{1-4}$alkyl, $OC_{0-2}$alkyleneC$_{3-5}$cycloalkyl, $OCH_2CH_2N(CH_3)_2$, $C_{1-4}$alkylOH, CN, $C_{1-3}$alkyleneOC$_{1-3}$alkyl, $C_{1-4}$haloalkyl, $OC_{1-4}$haloalkyl, $N(CH_3)_2$, $SO_2CH_3$, $C(O)N(CH_3)_2$, $NHC(O)C_{1-3}$alkyl or a $C_{3-6}$heterocycloalkyl comprising one nitrogen located at the point of attachment to Ar2; and $R_{13}$ is H, F, $CH_3$ or $OCH_3$;

or a salt, solvate, or salt and solvate thereof.

4. The compound, salt, solvate, or salt and solvate thereof according to claim 1, wherein $R_1$ is $C_{3-5}$cycloalkyl, optionally substituted by $CH_3$.

5. The compound, salt, solvate, or salt and solvate thereof according to claim 1, wherein $R_1$ is $C_{1-5}$alkyl.

6. The compound, salt, solvate, or salt and solvate thereof according to claim 1, wherein $R_3$ is H.

7. The compound, salt, solvate, or salt and solvate thereof according to claim 1, wherein $R_4$ is $C_{1-6}$alkyl.

8. The compound, salt, solvate, or salt and solvate thereof according to claim 1, wherein $R_5$ is H, methyl, ethyl or fluoro.

9. The compound, salt, solvate, or salt and solvate thereof according to claim 1, wherein $R_4$ is $OC_{1-6}$alkyl and $R_5$ is H; or $R_4$ is $C_{1-3}$alkylene$OC_{1-3}$alkyl and $R_5$ is H; or $R_4$ is $NR_{21}R_{22}$ and $R_5$ is H.

10. The compound, salt, solvate, or salt and solvate thereof according to claim 9 wherein $R_{21}$ is H, Me, C(O)OCH$_3$, C(O)CH$_3$ and $R_{22}$ is H or CH$_3$.

11. The compound, salt, solvate, or salt and solvate thereof according to claim 1 wherein $R_6$ is H.

12. The compound, salt, solvate, or salt and solvate thereof according to claim 1 wherein Ar1 is phenyl or 2-pyridyl.

13. The compound, salt, solvate, or salt and solvate thereof according to claim 1 wherein $R_{10}$ is H, F, Cl, CH$_3$, OCH$_3$ or OCF$_3$ and $R_1$ is H, F or CH$_3$.

14. The compound, salt, solvate, or salt and solvate thereof according to claim 1 wherein Ar2 is 3-pyridyl or pyrazinyl.

15. The compound, salt, solvate, or salt and solvate thereof according to claim 1 wherein $R_{12}$ is H, fluoro, chloro, CH$_3$, cyclopropyl, C≡CH, OCH$_3$, ethoxy, n-propoxy, isopropoxy, cyclopropoxy, CN, CF$_3$, OCHF$_2$, OCH$_2$CF$_3$ or pyrrolidinyl, and $R_{13}$ is H.

16. The compound, salt, solvate or salt and solvate thereof according to claim 4, wherein $R_1$ is cyclopropyl.

17. The compound, salt, solvate or salt and solvate thereof according to claim 9, wherein $R_4$ is $C_{1-3}$alkylene$OC_{1-3}$alkyl and $R_5$ is H.

18. A compound of formula (I):

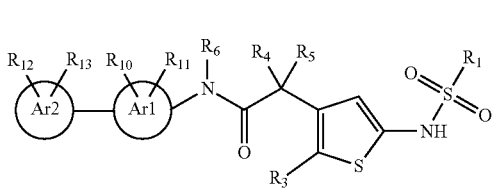

(I)

wherein
$R_1$ is $C_{1-5}$alkyl, $C_{0-2}$alkylene$C_{3-5}$cycloalkyl which cycloalkyl is optionally substituted by CH$_3$, $C_{1-3}$alkylene$OC_{1-2}$alkyl, or CF$_3$;

$R_3$ is H, halo, CH$_3$, $OC_{1-2}$alkyl or CF$_3$;
or $R_3$ together with $R_5$ forms a 5- or 6-membered cycloalkyl or 5 or 6 membered oxygen-containing heterocycloalkyl;

$R_4$ and $R_5$ are each independently H, halo, $C_{1-6}$alkyl, $C_{0-2}$alkylene$C_{3-6}$cycloalkyl, $C_{0-2}$alkylene$C_{3-6}$heterocycloalkyl, $OC_{1-6}$alkyl, $OC_{0-2}$alkylene$C_{3-6}$cycloalkyl, $C_{1-3}$alkylene$OC_{1-3}$alkyl, $C_{1-6}$alkylOH, $C_{1-6}$haloalkyl, $OC_{1-6}$haloalkyl or $NR_{21}R_{22}$,
or $R_4$ is H and $R_5$ together with $R_3$ form a 5- or 6-membered cycloalkyl or 5 or 6 membered oxygen-containing heterocycloalkyl,
or $R_4$ and $R_5$ together with the carbon atom to which they are attached form a $C_{3-6}$cycloalkyl or $C_{3-6}$heterocycloalkyl,
or $R_4$ is H and $R_5$ and $R_6$ are a $C_{2-3}$alkylene chain forming a 5- or 6-membered ring;
or $R_4$ is O and $R_5$ is absent;

$R_6$ is H or $C_{1-3}$alkyl,
or $R_6$ together with $R_{11}$ when in the ortho-position to the amide are a $C_2$alkylene chain forming a 5-membered ring, or $R_5$ and $R_6$ are a $C_{2-3}$alkylene chain forming a 5- or 6-membered ring and $R_4$ is H;

Ar1 is 6-membered aryl or 6-membered heteroaryl;
Ar2 is a 6-membered aryl or 6-membered heteroaryl and is attached to Ar1 in the para position relative to the amide;

$R_{10}$ is H, halo, $C_{1-3}$alkyl, $OC_{1-2}$alkyl, $C_{1-2}$haloalkyl, $OC_{1-2}$haloalkyl or CN;

$R_{11}$ is H, F, Cl, CH$_3$, ethyl, OCH$_3$, CF$_3$, OCF$_3$ or CN, or $R_{11}$, when in the ortho-position to the amide, together with $R_6$ are a $C_2$alkylene chain forming a 5-membered ring;

$R_{12}$ is attached to Ar2 in the ortho or meta position relative to Ar1 and $R_{12}$ is H, halo, $C_{1-4}$alkyl, $C_{2-4}$alkynyl, $C_{0-2}$alkylene$C_{3-5}$cycloalkyl, $OC_{1-4}$alkyl, $OC_{0-2}$alkylene$C_{3-5}$cycloalkyl, OCH$_2$CH$_2$N(CH$_3$)$_2$, OH, $C_{1-4}$alkylOH, CN, $C_{1-3}$alkyleneOC$_{1-3}$alkyl, $C_{1-4}$haloalkyl, $OC_{1-4}$haloalkyl, C(=O)$C_{1-2}$alkyl, $NR_{23}R_{24}$, SO$_2$C$_{1-4}$alkyl, SOC$_{1-4}$alkyl, SC$_{1-4}$alkyl, SH, C(O)N(CH$_3$)$_2$, NHC(O)C$_{1-3}$alkyl, $C_{3-6}$heterocycloalkyl comprising one nitrogen located at the point of attachment to Ar2, or $R_{12}$ together with a nitrogen atom to which it is attached forms an N-oxide (N$^+$—O$^-$);

$R_{13}$ is H, halo, CH$_3$ or OCH$_3$;
$R_{21}$ is H, $C_{1-5}$alkyl, C(O)C$_{1-5}$alkyl, C(O)OC$_{1-5}$alkyl;
$R_{22}$ is H or CH$_3$;
$R_{23}$ is H or $C_{1-2}$alkyl; and
$R_{24}$ is H or $C_{1-2}$alkyl.

19. A salt of a compound of formula (I):

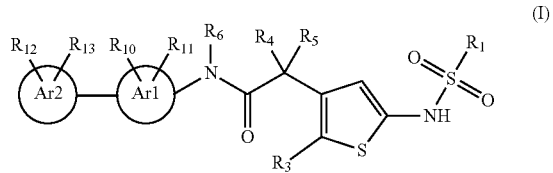

(I)

wherein
$R_1$ is $C_{1-5}$alkyl, $C_{0-2}$alkylene$C_{3-5}$cycloalkyl which cycloalkyl is optionally substituted by CH$_3$, $C_{1-3}$alkylene$OC_{1-2}$alkyl, or CF$_3$;

$R_3$ is H, halo, CH$_3$, $OC_{1-2}$alkyl or CF$_3$;
or $R_3$ together with $R_5$ forms a 5- or 6-membered cycloalkyl or 5 or 6 membered oxygen-containing heterocycloalkyl;

$R_4$ and $R_5$ are each independently H, halo, $C_{1-6}$alkyl, $C_{0-2}$alkylene$C_{3-6}$cycloalkyl, $C_{0-2}$alkylene$C_{3-6}$heterocycloalkyl, $OC_{1-6}$alkyl, $OC_{0-2}$alkylene$C_{3-6}$cycloalkyl, $C_{1-3}$alkylene$OC_{1-3}$alkyl, $C_{1-6}$alkylOH, $C_{1-6}$haloalkyl, $OC_{1-6}$haloalkyl or $NR_{21}R_{22}$,
or $R_4$ is H and $R_5$ together with $R_3$ form a 5- or 6-membered cycloalkyl or 5 or 6 membered oxygen-containing heterocycloalkyl,
or $R_4$ and $R_5$ together with the carbon atom to which they are attached form a $C_{3-6}$cycloalkyl or $C_{3-6}$heterocycloalkyl,
or $R_4$ is H and $R_5$ and $R_6$ are a $C_{2-3}$alkylene chain forming a 5- or 6-membered ring;
or $R_4$ is O and $R_5$ is absent;

$R_6$ is H or $C_{1-3}$alkyl,
or $R_6$ together with Rn when in the ortho-position to the amide are a $C_2$alkylene chain forming a 5-membered ring, or $R_5$ and $R_6$ are a $C_{2-3}$alkylene chain forming a 5- or 6-membered ring and $R_4$ is H;

Ar1 is 6-membered aryl or 6-membered heteroaryl;

Ar2 is a 6-membered aryl or 6-membered heteroaryl and is attached to Ar1 in the para position relative to the amide;

$R_{10}$ is H, halo, $C_{1-3}$alkyl, $OC_{1-2}$alkyl, $C_{1-2}$haloalkyl, $OC_{1-2}$haloalkyl or CN;

$R_{11}$ is H, F, Cl, $CH_3$, ethyl, $OCH_3$, $CF_3$, $OCF_3$ or CN, or $R_{11}$, when in the ortho-position to the amide, together with $R_6$ are a $C_2$alkylene chain forming a 5-membered ring;

$R_{12}$ is attached to Ar2 in the ortho or meta position relative to Ar1 and $R_{12}$ is H, halo, $C_{1-4}$alkyl, $C_{2-4}$alkynyl, $C_{0-2}$alkylene$C_{3-5}$cycloalkyl, $OC_{1-4}$alkyl, $OC_{0-2}$alkylene$C_{3-5}$cycloalkyl, $OCH_2CH_2N(CH_3)_2$, OH, $C_{1-4}$alkylOH, CN, $C_{1-3}$alkylene$OC_{1-3}$alkyl, $C_{1-4}$haloalkyl, $OC_{1-4}$haloalkyl, $C(=O)C_{1-2}$alkyl, $NR_{23}R_{24}$, $SO_2C_{1-4}$alkyl, $SOC_{1-4}$alkyl, $SC_{1-4}$alkyl, SH, $C(O)N(CH_3)_2$, $NHC(O)C_{1-3}$alkyl, $C_{3-6}$heterocycloalkyl comprising one nitrogen located at the point of attachment to Ar2, or $R_{12}$ together with a nitrogen atom to which it is attached forms an N-oxide ($N^+$—$O^-$);

$R_{13}$ is H, halo, $CH_3$ or $OCH_3$;

$R_{21}$ is H, $C_{1-5}$alkyl, $C(O)C_{1-5}$alkyl, $C(O)OC_{1-5}$alkyl;

$R_{22}$ is H or $CH_3$;

$R_{23}$ is H or $C_{1-2}$alkyl; and $R_{24}$ is H or $C_{1-2}$alkyl.

\* \* \* \* \*

SEQUENCE LISTING

```
<160> NUMBER OF SEQ ID NOS: 2

<210> SEQ ID NO 1
<211> LENGTH: 20
<212> TYPE: PRT
<213> ORGANISM: Artificial Sequence
<220> FEATURE:
<223> OTHER INFORMATION: synthetic

<400> SEQUENCE: 1

Gly Gly Asp Tyr Lys Asp Asp Asp Lys Gly Gly His His His
1               5                   10                  15

His His His His
            20

<210> SEQ ID NO 2
<211> LENGTH: 29
<212> TYPE: PRT
<213> ORGANISM: Artificial Sequence
<220> FEATURE:
<223> OTHER INFORMATION: synthetic

<400> SEQUENCE: 2

Asp Tyr Lys Asp Asp Asp Asp Lys His His His His His Gly Leu
1               5                   10                  15

Asn Asp Ile Phe Glu Ala Gln Lys Ile Glu Trp His Glu
            20                  25
```